US009290573B2

(12) United States Patent
Cong et al.

(10) Patent No.: US 9,290,573 B2
(45) **Date of Patent: *Mar. 22, 2016**

(54) THERAPEUTIC LOW DENSITY LIPOPROTEIN-RELATED PROTEIN 6 (LRP6) MULTIVALENT ANTIBODIES

(75) Inventors: Feng Cong, Quincy, MA (US); Seth Ettenberg, Melrose, MA (US); David Jenkins, Carlisle, MA (US); Ming Lei, Acton, MA (US); Andreas Loew, Somerville, MA (US); Karen Vincent, Basel (CH); Li Zhou, West Roxbury, MA (US)

(73) Assignee: NOVARTIS AG, BASEL (CH)

( * ) Notice: Subject to any disclaimer, the term of this patent is extended or adjusted under 35 U.S.C. 154(b) by 34 days.

This patent is subject to a terminal disclaimer.

(21) Appl. No.: 13/696,372

(22) PCT Filed: May 5, 2011

(86) PCT No.: PCT/EP2011/057200

§ 371 (c)(1),
(2), (4) Date: Nov. 6, 2012

(87) PCT Pub. No.: WO2011/138391

PCT Pub. Date: Nov. 10, 2011

(65) Prior Publication Data

US 2013/0064823 A1 Mar. 14, 2013

Related U.S. Application Data

(60) Provisional application No. 61/331,993, filed on May 6, 2010.

(51) Int. Cl.

| | |
|---|---|
| ***C07K 16/28*** | (2006.01) |
| ***C07K 16/46*** | (2006.01) |
| ***A61K 39/395*** | (2006.01) |
| *A61K 39/00* | (2006.01) |

(52) U.S. Cl.

CPC ........... *C07K 16/2863* (2013.01); *A61K 39/395* (2013.01); *A61K 39/3955* (2013.01); *C07K 16/28* (2013.01); *C07K 16/468* (2013.01); *A61K 2039/505* (2013.01); *C07K 2317/21* (2013.01); *C07K 2317/31* (2013.01); *C07K 2317/33* (2013.01); *C07K 2317/34* (2013.01); *C07K 2317/35* (2013.01); *C07K 2317/55* (2013.01); *C07K 2317/622* (2013.01); *C07K 2317/64* (2013.01); *C07K 2317/76* (2013.01); *C07K 2317/92* (2013.01); *C07K 2317/94* (2013.01); *C07K 2319/00* (2013.01)

(58) Field of Classification Search

None

See application file for complete search history.

(56) References Cited

U.S. PATENT DOCUMENTS

| | | | |
|---|---|---|---|
| 5,242,813 | A | 9/1993 | Pastan et al. |
| 5,624,659 | A | 4/1997 | Bigner et al. |
| 6,686,179 | B2 | 2/2004 | Fleer et al. |
| 6,780,609 | B1 | 8/2004 | Carulli et al. |
| 6,972,322 | B2 | 12/2005 | Fleer et al. |
| 6,987,006 | B2 | 1/2006 | Fleer et al. |
| 6,989,365 | B2 | 1/2006 | Fleer et al. |
| 7,041,478 | B2 | 5/2006 | Fleer et al. |
| 7,056,701 | B2 | 6/2006 | Fleer et al. |
| 7,081,354 | B2 | 7/2006 | Fleer et al. |
| 7,094,577 | B2 | 8/2006 | Fleer et al. |
| 7,105,160 | B1 | 9/2006 | Smith |
| 7,410,779 | B2 | 8/2008 | Fleer et al. |
| 7,416,849 | B2 | 8/2008 | Allen et al. |
| 7,435,410 | B2 | 10/2008 | Fleer et al. |
| 7,442,534 | B2 | 10/2008 | Abo et al. |
| 7,563,619 | B2 | 7/2009 | Williams et al. |
| 7,622,267 | B2 | 11/2009 | Williams et al. |
| 7,700,101 | B2 | 4/2010 | Allen et al. |
| 7,833,521 | B2 | 11/2010 | Fleer et al. |
| 7,906,121 | B2 | 3/2011 | Chang et al. |
| 7,951,918 | B2 | 5/2011 | Glaser et al. |
| 7,960,142 | B2 | 6/2011 | Glaser et al. |
| 2003/0138804 | A1 | 7/2003 | Boyle et al. |
| 2003/0194708 | A1 | 10/2003 | Binnerts et al. |
| 2004/0038860 | A1 | 2/2004 | Allen et al. |
| 2004/0176582 | A1 | 9/2004 | Carulli et al. |
| 2004/0244069 | A1 | 12/2004 | Askew et al. |
| 2005/0070699 | A1 | 3/2005 | Allen et al. |
| 2005/0084494 | A1 | 4/2005 | Prockop et al. |
| 2005/0142617 | A1 | 6/2005 | Carulli et al. |
| 2006/0051851 | A1 | 3/2006 | Kaminaka et al. |
| 2006/0094046 | A1 | 5/2006 | Abo et al. |
| 2006/0127393 | A1 | 6/2006 | Li et al. |
| 2006/0127919 | A1 | 6/2006 | Abo et al. |
| 2006/0198791 | A2 | 9/2006 | Wu et al. |

(Continued)

FOREIGN PATENT DOCUMENTS

| | | | |
|---|---|---|---|
| EP | 338395 | A2 | 10/1989 |
| EP | 1128847 | B1 | 9/2001 |

(Continued)

OTHER PUBLICATIONS

Ettenberg et al., Proceedings of the National Academy of Sciences, 107(35):15473-15478 (2010).

Abbas, et al: Cellular and Molecular Immunology (Eds. Abass et al.: 1991: WB Saunders: Philadelphia: p. 54).

Al et al: 'Reduced Affinity to and Inhibition by DKK1 Form a Common Mechanism by Which High Bone Mass-Associated Missense Mutations in LRP5 Affect Canonical WNT Signaling' Molecular and Cellular Biology vol. 25, No. 12, Jun. 15, 2005, pp. 4946 - 4955, XP055034028 DOI: 10.11281MCB.25.12.4946-4955.2005 ISSN: 0270-7306.

Binnerts et al: "The First Propeller Domain of LRP6 Regulates Sensitivity to DKK1", Molecular Biology of the Cell, vol. 20, No. 15, Aug. 1, 2009. pp. 3552-3560.

(Continued)

*Primary Examiner* — Zachary Howard

(74) *Attorney, Agent, or Firm* — John Prince

(57) ABSTRACT

The present disclosure relates to an antibody or antigen binding fragment having at least two receptor binding domains for two different binding sites of LRP6 and compositions and methods of use thereof.

9 Claims, 45 Drawing Sheets

(56) References Cited

U.S. PATENT DOCUMENTS

| | | | |
|---|---|---|---|
| 2006/0257892 | A1 | 11/2006 | Cohen et al. |
| 2006/0263375 | A1 | 11/2006 | Smith |
| 2007/0248628 | A1 | 10/2007 | Keller et al. |
| 2007/0280948 | A1 | 12/2007 | Williams et al. |
| 2007/0292348 | A1 | 12/2007 | Williams et al. |
| 2008/0014208 | A1 | 1/2008 | Reiter et al. |
| 2008/0050370 | A1 | 2/2008 | Glaser et al. |
| 2008/0227734 | A1 | 9/2008 | Westin et al. |
| 2009/0048122 | A1 | 2/2009 | Glaser et al. |
| 2009/0117108 | A1 | 5/2009 | Wang et al. |
| 2009/0130105 | A1 | 5/2009 | Glaser et al. |
| 2009/0130113 | A1 | 5/2009 | Kneissel et al. |
| 2009/0136507 | A1 | 5/2009 | Allen et al. |
| 2009/0155255 | A1 | 6/2009 | Glaser et al. |
| 2009/0163407 | A1 | 6/2009 | Bafico et al. |
| 2009/0181009 | A1 | 7/2009 | Abo et al. |
| 2009/0202433 | A1 | 8/2009 | Chang et al. |
| 2009/0280116 | A1 | 11/2009 | Smith et al. |
| 2009/0312253 | A1 | 12/2009 | Zheng |
| 2010/0092473 | A1 | 4/2010 | Muraca |
| 2010/0129928 | A1 | 5/2010 | Polakewicz et al. |
| 2010/0228335 | A1 | 9/2010 | Schorgl et al. |
| 2010/0254980 | A1 | 10/2010 | Cong et al. |
| 2011/0052488 | A1 | 3/2011 | Dennis, Jr. et al. |
| 2011/0059076 | A1 | 3/2011 | McDonagh et al. |
| 2011/0123532 | A1 | 5/2011 | Gurney et al. |
| 2011/0172398 | A1 | 7/2011 | Borges et al. |
| 2011/0195020 | A1 | 8/2011 | Chang et al. |
| 2011/0200623 | A1 | 8/2011 | Song et al. |
| 2011/0243963 | A1 | 10/2011 | Abo et al. |
| 2011/0256127 | A1 | 10/2011 | Bourhis et al. |
| 2011/0301331 | A1 | 12/2011 | Glaser et al. |
| 2012/0003221 | A1 | 1/2012 | McDonagh et al. |
| 2012/0014950 | A1 | 1/2012 | Migone et al. |
| 2012/0045437 | A1 | 2/2012 | Ma et al. |
| 2012/0076728 | A1 | 3/2012 | Wu et al. |
| 2012/0100074 | A1 | 4/2012 | Smith et al. |
| 2012/0100562 | A1 | 4/2012 | Bourhis et al. |
| 2013/0058934 | A1 | 3/2013 | Cong et al. |
| 2013/0064823 | A1 | 3/2013 | Cong et al. |
| 2014/0050725 | A1 | 2/2014 | Jenkins et al. |

FOREIGN PATENT DOCUMENTS

| | | | |
|---|---|---|---|
| EP | 1130094 | A2 | 9/2001 |
| EP | 1396543 | A2 | 3/2004 |
| EP | 1437410 | A1 | 7/2004 |
| EP | 0624195 | B1 | 9/2004 |
| EP | 1483288 | A2 | 12/2004 |
| EP | 1692167 | A2 | 8/2006 |
| EP | 1736484 | B1 | 12/2006 |
| EP | 2024392 | A2 | 2/2009 |
| EP | 2024507 | A2 | 2/2009 |
| EP | 2080812 | A1 | 7/2009 |
| EP | 2197490 | A2 | 6/2010 |
| EP | 2209491 | A2 | 7/2010 |
| EP | 2220122 | A2 | 8/2010 |
| EP | 2220247 | A2 | 8/2010 |
| EP | 2242853 | A2 | 10/2010 |
| EP | 2300501 | A2 | 3/2011 |
| EP | 2303303 | A2 | 4/2011 |
| EP | 2411412 | A1 | 2/2012 |
| EP | 2419120 | A2 | 2/2012 |
| EP | 2424567 | A2 | 3/2012 |
| JP | 2007-536938 | A | 12/2007 |
| WO | 9316178 | A2 | 8/1993 |
| WO | 9846743 | A1 | 10/1998 |
| WO | 0027435 | A1 | 5/2000 |
| WO | 0043419 | A2 | 7/2000 |
| WO | 0052165 | A2 | 9/2000 |
| WO | 02/092015 | A2 | 11/2002 |
| WO | 02092000 | A2 | 11/2002 |
| WO | 03029469 | A1 | 4/2003 |
| WO | 2005048913 | A2 | 6/2005 |
| WO | 2006/055635 | A2 | 5/2006 |
| WO | 2006/089114 | A2 | 8/2006 |
| WO | 2007109254 | A2 | 9/2007 |
| WO | 2007136778 | A2 | 11/2007 |
| WO | 2007140410 | A2 | 12/2007 |
| WO | 2007142987 | A2 | 12/2007 |
| WO | 2008013934 | A2 | 1/2008 |
| WO | 2008070047 | A2 | 6/2008 |
| WO | 2009032782 | A2 | 3/2009 |
| WO | 2009043051 | A2 | 4/2009 |
| WO | 2009051957 | A2 | 4/2009 |
| WO | 2009051974 | A1 | 4/2009 |
| WO | 2009/056634 | A2 | 5/2009 |
| WO | 2009064854 | A2 | 5/2009 |
| WO | 2009064944 | A2 | 5/2009 |
| WO | 2009126920 | A2 | 10/2009 |
| WO | 2009155055 | A2 | 12/2009 |
| WO | 2010011096 | A2 | 1/2010 |
| WO | 2010017472 | A1 | 2/2010 |
| WO | 2010/059315 | A1 | 5/2010 |
| WO | 2010111180 | A1 | 9/2010 |
| WO | 2010118169 | A2 | 10/2010 |
| WO | 2010129304 | A2 | 11/2010 |
| WO | 2011028945 | A1 | 3/2011 |
| WO | 2011039370 | A1 | 4/2011 |
| WO | 2011047180 | A1 | 4/2011 |
| WO | 2011084714 | A2 | 7/2011 |
| WO | 2011103426 | A2 | 8/2011 |
| WO | 2011/119661 | A1 | 9/2011 |
| WO | 2011106707 | A2 | 9/2011 |
| WO | 2011/138391 | A1 | 11/2011 |
| WO | 2011138392 | A1 | 11/2011 |
| WO | 2012054565 | A1 | 4/2012 |
| WO | 2012079093 | A2 | 6/2012 |
| WO | 2013/067355 | A1 | 5/2013 |

OTHER PUBLICATIONS

Bourhis et al., "Reconstitution of a frizzled8.Wnt3a.LRP6 signaling complex reveals multiple Wnt and Dkk1 binding sites on LRP6." Journal of Biological Chemistry, American Society for Biochemistry and Molecular Biology, 285 (12):9172-9179 (2010).

Davidson, et al "Kremen proteins interact with Dickkopf1 to regulate anteroposterior CNS patterning" Development, vol. 129, No. 24, 2002, pp. 5587-5596.

GenBank Accession No. AAA53291, Marget, M. et al., "Cloning and characterization of cDNAs coding for the heavy and light chains of a monoclonal antibody specific for Pseudomonas aeruginosa outer membrane protein 1," Gene, vol. 74:335-345 (1988), 2 pages, Nov. 28, 1994.

Gong et al: "Wnt Isoform-Specific Interactions with Coreceptor Specify Inhibition or Potentiation of Signaling by LRP6 Antibodies", Plos One. vol. 5, No. 9, Sep. 13, 2010. p. E12682.

He, et al. LDL Receptor-related proteins 5 and 6 Wnt/β-catenin signaling: Arrows point the way (Development, 131: 1663-1677, 2004).

International Preliminary Report on Patentability and Written Opinion for Application No. PCT/US2008/083486, 6 pages, dated May 18,2010.

International Preliminary Report on Patentability for PCT/EP2011/057202 dated Nov. 6, 2012.

International Preliminary Report on Patentablity & Written Opinion for PCT/EP2011/057200 dated Jul. 29, 2011.

International Search Report for Application No. PCT/US08/83486, 3 pages, dated Apr. 29, 2009.

International Search Report for PCT/EP2008/064821 dated Oct. 23, 2009.

International Search Report for PCT/EP2011/057200 dated Jul. 29, 2011.

International Search Report for PCT/EP2011/057202 dated Nov. 10, 2011.

International Search Report for PCT/US2012/063330 dated Apr. 10, 2013.

Li et al: "Second cysteine-rich domain of Dickkopf-2 activates canonical Wnt signaling pathway via LRP-6 independently of dishevelled." The Journal of Biological Chemistry Feb. 22, 2002, vol. 277, No. 8, Feb. 22, 2002, pp. 5977-5981, XP002538337 ISSN: 0021-9258.

(56) References Cited

OTHER PUBLICATIONS

Mao et al., "Kremen proteins are Dickkopf receptors that regulate Wntlbeta-catenin signalling", Nature: International Weekly Journal of Science, 417(6889):664-667 (2002).
Mao et al: "LDL-receptor-related protein 6 is a receptor for Dickkopf proteins" Nature, Nature Publishing Group; London, UK, vol. 411, No. 6835, May 17, 2001, pp. 321-325.
Mueller et al., "Improved pharmacokinetics of recombinant bispecific antibody molecules by fusion to human serum albumin." Journal of Biological Chemistry, American Society for Biochemistry and Molecular Biology, 282 (17:12650-12660 (2007).
Third Party Observations against European Patent Application No. 08 844 924.4 filed with the European Patent Office on Apr. 16, 2012.
Wei et al., "The LDL receptor-related protein LRP6 mediates internalization and lethality of anthrax toxin." Cell, 124:1141-1154 (2006).
Written Opinion for PCT/EP2008/064821 dated Oct. 23, 2009.
Written Opinion for PCT/EP2011/057202 dated Nov. 6, 2012.
Yaccoby, Shmuel et al., "Antibody-based inhibition of DKK1 suppresses tumor-induced bone resorption and multiple myeloma growth in vivo," Blood, vol. 109(5):2106-2111 (2007).
Zahid et al: "Analysis of endogenous LRP6 function reveals a novel feedback mechanism by which Wnt negatively regulates its receptor." Molecular and Cellular Biology Oct. 2007, vol. 27, No. 20, Oct. 2007, pp. 7291-7301, XP002538338 ISSN: 0270-7306.
Anraku, et al., "Validation of the chloramine-T induced oxidation of human serum umin as a model for oxidative damage in vivo," Pharmaceutical Research, 20(4): 684-92 (2003).
Barker at al., "Mininsg the Wnt pathway for cancer therapeutics," Nat. Rev. Drug Discov., 5(12): 997-1014, (2006).
Bhat et al., "Structure-based mutation analysis shows the importance of LRP5 beta-propeller 1 in modulating Dkk1-mediated inhibition of Wnt signaling" Gene 391: 103-112 (2007).
Binnerts et al., "R-Spondin I regulates Wnt signaling by inhibiting internalization of LRP6," Proc. Natl. Sci. USA, 104;14700-14705 (2007).
Boyden et al., "High bone density due to a mutation in LDL-receptor-related protein 5," New Engl. J. Med. 346: 1513-1521 (2002).
Brown et al., " Isolation and characterization of LRP6, a novel member of the density lipoprotein receptor gene family," Biochem. Biophys. Res. Commun, 248(3): 879-88 (1998).
Chen et al., "Modulating antibody pharmacokinetics using hydrophilic polymers" Expert Opinion on Drug Delivery 8(9): 1221-1236 (2011).
Cong et al., "Wnt Signals Across the Plasma Membrane to Activate the b-Catenin Pathway by Forming Oligomers Containing Its Receptors. Frizzled and LRP," Development 131(20): 5103-5115 (2004).
DasGupta et al., "Multiple Roles for Activated LEF/TCF Transcription Complexes During Hair Follicle Development and Differentiation," Development 126(20): 4557-4568 (1998).
Dianna et al., "Dickkopf-1 is a master regulator of joint remodeling," Nat. Med. 13: 156-163 (2007).
Ettenberg et al.,"Inhibition of tumorigenesis driven by different Wnt proteins requires blockade of distinct ligand-binding regions by LRP6 antibodies", Proc. Natl. Acad. Sci, USA 107(35): 15473-15478 (2010).
Evans et al., "The production, characterisation and enhanced pharmacokinetics of scFv-albumin fusions expressed in *Saccharomyces cerevisiae*" Protein Expression & Purification 73(2): 113-24 (2010).
Fathke et al., "Wnt signaling induces epithelial differentiation during cutaneous wound healing," BMC Cell Biology, 7:4 (2006).
GenBank Acc. No. NM_002336.2, GI:148727287, 2014.
Gong et al., "LDL receptor-related protein 5 (LRP5) affects bone accrual and eye developmeny," Cell 107: 513-523 (2001).
Harehaili et al., "Site-directed mutagenesis studies of human serum albumin define tryptophan at amino acid position 214 as the principal site for nitrosation. " Journal of Biomedical Science 9(1):47-58 (2002).
Hurst at al., "Phospholipid hydroperoxide cysteine peroxidase activity of human serum albumin" Biochem. J. 338: 723-728 (1999).
International Preliminary Report on Patentability and Written Opinion for PCT/EP2008/064821, issued May 4, 2010.
International Preliminary Report on Patentability and Written Opinion for PCTUS2012063330, issued May 6, 2014.
International Preliminary Report on Pate ablity and Written Opinion for PCT/EP2011/057200, issued Nov. 6, 2012.
International Search Report for PCT/EP2011/057200 mailed Jul. 29, 2011.
Ito et al., "Stem cells in the hair follicle bulge contribute to wound repair but not to homeostasis the epidermis " Nat. Med. 11: 1351-1354 (2005).
Jeon et al., "Implications for familial hypercholesteroiernia from the structure of the LDL receptor YWTD-EGF domain pair," Nat. Struct. Biol, 8:499-504 (2001).
Khan et al., "Analysis of Endogenous LRP6 Function Reveals a Novel Feedback Mechanism by Which Wnt Negatively Regulates its Receptor," Molecular and Cellular Biology 27(20): 7291-7301 (2007).
Kirikoshi et al.,"Expression profiles of 10 members of Frizzled gene family in human gastric cancer," Int. J Oncol. 19:767-771 (2001).
Kontermann et al., "Strategies to Extend Plasma Half-Lives of Recombinant Antibodies," Biodrugs 23(2): 93-109.
Korinek et al., "Depletion of epithelial stem-cell compartments in the small intestine of mice lacking Tcf-4," Nat. Genet. 19: 379-83 (1998).
Krishnan et al., "Regulation of bone mass by Wnt signaling," J. Clin. Invest. 116, 1202-1209 (2006).
Kuhnert et al., "Essential requirement for Wnt signaling in proliferation of adult small intestine and colon revealed by adenoviral expression of Dickkopf-1 ," Proc. Natl. Acad Sci. USA 101:266-71 (2004).
Kulkarni et al., "Orally bioavailable GSK-3alpha/beta dual inhibitor increases markers of cellular differentiation in vitro and bone mass in vivo," J. Bone Miner. Res. 21: 910-920 (2006).
Li et al., "Second Cysteine-rich Domain of Dickkopf-2 Activates Canonical Wnt Signaling Pathway via LRP-6 Independently of Dishevelled," The Journal of Biological Chemistry 277(8): 5977-5981 (2002).
Liu et al., "A novel bivalent single-chain variable fragment (scFV) inhibits the action of tumour necrosis factor alpha," Biotechnology and Applied Biochemistry 50: 173-179 (2008).
Lo Celso et al., "Transient activation of beta-catenin signalling in adult mouse epidermis is sufficient to induce new hair follicles but continuous activation is required to maintain hair follicle tumours," Development 131: 1787-1799 (2004).
MacDonald et al., "Wnt signal amplification via activity, cooperativity, and regulation of multiple intracellular PPPSP motifs in the Wnt co-receptor LRPfr" The Journal of Biological Chemistry 283: 16115-16123 (2008).
Mao, et al., "LDL-receptor-related protein 6 is a receptor for Dickkopf proteins," Nature 411(6835): 321-325 (2001).
Maretta et al., "Mapping Wnt/beta-catenin signaling during mouse development and in colorectal tumors," Proc. Nati. Acad. Sci. USA 100: 3299-3304 (2003).
Marget et al., "Cloning and characterization of cDNAs coding for the heavy and light chains of a monoclonal antibody specific for Pseudomonas aeruginosa outer membrane protein 1," Gene 74: 335-345 (1988).
McDonagh et al., "Antitumor activity of a novel bispecific antibody that targets the ErbB2/ErbB3 oncogenic unit and inhibits Heregulin-Induced activation of ErbB3" Mol. Cancer Ther. 11: 582-593 (2012).
Mukhopadhyay et al., "Dickkopfl is required for embryon head induction and limb morphogenesis in the mouse," Dev. Cell. 1 :423-434 (2001).
Munroe et al., "Prototypic G protein-coupled receptor for the intestinotrophic factor glucagon like peptide 2," Proc. Natl. Acad. Sci. USA 16: 1569-1573 (1999).
Pinson et al., "An LDL-receptor-related protein mediates Wnt signalling in mice," Nature 407: 535-538 (2000).
Poilu et al., "Serum concentrations of Dickkopf-1 protein are increased in patients with multiple myeloma and reduced after autologous stem cell transplantation," Int. J. Cancer 119: 1726-1731 (2006).

(56) References Cited

OTHER PUBLICATIONS

Reya et al., "Wnt signalling in stem cells and cancer," Nature 434: 643-850 (2005).
Reya et al., "A role for Wnt signallitttng in self-renewal of haematopoietic stem cells," Nature 423: 409-414 (2003).
Rudikoff et al.,"Single amino acid substitution altering antigen-binding specificity," Proc. Natl. Acad. Sci. USA 79: 1979-1983 (1982).
Sato et al., "Maintenance of piuripotency in human and mouse embryonic stern cells through activation of Wnt signaling by a pharmacological GSK-3-specific inhibitor," Nature Med. 10: 55-63 (2004).
Semenov et al., "DKK 1 antagonizes WNT signaling without promotion of LRP6 internalization and degradation," J. Biol. Chem. 283: 21427-21432 (2008).
Sher et al., "Structure-based mutational analyses in FGF7 identify new residues involved in specific interaction with FGFR2IIIb," FEBS Lett. 552: 150-154 (2003).
Sick et al., "WNT and DKK determine hair follicle spacing through a reaction-diffusion mechanism," Science 314: 1447-1450 (2006).
Smith et al., "Prolonged in vivo residence times of antibody fragments associated with albumin," Bioconjugate Chemistry 12(5): 750-756 (2001).
Springer et al., "An extracellular beta-propeller module predicted in lipoprotein and scavenger receptors, tyrosine kinases, epidermal growth factor precursor, and extracellular matrix components," J. Mat. Biol. 283: 837-862 (1998)
Subrarneniam et al., "Cellular oxidant stress and advanced glycation endproducts of albumin: caveats of the dichlorauoresoein assay," Archives of Biochemistry & Biophysics 400(1): 15-25 (2002).
Supplemental European Search Report for Application No. 08850109.3, dated Sep. 26, 2011.
Tamai et al., "LDL-receptor-related proteins in Wnt signal transduction," Nature 407: 530-535 (2000).
Tian et al., "The role of the Wnt-signaling antagonist DKK1 in the development of osteolytic lessions in multiple myeloma,"New Engl. J. Med. 349: 2483-2494 (2003).
van Genderen et al., "Development of several organs that require inductive epithelial-epitheliamesenchymal interactions is impaired in LEF-1 -deficient mice," Genes Dev. 8: 2691-2703 (1994).
Xu et al., "Deletion of beta-catenin impairs T cell development," Nature Immunol 4: 1177-1162 (2003).
Yaccoby et al., "Primary Myeloma Cells Growing in SCID-hu Mice: A Model for Studying the Biology and Treatment of Myeloma and Its Manifestations," Blood 92: 2908-2913 (1998).
Yacooby et al., "The Proliferative Potential of Myeloma Plasma Cells manifest in the SCID-hu Host." Blood 94: 3516-3582(999)
Yasui et al., "Detection of endogenous LRP6 expressed on human cells by monodonal antibodies specific for the native conformation" Journal of Immunological Methods 352: 153-160 (2010).
Yata et al.,"The SCID-rab model: a novel in vivo system for primary human myeloma demonstrating growth of CD 138-expressing malignant cells," Leukemia 18: 1891-1897 (2004).
Yazaki et al., "Biodistribution and tumor imaging of an anti-CEA single-chain antibody-albumin fusion protein." Nucl. Med. Biol. 35: 151-158 (2008).
Zechner et al., "beta-Catenin signals regulate cell growth and the balance between progenitor cell expansion and differentiation in the nervous system," Dev. Biol. 258: 406-418 (2003).
Zhao et al., "Elimination of the free sulfhydryl group in the human serum albumin (HSA) moiety of human interferon-alpha2b and HSA fusion protein increases its stability against mechanical and thermal stresses," European Journal of Pharmaceutics & Biopharmaceutics 72(2): 405-11 (2009).

MOR06475

MOR08193

MOR08473

| | Prop 1 | | | Prop 3 | | |
|---|---|---|---|---|---|---|
| | MOR08168 | MOR08545 | MOR06706 | MOR06475 | MOR08193 | MOR08473 |
| human LRP6 | 0.28 | 0.09 | 0.14 | 0.31 | 0.36 | 0.74 |
| mouse LRp6 | 0.12 | 0.06 | n/a | 0.96 | 0.08 | 0.46 |
| cynomolgus LRP6 | 0.88 | 0.30 | 0.46 | 0.22 | 0.20 | 0.52 |

$EC_{50}$ values expressed in nM.

Fig. 3

| Probe ID | Gene Symbol | Gene Title | Entrez Gene ID | log(2)fold change 0 h vs. 8 h | adj.P.Val 0 h vs. 8 h |
|---|---|---|---|---|---|
| 1435154_at | AU018091 | expressed sequence AU018091 | 245128 | 2.51 | 0.0081676 |
| 1418743_a_at | LOC100047138///Tesc | similar to Tescalcin /// tescalcin | 100047138 /// 57816 | 2.42 | 0.0007069 |
| 1418744_s_at | LOC100047138///Tesc | similar to Tescalcin /// tescalcin | 100047138 /// 57816 | 2.41 | 0.0011682 |
| 1447891_at | --- | --- | --- | 2.35 | 0.0012203 |
| 1417956_at | Cidea | cell death-inducing DNA fragmentation factor, alpha | 12683 | 2.32 | 0.0061736 |
| 1436279_at | --- | --- | --- | 2.25 | 0.0007424 |
| 1451139_at | Slc39a4 | solute carrier family 39 (zinc | 72027 | 2.04 | 0.0003359 |
| 1417130_s_at | Angptl4 | angiopoietin-like 4 | 57875 | 1.94 | 0.0007217 |
| 1434918_at | Sox6 | SRY-box containing gene 6 | 20679 | 1.79 | 0.0021073 |
| 1451612_at | Mt1 | metallothionein 1 | 17748 | 1.74 | 0.0046964 |
| 1451915_s_at | 2310076L09Rik | RIKEN cDNA 2310076L09 gene | 66968 | 1.71 | 0.0024997 |
| 1423860_at | Ptgds | prostaglandin D2 synthase (brain) | 19215 | 1.66 | 0.0012372 |
| 1428283_at | Cyp2s1 | cytochrome P450, family 2, subfamily s, polypeptide 1 | 74134 | 1.64 | 0.004778 |
| 1439036_a_at | Atp1b1 | ATPase, Na+/K+ transporting, beta 1 polypeptide | 11931 | 1.63 | 0.0070499 |
| 1451410_a_at | Crip3 | cysteine-rich protein 3 | 114570 | 1.62 | 0.000223 |
| 1459898_at | Sbsn | suprabasin | 282619 | 1.60 | 0.0022588 |
| 1433888_at | Atp2b2 | ATPase, Ca++ transporting, plasma membrane 2 | 11941 | 1.58 | 0.0099753 |
| 1450435_at | L1cam | L1 cell adhesion molecule | 16728 | 1.57 | 0.001168 |
| 1455506_at | Slc25a34 | solute carrier family 25, member 34 | 384071 | 1.55 | 7.26E-05 |
| 1422820_at | Lipe | lipase, hormone sensitive | 16890 | 1.52 | 0.0034308 |
| 1447655_x_at | Sox6 | SRY-box containing gene 6 | 20679 | 1.51 | 0.003772 |
| 1451204_at | Scara5 | scavenger receptor class A, | 71145 | 1.51 | 0.0017923 |
| 1451828_a_at | Acsl4 | acyl-CoA synthetase long-chain | 50790 | 1.48 | 6.46E-05 |
| 1451331_at | Ppp1r1b | protein phosphatase 1, regulatory (inhibitor) subunit 1B | 19049 | 1.44 | 0.0025364 |
| 1418453_a_at | Atp1b1 | ATPase, Na+/K+ transporting, beta 1 polypeptide | 11931 | 1.43 | 0.0049563 |
| 1419706_a_at | Akap12 | A kinase (PRKA) anchor protein (gravin) 12 | 83397 | 1.42 | 0.0001178 |
| 1418911_s_at | Acsl4 | acyl-CoA synthetase long-chain | 50790 | 1.40 | 0.003297 |
| 1439630_x_at | Sbsn | suprabasin | 282619 | 1.38 | 0.0007395 |
| 1438261_at | Cited4 | Cbp/p300-interacting transactivator, with Glu/Asp-rich carboxy-terminal domain, 4, mRNA (cDNA clone IMAGE:3670674) | 56222 | 1.36 | 0.0067834 |

Fig. 8A

| Probe ID | Gene Symbol | Gene Title | Entrez Gene ID | log(2)fold change 0 h vs. 8 h | adj.P.Val 0 h vs. 8 h |
|---|---|---|---|---|---|
| 1429952_at | Mospd4 | motile sperm domain containing 4 | 72076 | 1.36 | 0.0055785 |
| 1435595_at | 1810011O10Rik | RIKEN cDNA 1810011O10 gene | 69068 | 1.34 | 0.000592 |
| 1429352_at | Mocos | molybdenum cofactor sulfurase | 68591 | 1.32 | 0.0090359 |
| 1459897_a_at | Sbsn | suprabasin | 282619 | 1.32 | 0.0014474 |
| 1447845_s_at | Vnn1 | vanin 1 | 22361 | 1.31 | 0.004465 |
| 1421841_at | Fgfr3 | fibroblast growth factor receptor 3 | 14184 | 1.29 | 7.26E-05 |
| 1424937_at | 2310076L09Rik | RIKEN cDNA 2310076L09 gene | 66968 | 1.29 | 0.0001178 |
| 1449403_at | Pde9a | phosphodiesterase 9A | 18585 | 1.27 | 0.0097294 |
| 1424218_a_at | Creb3l4 | cAMP responsive element binding protein 3-like 4 | 78284 | 1.21 | 0.0020445 |
| 1424763_at | Rsph9 | radial spoke head 9 homolog (Chlamydomonas) | 75564 | 1.21 | 0.0067834 |
| 1420521_at | Papln | papilin, proteoglycan-like sulfated glycoprotein | 170721 | 1.21 | 0.0045018 |
| 1434442_at | Stbd1 | starch binding domain 1 | 52331 | 1.19 | 0.0047233 |
| 1438033_at | Tef | thyrotroph embryonic factor | 21685 | 1.17 | 0.0013355 |
| 1442335_at | --- | --- | --- | 1.16 | 0.0061736 |
| 1448227_at | Grb7 | growth factor receptor bound protein 7 | 14786 | 1.14 | 0.0012612 |
| 1416596_at | Slc44a4 | solute carrier family 44, member 4 | 70129 | 1.14 | 0.0088984 |
| 1439620_at | Car13 | carbonic anhydrase 13 | 71934 | 1.13 | 0.0032295 |
| 1418780_at | Cyp39a1 | cytochrome P450, family 39, subfamily a, polypeptide 1 | 56050 | 1.12 | 0.0061736 |
| 1460409_at | Cpt1a | carnitine palmitoyltransferase 1a, liver | 12894 | 1.10 | 0.003297 |
| 1449146_at | Notch4 | Notch gene homolog 4 (Drosophila) | 18132 | 1.10 | 0.0083512 |
| 1443841_x_at | Uap1l1 | UDP-N-acteylglucosamine pyrophosphorylase 1-like 1 | 227620 | 1.08 | 0.0076401 |
| 1417273_at | Pdk4 | pyruvate dehydrogenase kinase, isoenzyme 4 | 27273 | 1.08 | 0.0061736 |
| 1430278_a_at | Dqx1 | DEAQ RNA-dependent ATPase | 93838 | 1.07 | 0.0024997 |
| 1426065_a_at | Trib3 | tribbles homolog 3 (Drosophila) | 228775 | 1.04 | 0.0028588 |
| 1438038_at | 4930402H24Rik | RIKEN cDNA 4930402H24 gene | 228602 | 1.03 | 0.00599 |
| 1427537_at | Eppk1 | epiplakin 1 | 223650 | 1.02 | 0.0011399 |
| 1416457_at | Ddah2 | dimethylarginine dimethylaminohydrolase 2 | 51793 | 1.01 | 0.0057377 |

Fig. 8B

| Probe ID | Gene Symbol | Gene Title | Entrez Gene | log(2)fold change 0 h vs. 8h | adj.P.Val 0 h vs. 8h |
|---|---|---|---|---|---|
| 1449451_at | Serpinb11 | serine (or cysteine) peptidase inhibitor, clade B (ovalbumin), member 11 | 66957 | -3.95 | 7.37E-07 |
| 1451129_at | Calb2 | calbindin 2 | 12308 | -3.14 | 0.006783 |
| 1436845_at | Axin2 | axin2 | 12006 | -2.92 | 4.53E-07 |
| 1416468_at | Aldh1a1 | aldehyde dehydrogenase family 1, subfamily A1 | 11668 | -2.83 | 0.000506 |
| 1427508_at | Arsi | arylsulfatase i | 545260 | -2.55 | 0.000592 |
| 1418601_at | Aldh1a7 | aldehyde dehydrogenase family 1, subfamily A7 | 26358 | -2.55 | 0.005578 |
| 1432592_at | Pappa | pregnancy-associated plasma protein A | 18491 | -2.55 | 6.46E-05 |
| 1425985_s_at | Masp1 | mannan-binding lectin serine peptidase 1 | 17174 | -2.48 | 0.001787 |
| 1434802_s_at | Ntf3 | neurotrophin 3 | 18205 | -2.43 | 0.000914 |
| 1425978_at | Myocd | myocardin | 214384 | -2.39 | 0.00374 |
| 1436221_at | Ildr2 | immunoglobulin-like domain containing receptor 2 | 100039795 | -2.36 | 0.00296 |
| 1418678_at | Has2 | hyaluronan synthase 2 | 15117 | -2.31 | 0.000996 |
| 1436894_at | Ildr2 | immunoglobulin-like domain containing receptor 2 | 100039795 | -2.3 | 0.0025 |
| 1427633_a_at | Pappa | pregnancy-associated plasma protein A | 18491 | -2.21 | 0.002187 |
| 1436293_x_at | Ildr2 | immunoglobulin-like domain containing receptor 2 | 100039795 | -2.17 | 0.002799 |
| 1433959_at | Zmat4 | zinc finger, matrin type 4 | 320158 | -2.14 | 0.00638 |
| 1427600_at | --- | --- | --- | -2.12 | 6.46E-05 |
| 1432591_at | Pappa | pregnancy-associated plasma protein A | 18491 | -2.07 | 0.001159 |
| 1448397_at | Gjb6 | gap junction protein, beta 6 | 14623 | -2.06 | 0.002796 |
| 1449926_at | Cd70 | CD70 antigen | 21948 | -2.05 | 0.006174 |
| 1441807_s_at | --- | --- | --- | -2.02 | 0.004956 |
| 1438602_s_at | Masp1 | mannan-binding lectin serine peptidase 1 | 17174 | -2.01 | 0.00255 |
| 1425212_a_at | Tnfrsf19 | tumor necrosis factor receptor superfamily, member 19 | 29820 | -1.94 | 6.46E-05 |
| 1428223_at | Mfsd2 | major facilitator superfamily domain containing 2 | 76574 | -1.93 | 0.006536 |
| 1420006_at | Bmp15 | Bone morphogenetic protein 15 (8mp15), mRNA | 12155 | -1.91 | 0.000707 |
| 1429506_at | Nkd1 | naked cuticle 1 homolog (Drosophila) | 93960 | -1.91 | 0.001459 |
| 1433894_at | Jazf1 | JAZF zinc finger 1 | 231986 | -1.9 | 0.000592 |
| 1422699_at | Alox12 | arachidonate 12-lipoxygenase | 11684 | -1.89 | 0.001168 |
| 1460449_at | Anks1b | ankyrin repeat and sterile alpha motif domain containing 1B | 77531 | -1.87 | 0.00592 |

Fig. 8C

| Probe ID | Gene Symbol | Gene Title | Entrez Gene | log(2)fold change 0 h vs. 8h | adj.P.Val 0 h vs. 8h |
|---|---|---|---|---|---|
| 1417275_at | Mal | myelin and lymphocyte protein, T-cell differentiation protein | 17153 | -1.87 | 0.002349 |
| 1449169_at | Has2 | hyaluronan synthase 2 | 15117 | -1.8 | 0.000707 |
| 1420005_s_at | Bmp15 | bone morphogenetic protein 15 | 12155 | -1.78 | 0.002107 |
| 1449033_at | Tnfrsf11b | tumor necrosis factor receptor superfamily, member 11b (osteoprotegerin) | 18383 | -1.76 | 0.00402 |
| 1433990_at | Lhfpl3 | lipoma HMGIC fusion partner-like 3 | 269629 | -1.73 | 0.001503 |
| 1431229_at | Ipw | imprinted gene in the Prader-Willi syndrome region | 16353 | -1.71 | 0.0022 |
| 1429592_at | Lhfpl3 | lipoma HMGIC fusion partner-like 3 | 269629 | -1.7 | 0.004465 |
| 1457617_at | --- | --- | --- | -1.64 | 0.008658 |
| 1434265_s_at | Ank2 | ankyrin 2, brain | 109676 | -1.64 | 0.006936 |
| 1449634_a_at | Anks1b | ankyrin repeat and sterile alpha motif domain containing 1B | 77531 | -1.6 | 0.005666 |
| 1455436_at | Diras2 | DIRAS family, GTP-binding RAS-like 2 | 68203 | -1.56 | 0.00813 |
| 1457429_s_at | Gm106 | gene model 106, (NCBI) | 226866 | -1.56 | 0.000118 |
| 1425425_a_at | Wif1 | Wnt inhibitory factor 1 | 24117 | -1.55 | 0.000336 |
| 1415921_a_at | Tnfrsf19 | tumor necrosis factor receptor superfamily, member 19 | 29820 | -1.53 | 8.15E-05 |
| 1457948_at | Gas7 | Growth arrest-specific 7-cb protein (Gas7-cb) | 14457 | -1.53 | 0.006196 |
| 1439954_at | 6430514M23Rik | RIKEN cDNA 6430514M23 gene | 399595 | -1.52 | 0.006504 |
| 1417709_at | Cyp46a1 | cytochrome P450, family 46, subfamily a, polypeptide 1 | 13116 | -1.52 | 0.004364 |
| 1445247_at | C530044C16Rik | RIKEN cDNA C530044C16 gene | 319981 | -1.52 | 0.000604 |
| 1428665_at | Pfn4 | profilin family, member 4 | 382562 | -1.51 | 0.006174 |
| 1448147_at | Tnfrsf19 | tumor necrosis factor receptor superfamily, member 19 | 29820 | -1.47 | 2.14E-08 |
| 1456335_at | Gm106 | gene model 106, (NCBI) | 226866 | -1.47 | 0.001787 |
| 1440546_at | 9630002D21Rik | RIKEN cDNA 9630002D21 gene | 319560 | -1.44 | 0.003664 |
| 1450506_a_at | Aen | apoptosis enhancing nuclease | 68048 | -1.43 | 0.005422 |
| 1453041_at | Ano9 | anoctamin 9 | 71345 | -1.41 | 0.000592 |
| 1453700_s_at | 4933403O03Rik ///EG245263 | RIKEN c DNA 4933403O03 gene /// predicted gene, EG245263 | 245263///74: | -1.41 | 0.004956 |
| 1449478_at | Mmp7 | matrix metallopeptidase 7 | 17393 | -1.39 | 0.009569 |
| 1452938_at | Anks1b | ankyrin repeat and sterile alpha motif domain containing 1B | 77531 | -1.37 | 0.006568 |
| 1444541_at | --- | --- | --- | -1.37 | 0.000828 |
| 1450728_at | Fjx1 | four jointed box 1 (Drosophila) | 14221 | -1.36 | 0.00323 |
| 1452728_at | Kirrel3 | kin of IRRE like 3 (Drosophila) | 67703 | -1.36 | 0.005549 |

Fig. 8D

| Probe ID | Gene Symbol | Gene Title | Entrez Gene | log(2)fold change 0 h vs. 8h | adj.P.Val 0 h vs. 8h |
|---|---|---|---|---|---|
| 1430118_at | 2700046A07Rik | RIKEN cDNA 2700046A07 gene | 78449 | -1.31 | 0.008169 |
| 1441272_at | Matr3 | Martin 3, mRNA (cDNA clone MGC:28206 IMAGE:3989914) | 17184 | -1.29 | 0.002269 |
| 1419539_at | Irx4 | Iroquois related homeobox 4 (Drosophila) | 50916 | -1.26 | 0.005098 |
| 1442456_at | Spata5 | spermatogenesis associated 5 | 57815 | -1.26 | 0.006174 |
| 1456672_at | --- | --- | --- | -1.24 | 0.006783 |
| 1439026_at | Trpm3 | transient receptor potential cation channel, subfamily M, member 3 | 226025 | -1.23 | 0.006174 |
| 1440446_at | --- | --- | --- | -1.21 | 0.001125 |
| 1426139_a_at | Ccrl1 | chemokine (C-C motif) receptor-like 1 | 252837 | -1.2 | 0.009707 |
| 1435941_at | Rhbdl3 | rhomboid, veinlet-like 3 (Drosophila) | 246104 | -1.18 | 0.004465 |
| 1453645_at | 2700046A07Rik | RIKEN cDNA 2700046A07 gene | 78449 | -1.18 | 0.000692 |
| 1444905_at | D1Ertd705e | DNA segment, Chr 1, ERATO Doi 705, expressed | 51940 | -1.17 | 0.003297 |
| 1422733_at | Fjx1 | four jointed box 1 (Drosophila) | 14221 | -1.14 | 0.007138 |
| 1423957_at | Aen | apoptosis enhancing nuclease | 68048 | -1.07 | 0.000391 |
| 1433084_at | 4930402C16Rik | RIKEN cDNA 4930402C16 gene | 73812 | -1.07 | 0.006802 |
| 1421498_a_at | 2010204K13Rik | RIKEN cDNA 2010204K13 gene | 68355 | -1.07 | 0.007469 |
| 1426981_at | Pcsk6 | proprotein convertase subtilisin/kexin type 6 | 18553 | -1.06 | 0.000506 |
| 1446846_at | --- | --- | --- | -1.05 | 0.004364 |
| 1429861_at | Pcdh9 | protocadherin 9 | 211712 | -1.04 | 0.006174 |
| 1447958_at | --- | --- | --- | -1.02 | 0.000592 |
| 1435608_at | LOC631806/// Znrf3 | similar to Goliath homolog precursor (Ring finger protein 130) (R-goliath)/// zinc and ring finger 3 | 407821///63: | -1.02 | 0.000118 |
| 1456266_at | --- | --- | --- | -1.02 | 0.002282 |
| 1421341_at | Axin2 | axin2 | 12006 | -1.02 | 0.001447 |
| 1418495_at | Zc3h8 | zinc finger CCCH type containing 8 | 57432 | -1.01 | 0.000233 |

Fig. 8E

| | HEK STF IC50 (μg/ml) WNT1 | HEK STF IC50 (μg/ml) WNT3a |
|---|---|---|
| MOR06475-sc-fv-Vl-Vh | n/a | 0.07 |
| MOR06475-sc-fv-Vh-Vl | n/a | 0.06 |
| MOR06475-sc-fv-Vl-Vh-(GGGGS)3 | n/a | 0.08 |
| MOR06475-sc-fv-Vh-Vl-(GGGGS)3 | n/a | 0.08 |
| MOR06475-Fab | n/a | 0.11 |
| MOR08168-sc-fv-Vl-Vh | 0.05 | n/a |
| MOR08168-sc-fv-Vh-Vl | 0.06 | n/a |
| MOR08168-sc-fv-Vl-Vh-(GGGGS)3 | 0.07 | n/a |
| MOR08168-sc-fv-Vh-Vl-(GGGGS)3 | 0.1 | n/a |
| MOR08168-Fab | 0.15 | n/a |
| MOR08545-sc-fv-Vl-Vh | 0.53 | n/a |
| MOR08545-sc-fv-Vh-Vl | 0.06 | n/a |
| MOR08545-sc-fv-Vl-Vh-(GGGGS)3 | n/a | n/a |
| MOR08545-sc-fv-Vh-Vl-(GGGGS)3 | 0.05 | n/a |
| MOR08545-Fab | 0.05 | n/a |
| anti-LRP6_MOR08168_hIgG1 LALA_6475scfv_at_VL | 0.013 | 0.0071 |
| anti-LRP6_MOR06475_hIgG1 LALA_8168scfvatCH3_(VH-3-VL) | 0.013 | 0.0082 |
| anti-LRP6_MOR06475_hIgG1 LALA_8168scfvatCH3_(VH-4-VL) | 0.016 | 0.0094 |
| anti-LRP6_MOR08168_hIgG1 LALA_6475scfvatCH3_opt_DPtoDA | 0.02 | 0.0076 |
| anti-LRP6_MOR08168_hIgG1 LALA_6475scfvatCH3_opt_DPtoTA | 0.026 | 0.0098 |
| anti-LRP6_MOR08168_hIgG1 LALA_6475scfvatCH3_opt_w/o-K | 0.015 | 0.0064 |
| MOR06475 IgG | n/a | 0.0039 |
| MOR08168 IgG | 0.025 | n/a |
| MOR08168hIgG1LALA 6475 scfv | 0.016 | 0.011 |

Fig. 18

| **Antibody** | **$K_D$ [μM], binding of Ab's to FcRn** | | | |
|---|---|---|---|---|
| **FcRn** | **huFcRn, pH6.0** | **huFcRn, pH7.4** | **cynoFcRn, pH6.0** | **cynoFcRn, pH7.4** |
| MORO8168 | 0.023 | LLB | 0.28 | LLB |
| MORO8168/6475 BpAB | 0.021 | LLB | 0.12 | LLB |
| LLB: low level binding | | | | |

Fig. 19

PK/PD of MOR08168hIgG1LALA 6475 scfv
and MOR08168 in mouse MMTV-Wnt1 tumors

Summary of KD measurement of MOR08168 IgG LALA 6475scFv, MOR08168 and MOR06475 binding to PD1/2 and PD3/4

| Binding to PD1/2 | Ka (1/Ms) | Kd (1/s) | KD (M) | N |
|---|---|---|---|---|
| MOR08168 IgG LALA 6475scFV | 1.27E+05 | 6.10E-05 | 8.68E-10 | 3 |
| MOR08168 | 8.72E+04 | 9.05E-05 | 1.08-09 | 4 |

| Binding to PD3/4 | Ka (1/Ms) | Kd (1/s) | KD (M) | N |
|---|---|---|---|---|
| MOR08168 IgG LALA 6475scFV | 2.11E+05 | 3.14E-04 | 1.93E-09 | 3 |
| MOR06475 | 2.01E+04 | 2.17E-04 | 1.13E-09 | 4 |

Fig. 26A

Binding to PD1/2

901-MOR8168 IgG1 LALA 6475scFv

902-MOR6475 IgG1 LALA 8168scFv

Effect of leader sequences

Effect of Bacterial strains and constructs

Tm of single point mutations in scFv06475

| Construct ID | mutation[a] | $T_m$ on protein from E.coli | $T_m$ on protein from mammalian |
|---|---|---|---|
| scFv06475 WT | | 59 | 61 |
| 6475-S2 | VH:G34V | 61 | 64 |
| 6475-S3 | VH:I37F | 61 | 64.5 |
| 6475-S6 | VH:V85E | 60 | 62.5 |
| 6475-S8 | VH:M95F | 61.5 | 64.5 |
| 6475-S9 | VL:D93N | 59.5 | 60.5 |

[a]Both kabat and Chothia numbering system have been used. The numbering is the same for all mutations but VH: G34V in scFv6475. This would be VH: G32V in Chothia numbering system. The numbering system in the text is Kabat system.

Fig. 29

| Tm of single point mutations in scFv08168 | | |
|---|---|---|
| Construct ID | mutation | $T_m$ on protein from E.coli[a] |
| WT | WT | 48.50 |
| B02 | VH:V033N | 50.50 |
| B03-S1 | VH:I034M | 56.00 |
| B04 | VH:I034F | 52.50 |
| C05 | VH:S049A | 54.00 |
| C07 | VH:G050S | 51.50 |
| C08 | VH:W052aG | 55.50 |
| C10 | VH:H058Y | 52.00 |
| F11 | VL:V047L | 51.00 |
| G02 | VL:G064V | 50.50 |
| G07 | VL:T078V | 51.00 |

[a]Proteins were expressed from Acella strain. Samples were analyzed by DSF without removal of imidazole.

Fig. 30

Tm of single vs double mutations in scFv08168

| Construct ID | Mutation | $T_m$ on protein from E.coli[a] | $T_m$ on protein from mammalian[b] | $T_m$ on protein from mammalian |
|---|---|---|---|---|
| scFv08168 WT | WT | 48.50 | 49 | 49 |
| scFv8168 B02 | VH:V33N | 50.50 | | |
| scFv08168 B03-S1 | VH:I34M | 56.00 | 57 | 56.5 |
| scFv08168 B04 | VH:I34F | 52.50 | | |
| scFv08168 C05 | VH:S49A | 54.00 | | |
| scFv08168 C07 | VH:G50S | 51.50 | | |
| scFv08168 C10 | VH:H58Y | 52.00 | | |
| scFv08168 F11 | VL:V47L | 51.00 | | |
| scFv08168 G02 | VL:G64V | 50.50 | | |
| scFv08168 G07 | VL:T78V | 51.00 | | |
| scFv08168D1 | VH S49A, I34M | 61 | 61.5 | 62.5 |
| scFv08168D2 | VH S49A, I34F | 57.5 | 58 | 58.5 |
| scFv08168D4 | VH I34M, G50S | 59.5 | 59.5 | 60 |
| scFv08168D5 | VH I34M, H58Y | 59 | 59 | 59 |
| scFv08168D6 | VH I34M, V48I | 57 | 56 | 57.5 |
| scFv08168D7 | VH I34M, VL S22T | 57 | 57 | 58 |
| scFv08168D8 | VH I34M, VL V47L | 57.5 | 56 | 58.5 |
| scFv08168D9 | VH I34M, VL G64V | 57.5 | 58.5 | 57.5 |

[a]Proteins were expressed from Acella strain. Samples were analyzed by DSF without removal of imidazole.

[b]Protein expressed from 293T suspension cells. Samples were analyzed by DSF without removal of imidazole.

Fig. 31

| Activity of scFv06475, scFv08168 and the variants in different assays | | | | | |
|---|---|---|---|---|---|
| Construct ID | Mutations | EC50 by ELISA nM | Affinity by Proteon nM | IC50 by STF assay for Wnt1 inhibition (nM) | IC50 by STF assay for Wnt3a inhibition (nM) |
| scFv06475 WT | | 0.76 | - | - | 1.48 |
| scFv06475-S2 | VH:G34V | 27.4 | - | - | - |
| scFv06475-S3 | VH:I37F | 4.3 | - | - | - |
| scFv06475-S6 | VH:V85E | 0.73 | - | - | 1.33 |
| **scFv06475-S8** | **VH:M95F** | **1.0** | - | - | **0.96** |
| scFv06475-S9 | VL:D93N | 0.88 | - | - | |
| scFv08168 WT | | 2.04 | 3.82 | 7.41 | - |
| scFv08168 B03-S1 | VH:I34M | 0.98 | - | 5.19 | - |
| **scFv08168-D1** | **VH S49A, I34M** | **1.61** | **2.55** | **2.44** | - |
| scFv08168-D2 | VH S49A, I34F | 1.68 | - | 2.59 | - |
| scFv08168-D4 | VH I34M, G50S | 1.47 | - | 5.56 | - |
| scFv08168-D5 | VH I34M, H58Y | 1.22 | - | - | - |
| scFv08168-D6 | VH I34M, V48I | 1.24 | - | 0.74 | - |
| scFv08168-D7 | VH I34M, VL S22T | 1.15 | - | 4.81 | - |
| scFv08168-D8 | VH I34M, VL V47L | 0.91 | - | - | - |
| scFv08168-D9 | VH I34M, VL G64V | 1.26 | - | 11.11 | - |

Fig. 32

Selected examples of stabilizing mutations

| Thermostability measurement of HSA fusion and IgG based biparatopic molecules | | |
|---|---|---|
| | $T_m$ by DSF (ProteoSTAT) | $T_m$ by DSC |
| MOR6475 IgG1-scFv8168 (902wt) | 47, 72.5 | ND |
| MOR6475 IgG1-scFv8168 (902 mutant) | 62, 76 | ND |

Fig. 34

THERAPEUTIC LOW DENSITY LIPOPROTEIN-RELATED PROTEIN 6 (LRP6) MULTIVALENT ANTIBODIES

This application is a U.S. National Phase filing of International Application No. PCT/EP2011/057200 filed 5 May 2011, which claims priority to U.S. Provisional Application Ser. No. 61/331,993 filed 6 May 2010, the contents of which are incorporated herein by reference in their entirety.

RELATED APPLICATIONS

This application claims priority to U.S. Provisional Application Ser. No. 61/331,993 filed May 6, 2010, the contents of which are incorporated herein by reference in its entirety.

FIELD OF THE INVENTION

The present invention relates to multivalent antibodies comprising at least two receptor binding domains for two different binding sites on LRP6. The invention more specifically relates to multivalent antibodies that are LRP6 antagonists.

BACKGROUND OF THE INVENTION

The Wnt/β-catenin pathway regulates diverse biological processes during development and tissue homeostasis through modulating the protein stability of β-catenin (Clevers et al., (2006) Cell 127:469-480; and Logan et al., (2004) Annu. Rev Cell Dev. Bial 20:781-810). In the absence of Wnt signaling, cytoplasmic β-catenin is associated with the β-catenin destruction complex that contains multiple proteins including adenomatous polyposis coli (APC), Axin, and glycogen synthase kinase 3 (GSK3). In this complex, β-catenin is constitutively phosphorylated by GSK3 and degraded by the proteasome pathway. The Wnt signal is transduced across the plasma membrane through two distinct receptors, the serpentine receptor Frizzled, and the single-transmembrane protein LRP5 or LRP6. The Wnt proteins promote the assembly of the Frizzled-LRP5/6 signaling complex, and induce phosphorylation of the cytoplasmic PPPSPxS motifs of LRP5/6 by GSK3 and Casein Kinase I. Phosphorylated LRP5/6 bind to Axin and inactivate the β-catenin degradation complex. Stabilized β-catenin enters the nucleus, binds to the TCF family transcription factors, and turns on transcription.

The large extracellular domain of LRP5/6 contains four YWTD-type β-propeller regions that are each followed by an EGF-like domain, and the LDLR domain. Each propeller region contains six YWTD motifs that form a six-bladed β-propeller structure. Biochemical studies suggest that Wnt proteins physically interact with both Frizzled and LRP6 and induce formation of Frizzled-LRP6 signaling complex (Semenov et al., (2001) Curr. Biol 11, 951-961; and Tamai, et al. (2000) Nature 407, 530-535). Besides Wnt proteins, the large extracellular domain of LRP5/6 binds to multiple secreted Wnt modulators, including Wnt antagonist, DKK1 and Sclerostin (SOST), and Wnt agonist R-Spondins.

Mutations in pathway components such as APC and β-catenin have been associated with human cancers. Recent studies suggest that overexpression of Wnt proteins and/or silencing of Wnt antagonists such as DKK1, WISP and sFRPs promote cancer development and progression (Akiri et al., (2009) Oncogene 28:2163-2172; Bafico et al., (2004) Cancer Cell 6:497-506; Suzuki et al., (2004) Nat Genet. 36:417-422; Taniguchi et al., (2005) Oncogene. 24:7946-7952; Veeck et al., (2006) Oncogene. 25:3479-3488; Zeng et al., (2007) Hum. Pathol. 38:120-133). In addition, Wnt signaling has been implicated for the maintenance of cancer stem cells (Jamieson et al., (2004) Cancer Cell 6:531-533 and Zhao et al., (2007) Cancer Cell 12:528-541).

Antibody therapy has been used as a means to treat certain cancers. Efforts to increase the valency or the number of antigenic determinants that an individual antibody molecule can bind have lead to the development of bispecific antibodies (for examples see Jimenez et al., Molecular Cancer Therapeutics 2005:4427-434, Lu et al., J. of Immun. Methods 1999: 230, 159-171 and U.S. Patent Publication Nos. 20070014794 and 20050100543). Bispecific antibodies are immunoglobulin (Ig)-based molecules that bind to two different epitopes on either the same or distinct antigens. The antibodies, for example, could be specific for a tumor cell antigen and an effector cell such as an activated T-cell or two functional targets or epitopes.

A major obstacle in the development of bispecific antibodies as therapeutics has been difficulty in producing the antibodies in sufficient quantity and quality for clinical studies. In particular, traditional methods, including hybrid hybridoma, in which two distinct hybridomas are fused to create a cell expressing two sets of heavy and light chains, and chemical conjugation (Carter et al., (1995) J. Hematotherapy 4:463-70) have been inadequate. For example, coexpression of two different sets of IgG light and heavy chains in a hybrid hybridoma may produce up to 10 light- and heavy-chain pairs, with only one of these pairs forming the functional bispecific heterodimer (Suresh et al. (1986) Methods Enzymol. 121:210-28). In addition, purification of the antibodies from the non-functional species, such as homodimers and mispaired heterodimers of non-cognate Ig light and heavy chains produced by the hybrid hybridoma is cumbersome and inefficient.

Chemical crosslinking of two IgGs or their fragments is also inefficient and can lead to the loss of antibody activity (Zhu et al. (1994) Cancer Lett. 86:127-34). Multimeric aggregates resulting from chemical conjugation result in a poor yield (Cao et al. (1998) Bioconj. Chem. 9:635-44).

Accordingly, a need exists for functional multivalent antibodies capable of binding at least two or more epitopes with high affinity. In particular, there is need for functional multivalent antibodies that modify receptors with more then one modifying ligand, such as the canonical Wnt signaling co-receptor, LRP6.

SUMMARY OF THE INVENTION

The present invention provides novel multivalent antibodies that bind to multiple binding sites on the LRP6 receptor. In particular, the invention provides LRP6 multivalent antibodies that inhibit thecanonical Wnt signaling pathway.

The present invention is based on the discovery that the multivalent antibodies (e.g., a single LRP6 biparatopic antibody) have the ability to inhibit both propeller 1 (e.g., Wnt1) and propeller 3 (e.g., Wnt 3) ligands. Furthermore, and unexpectedly, the multivalent antibody (e.g., a single LRP6 biparatopic antibody) display no significant potentiation (enhancement) of a Wnt signal. The multivalent antibody binds to distinct LRP6 β-propeller domains. Propeller 1 antibodies bind to the β-propeller 1 domain and block propeller1-dependent Wnts such as Wnt1, Wnt2, Wnt6, Wnt7A, Wnt7B, Wnt9, Wnt10A, Wnt10B. Propeller 3 antibodies bind to the β-propeller 3 domain and block propeller3-dependent Wnts such as Wnt3a and Wnt3. LRP6 antibodies differentiate propeller 1 and propeller 3 ligands into two separate classes and bind to distinct binding sites of the LRP6 target receptor. Conversion of fragments of the LRP6 antibodies (e.g., Fabs) to full length IgG antibody results in an antibody that potentiates (enhances) a Wnt signal in the presence of another protein such as a Wnt1 or Wnt 3 ligand. Multivalent antibodies inhibit both propeller 1 (e.g., Wnt1) and propeller 3 (e.g., Wnt 3) ligands but without potentiation. In addition to Wnt ligands LRP6 Propeller 1 antibodies are expected to inhibit the interaction with other Propeller 1 binding ligands (e.g. Sclerostin, Dkk1). Similarly, Propeller 3 antibodies are expected to inhibit the interaction with other propeller 3 binding ligands (e.g. Dkk1). Furthermore, propeller 1 and 3 binding antibodies may be expected to affect the activity of other Wnt signaling modulators e.g. R-spondins.

Multivalent antibodies provide advantages over traditional antibodies for example, expanding the repertoire of targets, having new binding specificities, increased potency, and no signal potentiation. A single LRP6 multivalent antibody can bind to multiple β-propeller domains on a single LRP6 target receptor on the same cell, and inhibit Wnt signaling. In one embodiment, the multivalent antibody binds to any combination of a β-propeller domains selected from the group consisting of propeller 1, propeller 2, propeller 3, and propeller 4. In one embodiment, the multivalent antibody binds to propeller 1 and propeller 3 domains of LRP6. Thus, a single LRP6 multivalent antibody has increased potency of action by binding to multiple β-propeller domains and inhibiting Wnt signaling mediated by each domain. For example, a single LRP6 multivalent antibody inhibits both propeller 1 and propeller 3 mediated Wnt signaling binding to both propeller 1 and propeller 3 domains, respectively. The increased potency of action may be due to increased avidity or better binding of the LRP6 multivalent antibody.

Accordingly, in one aspect, the invention pertains to an isolated multivalent antibody having at least two receptor binding domains for two different binding sites of a target receptor, wherein the first receptor binding domain binds to a first binding site on the target receptor and the second receptor binding domain binds to a second binding site on the same target receptor, wherein the first and second receptor binding domains are linked together such that the binding of the first and second receptor binding domains to the first and second binding sites of the target receptor inhibits a canonical Wnt signal transduction pathway; and wherein the antibody or antigen binding fragment displays no significant potentiation of a Wnt signal.

The multivalent antibody has an affinity for target receptor of approximately nanomolar affinity, or of approximately 1 picomolar affinity. The multivalent antibody is a multivalent antibody, a bivalent antibody, a bispecific antibody, or a biparatopic antibody. In one embodiment, the first and second receptor binding domains is an IgG antibody, an scFv fragment, a single chain diabody, an antibody mimetic, or an antibody variable domain. The first and second receptor binding domains are linked together by a linker with a spatial distribution that permits the first and second receptor binding domains to bind to the first and second binding sites, respectively. In one embodiment, the linker is a Gly-Ser linker. In one embodiment, the multivalent antibody has the functional activity of inhibiting a canonical Wnt signal transduction pathway such as the Wnt1 signal pathway and/or the Wnt3 signal transduction pathway. In one embodiment, the multivalent antibody has the functional activity of depleting a cell population, inhibiting or reducing proliferation of a cell population, inhibiting or reducing secretion of inflammatory mediators from a cell population, inhibiting or reducing secretion of cytoplasmic granules from a cell population, wherein the cell population is selected from the group consisting of tumor cells, T cells B cells, and Wnt dependent cells.

In another aspect, the invention pertains to an isolated multivalent antibody having at least two receptor binding domains for two different binding sites of an LRP6 target receptor, where the first receptor binding domain binds to a first binding site on the target receptor and the second receptor binding domain binds to a second binding site on the same LRP6 target receptor. The first and second receptor binding domains are linked together such that the binding of the first and second receptor binding domains to the first and second binding sites of the LRP6 target receptor inhibits a canonical Wnt signal transduction pathway, and the antibody or antigen binding fragment displays no significant potentiation of a Wnt signal.

In one embodiment, the antibody has an affinity for target receptor of approximately nanomolar affinity. In another embodiment, the antibody has an affinity for target receptor of approximately 1 picomolar affinity.

In one embodiment, the first receptor binding domain is an IgG antibody and the second receptor binding domain is an scFv fragment, where the IgG antibody and scFv fragment are linked together by a linker with a spatial distribution that permits the IgG antibody and scFv fragment to bind to the first and second epitopes of LRP6, respectively. In one embodiment, the linker is a Gly-Ser linker selected from the group consisting of $(Gly_4Ser)_4$, and $(Gly_4Ser)_3$.

In one embodiment, the first epitope of the LRP6 target receptor is a β-propeller 1 domain and the second epitope of the LRP6 target receptor is a β-propeller 3 domain. In one embodiment, the antibody or antigen binding fragment binds to the LPR6 β-propeller 1 domain and comprises a heavy chain CDR1 selected from the group consisting of SEQ ID NO: 1, SEQ ID NO: 21, and SEQ ID NO: 47; a CDR2 selected from the group consisting of SEQ ID NO: 2, SEQ ID NO: 22, and SEQ ID NO: 48; and a CDR3 selected from the group consisting of SEQ ID NO: 3, SEQ ID NO: 23, and SEQ ID NO: 49; and a light chain CDR1 selected from the group consisting of SEQ ID NO: 4, SEQ ID NO: 24, and SEQ ID NO: 50; a CDR2 selected from the group consisting of SEQ ID NO: 5, SEQ ID NO: 25, and SEQ ID NO: 51; and a CDR3 selected from the group consisting of SEQ ID NO: 6, SEQ ID NO: 26, and SEQ ID NO: 52.

In one embodiment, the antibody or antigen binding fragment binds to the LPR6 β-propeller 3 domain and comprises a heavy chain CDR1 selected from the group consisting of SEQ ID NO: 69, SEQ ID NO: 93, and SEQ ID NO: 115; a CDR2 selected from the group consisting of SEQ ID NO: 70, SEQ ID NO: 94, and SEQ ID NO: 116; and a CDR3 selected from the group consisting of SEQ ID NO: 71, SEQ ID NO: 95, and SEQ ID NO: 117; and a light chain CDR1 selected from the group consisting of SEQ ID NO: 72, SEQ ID NO: 96, and SEQ ID NO: 118; a CDR2 selected from the group consisting of SEQ ID NO: 73, SEQ ID NO: 97, and SEQ ID NO: 119; and a CDR3 selected from the group consisting of SEQ ID NO: 74, SEQ ID NO: 98, and SEQ ID NO: 120. In one embodiment, the IgG heavy chain antibody is selected from the group consisting of SEQ ID NO: 18, and 66, and the light chain is selected from the group consisting of SEQ ID NO: 17, 86, and 85. In one embodiment, the scFv is selected from the group consisting of SEQ ID NO: 142, 144, 146, 148, 150, 152, 154, 156, 158, 160, 162, and 164. In one embodiment, the scFv fragment comprises at least one amino acid mutation that improves stability of the scFv compared with the unmutated scFv fragment, wherein the amino acid mutation is selected from FIGS. 29-32. In one embodiment, the multivalent antibody has the functional activity of inhibiting a canonical Wnt signal transduction pathway selected from the group consisting of Wnt1 signal pathway and Wnt3 signal transduction pathway. In another embodiment, the multivalent antibody has the functional activity of depleting a cell population, inhibiting or reducing proliferation of a cell population, inhibiting or reducing secretion of inflammatory mediators from a cell population, inhibiting or reducing secretion of cytoplasmic granules from a cell population, wherein the cell population is selected from the group consisting of tumor cells, T cells B cells, and Wnt dependent cells.

In another aspect, the invention pertains to an isolated biparatopic antibody comprising an IgG antibody that binds to a β-propeller 1 domain on an LRP6 target receptor and a scFv that binds to a β-propeller 3 domain on the LRP6 target, where the IgG antibody and the scFv are linked by a linker such that the binding of the IgG antibody and the scFv to the β-propeller 1 domain and the β-propeller 3 domains, respectively inhibits a canonical Wnt signal transduction pathway, and where the biparatopic antibody displays no significant potentiation of a Wnt signal.

In one embodiment, the antibody has an affinity for target receptor of approximately nanomolar affinity. In another embodiment, the antibody has an affinity for target receptor of approximately 1 picomolar affinity.

In one embodiment, the linker comprises a spatial distribution that permits binding of the IgG antibody and the scFv fragment to bind the β-propeller 1 domain of LRP6 and the 11-propeller 3 domain of LRP6, respectively. In one embodiment, the scFv is linked by a Ser-Gly linker to the Fc binding site of the IgG antibody, where the Ser-Gly linker is selected from the group consisting of $(Gly_4Ser)_4$, and $(Gly_4Ser)_3$. In another embodiment, the Fc binding site of the IgG antibody is a CH3 domain. In another embodiment, the scFv is linked by a Ser-Gly linker to the light chain of the IgG antibody, where the Ser-Gly linker is selected from the group consisting of $(Gly_4Ser)_4$, and $(Gly_4Ser)_3$. In one embodiment, the scFv comprises at least one amino acid mutation that improves stability of the scFv compared with the unmutated scFv fragment, wherein the amino acid mutation is selected from FIGS. 29-32.

In one embodiment, the antibody comprises a heavy chain variable region CDR1 of SEQ ID NO: 1; a heavy chain variable region CDR2 of SEQ ID NO: 2; a heavy chain variable region CDR3 of SEQ ID NO: 3; a light chain variable region CDR1 of SEQ ID NO: 4; a light chain variable region CDR2 of SEQ ID NO: 5; and a light chain variable region CDR3 of SEQ ID NO: 6, wherein the antibody binds to a β-propeller 1 domain of LRP6; and a scFv heavy chain variable region CDR1 of SEQ ID NO: 69; a heavy chain variable region CDR2 of SEQ ID NO: 70; a heavy chain variable region CDR3 of SEQ ID NO: 71; a light chain variable region CDR1 of SEQ ID NO: 72; a light chain variable region CDR2 of SEQ ID NO: 73; and a light chain variable region CDR3 of SEQ ID NO: 74, wherein the scFv binds to a β-propeller 3 domain of LRP6. In one embodiment, the antibody further comprises a Lys deletion from position 454 of SEQ ID NO: 166. In one embodiment, the antibody further comprises a Pro to Ala mutation at position 677 of SEQ ID NO: 166.

In one embodiment, the antibody comprises a heavy chain sequence selected from the group consisting of SEQ ID NOs: 166, 171, 173, 175, 195, 201 and 207 in combination with a light chain sequence selected from the group consisting of SEQ ID NOs: 170, 193, 199, and 205. In one embodiment, the antibody comprises a combination of heavy and light chain sequences selected from the group consisting of SEQ ID NOs: 166/170, 171/170, 173/170, 175/170, 201/199, 207/205, and 195/193. In one embodiment, the antibody comprises heavy and light chain sequences with SEQ ID NOs: 166/170. In one embodiment, the antibody comprising heavy and light chain sequences with SEQ ID NOs; 177/181.

In one embodiment, the antibody has the functional activity of inhibiting a canonical Wnt signal transduction pathway selected from the group consisting of Wnt1 signal pathway and Wnt3 signal transduction pathway. In another embodiment, the antibody has the functional activity of depleting a cell population, inhibiting or reducing proliferation of a cell population, inhibiting or reducing secretion of inflammatory mediators from a cell population, inhibiting or reducing secretion of cytoplasmic granules from a cell population, wherein the cell population is selected from the group consisting of tumor cells, T cells B cells, and Wnt dependent cells.

In another aspect, the invention pertains to an isolated biparatopic antibody comprising an IgG antibody that binds to a β-propeller 3 domain on an LRP6 target receptor and a scFv that binds to a β-propeller 1 domain on the LRP6 target, wherein the IgG antibody and the scFv are linked by a linker such that the binding of the IgG antibody and the scFv to the β-propeller 3 domain and the β-propeller 1 domains, respectively inhibits a canonical Wnt signal transduction pathway, and wherein the biparatopic antibody displays no significant potentiation of a Wnt signal.

In one embodiment, the antibody has an affinity for target receptor of approximately nanomolar affinity. In another embodiment, the antibody has an affinity for target receptor of approximately 1 picomolar affinity.

In one embodiment, the linker comprises a spatial distribution that permits binding of the IgG antibody and the scFv to bind the β-propeller 3 domain of LRP6 and the β-propeller 1 domain of LRP6, respectively. In one embodiment, the scFv is linked by a Ser-Gly linker to the Fc binding site of the IgG antibody, wherein the Ser-Gly linker is selected from the group consisting of $(Gly_4Ser)_4$, and $(Gly_4Ser)_3$. In one embodiment, the Fc binding site of the IgG antibody is a CH3 domain. In one embodiment, the scFv comprises at least one amino acid mutation that improves stability of the scFv compared with the unmutated scFv fragment, wherein the amino acid mutation is selected from FIGS. 29-32.

In one embodiment, the antibody comprises a heavy chain variable region CDR1 of SEQ ID NO: 69; a heavy chain variable region CDR2 of SEQ ID NO: 70; a heavy chain variable region CDR3 of SEQ ID NO: 71; a light chain variable region CDR1 of SEQ ID NO: 72; a light chain variable region CDR2 of SEQ ID NO: 73; and a light chain variable region CDR3 of SEQ ID NO: 74, wherein the antibody binds to a β-propeller 3 domain of LRP6; and an scFv with a heavy chain variable region CDR1 of SEQ ID NO: 1; a heavy chain variable region CDR2 of SEQ ID NO: 2; a heavy chain variable region CDR3 of SEQ ID NO: 3; a light chain variable region CDR1 of SEQ ID NO: 4; a light chain variable region CDR2 of SEQ ID NO: 5; and a light chain variable region CDR3 of SEQ ID NO: 6, wherein the scFv thereof binds to a β-propeller 1 domain of LRP6. In one embodiment, the scFv VH and VL are linked with a linker comprising 3 amino acids. In another embodiment, the scFv VH and VL are linked with a linker comprising 4 amino acids. In one embodiment, the antibody comprises a heavy chain sequence selected from the group consisting of SEQ ID NO: 187, and 189; and a light chain sequence comprising SEQ ID NO: 185. In one embodiment, the antibody has the functional activity of inhibiting a canonical Wnt signal transduction pathway selected from the group consisting of Wnt1 signal pathway and Wnt3 signal transduction pathway. In another embodiment, the antibody has the functional activity of depleting a cell population, inhibiting or reducing proliferation of a cell population, inhibiting or reducing secretion of inflammatory mediators from a cell population, inhibiting or reducing secretion of cytoplasmic granules from a cell population, wherein the cell population is selected from the group consisting of tumor cells, T cells B cells, and Wnt dependent cells.

In another aspect, the invention pertains to nucleic acid comprising a nucleotide sequence encoding a multivalent antibody.

In one aspect, the invention pertains to a nucleic acid comprising a nucleotide sequence encoding a multivalent antibody comprising a heavy chain sequence selected from the group consisting of SEQ ID NOs: 166, 171, 173, 175, 195, 201, and 207; and light chain sequences selected from the group consisting of SEQ ID NOs: 170, 193, 199, and 205.

In another aspect, the invention pertains to a nucleic acid comprising a nucleotide sequence encoding multivalent antibody comprising a heavy chain sequence selected from the group consisting of SEQ ID NOs: 166, 171, 173, 175, 193, 199, 201, and 207; and light chain sequences selected from the group consisting of SEQ ID NOs: 170, 195, and 205 least, where the antibody or antigen binding fragment has 98% sequence identity to SEQ ID NOs: 166, 171, 173, 175, 195, 201, and 207; and light chain sequences selected from the group consisting of SEQ ID NOs: 170, 193, 199, and 205.

In another aspect, the invention pertains to a nucleic acid comprising a nucleotide sequence encoding a multivalent antibody comprising a SEQ ID NO: 166 and SEQ ID NO: 170.

In another aspect, the invention pertains to a nucleic acid comprising a nucleotide sequence encoding a multivalent antibody comprising at least 98% sequence identity to a SEQ ID NO: 166 and SEQ ID NO: 170.

In another aspect, the invention pertains to a nucleic acid comprising a nucleotide sequence encoding a multivalent antibody comprising a sequence selected from the group consisting of SEQ ID NOs: 177, and; and a light chain sequence of SEQ ID NO: 181.

In another aspect, the invention pertains to a nucleic acid comprising a nucleotide sequence encoding a multivalent antibody comprising at least 98% sequence identity to SEQ ID NOs: 177; and a light chain sequence of SEQ ID NO: 181.

In another aspect, the invention pertains to a nucleic acid comprising a nucleotide sequence encoding a multivalent antibody comprising a sequence selected from the group consisting of SEQ ID NOs: 187, and 189; and a light chain sequence of SEQ ID NO: 185.

In another aspect, the invention pertains to a nucleotide sequence encoding a multivalent antibody comprising at least 98% sequence identity to SEQ ID NOs: 187, and 189; and a light chain sequence of SEQ ID NO: 185. In another aspect, the invention pertains to a vector comprising the nucleic acid of the invention.

In another aspect, the invention pertains to a pharmaceutical composition comprising a multivalent antibody having at least two receptor binding domains for two different binding sites of a target receptor and a pharmaceutically acceptable carrier.

In another aspect, the invention pertains to a method of obtaining a multivalent antibody of the invention by a) providing a first receptor binding domain which binds to a first binding site of an LRP6 target receptor; (b) providing a second receptor binding domain which binds to a second binding site of an LRP6 target receptor; and (c) linking the first receptor binding domain to the second receptor binding domain. In one embodiment, the first or second receptor binding domain are selected from the group consisting of an IgG antibody, an scFv fragment, a single chain diabody, an antibody mimetic, and an antibody variable domain. In one embodiment, the first and second receptor binding domains are linked together by a linker with a spatial distribution that permits the first and second receptor binding domains to bind to the first and second epitopes of LRP6, respectively. In one embodiment, the linker is a Gly-Ser linker selected from the group consisting of $(Gly_4Ser)_4$, and $(Gly_4Ser)_3$. In one embodiment, the method further comprises introducing at least one amino acid mutation to the first or second receptor binding domain, such that the amino acid mutation improves stability of the first or second receptor binding domain compared with the unmutated first or second receptor binding domain.

In one aspect, the invention pertains to a method of treating a cancer comprising selecting a subject (e.g., human) having an LRP6 expressing cancer, administering to a subject in need thereof an effective amount of a composition comprising a multivalent antibody having at least two receptor binding domains for two different binding sites of a target receptor.

In one aspect, the invention pertains to a method of treating a cancer comprising selecting a subject having an LRP6 expressing cancer, administering to a subject in need thereof an effective amount of a composition comprising a multivalent antibody having at least two receptor binding domains for two different binding sites of a target receptor, where the cancer is selected from the group consisting of breast cancer, lung cancer, multiple myeloma, ovarian cancer, liver cancer, bladder cancer, gastric cancer, prostate cancer, acute myeloid leukemia, chronic myeloid leukemia, osteosarcoma, squamous cell carcinoma, and melanoma. In one embodiment, the cancer is breast cancer.

In another aspect, the invention pertains to a method of treating a disease mediated by a canonical Wnt signaling pathway using a biparatopic antibody to LRP6.

In another aspect, the invention pertains to a method of treating a cancer comprising selecting a subject having an LRP6 expressing cancer, administering to said subject an effective amount of a composition comprising a antibody with heavy and light chain sequences selected from the group consisting of SEQ ID NOs: 166/170, 171/170, 173/170, 175/170, 201/199, 207/205, and 195/193 in combination with any standard of care cancer therapies.

In another aspect, the invention pertains to use of a multivalent antibody in the manufacture of a medicament for the treatment of a cancer selected from the group consisting of breast cancer, lung cancer, multiple myeloma, ovarian cancer, liver cancer, bladder cancer gastric cancer, prostate cancer, acute myeloid leukemia, chronic myeloid leukemia, osteosarcoma, squamous cell carcinoma, and melanoma.

In another aspect, the invention pertains to a multivalent antibody having VH of SEQ ID NO: 14; VL of SEQ ID NO: 13; VH of SEQ ID NO: 82; VL of SEQ ID NO: 81 for use in treating a cancer mediated by a canonical Wnt signaling pathway.

In another aspect, the invention pertains to a multivalent antibody having VH of SEQ ID NO: 14; VL of SEQ ID NO: 13; VH of SEQ ID NO: 82; VL of SEQ ID NO: 81 for use as a drug.

In another aspect, the invention pertains to a multivalent antibody having SEQ ID NO: 166 and SEQ ID NO: 170 for use in treating a cancer mediated by a canonical Wnt signaling pathway.

In another aspect, the invention pertains to a multivalent antibody having SEQ ID NO: 166 and SEQ ID NO: 170 for use as a drug.

In another aspect, the invention pertains to a multivalent antibody for use as a medicament. In another aspect, the invention pertains to a multivalent antibody for use as a medicament for treatment of an LRP6 expressing cancer. In another aspect, the invention pertains a multivalent antibody for use as a medicament for treatment of an LRP6 expressing cancer, wherein the cancer is selected from the group consisting of breast cancer, lung cancer, multiple myeloma, ovarian cancer, liver cancer, bladder cancer, gastric cancer, prostate cancer, acute myeloid leukemia, chronic myeloid leukemia, osteosarcoma, squamous cell carcinoma, and melanoma.

BRIEF DESCRIPTION OF FIGURES

FIG. 3 shows the cross-reactivity values of anti-LRP6 β-propeller 1 and β-propeller 3 antibodies for human, mouse and cymologous monkey;

FIGS. 8A-B is a table that shows genes in MMTV-Wnt1 tumors that were upregulated >2-fold relative to t=0 control with an adjusted P-value of <0.01 and FIGS. 8C-E is a table that shows genes that were downregulated >2-fold relative to t=0 control with an adjusted P-value of <0.01 8 h after administration of a single dose of MOR08168 (5 mg/kg) to MMTV-Wnt1 tumors bearing mice;

FIG. 18 shows activity in STF assay of linker length comparisons in scFv molecules;

FIG. 19 is a table showing the binding activity a biparatopic antibody;

FIGS. 26A-D show the affinity and binding kinetics of MOR08168, MOR06475 and MOR08168IgG1LALA 6475 scfv to recombinant LRP6 PD1/2 and PD3/4. FIG. 26A shows a summary table of the affinities and on/off rates as determined by Biacore analysis. FIGS. 26B-C show representative binding curves of the anti-LRP6 molecules for corresponding LRP6 receptor domains, PD1/2 and PD3/4. FIG. 26D shows sequential binding of LRP6 PD1/2 and PD3/4 to MOR08168IgG1LALA 6475 scfv;

FIG. 29 is a table showing the effect of single mutations in MOR06475 scFv on Tm;

FIG. 30 is a table showing the effect of single mutations in MOR08168 scfv on Tm;

FIG. 31 is a table showing the effect of double mutations in MOR08168 scFv on Tm in material expressed in both bacterial and mammalian systems;

FIG. 32 is a table summarizing the binding and functional activities of the WILD TYPE and single/double mutated versions of MOR06475 and MOR08168 scFvs in ELISA, Proteon affinity and STF reporter gene assays;

FIG. 34 is a table showing thermostability measurements of biparatopic antibodies.

DETAILED DESCRIPTION OF THE INVENTION

Definitions

Figure 1A:
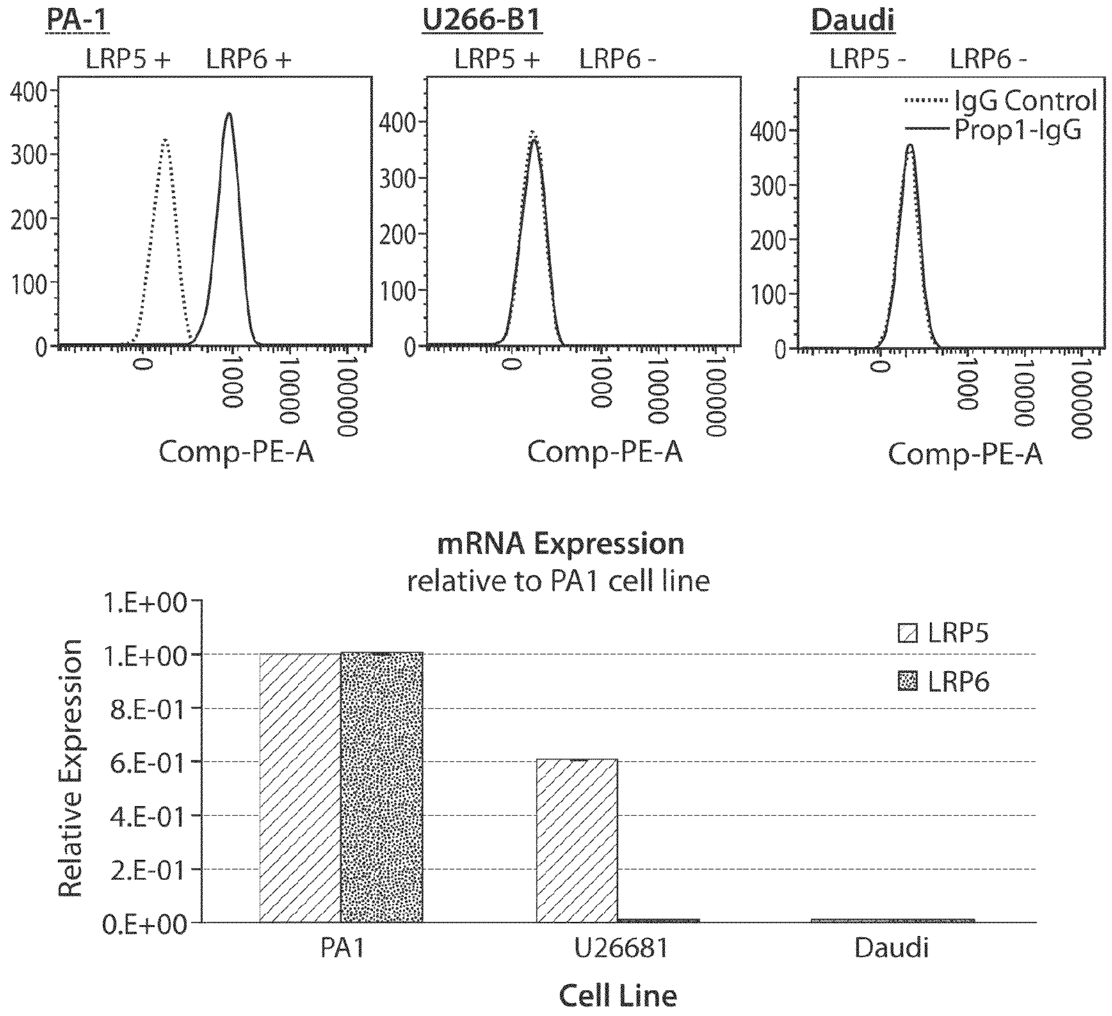
FIG. 1 is a graph showing FACS $EC_{50}$ determination of selected Fabs on PA1 cells, U266 cells and Daudi cells and the corresponding mRNA expression data (A) and knockdown of LRP6 by shRNA and the corresponding mRNA expression data (B).

In order that the present invention may be more readily understood, certain terms are first defined. Additional definitions are set forth throughout the detailed description.

The phrase "immune response" as used herein refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

The phrase "signal transduction pathway" or "signaling activity" as used herein refers to a biochemical causal relationship generally initiated by a protein-protein interaction such as binding of a growth factor to a receptor, resulting in transmission of a signal from one portion of a cell to another portion of a cell. For LRP6, the transmission involves specific phosphorylation of one or more tyrosine, serine, or threonine residues on one or more proteins in the series of reactions causing signal transduction. Penultimate processes typically include nuclear events, resulting in a change in gene expression.

The phrase "Wnt signaling pathway" as used herein refers to the canonical Wnt pathway in which members of the Wnt family of secreted protein ligands bind a receptor complex of LRP and Frizzled (FZD) allowing β-catenin to be translocated into the nucleus, interact with the LEF/TCF transcription factors and activate target gene expression. The Wnt signaling pathway can be measured using a Wnt reporter gene assay or other measure of Wnt directed signaling (e.g., LRP6 phosphorylation, β-catenin stabilization and nuclear translocation, cellular proliferation/survival) as described herein.

The phrase "Wnt 1 signaling pathway" refers to a canonical Wnt pathway that is activated by LRP6 interacting with the Wnt1 ligand and the class of Wnt1 binding ligands, such as Wnt2, Wnt6, Wnt7a, Wnt7b, Wnt9a, Wnt10a, or Wnt10b.

The phrase "Wnt 3 signaling pathway" refers to a canonical Wnt pathway that is activated by LRP6 interacting with the Wnt3 or a Wnt3a ligand.

The term "LRP6" refers to human LRP6 as defined in Accession No. NP002327.

The term "antibody" as used herein refers to whole antibodies that interact with (e.g., by binding, steric hinderance, stabilizing/destabilizing, spatial distribution) an LRP6 epitope and inhibit signal transduction. A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and $V_L$ regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. The term "antibody" includes for example, monoclonal antibodies, human antibodies, humanized antibodies, camelised antibodies, chimeric antibodies, Fab fragments, F(ab') fragments, and anti-idiotypic (anti-Id) antibodies (including, e.g., anti-Id antibodies to antibodies of the invention), and epitope-binding fragments of any of the above. The antibodies can be of any isotype (e.g., IgG, IgE, IgM, IgD, IgA and IgY), class (e.g., IgG1, IgG2, IgG3, IgG4, IgA1 and IgA2) or subclass.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminus is a variable region and at the C-terminus is a constant region; the CH3 and CL domains actually comprise the carboxy-terminus of the heavy and light chain, respectively. In particular, the term "antibody" specifically includes an IgG-scFv formats as shown in FIG. 12A-D.

The term "receptor binding domain" or "RBD" refers to portions of a binding molecule (e.g., an antibody), that specifically interacts with (e.g., by binding, steric hinderance, stabilizing/destabilizing, spatial distribution) a binding site on a target receptor. RBD also refers to one or more fragments of an antibody that retain the ability to specifically interact with (e.g., by binding, steric hinderance, stabilizing/destabilizing, spatial distribution) an LRP6 epitope and inhibit signal transduction. Examples of antibody fragments include, but are not limited to, an scFv, a Fab fragment, a monovalent fragment consisting of the VL, VH, CL and CH1 domains; a $F(ab)_2$ fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., (1989) Nature 341:544-546), which consists of a VH domain; and an isolated complementarity determining region (CDR).

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., (1988) Science 242:423-426; and Huston et al., (1988) Proc. Natl. Acad. Sci. 85:5879-5883).

Such single chain antibodies are also intended to be encompassed within the term "antibody fragment". These antibody fragments are obtained using conventional techniques known to those of skill in the art, and the fragments are screened for utility in the same manner as are intact antibodies.

Antibody fragments can also be incorporated into "single domain antibodies", "maxibodies", "minibodies", "diabodies", "triabodies", "tetrabodies", "v-NAR" and "bis-scFv" (see, e.g., Hollinger and Hudson, (2005) Nature Biotechnology 23: 1126-1136). Antibody fragments can be grafted into scaffolds based on polypeptides such as Fibronectin type III (Fn3) (see U.S. Pat. No. 6,703,199, which describes fibronectin polypeptide monobodies).

Antibody fragments can be incorporated into single chain molecules comprising a pair of tandem Fv segments (VH-CH1-VH-CH1) which, together with complementary light chain polypeptides, form a pair of antigen binding regions (Zapata et al., (1995) Protein Eng. 8:1057-1062; and U.S. Pat. No. 5,641,870).

RBDs also include single domain antibodies, maxibodies, unibodies, minibodies, triabodies, tetrabodies, v-NAR and bis-scFv (see, e.g., Hollinger and Hudson, (2005) Nature Biotechnology 23: 1126-1136), bispecific single chain diabodies, or single chain diabodies designed to bind two distinct epitopes. RBDs also include antibody-like molecules or antibody mimetics, which include, but not limited to minibodies, maxybodies, Fn3 based protein scaffolds, Ankrin repeats (also known as DARpins), VASP polypeptides, Avian pancreatic polypeptide (aPP), Tetranectin, Affililin, Knottins, SH3 domains, PDZ domains, Tendamistat, Neocarzinostatin, Protein A domains, Lipocalins, Transferrin, and Kunitz domains that specifically bind epitopes, which are within the scope of the invention.

The term "multivalent antibody" refers to a single binding molecule with more than one valency, where "valency" is described as the number of antigen-binding moieties present per molecule of an antibody construct. As such, the single binding molecule can bind to more than one binding site on a target receptor. Examples of multivalent antibodies include, but are not limited to bivalent antibodies, trivalent antibodies, tetravalent antibodies, pentavalent antibodies, and the like, as well as bispecific antibodies and biparatopic antibodies. For example, for the LRP6 receptor, the mutivalent antibody (e.g., an LRP6 biparatopic antibody) has a binding moiety for the β-propeller 1 domain binding site and a binding moiety for the β-propeller 3 domain binding site of LRP6, respectively.

The term "multivalent antibody" also refers to a single binding molecule that has more than one antigen-binding moieties for two separate target receptors. For example, an antibody that binds to both an LRP6 target receptor and a second target receptor that is not LRP6 (such as ErbB, cmet, IGFR1, Smoothened, Notch receptors). In one embodiment, a multivalent antibody is a tetravalent antibody that has four receptor binding domains. A tetravalent molecule may be bispecific and bivalent for each binding site on that target receptor.

The multivalent antibody mediates biological effect (e.g., which modulates cellular activation (e.g., by binding to a cell surface receptor and resulting in transmission or inhibition of an activating or inhibitory signal), which results in death of the cell (e.g., by a cell signal induced pathway), or which modulates a disease or disorder in a subject (e.g., by mediating or promoting cell killing, or by modulating the amount of a substance which is bioavailable.

The phrase "isolated antibody", as used herein, refers to antibody that is substantially free of other antibodies having different antigenic specificities (e.g., an isolated antibody that specifically binds LRP6 is substantially free of antibodies that specifically bind antigens other than LRP6). An isolated antibody that specifically binds LRP6 may, however, have cross-reactivity to other antigens, such as LRP6 molecules from other species. Moreover, an isolated antibody may be substantially free of other cellular material and/or chemicals.

The term "monovalent antibody" as used herein, refers to an antibody that binds to a single epitope on a target receptor such as LRP6.

The term "bivalent antibody" as used herein, refers to an antibody that binds to two epitopes on at least two identical target receptors (e.g., an antibody that binds to the β-propeller 1 domain of two LRP6 receptors, or an antibody that binds to the β-propeller 3 domain of two LRP6 receptors). The bivalent antibody may also crosslink the target receptors to one another. A "bivalent antibody" also refers to an antibody that bind to two different epitopes on at least two identical target receptors.

The term "biparatopic antibody" as used herein, refers to an antibody that binds to two different epitopes on the same target receptor, e.g., an antibody that binds to the 13-propeller 1 domain and the β-propeller 3 domain of a single LRP6 receptor. The term also includes an antibody, which binds to both the β-propeller 1 and β-propeller 3 domains of at least two LRP6 receptor(s) e.g., a tetravalent biparatopic antibody.

The term "bispecific antibody" as used herein, refers to an antibody that binds to two or more different epitopes on at least two different target receptors (e.g., an LRP6 receptor and a receptor that is not a LRP6 receptor).

The phrases "monoclonal antibody" or "monoclonal antibody composition" as used herein refers to polypeptides, including antibodies, antibody fragments, bispecific antibodies, etc. that have substantially identical to amino acid sequence or are derived from the same genetic source. This term also includes preparations of antibody molecules of single molecular composition. A monoclonal antibody composition displays a single binding specificity and affinity for a particular epitope.

The phrase "human antibody", as used herein, includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik, et al. (2000. J Mol Biol 296, 57-86). The structures and locations of immunoglobulin variable domains, e.g., CDRs, may be defined using well known numbering schemes, e.g., the Kabat numbering scheme, the Chothia numbering scheme, or a combination of Kabat and Chothia (see, e.g., Sequences of Proteins of Immunological Interest, U.S.

Department of Health and Human Services (1991), eds. Kabat et al.; Al Lazikani et al., (1997) J. Mol. Bio. 273:927 948); Kabat et al., (1991) Sequences of Proteins of Immunological Interest, 5th edit., NIH Publication no. 91-3242 U.S. Department of Health and Human Services; Chothia et al., (1987) J. Mol. Biol. 196:901-917; Chothia et al., (1989) Nature 342:877-883; and Al-Lazikani et al., (1997) J. Mal. Biol. 273:927-948.

The human antibodies of the invention may include amino acid residues not encoded by human sequences (e.g., mutations introduced by random or site-specific mutagenesis in vitro or by somatic mutation in vivo, or a conservative substitution to promote stability or manufacturing). However, the term "human antibody" as used herein, is not intended to include antibodies in which CDR sequences derived from the germline of another mammalian species, such as a mouse, have been grafted onto human framework sequences.

The phrase "recombinant human antibody" as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "linker" as used herein refers to a peptide linker that consists of glycine and serine residues used to link an scFv to an IgG. An exemplary Gly/Ser linker comprises the amino acid sequence $(Gly\text{-}Gly\text{-}Ser)_2$, i.e., $(Gly_2\,Ser)_n$ where n is a positive integer equal to or greater than 1. For example, n=1, n=2, n=3, n=4, n=5 and n=6, n=7, n=8, n=9 and n=10. In one embodiment, the linkers include, but are not limited to, $(Gly_4\,Ser)_4$ or $(Gly_4\,Ser)_3$. In another embodiment, the linkers Glu and Lys residues interspersed within the Gly-Ser linkers for better solubility. In another embodiment, the linkers include multiple repeats of $(Gly_2Ser)$, (GlySer) or $(Gly_3Ser)$. In another embodiment, the linkers include combinations and multiples of $(Gly_3Ser)$+$(Gly_4Ser)$+(GlySer). In another embodiment, Ser can be replaced with Ala e.g., $(Gly_4Ala)$ or $(Gly_3Ala)$. In another embodiment, the linker comprises any combination of Gly, Ser and Pro. In yet another embodiment, the linker comprises the motif $(GluAlaAlaAlaLys)_n$, where n is a positive integer equal to or greater than 1.

The term "Fc region" as used herein refers to a polypeptide comprising the CH3, CH2 and at least a portion of the hinge region of a constant domain of an antibody. Optionally, an Fc region may include a CH4 domain, present in some antibody classes. An Fc region, may comprise the entire hinge region of a constant domain of an antibody. In one embodiment, the invention comprises an Fc region and a CH1 region of an antibody. In one embodiment, the invention comprises an Fc region CH3 region of an antibody. In another embodiment, the invention comprises an Fc region, a CH1 region and a Ckappa/lambda region from the constant domain of an antibody. In one embodiment, a binding molecule of the invention comprises a constant region, e.g., a heavy chain constant region. In one embodiment, such a constant region is modified compared to a wild-type constant region. That is, the polypeptides of the invention disclosed herein may comprise alterations or modifications to one or more of the three heavy chain constant domains (CH1, CH2 or CH3) and/or to the light chain constant region domain (CL). Exemplary modifications include additions, deletions or substitutions of one or more amino acids in one or more domains. Such changes may be included to optimize effector function, half-life, etc.

The term "binding site" as used herein comprises an area on a target receptor to which an antibody or antigen binding fragment selectively binds. For example, the binding sites on LRP6 include the β-propeller 1 binding domain, β-propeller 2 binding domain, β-propeller 3 binding domain, and β-propeller 4 binding domain.

The term "epitope" as used herein refers to any determinant capable of binding with high affinity to an immunoglobulin. An epitope is a region of an antigen that is bound by an antibody that specifically targets that antigen, and when the antigen is a protein, includes specific amino acids that directly contact the antibody. Most often, epitopes reside on proteins, but in some instances, may reside on other kinds of molecules, such as nucleic acids. Epitope determinants may include chemically active surface groupings of molecules such as amino acids, sugar side chains, phosphoryl or sulfonyl groups, and may have specific three dimensional structural characteristics, and/or specific charge characteristics.

Generally, antibodies specific for a particular target antigen will bind to an epitope on the target antigen in a complex mixture of proteins and/or macromolecules.

Regions of a given polypeptide that include an epitope can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., (1984) Proc. Natl. Acad. Sci. USA 8:3998-4002; Geysen et al., (1985) Proc. Natl. Acad. Sci. USA 82:78-182; Geysen et al., (1986) Mol. Immunol. 23:709-715. Similarly, conformational epitopes are readily identified by determining spatial conformation of amino acids such as by, e.g., x-ray crystallography and two-dimensional nuclear magnetic resonance. See, e.g., Epitope Mapping Protocols, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., (1981) Proc. Natl. Acad. Sci USA 78:3824-3828; for determining antigenicity profiles, and the Kyte-Doolittle technique, Kyte et al., (1982) J. Mol. Biol. 157:105-132; for hydropathy plots.

The term "specific binding" between two entities means a binding with an equilibrium constant ($K_A$) ($k_{on}/k_{off}$) of at least $10^2M^{-1}$, at least $5\times10^2M^{-1}$, at least $10^3M^{-1}$, at least $5\times10^3M^{-1}$, at least $10^4M^{-1}$, at least $5\times10^4M^{-1}$, at least $10^5M^{-1}$, at least $5\times10^5M^{-1}$, at least $10^6M^{-1}$, at least $5\times10^6M^{-1}$, at least $10^7M^{-1}$, at least $5\times10^7M^{-1}$, at least $10^8M^{-1}$, at least 5×

$10^8M^{-1}$, at least $10^9M^{-1}$, at least $5\times10^9M^{-1}$, at least $10^{10}M^{-1}$, at least $5\times10^{10}M^{-1}$, at least $10^{11}M^{-1}$, at least $5\times10^{11}M^{-1}$, at least $10^{12}M^{-1}$, at least $5\times10^{12}M^{-1}$, at least $10^{13}M^{-1}$, at least $5\times10^{13}M^{-1}$, at least $10^{14}M^{-1}$, at least $5\times10^{14}M^{-1}$, at least $10^{15}M^{-1}$, or at least $5\times10^{15}M^{-1}$ The phrase "specifically (or selectively) binds" to a LRP6 multivalent antibody (e.g., a biparatopic antibody) refers to a binding reaction that is determinative of the presence of a cognate antigen (e.g., a human LRP6) in a heterogeneous population of proteins and other biologics. In addition to the equilibrium constant ($K_A$), an LRP6 multivalent antibody of the invention typically also has a dissociation rate constant ($K_D$) of about ($k_{off}/k_{on}$) of less than $5\times10^{-2}M$, less than $10^{-2}M$, less than $5\times10^{-3}M$, less than $10^{-3}M$, less than $5\times10^{-4}M$, less than $10^{-4}M$, less than $5\times10^{-5}M$, less than $10^{-5}M$, less than $5\times10^{-6}M$, less than $10^{-6}M$, less than $5\times10^{-7}M$, less than $10^{-7}M$, less than $5\times10^{-8}M$, less than $10^{-8}M$, less than $5\times10^{-9}M$, less than $10^{-9}M$, less than $5\times10^{-10}M$, less than $10^{-10}M$, less than $5\times10^{-11}M$, less than $10^{-11}M$, less than $5\times10^{-12}M$, less than $10^{-12}M$, less than $5\times10^{-13}M$, less than $10^{-13}M$, less than $5\times10^{-14}M$, less than $10^{-14}M$, less than $5\times10^{-15}M$, or less than $10^{-15}M$ or lower, and binds to LRP6 with an affinity that is at least two-fold greater than its affinity for binding to a non-specific antigen (e.g., HSA). In one embodiment, the LRP6 multivalent antibody has dissociation constant ($K_d$) of less than 3000 pM, less than 2500 pM, less than 2000 pM, less than 1500 pM, less than 1000 pM, less than 750 pM, less than 500 pM, less than 250 pM, less than 200 pM, less than 150 pM, less than 100 pM, less than 75 pM, less than 10 pM, less than 1 pM as assessed using a method described herein or known to one of skill in the art (e.g., a BIAcore assay, ELISA, FACS, SET) (Biacore International AB, Uppsala, Sweden).

The term "$K_{assoc}$" or "$K_a$", as used herein, refers to the association rate of a particular antibody-antigen interaction, whereas the term "$K_{dis}$" or "$K_d$" as used herein, refers to the dissociation rate of a particular antibody-antigen interaction. The term "$K_D$", as used herein, refers to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, or using a biosensor system such as a Biacore® system.

The term "affinity" as used herein refers to the strength of interaction between antibody and antigen at single antigenic sites. Within each antigenic site, the variable region of the antibody "arm" interacts through weak non-covalent forces with antigen at numerous sites; the more interactions, the stronger the affinity.

The term "avidity" as used herein refers to an informative measure of the overall stability or strength of the antibody-antigen complex. It is controlled by three major factors: antibody epitope affinity; the valence of both the antigen and antibody; and the structural arrangement of the interacting parts. Ultimately these factors define the specificity of the antibody, that is, the likelihood that the particular antibody is binding to a precise antigen epitope.

The term "Wnt 1" as used herein refers to Wnt1, Wnt2, Wnt6, Wnt7a, Wnt7b, Wnt9a, Wnt10a, or Wnt10b The term "Wnt 3a" as used herein refers to Wnt3a and Wnt3.

The term "potentiate" as used herein refers to a process whereby the Wnt signal is activated and enhanced upon conversion of a fragment of an antibody to a full length IgG LRP6 antibody in the presence of a Wnt ligand.

The term "no significant potentiation" or "avoids potentiation" refers to a Wnt signal that is not activated or enhanced compared with an control antibody or fragment thereof that binds to the same epitope. No significant potentiation can be at least 10% less than control antibody or fragment thereof, at least 20%, at least 30%, at least 40%, at least 50%, at least 60%, at least 70%, at least 80%, at least 90%, at least 100% less than then control antibody or fragment thereof.

The term "cluster" as used herein refers to any protein that gathers or groups together LRP6 receptors and potentiates Wnt signaling. Examples of such proteins include, but are not limited to, Wnt1 ligands, Wnt3a ligands and Wnt3 ligands. These proteins can cause multimerization, e.g., dimerization of two endogenous LRP6 receptors. This dimerization may result in increased avidity due to increased interactions of LRP6, which in the presence of a Wnt ligand can potentiate a Wnt signal.

The phrase "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). In some embodiments, the term "conservative sequence modifications" are used to refer to amino acid modifications that do not significantly affect or alter the binding characteristics of the antibody containing the amino acid sequence.

The terms "cross-block", "cross-blocked" and "cross-blocking" are used interchangeably herein to mean the ability of the multivalent antibody, to interfere with the binding of other antibodies or binding agents to LRP6 in a standard competitive binding assay.

The ability or extent to which an multivalent antibody is able to interfere with the binding of another antibody or binding molecule to LRP6, and therefore whether it can be said to cross-block according to the invention, can be determined using standard competition binding assays. One suitable assay involves the use of the Biacore technology (e.g. by using the BIAcore 3000 instrument (Biacore, Uppsala, Sweden)), which can measure the extent of interactions using surface plasmon resonance technology. Another assay for measuring cross-blocking uses an ELISA-based approach.

The term "optimized" as used herein refers to a nucleotide sequence has been altered to encode an amino acid sequence using codons that are preferred in the production cell or organism, generally a eukaryotic cell, for example, a cell of *Pichia*, a cell of *Trichoderma*, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence.

Standard assays to evaluate the binding ability of the multivalent antibodies toward LRP6 of various species are known in the art, including for example, ELISAs, western blots and RIAs. Suitable assays are described in detail in the Examples. The binding kinetics (e.g., binding affinity) of the multivalent antibodies also can be assessed by standard assays known in the art, such as by Biacore™ analysis. Assays to evaluate the effects of the multivalent antibodies on functional properties of LRP6 (e.g., receptor binding assays, modulating the Wnt pathway, or IgG production) are described in further detail in the Examples.

Accordingly, a multivalent antibody that "inhibits" one or more of these LRP6 functional properties (e.g., biochemical, immunochemical, cellular, physiological or other biological activities, or the like) as determined according to methodologies known to the art and described herein, will be understood to relate to a statistically significant decrease in the particular activity relative to that seen in the absence of the multivalent antibody (e.g., or when a control antibody of irrelevant specificity is present). A multivalent antibody that inhibits LRP6 activity effects such a statistically significant decrease by at least 10% of the measured parameter, by at least 50%, 80% or 90%, and in certain embodiments an antibody of the invention may inhibit greater than 95%, 98% or 99% of LRP6 functional activity.

The phrases "percent identical" or "percent identity," in the context of two or more nucleic acids or polypeptide sequences, refers to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., (2003) Current Protocols in Molecular Biology).

Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller (Comput. Appl. Biosci. 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol, Biol. 48:444-453 (1970)) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below.

Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., (1991) Nucleic Acid Res. 19:5081; Ohtsuka et al., (1985) J. Biol. Chem. 260:2605-2608; and Rossolini et al., (1994) Mol. Cell. Probes 8:91-98).

The phrase "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The term "anti-cancer agent" means any agent that can be used to treat a cell proliferative disorder such as cancer, including cytotoxic agents, chemotherapeutic agents, radiotherapy and radiotherapeutic agents, targeted anti-cancer agents, and immunotherapeutic agents.

"Tumor" refers to neoplastic cell growth and proliferation, whether malignant or benign, and all pre-cancerous and cancerous cells and tissues.

The term "anti-tumor activity" means a reduction in the rate of tumor cell proliferation, viability, or metastatic activity. A possible way of showing anti-tumor activity is show a decline in growth rate of abnormal cells that arises during therapy or tumor size stability or reduction. Such activity can be assessed using accepted in vitro or in vivo tumor models, including but not limited to xenograft models.

The term "malignancy" refers to a non-benign tumor or a cancer. As used herein, the term "cancer" includes a malignancy characterized by deregulated or uncontrolled cell growth. Exemplary cancers include: carcinomas, sarcomas, leukemias, and lymphomas. The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor).

Various aspects of the invention are described in further detail in the following sections and subsections.

LRP6 and the Wnt-Signaling Pathway

The invention pertains to LRP6 multivalent antibodies and uses thereof. Inhibition of Wnt signaling by molecules directed to LRP6 lead to a loss of canonical Wnt signaling. Therefore, antagonism of LRP6 receptor function with a multivalent antibody will inhibit Wnt ligand signaling and aid in diseases associated with aberrant canonical Wnt signaling, e.g., cancer. In particular, the LRP6 multivalent antibodies can specifically increase or decrease signaling mediated by Wnt1 or Wnt3a class proteins in different disease settings.

Misregulation of the Wnt/β-catenin signaling pathway has been linked to various human diseases such as cancer and bone disorders. Molecules that restore the balance of Wnt signaling in these diseases might have therapeutic potential. Using phage-based panning, LRP6 antibodies have been identified that either inhibit or enhance Wnt signaling. Remarkably, two classes of LRP6 antagonistic antibodies have been identified. One class of antibodies specifically inhibits Wnt proteins represented by Wnt1, while the second class specifically inhibits Wnt proteins represented by Wnt3a. Epitope mapping experiments indicate that Wnt1-specific and Wnt3a-specific LRP6 antibodies bind to the first β-propeller and the third β-propeller of LRP6 respectively, suggesting that Wnt1 and Wnt3a proteins bind to different β-propeller regions of LRP6 (See International Serial No. PCT/EP2008/064821 filed Oct. 31, 2008, the contents of which are incorporated herein by reference in their entirety).

Additional characterization of the Propeller 3 domain of LRP6 identified residues in this domain responsible for interaction with the antibodies. Antibody binding sites within YWTD-EGF region of Propeller 3 were identified using hydrogen-deuterium exchange (HDx) mass spectrometry (MS) and correspond to a concave surface between blade 1 and 6 of Propeller 3 domain.

The Wnt signaling pathway is important in embryonic development and postnatal tissue maintenance. This is achieved by directing a specific set of genes that control temporal and spatial regulation of cell growth, movement and cell survival (reviewed in Barker and Clevers (2006) Nature Rev. 5:997). Proper regulation of this pathway is important for maintaining tissue homeostasis. Chronic activation of this pathway promotes uncontrolled cell growth and survival and can consequently drive the development of cell proliferative diseases, such as cancer. Alternatively, abnormal inhibition of this pathway can result in many disease states, for example loss of bone mass and other bone diseases. Wnt proteins initiate downstream signaling by interacting with a Frizzled receptor and one of two cell-surface receptors, which are members of the low-density-lipoprotein receptor (LDLR)-related proteins (LRPs): LRP5 and LRP6 (reviewed in He et al., (2004) Development 31:1663-1677).

The role of LRP6 in canonical Wnt signaling was discovered via genetic studies. Mutant mice lacking LRP6 exhibited composite phenotypes similar to mutations in several individual Wnt genes (Pinson et al., (2000) Nature 407:535-538). In *Xenopus* embryos, dominant-negative LRP6 blocked signaling by several Wnt proteins, whereas overexpression of LRP6 activated Wnt/β-catenin signaling (Tamai et al., (2000) Nature 407:530-535). Furthermore, it has been shown that expression of either LRP6 or LRP5 is necessary for cells to respond to canonical Wnt signaling (reviewed in He et al., supra, 2004).

LRP5 and LRP6 are highly homologous and share 73% and 64% identity in their extra- and intracellular domains, respectively. They are widely co-expressed during embryogenesis and in adult tissues and share some functional redundancy.

The extracellular domains of LRP5 and LRP6 comprise three basic domains: 1) a YWTD (tyrosine, tryptophan, threonine, aspartic acid)-type β-propeller region, 2) an EGF (epidermal growth factor)-like domain, and 3) an LDLR type A (LA) domain.

The YWTD-type β-propeller region contains six YWTD repeats of 43-50 amino acid residues each and forms a six-bladed β-propeller structure. In LRP5 and LRP6, there are four YWTD-type β-propeller regions that are each followed by an EGF-like domain, which comprises about 40 amino acid residues with conserved cysteine residues, which in turn are followed by three LA domains. (Springer et al., (1998) J. MoI. Biol. 283:837-862; Jeon et al., (2001) Nat. Struct. Biol. 8:499-504). The β-propeller-EGF-like domains appear to bind extracellular ligands. The extracellular domain of LRP6 is defined by amino acid residues 19 to 1246 and contains four β-propeller domains at amino acid residues 43-324, 352-627, 654-929, and 957-1250, which correspond to β-propeller regions 1, 2, 3 and 4, respectively. Propeller domains 1-2 include amino acids 19-629, and Propeller domains 3-4 include amino acids 631-1246.

LRP6 Antibodies

The present invention provides antibodies that specifically bind to LRP6 (e.g., human LRP6, cynomologus LRP6). In some embodiments, the present invention provides antibodies that specifically bind to both human and cynomologus LRP6.

The Wnt proteins capable of activating β-catenin signaling can be divided into two classes and they require different β-propeller regions of LRP6 for signaling as described in International Serial No. PCT/EP2008/064821 filed Oct. 31, 2008, the contents of which are incorporated herein by reference in their entirety. In addition, dimeric LRP6 antibodies (e.g., IgG) strongly sensitize cells to Wnt signaling, for example through dimerization of endogenous LRP6. These results suggest that β-propeller 1 and β-propeller 3 are differentially required for signaling activity of Wnt1 and Wnt 3. These findings provide new insights on Wnt-induced LRP6 activation and pave the way for the development of LRP6 antibodies to modulate Wnt signaling in different diseases. Furthermore, conversion of fragments of the LRP6 antibodies into an IgG format results in an antibody that clusters LRP6 receptors and in the presence of a ligand protein can potentiate a Wnt signal.

In one embodiment, the antibodies potentiate a Wnt signal with the proviso that potentiation does not occur with biparatopic antibodies of the invention. In such an embodiment, the Wnt signal is activated and enhanced upon conversion of a fragment of an antibody to a full length IgG LRP6 antibody in the presence of a Wnt ligand. For example, a Wnt1 Fab binds to the β-propeller 1 domain of the LRP6 receptor and blocks the Wnt1 pathway in absence of a Wnt ligand, e.g., Wnt 3. In the presence of a Wnt ligand, e.g., Wnt 3, the Wnt1 Fab blocks signaling through the Wnt1 pathway, but signal activation may occur through the Wnt 3 pathway, thereby producing a signal. When the Wnt1 Fab is converted to a full length Wnt1 IgG, the Wnt1 IgG binds to the β-propeller 1 domains of two LRP6 receptors and blocks the Wnt1 pathway, however, in the presence of a Wnt ligand, e.g., Wnt 3; signal activation occurs through the Wnt 3 pathway and is also enhanced. While not required to provide a theory of action, one possible mechanism is that the IgG clusters together two or more LRP6 receptors by binding to the n-propeller 1 domains of each LRP6 receptor, which in the presence of a Wnt 3 ligand results in a stronger signal through the Wnt 3 pathway. Dimerization of the LRP6 receptors promotes Wnt signaling, perhaps through the increases avidity of the various interactions involving LRP6.

The reverse results are obtained with a Wnt 3 Fab that binds to the β-propeller 3 domain of the LRP6 receptor and blocks the Wnt 3 pathway. In the presence of a Wnt1 ligand, the Wnt 3 Fab blocks the Wnt 3 pathway, but activates the Wnt1 pathway to generate a signal. When the Wnt 3 Fab is converted to a full length Wnt 3 IgG, the Wnt 3 IgG binds to the β-propeller 3 regions of two LRP6 receptors, and in the presence of a Wnt1 ligand, inhibits signaling through the Wnt1 pathway. In one embodiment, the antibodies avoid potentiating a Wnt signal. In some embodiments, the present invention provides antibodies that specifically bind to both human and cynomologus LRP6. In one embodiment, the LRP6 antibodies are antagonistic antibodies. In another embodiment, the LRP6 antibodies are agonistic antibodies.

As different Wnt proteins require different β-propellers domains of LRP6 for signaling, and as clustering or dimerization of LRP6 potentiates Wnt signaling, therapy using the LRP6 antibodies can be regulated and "fine tuned" by using different combinations of antibodies.

In one embodiment, the LRP6 antibodies are used as monomeric antibodies or fragments thereof such as single chain antibodies, unibodies, and the like. In one embodiment, a monomeric LRP6 antibody that binds to the β-propeller 1 region of LRP6 is used in combination with a monomeric LRP6 antibody that binds to the β-propeller 3 region of LRP6. In another embodiment, the LRP6 antibodies are used as multimeric antibodies or fragments thereof such as bispecific, biparatopic LRP6 antibodies.

In addition to Wnt ligands LRP6 Propeller 1 antibodies are expected to inhibit the interaction with other Propeller 1 binding ligands (e.g. Sclerostin, Dkk1). Similarly, Propeller 3 antibodies are expected to inhibit the interaction with other propeller 3 binding ligands (e.g. Dkk1). Furthermore, propeller 1 and 3 binding antibodies may be expected to affect the activity of other Wnt signaling modulators e.g. R-spondins The present invention also provides antibodies that specifically bind to a LRP6 protein (e.g., human and/or cynomologus LRP6), the antibodies comprising a VH CDR having an amino acid sequence of any one of the VH CDRs listed in Table 1, infra. In particular, the invention provides antibodies that specifically bind to a LRP6 protein (e.g., human and/or cynomologus LRP6), the antibodies comprising (or alternatively, consisting of) one, two, three, four, five or more VH CDRs having an amino acid sequence of any of the VH CDRs listed in Table 1, infra.

The present invention provides antibodies that specifically bind a LRP6 protein (e.g., human and/or cynomologus LRP6), the antibodies comprising a VH domain having an amino acid sequence of SEQ ID NOs: 14, 34, 36, 44, 60 and 62. The present invention provides antibodies that specifically bind to a LRP6 protein (e.g., human and/or cynomologus LRP6), the antibodies comprising a VL domain having an amino acid sequence of SEQ ID NOs: 13, 33, 35, 43, 59, and 61.

The present invention provides antibodies that specifically bind a LRP6 protein (e.g., human and/or cynomologus LRP6), the antibodies comprising a VH domain having an amino acid sequence of SEQ ID NOs: 82, 89, 106, 108, 128, 130, and 138. The present invention provides antibodies that specifically bind to a LRP6 protein (e.g., human and/or cynomologus LRP6), the antibodies comprising a VL domain having an amino acid sequence of SEQ ID NOs: 81, 90, 105, 107, 127, and 129.

Other antibodies of the invention include amino acids that have been mutated, yet have at least 60%, 70%, 80%, 90%, 95% or 98% identity in the CDR regions with the CDR regions depicted in the sequences described in Table 1. In some embodiments, it includes mutant amino acid sequences wherein no more than 1, 2, 3, 4 or 5 amino acids have been mutated in the CDR regions when compared with the CDR regions depicted in the sequence described in Table 1, while still maintaining their specificity for the original antibody's epitope.

Other antibodies of the invention include amino acids that have been mutated, yet have at least 60%, 70%, 80%, 90%, 95% or 98% identity in the framework regions with the framework regions depicted in the sequences described in Table 1. In some embodiments, it includes mutant amino acid sequences wherein no more than 1, 2, 3, 4, 5, 6, or 7 amino acids have been mutated in the framework regions when compared with the framework regions depicted in the sequence described Table 1, while still maintaining their specificity for the original antibody's epitope The present invention also provides nucleic acid sequences that encode VH, VL, the full length heavy chain, and the full length light chain of the antibodies that specifically bind to a LRP6 protein (e.g., human and/or cynomologus LRP6). Such nucleic acid sequences can be optimized for expression in mammalian cells (for example, Table 1 for MOR08168, MOR08545, and MOR06706 for β-propeller 1 antibodies and MOR06475, MOR08193, and MOR08473 for β-propeller 3 antibodies).

The LRP6 antibodies of the invention bind to distinct LRP6 β-propeller regions. Propeller 1 antibodies bind to the β-propeller 1 domain and block Propeller1-dependent Wnts such as Wnt1, Wnt2, Wnt6, Wnt7A, Wnt7B, Wnt9, Wnt10A, Wnt10B. Propeller 3 antibodies bind to the β-propeller 3 domain and block Propeller 3-dependent Wnts such as Wnt3a and Wnt3.

TABLE 1

Examples of LRP6 Antibodies of the Present Invention

| SEQ ID NUMBER | Ab region | Sequence |
|---|---|---|
| MOR08168 Prop1 | | |
| SEQ ID NO: 1 (Kabat) | HCDR1 | DYVIN |
| SEQ ID NO: 2 (Kabat) | HCDR2 | GISWSGVNTHYADSVKG |
| SEQ ID NO: 3 (Kabat) | HCDR3 | LGATANNIRYKFMDV |
| SEQ ID NO: 4 (Kabat) | LCDR1 | SGDSLRNKVY |
| SEQ ID NO: 5 (Kabat) | LCDR2 | KNNRPS |
| SEQ ID NO: 6 (Kabat) | LCDR3 | QSYDGQKSLV |
| SEQ ID NO: 7 (Chothia) | HCDR1 | GFTFSDY |

TABLE 1-continued

Examples of LRP6 Antibodies of the Present Invention

| SEQ ID NUMBER | Ab region | Sequence |
|---|---|---|
| SEQ ID NO: 8<br>(Chothia) | HCDR2 | SWSGVN |
| SEQ ID NO: 9<br>(Chothia) | HCDR3 | LGATANNIRYKFMDV |
| SEQ ID NO: 10<br>(Chothia) | LCDR1 | DSLRNK |
| SEQ ID NO: 11<br>(Chothia) | LCDR2 | KN |
| SEQ ID NO: 12<br>(Chothia) | LCDR3 | YDGQKSL |
| SEQ ID NO: 13 | VL | DIELTQPPSVSVAPGQTARISCSGDSLRNKVYWYQQKPGQAPVLVIYKNNRPSGIPERFSGSN<br>SGNTATLTISGTQAEDEADYYCQSYDGQKSLVFGGGTKLTVL |
| SEQ ID NO: 14 | VH | QVQLVESGGGLVQPGGSLRLSCAASGFTFSDYVINWVRQAPGKGLEWVSGISWSGVNTHYADS<br>VKGRFTISRDNSKNTLYLQMNSLRAEDTAVYYCARLGATANNIRYKFMDVWGQGTLVTVSS |
| SEQ ID NO: 15 | DNA VL | GATATCGAACTGACCCAGCCGCCTTCAGTGAGCGTTGCACCAGGTCAGACCGCGCGTATCTCG<br>TGTAGCGGCGATTCTCTTCGTAATAAGGTTTATTGGTACCAGCAGAAACCCGGGCAGGCGCCA<br>GTTCTTGTGATTTATAAGAATAATCGTCCTCAGGCATCCCGGAACGCTTTAGCGGATCCAACA<br>GCGGCAACACCGCGACCCTGACCATTAGCGGCACTCAGGCGGAAGACGAAGCGGATTATTATT<br>GCCAGTCTTATGATGGTCAGAAGTCTCTTGTGTTTGGCGGCGGCACGAAGTTAACCGTCCTA |
| SEQ ID NO: 16 | DNA VH | CAGGTGCAATTGGTGGAAAGCGGCGGCGGCCTGGTGCAACCGGGCGGCAGCCTGCGTCTGAGC<br>TGCGCGGCCTCCGGATTTACCTTTTCTGATTATGTTATTAATTGGGTGCGCCAAGCCCCTGGG<br>AAGGGTCTCGAGTGGGTGAGCGGTATTTCTTGGTCTGGTGTTAATACTCATTATGCTGATTCT<br>GTTAAGGGTCGTTTTACCATTTCACGTGATAATTCGAAAAACACCCTGTATCTGCAAATGAAC<br>AGCCTGCGTGCGGAAGATACGGCCGTGTATTATTGCGCGCGTCTTGGTGCTACTGCTAATAAT<br>ATTCGTTATAAGTTTATGGATGTTTGGGGCCAAGGCACCCTGGTGACGGTTAGCTCA |
| SEQ ID NO: 17 | Light Lambda | DIELTQPPSVSVAPGQTARISCSGDSLRNKVYWYQQKPGQAPVLVIYKNNRPSGIPERFSGSN<br>SGNTATLTISGTQAEDEADYYCQSYDGQKSLVFGGGTKLTVLGQPKAAPSVTLFPPSSEELQA<br>NKATLVCLISDFYPGAVTVAWKADSSPVKAGVETTTPSKQSNNKYAASSYLSLTPEQWKSHRS<br>SCQVTHEGSTVEKTVAPTECS |
| SEQ ID NO: 18 | Heavy IgG1<br>LALA | QVQLVESGGGLVQPGGSLRLSCAASGFTFSDYVINWVRQAPGKGLEWVSGISWSGVNTHYADS<br>VKGRFTISRDNSKNTLYLQMNSLRAEDTAVYYCARLGATANNIRYKFMDVWGQGTLVTVSSAS<br>TKGPSVFPLAPSSKSTSGGTAALGCLVKDYFPEPVTVSWNSGALTSGVHTFPAVLQSSGLYLS<br>LLVVTVPSSSLGTQTYICNVNHKPSNTKVDVRVEPKSCDKTHTCPPCPAPEAAGGPSVFLFPP<br>KPKDTLMISRTPEVTCVVVDVSHEDPEVKFNWYVDGVEVHNAKTKPREEQYNSTYRVVSVLTV<br>LHQDWLNGKEYKCKVSNKKALPAPIEKTISKAKGQPREPQVYTLPPSREEMTKNQVSLTCLVK<br>GFYPSDIAVEWESNGQPENNYKTTPPVLDSDGSFFLYSKLTVDKSRWQQGNVFSCSVMHEALH<br>NHYTQKSLSLSPGK |
| SEQ ID NO: 19 | DNA<br>Light Lambda | GATATCGAACTGACCCAGCCGCCTTCAGTGAGCGTTGCACCAGGTCAGACCGCGCGTATCTCG<br>TGTAGCGGCGATTCTCTTCGTAATAAGGTTTATTGGTACCAGCAGAAACCCGGGCAGGCGCCA<br>GTTCTTGTGATTTATAAGAATAATCGTCCCTCAGGCATCCCGGAACGCTTTAGCGGATCCAAC<br>AGCGGCAACACCGCGACCCTGACCATTAGCGGCACTCAGGCGGAAGACGAAGCGGATTATTAT<br>TGCCAGTCTTATGATGGTCAGAAGTCTCTTGTGTTTGGCGGCGGCACGAAGTTAACCGTCCTA<br>GGTCAGCCCAAGGCTGCCCCCTCGGTCACTCTGTTCCCGCCCTCCTCTGAGGAGCTTCAAGCC<br>AACAAGGCCACACTGGTGTGTCTCATAAGTGACTTCTACCCGGGAGCCGTGACAGTGGCCTGG<br>AAGGCAGATAGCAGCCCCGTCAAGGCGGGAGTGGAGACCACCACACCCTCCAAACAAAGCAAC<br>AACAAGTACGCGGCCAGCAGCTATCTGAGCCTGACGCCTGAGCAGTGGAAGTCCCACAGAAGC<br>TACAGCTGCCAGGTCACGCATGAAGGGAGCACCGTGGAGAAGACAGTGGCCCCTACAGAATGT<br>TCA |
| SEQ ID NO: 20 | DNA<br>Heavy IgG1<br>LALA | CAGGTGCAATTGGTGGAAAGCGGCGGCGGCCTGGTGCAACCGGGCGGCAGCCTGCGTCTGAGC<br>TGCGCGGCCTCCGGATTTACCTTTTCTGATTATGTTATTAATTGGGTGCGCCAAGCCCCTGGG<br>AAGGGTCTCGAGTGGGTGAGCGGTATTTCTTGGTCTGGTGTTAATACTCATTATGCTGATTCT<br>GTTAAGGGTCGTTTTACCATTTCACGTGATAATTCGAAAAACACCCTGTATCTGCAAATGAAC<br>AGCCTGCGTGCGGAAGATACGGCCGTGTATTATTGCGCGCGTCTTGGTGCTACTGCTAATAAT<br>ATTCGTTATAAGTTTATGGATGTTTGGGGCCAAGGCACCCTGGTGACGGTTAGCTCAGCCTCC<br>ACCAAGGGTCCATCGGTCTTCCCCCTGGCACCCTCCTCCAAGAGCACCTCTGGGGGCACAGCG<br>GCCCTGGGCTGCCTGGTCAAGGACTACTTCCCCGAACCGGTGACGGTGTCGTGGAACTCAGGC<br>GCCCTGACCAGCGGCGTGCACACCTTCCCGGCTGTCCTACAGTCCTCAGGACTCTACTCCCTC<br>AGCAGCGTGGTGACCGTGCCCTCCAGCAGCTTGGGCACCCAGACCTACATCTGCAACGTGAAT<br>CACAAGCCCAGCAACACCAAGGTGGACAAGAGAGTTGAGCCCAAATCTTGTGACAAAACTCAC<br>ACATGCCCACCGTGCCCAGCACCTGAAGCAGCGGGGGGACCGTCAGTCTTCCTCTTCCCCCCA<br>AAACCCAAGGACACCCTCATGATCTCCCGGACCCCTGAGGTCACATGCGTGGTGGTGGACGTG<br>AGCCACGAAGACCCTGAGGTCAAGTTCAACTGGTACGTGGACGGCGTGGAGGTGCATAATGCC<br>AAGACAAAGCCGCGGGAGGAGCAGTACAACAGCACGTACCGGGTGGTCAGCGTCCTCACCGTC |

TABLE 1-continued

| Examples of LRP6 Antibodies of the Present Invention | | |
|---|---|---|
| SEQ ID NUMBER | Ab region | Sequence |
| | | CTGCACCAGGACTGGCTGAATGGCAAGGAGTACAAGTGCAAGGTCTCCAACAAAGCCCTCCCA GCCCCCATCGAGAAAACCATCTCCAAAGCCAAAGGGCAGCCCCGAGAACCACAGGTGTACACC CTGCCCCCATCCCGGGAGGAGATGACCAAGAACCAGGTCAGCCTGACCTGCCTGGTCAAAGGC TTCTATCCCAGCGACATCGCCGTGGAGTGGGAGAGCAATGGGCAGCCGGAGAACAACTACAAG ACCACGCCTCCCGTGCTGGACTCCGACGGCTCCTTCTTCCTCTACAGCAAGCTCACCGTGGAC AAGAGCAGGTGGCAGCAGGGGAACGTCTTCTCATGCTCCGTGATGCATGAGGCTCTGCACAAC CACTACACGCAGAAGAGCCTCTCCCTGTCTCCGGGTAAA |
| MOR08545 Prop1 | | |
| SEQ ID NO: 21 (Kabat) | HCDR1 | VNGMH |
| SEQ ID NO: 22 (Kabat) | HCDR2 | VIDGMGHTYYADSVKG |
| SEQ ID NO: 23 (Kabat) | HCDR3 | YDYIKYGAFDP |
| SEQ ID NO: 24 (Kabat) | LDCR1 | SGDNIGSKYVH |
| SEQ ID NO: 25 (Kabat) | LDCR2 | GDSNRPS |
| SEQ ID NO: 26 (Kabat) | LCDR3 | TRTSTPISGV |
| SEQ ID NO: 27 (Chothia) | HCDR1 | GFTFSVN |
| SEQ ID NO: 28 (Chothia) | HCDR2 | DGMGH |
| SEQ ID NO: 29 (Chothia) | HCDR3 | YDTIKYGAFDP |
| SEQ ID NO: 30 (Chothia) | LCDR1 | DNIGSKY |
| SEQ ID NO: 31 (Chothia) | LDCR2 | GDS |
| SEQ ID NO: 32 (Chothia) | LCDR3 | TSTPISG |
| SEQ ID NO: 33 | VL | DIELTQPPSVSVAPGQTARISCSGDNIGSKYVHWYQQKPGQAPVLVIYGDSNRPSGIPERFSG SNSGNTATLTISGTQAEDEADYYCTRTSTPISGVFGGGTKLTVL |
| SEQ ID NO: 34 | VH | QVQLVESGGGLVQPGGSLRLSCAASGFTFSVHGMHWVRQAPGKGLEWVSVIDGMGHTYYADSV KGRTFISRDNSKNTLYLQMNSLRAEDTAVYYCARYDYIKYGAFDPWGQGTLVTVSS |
| SEQ ID NO: 35 | VL Germlined | SYELTQPPSVSVSPGQTASITCSGDNIGSKYVHWYQQKPGQSPVLVIYGDSNRPSGIPERFSG SNSGNTATLTISGTQAMDEADYYCTRTSTPISGVFGGGTKLTVL |
| SEQ ID NO: 36 | VH Germlined | EVQLVESGGGLVQPGGSLRLSCAASGFTFSVNGMHWVRQAPGKGLEWVSVIDGMGHTYYADSV KGRFTISRDNSKNTLYLQMNSLRAEDTAVYYCARYDYIKYGAFDPWGQGTLVTVSS |
| SEQ ID NO: 37 | DNA VL | GATATCGAACTGACCCAGCCGCCTTCAGTGAGCGTTGCACCAGGTCAGACCGCGCGTATCTCG TGTAGCGGCGATAATATTGGTTCTAAGTATGTTCATTGGTACCAGCAGAAACCCGGGCAGGCG CCAGTTCTTGTGATTTATGGTGATTCTAATCGTCCCTCAGGCATCCCGGAACGCTTTAGCGGA TCCAACAGCGGCAACACCGCGACCCTGACCATTAGCGGCACTCAGGCGGAAGACGAAGCGGAT TATTATTGCACTCGTACTTCTACTCCTATTTCTGGTGTGTTTGGCGGCGGCACGAAGTTAACC GTTCTT |
| SEQ ID NO: 38 | DNA VH | CAGGTGCAATTGGTGGAAAGCGGCGGCGGCCTGGTGCAACCGGGCGGCAGCCTGCGTCTGAGC TGCGCGGCCTCCGGATTTACCTTTTCTGTTAATGGTATGCATTGGGTGCGCCAAGCCCCTGGG AAGGGTCTCGAGTGGGTGAGCGTTATTGATGGTATGGGTCATACTTATTATGCTGATTCTGTT AAGGGTCGTTTTACCATTTCACGTGATAATTCGAAAAACACCCTGTATCTGCAAATGAACAGC CTGCGTGCGGAAGATACGGCCGTGTATTATTGCGCGCGTTATGATTATATTAAGTATGGTGCT TTTGATCCTTGGGGCCAAGGCACCCTGGTGACGGTTAGCTCA |
| SEQ ID NO: 39 | Light lambda | DIELTQPPSVSVAPGQTARISCSGDNIGSKYVHWYQQKPGQAPVLVIYGDSNRPSGIPERFSG SNSGNTATLTISGTQAEDEADYYCTRTSTPISGVFGGGTKLTVLGQPKAAPSVLFPPSSEELQ |

TABLE 1-continued

Examples of LRP6 Antibodies of the Present Invention

| SEQ ID NUMBER | Ab region | Sequence |
|---|---|---|
| | | ANKATLVCLISDFYPGAVTVAWKADSSPVKAGVETTTPSKQSNNKYAASSYLSLTPEQWKSHR SYSCQVTHEGSTVEKTVAPTEA |
| SEQ ID NO: 40 | Heavy Fab | QVQLVESGGGLVQPGGSLRLSCAASGFTFSVNGMHWVRQAPGKGLEWVSVIDGMGHTYYADSV KGRFTISRDNSKNTLYLQMNSLRAEDTAVYYCARYDYIKYGAFDPWGQGTLVTVSSASTKGPS VFPLALSSKSTSGGTAALGCLVKFYFPEPVTVSWNSGALTSGVHTFPAVLQSSLGYSLSSVVT VPSSSLGTQTYICNVNHKPSNTKVDKKVEPKS |
| SEQ ID NO: 41 | DNA Light lambda | GATATCGAACTGACCCAGCCGCCTTCAGTGAGCGTTGCACCAGGTCAGACCGCGCGTATCTCG TGTAGCGGCGATAATATTGGTTCTAAGTATGTTCATTGGTACCAGCAGAAACCCGGGCAGGCG CCAGTTCTTGTGATTTATGGTGATTCTAATCGTCCCTCAGGCATCCCGGAACGCTTTAGCGGA TCCAACAGCGGCAACACCGCGACCCTGACCATTAGCGGCACTCAGGCGGAAGACGAAGCGGAT TATTATTGCACTCGTACTTCTACTCCTATTTCTGGTGTGTTTGGCGGCGGCACGAAGTTAACC GTTCTTGGCCAGCCGAAAGCCGCACCGAGTGTGACGCTGTTTCCGCCGAGCAGCAGAAGAATT GCAGGCGAACAAAGCGACCCTGGTGTGCCTGATTAGCGACTTTTATCCGGGAGCCGTGACAGT GGCCTGGAAGGCAGATAGCAGCCCCGTCAAGGCGGGAGTGGAGACCACCACACCCTCCAAACA AAGCAACAACAAGTACGCGGCCAGCAGCTATCTGAGCCTGACGCCTGAGCAGTGGAAGTCCCA CAGAAGCTACAGCTGCCAGGTCACGCATGAGGGGAGCACCGTGGAAAAAACCGTTGCGCCGAC TGAGGCC |
| SEQ ID NO: 42 | DNA Heavy Fab | CAGGTGCAATTGGTGGAAAGCGGCGGCGGCCTGGTGCAACCGGGCGGCAGCCTGCGTCTGAGC TGCGCGGCCTCCGGATTTACCTTTTCTGTTAATGGTATGCATTGGGTGCGCCAAGCCCCTGGG AAGGGTCTCGAGTGGGTGAGCGTTATTGATGGTATGGGTCATACTTATTATGCTGATTCTGTT AAGGGTCGTTTTACCATTTCACGTGATAATTCGAAAAACACCCTGTATCTGCAAATGAACAGC CTGCGTGCGGAAGATACGGCCGTGTATTATTGCGCGCGTTATGATTATATTAAGTATGGTGCT TTTGATCCTTGGGGCCAAGGCACCCTGGTGACGGTTAGCTCAGCGTCGACCAAAGGTCCAAGC GTGTTTCCGCTGGCTCCGAGCAGCAAAAGCACCAGCGGCGGCACGGCTGCCCTGGGCTGCCTG GTTAAAGATTATTTCCCGGAACCAGTCACCGTGAGCTGGAACAGCGGGGCGCTGACCAGCGGC GTGTATACCTTTCCGGCGGTGCTGCAAAGCAGCGGCCTGTATAGCCTGAGCAGCGTTGTGACC GTGCCGAGCAGCAGCTTAGGCACTCAGACCTATATTTGCAACGTGAACCATAAACCGAGCAAC ACCAAAGTGGATAAAAAAGTGGAACCGAAAAGC |
| SEQ ID NO: 43 | VL Germlined | SYELTQPLSVSVALGQTARITCGGDNIGSKYVHWYQQKPGQAPVLVIYGDSNRPSGIPERFSG SNSGNTATLTISRAQAGDEADYYCTRTSTPISGVFGGGTKLTVL |
| SEQ ID NO: 44 | VH Germlined | EVQLLESGGGLVQPGGSLRLSCAASGFTFSVNGMHWVRQAPGKGLEWVSVIDGMGHTYYADSV KGRFTISRDNSKNTLYLQMNSLRAEDTAVYYCARYDYIKYGAFDPWGQGTLVTVSS |
| SEQ ID NO: 45 | DNA VL Germlined | AGCTATGAACTGACCCAGCCGCTGTCTGTGAGCGTGGCGCTGGGCCAGACCGCGCGTATTACC TGCGGTGGCGATAACATTGGCAGCAAATATGTGCATTGGTATCAGCAGAAACCGGGCCAGGCG CCGGTGCTGGTGATTTATGGCGATAGCAACCGTCCGAGCGGCATTCCGGAACGTTTTAGCGGC AGCAACAGCGGCAACACCGCGACCCTGACCATTTCTCGCGCGCAGGCGGGTGATGAAGCGGAT TATTATTGCACCCGTACCAGCACCCCGATTAGCGGCGTGTTTGGCGGCGGTACGAAGTTAACC GTTCTT |
| SEQ ID NO: 46 | DNA VH Germlined | GAGGTGCAATTGCTGGAAAGCGGCGGCGGCCTGGTGCAACCGGGCGGCAGCCTGCGTCTGAGC TGCGCGGCCTCCGGATTTACCTTTTCTGTTAATGGTATGCATTGGGTGCGCCAAGCCCCTGGG AAGGGTCTCGAGTGGGTGAGCGTTATTGATGGTATGGGTCATACTTATTATGCTGATTCTGTT AAGGGTCGTTTTACCATTTCACGTGATAATTCGAAAAACACCCTGTATCTGCAAATGAACAGC CTGCGTGCGGAAGATACGGCCGTGTATTATTGCGCGCGTTATGATTATATTAAGTATGGTGCT TTTGATCCTTGGGGCCAAGGCACCCTGGTGACGGTTAGCTCA |
| MOR06706 Prop1 | | |
| SEQ ID NO: 47 (Kabat) | HCDR1 | DYAIH |
| SEQ ID NO: 48 (Kabat) | HCDR2 | GISYSGSSTHYADSVKG |
| SEQ ID NO: 49 (Kabat) | HCDR3 | GSHGNIMAKRYFDF |
| SEQ ID NO: 50 (Kabat) | LCDR1 | SGDNIRKKYVY |
| SEQ ID NO: 51 (Kabat) | LDCR2 | EDSKRPS |
| SEQ ID NO: 52 (Kabat) | LCDR3 | STADSGINNGV |
| SEQ ID NO: 53 (Chothia) | HCDR1 | GFTFSDY |

TABLE 1-continued

| Examples of LRP6 Antibodies of the Present Invention | | |
|---|---|---|
| SEQ ID NUMBER | Ab region | Sequence |
| SEQ ID NO: 54 (Chothia) | HCDR2 | SYSGSS |
| SEQ ID NO: 55 (Chothia) | HCDR3 | GSHGNIMAKRYFDF |
| SEQ ID NO: 56 (Chothia) | LCDR1 | DNIRKKY |
| SEQ ID NO: 57 (Chothia) | LDCR2 | EDS |
| SEQ ID NO: 58 (Chothia) | LCDR3 | ADSGINNG |
| SEQ ID NO: 59 | VL | DIELTQPPSVSVAPGQTARISCSGDNIRKKYVYWYQQKPGQAPVLVIYEDSKRPSGIPERFSG SNSGNTATLTISGTQAEDEADYYCSTADSGINNGVFGGGTKLTVL |
| SEQ ID NO: 60 | VH | QVQLVESGGGLVQPGGSLRLSCAASGFTFSDYAIHWVRQAPGKGLEWVSGISYSGSSTHYADS VKGRFTISRONSKNTLYLQMNSLRAEDTAVYYCARGSHGNIMAKRYFDFWGQGTLVTVSS |
| SEQ ID NO: 61 | VL Germlined | SYELTQPPSVSVSPGQTASITCSGDNIRKKYVYWYQQKPGQSPVLVIYEDSKRPSGIPERFSG SNSGNTATLTISGTQAMDEADYYCSTADSGINNGVFGGGTKLTVL |
| SEQ ID NO: 62 | VH Germlined | EVQLVESGGGLVQPGGSLRLSCAASGFTFSDYAIHWVRQAPGKGLEWVSGISYSGSSTHYADS VKGRFTISRDNSKNTLYLQMNSLRAEDTAVYYCARGSHGNIMAKRYFDFWGQGTLVTVSS |
| SEQ ID NO: 63 | DNA VL | GATATCGAACTGACCCAGCCGCCTTCAGTGAGCGTTGCACCAGGTCAGACCGCGCGTATCTCG TGTAGCGGCGATAATATTCGTAAGAAGTATGTTTATTGGTACCAGCAGAAACCCGGGCAGGCG CCAGTTCTTGTGATTTATGAGGATTCTAAGCGTCCCTCAGGCATCCCGGAACGCTTTAGCGGA TCCAACAGCGGCAACACCGCGACCCTGACCATTAGCGGCACTCAGGCGGAAGACGAAGCGGAT TATTATTGCTCTACTGCTGATTCTGGTATTAATAATGGTGTGTTTGGCGGCGGCACGAAGTTA ACCGTTCTT |
| SEQ ID NO: 64 | DNA VH | CAGGTGCAATTGGTGGAAAGCGGCGGCGGCCTGGTGCAACCGGGCGGCAGCCTGCGTCTGAGC TGCGCGGCCTCCGGATTTACCTTTTCTGATTATGCTATTCATTGGGTGCGCCAAGCCCCTGGG AAGGGTCTCGAGTGGGTGAGCGGTATCTCTTATTCTGGTAGCTCTACCCATTATGCGGATAGC GTGAAAGGCCGTTTTACCATTTCACGTGATAATTCGAAAAACACCCTGTATCTGCAAATGAAC AGCCTGCGTGCGGAAGATACGGCCGTGTATTATTGCGCGCGTGGTTCTCATGGTAATATTATG GCTAAGCGTTATTTTGATTTTTGGGGCCAAGGCACCCTGGTGACGGTTAGCTCA |
| SEQ ID NO: 65 | Light Lambda | DIELTQPPSVSVAPGQTARISCSGDNIRKKYVYWYQQKPGQAPVLVIYEDSKRPSGIPERFSG SNSGNTATLTISGTQAEDEADYYCSTADSGINNGVFGGGTKLTVLGQPKAAPSVLTLFPPSSE ELQANKATLVCLISDFYPGAVTVAWKADSSPVKAGVETTTPSKQSNNKYAASSYLSLTPEQWK SHRSYSCQVTHEGSTVEKTVAPTECS |
| SEQ ID NO: 66 | Heavy IgG1 LALA | QVQLVESGGGLVQPGGSLRLSCAASGFTFSDYAIHWVRQAPGKGLEWVSGISYSGSSTHYADS VKGRFTISRDNSKNTLYQMNSLRAEDTAVYYCARGSHGNIMAKRYFDFWGQGTLVTVSSASTK GPSVFPLAPSSKSTSGGTAALGCLVKDYFPEPVTVSWNSGALTSGVHTFPAVLQSSGLYSLSS VVTVPSSSLGTQTYICNVNHKPSNTKVDKRVEPKSCDKTHTCPPCPAPEAAGGPSVFLFPPKP KDTLMISRTPEVTCVVVDVSHEDPEVKFNWYVDGVEVHNAKTKPREEQYNSTYRVVSVLTVLH QDWLNGKEYCKVSNKALPAPIEKTISKAKGQPREPQVYTLPPSREEMTKNQVSLTCLVKGFYP SDIAVEWESNGQPENNYKTTPPVLDSDGSFFLYSKLTVDKSRWQQGNVFSCSVMHEALHNHYT QKSLSLSPGK |
| SEQ ID NO: 67 | DNA hlamda | GATATCGAACTGACCCAGCCGCCTTCAGTGAGCGTTGCACCAGGTCAGACCGCGCGTATCTCG TGTAGCGGCGATAATATTCGTAAGAAGTATGTTTATTGGTACCAGCAGAAACCCGGGCAGGCG CCAGTTCTTGTGATTTATGAGGATTCTAAGCGTCCCTCAGGCATCCCGGAACGCTTTAGCGGA TCCAACAGCGGCAACACCGCGACCCTGACCATTAGCGGCACTCAGGCGGAAGACGAAGCGGAT TATTATTGCTCTACTGCTGATTCTGGTATTAATAATGGTGTGTTTGGCGGCGGCACGAAGTTA ACCGTCCTAGGTCAGCCCAAGGCTGCCCCCTCGGTCACTCTGTTCCCGCCCTCCTCTGAGGAG CTTCAAGCCAACAAGGCCACACTGGTGTGTCTCATAAGTGACTTCTACCCGGGAGCCGTGACA GTGGCCTGGAAGGCAGATAGCAGCCCCGTCAAGGCGGGAGTGGAGACCACCACACCCTCCAAA CAAAGCAACAACAAGTACGCGGCCAGCAGCTATCTGAGCCTGACGCCTGAGCAGTGGAAGTCC CACAGAAGCTACAGCTGCCAGGTCACGCATGAAGGGAGCACCGTGGAGAAGACAGTGGCCCCT ACAGAATGTTCA |
| SEQ ID NO: 68 | DNA Heavy IgG1 LALA | CAGGTGCAATTGGTGGAAAGCGGCGGCGGCCTGGTGCAACCGGGCGGCAGCCTGCGTCTGAGC TGCGCGGCCTCCGGATTTACCTTTTCTGATTATGCTATTCATTGGGTGCGCCAAGCCCCTGGG AAGGGTCTCGAGTGGGTGAGCGGTATCTCTTATTCTGGTAGCTCTACCCATTATGCGGATAGC GTGAAAGGCCGTTTTACCATTTCACGTGATAATTCGAAAAACACCCTGTATCTGCAAATGAAC AGCCTGCGTGCGGAAGATACGGCCGTGTATTATTGCGCGCGTGGTTCTCATGGTAATATTATG GCCAAGCGTTATTTTGATTTTTGGGGCCAAGGCACCCTGGTGACGGTTAGCTCAGCCTCCACC AAGGGTCCATCGGTCTTCCCCCTGGCACCCTCCTCCAAGAGCACCTCTGGGGGCACAGCGGCC CTGGGCTGCCTGGTCAAGGACTACTTCCCCGAACCGGTGACGGTGTCGTGGAACTCAGGCGCC CTGACCAGCGGCGTGCACACCTTCCCGGCTGTCCTACAGTCCTCAGGACTCTACTCCCTCAGC |

TABLE 1-continued

Examples of LRP6 Antibodies of the Present Invention

| SEQ ID NUMBER | Ab region | Sequence |
|---|---|---|
| | | AGCGTGGTGACCGTGCCCTCCAGCAGCTTGGGCACCCAGACCTACATCTGCAACGTGAATCAC AAGCCCAGCAACACCAAGGTGGACAAGAGAGTTGAGCCCAAATCTTGTGACAAAACTCACACA TGCCCACCGTGCCCAGCACCTGAAGCAGCGGGGGGACCGTCAGTCTTCCTCTTCCCCCCAAAA CCCAAGGACACCCTCATGATCTCCCGGACCCCTGAGGTCACATGCGTGGTGGTGGACGTGAGC CACGAAGACCCTGAGGTCAAGTTCAACTGGTACGTGGACGGCGTGGAGGTGCATAATGCCAAG ACAAAGCCGCGGGAGGAGCAGTACAACAGCACGTACCGGGTGGTCAGCGTCCTCACCGTCCTG CACCAGGACTGGCTGAATGGCAAGGAGTACAAGTGCAAGGTCTCCAACAAAGCCCTCCCAGCC CCCATCGAGAAAACCATCTCCAAAGCCAAAGGGCAGCCCCGAGAACCACAGGTGTACACCCTG CCCCCATCCCGGGAGGAGATGACCAAGAACCAGGTCAGCCTGACCTGCCTGGTCAAAGGCTTC TATCCCAGCGACATCGCCGTGGAGTGGGAGAGCAATGGGCAGCCGGAGAACAACTACAAGACC ACGCCTCCCGTGCTGGACTCCGACGGCTCCTTCTTCCTCTACAGCAAGCTCACCGTGGACAAG AGCAGGTGGCAGCAGGGGAACGTCTTCTCATGCTCCGTGATGCATGAGGCTCTGCACAACCAC TACACGCAGAAGAGCCTCTCCCTGTCTCCGGGTAAA |
| MOR06475 Prop3 | | |
| SEQ ID NO: 69 (Kabat) | HCDR1 | NRGGGVG |
| SEQ ID NO: 70 (Kabat) | HCDR2 | WIDWDDDKSYSYSLKT |
| SEQ ID NO: 71 (Kabat) | HCDR3 | MHLPLVFDS |
| SEQ ID NO: 72 (Kabat) | LCDR1 | RASQFIGSRYLA |
| SEQ ID NO: 73 (Kabat) | LDCDR2 | GASNRAT |
| SEQ ID NO: 74 (Kabat) | LCDR3 | QQYYDYPQT |
| SEQ ID NO: 75 (Chothia) | HCDR1 | GFSLSNRGG |
| SEQ ID NO: 76 (Chothia) | HCDR2 | DWDDD |
| SEQ ID NO: 77 (Chothia) | HCDR3 | MHLPLVFDS |
| SEQ ID NO: 78 (Chothia) | LCDR1 | SQFIGSRY |
| SEQ ID NO: 79 (Chothia) | LDCR2 | GAS |
| SEQ ID NO: 80 (Chothia) | LCDR3 | YYDYPQ |
| SEQ ID NO: 81 | VL | DIVLTQSPATLSLSPGERATLSCRASQFIGSRYLAWYQQKPGQAPRLLIYGASNRATGVPARF SGSGSGTDFTLTISSLEPEDFATYYCQQYYDYPQTFGQGTKVEIK |
| SEQ ID NO: 82 | VH | QVQLKESGPALVKPTQTLTLTCTFSGSFLSNRGGGVGWIRQPPGKALEWLAWIDWDDDKSYST SLKTRLTISKDTSKNQVVLTMTNMDPVDTATYYCARMHLPLVFDSWGQGTLVTVSS |
| SEQ ID NO: 83 | DNA VL | GATATCGTGCTGACCCAGAGCCCGGCGACCCTGAGCCTGTCTCCGGGCGAACGTGCGACCCTG AGCTGCAGAGCGAGCCAGTTTATTGGTTCTCGTTATCTGGCTTGGTACCAGCAGAAACCAGGT CAAGCACCGCGTCTATTAATTTATGGTGCTTCTAATCGTGCAACTGGGGTCCCGGCGCGTTTT AGCGGCTCTGGATCCGGCACGGATTTTACCCTGACCATTAGCAGCCTGGAACCTGAAGACTTT GCGACTTATTATTGCCAGCAGTATTATGATTATCCTCAGACCTTTGGCCAGGGTACGAAAGTT GAAATTAAA |
| SEQ ID NO: 84 | DNA VH | CAGGTGCAATTGAAAGAAAGCGGCCCGGCCCTGGTGAAACCGACCCAAACCCTGACCCTGACC TGTACCTTTTCCGGATTTAGCCTGTCTAATCGTGGTGGTGGTGTGGGTTGGATTCGCCAGCCG CCTGGGAAAGCCCTCGAGTGGCTGGCTTGGATCGATTGGGATGATGATAAGTCTTATAGCACC AGCCTGAAAACGCGTCTGACCATTAGCAAAGATACTTCGAAAAATCAGGTGGTGCTGACTATG ACCAACATGGACCCGGTGGATACGGCCACCTATTATTGCGCGCGTATGCATCTTCCTCTTGTT TTTGATTCTTGGGGCCAAGGCACCCTGGTGACGGTTAGCTCA |
| SEQ ID NO: 85 | Light kappa | DIVLTQSPATLSLSPGERATLSCRASQFIGSRYLAWYQQKPGQAPRLLIYGASNRATGVPARF SGSGSGTDFTLTISSLEPEDFATYYCQQYYDYPQTFGQGTKVEIKRTVAAPSVFIFPPSDEQL |

TABLE 1-continued

| Examples of LRP6 Antibodies of the Present Invention | | |
|---|---|---|
| SEQ ID NUMBER | Ab region | Sequence |
| | | KSGTASVVCLLNNFYPREAKVQWKVDNALQSGNSQESVTEQDSKDSTYSLSSTLTLSKADYEK<br>HKVYACEVTHQGLSSPVTKSFNRGEC |
| SEQ ID NO: 86 | Heavy IgG1<br>LALA | QVQLKESGPALVKPTQTLTLTCTFSGFSLSNRGGGVGWIRQPPGKALEWLAWIDWDDDKSYST<br>SLKTRLTISKDTSKNQVVLTMTNMDPVDTATYYCARMHLPLVFDSWGQGTLVTVSSASTKGPS<br>VFPLAPSSKSTSGGTAALGCLVKDYFPEPVTVSWNSGALTSGVHTFPAVLQSSGLYSLSSVVT<br>VPSSSLGTQTYICNVNHKPSNTKVDKRVEPKSCDKTHTCPPCPAPEAAGGPSVLFPPKPKDTL<br>MISRTPEVTCVVVDVSHEDPEVKFNWYVDGVEVHNAKTKPREEQYNSTYRVVSVLTVLHQDWL<br>NGKEYKCKVSNKALPAPIEKTISKAKGQPREPQVYTLPPSREEMTKNQVSLTCLVKGFYPSDI<br>AVEWESNGQPENNYKTTPPVLDSGSFFLVSKLTVDKSRWQQGNVFSCSVMHEALHNHYTQKSL<br>SLSPGK |
| SEQ ID NO: 87 | DNA<br>Light kappa | GATATCGTGCTGACCCAGAGCCCGGCGACCCTGAGCCTGTCTCCGGGCGAACGTGCGACCCTG<br>AGCTGCAGAGCGAGCCAGTTTATTGGTTCTCGTTATCTGGCTTGGTACCAGCAGAAACCAGGT<br>CAAGCACCGCGTCTATTAATTTATGGTGCTTCTAATCGTGCAACTGGGGTCCCGGCGCGTTTT<br>AGCGGCTCTGGATCCGGCACGGATTTTACCCTGACCATTAGCAGCCTGGAACCTGAAGACTTT<br>GCGACTTATTATTGCCAGCAGTATTATGATTATCCTCAGACCTTTGGCCAGGGTACGAAAGTT<br>GAAATTAAACGTACGGTGGCTGCACCATCTGTCTTCATCTTCCCGCCATCTGATGAGCAGTTG<br>AAATCTGGAACTGCCTCTGTTGTGTGCCTGCTGAATAACTTCTATCCCAGAGAGGCCAAAGTA<br>CAGTGGAAGGTGGATAACGCCCTCCAATCGGGTAACTCCCAGGAGAGTGTCACAGAGCAGGAC<br>AGCAAGGACAGCACCTACAGCCTCAGCAGCACCCTGACGCTGAGCAAAGCAGACTACGAGAAA<br>CACAAAGTCTACGCCTGCGAAGTCACCCATCAGGGCCTGAGCTCGCCCGTCACAAAGAGCTTC<br>AACAGGGGAGAGTGT |
| SEQ ID NO: 88 | DNA<br>Heavy IgG1<br>LALA | CAGGTGCAATTGAAAGAAAGCGGCCCGGCCCTGGTGAAACCGACCCAAACCCTGACCCTGACC<br>TGTACCTTTTCCGGATTTAGCCTGTCTAATCGTGGTGGTGGTGTGGGTTGGATTCGCCAGCCG<br>CCTGGGAAAGCCCTCGAGTGGCTGGCTTGGATCGATTGGGATGATGATAAGTCTTATAGCACC<br>AGCCTGAAAACGCGTCTGACCATTAGCAAAGATACTTCGAAAAATCAGGTGGTGCTGACTATG<br>ACCAACATGGACCCGGTGGATACGGCCACCTATTATTGCGCGCGTATGCATCTTCCTCTTGTT<br>TTTGATTCTTGGGGCCAAGGCACCCTGGTGACGGTTAGCTCAGCCTCCACCAAGGGTCCATCG<br>GTCTTCCCCCTGGCACCCTCCTCCAAGAGCACCTCTGGGGGCACAGCGGCCCTGGGCTGCCTG<br>GTCAAGGACTACTTCCCCGAACCGGTGACGGTGTCGTGGAACTCAGGCGCCCTGACCAGCGGC<br>CACCTTCCCGGCTGTCCTACAGTCCTCAGGACTCTACTCCCTCAGCAGCGTGGTGACCGTGCC<br>CTCCAGCAGCTTGGGCACCCAGACCTACATCTGCAACGTGAATCACAAGCCCAGCAACACCAA<br>GGTGGACAAGAGAGTTGAGCCCAAATCTTGTGACAAAACTCACACATGCCCACCGTGCCCAGC<br>ACCTGAAGCAGCGGGGGGACCGTCAGTCTTCCTCTTCCCCCCAAAACCCAAGGACACCCTCAT<br>GATCTCCCGGACCCCTGAGGTCACATGCGTGGTGGTGGACGTGAGCCACGAAGACCCTGAGGT<br>CAAGTTCAACTGGTACGTGGACGGCGTGGAGGTGCATAATGCCAAGACAAAGCCGCGGGAGGA<br>GCAGTACAACAGCACGTACCGGGTGGTCAGCGTCCTCACCGTCCTGCACCAGGACTGGCTGAA<br>TGGCAAGGAGTACAAGTGCAAGGTCTCCAACAAAGCCCTCCCAGCCCCCATCGAGAAAACCAT<br>CTCCAAAGCCAAAGGGCAGCCCCGAGAACCACAGGTGTACACCCTGCCCCCATCCCGGGAGGA<br>GATGACCAAGAACCAGGTCAGCCTGACCTGCCTGGTCAAAGGCTTCTATCCCAGCGACATCGC<br>CGTGGAGTGGGAGAGCAATGGGCAGCCGGAGAACAACTACAAGACCACGCCTCCCGTGCTGGA<br>CTCCGACGGCTCCTTCTTCCTCTACAGCAAGCTCACCGTGGACAAGAGCAGGTGGCAGCAGGG<br>GAACGTCTTCTCATGCTCCGTGATGCATGAGGCTCTGCACAACCACTACACGCAGAAGAGCCT<br>CTCCCTGTCTCCGGGTAAA |
| SEQ ID NO: 89 | VH Germlined | QVTLKESGPALVKPTQTLTLTCTFSGFSLSNRGGGVGWIRQPPGKALEWLAWIDWDDDKSYST<br>SLKTRLTISKDTSKNQVVLTMTNMDPVDTATYYCARMHLPLVFDSWGQGTLVTVSS |
| SEQ ID NO: 90 | VL Germlined | EIVLTQSPATLSLSPGERATLSCRASQFIGSRYLAWYQQKPGQAPRLLIYGASNRATGIPARF<br>SGSGSGTDFTLTISSLEPEDFAVYYCQQYYDYPQTFGQGTKVEIK |
| SEQ ID NO: 91 | DNA VH<br>Germlined | CAGGTCACACTGAAAGAGTCCGGCCCTGCCCTGGTCAAACCCACCCAGACCCTGACCCTGACA<br>TGCACCTTCAGCGGCTTCAGCCTGAGCAACAGAGGCGGCGGAGTGGGCTGGATCAGACAGCCT<br>CCCGGCAAGGCCCTGGAATGGCTGGCCTGGATCGACTGGGACGACGACAAGAGCTACAGCACC<br>AGCCTGAAAACCCGGCTGACCATCAGCAAGGACACCAGCAAGAACCAGGTGGTGCTGACCATG<br>ACCAACATGGACCCCGTGGACACCGCCACCTACTACTGCGCCCGGATGCATCTGCCCCTGGTG<br>TTCGATAGCTGGGGCCAGGGCACCCTGGTCACCGTCAGCTCA |
| SEQ ID NO: 92 | DNA VL<br>Germlined | GAAATCGTGCTGACCCAGAGCCCCGCCACCCTGTCTCTGAGCCCTGGCGAGAGAGCCACCCTG<br>AGCTGCCGGGCCAGCCAGTTCATCGGCAGCAGATACCTGGCTTGGTATCAGCAGAAGCCCGGC<br>CAGGCCCCCAGACTGCTGATCTACGGCGCCAGCAACCGGGCCACCGGCATCCCTGCCAGATTT<br>TCTGGCAGCGGCAGCGGCACCGACTTCACCCTGACCATCAGCAGCCTGGAACCCGAGGACTTC<br>GCCGTGTACTACTGCCAGCAGTACTACGACTACCCCCAGACCTTCGGCCAGGGCACCAAGGTG<br>GAAATCAAG |
| MOR08193<br>Prop3 | | |
| SEQ ID NO: 93<br>(Kabat) | HCDR1 | NRGGGVG |
| SEQ ID NO: 94<br>(Kabat) | HCDR2 | WIDWDDDKSYSTSLKT |

TABLE 1-continued

Examples of LRP6 Antibodies of the Present Invention

| SEQ ID NUMBER | Ab region | Sequence |
|---|---|---|
| SEQ ID NO: 95 (Kabat) | HCDR3 | MHLPLVFDS |
| SEQ ID NO: 96 (Kabat) | LCDR1 | RASQFIGSRYLA |
| SEQ ID NO: 97 (Kabat) | LCDR2 | GASNRAT |
| SEQ ID NO: 98 (Kabat) | LCDR3 | QQYWSIPIT |
| SEQ ID NO: 99 (Chothia) | HCDR1 | GFSLSNRGG |
| SEQ ID NO: 100 (Chothia) | HCDR2 | DWDDD |
| SEQ ID NO: 101 (Chothia) | HCDR3 | MHLPLVFDS |
| SEQ ID NO: 102 (Chothia) | LCDR1 | SQFIGSRY |
| SEQ ID NO: 103 (Chothia) | LDCR2 | GAS |
| SEQ ID NO: 104 (Chothia) | LCDR3 | YWSIPI |
| SEQ ID NO: 105 | VL | DIVLTQSPATLSLSPGERATLSCRASQFIGSRYLAWYQQKPGQAPRLLIYGASNRATGVPARF SGSGSGTDFTLTISSLEPEDFAVYYCQQYWSIPITFGQGTKVEIK |
| SEQ ID NO: 106 | VH | QVQLKESGPALVKPTQTLTLTCTFSGFSLSNRGGGVGWIRQPPGKALEWLAWIDWDDDKSYST SLKTRLTISKDTSKNQVVLTMTNMDPVDTATYYCARMHLPLVFDSWGQGTLVTVSS |
| SEQ ID NO: 107 | VL Germlined | EIVLTQSPATLSLSPGERATLSCRASQFIGSRYLAWYQQKPGQAPRLLIYGASNRATGIPARF SGSGSGTDFTLTISSLEPEDFAVYYCQQYWSIPITFGQGTKVEIK |
| SEQ ID NO: 108 | VH Germlined | QVTLKESGPALVKPTQTLTLTCTFSGFSLSNRGGGVGWIRQPPGKALEWLAWIDWDDDKSYST SLKTRLTISKDTSKNQVVLTMTNMDPVDTATYYCARMHLPLVFDSWGQGTLVTVSS |
| SEQ ID NO: 109 | DNA VL | GATATCGTGCTGACCCAGAGCCCGGCGACCCTGAGCCTGTCTCCGGGCGAACGTGCGACCCTG AGCTGCAGAGCGAGCCAGTTTATTGGTTCTCGTTATCTGGCTTGGTACCAGCAGAAACCAGGT CAAGCACCGCGTCTATTAATTTATGGTGCTTCTAATCGTGCAACTGGGGTCCCGGCGCGTTTT AGCGGCTCTGGATCCGGCACGGATTTTACCCTGACCATTAGCAGCCTGGAACCTGAAGACTTT GCGGTGTATTATTGCCAGCAGTATTGGTCTATTCCTATTACCTTTGGCCAGGGTACGAAAGTT GAAATTAAA |
| SEQ ID NO: 110 | DNA VH | CAGGTGCAATTGAAAGAAAGCGGCCCGGCCCTGGTGAAACCGACCCAAACCCTGACCCTGACC TGTACCTTTTCCGGATTTAGCCTGTCTAATCGTGGTGGTGGTGTGGGTTGGATTCGCCAGCCG CCTGGGAAAGCCCTCGAGTGGCTGGCTTGGATCGATTGGGATGATGATAAGTCTTATAGCACC AGCCTGAAAACGCGTCTGACCATTAGCAAAGATACTTCGAAAAATCAGGTGGTGCTGACTATG ACCAACATGGACCCGGTGGATACGGCCACCTATTATTGCGCGCGTATGCATCTTCCTCTTGTT TTTGATTCTTGGGGCCAAGGCACCCTGGTGACGGTTAGCTCA |
| SEQ ID NO: 111 | Light kappa | DIVLTQSPATLSLSPGERATLSCRASQFIGSRYLAWYQQKPGQAPRLLIYGASNRATGVPARF SGSGSGTDFTLTISSLEPEDFAVYYCQQYWSIPITFGQGTKVEIKRTVAAPSVFIFPPSDEQL KSGTASVVCLLNNFYPREAKVQWKVDNALQSGNSQESVTEQDSKSDTYSLSSTLTLSKADTYE KHKVYACEVTHQGLSSPVTKSFNRGEA |
| SEQ ID NO: 112 | Heavy Fab | QVQLKESGPALVKPTQTLTLTCTFSGFSLSNRGGGVGWIRQPPGKALEWLAWIDWDDDKSYST SLKTRLTISKDTSKNQVVLTMTNMDPVDTATYYCARMHLPLVFDSWGQGTLVTVSSASTKGPS VFPLAPSSKSTSGGTAALGCLVKDYFPEPVTVSWNSGALTSGVHTFPAVLQSSGLYSLSSVVT VPSSSLGTQTYICNVNHKPSNTKVDKKVEPKS |
| SEQ ID NO: 113 | DNA Light kappa | GATATCGTGCTGACCCAGAGCCCGGCGACCCTGAGCCTGTCTCCGGGCGAACGTGCGACCCTG AGCTGCAGAGCGAGCCAGTTTATTGGTTCTCGTTATCTGGCTTGGTACCAGCAGAAACCAGGT CAAGCACCGCGTCTATTAATTTATGGTGCTTCTAATCGTGCAACTGGGGTCCCGGCGCGTTTT AGCGGCTCTGGATCCGGCACGGATTTTACCCTGACCATTAGCAGCCTGGAACCTGAAGACTTT GCGGTGTATTATTGCCAGCAGTATTGGTCTATTCCTATTACCTTTGGCCAGGGTACGAAAGTT GAAATTAAACGTACGGTGGCTGCTCCGAGCGTGTTTATTTTTCCGCCGAGCGATGAACAACTG AAAAGCGGCACGGCGAGCGTGGTGTGCCTGCTGAACAACTTTTATCCGCGTGAAGCGAAAGTT CAGTGGAAAGTAGACAACGCGCTGCAAAGCGGCAACAGCCAGGAAAGCGTGACCGAACAGGAT |

TABLE 1-continued

Examples of LRP6 Antibodies of the Present Invention

| SEQ ID NUMBER | Ab region | Sequence |
| --- | --- | --- |
| | | AGCAAAGATAGCACCTATTCTCTGAGCAGCACCCTGACCCTGAGCAAAGCGGATTATGAAAAA<br>CATAAAGTGTATGCGTGCGAAGTGACCCATCAAGGTCTGAGCAGCCCGGTGACTAAATCTTTT<br>AATCGTGGCGAGGCC |
| SEQ ID NO: 114 | DNA<br>Heavy Fab | CAGGTGCAATTGAAAGAAAGCGGCCCGGCCCTGGTGAAACCGACCCAAACCCTGACCCTGACC<br>TGTACCTTTTCCGGATTTAGCCTGTCTAATCGTGGTGGTGGTGTGGGTTGGATTCGCCAGCCG<br>CCTGGGAAAGCCCTCGAGTGGCTGGCTTGGATCGATTGGGATGATGATAAGTCTTATAGCACC<br>AGCCTGAAAACGCGTCTGACCATTAGCAAAGATACTTCGAAAAATCAGGTGGTGCTGACTATG<br>ACCAACATGGACCCGGTGGATACGGCCACCTATTATTGCGCGCGTATGCATCTTCCTCTTGTT<br>TTTGATTCTTGGGGCCAAGGCACCCTGGTGACGGTTAGCTCAGCGTCGACCAAAGGTCCAAGC<br>GTGTTTCCGCTGGCTCCGAGCAGCAAAAGCACCAGCGGCGGCACGGCTGCCCTGGGCTGCCTG<br>GTTAAAGATTATTTCCCGGAACCAGTCACCGTGAGCTGGAACAGCGGGGCGCTGACCAGCGGC<br>GTGCATACCTTTCCGGCGGTGCTGCAAAGCAGCGGCCTGTATAGCCTGAGCAGCGTTGTGACC<br>GTGCCGAGCAGCAGCTTAGGCACTCAGACCTATATTTGCAACGTGAACCATAAACCGAGCAAC<br>ACCAAAGTGGATAAAAAAGTGGAACCGAAAAGC |

MOR08473
Prop3

| SEQ ID NO: 115<br>(Kabat) | HCDR1 | SYGMS |
| --- | --- | --- |
| SEQ ID NO: 116<br>(Kabat) | HCDR2 | NISNDGHYTYYADSVKG |
| SEQ ID NO: 117<br>(Kabat) | HCDR3 | FQASYLDIMDY |
| SEQ ID NO: 118<br>(Kabat) | LCDR1 | SGDNIGSKYVH |
| SEQ ID NO: 119<br>(Kabat) | LDCR2 | NDSNRPS |
| SEQ ID NO: 120<br>(Kabat) | LCDR3 | QAWGDNGTRV |
| SEQ ID NO: 121<br>(Chothia) | HCDR1 | GFTFSSY |
| SEQ ID NO: 122<br>(Chothia) | HCDR2 | SNDGHY |
| SEQ ID NO: 123<br>(Chothia) | HCDR3 | FQASYLDIMDY |
| SEQ ID NO: 124<br>(Chothia) | LCDR1 | DNIGSKY |
| SEQ ID NO: 125<br>(Chothia) | LDCR2 | NDS |
| SEQ ID NO: 126<br>(Chothia) | LCDR3 | WGDNGTR |
| SEQ ID NO: 127 | VL | DIELTQPPSVSVAPGQSITISCSGDNIGSKYVHWYQQKPGQAPVLVIYNDSNRPSGIPERFSG<br>SNSGNTATLTISGTQAEDEADYYCQAWGDNGTRVFGGGTKLTVL |
| SEQ ID NO: 128 | VH | QVQLVESGGGLVQPGGSLRLSCAASGFTFSSYGMSWVRQAPGKGLEWVSNISNDGHYTYYADS<br>VKGRFTISRDNSKNTLYLQMNSLRAEDTAVYYCARFQASYLDIMDYWGQGTLVTVSS |
| SEQ ID NO: 129 | VL Germlined | SYELTQPPSVSVSPGQTASITCSGDNIGSKYVHWYQQKPGQSPVLVIYNDSNRPSGIPERFSG<br>SNSGNTATLTISGTQAMDEADYYCQAWGDNGTRVFGGGTKLTVL |
| SEQ ID NO: 130 | VH Germlined | EVQLVESGGGLVQPGGSLRLSCAASGFTFSSYGMSWVRQAPGKGLEWVSNISNDGHYTYYADS<br>VKGRFTISRDNSKNTLYLQMNSLRAEDTAVYYCARFQASYLDIMDYWGQGTLVTVSS |
| SEQ ID NO: 131 | DNA VL | GATATCGAACTGACCCAGCCGCCTTCAGTGAGCGTTGCACCAGGTCAGAGCATTACCATCTGT<br>GTAGCGGCGATAATATTGGTTCTAAGTATGTTCATTGGTACCAGCAGAAACCCGGGCAGGCGC<br>CAGTTCTTGTGATTTATAATGATTCTAATCGTCCCTCAGGCATCCCGGAACGCTTTAGCGGAT<br>CCAACAGCGGCAACACCGCGACCCTGACCATTAGCGGCACTCAGGCGGAAGACGAAGCGGATT<br>ATTATTGCCAGGCTTGGGGTGATAATGGTACTCGTGTGTTTGGCGGCGGCACGAAGTTAACCG<br>TTCTT |
| SEQ ID NO: 132 | DNA VH | CAGGTGCAATTGGTGGAAAGCGGCGGCGGCCTGGTGCAACCGGGCGGCAGCCTGCGTCTGAGC<br>TGCGCGGCCTCCGGATTTACCTTTTCTTCTTATGGTATGTCTTGGGTGCGCCAAGCCCCTGGG |

TABLE 1-continued

| Examples of LRP6 Antibodies of the Present Invention | | |
|---|---|---|
| SEQ ID NUMBER | Ab region | Sequence |
| | | AAGGGTCTCGAGTGGGTGAGCAATATTTCTAATGATGGTCATTATACTTATTATGCTGATTCT GTTAAGGGTCGTTTTACCATTTCACGTGATAATTCGAAAAACACCCTGTATCTGCAAATGAAC AGCCTGCGTGCGGAAGATACGGCCGTGTATTATTGCGCGCGTTTTCAGGCTTCTTATCTTGAT ATTATGGATTATTGGGGCCAAGGCACCCTGGTGACGGTTAGCTCA |
| SEQ ID NO: 133 | Light lambda | DIELTQPPSVSVAPGQSITISCSGDNIGSKYVHWYQQKPGQAPVLVIYNDSNRPSGIPERFSG SNSGNTATLTISGTQAEDEADYYCQAWGDNGTRVFGGGTKLTVLGQPKAAPSVTLFPPSSEEL QANKATLVCLISDFYPGAVTVAWKADSSPVKAGVETTTPSKQSNNKYAASSYLSLTPEQWKSH RSYSCQVTHEGSTVEKTVAPTEA |
| SEQ ID NO: 134 | Heavy Fab | QVQLVESGGGLVQPGGSLRLSCAASGFTFSSYGMSWVRQAPGKGLEWVSNISNDGHYTYYADS VKGRFTISRDNSKNTLYLQMNSLRAEDTAVYYCARFQASYLDIMDYWGQGTLVTVSSASTKGP SVFPLAPSSKSTSGGTAALGCLVKDYFPEPVTVSWNSGALTSGVHTFPAVLQSSGLYSLSSVV TVPSSSLGTQTYICNVNHKPSNTKVDKKVEPKS |
| SEQ ID NO: 135 | DNA<br>Light lambda | GATATCGAACTGACCCAGCCGCCTTCAGTGAGCGTTGCACCAGGTCAGAGCATTACCATCTCG TGTAGCGGCGATAATATTGGTTCTAAGTATGTTCATTGGTACCAGCAGAAACCCGGGCAGGCG CCAGTTCTTGTGATTTATAATGATTCTAATCGTCCCTCAGGCATCCCGGAACGCTTTAGCGGA TCCAACAGCGGCAACACCGCGACCCTGACCATTAGCGGCACTCAGGCGGAAGACGAAGCGGAT TATTATTGCCAGGCTTGGGGTGATAATGGTACTCGTGTGTTTGGCGGCGGCACGAAGTTAACC GTTCTTGGCCAGCCGAAAGCCGCACCGAGTGTGACGCTGTTTCCGCCGAGCAGCGAAGAATTG CAGGCGAACAAAGCGACCCTGGTGTGCCTGATTAGCGACTTTTATCCGGGAGCCGTGACAGTG GCCTGGAAGGCAGATAGCAGCCCCGTCAAGGCGGGAGTGGAGACCACCACACCCTCCAAACAA AGCAACAACAAGTACGCGGCCAGCAGCTATCTGAGCCTGACGCCTGAGCAGTGGAAGTCCCAC AGAAGCTACAGCTGCCAGGTCACGCATGAGGGGAGCACCGTGGAAAAAACCGTTGCGCCGACT GAGGCC |
| SEQ ID NO: 136 | DNA<br>Heavy Fab | CAGGTGCAATTGGTGGAAAGCGGCGGCGGCCTGGTGCAACCGGGCGGCAGCCTGCGTCTGAGC TGCGCGGCCTCCGGATTTACCTTTTCTTCTTATGGTATGTCTTGGGTGCGCCAAGCCCCTGGG AAGGGTCTCGAGTGGGTGAGCAATATTTCTAATGATGGTCATTATACTTATTATGCTGATTCT GTTAAGGGTCGTTTTACCATTTCACGTGATAATTCGAAAAACACCCTGTATCTGCAAATGAAC AGCCTGCGTGCGGAAGATACGGCCGTGTATTATTGCGCGCGTTTTCAGGCTTCTTATCTTGAT ATTATGGATTATTGGGGCCAAGGCACCCTGGTGACGGTTAGCTCAGCGTCGACCAAAGGTCCA AGCGTGTTTCCGCTGGCTCCGAGCAGCAAAAGCACCAGCGGCGGCACGGCTGCCCTGGGCTGC CTGGTTAAAGATTATTTCCCGGAACCAGTCACCGTGAGCTGGAACAGCGGGGCGCTGACCAGC GGCGTGCATACCTTTCCGGCGGTGCTGCAAAGCAGCGGCCTGTATAGCCTGAGCAGCGTTGTG ACCGTGCCGAGCAGCAGCTTAGGCACTCAGACCTATATTTGCAACGTGAACCATAAACCGAGC AACACCAAAGTGGATAAAAAAGTGGAACCGAAAAGC |
| SEQ ID NO: 137 | VL Germlined | SYELTQPLSVSVALGQTARITCGGDNIGSKYVHWYQQKPGQAPVLVIYNDSNRPSGIPERFSG SNSGNTATLTISRAQAGDEADYYCQAWGDNGTRVFGGGTKLTVL |
| SEQ ID NO: 138 | VH Germlined | EVQLLESGGGLVQPGGLSLRSCAASGFTFSSYGMSWVRQAPGKGLEWVSNISNDGHYTYYADS VKGRFTISRDNSKNTLYLQMNSLEAEDTAVYYCARFQASYLDIMDYWGQGTLVTVSS |
| SEQ ID NO: 139 | DNA<br>VL Germlined | AGCTATGAACTGACCCAGCCGCTGAGTGTTAGCGTTGCGCTGGGTCAGACCGCGCGTATTACC TGCGGCGGTGATAACATTGGCAGCAAATATGTGCATTGGTATCAGCAGAAACCGGGCCAGGCG CCGGTGCTGGTGATTTATAACGATAGCAACCGTCCGAGCGGCATTCCGGAACGTTTTAGCGGC AGCAACAGCGGCAATACCGCGACCCTGACCATTAGCCGTGCGCAGGCGGGTGATGAAGCGGAT TATTATTGCCAGGCGTGGGGCGATAATGGTACGCGTGTGTTTGGCGGTGGTACGAAGTTAACC GTTCTT |
| SEQ ID NO: 140 | DNA<br>VH Germlined | GAGGTGCAATTGCTGGAAAGCGGCGGCGGCCTGGTGCAACCGGGCGGCAGCCTGCGTCTGAGC TGCGCGGCCTCCGGATTTACCTTTTCTTCTTATGGTATGTCTTGGGTGCGCCAAGCCCCTGGG AAGGGTCTCGAGTGGGTGAGCAATATTTCTAATGATGGTCATTATACTTATTATGCTGATTCT GTTAAGGGTCGTTTTACCATTTCACGTGATAATTCGAAAAACACCCTGTATCTGCAAATGAAC AGCCTGCGTGCGGAAGATACGGCCGTGTATTATTGCGCGCGTTTTCAGGCTTCTTATCTTGAT ATTATGGATTATTGGGGCCAAGGCACCCTGGTGACGGTTAGCTCA |
| Biparatopic construction MOR06475 | | |
| SEQ ID NO: 141 | DNA VL-<br>(GGGGS)3-VH<br>scFv | Gatatcgttctgacccagagtccggcaaccctgagcctgagtccgggtgaacgtgccaccctg agctgtcgtgcaagccagtttattggtagccgttatctggcatggtatcagcagaaaccgggt caggcaccgcgtctgctgatttatggtgcaagcaatcgtgcaaccggtgttccggcacgtttt agcggtagcggtagtggcaccgattttaccctgaccattagcagcctggaaccggaagatttt gcaacctattattgccagcagtattatgattatccgcagacctttggtcagggcaccaaggtg gaaattaaaggtggtggtggtagcggtggtggtggctcaggtggtggcggtagtcaggttcaa ttgaaagaaagcggtccggcactggttaaaccgacccagaccctgaccctgacatgtaccttt agcggttttagcctgagcaatcgtggtggtggtgttggttggattcgtcagcctccgggtaaa gcactggaatggctggcatggattgattgggatgatgataaaagctatgcaccagcctgaaaa cccgtctgaccattagtaaagataccagcaaaaatcaggtggttctgaccatgaccaatatgg atccggttgataccgccacctattattgtgcacgtatgcatctgccgctggtttttgatagct ggggtcagggtacactagttaccgttagcagc |

TABLE 1-continued

Examples of LRP6 Antibodies of the Present Invention

| SEQ ID NUMBER | Ab region | Sequence |
| --- | --- | --- |
| SEQ ID NO: 142 | VL-(GGGGS)3-VH scFv | DIVLTQSPATLSLSPGERATLSCRASQFIGSRYLAWYQQKPGQAPRLLIYGASNRATGVPARF<br>SGSGSGTDFTLTISSLEPEDFATYYCQQYYDYPQTFGQGTKVEIKGGGGSGGGGSGGGGSQVQ<br>LKESGPALVKPTQTLTLTCTFSGFSLSNRGGGVGWIRQPPGKALEWLAWIDWDDDKSYSTSLK<br>TRTISKDTSKNQVVLTMTNMDPVDTATYYCARMHLPLVFDSWGQGTLVTVSS |
| SEQ ID NO: 143 | DNA VL-(GGGGS)4-VH scFv | Gatatcgtgctgacacagagccctgccaccctgtctctgagccctggcgagagagccaccctg<br>agctgccgggccagccagttcatcggctcccgctacctggcctggtatcagcagaagcccgga<br>caggctcccagactgctgatctacggcgccagcaacagagctaccggcgtgcccgccagattt<br>tctggcagcggcagcggcaccgacttcaccctgaccatcagcagcctggaacccgaggacttc<br>gccacctactactgccagcagtactacgactacccccagaccttcggccagggcaccaaggtg<br>gagatcaagggcggaggcggatccgggggtggcggaagtggaggcggaggaagcggagggggc<br>ggaagccaggtgcaattgaaagagtccggccctgccctggtgaagcctacccagaccctgacc<br>ctgacatgcaccttcagcggcttcagcctgagcaacagaggcggcggagtgggctggatcaga<br>cagcctcccggcaaggccctggaatggctggcctggatcgactgggacgacgacaagagctac<br>agcaccagcctgaaaacccggctgaccatctccaaggacaccagcaagaaccaggtggtgctc<br>accatgaccaacatggaccccgtggacaccgccacctattattgcgcccggatgcatctgccc<br>ctggtgttcgatagctggggccagggaaccctggtgacagtgtccagc |
| SEQ ID NO: 144 | VL-(GGGGS)4-VH scFc | DIVLTQSPATLSLSPGEERATLSCRASQFIGSRYLAWYQQKPGQAPRLLIYGASNRATGVPAR<br>FSGSGSGTDFTLTISSLEPEDFATYYCQQYYDYPQTFGQGTKVEIKGGGGSGGGGSGGGGSGG<br>GGSQVQLKESGPALVKPTQTLTLTCTFSGFSLSNRGGGVGWIRQPPGKALEWLAWIDWDDDKS<br>YSYSLKTRLTISKDTSKNQVVLTMTNMDPVDTATYYCARMHLPLVFDSWGQGTLVTVSS |
| SEQ ID NO: 145 | DNA VH-(GGGGS)3-VL scFv | Caggttcaattgaaagaaagcggtccggcactggttaaaccgacccagaccctgaccctgaca<br>tgtacctttagcggttttagcctgagcaatcgtggtggtggtgttggttggattcgtcagcct<br>ccgggtaaagcactggaatggctggcatggattgattgggatgatgataaaagctatagcacc<br>agcctgaaaacccgtctgaccattagcaaagataccagcaaaaatcaggttgttctgaccatg<br>accaatatggatccggttgataccgcaacctattattgtgcacgtatgcatctgccgctggtt<br>tttgatagctggggtcagggtacactagttaccgttagcagcggtggtggtggtagcggtggt<br>ggcggttcaggtggtggtggcagtgatatcgttctgacccagagtccggcaaccctgagcctg<br>agtccgggtgaacgtgccaccctgagctgtcgtgcaagccagtttattggtagccgttatctg<br>gcatggtatcagtcagaaaccgggtcaggcaccgcgtctgctgatttatggtgcaagcaatcg<br>tgcaaccggtgttccggcacgttttagcggtagcggtagtggcaccgattttaccctgaccat<br>tagtagcctggaaccggaagattttgccacctattattgccagcagtattatgattatccgca<br>gacctttggtcagggcaccaaggtggaaattaaa |
| SEQ ID NO: 146 | VH-(GGGGS)3-VL scFv | QVQLKESGPALVKPTQTLTLTCTFSGFSLSNRGGGVGWIRQPPGKALEWLAWIDWDDDKSYST<br>SLKTRLTISKDTSKNQVVLTMTNMDPVDTATYYCARMHLPLVFDSWGQGTLVTVSSGGGGSGG<br>GGSGGGGSDIVLTQSPATLSLSPGERATLSCRASQFIGSRYLAWYQQKPGQAPRLLIYGASNR<br>ATGVPARFSGSGSGTDFTLTISSLEPEDFATYYCQQYYDYPQTFGQGTKVEIK |
| SEQ ID NO: 147 | DNA VH-(GGGGS)4-VL scFv | Caggttcaattgaaagaaagcggtccggcactggttaaaccgacccagaccctgaccctgaca<br>tgtacctttagcggttttagcctgagcaatcgtggtggtggtgttggttggattcgtcagcct<br>ccgggtaaagcactggaatggctggcatggattgattgggatgatgataaaagctatagcacc<br>agcctgaaaacccgtctgaccattagcaaagataccagcaaaaatcaggttgttctgaccatg<br>accaatatggatccggttgataccgcaacctattattgtgcacgtatgcatctgccgctggtt<br>tttgatagctggggtcagggtacactagttaccgttagcagcggtggtggtggtagcggtggt<br>ggcggttcaggtggtggtggcagtggcggtggtggtagtgatatcgttctgacccagagtccg<br>gcaaccctgagcctgagtccgggtgaacgtgccaccctgagctgtcgtgcaagccagtttatt<br>ggtagccgttatctggcatggtatcagcagaaaccgggtcaggcaccgcgtctgctgatttat<br>ggtgcaagcaatcgtgcaaccggtgttccggcacgttttagcggtagcggtagtggcaccgat<br>tttaccctgaccattagtagcctggaaccggaagattttgccacctattattgccagcagtat<br>tatgattatccgcagacctttggtcagggcaccaaggtggaaattaaa |
| SEQ ID NO: 148 | VH-(GGGGS)4-VL scFv | QVQLKESGPALVKPTQTLTLTCTFSGFSLSNRGGGVGWIRQPPGKALEWLAWIDWDDDKSYST<br>SLKTRLTISKDTSKNQVVLTMTNMDPVDTATYYCARMHLPLVFDSWGQGTLVTVSSGGGGSGG<br>GGSGGGGSGGGGSDIVLTQSPATLSLSPGERATLSCRASQFIGSRYLAWYQQKPGQAPRLLIY<br>GASNRATGVPARFSGSGSGTDFTLTISSLEPEDFATYYCQQYYDYPQTFGQGTKVEIK |
| MOR08168 | | |
| SEQ ID NO: 149 | DNA VL-(GGGGS)3-VH scFv | Gatatcgaactgacccagcctccgagcgttagcgttgcaccgggtcagaccgcacgtattagc<br>tgtagcggtgatagcctgcgtaataaagtttattggtatcagcagaaaccgggtcaggcaccg<br>gttctggttatttataaaaaataatcgtccgagcggtattccggaacgttttagcggtagcaa<br>tagcggtaataccgcaaccctgaccattagcggcacccaggcagaagatgaagcagattatta<br>ttgccagagctatgatggtcagaaaagcctggttttttggtggtggcaccaagcttaccgttct<br>gggtggtggtggtagcggtggtggtggctcaggtggtggcggttctcaggttcaattggttga<br>aagtggtggtggtctggttcagcctggtggtagcctgcgtctgagctgtgcagcaagcggttt<br>tacctttagcgattatgtgattaattgggttcgccaggcaccgggtaaaggtctggaatgggt<br>tagcggtattagctggtcaggtgttaatacccattatgcagatagcgtgaaaggtcgttttac<br>cattagccgtgataatagcaaaaataccctgtatctgcagatgaatagcctgcgtgcagaaga<br>taccgcagtttattattgtgcacgtctgggtgcaaccgcaaataatattcgctataaatttat<br>ggatgtgtggggtcagggtacactagttaccgttagcagc |
| SEQ ID NO: 150 | VL-(GGGGS)3-VH scFv | DIELTQPPSVSVAPGQTARISCSGDSLRNKVYWYQQKPGQAPVLVIYKNNRPSGIPERFSGSN<br>SGNTATLTISGTQAEDEADYYCQSYDGQKSLVFGGGTKLTVLGGGGSGGGGSGGGGSQVQLVE |

TABLE 1-continued

Examples of LRP6 Antibodies of the Present Invention

| SEQ ID NUMBER | Ab region | Sequence |
|---|---|---|
| | | SGGGLVQPGGSLRLSCAASGFTFSDYVINWVRQAPGKGLEWVSGISWSGVNTHYADSVKGRFT<br>ISRDNSKNTLYLQMNSLRAEDTAVYYCARLGATANNIRYKFMDYWGQGTLVTVSS |
| SEQ ID NO: 151 | DNA VL-(GGGGS)4-VH scFv | Gatatcgaactgacccagcctccgagcgttagcgttgcaccgggtcagaccgcacgtattagc<br>tgtagcggtgatagcctgcgtaataaagtttattggtatcagcagaaaccgggtcaggcaccg<br>gttctggttatttataaaaataatcgtccgagcggtattccggaacgttttagcggtagcaat<br>agcggtaataccgcaaccctgaccattagcggcacccaggcagaagatgaagcagattattat<br>tgccagagctatgatggtcagaaaagcctggttttggtggtggcaccaagcttaccgttctgg<br>gtggtggtggtagcggtggtggtggctcaggtggtggcggttctggtggcggtggttcacagg<br>ttcaattggttgaaagtggtggtggtctggttcagcctggtggtagcctgcgtctgagctgtg<br>cagcaagcggttttacctttagcgattatgtgattaattgggttcgccaggcaccgggtaaag<br>gtctggaatgggttagcggtattagctggtcaggtgttaatacccattatgcagatagcgtga<br>aaggtcgttttaccattagccgtgataatagcaaaaataccctgtatctgcagatgaatagcc<br>tgcgtgcagaagataccgcagtttattattgtgcacgtctgggtgcaaccgcaaataatattc<br>gctataaatttatggatgtgtggggtcagggtacactagttaccgttagcagc |
| SEQ ID NO: 152 | VL-(GGGGS)4-VH scFv | DIELTQPPSVSVAPGQTARISCSGDSLRNKVYWYQQKPGQAPVLVIYKNNRPSGIPERFSGSN<br>SGNTATLTISGTQAEDEADYYCQSYDGQKSLVFGGGTKLTVLGGGGSGGGGSGGGGSGGGGSQ<br>VQLVESGGGLVQPGGSLRLSCAASGFTFSDYVINWVRQAPGKGLEWVSGISWSGVNTHYADSV<br>KGRFTISRDNSKNTLYLQMNSLRAEDTAVYYCARLGATANNIRYKFMDVWGQGTLVTVSS |
| SEQ ID NO: 153 | DNA VH-(GGGGS)3-VL | Caggttcaattggttgaaagcggtggtggtctggttcagcctggtggtagcctgcgtctgagc<br>tgtgcagcaagcggttttacctttagcgattatgtgattaattgggttcgtcaggcaccgggt<br>aaaggtctggaatgggttagcggtattagctggtcaggtgttaatacccattatgcagatagc<br>gtgaaaggtcgttttaccattagccgtgataatagcaaaaataccctgtatctgcagatgaat<br>agcctgcgtgcagaagataccgcagtttattattgtgcacgtctgggtgcaaccgcaaataat<br>attcgctataaatttatggatgtgtggggtcagggtacactagttaccgttagcagtggtggt<br>ggtggtagcggtggtggcggatctggtggcggtggcagtgatatcgaactgacccagcctccg<br>agcgttagcgttgcaccgggtcagaccgcacgtattagctgtagcggtgatagtctgcgtaat<br>aaagtttattggtatcagcagaaaccgggtcaggctccggttctggttatttataaaaataat<br>cgtccgagcggtattccggaacgttttagcggtagcaatagcggtaataccgcaaccctgacc<br>attagcggcacccaggcagaagatgaagccgattattattgtcagagctatgatggtcagaaa<br>agcctggtttttggtggtggcaccaagcttaccgttcta |
| SEQ ID NO: 154 | VH-(GGGGS)3-VL scFv | QVQLVESGGGLVQPGGSLRLSCAASGFTFSDYVINWVRQAPGKLGEWVSGISWSGVNTHYADS<br>VKGRFTISRDNSKNTLYLQMNSLRAEDTAVYYCARLGATANNIRYKFMDVWGQGTLVTVSSGG<br>GGSGGGGSGGGGSDIELTQPPSVSVAPGQTARISCSGDSLRNKVYWYQQKPGQAPVLVIYKNN<br>RPSGIPERFSGSNSGNTATLTISGTQAEDEADYYCQSYDGQKSLVFGGGTKLTVL |
| SEQ ID NO: 155 | DNA VH-(GGGGS)4-VL scFv | Caggttcaattggttgaaagcggtggtggtctggttcagcctggtggtagcctgcgtctgagc<br>tgtgcagcaagcggttttacctttagcgattaggtgattaattgggttcgtcaggcaccgggt<br>aaaggtctggaatgggttagcggtattagctggtcaggtgttaatacccattatgcagatagc<br>gtgaaaggtcgttttaccattagccgtgataatagcaaaaataccctgtatctgcagatgaat<br>agcctgcgtgcagaagataccgcagtttattattgtgcacgtctgggtgcaaccgcaaataat<br>attcgctataaatttatggatgtgtggggtcagggtacactagttaccgttagcagtggtggt<br>ggtggtagcggtggtggcggatctggtggcggtggttcaggtggtggtggcagtgatatcgaa<br>ctgacccagcctccgagcgttagcgttgcaccgggtcagaccgcacgtattagctgtagcggt<br>gatagtctgcgtaataaagtttattggtatcagcagaaaccgggtcaggctccggttctggtt<br>atttataaaaataatcgtccgagcggtattccggaacgttttagcggtagcaatagcggtaat<br>accgcaaccctgaccattagcggcacccaggcagaagatgaagccgattattattgtcagagc<br>tatgatggtcagaaaagcctggtttttggtggtggcaccaagcttaccgttctg |
| SEQ ID NO: 156 | VH-(GGGGS)4-VL scFv | QVQLVESGGGLVQPGGSLRLSCAASGFTFSDYVINWVRQAPGKGLEWVSGISWSGVNTHYADS<br>VKGRFTISRDNSKNTLYLQMNSLRAEDTAVYYCARLGATANNIRYKFMDVWGQGTLVTVSSGG<br>GGSGGGGSGGGGSGGGGSDIELTQPPSVSVAPGQTARISCSGDSLRNKVYWYQQKPGQAPVLV<br>IYKNNRPSGIPERFSGSNSGNTATLTISGTQAEDEADYYCQSYDGQKSLVFGGGTKLTVL |
| MOR08545 | | |
| SEQ ID NO: 157 | DNA VL-(GGGGS)3-VH scFv | Gatatcgaactgacccagcctccgagcgttagcgttgcaccgggtcagaccgcacgtattagc<br>tgtagcggtgataatattggcagcaaatatgtgcattggtatcagcagaaaccgggtcaggca<br>ccggttctggttatttatggtgatagcaatcgtccgagcggtattccggaacgttttagcggt<br>agcaatagcggtaataccgcaaccctgaccattagcggcacccaggcagaagatgaagcagat<br>tattattgtacccgtaccagcaccccgattagcggtgtttttggtggtggcaccaagcttacc<br>gttctgggtggtggtggtagcggtggtggtggctcaggtggtggtggttcacaggttcaattg<br>gttgaaagtggtggtggtctggttcagcctggtggtagcctgcgtctgagctgtgcagcaagc<br>ggttttacctttagcgttaatggtatgcattgggttcgccaggcaccgggtaaaggtctggaa<br>tgggttagcgttattgatggtatgggccatacctattatgccgatagcgttaaaggtcgtttt<br>accattagccgtgataatagcaaaaataccctgtatctgcagatgaatagcctgcgtgcagaa<br>gataccgcagtttattattgcgcacgctatgattatattaaatatggtgcctttgatccgtg<br>gggtcagggtacactagttaccgttagcagc |
| SEQ ID NO: 158 | VL-(GGGGS)3-VH scFv | DIELTQPPSVSVAPGQTARISCSGDNIGSKYVHWYQQKPGQAPVLVIYGDSNRPSGIPERFSG<br>SNGSNTATLTISGTQAEDEADYYCTRTSTPISGVFGGGTKLTVLGGGGSGGGGSGGGGSQVQL<br>VESGGGLVQPGGLSRLSCAASGFTFSVNGMHWVRQAPGKGLEWVSVIDGMGHTYYADSVKGRF<br>TISRDNSKNTLYLQMNSLRAEDTAVYYCARYDYIKYGAFDPWGQGTLVTVSS |

TABLE 1-continued

Examples of LRP6 Antibodies of the Present Invention

| SEQ ID NUMBER | Ab region | Sequence |
|---|---|---|
| SEQ ID NO: 159 | DNA VL-(GGGGS)4-VH scFv | Gatatcgaactgacccagcctccgagcgttagcgttgcaccgggtcagaccgcacgtattagc tgtagcggtgataatattggcagcaaatatgtgcattggtatcagcagaaaccgggtcaggca ccggttctggttatttatggtgatagcaatcgtccgagcggtattccggaacgttttagcggt agcaatagcggtaataccgcaaccctgaccattagcggcacccaggcagaagatgaagcagat tattattgtacccgtaccagcaccccgattagcggtgtttttggtggtggcaccaagcttacc gttctgggtggtggtggtagcggtggtggtggctcaggtggtggcggttctggtggcggtggt tcacaggttcaattggttgaaagtggtggtggtctggttcagcctggtggtagcctgcgtctg agctgtgcagcaagcggttttacctttagcgttaatggtatgcattgggttcgccaggcaccg ggtaaaggtctggaatgggttagcgttattgatggtatgggccatacctattatgccgatagc gttaaaggtcgttttaccattagccgtgataatagcaaaaataccctgtatctgcagatgaat agcctgcgtgcagaagataccgcagtttattattgcgcacgctatgattatattaaatatggt gcctttgatccgtggggtcagggtacactagttaccgttagcagc |
| SEQ ID NO: 160 | VL-(GGGGS)4-VH scFv | DIELTQPPSVSVAPGQTARISCSGDINIGSKYVHWYQQKPGQAPVLVIYGDSNRPSGIPERFS GSNSGNTATLTISGTQAEDEADYYCTRTSTPISGVFGGGTKLTVLGGGGSGGGGSGGGGSGGG GSQVQLVESGGGLVQPGGSLRLSCAASGFTFSVNGMHWVRQAPGKGLEWVSVIDGMGHTYYAD SVKGRFTISRDNSKNTLYLQMNSLRAEDTAVYYCARYKYIKYGAFDPWGQGTLVTVSS |
| SEQ ID NO: 161 | DNA VH-(GGGGS)3-VL | Caggttcaattggttgaaagcggtggtggtctggttcagcctggtggtagcctgcgtctgagc tgtgcagcaagcggttttacctttagcgttaatggtatgcattgggttcgtcaggcaccgggt aaaggtctggaatgggttagcgttattgatggtatgggccatacctattatgccgatagcgtt aaaggtcgttttaccattagccgtgataatagcaaaaataccctgtatctgcagatgaatagc ctgcgtgcagaagataccgcagtttattattgtgcccgttatgattatattaaatatggtgcc tttgatccgtggggtcagggtacactagttaccgttagcagtggtggtggtggtagcggtggt ggcggatctggtggcggtggttcagatatcgaactgacccagcctccgagcgttagcgttgca ccgggtcagaccgcacgtattagctgtagcggtgataatattggcagcaaatatgtgcattgg tatcagcagaaaccgggtcaggctccggttctggttatttatggtgatagcaatcgtccgagc ggtattccggaacgttttagcggtagcaatagcggtaataccgcaaccctgaccattagcggc acccaggcagaagatgaagccgattattattgcacccgtaccagcaccccgattagcggtgtt tttggtggtggcaccaagcttaccgttctg |
| SEQ ID NO: 162 | VH-(GGGGS)3-VL scFv | QVQLVESGGGLVQPGGSLRLSCAASGFTFSVNGMHWVRQAPGKGLEWVSIDGMGHTYYADSVK GRFTISRDNSKNTLYLQMNSLRAEDTAVYYCARDYIKYGAFDPQGQGTLVTVSSGGGGSGGGG SGGGGSDIELTQPPSVSVAPGQTARISCSGNIGSKYVHWYQQKPGQAPVLVIYGDSNRPSGIP ERFSGSNSGNTATLTISGTQAEDESDYYCTRTSTPISGVFGGGTKLTVL |
| SEQ ID NO: 163 | DNA VH-(GGGGS)4-VL scFv | Caggttcaattggttgaaagcggtggtggtctggttcagcctggtggtagcctgcgtctgagc tgtgcagcaagcggttttacctttagcgttaatggtatgcattgggttcgtcaggcaccgggt aaaggtctggaatgggttagcgttattgatggtatgggccatacctattatgccgatagcgtt aaaggtcgttttaccattagccgtgataatagcaaaaataccctgtatctgcagatgaatagc ctgcgtgcagaagataccgcagtttattattgtgcccgttatgattatattaaatatggtgcc tttgatccgtggggtcagggtacactagttaccgttagcagtggtggtggtggtagcggtggt ggcggatctggtggcggtggttcaggtggtggtggcagtgatatcgaactgacccagcctccg agcgttagcgttgcaccgggtcagaccgcacgtattagctgtagcggtgataatattggcagc aaatatgtgcattggtatcagcagaaaccgggtcaggctccggttctggttatttatggtgat agcaatcgtccgagcggtattccggaacgttttagcggtagcaatagcggtaataccgcaacc ctgaccattagcggcacccaggcagaagatgaagccgattattattgcacccgtaccagcacc ccgattagcggtgtttttggtggtggcaccaagcttaccgttctg |
| SEQ ID NO: 164 | VH-(GGGGS)4-VL scFv | QVQLVESGGGLVQPGGSLRLSCAASGFTFSVNGMHWVRQAPGKGLEWVSVIDGMGHTYYADSV KGRFTISRDNSKNTLYLQMNSLRAEDTAVYYCARYDYIKYGAFDPWGQGTLVTVSSGGGGSGG GGSGGGGSGGGGSDIELTQPPSVSVAPGQTARISCSGDNIGSKYVHWYQQKPGQAPVLVIYGD SNRPSGIPERSGSNSGNTATLTISGTQAEDEADYYCTRTSTPISGVFGGGTKLTVL |
| Biparatopic MOR08168/ MOR06475 | | |
| SEQ ID NO: 165 | DNA Heavy MOR08168 hlgG1 LALA MOR06475 scFv | caggtgcaattgtcgagtctggcggaggactggtgcagcctggtggcagcctgagactgagct gcgccgccagcggcttcaccttcagcgactacgtgatcaactgggtgcgacaggcccctggaa agggcctggaatgggtgtccggcatctcttggtctggcgtgaacacccactacgccgacagcg tgaagggccggttcaccatcagccgggacaacagcaagaacaccctgtacctgcagatgaaca gcctgagagccgaggacaccgccgtgtactactgtgccagactgggcgccaccgccaacaaca tccggtacaagttcatggacgtgtggggccagggcacactggtgaccgtcagctcagctagca ccaagggccccagcgtgttccccctggcccccagcagcaagagcaccagcggcggcacagccg ccctgggctgcctggtgaaggactacttccccgagcccgtgaccgtgtcctggaacagcggag ccctgacctccggcgtgcacaccttccccgccgtgctgcagagcagcggcctgtacagcctgt ccagcgtggtgacagtgcccagcagcagcctgggcacccagacctacatctgcaacgtgaacc acaagcccagcaacaccaaggtggacaagagagtggagcccaagagctgcgacaagacccaca cctgccccccctgcccagccccagaggcagcgggcggaccctccgtgttcctgttccccccca agcccaaggacaccctgatgatcagcaggacccccgaggtgacctgcgtggtggtggacgtga gccacgaggacccagaggtgaagttcaactggtacgtggacggcgtggaggtgcacaacgcca agaccaagcccagagaggagcagtacaacagcacctacagggtggtgtccgtgctgaccgtgc tgcaccaggactggctgaacggcaaggaatacaagtgcaaggtctccaacaaggccctgccag cccccatcgaaaagaccatcagcaaggccaagggccagccacgggagccccaggtgtacaccc |

TABLE 1-continued

| Examples of LRP6 Antibodies of the Present Invention | | |
|---|---|---|
| SEQ ID NUMBER | Ab region | Sequence |
| | | tgccccccctcccgggaggagatgaccaagaaccaggtgtccctgacctgtctggtgaagggct<br>tctaccccagcgacatcgccgtggagtgggagagcaacggccagcccgagaacaactacaaga<br>ccacccccccagtgctggacagcgacggcagcttcttcctgtacagcaagctgaccgtggaca<br>agtccaggtggcagcagggcaacgtgttcagctgcagcgtgatgcacgaagcgctgcacaacc<br>actacacccagaagagcctgagcctgtcccccggcaagggcggctccggcggaagcgatattc<br>gtgctgacacagagccctgccaccctgtctctgagccctggcgagagagccaccctgagctgc<br>cgggccagccagttcatcggctcccgctacctggcctggtatcagcagaagcccggacaggct<br>cccagactgctgatctacggcgccagcaacagagctaccggcgtgcccgccagattttctggc<br>agcggcagcggcaccgacttcaccctgaccatcagcagcctggaacccgaggacttcgccacc<br>tactactgccagcagtactacgactacccccagaccttcggccagggcaccaaggtggagatc<br>aagggcggaggcggatccgggggtggcggaagtggaggcggaggaagcggagggggcggaagc<br>caggtgcaattgaaagagtccggccctgccctggtgaagcctacccagaccctgaccctgaca<br>tgcaccttcaggcggcttcagcctgagcaacagaggcggcggagtgggctggatcagacagcc<br>tcccggcaaggccctggaatggctggcctggatcgactgggacgacgacaagagctacagcac<br>cagcctgaaaacccggctgaccatctccaaggacaccagcaagaaccaggtggtgctcaccat<br>gaccaacatggaccccgtggacaccgccacctattattgcgcccggatgcatctgcccctggt<br>gttcgatagctggggccagggaaccctggtgacagtgtccagc |
| SEQ ID NO: 166 | Heavy<br>MDR01868<br>hlgG1 LALA<br>MDR06475<br>scFv | QVQLVESGGGLVQPGGSLRLSCAASGFTFSDYVINWVRQAPGKGLEWVSGISWSGVNTHYADS<br>VKGRFTISRDNSKNTLYLQMNSLRAEDTAVYYCARLGATANNIRYKFMDVWGQGTLVTVSSAS<br>TKGPSVFPLAPSSKSTSGGTAALGCLVKDYFPEPVTVSWNSGALTSGVHTFPAVLQSSGLYSL<br>SSVVTVPSSSLGTQTYICNVNHKPSNTKVDKRVEPKSCDKTHTCPPCPAPEAAGGPSVFLFPP<br>KPKDTLMISRTPEVTCVVVDVSHEDPEVKFNWYDGVEVHNAKTKPREEQYNSTYRVVSVLTVL<br>QDWLNGKEYKCKVSNKALPAPIEKTISKAKGQPREPQVYTLPPSREEMTKNQVSLTCLVKGFY<br>PSDIAVEWESNGQPENNYKTTPPVLDSDGSFFLYSKLTVDKSRWQQGNVFSCSVMHEALHNHY<br>TQKSLSLSPGKGGSGGSDIVLTQSPATLSLSPGERATLSCRASQFIGSRYLAWYQQKPGQAPR<br>LLIYGASNRATGVPARFSGSGSGTDFTLTISSLEPEDFATYYCQQYYDYPQTFGQGTKVEIKG<br>GGGSGGGGSGGGGSGGGGSQVQLKESGPALVKPTQTLTLTCTFSGFSLSLNRGGGVGWIRQPP<br>GKALEWLAWIDWDDDKSYSTSLKTRLTISKDTSKNQVVLTMTNMDPVDTATYYCARMHLPLVF<br>DSWGQGTLVTVSS |
| SEQ ID NO: 167 | VL MDR08168 | DIELTQPPSVSVAPGQTARISCSGDSLRNKVYWYQQKPGQAPVLVIYKNNRPSGIPERFSGSN<br>SGNTATLTISGTQAEDEADYYCQSVDGQKSLVFGGGTKLTVL |
| SEQ ID NO: 168 | DNA VL<br>MOR08168 | GACATCGAGCTGACCCAGCCCCCTTCTGTGTCTGTGGCCCCTGGCCAGACCGCCAGAATCAGC<br>TGCAGCGGCGACAGCCTGCGGAACAAGGTGTACTGGTATCAGCAGAAGCCCGGCCAGGCTCCC<br>GTGCTGGTGATCTACAAGAACAACCGGCCCAGCGGCATCCCTGAGCGGTTCAGCGGCAGCAAC<br>AGCGGCAATACCGCCACCCTGACCATCAGCGGCACCCAGGCCGAAGATGAGGCCGACTACTAC<br>TGCCAGAGCTACGACGGCCAGAAAAGCCTGGTGTTCGGCGGAGGCACCAAGCTTACCGTGCTG |
| SEQ ID NO: 169 | DNA Light<br>lambda<br>MOR08168 | Gacatcgagctgacccagccccccttctgtgtctgtggcccctggccagaccgccagaatcagc<br>tgcagcggcgacagcctgcggaacaaggtgtactggtatcagcagaagcccggccaggctccc<br>gtgctggtgatctacaagaacaaccggcccagcggcatccctgagcggttcagcggcagcaac<br>agcggcaataccgccaccctgaccatcagcggcacccaggccgaagatgaggccgactactac<br>tgccagagctacgacggccagaaaagcctggtgttcggcggaggcaccaagcttaccgtgctg<br>ggccagcccaaagccgcccctagcgtgaccctgttccccccccagcagcgaggaactgcaggcc<br>aacaaggccaccctggtctgcctgatcagcgacttctaccctggcggccgtgaccgtggcctg<br>gaaggccgacagcagccccgtgaaggccggcgtggagacaaccacccccagcaagcagagcaa<br>caacaagtacgccgccagcagctacctgagcctgacccccgagcagtggaagagccacagaag<br>ctacagctgccaggtcacccacgagggcagcaccgtggagaaaaccgtggcccccaccgagtg<br>cagc |
| SEQ ID NO: 170 | Light lambda<br>MOR08168 | DIELTQPPSVSVAPGQTARISCSGDSLRNKVYWYQQKPGQAPVLVIYKNNRPSGIPERFSGSN<br>SGNTATLTISGTQAEDEADYYCQSYDGQKSLVFGGGTKLTVLGQPKAAPSVLTFPPSSEELQA<br>NKATLVCLISDFYPGAVTVAWKADSSPVKAGVETTTPSKQSNNKYAASSYLSLTPEQWKSHRS<br>YSCQVTHEGSTVEKTVAPTECS |
| SEQ ID NO: 171 | Heavy<br>MOR08168<br>hlgG1 LALA<br>(w/o K)<br>MOR06475<br>scFv | QVQLVESGGGLVQPGGSLRLSCAASGFTFSDYVINWYRQAPGKGLEWVSGISWSGVNTHYADS<br>VKGRFTISRDNSKNTLYLQMNSLRAEDTAVYYCARLGATANNIRYKFMDVWGQGTLVTVSSAS<br>TKGPSCFPLAPSSKSTSGGTAALGCLVKDYFPEPVTVSWNSGALTSGVHTFPAVLQSSGLYSL<br>SSVVTVPSSSLGTQTYICNVNHKPSNTKVDKRVEPKSCDKTHTCPPCPAPEAAGGPSVFLFPP<br>KPKDTLMISRTPEVTCVVVDVSHEDPEVKFNWYVDGVEVHNAKTKPREEQYNSTYRVVSVLTV<br>LHQDWLNGKEYKCKVSNKALPAPIEKTISKAKGQPREPQVYTLPPSREEMTKNQVSLTCLVKG<br>FYPSDIAVEWESNGQPENNYKTTPPVLDSDGSFFLYSKLTVDKSRWQQGNVFSCSVMHEALHN<br>HYTQKSLSLSPGGGSGGSDIVLTQSPATLSLSPGERATLSCRASQFIGSRYLAWYQQKPGQAP<br>RLLIYGASNRATGVPARFSGSGSGTDFTLTISSLEPEDFATYYCQQYYDYPQTFGQGTKVEIK<br>GGGGSGGGGSGGGGSGGGGSQVQLKESGPALVKPTQTLTLTCTFSGFSLSNRGGGVGWIRQPP<br>GKALEWLAWIDWDDDKSYSTSLKTRLTISKDTSKNQVVLTMTNMDPVDTATYYCARMHLPLVF<br>DSWGQGTLVTVSS |
| SEQ ID NO: 172 | DNA Heavy<br>MDR08168<br>hlgG1 LALA<br>(w/o K)<br>MOR06475<br>scFv | CAGGTGCAATTGGTCGAGTCTGGCGGAGGACTGGTGCAGCCTGGTGGCAGCCTGAGACTGAGC<br>TGCGCCGCCAGCGGCTTCACCTTCAGCGACTACGTGATCAACTGGGTGCGACAGGCCCCTGGA<br>AAGGGCCTGGAATGGGTGTCCGGCATCTCTTGGTCTGGCGTGAACACCCACTACGCCGACAGC<br>GTGAAGGGCCGGTTCACCATCAGCCGGGACAACAGCAAGAACACCCTGTACCTGCAGATGAAC<br>AGCCTGAGAGCCGAGGACACCGCCGTGTACTACTGTGCCAGACTGGGCGCCACCGCCAACAAC<br>ATCCGGTACAAGTTCATGGACGTGTGGGGCCAGGGCACACTGGTGACCGTCAGCTCAGCTAGC |

TABLE 1-continued

Examples of LRP6 Antibodies of the Present Invention

| SEQ ID NUMBER | Ab region | Sequence |
|---|---|---|
| | | ACCAAGGGCCCCAGCGTGTTCCCCCTGGCCCCCAGCAGCAAGAGCACCAGCGGCGGCACAGCC<br>GCCCTGGGCTGCCTGGTGAAGGACTACTTCCCCGAGCCCGTGACCGTGTCCTGGAACAGCGGA<br>GCCCTGACCTCCGGCGTGCACACCTTCCCCGCCGTGCTGCAGAGCAGCGGCCTGTACAGCCTG<br>TCCAGCGTGGTGACAGTGCCCAGCAGCAGCCTGGGCACCCAGACCTACATCTGCAACGTGAAC<br>CACAAGCCCAGCAACACCAAGGTGGACAAGAGAGTGGAGCCCAAGAGCTGCGACAAGACCCAC<br>ACCTGCCCCCCCTGCCCAGCCCCAGAGGCAGCGGGCGGACCCTCCGTGTTCCTGTTCCCCCCC<br>AAGCCCAAGGACACCCTGATGATCAGCAGGACCCCCGAGGTGACCTGCGTGGTGGTGGACGTG<br>AGCCACGAGGACCCAGAGGTGAAGTTCAACTGGTACGTGGACGGCGTGGAGGTGCACAACGCC<br>AAGACCAAGCCCAGAGAGGAGCAGTACAACAGCACCTACAGGGTGGTGTCCGTGCTGACCGTG<br>CTGCACCAGGACTGGCTGAACGGCAAGGAATACAAGTGCAAGGTCTCCAACAAGGCCCTGCCA<br>GCCCCCATCGAAAAGACCATCAGCAAGGCCAAGGGCCAGCCACGGGAGCCCCAGGTGTACACC<br>CTGCCCCCCTCCCGGGAGGAGATGACCAAGAACCAGGTGTCCCTGACCTGTCTGGTGAAGGGC<br>TTCTACCCCAGCGACATCGCCGTGGAGTGGGAGAGCAACGGCCAGCCCGAGAACAACTACAAG<br>ACCACCCCCCCAGTGCTGGACAGCGACGGCAGCTTCTTCCTGTACAGCAAGCTGACCGTGGAC<br>AAGTCCAGGTGGCAGCAGGGCAACGTGTTCAGCTGCAGCGTGATGCACGAAGCGCTGCACAAC<br>CACTACACCCAGAAGAGCCTGAGCCTGTCCCCCGGCGGCGGCTCCGGCGGAAGCGATATCGTG<br>CTGACACAGAGCCCTGCCACCCTGTCTCTGAGCCCTGGCGAGAGAGCCACCCTGAGCTGCCGG<br>GCCAGCCAGTTCATCGGCTCCCGCTACCTGGCCTGGTATCAGCAGAAGCCCGGACAGGCTCCC<br>AGACTGCTGATCTACGGCGCCAGCAACAGAGCTACCGGCGTGCCCGCCAGATTTTCTGGCAGC<br>GGCAGCGGCACCGACTTCACCCTGACCATCAGCAGCCTGGAACCCGAGGACTTCGCCACCTAC<br>TACTGCCAGCAGTACTACGACTACCCCCAGACCTTCGGCCAGGGCACCAAGGTGGAGATCAAG<br>GGCGGAGGCGGATCCGGGGGTGGCGGAAGTGGAGGCGGAGGAAGCGGAGGGGGCGGAAGCCAG<br>GTGCAATTGAAAGAGTCCGGCCCTGCCCTGGTGAAGCCTACCCAGACCCTGACCCTGACATGC<br>ACCTTCAGCGGCTTCAGCCTGAGCAACAGAGGCGGCGGAGTGGGCTGGATCAGACAGCCTCCC<br>GGCAAGGCCCTGGAATGGCTGGCCTGGATCGACTGGGACGACGACAAGAGCTACAGCACCAGC<br>CTGAAAACCCGGCTGACCATCTCCAAGGACACCAGCAAGAACCAGGTGGTGCTCACCATGACC<br>AACATGGACCCCGTGGACACCGCCACCTATTATTGCGCCCGGATGCATCTGCCCCTGGTGTTC<br>GATAGCTGGGGCCAGGGAACCCTGGTGACAGTGTCCAGC |
| SEQ ID NO: 173 | Heavy<br>MDR08168<br>hlgG1 LALA<br>MDR06475<br>scFv<br>(DP to DA) | QVQLVESGGGLVQPGGSLRLSCAASGFTFSDYVINWVRQAPGKLGEWVSGISWSGVNTHYADS<br>VKGRFTISRDNSKNTLYLQMNSLRAEDTAVYYCARLGATANNIRYKFMDVWGQGTLVTVSSAS<br>TKGPSVFPLAPSSKSTSGGTAALGCLVKDYFPEPVTVSWNSGALTSGVHTFPAVLQSSGLYSL<br>SSVVTVPSSSLGTQTYICNVNHKPSNTKVDKRVEPKSCDKTHTCPPCPAPEAAGGPSVFLFPP<br>KPKDTLMISRTPEVTCVVVDVSHEDPEVKFNWYVDGVEVHNAKTKPREEQYNSTYRVVSVTLV<br>LHQDWLNGKEYKCKVSNKALPAPIEKTISKAKGQPREPQVYTLPPSREEMTKNQVSLTCLVKG<br>FYPSDIAVEWESNGQPENNYKTTPPVLDSDGSFFLYSKLTVDKSRWQQGNVFSCSVMHEALHN<br>HYTQSLSLSLPGKGGSGGSDIVLTQSPATLSLSPGERATLSCRASQFIGSRYLAWYQQKPGQA<br>PRLLIYGASNRATGVPARFSGSGSGTDFTLTISSLEPEDFATYYCQQYYDYPQTFGQGTKVEI<br>KGGGGSGGGGSGGGGSGGGGSQVQLKESGPALVKPTQTLTLTCTFSGFSLSNRGGGVGWIRQP<br>PGKALEWLAWIDWDDDKSYSTSLKTRLTISKDTSKNQVVLTMTNMDAVDTATYYCARMHLPLV<br>FDSWGQGTLVTVSS |
| SEQ ID NO: 174 | DNA Heavy<br>MOR08168<br>hlgG1 LALA<br>MDR06475<br>scFv<br>(DP to DA) | CAGGTGCAATTGGTCGAGTCTGGCGGAGGACTGGTGCAGCCTGGTGGCAGCCTGAGACTGAGC<br>TGCGCCGCCAGCGGCTTCACCTTCAGCGACTACGTGATCAACTGGGTGCGACAGGCCCCTGGA<br>AAGGGCCTGGAATGGGTGTCCGGCATCTCTTGGTCTGGCGTGAACACCCACTACGCCGACAGC<br>GTGAAGGGCCGGTTCACCATCAGCCGGGACAACAGCAAGAACACCCTGTACCTGCAGATGAAC<br>AGCCTGAGAGCCGAGGACACCGCCGTGTACTACTTGCCAGACTGGGCGCCACCGCCAACAACA<br>TCCGGTACAAGTTCATGGACGTGTGGGGCCAGGGCACACTGGTGACCGTCAGCTCAGCTAGCA<br>CCAAGGGCCCCAGCGTGTTCCCCCTGGCCCCCAGCAGCAAGAGCACCAGCGGCGGCACAGCCG<br>CCCTGGGCTGCCTGGTGAAGGACTACTTCCCCGAGCCCGTGACCGTGTCCTGGAACAGCGGAG<br>CCCTGACCTCCGGCGTGCACACCTTCCCCGCCGTGCTGCAGAGCAGCGGCCTGTACAGCCGTC<br>CAGCGTGGTGACAGTGCCCAGCAGCAGCCTGGGCACCCAGACCTACATCTGCAACGTGAACCA<br>CAAGCCCAGCAACACCAAGGTGGACAAGAGAGTGGAGCCCAAGAGCTGCGACAAGACCCACAC<br>CTGCCCCCCCTGCCCAGCCCCAGAGGCAGCGGGCGGACCCTCCGTGTTCCTGTTCCCCCCCAA<br>GCCCAAGGACACCCTGATGATCAGCAGGACCCCCGAGGTGACCTGCGTGGTGGTGGACGTGAG<br>CCACGAGGACCCAGAGGTGAAGTTCAACTGGTACGTGGACGGCGTGGAGGTGCACAACGCCAA<br>GACCAAGCCCAGAGAGGAGCAGTACAACAGCACCTACAGGGTGGTGTCCGTGCTGACCGTGCT<br>GCACCAGGACTGGCTGAACGGCAAGGAATACAAGTGCAAGGTCTCCAACAAGGCCCTGCCAGC<br>CCCCATCGAAAAGACCATCAGCAAGGCCAAGGGCCAGCCACGGGAGCCCCAGGTGTACACCCT<br>GCCCCCCTCCCGGGAGGAGATGACCAAGAACCAGGTGTCCCTGACCTGTCTGGTGAAGGGCTT<br>CTACCCCAGCGACATCGCCGTGGAGTGGGAGAGCAACGGCCAGCCCGAGAACAACTACAAGAC<br>CACCCCCCCAGTGCTGGACAGCGACGGCAGCTTCTTCCTGTACAGCAAGCTGACCGTGGACAA<br>GTCCAGGTGGCAGCAGGGCAACGTGTTCAGCTGCAGCGTGATGCACGAAGCGCTGCACAACCA<br>CTACACCCAGAAGAGCCTGAGCCTGTCCCCCGGCAAGGGCGGCTCCGGCGGAAGCGATATCGT<br>GCTGACACAGAGCCCTGCCACCCTGTCTCTGAGCCCTGGCGAGAGAGCCACCCTGAGCTGCCG<br>GGCCAGCCAGTTCATCGGCTCCCGCTACCTGGCCTGGTATCAGCAGAAGCCCGGACAGGCTCC<br>CAGACTGCTGATCTACGGCGCCAGCAACAGAGCTACCGGCGTGCCCGCCAGATTTTCTGGCAG<br>CGGCAGCGGCACCGACTTCACCCTGACCATCAGCAGCCTGGAACCCGAGGACTTCGCCACCTA<br>CTACTGCCAGCAGTACTACGACTACCCCCAGACCTTCGGCCAGGGCACCAAGGTGGAGATCAA<br>GGGCGGAGGCGGATCCGGGGGTGGCGGAAGTGGAGGCGGAGGAAGCGGAGGGGGCGGAAGCCA<br>GGTGCAATTGAAAGAGTCCGGCCCTGCCCTGGTGAAGCCTACCCAGACCCTGACCCTGACATG<br>CACCTTCAGCGGCTTCAGCCTGAGCAACAGAGGCGGCGGAGTGGGCTGGATCAGACAGCCTCC<br>CGGCAAGGCCCTGGAATGGCTGGCCTGGATCGACTGGGACGACAGACAAGAGCTACAGCACCA<br>GCCTGAAAACCCGGCTGACCATCTCCAAGGACACCAGCAAGAACCAGGTGGTGCTCACCATGA<br>CCAACATGGACGCCGTGGACACCGCCACCTATTATTGCGCCCGGATGCATCTGCCCCTGGTGT<br>TCGATAGCTGGGGCCAGGGAACCCTGGTGACAGTGTCCAGC |

TABLE 1-continued

Examples of LRP6 Antibodies of the Present Invention

| SEQ ID NUMBER | Ab region | Sequence |
|---|---|---|
| SEQ ID NO: 175 | Heavy<br>MOR08168<br>hlgG1 LALA<br>MOR06475<br>scFv<br>(DP to TA) | QVQLVESGGGLVQPGGSLRLSCAASGFTFSDVINWVRQAPGKGLEWVSGISWSGNTHYADSVK<br>GRFTISRDNSKNTLYLQMNSLRAEDTAVVYCARLGATANNIRYKFMDVWGQGTLVTVSSASTK<br>GPSVFPLAPSSKSTSGGTAALGCLVKDYFPEPVTVSWNSGALTSGVHTFPAVLQSSGLYSLSS<br>VVTVPSSSLGTQTYICNVNHKPSNTKVDKRVEPKSCDKTHTCPPCPAPEAAGGPSVFLFPPKP<br>KDTLMISRTPEVTCVVVDVSHEDPEVKFNWYVDGVEVHNAKTKPREEQYNSTYRVVSVLTVLH<br>QDWLNGKEYKCKVSNKALPAPIEKTISKAKGQPREPQVYTLPPSREEMTKNQVSLTCVKGFYP<br>SDIAVEWESNGQPENNYKTTPPVLDSDGSFFLYSKLTVDKSRWQQGNVFSCSVMHEALHNHYT<br>QKSLSLSPGKGGSGGSDIVLTQSPATLSLSPGERATLSCRASQFIGSRYLAWYQQKPGQAPRL<br>LIYGASNRATGVPARFSGSGSGTDFTLTISSLEPEDFATYYCQQYYDYPQTFGQGTKVEIKGG<br>GGSGGGGSGGGGSGGGGSQVQLKESGPALVKPTQTLTLTCTFSGFSLSNRGGGVGWIRQPPGK<br>ALEWLAWIDWDDDKSYSTSLKTRLTISKDTSKNQVVLTMTNMTAVDTATYYCARMHLPLVFDS<br>WGQGTLVIVSS |
| SEQ ID NO: 176 | DNA Heavy<br>MOR08168<br>hlgG1 LALA<br>MOR06475<br>scFv<br>(DP to TA) | CAGGTGCAATTGGTCGAGTCTGGCGGAGGACTGGTGCAGCCTGGTGGCAGCCTGAGACTGAGC<br>TGCGCCGCCAGCGGCTTCACCTTCAGCGACTACGTGATCAACTGGGTGCGACAGGCCCCTGGA<br>AAGGGCCTGGAATGGGTGTCCGGCATCTCTTGGTCTGGCGTGAACACCCACTACGCCGACAGC<br>GTGAAGGGCCGGTTCACCATCAGCCGGGACAACAGCAAGAACACCCTGTACCTGCAGATGAAC<br>AGCCTGAGAGCCGAGGACACCGCCGTGTACTACTGTGCCAGACTGGGCGCCACCGCCAACAAC<br>ATCCGGTACAAGTTCATGGACGTGTGGGGCCAGGGCACACTGGTGACCGTCAGCTCAGCTAGC<br>ACCAAGGGCCCCAGCGTGTTCCCCCTGGCCCCCAGCAGCAAGAGCACCAGCGGCGGCACAGCC<br>GCCCTGGGCTGCCTGGTGAAGGACTACTTCCCCGAGCCCGTGACCGTGTCCTGGAACAGCGGA<br>GCCCTGACCTCCGGCGTGCACACCTTCCCCGCCGTGCTGCAGAGCAGCGGCCTGTACAGCCTG<br>TCCAGCGTGGTGACAGTGCCCAGCAGCAGCCTGGGCACCCAGACCTACATCTGCAACGTGAAC<br>CACAAGCCCAGCAACACCAAGGTGGACAAGAGAGTGGAGCCCAAGAGCTGCGACAAGACCCAC<br>ACCTGCCCCCCCTGCCCAGCCCCAGAGGCAGCGGGCGGACCCTCCGTGTTCCTGTTCCCCCCC<br>AAGCCCAAGGACACCCTGATGATCAGCAGGACCCCCGAGGTGACCTGCGTGGTGGTGGACGTG<br>AGCCACGAGGACCCAGAGGTGAAGTTCAACTGGTACGTGGACGGCGTGGAGGTGCACAACGCC<br>AAGACCAAGCCCAGAGAGGAGCAGTACAACAGCACCTACAGGGTGGTGTCCGTGCTGACCGTG<br>CTGCACCAGGACTGGCTGAACGGCAAGGAATACAAGTGCAAGGTCTCCAACAAGGCCCTGCCA<br>GCCCCCATCGAAAAGACCATCAGCAAGGCCAAGGGCCAGCCACGGGAGCCCCAGGTGTACACC<br>CTGCCCCCCTCCCGGGAGGAGATGACCAAGAACCAGGTGTCCCTGACCTGTCTGGTGAAGGGC<br>TTCTACCCCAGCGACATCGCCGTGGAGTGGGAGAGCAACGGCCAGCCCGAGAACAACTACAAG<br>ACCACCCCCCCAGTGCTGGACAGCGACGGCAGCTTCTTCCTGTACAGCAAGCTGACCGTGGAC<br>AAGTCCAGGTGGCAGCAGGGCAACGTGTTCAGCTGCAGCGTGATGCACGAAGCGCTGCACAAC<br>CACTACACCCAGAAGAGCCTGAGCCTGTCCCCCGGCAAGGGCGGCTCCGGCGGAAGCGATATC<br>GTGCTGACACAGAGCCCTGCCACCCTGTCTCTGAGCCCTGGCGAGAGAGCCACCCTGAGCTGC<br>CGGGCCAGCCAGTTCATCGGCTCCCGCTACCTGGCCTGGTATCAGCAGAAGCCCGGACAGGCT<br>CCCAGACTGCTGATCTACGGCGCCAGCAACAGAGCTACCGGCGTGCCCGCCAGATTTTCTGGC<br>AGCGGCAGCGGCACCGACTTCACCCTGACCATCAGCAGCCTGGAACCCGAGGACTTCGCCACC<br>TACTACTGCCAGCAGTACTACGACTACCCCCAGACCTTCGGCCAGGGCACCAAGGTGGAGATC<br>AAGGGCGGAGGCGGATCCGGGGGTGGCGGAAGTGGAGGCGGAGGAAGCGGAGGGGGCGGAAGC<br>CAGGTGCAATTGAAAGAGTCCGGCCCTGCCCTGGTGAAGCCTACCCAGACCCTGACCCTGACA<br>TGCACCTTCAGCGGCTTCAGCCTGAGCAACAGAGGCGGCGGAGTGGGCTGGATCAGACAGCCT<br>CCCGGCAAGGCCCTGGAATGGCTGGCCTGGATCGACTGGGACGACGACAAGAGCTACAGCACC<br>AGCCTGAAAACCCGGCTGACCATCTCCAAGGACACCAGCAAGAACCAGGTGGTGCTCACCATG<br>ACCAACATGACCGCCGTGGACACCGCCACCTATTATTGCGCCCGGATGCATCTGCCCCTGGTG<br>TTCGATAGCTGGGGCCAGGGAACCCTGGTGACAGTGTCCAGC |
| SEQ ID NO: 177 | Light<br>MOR06475<br>scFv<br>MOR08168<br>lambda | DIVLTQSPATLSLSPGERATLSCRASQFIGSRYLAWYQQKPGQAPRLLIYGASNRATGVPARF<br>SGSGSGTDFTLTISSLEPEDFATYYCQQYYDYPQTFGQGTKVEIKGGGGSGGGGSGGGGSGGG<br>GSQVQLKESGPALVKPTQTLTLTCTFSGFSLSNRGGGVGWIRQPPGKALEWLAWIDWDDDKSY<br>STSLKTRLTISKDTSKNQVVLTMTNMDPVDTATYYCARMHLPLVFDSWGQGTLVTVSSGGSGG<br>SDIELTQPPSVSVAPGQTARISCSGDSLRNKVYWYQQKPGQAPVLVIYKNNRPSGIPERFSGS<br>NSGNTATLTISGTQAEDEADYYCQSYDGQKSLVFGGGTKLTVLGQPKAAPSVTLFPPSSEELQ<br>ANKATLVCLISDFYPGAVTVAWKADSSPVKAGVETTTPSKQSNNKYAASSYLSLTPEQWKSHR<br>SYSCQVTHEGSTVEKTVAPTECS |
| SEQ ID NO: 178 | DNA Light<br>MOR06475<br>scFv<br>MOR08168<br>lambda | GATATCGTGCTGACACAGAGCCCTGCCACCCTGTCTCTGAGCCCTGGCGAGAGAGCCACCCTG<br>AGCTGCCGGGCCAGCCAGTTCATCGGCTCCCGCTACCTGGCCTGGTATCAGCAGAAGCCCGGA<br>CAGGCTCCCAGACTGCTGATCTACGGCGCCAGCAACAGAGCTACCGGCGTGCCCGCCAGATTT<br>TCTGGCAGCGGCAGCGGCACCGACTTCACCCTGACCATCAGCAGCCTGGAACCCGAGGACTTC<br>GCCACCTACTACTGCCAGCAGTACTACGACTACCCCCAGACCTTCGGCCAGGGCACCAAGGTG<br>GAGATCAAGGGCGGAGGCGGATCCGGGGGTGGCGGAAGTGGAGGCGGAGGAAGCGGAGGGGGC<br>GGAAGCCAGGTGCAATTGAAAGAGTCCGGCCCTGCCCTGGTGAAGCCTACCCAGACCCTGACC<br>CTGACATGCACCTTCAGCGGCTTCAGCCTGAGCAACAGAGGCGGCGGAGTGGGCTGGATCAGA<br>CAGCCTCCCGGCAAGGCCCTGGAATGGCTGGCCTGGATCGACTGGGACGACGACAAGAGCTAC<br>AGCACCAGCCTGAAAACCCGGCTGACCATCTCCAAGGACACCAGCAAGAACCAGGTGGTGCTC<br>ACCATGACCAACATGGACCCCGTGGACACCGCCACCTATTATTGCGCCCGGATGCATCTGCCC<br>CTGGTGTTCGATAGCTGGGGCCAGGGAACCCTGGTGACAGTGTCCAGCGGCGGCTCCGGCGGA<br>AGCGACATCGAGCTGACCCAGCCCCCTTCTGTGTCTGTGGCGCCCGGGCAGACCGCCAGAATC<br>AGCTGCAGCGGCGACAGCCTGCGGAACAAGGTGTACTGGTATCAGCAGAAGCCCGGCCAGGCT<br>CCCGTGCTGGTGATCTACAAGAACAACCGGCCCAGCGGCATCCCTGAGCGGTTCAGCGGCAGC<br>AACAGCGGCAATACCGCCACCCTGACCATCAGCGGCACCCAGGCCGAAGATGAGGCCGACTAC<br>TACTGCCAGAGCTACGACGGCCAGAAAAGCCTGGTGTTCGGCGGAGGCACCAAGCTTACCGTG<br>CTGGGCCAGCCCAAAGCCGCCCCTAGCGTGACCCTGTTCCCCCCCAGCAGCGAGGAACTGCAG |

TABLE 1-continued

Examples of LRP6 Antibodies of the Present Invention

| SEQ ID NUMBER | Ab region | Sequence |
|---|---|---|
| | | GCCAACAAGGCCACCCTGGTCTGCCTGATCAGCGACTTCTACCCTGGCGCCGTGACCGTGGCC<br>TGGAAGGCCGACAGCAGCCCCGTGAAGGCCGGCGTGGAGACAACCACCCCCAGCAAGCAGAGC<br>AACAACAAGTACGCCGCCAGCAGCTACCTGAGCCTGACCCCCGAGCAGTGGAAGAGCCACAGA<br>AGCTACAGCTGCCAGGTCACCCACGAGGGCAGCACCGTGGAGAAAACCGTGGCCCCCACCGAG<br>TGCAGC |
| SEQ ID NO: 179 | VH<br>MDR08168 | QVQLVESGGGLVQPGGSLRLSCAASGFTFSDYVINWVRQAPGKGLEWVSGISWSGVNTHYADS<br>VKGRFTISRDNSKNTLYLQMNSLRAEDTAVYYCARLGATANNIRYKFMDVWGQGTLVTVSS |
| SEQ ID NO: 180 | DNA VH<br>MDR08168 | Caggtgcaattggtcgagtctggcggaggactggtgcagcctggtggcagcctgagactgagc<br>tgcgccgccagcggcttcaccttcagcgactacgtgatcaactgggtgcgacaggcccctgga<br>aagggcctggaatgggtgtccggcatctcttggtctggcgtgaacacccactacgccgacagc<br>gtgaagggccggttcaccatcagccgggacaacagcaagaacaccctgtacctgcagatgaac<br>agcctgagagccgaggacaccgccgtgtactactgtgccagactgggcgccaccgccaacaac<br>atccggtacaagttcatggacgtgtggggccagggcacactggtgaccgtcagctca |
| SEQ ID NO: 181 | Heavy<br>MDR08168<br>hlgG1 LALA | QVQLVESGGGLVQPGGSLRLSCAASGFTFSDYVINWVRQAPGKGLEWVSGISWSGVNTHYADS<br>VKGRFTISRDNSKNTLYLQMNSLRAEDTAVYYCARLGATANNIRVKFMDVWGQGTLVTVSSAS<br>TKGPSVFPLAPSSKSTSGGTAALGCLVKDYFPEPVTVSWNSGALTSGVHTFPAVLQSSGLYSL<br>SSVVTVPSSSLGTQTYICNVNHKPSNTKVDKRVEPKSCDKTHTCPPCPAPEAAGGPSVFLFPP<br>KPKDTLMISRTPEVTCVVVDVSHEDPEVKFNWYVDGVEVHNAKTKPREEQYNSTYRVVSVLTV<br>LHQDWLNGKEYKCKVSNKALPAPIEKTISKAKGQPREPQVYTLPPSREEMTKNQVSLTCLVKG<br>FYPSDIAVEWESNGQPENNYKTTPPVLDSDGSFFLYSKLTVDKSRWQQGNVFSCSVMHEALHN<br>HYTQSLSLSLPGK |
| SEQ ID NO: 182 | DNA Heavy<br>MDR08168<br>hlgG1 LALA | CAGGTGCAATTGGTCGAGTCTGGCGGAGGACTGGTGCAGCCTGGTGGCAGCCTGAGACTGAGC<br>TGCGCCGCCAGCGGCTTCACCTTCAGCGACTACGTGATCAACTGGGTGCGACAGGCCCCTGGA<br>AAGGGCCTGGAATGGGTGTCCGGCATCTCTTGGTCTGGCGTGAACACCCACTACGCCGACAGC<br>GTGAAGGGCCGGTTCACCATCAGCCGGGACAACAGCAAGAACACCCTGTACCTGCAGATGAAC<br>AGCCTGAGAGCCGAGGACACCGCCGTGTACTACTGTGCCAGACTGGGCGCCACCGCCAACAAC<br>ATCCGGTACAAGTTCATGGACGTGTGGGGCCAGGGCACACTGGTGACCGTCAGCTCAGCTAGC<br>ACCAAGGGCCCCAGCGTGTTCCCCCTGGCCCCCAGCAGCAAGAGCACCAGCGGCGGCACAGCC<br>GCCCTGGGCTGCCTGGTGAAGGACTACTTCCCCGAGCCCGTGACCGTGTCCTGGAACAGCGGA<br>GCCCTGACCTCCGGCGTGCACACCTTCCCCGCCGTGCTGCAGAGCAGCGGCCTGTACAGCCTG<br>TCCAGCGTGGTGACAGTGCCCAGCAGCAGCCTGGGCACCCAGACCTACATCTGCAACGTGAAC<br>CACAAGCCCAGCAACACCAAGGTGGACAAGAGAGTGGAGCCCAAGAGCTGCGACAAGACCCAC<br>ACCTGCCCCCCCTGCCCAGCCCCAGAGGCAGCGGGCGGACCCTCCGTGTTCCTGTTCCCCCCC<br>AAGCCCAAGGACACCCTGATGATCAGCAGGACCCCCGAGGTGACCTGCGTGGTGGTGGACGTG<br>AGCCACGAGGACCCAGAGGTGAAGTTCAACTGGTACGTGGACGGCGTGGAGGTGCACAACGCC<br>AAGACCAAGCCCAGAGAGGAGCAGTACAACAGCACCTACAGGGTGGTGTCCGTGCTGACCGTG<br>CTGCACCAGGACTGGCTGAACGGCAAGGAATACAAGTGCAAGGTCTCCAACAAGGCCCTGCCA<br>GCCCCCATCGAAAAGACCATCAGCAAGGCCAAGGGCCAGCCACGGGAGCCCCAGGTGTACACC<br>CTGCCCCCCTCCCGGGAGGAGATGACCAAGAACCAGGTGTCCCTGACCTGTCTGGTGAAGGGC<br>TTCTACCCCAGCGACATCGCCGTGGAGTGGGAGAGCAACGGCCAGCCCGAGAACAACTACAAG<br>ACCACCCCCCCAGTGCTGGACAGCGACGGCAGCTTCTTCCTGTACAGCAAGCTGACCGTGGAC<br>AAGTCCAGGTGGCAGCAGGGCAACGTGTTCAGCTGCAGCGTGATGCACGAGGCCCTGCACAAC<br>CACTACACCCAGAAGAGCCTGAGCCTGTCCCCCGGCAAG |
| SEQ ID NO: 183 | VL<br>MOR06475 | DIVLTQSPATLSLSPGERATLSCRASQFIGSRYLAWYQQKPGQAPRLLIYGASNRATGVPARF<br>SGSGSGTDFTLTISSLEPEDFATYYCQQYYDYPQTFGQGTKVEIK |
| SEQ ID NO: 184 | DNA VL<br>MOR06475 | Gatatcgtgctgacccagagcccggcgaccctgagcctgtctccgggcgaacgtgcgaccctg<br>agctgcagagcgagccagtttattggttctcgttatctggcttggtaccagcagaaaccaggt<br>caagcaccgcgtctattaatttatggtgcttctaatcgtgcaactggggtcccggcgcgtttt<br>agcggctctggatccggcacggattttaccctgaccattagcagcctggaacctgaagacttt<br>gcgacttattattgccagcagtattatgattatcctcagacctttggccagggtacgaaagtt<br>gaaattaaa |
| SEQ ID NO: 185 | Light<br>MDR06475<br>kappa | DIVLTQSPATLSLSPGERATLSCRASQFIGSRYLAWYQQKPGQAPRLLIYGASNRATGVPARF<br>SGSGSGTDFTLTISSLEPEDFATYYCQQYYDYPQTFGQGTKVEIKRTVAAPSVFIFPPSDEQL<br>KSGTASVVCLLNNFYPREAKVQWKVDNALQSGNSQESVTEQDSKDSTYSLSSTLTLSKADYEK<br>HKVYACEVTHQGLSSPVTKSFNRGEC |
| SEQ ID NO: 186 | DNA Light<br>MDR06475<br>kappa | GATATCGTGCTGACCCAGAGCCCGGCGACCCTGAGCCTGTCTCCGGGCGAACGTGCGACCCTG<br>AGCTGCAGAGCGAGCCAGTTTATTGGTTCTCGTTATCTGGCTTGGTACCAGCAGAAACCAGGT<br>CAAGCACCGCGTCTATTAATTTATGGTGCTTCTAATCGTGCAACTGGGGTCCCGGCGCGTTTT<br>AGCGGCTCTGGATCCGGCACGGATTTTACCCTGACCATTAGCAGCCTGGAACCTGAAGACTTT<br>GCGACTTATTATTGCCAGCAGTATTATGATTATCCTCAGACCTTTGGCCAGGGTACGAAAGTT<br>GAAATTAAACGTACGGTGGCCGCTCCCAGCGTGTTCATCTTCCCCCCCAGCGACGAGCAGCTG<br>AAGAGCGGCACCGCCAGCGTGGTGTGCCTGCTGAACAACTTCTACCCCCGGGAGGCCAAGGTG<br>CAGTGGAAGGTGGACAACGCCCTGCAGAGCGGCAACAGCCAGGAGAGCGTCACCGAGCAGGAC<br>AGCAAGGACTCCACCTACAGCCTGAGCAGCACCCTGACCCTGAGCAAGGCCGACTACGAGAAG<br>CATAAGGTGTACGCCTGCGAGGTGACCCACCAGGGCCTGTCCAGCCCCGTGACCAAGAGCTTC<br>AACAGGGGCGAGTGC |

TABLE 1-continued

| Examples of LRP6 Antibodies of the Present Invention | | |
|---|---|---|
| SEQ ID NUMBER | Ab region | Sequence |
| SEQ ID NO: 187 | Heavy<br>MOR06475<br>hlgG1LALA<br>MOR08168<br>scFv<br>(VH-3-VL) | QVQLKESGPALVKPTQTLTLTCTFSGFSLSNRGGGVGWIRQPPGKALEWLAWIDWDDDKSYST<br>SLKTRLTISKDTSKNQVVLTMTNMDPVDTATYYCARMHLPLVFDSWGQGTLVTVSSASTKGPS<br>VFPLAPSSKSTSGGTAALGCLVKDYFPEPVTVSWNSGALTSGVHTFPAVLQSSGLYSLSSVVT<br>VPSSSLGTQTYICNVNHKPSNTKVDKRVEPKSCDKTHTCPPCPAPEAAGGPSVFLFPPKPKDT<br>LMISRTPEVTCVVVDVSHEDPEVKFNWYVDGVEVHNAKTKPREEQYNSTYRVVSVLTVLHQDW<br>LNGKEYKCKVSNKALPAPIEKTISKAKGQPREPQVYTLPPSREEMTKNQVSLTCLVKGFYPSD<br>IAVEWESNGQPENNYKTTPPVLDSDGSFFLYSKLTVDKSRWQQGNVFSCSVMHEALHNHYTQK<br>SLSLSPGKGGSGGSQVQLVESGGGLVQPGGSLRLSCAASGFTFSDYINWVRQAPGKGLEWVSG<br>ISWSGVNTHYADSVKGRFTISRDNSKNTLYLQMNSLRAEDTAVYYCARLGATANNIRYKFMDV<br>WGQGTLVTVSSGGGGSGGGGSGGGGSDIELTQPPSVSVAPGQTARISCSGDSLRNKVYWYQQK<br>PGQAPVLVIYKNNRPSGIPERFSGSNSGNTATLTISGTQAEDEADYYCQYSYDGQKSLVFGGG<br>TKLTVL |
| SEQ ID NO: 188 | DNA Heavy<br>MOR06475<br>hlgG1LALA<br>MOR08168<br>scFv<br>(VH-3-VL) | CAGGTGCAATTGAAAGAAAGCGGCCCGGCCCTGGTGAAACCGACCCAAACCCTGACCCTGACC<br>TGTACCTTTTCCGGATTTAGCCTGTCTAATCGTGGTGGTGGTGTGGGTTGGATCGCCAGCCGC<br>CTGGGAAAGCCCTCGAGTGGCTGGCTTGGATCGATTGGGATGATGATAAGTCTTATAGCACCA<br>GCCTGAAAACGCGTCTGACCATTAGCAAAGATACTTCGAAAAATCAGGTGGTGCTGACTATGA<br>CCAACATGGACCCGGTGGATACGGCCACCTATTATTGCGCGCGTATGCATCTTCCTCTTGTTT<br>TTGATTCTTGGGGCCAAGGCACCCTGGTGACGGTTAGCTCAGCTAGCACCAAGGGCCCCAGCG<br>TGTTCCCCCTGGCCCCCAGCAGCAAGAGCACCAGCGGCGGCACAGCCGCCCTGGGCTGCCTGG<br>TGAAGGACTACTTCCCCGAGCCCGTGACCGTGTCCTGGAACAGCGGAGCCCTGACCTCCGGCG<br>TGCACACCTTCCCCGCCGTGCTGCAGAGCAGCGGCCTGTACAGCCTGTCCAGCGTGGTGACAG<br>TGCCCAGCAGCAGCCTGGGCACCCAGACCTACATCTGCAACGTGAACCACAAGCCCAGCAACA<br>CCAAGGTGGACAAGAGAGTGGAGCCCAAGAGCTGCGACAAGACCCACACCTGCCCCCCCTGCC<br>CAGCCCCAGAGGCAGCGGGCGGACCCTCCGTGTTCCTGTTCCCCCCCAAGCCCAAGGACACCC<br>TGATGATCAGCAGGACCCCCGAGGTGACCTGCGTGGTGGTGGACGTGAGCCACGAGGACCCAG<br>AGGTGAAGTTCAACTGGTACGTGGACGGCGTGGAGGTGCACAACGCCAAGACCAAGCCCAGAG<br>AGGAGCAGTACAACAGCACCTACAGGGTGGTGTCCGTGCTGACCGTGCTGCACCAGGACTGGC<br>TGAACGGCAAGGAATACAAGTGCAAGGTCTCCAACAAGGCCCTGCCAGCCCCCATCGAAAAGA<br>CCATCAGCAAGGCCAAGGGCCAGCCACGGGAGCCCCAGGTGTACACCCTGCCCCCCTCCCGGG<br>AGGAGATGACCAAGAACCAGGTGTCCCTGACCTGTCTGGTGAAGGGCTTCTACCCCAGCGACA<br>TCGCCGTGGAGTGGGAGAGCAACGGCCAGCCCGAGAACAACTACAAGACCACCCCCCCAGTGC<br>TGGACAGCGACGGCAGCTTCTTCCTGTACAGCAAGCTGACCGTGGACAAGTCCAGGTGGCAGC<br>AGGGCAACGTGTTCAGCTGCAGCGTGATGCACGAAGCGCTGCACAACCACTACACCCAGAAGA<br>GCCTGAGCCTGTCCCCCGGCAAGGGCGGCTCCGGCGGAAGCCAGGTTCAATTGGTTGAAAGCG<br>GTGGTGGTCTGGTTCAGCCTGGTGGTAGCCTGCGTCTGAGCTGTGCAGCAAGCGGTTTTACCT<br>TTAGCGATTATGTGATTAATTGGGTTCGTCAGGCACCGGGTAAAGGTCTGGAATGGGTTAGCG<br>GTATTAGCTGGTCAGGTGTTAATACCCATTATGCAGATAGCGTGAAAGGTCGTTTTACCATTA<br>GCCGTGATAATAGCAAAAATACCCTGTATCTGCAGATGAATAGCCTGCGTGCAGAAGATACCG<br>CAGTTTATTATTGTGCACGTCTGGGTGCAACCGCAAATAATATTCGCTATAAATTTATGGATG<br>TGTGGGGTCAGGGTACACTAGTTACCGTTAGCAGTGGTGGTGGTGGTAGCGGTGGTGGCGGAT<br>CTGGTGGCGGTGGCAGTGATATCGAACTGACCCAGCCTCCGAGCGTTAGCGTTGCACCGGGTC<br>AGACCGCACGTATTAGCTGTAGCGGTGATAGTCTGCGTAATAAAGTTTATTGGTATCAGCAGA<br>AACCGGGTCAGGCTCCGGTTCTGGTTATTTATAAAAATAATCGTCCGAGCGGTATTCCGGAAC<br>GTTTTAGCGGTAGCAATAGCGGTAATACCGCAACCCTGACCATTAGCGGCACCCAGGCAGAAG<br>ATGAAGCCGATTATTATTGTCAGAGCTATGATGGTCAGAAAAGCCTGGTTTTTGGTGGTGGCA<br>CCAAGCTTACCGTTCTG |
| SEQ ID NO: 189 | Heavy<br>MOR06475<br>hlgG1 LALA<br>MOR08168<br>scFv<br>(VH-4-VL) | QVQLKESGPALVKPTQTLTLTCTFSGFSLSNRGGGVGWIRQPPGKALEWLAWIDWDDDKSYST<br>SLKTRLTISKDTSKNQVVLTMTNMDPVDTATYYCARMHLPLVFDSWGQGTLVTVSSASTKGPS<br>VFPLAPSSKSTSGGTAALGCLVKDYFPEPVTVSWNSGALTSGVHTFPAVLQSSGLYSLSSVVT<br>VPSSSLGTQTYICNVNHKPSNTKVDKRVEPKSCDKTHTCPPCPAPEAAGGPSVFLFPPKPKDT<br>LMISRTPEVTCVVVDVSHEDPEVKFNWYVDGVEVHNAKTKPREEQYNSTYRVVSVLTVLHQDW<br>LNGKEYKCKVSNKALPAPIEKTISKAKGQPREPQVYTLPPSREEMTKNQVSLTCLVKGFYPSD<br>IAVEWESNGQPENNYKTTPPVLDSDGSFFLYSKLTVDKSRWGGGNVFSCSVMHEALHNHYTQK<br>SLSLSPGKGGSGGSQVQLVESGGGLVQPGGSLRLSCAASGFTFSDYVINWVRQAPGKGLEWVS<br>GISWSGVNTHYADSVKGRFTISRDNSKNTLYLQMNSLRAEDTAVYYCARLGATANNIRYKFMD<br>VWGQGTLVTVSSGGGGSGGGGSGGGGSGGGGSDIELTQPPSVSVAPGQTARISCSGDSLRNKV<br>YWYQQKPGQAPVLVIYKNNRPSGIPERFSGSNSGNTATLTISGTQAEDEADYYCQSYDGQKSL<br>VFGGGTKLTVL |
| SEQ ID NO: 190 | DNA Heavy<br>MOR06475<br>hlgG1 LALA<br>MOR08168<br>scFv<br>(VH-4-VL) | CAGGTGCAATTGAAAGAAAGCGGCCCGGCCCTGGTGAAACCGACCCAAACCCTGACCCTACCT<br>GTACCTTTTCCGGATTTAGCCTGTCTAATCGTGGTGGTGGTGTGGGTTGGATTCGCCAGCCGC<br>CTGGGAAAGCCCTCGAGTGGCTGGCTTGGATCGATTGGGATGATGATAAGTCTTATAGCACCA<br>GCCTGAAAACGCGTCTGACCATTAGCAAAGATACTTCGAAAAATCAGGTGGTGCTGACTATGA<br>CCAACATGGACCCGGTGGATACGGCCACCTATTATTGCGCGCGTATGCATCTTCCTCTTGTTT<br>TTGATTCTTGGGGCCAAGGCACCCTGGTGACGGTTAGCTCAGCTAGCACCAAGGGCCCCAGCG<br>TGTTCCCCCTGGCCCCCAGCAGCAAGAGCACCAGCAGGCGGCACAGCCGCCCTGGGCTGCCTG<br>GTGAAGGACTACTTCCCCGAGCCCGTGACCGTGTCCTGGAACAGCGGAGCCCTGACCTCCGGC<br>GTGCACACCTTCCCCGCCGTGCTGCAGAGCAGCGGCCTGTACAGCCTGTCCAGCGTGGTGACA<br>GTGCCCAGCAGCAGCCTGGGCACCCAGACCTACATCTGCAACGTGAACCACAAGCCCAGCAAC<br>ACCAAGGTGGACAAGAGAGTGGAGCCCAAGAGCTGCGACAAGACCCACACCTGCCCCCCCTGC<br>CCAGCCCCAGAGGCAGCGGGCGGACCCTCCGTGTTCCTGTTCCCCCCCAAGCCCAAGGACACC<br>CTGATGATCAGCAGGACCCCCGAGGTGACCTGCGTGGTGGTGGACGTGAGCCACGAGGACCCA<br>GAGGTGAAGTTCAACTGGTACGTGGACGGCGTGGAGGTGCACAACGCCAAGACCAAGCCCAGA |

TABLE 1-continued

Examples of LRP6 Antibodies of the Present Invention

| SEQ ID NUMBER | Ab region | Sequence |
|---|---|---|
| | | GAGGAGCAGTACAACAGCACCTACAGGGTGGTGTCCGTGCTGACCGTGCTGCACCAGGACTGG CTGAACGGCAAGGAATACAAGTGCAAGGTCTCCAACAAGGCCCTGCCAGCCCCCATCGAAAAG ACCATCAGCAAGGCCAAGGGCCAGCCACGGGAGCCCCAGGTGTACACCCTGCCCCCCTCCCGG GAGGAGATGACCAAGAACCAGGTGTCCCTGACCTGTCTGGTGAAGGGCTTCTACCCCAGCGAC ATCGCCGTGGAGTGGGAGAGCAACGGCCAGCCCGAGAACAACTACAAGACCACCCCCCCAGTG CTGGACAGCGACGGCAGCTTCTTCCTGTACAGCAAGCTGACCGTGGACAAGTCCAGGTGGCAG CAGGGCAACGTGTTCAGCTGCAGCGTGATGCACGAAGCGCTGCACAACCACTACACCCAGAAG AGCCTGAGCCTGTCCCCCGGCAAGGGCGGCTCCGGCGGAAGCCAGGTTCAATTGGTTGAAAGC GGTGGTGGTCTGGTTCAGCCTGGTGGTAGCCTGCGTCTGAGCTGTGCAGCAAGCGGTTTTACC TTTAGCGATTATGTGATTAATTGGGTTCGTCAGGCACCGGGTAAAGGTCTGGAATGGGTTAGC GGTATTAGCTGGTCAGGTGTTAATACCCATTATGCAGATAGCGTGAAAGGTCGTTTTACCATT AGCCGTGATAATAGCAAAAATACCCTGTATCTGCAGATGAATAGCCTGCGTGCAGAAGATACC GCAGTTTATTATTGTGCACGTCTGGGTGCAACCGCAAATAATATTCGCTATAAATTTATGGAT GTGTGGGGTCAGGGTACACTAGTTACCGTTAGCAGTGGTGGTGGTGGTAGCGGTGGTGGCGGA TCTGGTGGCGGTGGTTCAGGTGGTGGTGGCAGTGATATCGAACTGACCCAGCCTCCGAGCGTT AGCGTTGCACCGGGTCAGACCGCACGTATTAGCTGTAGCGGTGATAGTCTGCGTAATAAAGTT TATTGGTATCAGCAGAAACCGGGTCAGGCTCCGGTTCTGGTTATTTATAAAAATAATCGTCCG AGCGGTATTCCGGAACGTTTTAGCGGTAGCAATAGCGGTAATACCGCAACCCTGACCATTAGC GGCACCCAGGCAGAAGATGAAGCCGATTATTATTGTCAGAGCTATGATGGTCAGAAAAGCCTG GTTTTTGGTGGTGGCACCAAGCTTACCGTTCTG |
| SEQ ID NO: 191 | VL MDR08168 wt | DIELTQPPSVSVAPGQTARISCSGDSLRNKVYWYQQKPGQAPVLVIYKNNRPSGIPERFSGSN SGNTATLTISGTQAEDEADYYCQSYDGQKSLVFGGGTKLTVL |
| SEQ ID NO: 192 | DNA VL MOR08186 wt | GACATCGAGCTGACTCAGCCCCCTAGCGTGTCAGTGGCTCCTGGCCAGACCGCTAGAATTAGC TGTAGCGGCGATAGCCTGCGTAACAAGGTCTACTGGTATCAGCAGAAGCCCGGCCAGGCCCCT GTGCTGGTCATCTATAAGAACAATAGGCCTAGCGGCATCCCCGAGCGGTTTAGCGGCTCTAAT AGCGGCAACACCGCTACCCTGACTATTAGCGGCACTCAGGCCGAGGACGAGGCCGACTACTAC TGTCAGTCCTACGACGGCCAGAAGTCACTGGTCTTTGGCGGCGGAACTAAGCTGACCGTGCTG |
| SEQ ID NO: 193 | Light lambda MDR08168 wt | DIELTQPPSVSVAPGQTARISCSGDSLRNKVYWYQQKPGQAPVLVIYKNNRPSGIPERFGSNS GNTATLTISGTQAEDEADYYCQSYDGQKSLVFGGGTKLTVLGQPKAAPSVTLFPPSSEELQAN KATLVCLISDFYPGAVTVAWKADSSPVKAGVETTTPSKQSNNKYAASSYLSLTPEQWKSHRSY SCQVTHEGSTVEKTVAPTECS |
| SEQ ID NO: 194 | DNA Light lambda MOR08168 wt | GACATCGAGCTGACTCAGCCCCCTAGCGTGTCAGTGGCTCCTGGCCAGACCGCTAGAATTAGC TGTAGCGGCGATAGCCTGCGTAACAAGGTCTACTGGTATCAGCAGAAGCCCGGCCAGGCCCCT GTGCTGGTCATCTATAAGAACAATAGGCCTAGCGGCATCCCCGAGCGGTTTAGCGGCTCTAAT AGCGGCAACACCGCTACCCTGACTATTAGCGGCACTCAGGCCGAGGACGAGGCCGACTACTAC TGTCAGTCCTACGACGGCCAGAAGTCACTGGTCTTTGGCGGCGGAACTAAGCTGACCGTGCTG GGACAGCCTAAGGCTGCCCCCAGCGTGACCCTGTTCCCCCCCAGCAGCGAGGAGCTGCAGGCC AACAAGGCCACCCTGGTGTGCCTGATCAGCGACTTCTACCCAGGCGCCGTGACCGTGGCCTGG AAGGCCGACAGCAGCCCCGTGAAGGCCGGCGTGGAGACCACCACCCCCAGCAAGCAGAGCAAC AACAAGTACGCCGCCAGCAGCTACCTGAGCCTGACCCCCGAGCAGTGGAAGAGCCACAGGTCC TACAGCTGCCAGGTGACCCACGAGGGCAGCACCGTGGAAAAGACCGTGGCCCCAACCGAGTGC AGC |
| SEQ ID NO: 195 | Heavy MOR08168IgG 1LALA_6475sc Fv wt | QVQLVESGGGLVQPGGSLRLSCAASGFTFSDYVINIWVRQAPGKGLEWVSGISWSGVNTHYAD SVKGRFTISRDNSKNTLYLQMNSLRAEDTAVYYCARLGATANNIRYKFMDVWGQGTLVTVSSA STKGPSVFPLAPSSKSTSGGTAALGCLVKDYFPEPVTVSWNSGALTSGVHTFPAVLQSSGLYS LSSVVTVPSSSLGTQTYICNVNHKPSNTKVDKRVEPKSCDKTHTCPPCPAPEAAGGPSVFLFP PKPKDTLMISRTPEVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSREEMTKNQVSLTCLVK GFYPSDIAVEWESNGQPENNYKTTPPVLDSDGSFFLYSKLTVDKSRWQQGNVFSCSVMHEALH NHYTQKSLSLSPGKGGSGGSDIVLTQSPATLSLSPGERATLSCRASQFIGSRYLAWYQQKPGQ APRLLIYGASNRATGVPARFSGSGSGTDFTLTISSLEPEDFATYYCQQYYDYPQTFGQGTKVE IKGGGGSGGGGSGGGGSGGGGSQVQLKESGPALVKPTQTLTLTCTFSGFSLSNRGGGVGWIRQ PPGKALEWLAWIDWDDDKSYSTSLKTRLTISKDTSKNQVVLTMTNMDPVDTATYYCARMHLPL VFDSWGQGTLVTVSS |
| SEQ ID NO: 196 | DNA Heavy MOR08168IgG 1LALA_6475sc Fv wt | CAGGTGCAGCTGGTGGAATCAGGCGGAGGACTGGTCCAGCCTGGCGGATCACTTAGACTGAGC TGTGCCGCTAGTGGCTTCACCTTTTAGCGACTATGTGATTAACTGGGTCCGACAGGCCCCTGG CAAGGGACTGGAATGGGTGTCAGGCATTAGTTGGAGCGGCGTGAACACTCACTACGCCGATAG CGTGAAGGGCCGGTTCACTATTAGCCGGGATAACTCTAAGAACACCCTGTACCTGCAGATGAA TAGCCTGAGAGCCGAGGACACCGCCGTCTACTACTGCGCTAGACTGGGCGCTACCGCTAACAA CATCCGCTATAAGTTCATGGACGTGTGGGGCCAGGGCACCCTGGTCACAGTGTCTTCAGCTAG CACTAAGGGCCCCTCAGTGTTCCCCCTGGCCCCTAGCTCTAAGTCTACTAGCGGTGGCACCGC CGCTCTGGGCTGCCTGGTCAAGGACTACTTCCCCGAGCCCGTGACCGTGTCTTGGAATAGCGG CGCTCTGACTAGCGGAGTGCACACCTTCCCCGCCGTGCTGCAGTCTAGCGGCCTGTATAGCCT GTCTAGCGTCGTGACCGTGCCTAGCTCTAGCCTGGGCACTCAGACCTATATCTGTAACGTGAA CCACAAGCCTAGTAACACTAAGGTGGACAAGCGGGTGGAACCTAAGTCTTGCGATAAGACTCA CACCTGTCCCCCCTGCCCTGCCCCAGAAGCTGCTGGCGGACCTAGCGTGTTCCTGTTCCCACC TAAGCCTAAAGACACCCTGATGATTAGTAGGACCCCCGAAGTGACCTGCGTGGTGGTGGACGT CAGCCACGAGGACCCTGAAGTGAAGTTCAATTGGTATGTGGACGGCGTGGAAGTGCACAACGC TAAGACTAAGCCTAGAGAGGAACAGTATAACTCCACCTATAGGGTGGTGTCAGTGCTGACCGT GCTGCACCAGGACTGGCTGAACGGCAAAGAGTATAAGTGTAAAGTCTCTAACAAGGCCCTGCC |

TABLE 1-continued

Examples of LRP6 Antibodies of the Present Invention

| SEQ ID NUMBER | Ab region | Sequence |
|---|---|---|
| | | TGCCCCTATCGAAAAGACTATCTCTAAGGCTAAGGGCCAGCCTAGAGAACCCCAGGTCTACAC CCTGCCCCCTAGTAGAGAAGAGATGACTAAGAATCAGGTGTCCCTGACCTGTCTGGTCAAGGG CTTCTACCCTAGCGATATCGCCGTGGAGTGGGAGTCTAACGGCCAGCCCGAGAACAACTATAA GACTACCCCCCCTGTGCTGGATAGCGACGGCTCTTTCTTCCTGTACTCTAAACTGACCGTGGA CAAGTCTAGGTGGCAGCAGGGCAACGTGTTCAGCTGTAGCGTGATGCACGAGGCCCTGCACAA TCACTACACTCAGAAGTCACTGAGCCTGAGTCCCGGCAAGGGCGGCTCAGGCGGTAGCGATAT CGTGCTGACTCAGTCACCCGCTACCCTGAGTCTGAGCCCTGGCGAGCGGGCTACACTGAGCTG TAGAGCTAGTCAGTTTATCGGCTCACGCTACCTGGCCTGGTATCAGCAGAAGCCCGGCCAGGC CCCTAGACTGCTGATCTACGGCGCTAGTAATAGAGCTACCGGCGTGCCCGCTAGGTTTAGCGG CTCAGGATCAGGCACCGACTTTACCCTGACTATTAGTAGCCTGGAACCCGAGGACTTCGCTAC CTACTACTGTCAGCAGTACTACGACTACCCTCAGACCTTCGGCCAGGGAACTAAGGTCGAGAT TAAGGGCGGTGGCGGTAGCGGCGGAGGCGGATCAGGTGGTGGTGGTAGTGGCGGCGGAGGTAG TCAGGTCCAGCTGAAAGAGTCAGGCCCTGCCCTGGTCAAGCCTACTCAGACCCTGACCCTGAC CTGCACTTTTAGCGGCTTTAGCCTGAGTAATAGAGGCGGCGGAGTGGGCTGGATTAGACAGCC TCCAGGCAAAGCCCTGGAGTGGCTGGCCTGGATCGACTGGGACGACGATAAGTCCTACTCCAC TAGCCTGAAAACTAGGCTGACAATCAGCAAGGACACTAGTAAAAACCAGGTGGTGCTGACTAT GACTAATATGGACCCCGTGGACACCGCTACCTATTATTGCGCTAGAATGCACCTCCCACTGGT GTTCGATAGCTGGGGTCAGGGAACTCTGGTCACAGTCAGTAGC |
| SEQ ID NO: 197 | VL MOR08168 DI | SYELTQPPSVSVAPGQTARISCSGDSLRNKVYWYQQKPGQPAVLVIYKNNRPSGIPERFSGSN SGNTATLTISGTQAEDEADYYCQSYDGQKSLVFGGGTKLTVL |
| SEQ ID NO: 198 | DNA VL MOR08168 DI | TCTTACGAGCTGACCCAGCCCCCTTCCGTGTCTGTGGCTCCTGGCCAGACCGCCAGAATCTCT TGCTCCGGCGACTCCCTGCGGAACAAGGTGTACTGGTATCAGCAGAAGCCCGGCCAGGCCCCT GTGCTGGTCATCTACAAGAACAACCGGCCCTCCGGCATCCCCGAGAGATTCTCTGGCTCCAAC TCCGGCAACACCGCCACCCTGACAATCTCTGGCACACAGGCCGAGGACGAGGCCGACTACTAC TGCCAGTCCTACGACGGCCAGAAATCACTGGTGTTCGGCGGAGGCACCAAGCTGACAGTGCTG |
| SEQ ID NO: 199 | Light lambda MOR08168 DI | SYELTQPPSVSVAPGQTARISCSGDSLRNKVYWYQQKPGQAPVLVIYKNNRPSGIPERFSGSN SGNTATLTISGTQAEDEADYYCQSYDGQKSLVFGGGTKLTVLGQPKAAPSVTLFPPSSEELQA NKATLVCLISDFYPGAVTVAWKADSSPVKAGVETTTPSKQSNNKYAASSYLSLTPEQWKSHRS YSCQVTHEGSTVEKTVAPTECS |
| SEQ ID NO: 200 | DNA light lambda MOR08168 DI | TCTTACGAGCTGACCCAGCCCCCTTCCGTGTCTGTGGCTCCTGGCCAGACCGCCAGAATCTCT TGCTCCGGCGACTCCCTGCGGAACAAGGTGTACTGGTATCAGCAGAAGCCCGGCCAGGCCCCT GTGCTGGTCATCTACAAGAACAACCGGCCCTCCGGCATCCCCGAGAGATTCTCTGGCTCCAAC TCCGGCAACACCGCCACCCTGACAATCTCTGGCACACAGGCCGAGGACGAGGCCGACTACTAC TGCCAGTCCTACGACGGCCAGAAATCACTGGTGTTCGGCGGAGGCACCAAGCTGACAGTGCTG GGACAGCCTAAGGCTGCCCCCAGCGTGACCCTGTTCCCCCCCAGCAGCGAGGAGCTGCAGGCC AACAAGGCCACCCTGGTGTGCCTGATCAGCGACTTCTACCCAGGCGCCGTGACCGTGGCCTGG AAGGCCGACAGCAGCCCCGTGAAGGCCGGCGTGGAGACCACCACCCCCAGCAAGCAGAGCAAC AACAAGTACGCCGCCAGCAGCTACCTGAGCCTGACCCCCGAGCAGTGGAAGAGCCACAGGTCC TACAGCTGCCAGGTGACCCACGAGGGCAGCACCGTGGAAAAGACCGTGGCCCCAACCGAGTGC AGC |
| SEQ ID NO: 201 | Heavy MOR08168IgG 1LALA_6475sc Fv DI | QVQLVESGGGLVQPGGSLRLSCAASGFTFSDYVINWVRQAPGKGLEWVSGISWSGVNTHYADS VKGRFTISRDNSKNTLYLQMNSLRAEDTAVYYCARLGATANNIRYKFMDVWGQGTLVTVSSAS TKGPSVFPLAPSSKSTSGGTAALGCLVKDYFPEPVTVSWNSGALTSGVHTFPAVLQSSGLYSL SSVVTVPSSSLGTQTYICNVNHKPSNTKVDKRVEPKSCDKTHTCPPCPAPEAAGGPSVFLFPP KPKDTLMISRTPEVTCVVVDVSHEDPEVKFNWYVDGVEVHNAKTKPREEQYNSTYRVVSVLTV LHQDWLNGKEYKCKVSNKALPAPIEKTISKAKGQPREPQVYTLPPSREEMTKNQVSLTCLVKG FYPSDIAVEWESNGQPENNYKTTPPVLDSDGSFFLYSKLTVDKSRWQQGNVFSCSVMHEALHN HYTQKSLSLSPGKGGSGGSDIVLTQSPATLSLSPGERATLSCRASQFIGSRVLAWYQQKPGQA PRLLIYGASNRATGVPARFSGSGSGTDFTLTISSLEPEDFATYYCQQYYDYPQTFGQGTKVEI KGGGGSGGGGSGGGGSGGGGSQVQLKESGPALVKPTQTLTLTCTFSGFSLSNRGGGVGWIRQP PGKALEWLAWIDWDDDKSYSTSLKTRLTISKDTSKNQVVLTMTNMDPVDTATYYCARMHLPLV FDSWGQGTLVTVSS |
| SEQ ID NO: 202 | DNA Heavy MOR08168IgG 1LALA_6475sc Fv DI | CAGGTGCAGCTGGTGGAATCAGGCGGAGGACTGGTCCAGCCTGGCGGATCACTTAGACTGAGC TGTGCCGCTAGTGGCTTCACCTTTAGCGACTATGTGATTAACTGGGTCCGACAGGCCCCTGGC AAGGGACTGGAATGGGTGTCAGGCATTAGTTGGAGCGGCGTGAACACTCACTACGCCGATAGC GTGAAGGGCCGGTTCACTATTAGCCGGGATAACTCTAAGAACACCCTGTACCTGCAGATGAAT AGCCTGAGAGCCGAGGACACCGCCGTCTACTACTGCGCTAGACTGGGCGCTACCGCTAACAAC ATCCGCTATAAGTTCATGGACGTGTGGGGCCAGGGCACCCTGGTCACAGTGTCTTCAGCTAGC ACTAAGGGCCCCTCAGTGTTCCCCCTGGCCCCTAGCTCTAAGTCTACTAGCGGTGGCACCGCC GCTCTGGGCTGCCTGGTCAAGGACTACTTCCCCGAGCCCGTGACCGTGTCTTGGAATAGCGGC GCTCTGACTAGCGGAGTGCACACCTTCCCCGCCGTGCTGCAGTCTAGCGGCCTGTATAGCCTG TCTAGCGTCGTGACCGTGCCTAGCTCTAGCCTGGGCACTCAGACCTATATCTGTAACGTGAAC CACAAGCCTAGTAACACTAAGGTGGACAAGCGGGTGGAACCTAAGTCTTGCGATAAGACTCAC ACCTGTCCCCCCTGCCCTGCCCCAGAAGCTGCTGGCGGACCTAGCGTGTTCCTGTTCCCACCT AAGCCTAAAGACACCCTGATGATTAGTAGGACCCCCGAAGTGACCTGCGTGGTGGTGGACGTC AGCCACGAGGACCCTGAAGTGAAGTTCAATTGGTATGTGGACGGCGTGGAAGTGCACAACGCT AAGACTAAGCCTAGAGAGGAACAGTATAACTCCACCTATAGGGTGGTGTCAGTGCTGACCGTG CTGCACCAGGACTGGCTGAACGGCAAAGAGTATAAGTGTAAAGTCTCTAACAAGGCCCTGCCT GCCCCTATCGAAAAGACTATCTCTAAGGCTAAGGGCCAGCCTAGAGAACCCCAGGTCTACACC CTGCCCCCTAGTAGAGAAGAGATGACTAAGAATCAGGTGTCCCTGACCTGTCTGGTCAAGGGC |

TABLE 1-continued

Examples of LRP6 Antibodies of the Present Invention

| SEQ ID NUMBER | Ab region | Sequence |
|---|---|---|
| | | TTCTACCCTAGCGATATCGCCGTGGAGTGGGAGTCTAACGGCCAGCCCGAGAACAACTATAAG<br>ACTACCCCCCCTGTGCTGGATAGCGACGGCTCTTTCTTCCTGTACTCTAAACTGACCGTGGAC<br>AAGTCTAGGTGGCAGCAGGGCAACGTGTTCAGCTGTAGCGTGATGCACGAGGCCCTGCACAAT<br>CACTACACTCAGAAGTCACTGAGCCTGAGTCCCGGCAAGGGCGGCTCAGGCGGTAGCGATATC<br>GTGCTGACTCAGTCACCCGCTACCCTGAGTCTGAGCCCTGGCGAGCGGGCTACACTGAGCTGT<br>AGAGCTAGTCAGTTTATCGGCTCACGCTACCTGGCCTGGTATCAGCAGAAGCCCGGCCAGGCC<br>CCTAGACTGCTGATCTACGGCGCTAGTAATAGAGCTACCGGCGTGCCCGCTAGGTTTAGCGGC<br>TCAGGATCAGGCACCGACTTTACCCTGACTATTAGTAGCCTGGAACCCGAGGACTTCGCTACC<br>TACTACTGTCAGCAGTACTACGACTACCCTCAGACCTTCGGCCAGGGAACTAAGGTCGAGATT<br>AAGGGCGGTGGCGGTAGCGGCGGAGGCGGATCAGGTGGTGGTGGTAGTGGCGGCGGAGGTAGT<br>CAGGTCCAGCTGAAAGAGTCAGGCCCTGCCCTGGTCAAGCCTACTCAGACCCTGACCCTGACC<br>TGCACTTTTAGCGGCTTTAGCCTGAGTAATAGAGGCGGCGGAGTGGGCTGGATTAGACAGCCT<br>CCAGGCAAAGCCCTGGAGTGGCTGGCCTGGATCGACTGGGACGACGATAAGTCCTACTCCACT<br>AGCCTGAAAACTAGGCTGACAATCAGCAAGGACACTAGTAAAAACCAGGTGGTGCTGACTATG<br>ACTAATATGGACCCCGTGGACACCGCTACCTATTATTGCGCTAGAATGCACCTCCCACTGGTG<br>TTCGATAGCTGGGGTCAGGGAACTCTGGTCACAGTCAGTAGC |
| SEQ ID NO: 203 | VL<br>MOR08168 GL | SYELTQPLSVSVALGQTARITCSGDSLRNKVYWYQQKPGQAPVLVIYKNNRPSGIPERFSGSN<br>SGNTATLTISRAQAGDEADYYCQSYDGQKSLVFGGGTKLTVL |
| SEQ ID NO: 204 | DNA VL<br>MOR08168 GL | AGCTACGAGCTGACTCAGCCCCTGAGCGTGTCAGTGGCTCTGGGCCAGACCGCTAGAATCACC<br>TGTAGCGGCGATAGCCTGAGAAACAAGGTCTACTGGTATCAGCAGAAGCCCGGCCAGGCCCCT<br>GTGCTGGTCATCTATAAGAACAATAGGCCTAGCGGCATCCCCGAGCGGTTTAGCGGCTCTAAT<br>AGCGGCAACACCGCTACCCTGACTATTAGTAGGGCTCAGGCCGGCGACGAGGCCGACTACTAC<br>TGTCAGTCCTACGACGGCCAGAAGTCACTGGTCTTTGGCGGCGGAACTAAGCTGACCGTGCTG |
| SEQ ID NO: 205 | Light lambda<br>MDR08168 GL | SYELTQPLSVSVALGQTARITCSGDSLRNKVYWYQQKPGQAPVLVIYKNNRPSGIPERFSGSN<br>SGNTATLTISRAQAGDEADYYCQSYDGQKSLVFGGGTKLTVLGQPKAAPSVTLFPPSSEELQA<br>NKATLVCLISDFYPGAVTVAWKADSSPVKAGVETTTPSKQSNNKYAASSYLSLTPEQWKSHRS<br>YSCQVTHEGSTVEKTVAPTECS |
| SEQ ID NO: 206 | DNA Light<br>lambda<br>MOR08168 GL | AGCTACGAGCTGACTCAGCCCCTGAGCGTGTCAGTGGCTCTGGGCCAGACCGCTAGAATCACC<br>TGTAGCGGCGATAGCCTGAGAAACAAGGTCTACTGGTATCAGCAGAAGCCCGGCCAGGCCCCT<br>GTGCTGGTCATCTATAAGAACAATAGGCCTAGCGGCATCCCCGAGCGGTTTAGCGGCTCTAAT<br>AGCGGCAACACCGCTACCCTGACTATTAGTAGGGCTCAGGCCGGCGACGAGGCCGACTACTAC<br>TGTCAGTCCTACGACGGCCAGAAGTCACTGGTCTTTGGCGGCGGAACTAAGCTGACCGTGCTG<br>GGACAGCCTAAGGCTGCCCCCAGCGTGACCCTGTTCCCCCCCAGCAGCGAGGAGCTGCAGGCC<br>AACAAGGCCACCCTGGTGTGCCTGATCAGCGACTTCTACCCAGGCGCCGTGACCGTGGCCTGG<br>AAGGCCGACAGCAGCCCCGTGAAGGCCGGCGTGGAGACCACCACCCCCAGCAAGCAGAGCAAC<br>AACAAGTACGCCGCCAGCAGCTACCTGAGCCTGACCCCCGAGCAGTGGAAGAGCCACAGGTCC<br>TACAGCTGCCAGGTGACCCACGAGGGCAGCACCGTGGAAAAGACCGTGGCCCCAACCGAGTGC<br>AGC |
| SEQ ID NO: 207 | Heavy<br>MOR01868IgG<br>1LALA_6475sc<br>Fv GL | EVQLLESGGGLVQPGGSLRLSCAASGFTFSDYVINWVRQAPGKGLEWVSGISWSGVNTHYADS<br>VKGRFTISRDNSKNTLYQMNSLRAEDTAVYYCARLGATANNIRYKFMDVWGQGTLVTVSSAST<br>KGPSVFPLAPSSKSTSGGTAALGCLVKDYFPEPVTVSWNSGALTSGVHTFPAVLQSSGLYSLS<br>SVVTVPSSSLGTQTYICNVNHKPSNTKVDKRVEPKSCDKTHTCPPCPAPEAAGGPSVFLFPPK<br>PKDTLMISRTPEVTCVVVDVSHEDPEVKFNWYVDGVEVHNAKTKPREEQYNSTYRVVSVLTVL<br>HQDWLNGKEYKCKVSNKALPAPIEKTISKAKGQPREPQVYTLPPSREEMTKNQVSLTCLVKGF<br>YPSDIAVEWESNGQPENNYKTTPPVLDSDGSFFLYSKLTVDKSRWQQGNVFSCSVMHEALHNH<br>YTQKSLSLSPGKGGSGGSDIVLTQSPATLSLSPGERATLSCRASQFIGSRYLAWYQQKPGQAP<br>RLLIYGASNRATGVPARFSGSGSGTDFTLTISSLEPEDFATYYCQQYYDYPQTFGQGTKVEIK<br>GGGGSGGGGSGGGGSGGGGSQVQLKESGPALVKPTQTLTLTCTFSGFSLSNRGGGVGWIRQPP<br>GKALEWLAWIDWDDDKSYSTSLKTRLTISKDTSKNQVVLTMTNMDPVDTATYYCARMHLPLVF<br>DSWGQGTLVTVSS |
| SEQ ID NO: 208 | DNA Heavy<br>MDR08168IgG<br>1LALA_6475sc<br>FvGL | GAGGTGCAGCTGCTGGAATCAGGCGGAGGACTGGTGCAGCCTGGCGGATCACTGAGACTGAGC<br>TGTGCCGCTAGTGGCTTCACCTTTAGCGACTATGTGATTAACTGGGTCCGACAGGCCCCTGGC<br>AAGGGACTGGAATGGGTGTCAGGCATTAGTTGGAGCGGCGTGAACACTCACTACGCCGATAGC<br>GTGAAGGGCCGGTTCACTATTAGCCGGGATAACTCTAAGAACACCCGTACCTGCAGATGAATA<br>GCCTGAGAGCCGAGGACACCGCCGTCTACTACTGCGCTAGACTGGGCGCTACCGCTAACAACA<br>TCCGCTATAAGTTCATGGACGTGTGGGGCCAGGGCACCCTGGTCACAGTGTCTTCAGCTAGCA<br>CTAAGGGCCCCTCAGTGTTCCCCCTGGCCCCTAGCTCTAAGTCTACTAGCGGTGGCACCGCCG<br>CTCTGGGCTGCCTGGTCAAGGACTACTTCCCCGAGCCCGTGACCGTGTCTTGGAATAGCGGCG<br>CTCTGACTAGCGGAGTGCACACCTTCCCCGCCGTGCTGCAGTCTAGCGGCCTGTATAGCCTGT<br>CTAGCGTCGTGACCGTGCCTAGCTCTAGCCTGGGCACTCAGACCTATATCTGTAACGTGAACC<br>ACAAGCCTAGTAACACTAAGGTGGACAAGCGGGTGGAACCTAAGTCTTGCGATAAGACTCACA<br>CCTGTCCCCCCTGCCCTGCCCCAGAAGCTGCTGGCGGACCTAGCGTGTTCCTGTTCCCACCTA<br>AGCCTAAAGACACCCTGATGATTAGTAGGACCCCCGAAGTGACCTGCGTGGTGGTGGACGTCA<br>GCCACGAGGACCCTGAAGTGAAGTTCAATTGGTATGTGGACGGCGTGGAAGTGCACAACGCTA<br>AGACTAAGCCTAGAGAGGAACAGTATAACTCCACCTATAGGGTGGTGTCAGTGCTGACCGTGC<br>TGCACCAGGACTGGCTGAACGGCAAAGAGTATAAGTGTAAAGTCTCTAACAAGGCCCTGCCTG<br>CCCCTATCGAAAAGACTATCTCTAAGGCTAAGGGCCAGCCTAGAGAACCCCAGGTCTACACCC<br>TGCCCCCTAGTAGAGAAGAGATGACTAAGAATCAGGTGTCCCTGACCTGTCTGGTCAAGGGCT<br>TCTACCCTAGCGATATCGCCGTGGAGTGGGAGTCTAACGGCCAGCCCGAGAACAACTATAAGA<br>CTACCCCCCCTGTGCTGGATAGCGACGGCTCTTTCTTCCTGTACTCTAAACTGACCGTGGACA |

TABLE 1-continued

Examples of LRP6 Antibodies of the Present Invention

| SEQ ID NUMBER | Ab region | Sequence |
|---|---|---|
| | | AGTCTAGGTGGCAGCAGGGCAACGTGTTCAGCTGTAGCGTGATGCACGAGGCCCTGCACAATC ACTACACTCAGAAGTCACTGAGCCTGAGTCCCGGCAAGGGCGGCTCAGGCGGTAGCGATATCG TGCTGACTCAGTCACCCGCTACCCTGAGTCTGAGCCCTGGCGAGCGGGCTACACTGAGCTGTA GAGCTAGTCAGTTTATCGGCTCACGCTACCTGGCCTGGTATCAGCAGAAGCCCGGCCAGGCCC CTAGACTGCTGATCTACGGCGCTAGTAATAGAGCTACCGGCGTGCCCGCTAGGTTTAGCGGCT CAGGATCAGGCACCGACTTTACCCTGACTATTAGTAGCCTGGAACCCGAGGACTTCGCTACCT ACTACTGTCAGCAGTACTACGACTACCCTCAGACCTTCGGCCAGGGAACTAAGGTCGAGATTA AGGGCGGTGGCGGTAGCGGCGGAGGCGGATCAGGTGGTGGTGGTAGTGGCGGCGGAGGTAGTC AGGTCCAGCTGAAAGAGTCAGGCCCTGCCCTGGTCAAGCCTACTCAGACCCTGACCCTGACCT GCATTTTAGCGGCTTTAGCCTGAGTAATAGAGGCGGCGGAGTGGGCTGGATTAGACAGCCTCC AGGCAAAGCCCTGGAGTGGCTGGCCTGGATCGACTGGGACGACGATAAGTCCTACTCCACTAG CCTGAAAACTAGGCTGACAATCAGCAAGGACACTAGTAAAAACCAGGTGGTGCTGACTATGAC TAATATGGACCCCGTGGACACCGCTACCTATTATTGCGCTAGAATGCACCTCCCACTGGTGTT CGATAGCTGGGGTCAGGGAACTCTGGTCACAGTCAGTAGC |

Other antibodies of the invention include those where the amino acids or nucleic acids encoding the amino acids have been mutated, yet have at least 60%, 70%, 80%, 90%, 95% or 98% identity to the sequences described in Table 1. In some embodiments, it include mutant amino acid sequences wherein no more than 1, 2, 3, 4 or 5 amino acids have been mutated in the variable regions when compared with the variable regions depicted in the sequence described in Table 1, while retaining substantially the same therapeutic activity.

Since each of these antibodies can bind to LRP6, the VH, VL, full length light chain, and full length heavy chain sequences (amino acid sequences and the nucleotide sequences encoding the amino acid sequences) can be "mixed and matched" to create other LRP6 antibodies of the invention. Such "mixed and matched" LRP6 antibodies can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise a full length light chain sequence from a particular full length heavy chain/full length light chain pairing should be replaced with a structurally similar full length light chain sequence. Accordingly, in one aspect, the invention provides an isolated monoclonal antibody or fragment thereof having: a heavy chain variable region comprising an amino acid sequence selected from the group consisting of SEQ ID NOs: 14, 34, 36, 44, 60, and 62; and a light chain variable region comprising an amino acid sequence selected from the group consisting of SEQ ID NOs: 13, 33, 35, 43, 59 and 61; a heavy chain selected from the group consisting of SEQ ID NOs: 82, 106, 108, 128, 130 and 138; and a light chain variable region comprising an amino acid sequence selected from the group consisting of SEQ ID NOs: 81, and 90, 105, 107, 127, 129, and 137; wherein the antibody specifically binds to LRP6 (e.g., human and/or cynomologus LRP6).

In another aspect, the present invention provides LRP6 antibodies that bind to the β propeller 1 domain of LRP6 that comprise the heavy chain and light chain CDR1s, CDR2s and CDR3s as described in Table 1, or combinations thereof. The amino acid sequences of the VH CDR1s of the antibodies are shown in SEQ ID NOs: 1, 21, and 47. The amino acid sequences of the VH CDR2s of the antibodies and are shown in SEQ ID NOs: 2, 22, and 48. The amino acid sequences of the VH CDR3s of the antibodies are shown in SEQ ID NOs: 3, 23, and 49. The amino acid sequences of the VL CDR1s of the antibodies are shown in SEQ ID NOs: 4, 24, and 50. The amino acid sequences of the VL CDR2s of the antibodies are shown in SEQ ID NOs: 5, 25, and 51. The amino acid sequences of the VL CDR3s of the antibodies are shown in SEQ ID NOs: 6, 26, and 52. The CDR regions are delineated using the Kabat system (Kabat et al., (1991) Sequences of Proteins of Immunological Interest, Fifth Edition, U.S. Department of Health and Human Services, NIH Publication No. 91-3242; Chothia et al., (1987) J. Mol. Biol. 196: 901-917; Chothia et al., (1989) Nature 342: 877-883; and Al-Lazikani et al., (1997) J. Mol. Biol. 273, 927-948).

In another aspect, the present invention provides LRP6 antibodies that bind to the β propeller 3 domain of LRP6 that comprise the heavy chain and light chain CDR1s, CDR2s and CDR3s as described in Table 1, or combinations thereof. The amino acid sequences of the VH CDR1s of the antibodies are shown in SEQ ID NOs: 69, 93, and 115. The amino acid sequences of the VH CDR2s of the antibodies and are shown in SEQ ID NOs: 70, 94, and 116. The amino acid sequences of the VH CDR3s of the antibodies are shown in SEQ ID NOs: 71, 95, and 117. The amino acid sequences of the VL CDR1s of the antibodies are shown in SEQ ID NOs: 72, 96, and 118. The amino acid sequences of the VL CDR2s of the antibodies are shown in SEQ ID NOs: 73, 97, and 119. The amino acid sequences of the VL CDR3s of the antibodies are shown in SEQ ID NOs: 74, 98, and 120. The CDR regions are delineated using the Kabat system (Kabat et al., (1991) Sequences of Proteins of Immunological Interest, Fifth Edition, U.S. Department of Health and Human Services, NIH Publication No. 91-3242; Chothia et al., (1987) J. Mol. Biol. 196: 901-917; Chothia et al., (1989) Nature 342: 877-883; and Al-Lazikani et al., (1997) J. Mol. Biol. 273, 927-948).

Given that each of these antibodies can bind to LRP6 and that antigen-binding specificity is provided primarily by the CDR1, 2 and 3 regions, the VH CDR1, 2 and 3 sequences and VL CDR1, 2 and 3 sequences can be "mixed and matched" (i.e., CDRs from different antibodies can be mixed and match, although each antibody must contain a VH CDR1, 2 and 3 and a VL CDR1, 2 and 3 to create other LRP6 binding molecules of the invention. Such "mixed and matched" LRP6 antibodies can be tested using the binding assays known in the art and those described in the Examples (e.g., ELISAs). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by substituting one or more VH and/or VL CDR region sequences with structurally similar sequences from the CDR sequences shown herein for monoclonal antibodies of the present invention.

Accordingly, the present invention provides an isolated LRP6 β-propeller 1 monoclonal antibody or fragment thereof comprising a heavy chain variable region CDR1 comprising an amino acid sequence selected from the group consisting of SEQ ID NOs: 1, 21, and 47; a heavy chain variable region CDR2 comprising an amino acid sequence selected from the group consisting of SEQ ID NOs: 2, 22, and 48; a heavy chain variable region CDR3 comprising an amino acid sequence selected from the group consisting of SEQ ID NOs: 3, 23, and 49; a light chain variable region CDR1 comprising an amino acid sequence selected from the group consisting of SEQ ID NOs: 4, 24, and 50; a light chain variable region CDR2 comprising an amino acid sequence selected from the group consisting of SEQ ID NOs: 5, 25, and 51; and a light chain variable region CDR3 comprising an amino acid sequence selected from the group consisting of SEQ ID NOs: 6, 26, and 52; wherein the antibody binds LRP6.

Accordingly, the present invention provides an isolated LRP6 β-propeller 3 monoclonal antibody or fragment thereof comprising a heavy chain variable region CDR1 comprising an amino acid sequence selected from the group consisting of SEQ ID NOs: 69, 93, and 115; a heavy chain variable region CDR2 comprising an amino acid sequence selected from the group consisting of SEQ ID NOs: 70, 94, and 116; a heavy chain variable region CDR3 comprising an amino acid sequence selected from the group consisting of SEQ ID NOs: 71, 95, and 117; a light chain variable region CDR1 comprising an amino acid sequence selected from the group consisting of SEQ ID NOs: 72, 96, and 118; a light chain variable region CDR2 comprising an amino acid sequence selected from the group consisting of SEQ ID NOs: 73, 97, and 119; and a light chain variable region CDR3 comprising an amino acid sequence selected from the group consisting of SEQ ID NOs: 74, 98, and 120; wherein the antibody binds LRP6.

In a specific embodiment, an antibody that binds to LRP6 comprises a heavy chain variable region CDR1 of SEQ ID NO: 1; a heavy chain variable region CDR2 of SEQ ID NO: 2; a heavy chain variable region CDR3 of SEQ ID NO: 3; a light chain variable region CDR1 of SEQ ID NO: 4; a light chain variable region CDR2 of SEQ ID NO: 5; and a light chain variable region CDR3 of SEQ ID NO: 6.

In a specific embodiment, an antibody that binds to LRP6 comprises a heavy chain variable region CDR1 of SEQ ID NO: 21; a heavy chain variable region CDR2 of SEQ ID NO: 22; a heavy chain variable region CDR3 of SEQ ID NO: 23; a light chain variable region CDR1 of SEQ ID NO: 24; a light chain variable region CDR2 of SEQ ID NO: 25; and a light chain variable region CDR3 of SEQ ID NO: 26.

In a specific embodiment, an antibody that binds to LRP6 comprises a heavy chain variable region CDR1 of SEQ ID NO: 47; a heavy chain variable region CDR2 of SEQ ID NO: 48; a heavy chain variable region CDR3 of SEQ ID NO: 49; a light chain variable region CDR1 of SEQ ID NO: 50; a light chain variable region CDR2 of SEQ ID NO: 51; and a light chain variable region CDR3 of SEQ ID NO: 52.

In a specific embodiment, an antibody that binds to LRP6 comprises a heavy chain variable region CDR1 of SEQ ID NO: 69; a heavy chain variable region CDR2 of SEQ ID NO: 70; a heavy chain variable region CDR3 of SEQ ID NO: 71; a light chain variable region CDR1 of SEQ ID NO: 72; a light chain variable region CDR2 of SEQ ID NO: 73; and a light chain variable region CDR3 of SEQ ID NO: 74.

In a specific embodiment, an antibody that binds to LRP6 comprises a heavy chain variable region CDR1 of SEQ ID NO: 93; a heavy chain variable region CDR2 of SEQ ID NO: 94; a heavy chain variable region CDR3 of SEQ ID NO: 95; a light chain variable region CDR1 of SEQ ID NO: 96; a light chain variable region CDR2 of SEQ ID NO: 97; and a light chain variable region CDR3 of SEQ ID NO: 98.

In a specific embodiment, an antibody that binds to LRP6 comprises a heavy chain variable region CDR1 of SEQ ID NO: 115; a heavy chain variable region CDR2 of SEQ ID NO: 116; a heavy chain variable region CDR3 of SEQ ID NO: 117; a light chain variable region CDR1 of SEQ ID NO: 118; a light chain variable region CDR2 of SEQ ID NO: 119; and a light chain variable region CDR3 of SEQ ID NO: 120.

In a specific embodiment, an antibody that binds to LRP6 comprises a VH of SEQ ID NO: 14 and VL of SEQ ID NO: 13. In a specific embodiment, an antibody that binds to LRP6 comprises a VH of SEQ ID NO: 34 and VL of SEQ ID NO: 33. In a specific embodiment, an antibody that binds to LRP6 comprises a VH of SEQ ID NO: 35 and VL of SEQ ID NO: 36. In a specific embodiment, an antibody that binds to LRP6 comprises a VH of SEQ ID NO; 43 and VL of SEQ ID NO: 44. In a specific embodiment, an antibody that binds to LRP6 comprises aVH of SEQ ID NO: 60 and VL of SEQ ID NO: 59. In a specific embodiment, an antibody that binds to LRP6 comprises a VH of SEQ ID NO; 62 and VL of SEQ ID NO: 61. In a specific embodiment, an antibody that binds to LRP6 comprises a SEQ ID NO: 82 and VL of SEQ ID NO: 81. In a specific embodiment, an antibody that binds to LRP6 comprises a VH of SEQ ID NO; 90 and VL of SEQ ID NO: 89. In a specific embodiment, an antibody that binds to LRP6 comprises a VH of SEQ ID NO: 106 and VL of SEQ ID NO: 105. In a specific embodiment, an antibody that binds to LRP6 comprises a VH of SEQ ID NO: 108 and VL of SEQ ID NO: 107. In a specific embodiment, an antibody that binds to LRP6 comprises aVH of SEQ ID NO: 128 and VL of SEQ ID NO: 127. In a specific embodiment, an antibody that binds to LRP6 comprises a VH of SEQ ID NO: 130 and VL of SEQ ID NO: 129. In a specific embodiment, an antibody that binds to LRP6 comprises a VH of SEQ ID NO: 138 and VL of SEQ ID NO: 137.

In one embodiment, the LRP6 antibodies are antagonist antibodies. In one embodiment, the LRP6 antibodies are agonist antibodies. In certain embodiments, an antibody that binds to LRP6 is an antibody that is described in Table 1.

As used herein, a human antibody comprises heavy or light chain variable regions or full length heavy or light chains that are "the product of" or "derived from" a particular germline sequence if the variable regions or full length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally occurring somatic mutations or intentional introduction of site-directed mutations. However, in the VH or VL framework regions, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Typically, a recombinant human antibody will display no more than 10 amino acid differences from the amino acid sequence encoded by the human germline immunoglobulin gene in the VH or VL framework regions. In certain cases, the human antibody may display no more than 5, or even no more than 4, 3, 2, or 1 amino acid difference from the amino acid sequence encoded by the germline immunoglobulin gene.

The antibodies disclosed herein can be derivatives of single chain antibodies, diabodies, domain antibodies, nanobodies, and unibodies. A "single-chain antibody" (scFv) consists of a single polypeptide chain comprising a VL domain linked to a V-domain wherein VL domain and VH domain are paired to form a monovalent molecule. Single chain antibody can be prepared according to method known in the art (see, for example, Bird et al., (1988) Science 242:423-426 and Huston et al., (1988) Proc. Natl. Acad. Sci. USA 85:5879-5883). A "disbud" consists of two chains, each chain comprising a heavy chain variable region connected to a light chain variable region on the same polypeptide chain connected by a short peptide linker, wherein the two regions on the same chain do not pair with each other but with complementary domains on the other chain to form a bispecific molecule. Methods of preparing diabodies are known in the art (See, e.g., Holliger et al., (1993) Proc. Natl. Acad. Sci. USA 90:6444-6448, and Poljak et al., (1994) Structure 2:1121-1123). Domain antibodies (dAbs) are small functional binding units of antibodies, corresponding to the variable regions of either the heavy or light chains of antibodies. Domain antibodies are well expressed in bacterial, yeast, and mammalian cell systems. Further details of domain antibodies and methods of production thereof are known in the art (see, for example, U.S. Pat. Nos. 6,291,158; 6,582,915; 6,593,081; 6,172,197; 6,696,245; European Patents 0368684 & 0616640; WO05/035572, WO04/101790, WO04/081026, WO04/058821, WO04/003019 and WO03/002609. Nanobodies are derived from the heavy chains of an antibody. A nanobody typically comprises a single variable domain and two constant domains (CH2 and CH3) and retains antigen-binding capacity of the original antibody. Nanobodies can be prepared by methods known in the art (See e.g., U.S. Pat. No. 6,765,087, U.S. Pat. No. 6,838,254, WO 06/079372). Unibodies consist of one light chain and one heavy chain of a IgG4 antibody. Unibodies may be made by the removal of the hinge region of IgG4 antibodies. Further details of unibodies and methods of preparing them may be found in WO2007/059782.

In addition to Wnt ligands LRP6 Propeller 1 antibodies are expected to inhibit the interaction with other Propeller 1 binding ligands (e.g. Sclerostin, Dkk1). Similarly, Propeller 3 antibodies are expected to inhibit the interaction with other propeller 3 binding ligands (e.g. Dkk1). Furthermore, propeller 1 and 3 binding antibodies may be expected to affect the activity of other Wnt signaling modulators e.g. R-spondins Homologous Antibodies In yet another embodiment, the present invention provides an antibody or fragment thereof comprising amino acid sequences that are homologous to the sequences described in Table 1, and the antibody binds to a LRP6 protein (e.g., human and/or cynomologus LRP6), and retains the desired functional properties of those antibodies described in Table 1.

For example, the invention provides an isolated monoclonal antibody (or a functional fragment thereof) comprising a heavy chain variable region and a light chain variable region, wherein the heavy chain variable region comprises an amino acid sequence that is at least 80%, at least 90%, or at least 95% identical to an amino acid sequence selected from the group consisting of SEQ ID NOs: 14, 34, 36, 44, 60, and 62; the light chain variable region comprises an amino acid sequence that is at least 80%, at least 90%, at least 95%, or at least 98% identical to an amino acid sequence selected from the group consisting of SEQ ID NOs: 13, 33, 37, 43, 59, and 61; the antibody binds to β-propeller 1 of LRP6 (e.g., human and/or cynomologus LRP6), and inhibits the signaling activity of β-propeller 1 dependent Wnt proteins, which can be measured in Wnt reporter gene assay or other measure of Wnt directed signaling (e.g., LRP6 phosphorylation, β-catenin stabilization and nuclear translocation, cellular proliferation/survival) as described herein. In a specific example, such antibodies have an $EC_{50}$ value in a Wnt1 assay of less than 10 nM when using conditioned medium or using transfected cells.

For example, the invention provides an isolated monoclonal antibody (or a functional fragment thereof) comprising a heavy chain variable region and a light chain variable region, wherein the heavy chain variable region comprises an amino acid sequence that is at least 80%, at least 90%, at least 95%, or at least 98% identical to an amino acid sequence selected from the group consisting of SEQ ID NOs: 82, 89, 106, 108, 128, 130, and 138; the light chain variable region comprises an amino acid sequence that is at least 80%, at least 90%, at least 95%, or at least 98% identical to an amino acid sequence selected from the group consisting of SEQ ID NOs: 81, 90, 105, 107, 127, 129, and 137; the antibody binds to β-propeller 3 of LRP6 (e.g., human and/or cynomologus LRP6), and inhibits the signaling activity of β-propeller 3 dependent Wnt proteins, which can be measured in Wnt reporter gene assay or other measure of Wnt directed signaling (e.g., LRP6 phosphorylation, β-catenin stabilization and nuclear translocation, cellular proliferation/survival) as described herein. In a specific example, such antibodies have an $EC_{50}$ value in a Wnt3a assay of less than 10 nM when using conditioned medium or using transfected cells.

Further for Propeller 1 antibodies, variable heavy chain parental nucleotide sequences are shown in SEQ ID NOs: 16, 38, and 64. Variable light chain parental nucleotide sequences are shown in SEQ ID NOs: 15, 37, and 63. Full length heavy chain sequences optimized for expression in a mammalian cell are shown in SEQ ID NOs: 20, 42, and 68. Full length light chain sequences optimized for expression in a mammalian cell are shown in SEQ ID NOs: 19, 41, and 67. Other antibodies of the invention include amino acids or nucleic acids that have been mutated, yet have at least 60%, 70%, 80%, 90%, 95% or 98% identity to the sequences described above. In some embodiments, it include mutant amino acid sequences wherein no more than 1, 2, 3, 4 or 5 amino acids have been mutated by amino acid deletion, insertion or substitution in the variable regions when compared with the variable regions depicted in the sequence described above.

Further for Propeller 3 antibodies, variable heavy chain parental nucleotide sequences are shown in SEQ ID NO: 84, 110, and 132. Variable light chain parental nucleotide sequences are shown in SEQ ID NO: 83, 109, and 131. Full length heavy chain sequences optimized for expression in a mammalian cell are shown in SEQ ID NO: 88, 91, 114, 136, and 140. Full length light chain nucleotide sequences optimized for expression in a mammalian cell are shown in SEQ ID NO: 87, 92, 113, 135, and 139. Other antibodies of the invention include amino acids or nucleic acids that have been mutated, yet have at least 60%, 70%, 80%, 90%, 95% or 98% identity to the sequences described above. In some embodiments, it include mutant amino acid sequences wherein no more than 1, 2, 3, 4 or 5 amino acids have been mutated by amino acid deletion, insertion or substitution in the variable regions when compared with the variable regions depicted in the sequence described above.

In other embodiments, the VH and/or VL amino acid sequences may be 50%, 60%, 70%, 80%, 90%, 95%, 96%, 97%, 98% or 99% identical to the sequences set forth in Table 1.

In other embodiments, the VH and/or VL amino acid sequences may be identical except an amino acid substitution in no more than 1, 2, 3, 4 or 5 amino acid position.

An antibody having VH and VL regions having high (i.e., 80% or greater) identity to the VH and VL regions of those Propeller 1 antibodies described in Table 1 can be obtained by mutagenesis (e.g., site-directed or PCR-mediated mutagenesis) of nucleic acid molecules encoding SEQ ID NOs: 14, 34, 60, 13, 33, and 59 respectively, followed by testing of the encoded altered antibody for retained function using the functional assays described herein.

An antibody having VH and VL regions having high (i.e., 80% or greater) identity to the VH and VL regions of those Propeller 3 antibodies described in Table 1 can be obtained by mutagenesis (e.g., site-directed or PCR-mediated mutagenesis) of nucleic acid molecules encoding SEQ ID NOs: 82, 106, 128, 81, 105, and 127 respectively, followed by testing of the encoded altered antibody for retained function using the functional assays described herein.

In other embodiments, the variable regions of heavy chain and/or light chain nucleotide sequences may be 60%, 70%, 80%, 90%, 95%, 96%, 97%, 98% or 99% identical to the sequences set forth above As used herein, "percent identity" between the two sequences is a function of the number of identical positions shared by the sequences (i.e., % identity equals number of identical positions/total number of positions×100), taking into account the number of gaps, and the length of each gap, which needs to be introduced for optimal alignment of the two sequences. The comparison of sequences and determination of percent identity between two sequences can be accomplished using a mathematical algorithm, as described in the non-limiting examples below.

Additionally or alternatively, the protein sequences of the present invention can further be used as a "query sequence" to perform a search against public databases to, for example, identifies related sequences. For example, such searches can be performed using the BLAST program (version 2.0) of Altschul et al. (1990) J. Mol. Biol. 215:403-10.

Antibodies with Conservative Modifications

In certain embodiments, an antibody of the invention has a heavy chain variable region comprising CDR1, CDR2, and CDR3 sequences and a light chain variable region comprising CDR1, CDR2, and CDR3 sequences, wherein one or more of these CDR sequences have specified amino acid sequences based on the antibodies described herein or conservative modifications thereof, and wherein the antibodies retain the desired functional properties of the LRP6 antibodies of the invention.

Accordingly, the invention provides an isolated Propeller 1 monoclonal antibody, or a functional fragment thereof, consisting of a heavy chain variable region comprising CDR1, CDR2, and CDR3 sequences and a light chain variable region comprising CDR1, CDR2, and CDR3 sequences, wherein: the heavy chain variable region CDR1 amino acid sequences are selected from the group consisting of SEQ ID NOs: 1, 21, and, 47, and conservative modifications thereof; the heavy chain variable region CDR2 amino acid sequences are selected from the group consisting of SEQ ID NOs: 2, 22, and 48, and conservative modifications thereof; the heavy chain variable region CDR3 amino acid sequences are selected from the group consisting of SEQ ID NOs: 3, 23, and 49, and conservative modifications thereof; the light chain variable regions CDR1 amino acid sequences are selected from the group consisting of SEQ ID NOs: 4, 24, 50, and conservative modifications thereof; the light chain variable regions CDR2 amino acid sequences are selected from the group consisting of SEQ ID NOs: 5, 25, and 51, and conservative modifications thereof; the light chain variable regions of CDR3 amino acid sequences are selected from the group consisting of SEQ ID NOs: 6, 26, and 52, and conservative modifications thereof; the antibody or fragment thereof specifically binds to LRP6, and inhibits LRP6 activity by inhibiting a Wnt signaling pathway, which can be measured in Wnt reporter gene assay or other measure of Wnt directed signaling (e.g., LRP6 phosphorylation, β-catenin stabilization and nuclear translocation, cellular proliferation/survival) as described herein.

Accordingly, the invention provides an isolated Propeller 3 monoclonal antibody, or a fragment thereof, consisting of a heavy chain variable region comprising CDR1, CDR2, and CDR3 sequences and a light chain variable region comprising CDR1, CDR2, and CDR3 sequences, wherein: the heavy chain variable region CDR1 amino acid sequences are selected from the group consisting of SEQ ID NOs: 69, 93, and 115, and conservative modifications thereof; the heavy chain variable region CDR2 amino acid sequences are selected from the group consisting of SEQ ID NOs: 70, 94, and 116, and conservative modifications thereof; the heavy chain variable region CDR3 amino acid sequences are selected from the group consisting of SEQ ID NOs: 71, 95, and 117, and conservative modifications thereof; the light chain variable regions CDR1 amino acid sequences are selected from the group consisting of SEQ ID NOs: 72, 96, and 118, and conservative modifications thereof; the light chain variable regions CDR2 amino acid sequences are selected from the group consisting of SEQ ID NOs: 73, 97, and 119, and conservative modifications thereof; the light chain variable regions of CDR3 amino acid sequences are selected from the group consisting of SEQ ID NOs: 74, 98, and 120, and conservative modifications thereof; the antibody or fragment thereof specifically binds to LRP6, and inhibits activities of Propeller 3-dependent Wnt proteins, which can be measured in Wnt reporter gene assay or other measure of Wnt directed signaling (e.g., LRP6 phosphorylation, β-catenin stabilization and nuclear translocation, cellular proliferation/survival) as described herein.

Antibodies that Bind to the Same Epitope

The present invention provides antibodies that bind to the same epitope as do the LRP6 antibodies described in Table 1. Additional antibodies can therefore be identified based on their ability to cross-compete (e.g., to competitively inhibit the binding of, in a statistically significant manner) with other antibodies of the invention in LRP6 binding assays. The ability of a test antibody to inhibit the binding of antibodies of the present invention to a LRP6 protein (e.g., human and/or cynomologus LRP6) demonstrates that the test antibody can compete with that antibody for binding to LRP6; such an antibody may, according to non-limiting theory, bind to the same or a related (e.g., a structurally similar or spatially proximal) epitope on the LRP6 protein as the antibody with which it competes. In an embodiment, the antibody that binds to the same epitope on LRP6 as the antibodies of the present invention is a human monoclonal antibody. Such human monoclonal antibodies can be prepared and isolated as described herein.

Engineered and Modified Antibodies

An antibody of the invention further can be prepared using an antibody having one or more of the VH and/or VL sequences shown herein as starting material to engineer a modified antibody, which modified antibody may have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al., (1998) Nature 332:323-327; Jones et al., (1986) Nature 321:522-525; Queen et al., (1989) Proc. Natl. Acad., U.S.A. 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of the invention pertains to an isolated Propeller 1 monoclonal antibody, or fragment thereof, comprising a heavy chain variable region comprising CDR1 sequences having an amino acid sequence selected from the group consisting of SEQ ID NOs: 1, 21, and 47; CDR2 sequences having an amino acid sequence selected from the group consisting of SEQ ID NOs: 2, 22, and 48; CDR3 sequences having an amino acid sequence selected from the group consisting of SEQ ID NOs: 3, 23, and 49, respectively; and a light chain variable region having CDR1 sequences having an amino acid sequence selected from the group consisting of SEQ ID NOs: 4, 24, and 50; CDR2 sequences having an amino acid sequence selected from the group consisting of SEQ ID NOs: 5, 25, and 51; and CDR3 sequences consisting of an amino acid sequence selected from the group consisting of SEQ ID NOs: 6, 26, and 52, respectively. Thus, such antibodies contain the VH and VL CDR sequences of monoclonal antibodies, yet may contain different framework sequences from these antibodies.

Accordingly, another embodiment of the invention pertains to an isolated Propeller 3 monoclonal antibody, or fragment thereof, comprising a heavy chain variable region comprising CDR1 sequences having an amino acid sequence selected from the group consisting of SEQ ID NOs: 69, 93, and 115; CDR2 sequences having an amino acid sequence selected from the group consisting of SEQ ID NOs: 70, 76, 100, and 116; CDR3 sequences having an amino acid sequence selected from the group consisting of SEQ ID NOs: 71, 95, and 117, respectively; and a light chain variable region having CDR1 sequences having an amino acid sequence selected from the group consisting of SEQ ID NOs: 72, 96, and 118; CDR2 sequences having an amino acid sequence selected from the group consisting of SEQ ID NOs: 73, 97, and 119; and CDR3 sequences consisting of an amino acid sequence selected from the group consisting of SEQ ID NOs: 74, 98, and 120, respectively. Thus, such antibodies contain the VH and VL CDR sequences of monoclonal antibodies, yet may contain different framework sequences from these antibodies.

Such framework sequences can be obtained from public DNA databases or published references that include germline antibody gene sequences. For example, germline DNA sequences for human heavy and light chain variable region genes can be found in the "Vase" human germline sequence database (available on the Internet at www.mrc-cpe.cam.ac.uldvbase), as well as in Kabat et al., (1991) Sequences of Proteins of Immunological Interest, Fifth Edition, U.S. Department of Health and Human Services, NIH Publication No. 91-3242; Chothia et al, (1987) J. Mol. Biol. 196:901-917; Chothia et al., (1989) Nature 342:877-883; and Al-Lazikani et al., (1997) J. Mol. Biol. 273:927-948; Tomlinson et al., (1992) J. fol. Biol. 227:776-798; and Cox et al., (1994) Eur. J Immunol. 24:827-836; the contents of each of which are expressly incorporated herein by reference.

An example of framework sequences for use in the antibodies of the invention are those that are structurally similar to the framework sequences used by selected antibodies of the invention, e.g., consensus sequences and/or framework sequences used by monoclonal antibodies of the invention. The VH CDR1, 2 and 3 sequences, and the VL CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the VH and/or VL CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications (as discussed above) can be introduced. The mutations may be amino acid substitutions, additions or deletions. Moreover, typically no more than one, two, three, four or five residues within a CDR region are altered.

Accordingly, in another embodiment, the invention provides isolated Propeller 1 monoclonal antibodies, or fragment thereof, consisting of a heavy chain variable region having: a VH CDR1 region consisting of an amino acid sequence selected from the group having SEQ ID NOs: 1, 21, and 47 or an amino acid sequence having one, two, three, four or five amino acid substitutions, deletions or additions as compared to SEQ ID NOs: 1, 21, and 47; a VH CDR2 region having an amino acid sequence selected from the group consisting of SEQ ID NOs: 2, 22, and 48, or an amino acid sequence having one, two, three, four or five amino acid substitutions, deletions or additions as compared to SEQ ID NOs: 2, 22, and 48; a VH CDR3 region having an amino acid sequence selected from the group consisting of SEQ ID NOs: 3, 23, and 49, or an amino acid sequence having one, two, three, four or five amino acid substitutions, deletions or additions as compared to SEQ ID NOs: 3, 23, and 49; a VL CDR1 region having an amino acid sequence selected from the group consisting of SEQ ID NOs: 4, 24, and 50, or an amino acid sequence having one, two, three, four or five amino acid substitutions, deletions or additions as compared to SEQ ID NOs: 4, 24, and 50; a VL CDR2 region having an amino acid sequence selected from the group consisting of SEQ ID NOs: 5, 25, and 51, or an amino acid sequence having one, two, three, four or five amino acid substitutions, deletions or additions as compared to SEQ ID NOs: 5, 25, and 51; and a VL CDR3 region having an amino acid sequence selected from the group consisting of SEQ ID NOs: 6, 26, and 52, or an amino acid sequence having one, two, three, four or five amino acid substitutions, deletions or additions as compared to SEQ ID NOs: 6, 26, and 52.

Accordingly, in another embodiment, the invention provides isolated Propeller 3 monoclonal antibodies, or fragment thereof, consisting of a heavy chain variable region having: a VH CDR1 region consisting of an amino acid sequence selected from the group having SEQ ID NOs: 69, 93, and 115 or an amino acid sequence having one, two, three, four or five amino acid substitutions, deletions or additions as compared to SEQ ID NOs: 69, 93, and 115; a VH CDR2 region having an amino acid sequence selected from the group consisting of SEQ ID NOs: 70, 94, and 116, or an amino acid sequence having one, two, three, four or five amino acid substitutions, deletions or additions as compared to SEQ ID NOs: 70, 94, and 116; a VH CDR3 region having an amino acid sequence selected from the group consisting of SEQ ID NOs: 71, 95, and 117, or an amino acid sequence having one, two, three, four or five amino acid substitutions, deletions or additions as compared to SEQ ID NOs: 71, 95, and 117; a VL CDR1 region having an amino acid sequence selected from the group consisting of SEQ ID NOs: 72, 96, and 118, or an amino acid sequence having one, two, three, four or five amino acid substitutions, deletions or additions as compared to SEQ ID NOs: 72, 96, and 118; a VL CDR2 region having an amino acid sequence selected from the group consisting of SEQ ID NOs: 73, 97, and 119, or an amino acid sequence having one, two, three, four or five amino acid substitutions, deletions or additions as compared to SEQ ID NOs: 73, 97, and 119; and a VL CDR3 region having an amino acid sequence selected from the group consisting of SEQ ID NOs: 74, 98, and 120, or an amino acid sequence having one, two, three, four or five amino acid substitutions, deletions or additions as compared to SEQ ID NOs: 74, 98, and 120.

Grafting Antibody Fragments into Alternative Frameworks or Scaffolds

A wide variety of antibody/immunoglobulin frameworks or scaffolds can be employed so long as the resulting polypeptide includes at least one binding region which specifically binds to LRP6. Such frameworks or scaffolds include the 5 main idiotypes of human immunoglobulins, or fragments thereof, and include immunoglobulins of other animal species, preferably having humanized aspects. Novel frameworks, scaffolds and fragments continue to be discovered and developed by those skilled in the art.

In one aspect, the invention pertains to generating non-immunoglobulin based antibodies using non-immunoglobulin scaffolds onto which CDRs of the invention can be grafted. Known or future non-immunoglobulin frameworks and scaffolds may be employed, as long as they comprise a binding region specific for the target LRP6 protein (e.g., human and/or cynomologus LRP6). Known non-immunoglobulin frameworks or scaffolds include, but are not limited to, fibronectin (Compound Therapeutics, Inc., Waltham, Mass.), ankyrin (Molecular Partners AG, Zurich, Switzerland), domain antibodies (Domantis, Ltd., Cambridge, Mass., and Ablynx nv, Zwijnaarde, Belgium), lipocalin (Pieris Proteolab AG, Freising, Germany), small modular immuno-pharmaceuticals (Trubion Pharmaceuticals Inc., Seattle, Wash.), maxybodies (Avidia, Inc., Mountain View, Calif.), Protein A (Affibody AG, Sweden), and affilin (gamma-crystallin or ubiquitin) (Scil Proteins GmbH, Halle, Germany).

The fibronectin scaffolds are based on fibronectin type III domain (e.g., the tenth module of the fibronectin type III ($^{10}$Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (see U.S. Pat. No. 6,818,418). These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the invention using standard cloning techniques.

The ankyrin technology is based on using proteins with ankyrin derived repeat modules as scaffolds for bearing variable regions which can be used for binding to different targets. The ankyrin repeat module is a 33 amino acid polypeptide consisting of two anti-parallel α-helices and a 0-turn. Binding of the variable regions is mostly optimized by using ribosome display.

Avimers are derived from natural A-domain containing protein such as LRP6. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, U.S. Patent Application Publication Nos. 20040175756; 20050053973; 20050048512; and 20060008844.

Affibody affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate affibody libraries with a large number of ligand variants (See e.g., U.S. Pat. No. 5,831,012). Affibody molecules mimic antibodies, they have a molecular weight of 6 kDa, compared to the molecular weight of antibodies, which is 150 kDa. In spite of its small size, the binding site of affibody molecules is similar to that of an antibody.

Anticalins are products developed by the company Pieris ProteoLab AG. They are derived from lipocalins, a widespread group of small and robust proteins that are usually involved in the physiological transport or storage of chemically sensitive or insoluble compounds. Several natural lipocalins occur in human tissues or body liquids. The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain. The set of four loops, which makes up the binding pocket, shows pronounced structural plasticity and tolerates a variety of side chains. The binding site can thus be reshaped in a proprietary process in order to recognize prescribed target molecules of different shape with high affinity and specificity. One protein of lipocalin family, the bilin-binding protein (BBP) of Pieris Brassicae has been used to develop anticalins by mutagenizing the set of four loops. One example of a patent application describing anticalins is in PCT Publication No. WO 199916873.

Affilin molecules are small non-immunoglobulin proteins which are designed for specific affinities towards proteins and small molecules. New affilin molecules can be very quickly selected from two libraries, each of which is based on a different human derived scaffold protein. Affilin molecules do not show any structural homology to immunoglobulin proteins. Currently, two affilin scaffolds are employed, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368.

Protein epitope mimetics (PEM) are medium-sized, cyclic, peptide-like molecules (MW 1-2 kDa) mimicking beta-hairpin secondary structures of proteins, the major secondary structure involved in protein-protein interactions.

In some embodiments, the Fabs are converted to silent IgG1 format by changing the Fc region. For example, antibodies MOR08168, MOR08545, MOR06706, MOR06475, MOR08193, and MOR08473 in Table 1 can be converted to IgG1 format by adding the amino acid sequence:

```
                                          (SEQ ID NO: 209)
CDKTHTCPPCPAPEAAGGPSVFLFPPKPKDTLMISRTPEVTCVVVDV

SHEDPEVKFNWYVDGVEVHNAKTKPREEQYNSTYRVVSVLTVLHQDW

LNGKEYKCKVSNKALPAPIEKTISKAKGQPREPQVYTLPPSREEMTK

NQVSLTCLVKGFYPSDIAVEWESNGQPENNYKTTPPVLDSDGSFFLY

SKLTVDKSRWQQGNVESCSVMHEALHNHYTQKSLSLSPGK.
```

and substituting the light chain with: CS if the light chain is lambda, or C if the light chain is kappa. As used herein, a "silent IgG1" is an IgG1 Fc sequence in which the amino acid sequence has been altered to decrease Fc-mediated effector functions (for example ADCC and/or CDC). Such an antibody will typically have decreased binding to Fc receptors. In some other embodiments, the Fabs are converted to IgG2 format. For example, antibodies MOR08168, MOR08545, MOR06706, MOR06475, MOR08193, and MOR08473 in Table 1 can be converted to IgG2 format by substituting the constant sequence with the constant sequence for the heavy chain of IgG2:

```
                                          (SEQ ID NO: 210)
ASTKGPSVFPLAPCSRSTSESTAALGCLVKDYFPEPVTVSWNSGALT

SGVHTFPAVLQSSGLYSLSSVVTVPSSNFOTQTYTCNVDHKPSNTKV

DKTVERKCCVECPPCPAPPVAGPSVFLFPPKPKDTLMISRTPEVTCV

VVDVSHEDPEVQFNWYVDGVEVHNAKTKPREEQFNSTFRVVSVLTVV

HQDWLNGKEYKCKVSNKGLPAPIEKTISKTKGQPREPQVYTLPPSRE

EMTKNQVSLTCLVKGFYPSDIAVEWESNGQPENNYKTTPPMLDSDGS

FFLYSKLTVDKSRWQQGNVFSCSVMHEALHNHYTQKSLSLSPGK.
```

Human or Humanized Antibodies

The present invention provides fully human antibodies that specifically bind to a LRP6 protein (e.g., human and/or cynomologus LRP6). Compared to the chimeric or humanized antibodies, the human LRP6 antibodies of the invention have further decreased antigenicity when administered to human subjects.

The human LRP6 antibodies can be generated using methods that are known in the art. For example, the humaneering technology used to converting non-human antibodies into engineered human antibodies. U.S. Patent Publication No. 20050008625 describes an in vivo method for replacing a nonhuman antibody variable region with a human variable region in an antibody while maintaining the same or providing better binding characteristics relative to that of the non-human antibody. The method relies on epitope guided replacement of variable regions of a non-human reference antibody with a fully human antibody. The resulting human antibody is generally unrelated structurally to the reference nonhuman antibody, but binds to the same epitope on the same antigen as the reference antibody. Briefly, the serial epitope-guided complementarity replacement approach is enabled by setting up a competition in cells between a "competitor" and a library of diverse hybrids of the reference antibody ("test antibodies") for binding to limiting amounts of antigen in the presence of a reporter system which responds to the binding of test antibody to antigen. The competitor can be the reference antibody or derivative thereof such as a single-chain Fv fragment. The competitor can also be a natural or artificial ligand of the antigen which binds to the same epitope as the reference antibody. The only requirements of the competitor are that it binds to the same epitope as the reference antibody, and that it competes with the reference antibody for antigen binding. The test antibodies have one antigen-binding V-region in common from the nonhuman reference antibody, and the other V-region selected at random from a diverse source such as a repertoire library of human antibodies. The common V-region from the reference antibody serves as a guide, positioning the test antibodies on the same epitope on the antigen, and in the same orientation, so that selection is biased toward the highest antigen-binding fidelity to the reference antibody.

Many types of reporter system can be used to detect desired interactions between test antibodies and antigen. For example, complementing reporter fragments may be linked to antigen and test antibody, respectively, so that reporter activation by fragment complementation only occurs when the test antibody binds to the antigen. When the test antibody- and antigen-reporter fragment fusions are co-expressed with a competitor, reporter activation becomes dependent on the ability of the test antibody to compete with the competitor, which is proportional to the affinity of the test antibody for the antigen. Other reporter systems that can be used include the reactivator of an auto-inhibited reporter reactivation system (RAIR) as disclosed in U.S. patent application Ser. No. 10/208,730 (Publication No. 20030198971), or competitive activation system disclosed in U.S. patent application Ser. No. 10/076,845 (Publication No. 20030157579).

With the serial epitope-guided complementarity replacement system, selection is made to identify cells expresses a single test antibody along with the competitor, antigen, and reporter components. In these cells, each test antibody competes one-on-one with the competitor for binding to a limiting amount of antigen. Activity of the reporter is proportional to the amount of antigen bound to the test antibody, which in turn is proportional to the affinity of the test antibody for the antigen and the stability of the test antibody. Test antibodies are initially selected on the basis of their activity relative to that of the reference antibody when expressed as the test antibody. The result of the first round of selection is a set of "hybrid" antibodies, each of which is comprised of the same non-human V-region from the reference antibody and a human V-region from the library, and each of which binds to the same epitope on the antigen as the reference antibody. One of more of the hybrid antibodies selected in the first round will have an affinity for the antigen comparable to or higher than that of the reference antibody.

In the second V-region replacement step, the human V-regions selected in the first step are used as guide for the selection of human replacements for the remaining non-human reference antibody V-region with a diverse library of cognate human V-regions. The hybrid antibodies selected in the first round may also be used as competitors for the second round of selection. The result of the second round of selection is a set of fully human antibodies which differ structurally from the reference antibody, but which compete with the reference antibody for binding to the same antigen. Some of the selected human antibodies bind to the same epitope on the same antigen as the reference antibody. Among these selected human antibodies, one or more binds to the same epitope with an affinity which is comparable to or higher than that of the reference antibody.

Using one of the mouse or chimeric LRP6 antibodies described above as the reference antibody, this method can be readily employed to generate human antibodies that bind to human LRP6 with the same binding specificity and the same or better binding affinity. In addition, such human LRP6 antibodies can also be commercially obtained from companies which customarily produce human antibodies, e.g., KaloBios, Inc. (Mountain View, Calif.).

Camelid Antibodies

Antibody proteins obtained from members of the camel and dromedary (*Camelus bactrianus* and *Calelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994).

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans et al., (2004) J Biol Chem 279:1256-1261; Dumoulin et al., (2003) Nature 424:783-788; Pleschberger et al. (2003) Bioconjugate Chem 14:440-448; Cortez-Retamozo et al. (2002) Int J Cancer 89:456-62; and Lauwereys et all (1998) EMBO J. 17:3512-3520. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further decreased.

The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitated drug transport across the blood brain barrier. See U.S. patent application 20040161738 published Aug. 19, 2004. These features combined with the low antigenicity to humans indicate great therapeutic potential. Further, these molecules can be fully expressed in prokaryotic cells such as *E. coli* and are expressed as fusion proteins with bacteriophage and are functional.

Accordingly, a feature of the present invention is a camelid antibody or nanobody having high affinity for LRP6. In certain embodiments herein, the camelid antibody or nanobody is naturally produced in the camelid animal, i.e., is produced by the camelid following immunization with LRP6 or a peptide fragment thereof, using techniques described herein for other antibodies. Alternatively, the LRP6 camelid nanobody is engineered, i.e., produced by selection for example from a library of phage displaying appropriately mutagenized camelid nanobody proteins using panning procedures with LRP6 as a target as described in the examples herein. Engineered nanobodies can further be customized by genetic engineering to have a half life in a recipient subject of from 45 minutes to two weeks. In a specific embodiment, the camelid antibody or nanobody is obtained by grafting the CDRs sequences of the heavy or light chain of the human antibodies of the invention into nanobody or single domain antibody framework sequences, as described for example in PCT/EP93/02214.

Multivalent Antibodies

The present invention features multivalent antibodies (e.g., biparatopic, bispecific antibodies) comprising at least two receptor binding domains for two different binding sites on one or more target(s) receptors. Clinical benefits may be provided by the binding of two or more binding specificities within one antibody (Morrison et al., (1997) Nature Biotech.

15:159-163; Alt et al. (1999) FEBS Letters 454: 90-94; Zuo et al, (2000) Protein Engineering 13:361-367; Lu et al., (2004) JBC 279:2856-2865; Lu et al., (2005) JBC 280:19665-19672; Marvin et al., (2005) Acta Pharmacologica Sinica 26:649-658; Marvin et al., (2006) Curr Opin Drug Disc Develop 9:184-193; Shen et al., (2007) J Immun Methods 218:65-74; Wu et al., (2007) Nat Biotechnol. 11:1290-1297; Dimasi et al., (2009) J. Mal Biol. 393:672-692; and Michaelson et al., (2009) mAbs 1:128-141.

The present invention is based on the discovery that the multivalent antibodies (e.g., a single LRP6 biparatopic or bispecific antibody) have the ability to inhibit both propeller 1 (e.g. Wnt1 and propeller 3 (e.g. Wnt3) ligand-mediated signaling. Furthermore, and unexpectedly, the multivalent antibodies (e.g., a single LRP6 biparatopic or bispecific antibody) display no significant potentiation of a Wnt signal. The multivalent antibodies bind to distinct LRP6 β-propeller regions. Propeller 1 antibodies bind to the β-propeller 1 domain and block propeller1-dependent Wnts such as Wnt1, Wnt2, Wnt6, Wnt7A, Wnt7B, Wnt9, Wnt10A, Wnt10B and inhibit a Wnt1 signal transduction pathway. Propeller 3 antibodies bind to the β-propeller 3 domain and block propeller3-dependent Wnts such as Wnt3a and Wnt3 and inhibit a Wnt3 signal transduction pathway. LRP6 antibodies differentiate propeller 1 and propeller 3 ligands into two separate classes and bind to distinct epitopes of the LRP6 target receptor. Conversion of fragments of the LRP6 antibodies (e.g., Fabs) to full length IgG antibody results in an antibody that potentiates (enhances) a Wnt signal in the presence of another protein such as a Wnt1 or Wnt 3 ligand.

Multivalent antibodies provide advantages over traditional antibodies for example, expanding the repertoire of targets, having new binding specificities, increased potency, and no signal potentiation. A single LRP6 multivalent antibody can bind to multiple propeller regions on a single LRP6 target receptor on the same cell, and inhibit Wnt signaling. In one embodiment, the multivalent antibody binds to any combination of a β-propeller regions selected from the group consisting of propeller 1, propeller 2, propeller 3, and propeller 4. In one embodiment, the multivalent antibody binds to propeller 1 and propeller 3 domains of LRP6. Thus, a single LRP6 multivalent antibody has increased potency of action by binding to multiple β-propeller regions and inhibiting Wnt signaling mediated by each domain. For example, a single LRP6 multivalent antibody inhibits both propeller 1 and propeller 3 mediated Wnt signaling by binding to both propeller 1 and propeller 3 domains, respectively. The increased potency of action may be due to increased avidity or better binding of the LRP6 multivalent antibody.

In one embodiment, multivalent antibodies are produced by linking an scFv to an IgG antibody. The VH and VL domains used to make an scFv may be derived from the same or from different antibodies. The scFv comprises at least one, two, three, four, five, or six CDRs.

The Fc region of the IgG antibody and the scFv fragment may be linked together in many different orientations. In one embodiment, the scFv is linked to the C-terminus of the Fc region. In other embodiments, the scFv is linked to the N-terminus of the Fc region. In other embodiments, scFvs are linked to both the N-terminus and C-terminus of the Fc region. In another embodiment, the scFv can be linked to a light chain of an antibody. The multivalent antibodies of the invention can bind multiple binding sites of a target receptor concurrently. The receptor binding domains of multivalent antibodies of the invention may bind at least 1, 2, 3, 4, 5, 6, 7, 8 or more binding sites. Each receptor binding domain can be specific for the same binding site. The multivalent antibodies of the invention comprise one or more receptor binding domains that are specific for distinct epitopes on the same target receptor, e.g., β-propeller 1 domain or β-propeller 3 domain of LRP6. Alternatively, the multivalent antibodies of the invention comprise one or more receptor binding domains that are specific for epitopes on different target receptors, e.g., LRP6 and a receptor that is not LRP6 such as Erb, cmet, IGFR1, Smoothened, and Notch receptors.

Each receptor binding domain within the multivalent antibodies of the invention can also have different (i.e. a higher or lower) affinity for the antigen compared to the traditional antibodies.

In one embodiment, the multivalent antibodies of the invention are biparatopic antibody comprising at least one receptor binding domain for a first eptiope on LRP6 target receptor and a second receptor binding domain for a second epitope on the same LRP6 target receptor.

The multivalent antibody of the invention comprises at least one CDR of an antibody, at least two CDRs of a given antibody, or at least three CDRs of a given antibody, at least four CDRs of a given antibody, at least five CDRs of a given antibody, or at least six CDRs of a given antibody. The multivalent antibody of the invention comprises at least one VH domain of an antibody, at least one VL domain of a given antibody, or at least one VH domain and one VL domain of an antibody. ScFv molecules can be constructed in a VH-linker-VL orientation or VL-linker-VH orientation.

The stability of scFv molecules of the invention or fusion proteins comprising them can be evaluated in reference to the biophysical properties (e.g., thermal stability) of a conventional control scFv molecule or a full length antibody. In one embodiment, the multivalent antibodies of the invention have a thermal stability that is greater than about 0.1, about 0.25, about 0.5, about 0.75, about 1, about 1.25, about 1.5, about 1.75, about 2, about 2.5, about 3, about 3.5, about 4, about 4.5, about 5, about 5.5, about 6, about 6.5, about 7, about 7.5, about 8, about 8.5, about 9, about 9.5, about 10 degrees, about 11 degrees, about 12 degrees, about 13 degrees, about 14 degrees, or about 15 degrees Celsius than a control binding molecule (e.g. a conventional scFv molecule).

The scFv molecules comprise an scFv linker with an optimized length and/or amino acid composition. Preferred scFv linkers of the invention improve the thermal stability of a multivalent antibody of the invention by at least about 2° C. or 3° C. as compared to a conventional antibody. In one embodiment, a multivalent antibody of the invention has a 1° C. improved thermal stability as compared to a conventional antibody. In another embodiment, a multivalent antibody of the invention has a 2° C. improved thermal stability as compared to a conventional antibody. In another embodiment, a multivalent antibody of the invention has a 4, 5, 6, 7, 8, 9, 10, 11, 12, 13, 14, 15° C. improved thermal stability as compared to a conventional antibody. Comparisons can be made, for example, between the scFv molecules of the invention and scFv molecules made using prior art methods or between scFv molecules and Fab fragments of an antibody from which the scFv VH and VL were derived. Thermal stability can be measured using methods known in the art. For example, in one embodiment, Tm can be measured. Methods for measuring Tm and other methods of determining protein stability are described in more detail below.

In one embodiment, the scFv linker consists of the amino acid sequence $(Gly_4Ser)_3$ or comprises a $(Gly_4Ser)_4$ sequence. Other exemplary linkers comprise or consist of $((Gly_4Ser)_5$ and $(Gly_4Ser)_6$ sequences. scFv linkers of the invention can be of varying lengths. In one embodiment, an scFv linker of the invention is from about 5 to about 50 amino acids in length. In another embodiment, an scFv linker of the invention is from about 10 to about 40 amino acids in length. In another embodiment, an scFv linker of the invention is from about 15 to about 30 amino acids in length. In another embodiment, an scFv linker of the invention is from about 15 to about 20 amino acids in length. Variation in linker length may retain or enhance activity, giving rise to superior efficacy in activity studies. scFv linkers can be introduced into polypeptide sequences using techniques known in the art. For example, PCR mutagenesis can be used. Modifications can be confirmed by DNA sequence analysis. Plasmid DNA can be used to transform host cells for stable production of the polypeptides produced.

In one embodiment, a scFv molecule of the invention comprises an scFv linker having the amino acid sequence of $(Gly_4Ser)_3$ or $(Gly_4Ser)_4$ interposed between a VH domain and a VL domain, wherein the VH and VL domains are linked by a disulfide bond.

The scFv molecules of the invention can further comprise at least one disulfide bond which links an amino acid in the VL domain with an amino acid in the VH domain. Cysteine residues are necessary to provide disulfide bonds. Disulfide bonds can be included in an scFv molecule of the invention, e.g., to connect FR4 of VL and FR2 of VH or to connect FR2 of VL and FR4 of VH. Exemplary positions for disulfide bonding include: 43, 44, 45, 46, 47, 103, 104, 105, and 106 of VH and 42, 43, 44, 45, 46, 98, 99, 100, and 101 of VL, Kabat numbering. Modifications of the genes which encode the VH and VL domains may be accomplished using techniques known in the art, for example, site-directed mutagenesis.

Mutations in scFv alter the stability of the scFv and improve the overall stability of the multivalent antibody comprising the mutated scFv compared to a multivalent antibody without the mutated in the scFv. Mutations to the scFv can be generated as shown in the Examples. Stability of the mutated scFv is compared against the unmutated scFv using measurements such as Tm, temperature denaturation and temperature aggregation as described in the Examples. The binding capacity of the mutant scFvs can be determined using assays such as ELISA.

In one embodiment, a multivalent antibody of the invention comprises at least one mutation in an scFv such that the mutated scFv confers improved stability to the multivalent antibody. In another embodiment, a multivalent antibody of the invention comprises at least 1, 2, 3, 4, 5, 6, 7, 8, 9, 10 mutations in an scFv such that the mutated scFv confers improved stability to the multivalent antibody. In another embodiment, a multivalent antibody of the invention comprises a combination of mutations in an scFv such that the mutated scFv confers improved stability to the multivalent antibody.

Multivalent antibodies, such as biparatopic antibodies of the invention are disclosed herein. These biparatopic antibodies bind to one or more epitopes of LRP6. ScFvs are linked to an Fc region, for example at the hinge region, using linkers such as GlySer linkers. In one embodiment, the invention pertains to an antibody or antigen binding fragment that binds to the β-propeller 1 domain of LRP6 linked to an scFv that binds to the β-propeller 3 domain of LRP6 using a $(GlyGlySer)_2$ linker lined to the CH3 region of the Fc. In one embodiment, a full length IgG antibody that binds to the LPR6 β-propeller 1 domain is used to attach a scFv fragment of an antibody that binds to the LRP6 β-propeller 3 domain.

Multivalent antibodies, such as biparatopic antibodies of the invention can be constructed using any combination of heavy and light chain sequences shown in Table 2.

TABLE 2

Biparatopic Constructs of the Invention

| Construct | Heavy Chain SEQ ID NO: | Light Chain SEQ ID NO: |
|---|---|---|
| BiPa Propeller 1 IgG/Propeller 3 scFv attached to Fc | 166, 171, 173, 175, 195, 201, and 207 | 170, 193, 199, and 205 |
| Alternative BiPa Propeller 1 IgG/Propeller 3 scFv attached to light chain | 177 | 181 |
| Reverse BiPa Propeller 3 IgG/Propeller 1 scFv attached to Fc | 187, and 189 | 185 |

Accordingly, the invention pertains to biparatopic antibodies constructed using a Propeller 1 IgG antibody and a Propeller 3 scFv. In one embodiment, the biparatopic antibody is constructed using any heavy chains sequence selected from the group consisting of SEQ ID NOs: 166, 171, 173, 175, 195, 201, and 207; and any light chain sequence selected from the group consisting of SEQ ID NOs: 170, 193, 199, and 205. In one embodiment, the biparatopic antibody comprises heavy and light chain sequences selected from the group consisting of SEQ ID NOs: 166/170, 171/170, 173/170, 175/170, 201/199, 207/205, and 195/193.

In one embodiment, the biparatopic antibody comprises heavy chain SEQ ID NO: 166 and light chain SEQ ID NO: 170. In one embodiment, the biparatopic antibody comprises heavy chain SEQ ID NO: 171 and light chain SEQ ID NO: 170. In one embodiment, the biparatopic antibody comprises heavy chain SEQ ID NO: 173 and light chain SEQ ID NO: 170. In one embodiment, the biparatopic antibody comprises heavy chain SEQ ID NO: 175 and light chain SEQ ID NO: 170. In one embodiment, the biparatopic antibody comprises heavy chain SEQ ID NO: 201 and light chain SEQ ID NO: 199. In one embodiment, the biparatopic antibody comprises heavy chain SEQ ID NO: 207 and light chain SEQ ID NO: 205. In one embodiment, the biparatopic antibody comprises heavy chain SEQ ID NO: 195 and light chain SEQ ID NO: 193.

In another embodiment, the biparatopic antibody is an "alternative biparatopic antibody" whereby the scFv is attached to the light chain of IgG. In one embodiment, the biparatopic antibody comprises heavy chain SEQ ID NO: 177 and light chain SEQ ID NO: 181.

In another embodiment, a full length IgG antibody that binds to the LPR6 β-propeller 3 domain is used to attach a scFv fragment of an antibody that binds to the LRP6 β-propeller 1 domain, referred to as "reverse biparatopic". In one embodiment, reverse biparatopic antibodies of the invention are constructed using a Propeller 3 IgG antibody and a Propeller 1 scFv. In one embodiment, a reverse biparatopic antibody is constructed using any heavy chains sequence selected from the group consisting of SEQ ID NOs: 187 and 189; and a light chain sequence SEQ ID NO: 185. In one embodiment, the reverse biparatopic antibody comprises heavy SEQ ID NO: 187 and light chain SEQ ID NO: 185. In one embodiment, the reverse biparatopic antibody comprises heavy chain SEQ ID NO: 189 and light chain SEQ ID NO: 185.

The invention also pertains to biparatopic antibodies having a heavy chain variable region comprising a CDR1 sequences having an amino acid sequence selected from the group consisting of 1, 21, and 47, CDR2 sequences having an amino acid sequence selected from the group consisting of 2, 22, and 48, CDR3 sequences having an amino acid sequence selected from the group consisting of 3, 23, and 49, respectively; a light chain a light chain variable region comprising a CDR1 sequences having an amino acid sequence selected from the group consisting of 4, 24, and 50, CDR2 sequences having an amino acid sequence selected from the group consisting of 5, 25, and, 51, CDR3 sequences having an amino acid sequence selected from the group consisting of 6, 26, and 52; combined with a heavy chain variable region comprising a CDR1 sequences having an amino acid sequence selected from the group consisting of 69, 93, and 115, CDR2 sequences having an amino acid sequence selected from the group consisting of 70, 94, and 116, CDR3 sequences having an amino acid sequence selected from the group consisting of 71, 95, and 117, respectively; a light chain a light chain variable region comprising a CDR1 sequences having an amino acid sequence selected from the group consisting of 72, 96, and 118, CDR2 sequences having an amino acid sequence selected from the group consisting of 73, 97, and 119, CDR3 sequences having an amino acid sequence selected from the group consisting of 74, 98 and 120; the antibody binds to LRP6 (e.g., human and/or cynomologous LRP6) and inhibits LRP6 biological activity which can be measured in a Wnt reporter gene assay or any other measure of Wnt directed signaling (e.g., LRP6 phosphorylation, β-catenin stabilization and nuclear translocation, cellular proliferation/survival) as described herein.

Antibodies that can be employed in the multivalent antibodies of the invention are human, murine, chimeric and humanized monoclonal antibodies.

The multivalent antibodies of the present invention can be prepared by conjugating the constituent receptor binding domains, using methods known in the art. For example, each receptor binding domain of the multivalent antibody can be generated separately and then conjugated to one another. When the receptor binding domains are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohaxane-1-carboxylate (sulfo-SMCC) (see e.g., Karpovsky et al., (1984) J. Exp. Med. 160:1686; Liu et al. (1985) Proc. Natl. Acad. Sci. USA 82:8648). Other methods include those described in Paulus (1985) Behring Ins. Mitt. No. 78:118-132; Brennan et al., (1985) Science 229:81-83), and Glennie et al., (1987) J. Immunol. 139: 2367-2375). Conjugating agents are SATA and sulfo-SMCC, both available from Pierce Chemical Co. (Rockford, Ill.).

When the receptor binding domains are antibodies, they can be conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, the receptor binding domains can be encoded in the same vector and expressed and assembled in the same host cell. This method is particularly useful where the multivalent antibody is a mAb×mAb, mAb×Fab, Fab×F$(ab')_2$ or ligand x Fab fusion protein. Methods for preparing multivalent antibodies are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the multivalent antibodies to their targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

In another aspect, the present invention provides multivalent antibodies comprising at least two different receptor binding domains of the antibodies of the invention binding to LRP6. The receptor binding domains can be linked together via protein fusion or covalent or non covalent linkage. Tetravalent antibodies can be obtained for example by cross-linking the antibodies of the invention with an antibody that binds to the constant regions of the antibodies of the invention, for example the Fc or hinge region.

Multivalent Antibody Orientation

The invention pertains to multivalent antibodies that have multiple receptor binding domains ("RBD"), which include for example, antibody variable regions, antibody fragments (e.g., Fabs), scFvs, single chain diabodies, or IgG antibodies. Examples of RBDs are components of a Fab fragment, a monovalent fragment consisting of the VL, VH, CL and CH1 domains; a $F(ab)_2$ fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., (1989) Nature 341:544-546), which consists of a VH domain; and an isolated complementarity determining region (CDR). RBDs also are also components of single domain antibodies, maxibodies, unibodies, minibodies, diabodies, triabodies, tetrabodies, v-NAR and bis-scFv (see, e.g., Hollinger and Hudson, (2005) Nature Biotechnology 23: 1126-1136.

The multivalent antibodies of the invention are generated in any orientation using at least one receptor binding domain (e.g., an scFv, a single chain diabody, an antibody variable region) as long as the resulting multivalent antibodies retain functional activity (e.g., inhibiting Wnt signaling). It should be understood that any number of receptor binding domains can be added to the C-terminus and/or N-terminus of the Fc as long as the resulting multivalent antibodies retain functional activity (e.g., inhibiting Wnt signaling). In an embodiment, one, two, three, or more receptor binding domains are linked to the C-terminus of the Fc region. In other embodiments one, two, three, or more receptor binding domains are linked to the N-terminus of the Fc region. In other embodiments, one, two, three, or more receptor binding domains are linked to both the N-terminus and C-terminus of the Fc region. For example, multivalent antibodies of the invention can comprise more than one receptor binding domain of the same type linked to the C-terminus and/or N-terminus of an Fc region, e.g., scFv-scFv-Fc-IgG. Alternatively, the multivalent antibodies of the invention can comprise more than one receptor binding domain of a different type linked to the C-terminus and/or N-terminus of the Fc region, e.g., scFv-diabody-Fc-IgG. In another embodiment, one, two, three or more receptor binding domains (e.g., scFv) are linked to the C-terminus of an IgG. In another embodiment, one, two, three or more receptor binding domains (e.g., scFv) are linked to the N-terminus of an IgG. In another embodiment, one, two, three or more receptor binding domains (e.g., scFv) are linked to the N-terminus and C-terminus of an IgG.

In other embodiments, the multivalent antibodies of the invention are generated using more than one receptor binding domain of a different type linked to the C-terminus, e.g., scFv-diabody-Fc-IgG; diabody-scFv-Fc-IgG; scFv-scFv-diabody-Fc-IgG; scFv-diabody-scFv-Fc-IgG; diabody-scFv-scFv-Fc-IgG; antibody variable region-scFv-diabody-Fc-IgG; and the like. Multivalent antibodies with any number of permutations of receptor binding domains can be generated. These multivalent antibodies can be tested for functionality using the methods and assays described within.

In other embodiments, the multivalent antibodies of the invention are generated using more than one receptor binding domain of a different type linked to the N-terminus, e.g., IgG-Fc-scFv-diabody; IgG-Fc-diabody-scFv; IgG-Fc-scFv-scFv-diabody; IgG-Fc-scFv-diabody-scFv; IgG-Fc-diabody-scFv-scFv; IgG-Fc-antibody variable region-scFv-diabody; and the like.

In yet other embodiments, multivalent antibodies of the invention are generated using a single receptor binding domain (e.g., an scFv, a single chain diabody, an antibody variable region) linked to the C-terminus and N-terminus of the Fc region. In another embodiment, multiple receptor binding domains are linked to the N-terminus of the Fc region, for example, at least 1, 2, 3, 4, 5, 6, 7, 8 or more receptor binding domains linked to the C-terminus and N-terminus of the Fc region. For example, the multivalent antibodies of the invention can comprise one or more scFvs linked to the C-terminus and N-terminus of the Fc region, e.g., scFv-Fc-scFv-scFv; -scFv-scFv-Fc-scFv-scFv, and the like. In other embodiments, the multivalent antibodies of the invention are generated using more than one receptor binding domain of a different type linked to the N-terminus, e.g., scFv-Fc-scFv-diabody; scFv-Fc-diabody-scFv; scFv-Fc-scFv-scFv-diabody; scFv-Fc-scFv-diabody-scFv; scFv-Fc-diabody-scFv-scFv; scFv-Fc-antibody variable region-scFv-diabody; and the like Multivalent antibodies with any number of permutations of receptor binding domains can be generated. These multivalent antibodies can be tested for functionality using the methods and assays described within.

Linker Length

It is known that linker length can greatly affect how the variable regions of an scFv fold and interact. In fact, if a short linker is employed (e.g., between 5-10 amino acids; between 5-20 amino acids) intrachain folding is prevented and interchain folding is required to bring the two variable regions together to form a functional epitope binding site. For examples of linker orientation and size see, e.g., Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, is incorporated herein by reference.

It is also understood that the receptor binding domains may be separated by linker regions of various lengths. The receptor binding domains can be separated from each other, a Ckappa/lambda, CH1, Hinge, CH2, CH3, or the entire Fc region by a linker sequence. Such linker sequence may comprise a random assortment of amino acids, or a restricted set of amino acids. Such linker sequence may be flexible or rigid.

The multivalent antibodies of the invention comprise a linker sequence of at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, or more amino acid residues between one or more of its receptor binding domains, Ckappa/lambda domains, CH1 domains, Hinge region, CH2 domains, CH3 domains, or Fc regions. The linker sequence may be comprised of any naturally occurring amino acid. In some embodiments, the amino acids glycine and serine comprise the amino acids within the linker sequence. In another embodiment, the linker region orientation comprises sets of glycine repeats $(Gly_4Ser)_n$, where n is a positive integer equal to or greater than 1.

In one embodiment, the linkers include, but are not limited to, $(Gly_4\ Ser)_4$ or $(Gly_4Ser)_3$. In another embodiment, the linkers Glu and Lys residues can be interspersed within the Gly-Ser linkers for better solubility. In another embodiment, the linkers include multiple repeats of $(Gly_2Ser)$, (GlySer) or $(Gly_3Ser)$. In another embodiment, the linkers include combinations and multiples of $(Gly_3Ser)+(Gly_4Ser)+(GlySer)$. In another embodiment, Ser can be replaced with Ala e.g., $(Gly_4Ala)$ or $(Gly_3Ala)$. In yet another embodiment, the linker comprises the motif $(GluAlaAlaAlaLys)_n$, where n is a positive integer equal to or greater than 1.

Hinge Region

The multivalent antibodies of the invention may comprise all or at least a portion of an antibody Hinge region. The Hinge region or portion thereof may be connected directly to an receptor binding domain, a CH1, a Ckappa/lambda, a CH2, or a CH3. In one embodiment, the Hinge region, or portion thereof may be connected through a variable length linker region to a receptor binding domain, a CH1, a Ckappa/lambda, a CH2, or a CH3.

The multivalent antibodies of the invention can comprise 1, 2, 3, 4, 5, 6, or more Hinge regions or portions thereof. The Hinge regions or portions thereof can either be identical or be different. In one embodiment, the multivalent antibodies of the invention comprise a Hinge region or portion thereof from a human IgG1 molecule. In further embodiments, the Hinge region or portion thereof may be engineered to remove a naturally occurring cysteine residue, introduce a non-naturally occurring cysteine residue, or substitute a naturally occurring residue for a non-naturally occurring cysteine residue. In some embodiments, the multivalent antibodies of the invention contain at least one Hinge region or portion thereof that comprises the following amino acids sequence comprising: EPKSCDKTHTCPPCP (SEQ ID NO: 211) or EPKSC (SEQ ID NO: 212). In some embodiments, at least one Hinge region or portion thereof is engineered to substitute at least one naturally occurring cysteine residue with another amino acid residue. In some embodiments, at least one naturally occurring cysteine residue is substituted with serine.

Non-naturally occurring cysteine residues useful for site-specific conjugation can be engineered into the multivalent antibodies of the invention. Such approaches, compositions and methods are exemplified in U.S. Provisional Patent Application Ser. No. 61/022,073 filed Jan. 18, 2008, entitled “Cysteine Engineered Antibodies for Site-Specific Conjugation” and U.S. Patent Application Publication No. 20070092940, filed Sep. 22, 2005, each of which are hereby incorporated by reference in its entirety for all purposes.

Methods of Evaluating Protein Stability

To assess the stability of multivalent antibodies, the stability of the least stable domain of a multidomain protein is predicted using the methods of the invention and those described below.

Such methods allow for the determination of multiple thermal unfolding transitions where the least stable domain either unfolds first or limits the overall stability threshold of a multidomain unit that unfolds cooperatively (i.e. a multidomain protein which exhibits a single unfolding transition). The least stable domain can be identified in a number of additional ways. Mutagenesis can be performed to probe which domain limits the overall stability. Additionally, protease resistance of a multidomain protein can be performed under conditions where the least stable domain is known to be intrinsically unfolded via DSC or other spectroscopic methods (Fontana, et al., (1997) Fold. Des., 2: R17-26; Dimasi et al. (2009) J.

Mal. Biol. 393: 672-692). Once the least stable domain is identified, the sequence encoding this domain (or a portion thereof) may be employed as a test sequence in the methods of the invention.

a) Thermal Stability

The thermal stability of the compositions of the invention may be analyzed using a number of non-limiting biophysical or biochemical techniques known in the art. In certain embodiments, thermal stability is evaluated by analytical spectroscopy.

An exemplary analytical spectroscopy method is Differential Scanning calorimetry (DSC). DSC employs a calorimeter which is sensitive to the heat absorbances that accompany the unfolding of most proteins or protein domains (see, e.g. Sanchez-Ruiz, et al., Biochemistry, 27: 1648-52, 1988). To determine the thermal stability of a protein, a sample of the protein is inserted into the calorimeter and the temperature is raised until the Fab or scFv unfolds. The temperature at which the protein unfolds is indicative of overall protein stability.

Another exemplary analytical spectroscopy method is Circular Dichroism (CD) spectroscopy. CD spectrometry measures the optical activity of a composition as a function of increasing temperature. Circular dichroism (CD) spectroscopy measures differences in the absorption of left-handed polarized light versus right-handed polarized light which arise due to structural asymmetry. A disordered or unfolded structure results in a CD spectrum very different from that of an ordered or folded structure. The CD spectrum reflects the sensitivity of the proteins to the denaturing effects of increasing temperature and is therefore indicative of a protein's thermal stability (see van Mierlo and Steemsma, J. Biotechnol., 79(3):281-98, 2000).

Another exemplary analytical spectroscopy method for measuring thermal stability is Fluorescence Emission Spectroscopy (see van Mierlo and Steemsma, supra). Yet another exemplary analytical spectroscopy method for measuring thermal stability is Nuclear Magnetic Resonance (NMR) spectroscopy (see, e.g. van Mierlo and Steemsma, supra).

The thermal stability of a composition of the invention can be measured biochemically. An exemplary biochemical method for assessing thermal stability is a thermal challenge assay. In a "thermal challenge assay", a composition of the invention is subjected to a range of elevated temperatures for a set period of time. For example, in one embodiment, test scFv molecules or molecules comprising scFv molecules are subject to a range of increasing temperatures, e.g., for 1-1.5 hours. The activity of the protein is then assayed by a relevant biochemical assay. For example, if the protein is a binding protein (e.g. an scFv or scFv-containing polypeptide of the invention) the binding activity of the binding protein may be determined by a functional or quantitative ELISA.

Such an assay may be done in a high-throughput format and those disclosed in the Examples using *E. coli* and high throughput screening. A library of scFv variants may be created using methods known in the art. scFv expression may be induced an scFvs may be subjected to thermal challenge. The challenged test samples may be assayed for binding and those scFvs which are stable may be scaled up and further characterized.

Thermal stability is evaluated by measuring the melting temperature (Tm) of a composition of the invention using any of the above techniques (e.g. analytical spectroscopy techniques). The melting temperature is the temperature at the midpoint of a thermal transition curve wherein 50% of molecules of a composition are in a folded state (See e.g., Dimasi et al. (2009) J. Mol Biol. 393: 672-692). In one embodiment, Tm values for a scFv are about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C. In one embodiment, Tim values for an IgG is about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C. In one embodiment, Tm values for an multivalent antibody is about 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C.

Thermal stability is also evaluated by measuring the specific heat or heat capacity (Cp) of a composition of the invention using an analytical calorimetric technique (e.g. DSC). The specific heat of a composition is the energy (e.g. in kcal/mol) required to raise by 1° C., the temperature of 1 mol of water. As large Cp is a hallmark of a denatured or inactive protein composition. The change in heat capacity (ΔCp) of a composition is measured by determining the specific heat of a composition before and after its thermal transition. Thermal stability may also be evaluated by measuring or determining other parameters of thermodynamic stability including Gibbs free energy of unfolding (ΔG), enthalpy of unfolding (ΔH), or entropy of unfolding (ΔS).

One or more of the above biochemical assays (e.g. a thermal challenge assay) is used to determine the temperature (i.e. the $T_C$ value) at which 50% of the composition retains its activity (e.g. binding activity).

In addition, mutations to the scFv alter the thermal stability of the scFv compared with the unmutated scFv. When the mutated scFv is incorporated into a multivalent antibody, the mutated scFv confers thermal stability to the overall multivalent antibody. In one embodiment, the scFv comprises a single mutation that confers thermal stability to the scFv. In another embodiment, the scFv comprises multiple mutations that confer thermal stability to the scFv. In one embodiment, the multiple mutations in the scFv have an additive effect on thermal stability of the scFv.

b) % Aggregation

The stability of a composition of the invention can be determined by measuring its propensity to aggregate. Aggregation can be measured by a number of non-limiting biochemical or biophysical techniques. For example, the aggregation of a composition of the invention may be evaluated using chromatography, e.g. Size-Exclusion Chromatograpy (SEC). SEC separates molecules on the basis of size. A column is filled with semi-solid beads of a polymeric gel that will admit ions and small molecules into their interior but not large ones. When a protein composition is applied to the top of the column, the compact folded proteins (ie. non-aggregated proteins) are distributed through a larger volume of solvent than is available to the large protein aggregates. Consequently, the large aggregates move more rapidly through the column, and in this way the mixture can be separated or fractionated into its components. Each fraction can be separately quantified (e.g. by light scattering) as it elutes from the gel. Accordingly, the % aggregation of a composition of the invention can be determined by comparing the concentration of a fraction with the total concentration of protein applied to the gel. Stable compositions elute from the column as essentially a single fraction and appear as essentially a single peak in the elution profile or chromatogram.

c) Binding Affinity

The stability of a composition of the invention can be assessed by determining its target binding affinity. A wide variety of methods for determining binding affinity are known in the art. An exemplary method for determining binding affinity employs surface plasmon resonance. Surface plasmon resonance is an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jonsson, U., et al. (1993) Ann. Biol. Clin. 51:19-26; Jonsson, U., i (1991) Biotechniques 11:620-627; Johnsson, B., et al. (1995) J. Mol. Recognit. 8:125-131; and Johnnson, B., et al. (1991) Anal. Biochem. 198:268-277.

Antibodies with Extended Half Life

The present invention provides for antibodies and multivalent antibodies that specifically bind to LRP6 protein which have an extended half-life in vivo. Many factors may affect a protein's half life in vivo. For examples, kidney filtration, metabolism in the liver, degradation by proteolytic enzymes (proteases), and immunogenic responses (e.g., protein neutralization by antibodies and uptake by macrophages and dentritic cells). A variety of strategies can be used to extend the half life of the antibodies of the present invention. For example, by chemical linkage to polyethyleneglycol (PEG), reCODE PEG, antibody scaffold, polysialic acid (PSA), hydroxyethyl starch (HES), albumin-binding ligands, and carbohydrate shields; by genetic fusion to proteins binding to serum proteins, such as albumin, IgG, FcRn, and transferring; by coupling (genetically or chemically) to other binding moieties that bind to serum proteins, such as nobodies, Fabs, DARPins, avimers, affibodies, and anticalins; by genetic fusion to rPEG, albumin, domain of albumin, albumin-binding proteins, and Fc; or by incorporation into nancarriers, slow release formulations, or medical devices.

To prolong the serum circulation of antibodies in vivo, inert polymer molecules such as high molecular weight PEG can be attached to the antibodies with or without a multifunctional linker either through site-specific conjugation of the PEG to the N- or C-terminus of the antibodies or via epsilon-amino groups present on lysine residues. To pegylate, a antibody typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Linear or branched polymer derivatization that results in minimal loss of biological activity will be used. The degree of conjugation can be closely monitored by SDS-PAGE and mass spectrometry to ensure proper conjugation of PEG molecules to the antibody. Unreacted PEG can be separated from antibody-PEG conjugates by size-exclusion or by ion-exchange chromatography. PEG-derivatized antibodies can be tested for binding activity as well as for in vivo efficacy using methods well-known to those of skill in the art, for example, by immunoassays described herein. Methods for pegylating proteins are known in the art and can be applied to the antibodies of the invention. See for example, EP 0 154 316 by Nishimura et al. and EP 0 401 384 by Ishikawa et al.

Other modified pegylation technologies include reconstituting chemically orthogonal directed engineering technology (ReCODE PEG), which incorporates chemically specified side chains into biosynthetic proteins via a reconstituted system that includes tRNA synthetase and tRNA. This technology enables incorporation of more than 30 new amino acids into biosynthetic proteins in *E. coli*, yeast, and mammalian cells. The tRNA incorporates a normative amino acid any place an amber codon is positioned, converting the amber from a stop codon to one that signals incorporation of the chemically specified amino acid.

Recombinant pegylation technology (rPEG) can also be used for serum halflife extension. This technology involves genetically fusing a 300-600 amino acid unstructured protein tail to an existing pharmaceutical protein. Because the apparent molecular weight of such an unstructured protein chain is about 15-fold larger than its actual molecular weight, the serum halflife of the protein is greatly increased. In contrast to traditional PEGylation, which requires chemical conjugation and repurification, the manufacturing process is greatly simplified and the product is homogeneous.

Polysialytion is another technology, which uses the natural polymer polysialic acid (PSA) to prolong the active life and improve the stability of therapeutic peptides and proteins, such as antibodies of the invention. PSA is a polymer of sialic acid (a sugar). When used for protein and therapeutic peptide drug delivery, polysialic acid provides a protective microenvironment on conjugation. This increases the active life of the therapeutic protein in the circulation and prevents it from being recognized by the immune system. The PSA polymer is naturally found in the human body. It was adopted by certain bacteria which evolved over millions of years to coat their walls with it. These naturally polysialylated bacteria were then able, by virtue of molecular mimicry, to foil the body's defense system. PSA, nature's ultimate stealth technology, can be easily produced from such bacteria in large quantities and with predetermined physical characteristics. Bacterial PSA is completely non-immunogenic, even when coupled to proteins, as it is chemically identical to PSA in the human body.

Another technology include the use of hydroxyethyl starch ("HES") derivatives linked to antibodies. HES is a modified natural polymer derived from waxy maize starch and can be metabolized by the body's enzymes. HES solutions are usually administered to substitute deficient blood volume and to improve the rheological properties of the blood. Hesylation of an antibody enables the prolongation of the circulation half-life by increasing the stability of the molecule, as well as by reducing renal clearance, resulting in an increased biological activity. By varying different parameters, such as the molecular weight of HES, a wide range of HES antibodies conjugates can be customized.

Antibodies having an increased half-life in vivo can also be generated introducing one or more amino acid modifications (i.e., substitutions, insertions or deletions) into an IgG constant domain, or FcRn binding fragment thereof (preferably a Fc or hinge Fc domain fragment). See, e.g., International Publication No. WO 98/23289; International Publication No. WO 97/34631; and U.S. Pat. No. 6,277,375.

Further, antibodies can be conjugated to albumin in order to make the antibodies more stable in vivo or have a longer half life in vivo. The techniques are well-known in the art, see, e.g., International Publication Nos. WO 93/15199, WO 93/15200, and WO 01/77137; and European Patent No. EP 413,622.

Antibody Conjugates

The present invention provides antibodies and multivalent antibodies thereof that specifically bind to a LRP6 protein recombinantly fused or chemically conjugated (including both covalent and non-covalent conjugations) to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. In particular, the invention provides fusion proteins comprising an antigen-binding fragment of antibodies described herein (e.g., a Fab fragment, Fd fragment, Fv fragment, $F(ab)_2$ fragment, a VH domain, a VH CDR, a VL domain or a VL CDR) and a heterologous protein, polypeptide, or peptide. Methods for fusing or conjugating proteins, polypeptides, or peptides to an antibody or an antibody fragment are known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International Publication Nos. WO 96/04388 and WO 91/06570; Ashkenazi et al., (1991) Proc. Natl. Acad. Sci. USA 88:10535-10539; Zheng et al., (1995) J. Immunol. 154:5590-5600; and Vil et al., (1992) Proc. Natl. Acad. Sci. USA 89:11337-11341.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention (e.g., multivalent, biparatopic or bispecific antibodies or fragments thereof with higher affinities and lower dissociation rates). See, generally, U.S. Pat. Nos. 5,605,793; 5,811,238; 5,830,721; 5,834,252; and 5,837,458; Patten et al., (1997) Curr. Opinion Biotechnol. 8:724-33; Harayama, (1998) Trends Biotechnol. 16(2):76-82; Hansson et al., (1999) J. Mol. Biol. 287:265-76; and Lorenzo and Blasco, (1998) Biotechniques 24(2):308-313 (each of these patents and publications are hereby incorporated by reference in its entirety). Antibodies or fragments thereof, or the encoded antibodies or fragments thereof, may be altered by being subjected to random mutagenesis by error-prone PCR, random nucleotide insertion or other methods prior to recombination. A polynucleotide encoding a multivalent antibody or fragment thereof that specifically binds to a LRP6 protein may be recombined with one or more components, motifs, sections, parts, domains, fragments, etc. of one or more heterologous molecules.

Moreover, the antibodies or fragments thereof can be fused to marker sequences, such as a peptide to facilitate purification. In one embodiment, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., (1989) Proc. Natl. Acad. Sci. USA 86:821-824, for instance, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., (1984) Cell 37:767), and the "flag" tag.

In other embodiments, antibodies of the present invention or fragments thereof conjugated to a diagnostic or detectable agent. Such antibodies can be useful for monitoring or prognosing the onset, development, progression and/or severity of a disease or disorder as part of a clinical testing procedure, such as determining the efficacy of a particular therapy. Such diagnosis and detection can accomplished by coupling the antibodies to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine ($^{131}I$, $^{125}I$, $^{123}I$, and $^{121}I$,), carbon ($^{14}C$), sulfur ($^{35}S$), tritium ($^{3}H$), indium ($^{115}In$, $^{113}In$, $^{112}In$, and $^{111}In$,), technetium ($^{99}Tc$), thallium ($^{201}Ti$), gallium ($^{68}Ga$, $^{67}Ga$), palladium ($^{103}Pd$), molybdenum ($^{99}Mo$), xenon ($^{133}Xe$), fluorine ($^{18}F$), $^{153}Sm$, 171Lu, $^{159}Gd$, 149Pm, $^{140}La$, $^{175}Yb$, $^{166}Ho$, $^{90}Y$, 47Sc, $^{186}Re$, $^{188}Re$, $^{142}Pr$, $^{105}Rh$, $^{97}Ru$, $^{68}Ge$, $^{57}Co$, $^{65}Zn$, $^{85}Sr$, $^{32}P$, $^{153}Gd$, $^{169}Yb$, $^{51}Cr$, $^{54}Mn$, $^{75}Se$, $^{113}Sn$, and $^{117}Tin$; and positron emitting metals using various positron emission tomographies, and noradioactive paramagnetic metal ions.

The present invention further encompasses uses of antibodies or fragments thereof conjugated to a therapeutic moiety. The antibodies or fragment thereof may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells.

Further, antibodies or fragments thereof may be conjugated to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, *pseudomonas* exotoxin, cholera toxin, or diphtheria toxin; a protein such as tumor necrosis factor, α-interferon, β-interferon, nerve growth factor, platelet derived growth factor, tissue plasminogen activator, an apoptotic agent, an anti-angiogenic agent; or, a biological response modifier such as, for example, a lymphokine.

In one embodiment, the antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxon, cytochalasin B, gramicidin D, ethidium bromide, emetine, mitomycin, etoposide, tenoposide, vincristine, vinblastine, t. colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), ablating agents (e.g., mechlorethamine, thioepa chloraxnbucil, meiphalan, carmustine (BSNU) and lomustine (CCNU), cyclothosphamide, busulfan, dibromomannitol, streptozotocin, mitomycin C, and cis-dichlorodiamine platinum (II) (DDP) cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other examples of therapeutic cytotoxins that can be conjugated to a antibody of the invention include duocarmycins, calicheamicins, maytansines and auristatins, and derivatives thereof. An example of a calicheamicin antibody conjugate is commercially available (Mylotarg™; Wyeth-Ayerst).

Cytoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito et al., (2003) Adv. Drug Deliv. Rev. 55:199-215; Trail et al., (2003) Cancer Immunol. Immunother. 52:328-337; Payne, (2003) Cancer Cell 3:207-212; Allen, (2002) Nat. Rev. Cancer 2:750-763; Pastan and Kreitman, (2002) Curr. Opin. Investig. Drugs 3:1089-1091; Senter and Springer, (2001) Adv. Drug Deliv. Rev. 53:247-264.

Antibodies of the present invention also can be conjugated to a radioactive isotope to generate cytotoxic radiopharmaceuticals, also referred to as radioimmunoconjugates.

Examples of radioactive isotopes that can be conjugated to antibodies for use diagnostically or therapeutically include, but are not limited to, iodine$^{131}$, indium$^{111}$, yttrium$^{90}$, and lutetium$^{177}$. Method for preparing radioimmunconjugates are established in the art. Examples of radioimmunoconjugates are commercially available, including Zevalin™ (DEC Pharmaceuticals) and Bexxar™ (Corixa Pharmaceuticals), and similar methods can be used to prepare radioimmunoconjugates using the antibodies of the invention. In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., (1998) Clin Cancer Res. 4(10):2483-90; Peterson et al., (1999) Bioconjug. Chem. 10(4):553-7; and Zimmerman et al., (1999) Nucl. Med. Biol. 26(8):943-50, each incorporated by reference in their entireties.

Techniques for conjugating therapeutic moieties to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., (1982) Immunol. Rev. 62:119-58.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Methods of Producing Antibodies (i) Nucleic Acids Encoding the Antibodies

The invention provides substantially purified nucleic acid molecules which encode multiple epitope binding proteins, e.g., antibodies and antigen binding fragments thereof comprising segments or domains of the LRP6 antibody chains described above. Some of the nucleic acids of the invention comprise the nucleotide sequence encoding the propeller 1 antibody heavy chain variable region shown in SEQ ID NO: 14, 19, 34, and 60, and/or the nucleotide sequence encoding the light chain variable region shown in SEQ ID NO:13, 20, 33, and 59. In a specific embodiment, the nucleic acid molecules are those identified in Table 1. Some other nucleic acid molecules of the invention comprise nucleotide sequences that are substantially identical (e.g., at least 65, 80%, 95%, or 99%) to the nucleotide sequences of those identified in Table 1. Some of the nucleic acids of the invention comprise the nucleotide sequence encoding the heavy chain variable region shown in SEQ ID NO: 82, 106, and 128, and/or the nucleotide sequence encoding the light chain variable region shown in SEQ ID NO: 81, 105, and 127. In a specific embodiment, the nucleic acid molecules are those identified in Table 1. Some other nucleic acid molecules of the invention comprise nucleotide sequences that are substantially identical (e.g., at least 65, 80%, 95%, or 99%) to the nucleotide sequences of those identified in Table 1. When expressed from appropriate expression vectors, polypeptides encoded by these polynucleotides are capable of exhibiting LRP6 antigen binding capacity.

Also provided in the invention are polynucleotides which encode at least one CDR region and usually all three CDR regions from the heavy or light chain of the LRP6 antibody set forth above. Some other polynucleotides encode all or substantially all of the variable region sequence of the heavy chain and/or the light chain of the LRP6 antibody set forth above. Because of the degeneracy of the code, a variety of nucleic acid sequences will encode each of the immunoglobulin amino acid sequences.

The nucleic acid molecules of the invention can encode both a variable region and a constant region of the antibody. Some of nucleic acid sequences of the invention comprise nucleotides encoding a mature heavy chain variable region sequence that is substantially identical (e.g., at least 80%, 90%, or 99%) to the mature heavy chain variable region sequence set forth in SEQ ID NO: 14, 19, 34, and 60. Some other nucleic acid sequences comprising nucleotide encoding a mature light chain variable region sequence that is substantially identical (e.g., at least 80%, 90%, or 99%) to the mature light chain variable region sequence set forth in SEQ ID NO: 13, 20, 33, and 59.

The nucleic acid molecules of the invention can encode both a variable region and a constant region of the antibody. Some of nucleic acid sequences of the invention comprise nucleotides encoding a mature heavy chain variable region sequence that is substantially identical (e.g., at least 80%, 90%, or 99%) to the mature heavy chain variable region sequence set forth in SEQ ID NO: 82, 106, and 128. Some other nucleic acid sequences comprising nucleotide encoding a mature light chain variable region sequence that is substantially identical (e.g., at least 80%, 90%, or 99%) to the mature light chain variable region sequence set forth in SEQ ID NO: 81, 105, and 129.

The polynucleotide sequences can be produced by de novo solid-phase DNA synthesis or by PCR mutagenesis of an existing sequence (e.g., sequences as described in the Examples below) encoding an LRP6 antibody or its binding fragment. Direct chemical synthesis of nucleic acids can be accomplished by methods known in the art, such as the phosphotriester method of Narang et al., (1979) Meth. Enzymol. 68:90; the phosphodiester method of Brown et al., (1979) Meth. Enzymol. 68:109; the diethylphosphoramidite method of Beaucage et al., (1981) Tetra. Lett., 22:1859; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Mattila et al., (1991) Nucleic Acids Res. 19:967; and Eckert et al., (1991) PCR Methods and Applications 1:17.

Also provided in the invention are expression vectors and host cells for producing the antibodies described above. Various expression vectors can be employed to express the polynucleotides encoding the antibody fragments thereof. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., (1997) Nat Genet 15:345). For example, nonviral vectors useful for expression of the antibody polynucleotides and polypeptides in mammalian (e.g., human) cells include pThioHis A, B & C, pcDNA3.1/His, pEBVHis A, B & C, (Invitrogen, San Diego, Calif.), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., (1995) supra; Smith, Annu. Rev. Microbiol. 49:807; and Rosenfeld et al., (1992) Cell 68:143.

The choice of expression vector depends on the intended host cells in which the vector is to be expressed. Typically, the expression vectors contain a promoter and other regulatory sequences (e.g., enhancers) that are operably linked to the polynucleotides encoding a antibody or fragment thereof. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of the antibody or fragment thereof. These elements typically include an ATG initiation codon and adjacent ribosome binding site or other sequences. In addition, the efficiency of expression may be enhanced by the inclusion of enhancers appropriate to the cell system in use (see, e.g., Scharf et al., (1994) Results Probl. Cell Differ. 20:125; and Bittner et al., (1987) Meth. Enzymol., 153:516). For example, the SV40 enhancer or CMV enhancer may be used to increase expression in mammalian host cells.

The expression vectors may also provide a secretion signal sequence position to form a fusion protein with polypeptides encoded by inserted LRP6 antibody sequences. More often, the inserted LRP6 antibody sequences are linked to a signal sequences before inclusion in the vector. Vectors to be used to receive sequences encoding LRP6 antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the antibodies can be either prokaryotic or eukaryotic. *E. coli* is one prokaryotic host useful for cloning and expressing the polynucleotides of the present invention. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express LRP6 antibodies of the invention. Insect cells in combination with baculovirus vectors can also be used.

In some preferred embodiments, mammalian host cells are used to express and produce the antibodies of the present invention. For example, they can be either a hybridoma cell line expressing endogenous immunoglobulin genes (e.g., the 1D6.C9 myeloma hybridoma clone as described in the Examples) or a mammalian cell line harboring an exogenous expression vector (e.g., the SP2/0 myeloma cells exemplified below). These include any normal mortal or normal or abnormal immortal animal or human cell. For example, a number of suitable host cell lines capable of secreting intact immunoglobulins have been developed including the CHO cell lines, various Cos cell lines, HeLa cells, myeloma cell lines, transformed B-cells and hybridomas. The use of mammalian tissue cell culture to express polypeptides is discussed generally in, e.g., Winnacker, FROM GENES TO CLONES, VCH Publishers, N.Y., N.Y., 1987. Expression vectors for mammalian host cells can include expression control sequences, such as an origin of replication, a promoter, and an enhancer (see, e.g., Queen et al., (1986) Immunol. Rev. 89:49-68), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, (1997) Cell 88:223), agent-enhanced uptake of DNA, and ex vivo transduction. For long-term, high-yield production of recombinant proteins, stable expression will often be desired. For example, cell lines which stably express antibody domains or binding fragments can be prepared using expression vectors of the invention which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

(ii) Generation of Antibodies

Monoclonal antibodies be produced using the methods disclosed in the Examples. These antibodies or fragments thereof can be used to generate multivalent antibodies, (e.g., bispecific/biparatopic) as disclosed in the Examples section. For example, a biparatopic LRP6 antibody can be generated by linking scFvs, e.g., an scFv that binds to the 3-propeller 3 domain of LRP6, to a full length IgG monoclonal antibody.

Alternatively, monoclonal antibodies can be produced by a variety of techniques, including conventional monoclonal antibody methodology e.g., the standard somatic cell hybridization technique of Kohler and Milstein, (1975) Nature 256: 495. Many techniques for producing monoclonal antibody can be employed e.g., viral or oncogenic transformation of B lymphocytes.

An animal system for preparing hybridomas is the murine system. Hybridoma production in the mouse is a well established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art. See e.g., U.S. Pat. No. 5,225,539 to Winter, and U.S. Pat. Nos. 5,530,101; 5,585,089; 5,693,762 and 6,180,370 to Queen et al.

In a certain embodiment, the antibodies of the invention are human monoclonal antibodies. Such human monoclonal antibodies directed against LRP6 can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode un-rearranged human heavy (μ and γ) and κ light chain immunoglobulin sequences, together with targeted mutations that inactivate the endogenous μ and κ chain loci (see e.g., Lonberg, et al., (1994) Nature 368(6474): 856-859). Accordingly, the mice exhibit decreased expression of mouse IgM or κ, and in response to immunization, the introduced human heavy and light chain transgenes undergo class switching and somatic mutation to generate high affinity human IgGκ monoclonal (Lonberg et al., (1994) supra; reviewed in Lonberg, (1994) Handbook of Experimental Pharmacology 113:49-101; Lonberg and Huszar, (1995) Intern. Rev. Immunol. 13: 65-93, and Harding and Lonberg, (1995) Ann. N.Y. Acad. Sci. 764:536-546). The preparation and use of HuMAb mice, and the genomic modifications carried by such mice, is further described in Taylor et al., (1992) Nucleic Acids Research 20:6287-6295; Chen et al., (1993) International Immunology 5: 647-656; Tuaillon et al., (1993) Proc. Natl. Acad. Sci. USA 94:3720-3724; Choi et al., (1993) Nature Genetics 4:117-123; Chen et al., (1993) EMBO J. 12:821-830; Tuaillon et al., (1994) J. Immunol. 152:2912-2920; Taylor et al., (1994) International Immunology 579-591; and Fishwild et al., (1996) Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92103918, WO 93/12227, WO 94/25585, WO 97113852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchomosomes such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise LRP6 antibodies of the invention. For example, an alternative transgenic system referred to as the Xenomouse (Abgenix, Inc.) can be used. Such mice are described in, e.g., U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise LRP6 antibodies of the invention. For example, mice carrying both a human heavy chain transchromosome and a human light chain tranchromosome, referred to as "TC mice" can be used; such mice are described in Tomizuka et al., (2000) Proc. Natl. Acad. Sci. USA 97:722-727. Furthermore, cows carrying human heavy and light chain transchromosomes have been described in the art (Kuroiwa et al., (2002) Nature Biotechnology 20:889-894) and can be used to raise LRP6 antibodies of the invention.

Human monoclonal antibodies of the invention can also be prepared using phage display methods for screening libraries of human immunoglobulin genes. Such phage display methods for isolating human antibodies are established in the art or described in the examples below. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

(iii) Framework or Fc Engineering

Engineered antibodies of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis. Such "backmutated" antibodies are also intended to be encompassed by the invention.

Another type of framework modification involves mutating one or more residues within the framework region, or even within one or more CDR regions, to remove T cell-epitopes to thereby decrease the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that Kabat (Supra).

The Hinge region of CH1 can be modified such that the number of cysteine residues in the Hinge region is altered, e.g., increased or decreased. This approach is described further in U.S. Pat. No. 5,677,425 by Bodmer et al. The number of cysteine residues in the Hinge region of CH1 is altered to, for example, facilitate assembly of the light and heavy chains or to increase or decrease the stability of the antibody.

The Fc-hinge region of a multivalent antibody can be modified to increase its biological half-life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. The Fc-hinge region of the multivalent antibody can be modified to decrease its biological half-life, for example to control dose, toxicity, and clearance therefore allowing for better clinical management through control of dose.

The Fc region can be altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

One or more amino acids can be replaced with a different amino acid residue such that the antibody has altered Clq binding and/or decreased or abolished complement dependent cytotoxicity (CDC). This approach is described in further detail in U.S. Pat. No. 6,194,551 by Idusogie et al.

One or more amino acid residues can be altered to alter the ability of the m antibody to fix complement. This approach is described further in PCT Publication WO 94/29351 by Bodmer et al.

The Fc region can be modified to increase the ability of the antibody to mediate antibody dependent cellular cytotoxicity (ADCC) and/or to increase the affinity of the multivalent antibody for an Fcγ receptor by modifying one or more amino acids. This approach is described further in PCT Publication WO 00/42072 by Presta. Moreover, the binding sites on human IgG1 for FcγRI, FcγRII, FcγRIII and FcRn have been mapped and variants with improved binding have been described (see Shields et al., (2001) J. Biol. Chen. 276:6591-6604).

The glycosylation of an antibody can be modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lecl3 cells, with reduced ability to attach fucose to Asn(297)-linked carbohydrates, also resulting in hypofucosylation of antibodies expressed in that host cell (see also Shields et al., (2002) J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., (1999) Nat. Biotech. 17:176-180).

The antibody can be modified to increase its biological half-life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

(iv) Methods of Engineering Altered Antibodies

As discussed above, antibodies having VH and VL sequences or full length heavy and light chain sequences shown herein can be used to create new antibodies by modifying full length heavy chain and/or light chain sequences, VH and/or VL sequences, or the constant region(s) attached thereto. Thus, in another aspect of the invention, the structural features of a antibody of the invention are used to create structurally related antibody that retain at least one functional property of the antibodies of the invention, such as binding to human LRP6 and also inhibiting one or more functional properties of LRP6 (e.g., Wnt signaling activity).

For example, one or more CDR regions of the antibodies of the present invention, or mutations thereof, can be combined recombinantly with known framework regions and/or other CDRs to create additional, recombinantly-engineered, antibodies of the invention, as discussed above. Other types of modifications include those described in the previous section. The starting material for the engineering method is one or more of the VH and/or VL sequences provided herein, or one or more CDR regions thereof. To create the engineered antibody, it is not necessary to actually prepare (i.e., express as a protein) a antibody having one or more of the VH and/or VL sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing a propeller 1 LRP6 antibody consisting of: a heavy chain variable region antibody sequence having a CDR1 sequence selected from the group consisting of SEQ ID NOs: 1, 21, and 47, a CDR2 sequence selected from the group consisting of SEQ JD NOs: 2, 22, and 48, and/or a CDR3 sequence selected from the group consisting of SEQ ID NOs: 3, 23, and 49; and a light chain variable region antibody sequence having a CDR1 sequence selected from the group consisting of SEQ ID NOs: 4, 24, and 50, a CDR2 sequence selected from the group consisting of SEQ ID NOs: 5, 25 and, 51, and/or a CDR3 sequence selected from the group consisting of SEQ ID NOs: 6, 26, and 52; altering at least one amino acid residue within the heavy chain variable region antibody sequence and/or the light chain variable region antibody sequence to create at least one altered antibody sequence; and expressing the altered antibody sequence as a protein.

Accordingly, in another embodiment, the invention provides a method for preparing a propeller 3 LRP6 antibody consisting of: a heavy chain variable region antibody sequence having a CDR1 sequence selected from the group consisting of SEQ ID NOs: 69, 93, and 115, a CDR2 sequence selected from the group consisting of SEQ ID NOs: 70, 94, and 116, and/or a CDR3 sequence selected from the group consisting of SEQ ID NOs: 71, 95, and 117; and a light chain variable region antibody sequence having a CDR1 sequence selected from the group consisting of SEQ ID NOs: 91, 107, and 118, a CDR2 sequence selected from the group consisting of SEQ ID NOs: 73, 97, and 121, and/or a CDR3 sequence selected from the group consisting of SEQ ID NOs: 74, 98, and 120; altering at least one amino acid residue within the heavy chain variable region antibody sequence and/or the light chain variable region antibody sequence to create at least one altered antibody sequence; and expressing the altered antibody sequence as a protein.

Accordingly, in another embodiment, the invention provides a method for preparing a multispecific (e.g., a biparatopic) LRP6 antibody consisting of: a heavy chain variable region antibody sequence having a CDR1 sequence selected from the group consisting of SEQ ID NOs: 1, 21, 47, 69, 93, and 115, a CDR2 sequence selected from the group consisting of SEQ ID NOs: 2, 22, 48, 70, 94, and 116, and/or a CDR3 sequence selected from the group consisting of SEQ ID NOs: 3, 23, 49, 71, 95, and 117; and a light chain variable region antibody sequence having a CDR1 sequence selected from the group consisting of SEQ ID NOs: 4, 24, 50, 72, 96, and 118, a CDR2 sequence selected from the group consisting of SEQ ID NOs: 5, 25, 51, 73, 97, and 119, and/or a CDR3 sequence selected from the group consisting of SEQ ID NOs: 6, 26, 52, 74, 98, and 120; altering at least one amino acid residue within the heavy chain variable region antibody sequence and/or the light chain variable region antibody sequence to create at least one altered antibody sequence; and expressing the altered antibody sequence as a protein. The altered antibody sequence can also be prepared by screening antibody libraries having fixed CDR3 sequences or minimal essential binding determinants as described in US20050255552 and diversity on CDR1 and CDR2 sequences. The screening can be performed according to any screening technology appropriate for screening antibodies from antibody libraries, such as phage display technology.

Standard molecular biology techniques can be used to prepare and express the altered antibody sequence. The antibody encoded by the altered antibody sequence(s) is one that retains one, some or all of the functional properties of the antibodies described herein, which functional properties include, but are not limited to, specifically binding to human and/or cynomolgus LRP6; the antibody binds to LRP6 and inhibits LRP6 biological activity by inhibiting the canonical Wnt signaling activity in a Wnt gene assay.

The functional properties of the altered antibodies can be assessed using standard assays available in the art and/or described herein, such as those set forth in the Examples (e.g., ELISAs).

In certain embodiments of the methods of engineering antibody of the invention, mutations can be introduced randomly or selectively along all or part of an antibody coding sequence and the resulting modified antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Characterization of the Antibodies

The antibodies and multivalent antibodies of the invention can be characterized by various functional assays. For example, they can be characterized by their ability to inhibit biological activity by inhibiting canonical Wnt signaling in a Wnt gene assay as described herein, their affinity to a LRP6 protein (e.g., human and/or cynomolgus LRP6), the epitope binning, their resistance to proteolysis, and their ability to block the Wnt pathway. In addition, the antibodies are characterized by ability to potentiate an agonistic effect after cross linking to Fab fragments The multivalent antibodies (e.g., a single biparatopic or a bispecific antibody) has the ability to inhibit both propeller 1 (e.g., Wnt 1) and propeller 3 (e.g., Wnt 3) ligands. Furthermore and unexpectedly, the multivalent antibodies (e.g., a single biparatopic or a bispecific antibody) displays no significant potentiation of a Wnt signal. The multivalent antibodies bind to distinct LRP6 β-propeller regions. For example a biparatopic antibody comprises an receptor binding domain that binds to the β-propeller 1 domain of LRP6 and blocks Propeller1-dependent Wnts such as Wnt1, Wnt2, Wnt6, Wnt7A, Wnt7B, Wnt9, Wnt10A, Wnt10B to inhibit Wnt1 signal transduction, and also has an epitope binding domain that binds to the β-propeller 3 domain of LRP6 to block Propeller3-dependent Wnts such as Wnt3a and Wnt3 to inhibit Wnt 3 signal transduction.

The multivalent antibodies provide advantages over traditional antibodies for example, by expanding the repertoire of targets, having new binding specificities, increased potency and no signal potency. A single LRP6 multivalent antibody can bind to multiple β-propeller regions on a single LRP6 target on the same cell and inhibit Wnt signaling. In one embodiment, the multivalent antibody binds to any combination of β-propeller regions selected from the group consisting of propeller 1, propeller 2, propeller 3, and propeller 4. In one embodiment, the multivalent antibody binds to propeller 1 and propeller 3 domains of LRP6. Thus, a single LRP6 multivalent antibody has increased potency of action by binding to multiple β-propeller regions and inhibiting Wnt signaling mediated by each region. For example, an LRP6 biparatopic antibody inhibits both propeller 1 and propeller 3 mediated Wnt signaling by binding to both β-propeller 1 and β-propeller 3 domains, respectively. The increased potency of action may be due to increased avidity or better binding of the biparatopic antibody compared to a monospecific antibody.

Various methods can be used to measure LRP6-mediated Wnt signaling. For example, the Wnt signaling pathway can be monitored by (i) measurement of abundance and localization of β-catenin; and (ii) measurement of phosphorylation of LRP6 or other downstream Wnt signaling proteins (e.g. DVL), and (iii) measurement of specific gene signatures or gene targets (e.g. c-myc, Cyclin-D, Axin2).

The ability of antibodies to bind to LRP6 can be detected by labelling the antibodies of interest directly, or the antibodies may be unlabelled and binding detected indirectly using various sandwich assay formats known in the art.

In some embodiments, antibodies of the invention block or compete with binding of a reference LRP6 antibody to a LRP6 polypeptide. These can be fully human antibodies described above. They can also be other mouse, chimeric or humanized t antibodies which bind to the same epitope as the reference antibody. The capacity to block or compete with the reference antibody binding indicates that the antibodies under test binds to the same or similar epitope as that defined by the reference antibody, or to an epitope which is sufficiently proximal to the epitope bound by the reference LRP6 antibody. Such antibodies are especially likely to share the advantageous properties identified for the reference antibody. The capacity to block or compete with the reference antibody may be determined by, e.g., a competition binding assay. With a competition binding assay, the antibody under test is examined for ability to inhibit specific binding of the reference antibody to a common antigen, such as a LRP6 polypeptide. A test antibody competes with the reference antibody for specific binding to the antigen if an excess of the test antibody substantially inhibits binding of the reference antibody. Substantial inhibition means that the test antibody decreases specific binding of the reference antibody usually by at least 10%, 25%, 50%, 75%, or 90%.

There are a number of known competition binding assays that can be used to assess competition of a antibodies with the reference LRP6 antibody for binding to a LRP6 protein. These include, e.g., solid phase direct or indirect radioimmunoassay (RIA), solid phase direct or indirect enzyme immunoassay (EIA), sandwich competition assay (see Stahli et al., (1983) Methods in Enzymology 9:242-253); solid phase direct biotin-avidin EIA (see Kirkland et al., (1986) J. Immunol. 137:3614-3619); solid phase direct labeled assay, solid phase direct labeled sandwich assay (see Harlow & Lane, supra); solid phase direct label RIA using 1-125 label (see Morel et al., (1988) Molec. Immunol. 25:7-15); solid phase direct biotin-avidin EIA (Cheung et al., (1990) Virology 176: 546-552); and direct labeled RIA (Moldenhauer et al., (1990) Scand. J. Immunol. 32:77-82). Typically, such an assay involves the use of purified antigen bound to a solid surface or cells bearing either of these, an unlabelled test antibody and a labelled reference antibody. Competitive inhibition is measured by determining the amount of label bound to the solid surface or cells in the presence of the test antibody. Usually the test antibody is present in excess. Antibodies, e.g., a bispecific or biparatopic LRP6 antibodies identified by competition assay (competing antibodies) include antibodies binding to the same epitope as the reference antibody and antibodies binding to an adjacent epitope sufficiently proximal to the epitope bound by the reference antibody for steric hindrance to occur.

To determine if the selected antibody binds to unique epitopes, each antibody can be biotinylated using commercially available reagents (e.g., reagents from Pierce, Rockford, Ill.). Competition studies using unlabeled antibodies and biotinylated antibodies can be performed using a LRP6 polypeptide coated-ELISA plates. Biotinylated antibodies binding can be detected with a strep-avidin-alkaline phosphatase probe. To determine the isotype of purified antibodies, isotype ELISAs can be performed. For example, wells of microtiter plates can be coated with 1 μg/ml of anti-human IgG overnight at 4° C. After blocking with 1% BSA, the plates are reacted with 1 mg/ml or less of the antibody or purified isotype controls, at ambient temperature for one to two hours. The wells can then be reacted with either human IgG1 or human IgM-specific alkaline phosphatase-conjugated probes. Plates are then developed and analyzed so that the isotype of the purified antibody can be determined.

To demonstrate binding of antibodies to live cells expressing a LRP6 polypeptide, flow cytometry can be used. Briefly, cell lines expressing LRP6 (grown under standard growth conditions) can be mixed with various concentrations of at antibodies in PBS containing 0.1% BSA and 10% fetal calf serum, and incubated at 37° C. for 1 hour. After washing, the cells are reacted with Fluorescein-labeled anti-human IgG antibody under the same conditions as the primary antibody staining. The samples can be analyzed by FACScan instrument using light and side scatter properties to gate on single cells. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

The antibodies can be further tested for reactivity with a LRP6 polypeptide or antigenic fragment by Western blotting. Briefly, purified LRP6 polypeptides or fusion proteins, or cell extracts from cells expressing LRP6 can be prepared and subjected to sodium dodecyl sulfate polyacrylamide gel electrophoresis. After electrophoresis, the separated antigens are transferred to nitrocellulose membranes, blocked with 10% fetal calf serum, and probed with the antibodies to be tested. Human IgG binding can be detected using anti-human IgG alkaline phosphatase and developed with BCIP/NBT substrate tablets (Sigma Chem. Co., St. Louis, Mo.). Other examples of functional assays are also described in the Example section below.

Binding Characteristics of Antibodies of the Invention (i) Binding Specificities The invention provides antibodies and multivalent antibodies comprising multiple receptor binding domains (e.g., scFvs, single chain diabodies, antibody variable regions) that have specificities for different binding sites on one or more target receptor(s).

In one embodiment, multivalent antibodies of the invention comprise receptor binding domains (e.g., scFvs) with identical binding specificities. In another embodiment, multivalent antibodies of the invention comprise scFvs with non-identical binding specificities.

(ii) Binding Affinity

The antibodies or multivalent antibodies of the invention may have a high binding affinity to one or more of its cognate antigens. For example, an epitope binding protein described herein may have an association rate constant or $k_{on}$ rate (epitope binding protein (RBP)+antigen→RBP-Ag) of at least $2\times10^5M^1s^{-1}$, at least $5\times10^5M^1s^{-1}$, at least $10^6M^1s^{-1}$, at least $5\times10^6M^1s^{-1}$, at least $10^7M^1s^{-1}$, at least $5\times10^7M^1s^{-1}$, or at least $10^8M^1s^{-1}$.

In one embodiment, the antibodies or multivalent antibody may have a $k_{off}$ rate (RBP-Ag→RBP+Ag) of less than $5\times10^{-1}$ $s^{-1}$, less than $10^{-1}$ $s^{-1}$, less than $5\times10^{-2}$ $s^{-1}$, less than $10^{-2}$ $s^{-1}$, less than $5\times10^{-3}s^{-1}$, less than $10^{-3}s^{-1}$, less than $5\times10^{-4}$ $s^{-1}$, or less than $5\times10^{-4}$ $s^{-1}$. The antibodies or multivalent antibodies have a $k_{off}$ of less than $5\times10^{-5}$ $s^{-1}$, less than $10^{-5}$ $s^{-1}$, less than $5\times10^{-6}$ $s^{-1}$, less than $10^{-6}$ $s^{-1}$, less than $5\times10^{-7}$ $s^{-1}$, less than $5\times10^{-7}$ $s^{-1}$, less than $5\times10^{-8}$ $s^{-1}$, less than $10^{-8}$ $s^{-1}$, less than $5\times10^{-9}$ $s^{-1}$, less than $10^{-9}$ $s^{-1}$, or less than $10^{-9}$ $s^{-1}$.

In another embodiment, the antibodies or multivalent antibody may have an affinity constant or $K_a$ ($k_{on}/k_{off}$) of at least $10^2M^{-1}$, at least $5\times10^2M^{-1}$, at least $10^3M^{-1}$, at least $5\times10^3$ $M^{-1}$, at least $10^4M^{-1}$, at least $5\times10^4M^{-1}$, at least $10^5M^{-1}$, at least $5\times10^5M^{-1}$, at least $10^6M^{-1}$, at least $5\times10^6M^{-1}$, at least $10^7M^{-1}$, at least $5\times10^7M^{-1}$, at least $10^8M^{-1}$, at least $5\times10^8$ $M^{-1}$, at least $10^9M^{-1}$, at least $5\times10^9M^{-1}$, at least $10^{10}$ $M^{-1}$, at least $5\times10^{10}M^{-1}$, at least $10^{11}M^{-1}$, at least $5\times10^{11}M^{-1}$, at least $10^{12}M^{-1}$, at least $5\times10^{12}M^{-1}$, at least $10^{13}M^{-1}$, at least $5\times10^{13}$ $M^{-1}$, at least $10^{14}M^{-1}$, at least $5\times10^{14}M^{-1}$, at least $10^{15}M^{-1}$, or at least $5\times10^{15}M^{-1}$.

In yet another embodiment, the antibody or multivalent antibody may have a dissociation constant or IQ ($k_{off}/k_{on}$) of less than $5\times10^{-2}M$, less than $10^{-2}M$, less than $5\times10^{-3}M$, less than $10^{-3}M$, less than $5\times10^{-4}M$, less than $10^{-4}M$, less than $5\times10^{-5}M$, less than $10^{-5}M$, less than $5\times10^{-6}M$, less than $10^{-6}M$, less than $5\times10^{-7}M$, less than $10^{-7}M$, less than $5\times10^{-8}M$, less than $10^{-8}M$, less than $5\times10^{-9}M$, less than $10^{-9}M$, less than $5\times10^{-10}$ M, less than $10^{-10}$ M, less than $5\times10^{-11}M$, less than $10^{-11}M$, less than $5\times10^{-12}M$, less than $10^{-12}M$, less than $5\times10^{-13}M$, less than $10^{-13}M$, less than $5\times10^{-14}M$, less than $10^{-14}M$, less than $5\times10^{-15}M$, or less than $10^{-15}M$.

The antibody or multivalent antibody used in accordance with a method described herein may have a dissociation constant (IQ) of less than 3000 pM, less than 2500 pM, less than 2000 pM, less than 1500 pM, less than 1000 pM, less than 750 pM, less than 500 pM, less than 250 pM, less than 200 pM, less than 150 pM, less than 100 pM, less than 75 pM, less than 10 pM, less than 1 pM as assessed using a method described herein or known to one of skill in the art (e.g., a BIAcore assay, ELISA, FACS, SET) (Biacore International AB, Uppsala, Sweden). The antibody or multivalent antibodies used in accordance with a method described herein may have a dissociation constant ($K_d$) of between 25 to 3400 pM, 25 to 3000 pM, 25 to 2500 pM, 25 to 2000 pM, 25 to 1500 pM, 25 to 1000 pM, 25 to 750 pM, 25 to 500 pM, 25 to 250 pM, 25 to 100 pM, 25 to 75 pM, 25 to 50 pM as assessed using a method described herein or known to one of skill in the art (e.g., a BIAcore assay, ELISA, FACS, SET). The antibody or multivalent antibodies used in accordance with a method described herein may have a dissociation constant ($K_d$) of 500 pM, 100 pM, 75 pM or 50 pM as assessed using a method described herein or known to one of skill in the art (e.g., a BIAcore assay, ELISA, FACS, SET).

(Iii) Relative Binding Affinities of Multivalent Antibodies

It is to be understood that the invention provides proteins carrying multiple receptor binding domains that may retain functionality within the protein in a similar fashion or better to the functionalities exhibited in an isolated state (i.e. the receptor binding domain exhibits similar properties as part of the multivalent antibody as compared to the domain if expressed or isolated independently). For example, an isolated scFv specific for epitope Y exhibits a specific functional profile including binding affinity, agonistic or antagonistic functions. It is to be understood that the same scFv expressed as a receptor binding domain within a multivalent antibody of the invention would exhibit similar binding affinity or better and/or agonistic or antagonistic properties as compared to the isolated scFv.

In one embodiment, the multivalent antibodies of the invention comprise receptor binding domains (e.g., scFvs) with binding affinities lower than the same isolated (free from other components of the multivalent antibody) receptor binding domains (e.g., scFvs). In another embodiment, multivalent antibodies of the invention comprise receptor binding domains (e.g., scFvs), with binding affinities higher than the same isolated (free from other components of the multivalent antibody) receptor binding domains (e.g., scFvs). In another embodiment, multivalent antibodies of the invention comprise receptor binding domains (e.g., scFvs), with binding affinities essentially the same as the corresponding isolated (free from other components of the multivalent antibody) receptor binding domains (e.g., scFvs).

Binding affinities can be routinely assayed by many techniques known in the art, such as ELISA, BiaCore™, KinExA™, cell surface receptor binding, competitive inhibition of binding assays, SET. The binding affinities of the multivalent antibodies of the invention can be assayed by the techniques presented in the Examples.

An receptor binding domain (e.g., scFv) of a multivalent antibody exhibits a binding affinity less than 99%, less than 95%, less than 90%, less than 80%, less than 70%, less than 60%, less than 50%, less than 40%, less than 30%, less than 20%, or less than 10% to a specific epitope than an identical functional isolated receptor binding domain (e.g., scFv) as measured by any assay known in the art. In another embodiment, a receptor binding domain (e.g., scFv) of a multivalent antibody exhibits a binding affinity less than 99%, less than 95%, less than 90%, less than 80%, less than 70%, less than 60%, less than 50%, less than 40%, less than 30%, less than 20%, or less than 10% to a specific epitope than an identical functional isolated receptor binding domain (e.g., scFv) as measured by the techniques presented in any of the Examples.

A receptor binding domain (e.g., scFv) of a multivalent antibody exhibits a binding affinity more than 99%, more than 95%, more than 90%, more than 80%, more than 70%, more than 60%, more than 50%, more than 40%, more than 30%, more than 20%, or more than 10% to a specific epitope than an identical functional isolated receptor binding domain (e.g., scFv) as measured by any assay known in the art. In another embodiment, an receptor binding domain (e.g., scFv) of a multivalent antibody exhibits a binding affinity more than 99%, more than 95%, more than 90%, more than 80%, more than 70%, more than 60%, more than 50%, more than 40%, more than 30%, more than 20%, or more than 10% to a specific epitope than an identical functional isolated receptor binding domain (e.g., scFv) as measured by the techniques presented in any of the Examples.

(iv) Assays for Epitope Binding and Activity

The antibodies and multivalent antibodies of the invention may be assayed for specific (i.e., immunospecific) binding by any method known in the art. The immunoassays which can be used, include but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and known in the art (see, e.g., Ausubel et al, eds, 1994, Current Protocols in Molecular Biology, Vol. 1, John Wiley & Sons, Inc., New York). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the epitope binding protein of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the protein of interest to immunoprecipitate a particular antigen can be assessed by, e.g., western blot analysis. One of skill in the art would be knowledgeable as to the parameters that can be modified to increase the binding of the epitope binding protein to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody diluted in blocking buffer, washing the membrane in washing buffer, blocking the membrane with a secondary antibody (which recognizes the primary antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microliter plate with the antigen, adding the epitope binding protein of interest conjugated to a detectable compound such as an enzymatic substrate (e.g., horseradish peroxidase or alkaline phosphatase) to the well and incubating for a period of time, and detecting the presence of the antigen. In ELISAs the epitope binding protein of interest does not have to be conjugated to a detectable compound; instead, a second antibody (which recognizes the protein of interest) conjugated to a detectable compound may be added to the well. Further, instead of coating the well with the antigen, the protein of interest may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity and other binding properties of an antibody or multivalent antibody to an antigen may be determined by a variety of in vitro assay methods known in the art including for example, equilibrium methods (e.g., enzyme-linked immunoabsorbent assay (ELISA; or radioimmunoassay (RIA)), or kinetics (e.g., BIACORE™ analysis), and other methods such as indirect binding assays, competitive binding assays fluorescence resonance energy transfer (FRET), gel electrophoresis and chromatography (e.g., gel filtration), FACS. These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions. One example of a competitive binding assay is a radioimmunoassay comprising the incubation of labeled antigen with the epitope binding protein of interest in the presence of increasing amounts of unlabeled antigen, and the detection of the epitope binding protein bound to the labeled antigen. The affinity of the epitope binding protein of interest for a particular antigen and the binding off-rates can be determined from the data by scatchard plot analysis. Competition with a second antibody can also be determined using radioimmunoassays. In this case, the antigen is incubated with epitope binding protein of interest conjugated to a labeled compound in the presence of increasing amounts of an unlabeled second antibody.

Prophylactic and Therapeutic Uses

The present invention also encompasses the use of antibodies or multivalent antibodies of the invention for the prevention, diagnosis, management, treatment or amelioration of one or more symptoms associated with diseases, disorders of diseases or disorders, including but not limited to cancer, inflammatory and autoimmune diseases either alone or in combination with other therapies. The invention also encompasses the use of antibodies of the invention conjugated or fused to a moiety (e.g., therapeutic agent or drug) for prevention, management, treatment or amelioration of one or more symptoms associated with diseases, disorders or infections, including but not limited to cancer, inflammatory and autoimmune diseases either alone or in combination with other therapies.

Many cell types express various common cell surface antigens and it is the specific combination of antigens that distinguish a defined subset of cells. Using the multivalent antibodies of the invention, it is possible to target specific subsets of cells without cross-reacting with other unrelated populations of cells. Further, it is possible that multivalent antibodies of the invention comprise one to several (two, three, four, five, six, seven, eight, nine, ten, etc.) receptor binding domains that bind cell surface antigens present on non-target cell populations, however, it is the combined avidity of the set of receptor binding domains, which confer an effective level of binding (i.e., a therapeutically effective level of binding) to the target cell population. In other words, several of the receptor binding domains are engaged to facilitate the targeting of a particular cell type, which would not be achieved by binding of an individual isolated domain (e.g., isolated from the multivalent antibody) or not achieved by one or more, but not all (i.e., a subset) of receptor binding domains (control peptides) exposed to the same cell, but not as part of a multivalent antibody. It is envisioned that the relative avidity contribution of each receptor binding domain may be tailored to only target the specific cell population of interest. Such affinity alterations may be performed by art-accepted techniques, such as affinity maturation, site-specific mutagenesis, and others known in art. It is also contemplated that the relative avidity contribution of each receptor binding domain may also be altered by changing the relative orientation of the receptor binding domains in the multivalent antibody.

Accordingly, provided herein in one embodiment are methods of using multivalent antibodies of the invention to identify, deplete, modulate (e.g., activate, inhibit) a cell population (e.g., in vivo in a mammal (e.g., a human) and/or in vitro). In some embodiments, the increase in avidity exhibited by the multivalent antibodies of the invention for a target cell population in vitro or when administered to a mammal (e.g., a human) is at least 2 fold, at least 3 fold, at least 4 fold, at least 5 fold, at least 6, fold, at least 7 fold, at least 8 fold, at least 9 fold, at least 10 fold, at least 15 fold, at least 20 fold, or at least 25 fold as compared to a "control epitope binding protein" which comprises one or more, but not all (i.e., a subset) of receptor binding domains isolated from the multivalent antibody. In some embodiments, the increase in avidity exhibited by the multivalent antibodies of the invention is at least 5%, at least 10%, at least 15%, at least 20%, at least 30%, fold, at least 40%, at least 50%, at least 75%, at least 85%, at least 90%, at least 95%, or at least 150% over the "control epitope binding protein".

In some embodiments, multivalent antibodies of the invention have an increase in avidity for a particular antigen compared to a control receptor binding protein, which comprises one or more, but not all (i.e., a subset) of receptor binding domains isolated from the multivalent antibody. In some embodiments, the increase in avidity exhibited by the multivalent antibodies of the invention is at least 2 fold, at least 3 fold, at least 4 fold, at least 5 fold, at least 6, fold, at least 7 fold, at least 8 fold, at least 9 fold, at least 10 fold, at least 15 fold, at least 20 fold, or at least 100 fold over or at least 1000 fold over the control receptor binding protein. In some embodiments, the increase in avidity exhibited by the multivalent antibodies of the invention is at least 5%, at least 10%, at least 15%, at least 20%, at least 30%, fold, at least 40%, at least 50%, at least 75%, at least 85%, at least 90%, at least 95%, 100% over the control receptor binding protein.

In other embodiments, multivalent antibodies of the invention comprising X number of receptor binding domains (where X is any positive integer from 2 through 6) exhibit an increase in avidity (in vitro or when administered to a mammal (e.g., a human) for a particular antigen compared to a control receptor binding protein (such as, but not limited to an antibody, an scFv) wherein the control receptor binding protein comprises X—Y (where X and Y are any positive integer from 2 through 6 and X is greater than Y) receptor binding domains, wherein at least one receptor binding domain in the control receptor binding domain protein is specific for the same epitope as the receptor binding domain present in the protein of the invention. In other words, the invention provides multivalent antibodies with increased avidity for a particular target as compared to control receptor binding proteins with greater or fewer receptor binding domains wherein at least one receptor binding domain is specific for a common antigen with the protein of the invention.

Such avidity changes in multivalent antibodies allow for the decrease of toxicity of such therapeutic proteins (for example, combinations of any antibodies listed in Table 1. It is understood that the proteins of the invention may exhibit a "tailor-fit" avidity and/or affinity to decrease toxicity in vivo. As such, the invention also provides multivalent antibodies of the invention that exhibit a lower toxicity in an animal, than a control receptor binding protein.

It is also appreciated that avidity changes may be evaluated by readily available in vitro methods such as functional assays (including but not limited to cytokine expression/release/binding, gene expression, morphology changes, chemotaxis, calcium flux, and the like, growth and signaling), binding measurements determined by BIAcore or KinExa measurements with control receptor binding domain proteins. In some embodiments, control receptor binding proteins may contain a subset of receptor binding domains from the proteins of the invention. In other embodiments, control receptor binding proteins may comprise at least one or more isolated receptor binding domains from the multivalent antibodies of the invention. For example, for a protein of the invention with 8 epitope binding domains, a control receptor binding protein may comprise 1, 2, 3, 4, 5, or 6 receptor binding domains, with at least one receptor binding domain having specificity for an antigen recognized by both the protein of the invention and the control protein.

In one embodiment, the multivalent antibodies of the invention are used to specifically identify, deplete, activate, inhibit, or target for neutralization cells which are defined by the expression of multiple cell surface antigens.

In a specific embodiment, the present invention provides methods of treating cancers associated with a Wnt signaling pathway that include, but are not limited to breast cancer, lung cancer, multiple myeloma, ovarian cancer, liver cancer, bladder cancer gastric cancer, prostate cancer, acute myeloid leukemia, chronic myeloid leukemia, osteosarcoma, squamous cell carcinoma, and melanoma.

Antibodies can also be used to treat or prevent other disorders associated with aberrant or defective Wnt signaling, including but are not limited to osteoporosis, osteoarthritis, polycystic kidney disease, diabetes, schizophrenia, vascular disease, cardiac disease, non-oncogenic proliferative diseases, fibrosis, and neurodegenerative diseases such as Alzheimer's disease. The Wnt signaling pathway plays a critical role in tissue repair and regeneration. Agents that sensitize cells to Wnt signaling can be used to promote tissue regeneration for many conditions such as bone diseases, mucositis, acute and chronic kidney injury, and others.

Suitable agents for combination treatment with LRP6 antibodies include standard of care agents known in the art that are able to modulate the activities of canonical Wnt signaling pathway (e.g., PI3 kinase agents).

Diagnostic Uses

In one aspect, the invention encompasses diagnostic assays for determining LRP6 protein and/or nucleic acid expression as well as LRP6 protein function, in the context of a biological sample (e.g., blood, serum, cells, tissue) or from individual afflicted with cancer, or is at risk of developing cancer.

Diagnostic assays, such as competitive assays rely on the ability of a labelled analogue (the "tracer") to compete with the test sample analyte for a limited number of binding sites on a common binding partner. The binding partner generally is insolubilized before or after the competition and then the tracer and analyte bound to the binding partner are separated from the unbound tracer and analyte. This separation is accomplished by decanting (where the binding partner was preinsolubilized) or by centrifuging (where the binding partner was precipitated after the competitive reaction). The amount of test sample analyte is inversely proportional to the amount of bound tracer as measured by the amount of marker substance. Dose-response curves with known amounts of analyte are prepared and compared with the test results in order to quantitatively determine the amount of analyte present in the test sample. These assays are called ELISA systems when enzymes are used as the detectable markers. In an assay of this form, competitive binding between antibodies and LRP6 antibodies results in the bound LRP6 protein, being a measure of antibodies in the serum sample, most particularly, antibodies in the serum sample.

A significant advantage of the assay is that measurement is made of neutralising antibodies directly (i.e., those which interfere with binding of LRP6 protein, specifically, epitopes). Such an assay, particularly in the form of an ELISA test has considerable applications in the clinical environment and in routine blood screening.

The invention also provides for prognostic (or predictive) assays for determining whether an individual is at risk of developing a disorder associated with LRP6. For example, mutations in a LRP6 gene can be assayed in a biological sample. Such assays can be used for prognostic or predictive purpose to thereby prophylactically treat an individual prior to the onset of a disorder characterized by or associated with LRP6 protein, nucleic acid expression or activity.

Another aspect of the invention provides methods for determining LRP6 nucleic acid expression or LRP6 protein activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs) on the expression or activity of LRP6 protein in clinical trials.

Pharmaceutical Compositions

To prepare pharmaceutical or sterile compositions including an antibody or multivalent antibodies of the invention mixed with a pharmaceutically acceptable carrier or excipient. The compositions can additionally contain one or more other therapeutic agents that are suitable for treating or preventing cancer (breast cancer, lung cancer, multiple myeloma, ovarian cancer, liver cancer, bladder cancer gastric cancer, prostate cancer, acute myeloid leukemia, chronic myeloid leukemia, osteosarcoma, squamous cell carcinoma, and melanoma).

Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

Selecting an administration regimen for a therapeutic depends on several factors, including the serum or tissue turnover rate of the entity, the level of symptoms, the immunogenicity of the entity, and the accessibility of the target cells in the biological matrix. In certain embodiments, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak (1996) Antibody Therapy, Bios Scientific Pub. Ltd, Oxfordshire, UK; Kresina (ed.) (1991) Monoclonal Antibodies, Cytokines and Arthritis, Marcel Dekker, New York, N.Y.; Bach (ed.) (1993) Monoclonal Antibodies and Peptide Therapy in Autoimmune Diseases, Marcel Dekker, New York, N.Y.; Baert et al., (2003) New Engl. J. Med. 348:601-608; Milgrom et al., (1999) New Engl. J. Med. 341:1966-1973; Slamon et al., (2001) New Engl. J. Med. 344:783-792; Beniaminovitz et al., (2000) New Engl. J. Med. 342:613-619; Ghosh et al., (2003) New Engl. J. Med. 348: 24-32; Lipsky et al., (2000) New Engl. J. Med. 343:1594-1602).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors known in the medical arts.

Compositions comprising antibodies of the invention can be provided by continuous infusion, or by doses at intervals of, e.g., one day, one week, or 1-7 times per week. Doses may be provided intravenously, subcutaneously, topically, orally, nasally, rectally, intramuscular, intracerebrally, or by inhalation. A specific dose protocol is one involving the maximal dose or dose frequency that avoids significant undesirable side effects. A total weekly dose may be at least 0.05 μg/kg body weight, at least 0.2 μg/kg, at least 0.5 μg/kg, at least 1 μg/kg, at least 10 μg/kg, at least 100 μg/kg, at least 0.2 mg/kg, at least 1.0 mg/kg, at least 2.0 mg/kg, at least 10 mg/kg, at least 25 mg/kg, or at least 50 mg/kg (see, e.g., Yang et al., (2003) New Engl. J. Med. 349:427-434; Herold et al., (2002) New Engl. J. Med. 346:1692-1698; Liu et al., (1999) J. Neurol. Neurosurg. Psych. 67:451-456; Portielji et al., (20003) Cancer Immunol. Immunother. 52:133-144). The desired dose of multivalent antibody is about the same as for an antibody or polypeptide, on a moles/kg body weight basis. The desired plasma concentration of a multivalent antibody is about the same as for an antibody, on a moles/kg body weight basis. The dose may be at least 15 μg at least 20 μg, at least 25 μg, at least 30 μg, at least 35 μg, at least 40 μg, at least 45 μg, at least 50 μg, at least 55 μg, at least 60 μg, at least 65 μg, at least 70 μg, at least 75 μg, at least 80 μg, at least 85 μg, at least 90 μg, at least 95 μg, or at least 100 μg. The doses administered to a subject may number at least 1, 2, 3, 4, 5, 6, 7, 8, 9, 10, 11, or 12, or more.

For antibodies of the invention, the dosage administered to a patient may be 0.0001 mg/kg to 100 mg/kg of the patient's body weight. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight.

The dosage of the antibody of the invention may be calculated using the patient's weight in kilograms (kg) multiplied by the dose to be administered in mg/kg. The dosage of the antibodies of the invention may be 150 μg/kg or less, 125 μg/kg or less, 100 μg/kg or less, 95 μg/kg or less, 90 μg/kg or less, 85 μg/kg or less, 80 μg/kg or less, 75 μg/kg or less, 70 μg/kg or less, 65 μg/kg or less, 60 μg/kg or less, 55 μg/kg or less, 50 μg/kg or less, 45 μg/kg or less, 40 μg/kg or less, 35 μg/kg or less, 30 μg/kg or less, 25 μg/kg or less, 20 μg/kg or less, 15 μg/kg or less, 10 μg/kg or less, 5 μg/kg or less, 2.5 μg/kg or less, 2 μg/kg or less, 1.5 μg/kg or less, 1 μg/kg or less, 0.5 μg/kg or less, or 0.5 μg/kg or less of a patient's body weight.

Unit dose of the antibodies of the invention may be 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 mg, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

The dosage of the antibodies of the invention may achieve a serum titer of at least 0.1 μg/ml, at least 0.5 μg/ml, at least 1 μg/ml, at least 2 μg/ml, at least 5 μg/ml, at least 6 μg/ml, at least 10 μg/ml, at least 15 μg/ml, at least 20 μg/ml, at least 25 μg/ml, at least 50 μg/ml, at least 100 μg/ml, at least 125 μg/ml, at least 150 μg/ml, at least 175 μg/ml, at least 200 μg/ml, at least 225 μg/ml, at least 250 μg/ml, at least 275 μg/ml, at least 300 μg/ml, at least 325 μg/ml, at least 350 μg/ml, at least 375 μg/ml, or at least 400 μg/ml in a subject. Alternatively, the dosage of the antibodies of the invention may achieve a serum titer of at least 0.1 μg/ml, at least 0.5 μg/ml, at least 1 μg/ml, at least, 2 μg/ml, at least 5 μg/ml, at least 6 μg/ml, at least 10 μg/ml, at least 15 μg/ml, at least 20 .mu.g/ml, at least 25 μg/ml, at least 50 μg/ml, at least 100 μg/ml, at least 125 μg/ml, at least 150 μg/ml, at least 175 μg/ml, at least 200 μg/ml, at least 225 μg/ml, at least 250 μg/ml, at least 275 μg/ml, at least 300 μg/ml, at least 325 μg/ml, at least 350 μg/ml, at least 375 μg/ml, or at least 400 μg/ml in the subject.

Doses of antibodies of the invention may be repeated and the administrations may be separated by at least 1 day, 2 days, 3 days, 5 days, 10 days, 15 days, 30 days, 45 days, 2 months, 75 days, 3 months, or at least 6 months.

An effective amount for a particular patient may vary depending on factors such as the condition being treated, the overall health of the patient, the method route and dose of administration and the severity of side affects (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

The route of administration may be by, e.g., sutaneous application, injection or infusion by intravenous, intraperitoneal, intracerebral, intramuscular, intraocular, intraarterial, intracerebrospinal, intralesional, or by sustained release systems or an implant (see, e.g., Sidman et al., (1983) Biopolymers 22:547-556; Langer et al., (1981) J. Biomed. Mater. Res. 15:167-277; Langer, (1982) Chem. Tech. 12:98-105; Epstein et al., (1985) Proc. Natl. Acad. Sci. USA 82:3688-3692; Hwang et al., (1980) Proc. Natl. Acad. Sci. USA 77:4030-4034; U.S. Pat. Nos. 6,350,466 and 6,316,024). Where necessary, the composition may also include a solubilizing agent and a local anesthetic such as lidocaine to ease pain at the site of the injection. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

A composition of the present invention may also be administered via one or more routes of administration using one or more of a variety of methods known in the art. As will be appreciated by the skilled artisan, the route and/or mode of administration will vary depending upon the desired results. Selected routes of administration for antibodies of the invention include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. In one embodiment, the antibody of the invention is administered by infusion. In another embodiment, the antibody of the invention is administered subcutaneously.

If the antibodies of the invention are administered in a controlled release or sustained release system, a pump may be used to achieve controlled or sustained release (see Langer, supra; Sefton, (1987) CRC Crit. Ref Biomed. Eng. 14:20; Buchwald et al., (1980) Surgery 88:507; Saudek et al., (1989) N. Engl. J. Med. 321:574). Polymeric materials can be used to achieve controlled or sustained release of the therapies of the invention (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one embodiment, the polymer used in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer ((1990), Science 249:1527-1533). Any technique known to one of skill in the art can be used to produce sustained release formulations comprising one or more antibodies of the invention. See, e.g., U.S. Pat. No. 4,526,938, PCT publication WO 91/05548, PCT publication WO 96/20698, Ning et al., (1996) "Intratumoral Radioimmunotheraphy of a Human Colon Cancer Xenograft Using a Sustained-Release Gel," Radiotherapy & Oncology 39:179-189, Song et al., (1995), "Antibody Mediated Lung Targeting of Long-Circulating Emulsions," PDA Journal of Pharmaceutical Science & Technology 50:372-397, Cleek et al., (1997), "Biodegradable Polymeric Carriers for a bFGF Antibody for Cardiovascular Application," Pro. Int'l. Symp. Control. Rel. Bioact. Mater. 24:853-854, and Lam et al., (1997), "Microencapsulation of Recombinant Humanized Monoclonal Antibody for Local Delivery," Proc. Intl. Symp. Control Rel. Bioact. Mater. 24:759-760, each of which is incorporated herein by reference in their entirety.

If the antibodies of the invention are administered topically, they can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in some instances, in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the compositions comprising antibodies are administered intranasally, it can be formulated in an aerosol form, spray, mist or in the form of drops.

Methods for co-administration or treatment with a second therapeutic agent, e.g., a cytokine, steroid, chemotherapeutic agent, antibiotic, or radiation, are known in the art (see, e.g., Hardman et al., (eds.) (2001) Goodman and Gilman's The Pharmacological Basis of Therapeutics, 10.sup.th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). An effective amount of therapeutic may decrease the symptoms by at least 10%; by at least 20%; at least about 30%; at least 40%, or at least 50%.

Additional therapies (e.g., prophylactic or therapeutic agents), which can be administered in combination with the antibodies of the invention may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the antibodies of the invention. The two or more therapies may be administered within one same patient visit.

The antibodies of the invention and the other therapies may be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In certain embodiments, the multivalent antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al); mannosides (Umezawa et al., (1988) Biochem. Biophys. Res. Commun. 153:1038); antibodies (P. G. Bloeman et al. (1995) FEBS Lett. 357:140; M. Owais et al., (1995) Antimicrob. Agents Chemother. 39:180); surfactant protein A receptor (Briscoe et al., (1995) Am. J. Physiol. 1233:134); p 120 (Schreier et al., (1994) J. Biol. Chem. 269:9090); see also Keinanen et al., (1994) FEBS Lett. 346:123; Killion et al., (1994) Immunomethods 4:273.

The invention provides protocols for the administration of pharmaceutical composition comprising antibodies of the invention alone or in combination with other therapies to a subject in need thereof. The therapies (e.g., prophylactic or therapeutic agents) of the combination therapies of the present invention can be administered concomitantly or sequentially to a subject. The therapy (e.g., prophylactic or therapeutic agents) of the combination therapies of the present invention can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies of the invention can be administered to a subject concurrently. The term "concurrently" is not limited to the administration of therapies (e.g., prophylactic or therapeutic agents) at exactly the same time, but rather it is meant that a pharmaceutical composition comprising antibodies of the invention are administered to a subject in a sequence and within a time interval such that the antibodies of the invention can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various embodiments, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other embodiments, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

The invention having been fully described, it is further illustrated by the following examples and claims, which are illustrative and are not meant to be further limiting.

EXAMPLES

Methods and Materials

1: Pannings, Antibody Identification and Characterization (a) Panning (i) HuCAL GOLD® Pannings For the selection of antibodies recognizing human LRP6 several panning strategies were applied. Therapeutic antibodies against human LRP6 protein were generated by selection of clones having high binding affinities, using as the source of antibody variant proteins a commercially available phage display library, the MorphoSys HuCAL GOLD® library.

The phagemid library is based on the HuCAL® concept (Knappik et al., (2000) J Mol Biol 296:57-86) and employs the CysDisplay™ technology for displaying the Fab on the phage surface (WO01/05950 to Lohning).

In detail, the HuCAL GOLD® library used in the current project is described in (Rothe et al., (2007) J Mal Biol) Either phagemids produced with helper phage VCSM13 or produced with Hyperphage (Rondot et al., (2001) Nat Biotechnol 19:75-78) were used for selection of anti-LRP6 antibodies.

(ii) Whole Cell Panning Against LRP6

For whole cell pannings, the cell line HEK293-hLRP6ΔC-eGFP was used expressing the amino terminal fragment (amino acid 1-1482) of LRP6 fused to eGFP. Specific HuCAL GOLD® antibody phagemids were eluted after incubation to the LRP6 expressing cell line followed by post-adsorption to HEK293-LRP5/6-shRNA cells. The resulting HuCAL phage-containing supernatant was titered on *E. coli* TG1 cells and rescued after infection of *E. coli* TG1 cells using helper phage. The polyclonal amplified phage output was titered again and used in consecutive selection steps.

(Iii) Fc Capture Panning Against LRP6

For Fc capture pannings, blocked phage were incubated with the Fc-captured LRP6-Fc and unspecific phage were washed away using different concentrations of PBST, and PBS at different times.

The remaining phage were eluted, and used immediately for infection of *E. coli* TG1 bacteria. Amplification, phage production and output titer determination were conducted as described above in whole cell panning against LRP6.

(iv) Differential Whole Cell Panning Against LRP6

Differential whole cell pannings with antibody selection on HEK293-hLRP6ΔC-eGFP cells and selection on recombinant human LRP6-Fc were performed as described above for whole cell pannings and for Fc capture pannings.

During the selection process, unspecific phage were removed using different concentrations of PBS and PBST for different time periods.

Phage infection of *E. coli* TG1, amplification, phage production and output titer determination were conducted as described above in whole cell panning against LRP6.

(v) Semi-Solution Panning Against LRP6

For semi-solution pannings, recombinant human LRP6-Fc and BSA were covalently linked to tosylactivated M-280-Dynabeads.

Pre-cleared phage were incubated with LRP6-coated beads on a rotator. Beads were then collected using a magnetic separator and washed with PBST and PBS. Bead-bound phage were eluted and immediately used for infection of *E. coli* TG1 bacteria. Phage infection, amplification, phage production and output titer determination were conducted as described above in whole cell panning against LRP6.

(b) Subcloning and Microexpression of Selected Fab Fragments

To facilitate rapid expression of soluble Fab, the Fab encoding inserts of the selected HuCAL GOLD® phage were subcloned into an expression vector pMORPH®X9_FH or pMORPH®X9_FS. After transformation of TG1-F single clone expression and preparation of periplasmic extracts containing HuCAL®-Fab fragments were performed as described previously (Rauchenberger et al., (2003)).

2: Screening (i) FACS Screening on HEK293-hLRP6ΔC-eGFP Cells

Clones selected by the panning strategies whole cell panning, differential whole cell panning, and semi-solution panning were screened by flow cytometry on HEK293-hLRP6ΔC-eGFP cells and HEK293-LRP5/6-shRNA cells for counter screening. Primary hits of Fc capture panning strategy as described above were also tested by flow cytometry.

Cells were harvested at 70 to 80% confluency, resuspended in FACS buffer, and stained with bacterial cell lysates in 96 well U-bottom microtiter plates. Antibody binding was revealed with fluorochrome-conjugated detection antibodies. Stained cells were washed twice and mean fluorescence intensity was measured and analyzed using a FACSArray instrument (BectonDickinson).

(ii) Fc-Capture Screening on Recombinant Human LRP6-Fc

Clones selected in the Fc-capture panning were screened in an Fc-capture-ELISA setup. Maxisorp (Nunc, Rochester, N.Y., USA) 384 well plates were coated with goat anti-human IgG, Fc fragment specific antibody. After washing with PBST and blocking the wells, recombinant human LRP6-Fc was added. After washing the coated plates, cell lysates were added and bound Fab fragments were detected using AP-conjugated goat IgG anti-human IgG $F(ab')_2$ with the substrate AttoPhos. Fluorescence was read at 535 nm using a Tecan Plate Reader.

3: Expression and Purification of HuCAL®-Fab Antibodies in *E. coli*

Expression of Fab fragments encoded by pMORPH®X9_Fab_FH or pMORPH®X11_Fab_FH in TG-1 cells was induced by addition of IPTG. Cells were disrupted using lysozyme and Fab fragments isolated by Ni-NTA chromatography (Bio-Rad, Germany). Protein concentrations were determined by UV-spectrophotometry. Purity of Fab fragments was analyzed in denatured, reduced state using SDS-PAGE and in native state by HP-SEC.

4: Affinity Determination (i) Surface Plasmon Resonance Measurements

For determination of $K_D$ values, surface plasmon resonance technology was applied. Anti-human-Fc-capture CM5 chip (Biacore, Sweden) was used for capturing LRP6-Fc-Fusion followed by ligand (Fab) injection at different concentrations.

(ii) Solution Equilibrium Titration (SET) Method for $K_D$ Determination Using Sector Imager 6000 (MSD)

For $K_D$ determination by solution equilibrium titration (SET), monomer fractions of antibody protein were used (at least 90% monomer content, analyzed by analytical SEC; Superdex75 (Amersham Pharmacia) for Fab, or Tosoh G3000SWXL (Tosoh Bioscience) for IgG, respectively).

Affinity determination in solution was basically performed as described in the literature (Friguet et al., (1985) J Immunol Methods 77:305-319). In order to improve the sensitivity and accuracy of the SET method, it was transferred from classical ELISA to ECL based technology (Haenel et al., (2005) Anal Biochem. 339:182-184).

The data was evaluated with XLfit (IDBS) software applying customized fitting models. For $K_D$ determination of Fab molecules the fit model was used (according to Haenel et al supra), modified according to Abraham et al. (1996) Journal of Molecular Recognition 9:456-461.

$$y = B_{max} - \left( \frac{B_{max}}{2[Fab]_t} \left( [Fab]_t + x + K_D - \sqrt{([Fab]_t + x + K_D)^2 - 4x[Fab]_t} \right) \right)$$

$[Fab]_t$: applied total Fab concentration x: applied total soluble antigen concentration (binding sites)

$B_{max}$: maximal signal of Fab without antigen $K_D$: affinity

5: Screening after Affinity Maturation $EC_{50}$ Determination on HEK293T/17 Cells $EC_{50}$ values were determined on parental HEK293T/17 cells in FACS measurements. A typical antibody titration curve contained ten to twelve different antibody dilutions, and titrations started at concentrations of approx. 150 to 200 μg/mL (final concentration). Cells were harvested using Accutase, resuspended in FACS buffer, distributed to the wells of a 96-well plate, and stained with antibody dilutions. $EC_{50}$ values were determined with the program GraphPad Prism using non-linear regression analysis.

6: Conversion to IgG

In order to express full length IgG, variable domain fragments of heavy (VH) and light chains (VL) were subcloned from Fab expression vectors into appropriate pMORPH®_hIg vectors for human IgG2, human IgG4, human IgG4_Pro, and human IgG1f LALA.

7: Transient Expression and Purification of Human IgG

Eukaryotic HKB11 cells were transfected with equal amounts of IgG heavy and light chain expression vector (pMORPH2) or expression vector DNA encoding for heavy and light chains of IgGs (pMORPH4). After sterile filtration, the solution was subjected to standard protein A affinity chromatography (MabSelect SURE, GE Healthcare). Protein concentrations were determined by UV-spectrophotometry. Purity of IgG was analyzed under denaturing, reducing and non-reducing conditions in SDS-PAGE or by using Agilent BioAnalyzer and in native state by HP-SEC.

8: Wnt Reporter Gene Assay

The ability of anti-LRP6 antibodies to inhibit Wnt signaling was tested in a Wnt1 and Wnt3a responsive luciferase reporter gene assay. Cells were either stimulated with Wnt3a conditioned medium or by co-transfection of Wnt1, Wnt3a, or other Wnt expression plasmids.

(i) Wnt3a Reporter Gene Assay with Conditioned Medium $10^4$ HEK293-STF cells/well were seeded into a 96 well tissue culture plate, and cells were incubated overnight at 37° C./5% $CO_2$ in 100 μL medium.

The following day, various anti-LRP6 antibody dilutions and DKK1 dilutions (positive control) were prepared either in pure or in diluted in Wnt3a-conditioned medium. 60 μL/well of the supernatant was removed from the 96 well tissue culture plate and replaced by 60 μL/well of the conditioned medium/antibody dilutions.

After Incubation for 16 to 24 h at 37° C./5% $CO_2$, 100 μL BrightGlo Luciferase reagent (Promega) were added and plates were incubated for 10 min. For luminescence readout (Tecan Plate Reader), the cell lysates were transferred into a 96 well microtiter plate (Costar, Cat #3917).

A similar assay can also be performed using co-culture of Wnt3 or Wnt3a over-expressing cells (e.g. CHO-K1, TM3, L or HEK293 cells)

(ii) Wnt1/Wnt3a Reporter Gene Assay with Transiently Transfected Cells $3\times10^4$ HEK293T/17 cells/well were seeded into a 96 well tissue culture plate (Costar), and cells were incubated at 37° C./5% $CO_2$ in 100 μL medium as described in Table 3. After 12 to 16 h, cells were transfected with empty vector Wnt expression plasmid1 ng/well; pTA-Luc-10×STF (Firefly luciferase construct) 50 ng/well; or phRL-SV40 (Renilla luciferase construct) 0.5 ng/well.

A transfection premix (10 μL/well) was prepared containing the plasmids listed above and 0.2 μL FuGene6/well (Roche). The transfection premix was incubated 15 min at RT and then distributed into the wells. The plate was rocked at 400 rpm for 2 min at RT and then incubated for 4 h at 37° C./5% $CO_2$. In the meantime, antibodies were diluted in medium and added to the transfected cells (75 μL/well).

After 18 to 24 h, 75 μL/well DualGlo Luciferase reagent (Promega) were added and the plate was rocked for 10 min for cell lysis before readout of the Firefly luciferase activity. After luminescence readout, 75 μL/well DualGlo Stop&Glow reagent (Promega) were added and luminescence was measured again to determine *Renilla* luciferase activity.

For analysis, the ratio between Firefly luciferase activity and *Renilla* luciferase activity was calculated. For $IC_{50}$-determination of the anti-LRP6 antibodies, the relative luciferase values were analyzed using GraphPad Prism.

A similar assay can also be performed using co-culture of Wnt1 or other Wnt1 class ligand over-expressing cells (e.g. CHO-K1, TM3, L or HEK293 cells).

9: FACS Cross-Reactivity Studies

Cross-species reactivity to murine and cynomologus LRP6 was determined on cells by FACS analysis. FACS staining was performed essentially as described above. Human U266 cells (no expression of LRP6) were used as a negative control.

Cross-reactivity to murine LRP6 was tested on murine NIH-3T3 cells. Cross-reactivity to cynomologus LRP6 was tested on the cynomologus cell line Cynom-K1 and on transiently transfected HEK293T/17 cells:

For testing cynomologus cross-reactivity on the human cell line HEK293T/17, the cells were transiently transfected using Lipofectamine (Invitrogen) according to the manufacturer's instructions. Cells were either transfected with a mixture of the human LRP6 expression plasmid pCMV6_XL4_LRP6 and the chaperone-encoding plasmid pcDNA3.1-flag_MESD or with a mixture of pcDNA3.1-nV5-DEST_cynoLRP6 and pcDNA3.1-flag_MESD (overexpression of cynomologus LRP6). 50 μg of LRP6 expression plasmid and 20 μg of MESD expression plasmid were used per T175 flask. After 24 h, cells were detached and stained with the goat anti human LRP6 control antibody (R&D Systems) and with anti-LRP6 HuCAL antibodies. Mock-transfected HEK293T/17 cells were used for negative control stainings (low endogenous LRP6 expression).

10: Binder Optimization

Generation of Affinity Maturation Libraries

To increase affinity and biological activity of selected antibody fragments, L-CDR3 and HCDR2 regions were optimized in parallel by cassette mutagenesis using trinucleotide directed mutagenesis, while the framework regions were kept constant.

The different affinity maturation libraries were generated by standard cloning procedures and transformation of the diversified clones into electro-competent *E. coli* TOP10F cells (Invitrogen). Sequencing of randomly picked clones showed a diversity of 100%. No parental binders were found among the picked clones. Finally phage of all libraries were prepared separately.

11: MMTV-Wnt1 Xenografts

Tumours from MMTV-Wnt1 transgenic mice were passaged as tumour pieces in the mammary fat pad of FVB mice for 5 passages prior to implantation into the mammary fat pad of nude mice. Eleven days post-implant, when tumours reached a mean volume of approximately 110 $mm^3$, mice were randomized into 3 groups with 8 mice per group and dosed every three days (DeAlmeida et al. (2007); Cancer Res. 67:5371-9).

12: Inhibition in Biochemical Assays

HEK293 cells were grown in D-MEM supplemented with 10% fetal bovine serum at 37° C. with 5% $CO_2$. Cells were seeded into a 96 well tissue culture plate (Costar) at $3\times10^4$/well and transfected with 0.1 ng/well Wnt expression plasmid, 50 ng/well STF reporter, and 0.5 ng/ml phRL-SV40 (Promega) mixed with 0.2 μL/well FuGene6 (Roche). Four hours after transfection, antibodies were diluted in PBS and added to the transfected cells. After 18 h incubation, Firefly luciferase and *Renilla* luciferase activities were measured using DualGlo Luciferase reagent (Promega). *Renilla* luciferase was used to normalize transfection efficiency All IgG formats tested have potent and complete inhibition of Wnt1 (2, 6, 7A, 7B, 9, 10A, 10B) generated canonical signal. All give rise to a bell shaped potentiation curve in the presence of a Wnt3/3A generated signal.

13: FACS-Based Competition Assay

For FACS-based competition assay, anti-LRP6 Fabs and the negative control Fab MOR03207 were biotinylated using the ECL protein biotinylation module (GE Healthcare) according to the manufacturer's instructions. The biotinylated Fabs were used for FACS staining on HEK293-hLRP6ΔC-eGFP cells at a constant Fab concentration (20 nM final concentration) and were competed with a 100-fold molar excess of unlabelled Fab. Cells were incubated with the Fab dilutions for 1 hour at 4° C. on a plate shaker. After washing the cells 1× with FACS buffer, they were incubated with PE-conjugated Streptavidin (Dianova) for 1 hour at 4° C. on a plate shaker in the dark. Cells were washed twice with FACS buffer and fluorescence was measured using FACS Array (BD). Similarly, unbiotinylated anti-LRP6 Fabs were competed with a 100-fold molar excess of the LRP6-binding protein SOST and binding of the Fabs to the cells was monitored by PE-conjugated anti human IgG antibody (Dianova).

14: Immunoblotting Assay

Total cell lysates were prepared in RIPA buffer (50 mM Tris-HCl, pH 7.4, 150 mM NaCl, 1% NP-40, 0.5% sodium deoxycholate, 0.1% SDS, 1 mM EDTA). Lysates were normalized for protein concentration, resolved by SDS-PAGE, transferred onto nitrocellulose membranes and probed with the indicated antibodies. pT1479 LRP6 antibody requires generation of membrane extracts to achieve satisfactory results. To generate membrane extracts, cells were lysed in hypotonic buffer (10 mM Tris-HCl pH7.5, 10 mM KCl) by performing four freeze-thaw cycles, and insoluble membrane fraction was solubilized using RIPA buffer. Protease inhibitor cocktail (Sigma) and 1× phosphatase inhibitor cocktail (Upstate) were added into the lysis buffers. Commercial antibodies used in the western blot assay include rabbit anti-LRP6, rabbit anti-pT1479 LRP6, and rabbit anti-pS1490 LRP6 antibodies (Cell Signaling Technology).

Example 1

Specific Binding of Anti-LRP6 Antibodies to Endogenous LRP6 by FACS

Detection of endogenous cell surface expression of LRP6 was examined on a number of tumor cells using the anti- LRP6 antibodies and FACS analysis. As shown in FIG. 1A, PA1 cells express both LRP5 and LRP6 mRNA, while U266 and Daudi cells do not express LRP6 mRNA. PA1 cells, but not U266 and Daudi cells, show significant staining with a Propeller 1 anti-LRP6 IgG. More importantly, U266 cells are not stained by anti-LRP6 antibody, although they express LRP6, demonstrating the specificity of anti-LRP6 antibody. Furthermore, anti-LRP6 antibody staining of PA1 cells is significantly reduced upon depletion of endogenous LRP6 using LRP6 shRNA, further demonstrating the specificity of the LRP6 antibody.

Figure 1B:
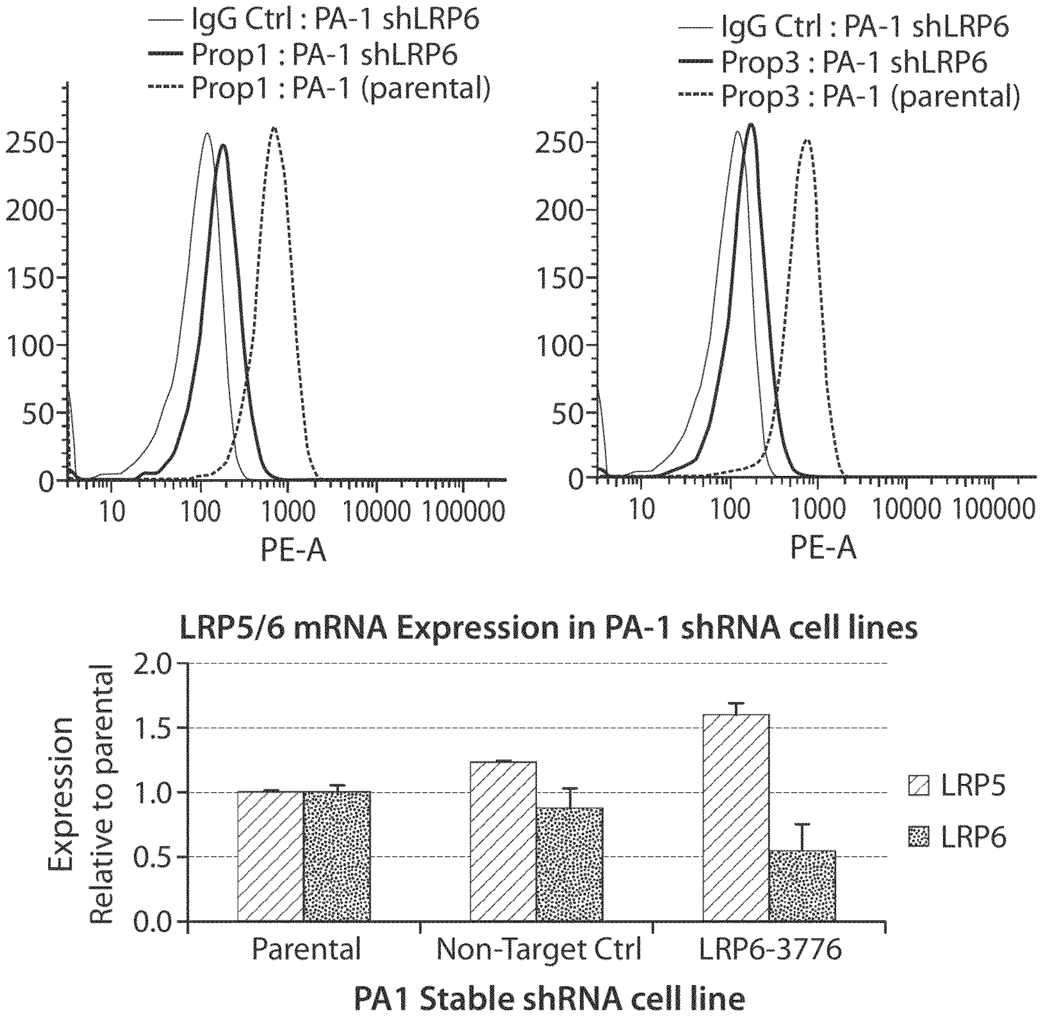

In additional studies, knockdown of LRP6 by shRNA in PA1 cells further confirms specificity of Prop1 and Prop3 antibodies for LRP6 (See FIG. 1B). Knockdown was achieved by infecting cells with lentivirus encoding short hairpin RNA directed to LRP6, and selecting a stable pool of infected cells. The shRNA infection method used for the study is described in Wiederschain et al. in 2009 Cell Cycle 8: 498-504. Epub 2009 Feb. 25.

Example 2

Figure 2A:
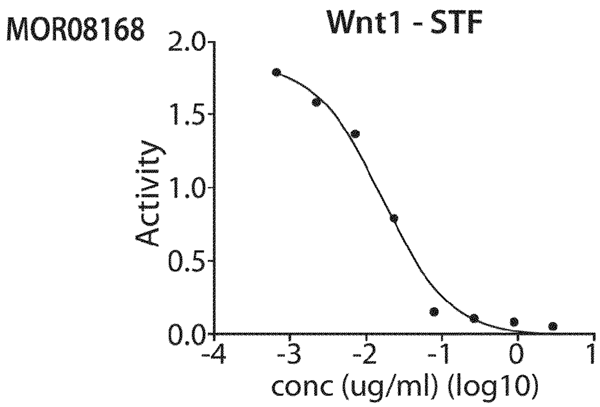
FIG. 2A-L are graphs showing anti-LRP6 Fab fragments activity in HEK293T/17 STF cells (gene reporter assay) expressing Wnt1 or Wnt3A ligands The data shows that anti-LRP6 Fabs selectively block Wnt1 or Wnt3 signaling.
Figure 2B:
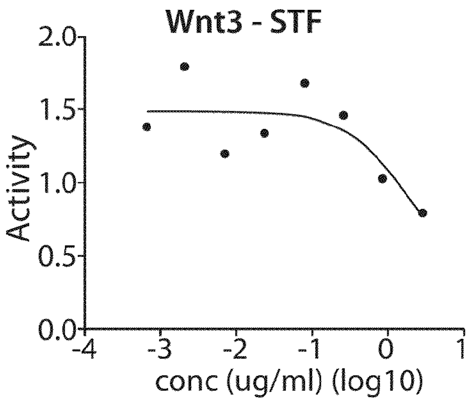
Figure 2C:
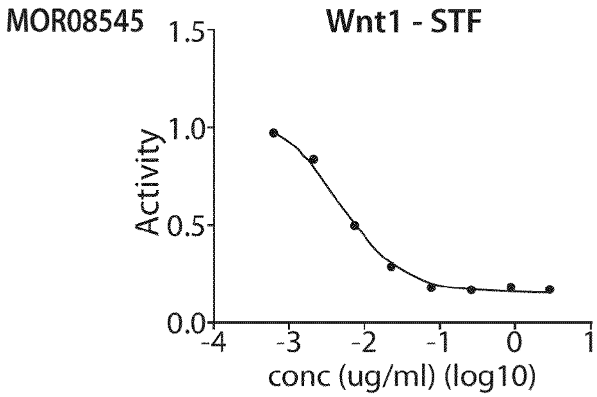
Figure 2D:
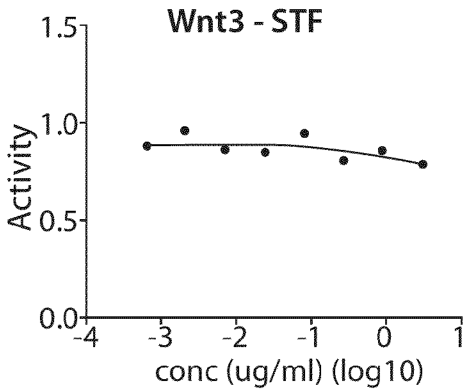
Figure 2E:
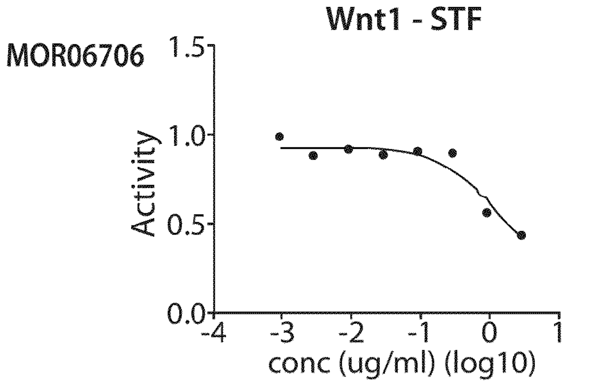
Figure 2F:
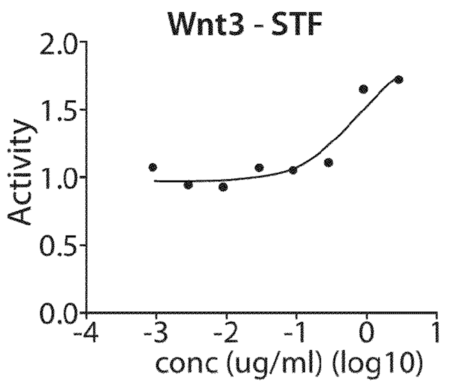
Figure 2G:
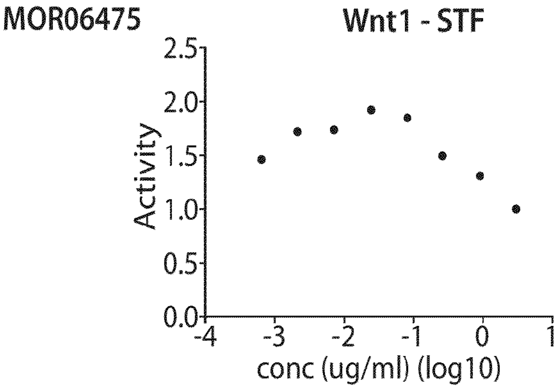
Figure 2H:
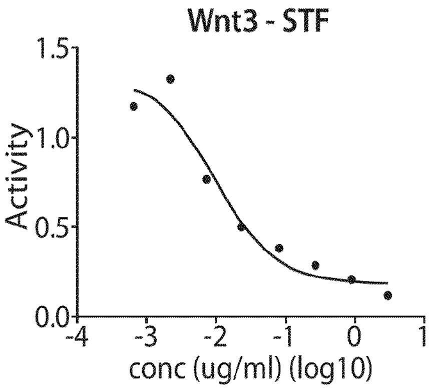
Figure 2I:
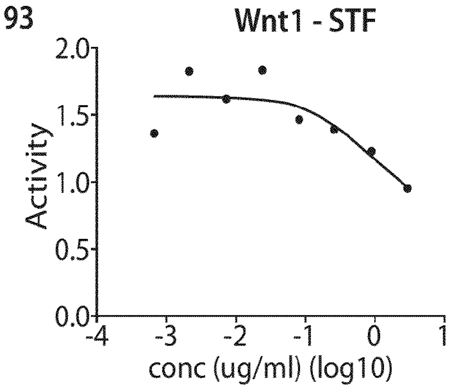
Figure 2J:
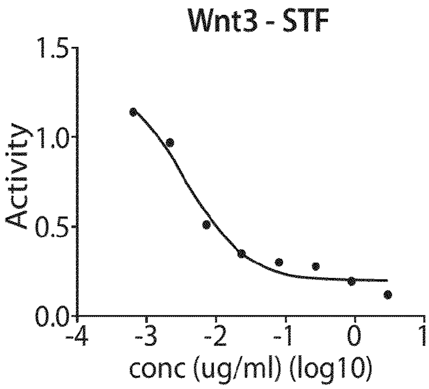
Figure 2K:
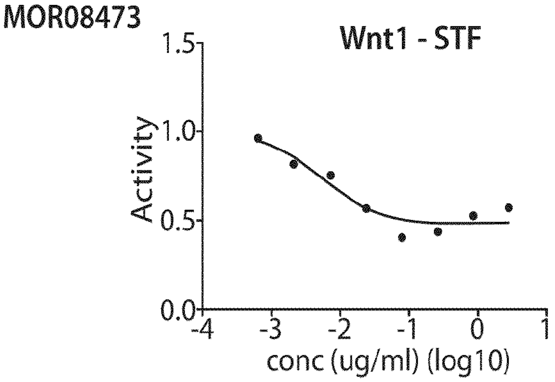
Figure 2L:
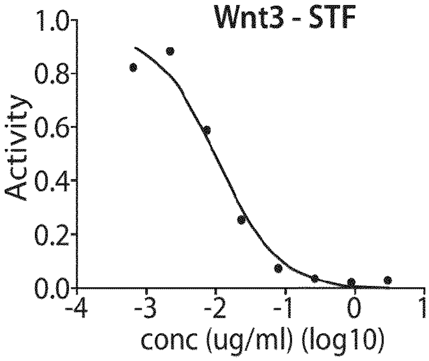

Differential Inhibition of Wnt1 and Wnt3a Reporter Gene Assays by Propeller 1 and Propeller 3 Anti-LRP6 Fabs Different anti-LRP6 Fabs were tested in in vitro Wnt reporter assays. Wnt1 or Wnt3A ligands were transiently expressed in HEK293T/17 STF cells (gene reporter assay) and treated with varying concentrations of anti-LRP6 Fab fragments. STF assays were conducted using the protocols described by Huang et al. (2009), Nature; 461:614-20. Epub 2009 Sep. 16. As seen in FIG. 2A, Propeller 1 anti-LRP6 Fabs (MOR08168, MOR08545, MOR06706) specifically reduced Wnt1-dependent signaling without much effect on Wnt3A-dependent signaling. Conversely as shown in FIG. 2B, Propeller 3 anti-LRP6 Fabs (MOR06475, MOR08193, MOR08473) specifically reduced Wnt3A-dependent signaling without significant effects on Wnt1-dependent Wnt1-dependent signaling. The results demonstrate that Wnt1 and Wnt3A activities are blocked separately by different LRP6 Fab fragment (epitopes).

Example 3

Binding of Anti-LRP6 Antibodies to LRP6 of Different Species

To show cross-reactivity, cells expressing endogenous LRP6 of human (HEK293T/17) and mouse origin (NIH 3T3), or transiently transfected HEK293/T17 cells expressing cynomolgus LRP6, were treated and subjected to flow cytometry as described above. FIG. 3 summarizes the results of the findings of the results and show that all anti-LRP6 antibodies bind to human, mouse, and cynomologus LRP6.

Example 4

Figure 4:
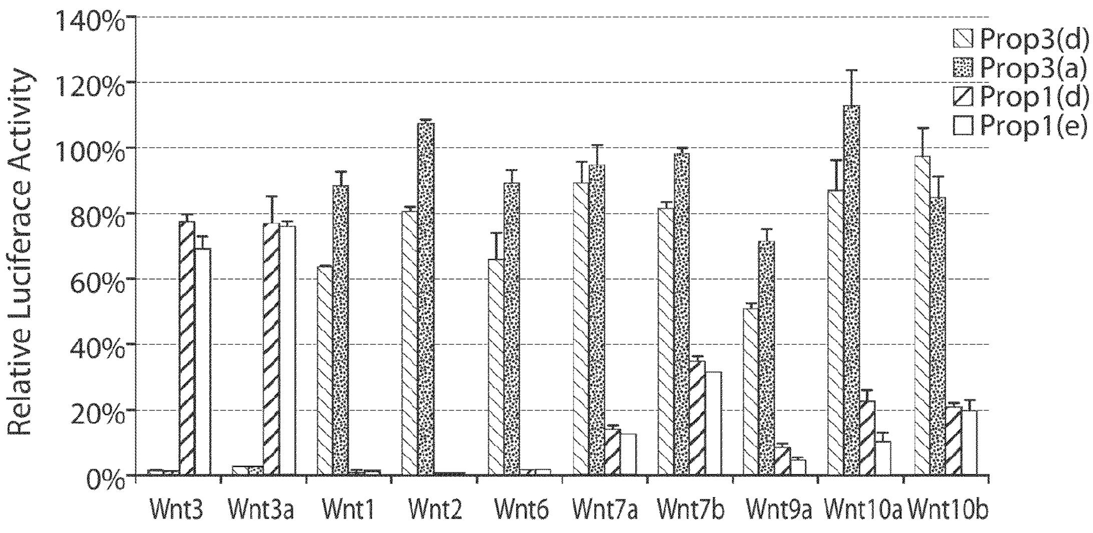
FIG. 4 is a graph showing transient expression of various WNT ligands in HEK293T/17 STF cells (gene reporter assay) and treatment with anti-LRP6 antibodies, showing activity inhibition of particular WNTs based on antibody binding/blocking to specific β-propeller regions of LRP6.

Classification of Wnts Based on their Sensitivity to Propeller 1 and Propeller 3 Anti-LRP6 Antibodies To evaluate Wnts based on their sensitivity Propeller 1 and Propeller 3 anti-LRP6 antibodies, various Wnt ligands were transiently expressed into HEK293T/17 STF cells (gene reporter assay) and treated with Propeller 1 or Propeller 3 anti-LRP6 antibodies. STF assays were conducted using the protocols described by Huang et al. (2009), Nature; 461:614-20. Epub 2009 Sep. 16. The results are shown in FIG. 4 which depicts the activity inhibition of particular Wnts based on antibody binding/blocking to specific propeller regions of LRP6. FIG. 4 shows that signaling induced by Wnt1, Wnt2, Wnt6, Wnt7A, Wnt7B, Wnt9, Wnt10A, Wnt10B can be specifically inhibited by Propeller 1 anti-LRP6 Fabs, while signaling induced by Wnt3 and Wnt3A can be specifically inhibited by Propeller 3 anti-LRP6 Fabs.

Example 5

Figure 5:
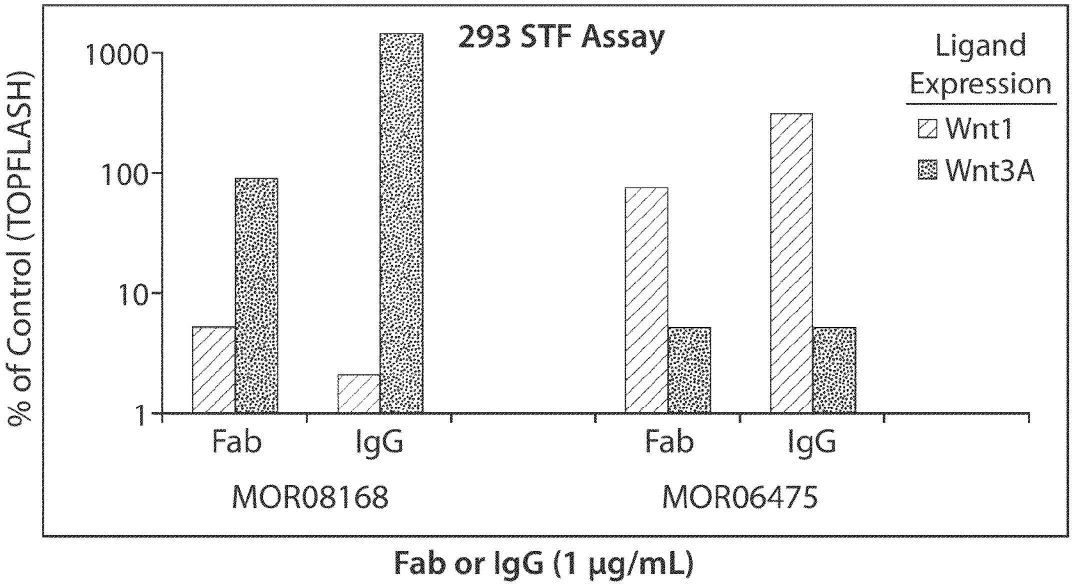
FIG. 5 is a bar chart showing that Fab conversion to IgG results in potentiation of signal from the non-blocked Wnt ligand.

Conversion of LRP6 Antibodies from Fab Fragments to IgG Potentiates Wnt Signaling Induced by the Other Class of Wnt In a rather unexpected observation, conversion of LRP6 antibodies from Fab fragments to IgG potentiates WNT signaling. Propeller 1 anti-LRP6 IgG inhibits Wnt1-dependent and potentiates Wnt3A-dependent signaling in a 293T/17 STF reporter assay. Similarly, Propeller 3 anti-LRP6 IgG inhibits Wnt3A-dependent and potentiates Wnt1-dependent signaling as shown in FIG. 5. This finding suggests that the Wnt signaling pathway may be modified or "fine tuned" using Propeller 1 and Propeller 3 antibodies. Similar effects were observed in STF reporter assays in other cellular backgrounds (e.g. MDA-MB231, MDA-MB435, PA-1, TM3 and 3t3 cells—data not shown)

Example 6

Figure 6:
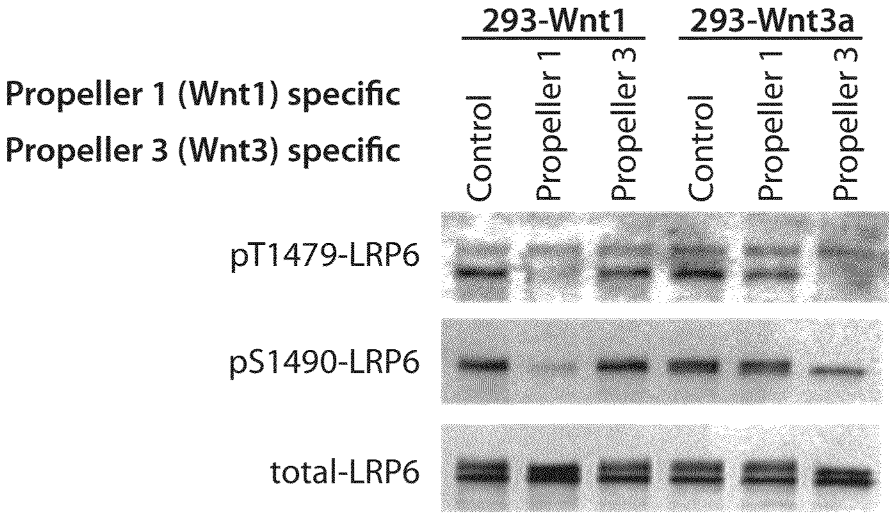
FIG. 6 is a western blot showing selective target inhibition of LRP6 in cellular systems.

Propeller1 or Propeller 3 Anti-LRP6 Fabs Specifically Inhibits Wnt1 or Wnt3A-Induced LRP6 Phosphorylation HEK293T/17 cells were transiently transfected with Wnt1 or Wnt3A expression plasmids and treated with Propeller for Propeller 3 anti-LRP6 Fabs. As seen in FIG. 6, Propeller 1 anti-LRP6 Fabs specifically inhibits Wnt1-induced phosphorylation of LRP6, for example, T1479 and 51490 sites and Propeller 3 antibodies do not. In contrast, Propeller 3 anti-LRP6 specifically inhibits Wnt3A-induced phosphorylation of LRP6 and Propeller 1 antibodies do not. These results support that antibodies bind to distinct propeller domains of LRP6 and block specific Wnt ligands.

Example 7

Figure 7:
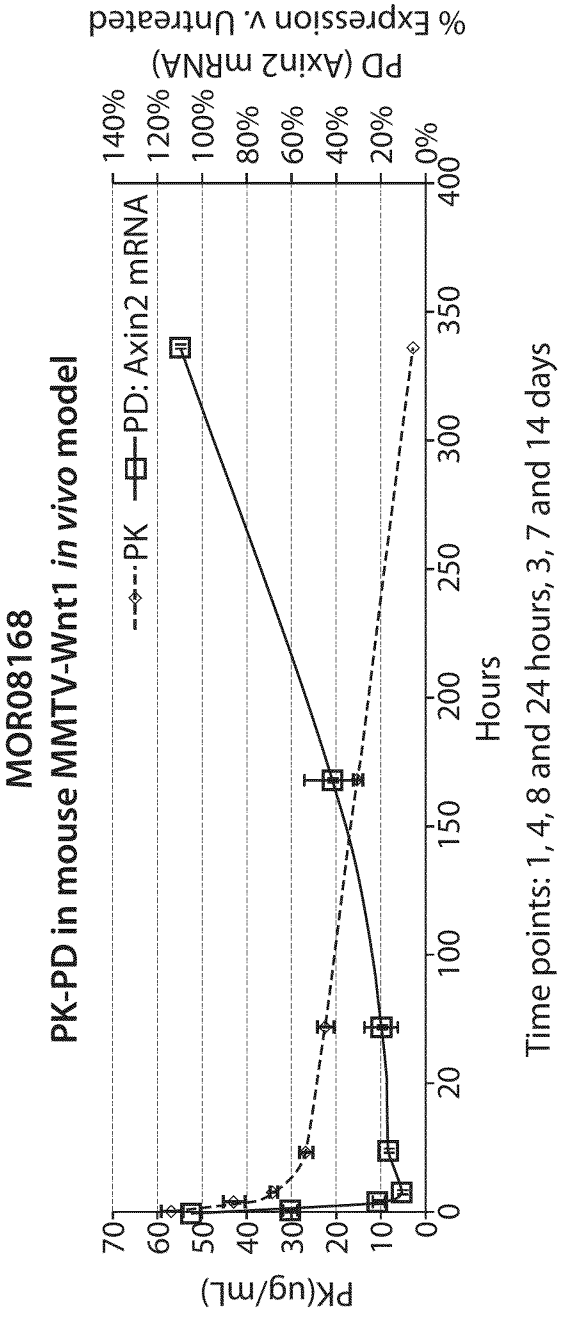
FIG. 7 is a graph showing a single i.v. dose of an LRP6 antibody that binds to β-propeller 1 region at 5 mg/kg in a rodent.

Inhibition of Expression of Wnt1 Target Gene in a MMTV-Wnt1 Tumor Xenograft Model Using a Propeller 1 Anti-LRP6 IgG The LRP6 antibodies were further characterized in vivo in an art recognized genetically engineered mouse model known as MMTV-Wnt1. Experiments were conducted to determine if the anti-LRP6 antibodies in the IgG format could inhibit Wnt signaling and tumor growth in vivo. Mammary tumors derived from MMTV-Wnt1 transgenic mice are Wnt1 dependent; turning off Wnt1 expression using a tetracyclin-regulated system (Gunther et al. (2003), supra) or blocking Wnt activity using Fz8CRDFc (DeAlmeida et al. (2007) Cancer Research 67:5371-5379) inhibits tumor growth in vivo. To measure the effect of anti-LRP6 antibodies on Wnt signaling in MMTV-Wnt 1 tumors, mice implanted with MMTV-Wnt1 tumors were dosed i.v. with a single dose of 5 mg/kg Wnt1 class-specific antagonistic anti-LRP6 antibody. Serum concentrations of the antibody as well as the mRNA expression of β-catenin target gene Axin2 were analyzed over a period of two weeks. The terminal β-phase half-life of the LRP6 antibody was about 108 hours. Corresponding to the antibody injection, a significant decrease of Axin2 mRNA expression was observed in tumors, and Axin2 expression gradually recovered one week after the antibody injection when the antibody level in serum decreased. These results suggest that Wnt1class-specific anti-LRP6 antibody suppresses Wnt signaling in MMTV-Wnt1 xenografts and this suppression is correlated with the concentration of LRP6 antibody in serum. To test the effect of anti-LRP6 antibodies on tumor growth, mice were dosed with Propeller 1-, Propeller 3-specific anti-LRP6 antibodies, or isotype matched control antibodies. Mice were dosed i.v. with an initial dose of 20 mg/kg, followed every third day with 10 mg/kg. In this experiment Propeller 1, but not Propeller 3-specific anti-LRP6 antibody caused tumor regression. Together, these results demonstrate that Propeller 1-specific anti-LRP6 antibody induces regression of MMTV-Wnt1 xenografts, MMTV-Wnt1 tumor xenografts in nude mice were treated with MOR08168, a Propeller 1 anti-LRP6 IgG at different timepoints ranging from 1 hour to 14 days. FIG. 7 shows an inverse correlation with PK serum concentration of the antibody and mRNA expression of Wnt target gene Axin2. Axin2 gene expression levels in tumors are inhibited with MOR08168 treatment, and return as antibody is cleared from the serum.

In addition to Axin2, the effect of MOR08168 on the expression of additional genes was evaluated. Affymetrix Mouse430 2.0 Arrays were used to profile a time course experiment of MMTV-Wnt1 allograft Tumors plus or minus a single dose of MOR08168 (5 mg/kg). There were six time points in all (0, 1, 3, 8, 24, 336 hours) and there were three replicates per time point. Based on data demonstrating maximal inhibition of Axin upon treatment with antibody, 8 h was chosen as best representative time point to determine differentially expressed genes putatively responding to Wnt pathway inhibition. The R/Bioconductor framework was utilized and Limma package was employed to determine differentially expressed genes between the 0 hour time point and the 8 hour time point. An adjusted P-value of 0.05 was used as the threshold to determine the set of differentially expressed genes. Based on this cutoff there are 1270 probe sets called differentially expressed mapped to 972 gene(s). FIG. 5A is a table that shows genes that were upregulated >2-fold with an adjusted P-value of <0.01 and FIG. 8B is a table that shows genes that were downregulated >2-fold with an adjusted P-value of <0.01.

Example 8

Figure 9A:
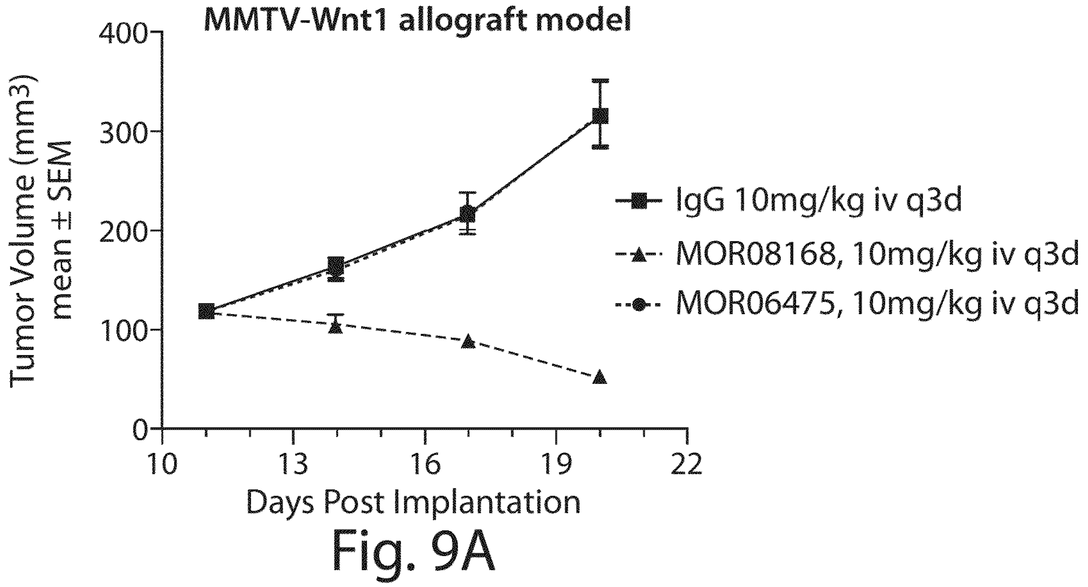
FIG. 9A is a graph showing Propeller 1, but not Propeller 3 mAb, causes in vivo tumor regression in MMTV-Wnt1 model.
Figure 9B:
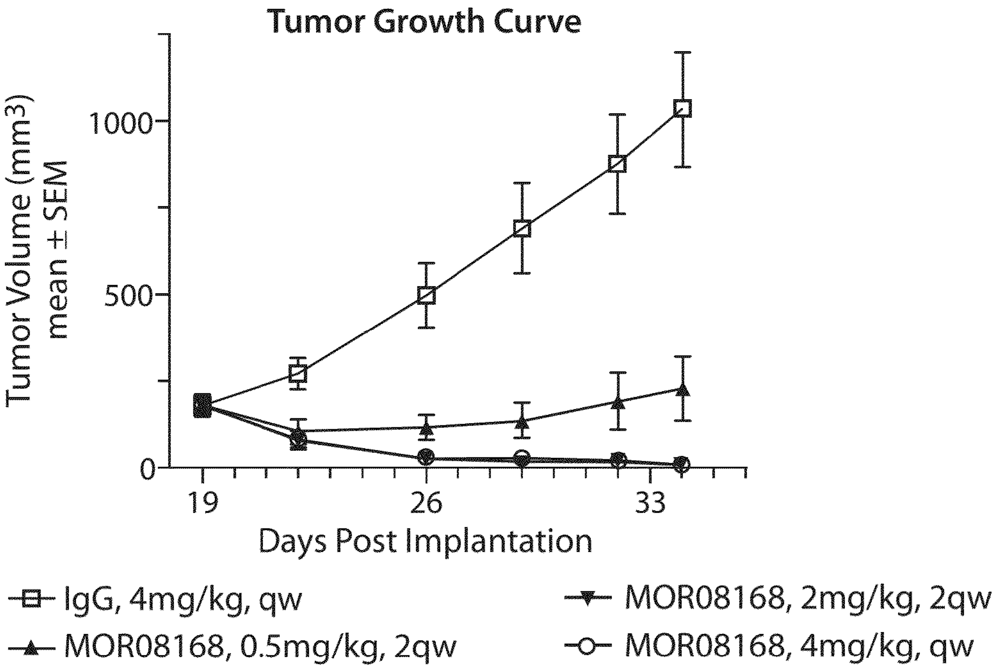
FIG. 9B is a graph showing the effect of different doses of the Propeller 1 mAb on the growth of the MMTV-Wnt1 tumor model.

Anti-Tumor Activities of Propeller 1 and Propeller 3 anti-LRP6 Antibodies in MMTV-Wnt1 Allograft Model Anti-tumor activity of LRP6 Propeller 1 and 3 antibodies was evaluated in the MMTV-Wnt1 allograft model. MMTV-Wnt1 tumor fragments were implanted subcutaneously (s.c.) into female nude mice. 11 days after implantation, mice carrying MMTV-Wnt1 tumors (n=8, average 121 $mm^3$; range: 100-147 $mm^3$) were treated with vehicle IgG (10 mg/kg, intravenously (i.v.), every third day (q3d), LRP6-Propeller 1 Ab MOR08168 (10 mg/kg, i.v., q3d), or LRP6-Propeller 3 Ab MOR06475 (10 mg/kg, i.v., q3d), and tumors calipered every third day. LRP6-Propeller 1 MOR08168 Ab dose-dependently induced tumor regressions (−55%, p<0.05) (See FIG. 9).

Example 9

Figure 10:
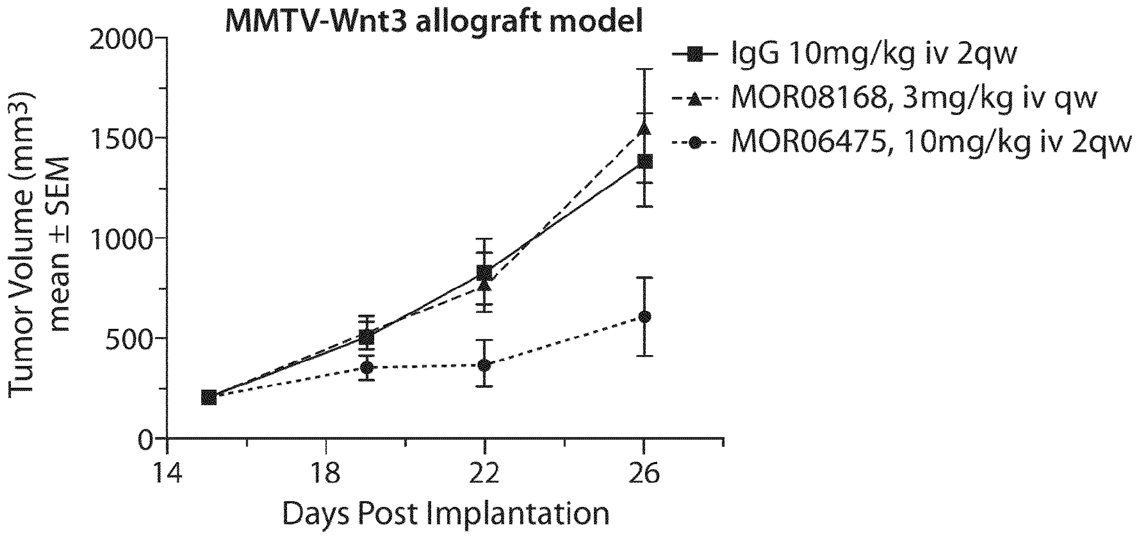
FIG. 10 is a graph showing Propeller 3, but not Propeller 1 mAb, causes inhibition of tumor growth in a MMTV-Wnt3 model.

Anti-Tumor Activities of Propeller 1 and Propeller 3 Anti-LRP6 Antibodies in MMTV-Wnt3 Allograft Model Anti-tumor activity of LRP6 Propeller 1 and 3 antibodies was evaluated in the MMTV-Wnt3 allograft model. MMTV-Wnt3 tumor fragments were implanted subcutaneously (s.c.) into female nude mice. 15 days after implantation, mice carrying MMTV-Wnt3 tumors (n=6, average 209 $mm^3$; range: 113-337 $mm^3$) were treated with vehicle IgG (10 mg/kg, intravenously (i.v.), twice a week (2qw), MOR08168 LRP6-Propeller 1 Ab (3 mg/kg, i.v., qw), or MOR06475 LRP6-Propeller 3 Ab (10 mg/kg, i.v., 2qw) and tumors calipered twice per week. MOR06475 LRP6-Propeller 3 Ab demonstrated antitumor activity (T/C=34%, p<0.05) (See FIG. 10).

Example 10

Figure 11:
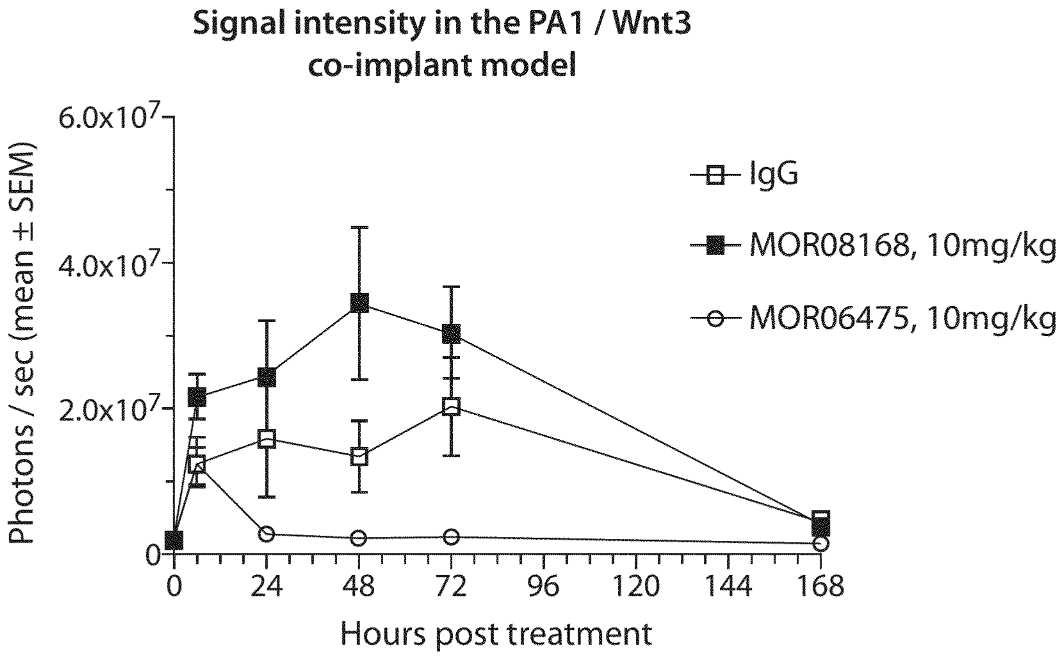
FIG. 11 is a graph showing Propeller 3, but not Propeller 1 mAb causes inhibition of Wnt3A-induced Super Top Flash activity in PA-1 cells in vivo.

Evaluation of Ability of Propeller 1 and 3 Anti-LRP6 Antibodies to Inhibit Wnt3A In Vivo The ability of LRP6-Propeller 1 and 3 antibodies to inhibit Wnt3 class Wnt signaling in vivo was tested in a co-implant system consisting of PA1-STF reporter cells co-implanted with Wnt3A secreting L cells. Female nude mice were implanted subcutaneously with 10×10e6 PA1-STF cells and 0.5×10e6 L-Wnt3A cells and randomized in groups of 5. 24 hours later, mice received a single intravenous dose of vehicle, MOR08168 LRP6-Propeller 1 Ab (10 mg/kg), or MOR06475 LRP6-Propeller 3 Ab (10 mg/kg) and were imaged by Xenogen 6 hours, 24 hours, 48 hours, 72 hours and 168 hours later. MOR06475 was able to inhibit Wnt3a induced signaling for at least 72 hours, whereas Mor08168 increased Wnt3A induced signaling (FIG. 11).

Example 11

Epitope Mapping of LRP6 PD3/4 and its Antibody Complex by HDx MS

Figure 12A:
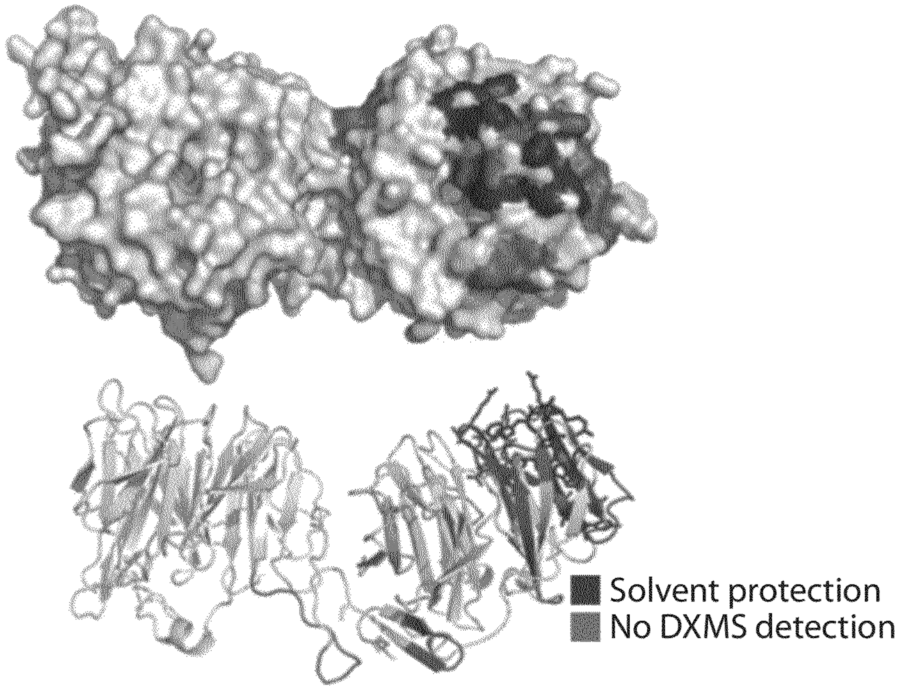
FIG. 12 is a figure showing solvent protected regions of LRP6 PD3-4 by MOR06475 by HDx MS (A) and that mutations of specific residues result in loss of binding of scFv MOR06475 (B)
Figure 12B:
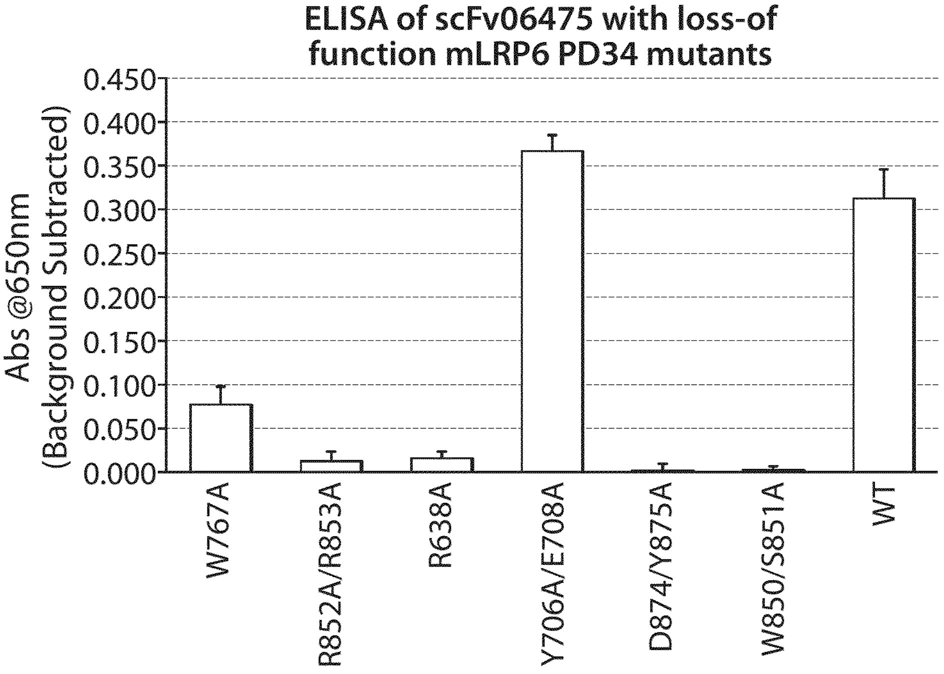

To identify antibody binding sites within YWTD-EGF region of Propeller 3, hydrogen-deuterium exchange (HDx) mass spectrometry (MS) was employed. LRP6 Propeller domains 3-4 (PD3/4) has 12 cysteines and 4 N-linked glycosylation sites. All 4 N-linked glycosylation sites are positioned in Propeller 3 domain (631-932). By HDx MS, close to 100% coverage (amount of protein it was possible to get structural information for) was mapped on the Propeller 4 domain, and about 70% coverage on Propeller 3 domain. Regions immediately surrounding the 4 glycosylated sites remain undetected (FIG. 12A). In the presence of Fab 06745, 2 weakly solvent protected peptides were found in Propeller 3 ($Phe^{636}$-$Leu^{647}$, $Tyr^{844}$-$Glu^{856}$; FIG. 11A). This suggests that the residues or a fraction of the residues responsible for the epitope are either on the protected peptides or spatially nearby. Based on the crystal structure of LRP6 PD34, the solvent protected regions correspond to the concave surface between blade 1 and 6 of Prop 3.

Mutations that Disrupt the Interaction of ScFv06475 with LRP6 PD34

To confirm that the rim of blade 1 and 6 is responsible for antibody mediated inhibition of Wnt3a signaling, a series of LRP6 surface mutations were constructed (R638A, W767A, Y706A/E708A, W850A/S851A, R852/R853A, and D874A/Y875A) that also approximately covered the region implicated by HDx in binding. To ensure that the mutant proteins are properly folded, differential static light scattering (DSLS) thermal-melt assay was performed. Temperature denaturation experiment showed that the aggregation temperature, $T_{agg}$, (the temperature at which 50% of the protein is denatured) of wild-type and mutant proteins was similar. Thus, the mutations had no effect on the folding or stability of the protein.

The binding capacity of mutant LRP6 to scFv MOR06475 was determined by ELISA. Mutation of residues (R638, W850/5851, and R852/R853) that are located on peptides that showed solvent protection in HDx MS experiments also showed dramatic decrease in antibody binding (See FIG. 12B). Mutation of residues (Y706/E708) that are located on peptides showing no solvent protection in HDx also showed no change in antibody binding capability (FIG. 11B). Thus the binding assay data are in good agreement with the binding interface as mapped by HDx MS suggesting the residues R638, W850, S851, R852, and R853 participate directly in the epitope.

Figure 13:
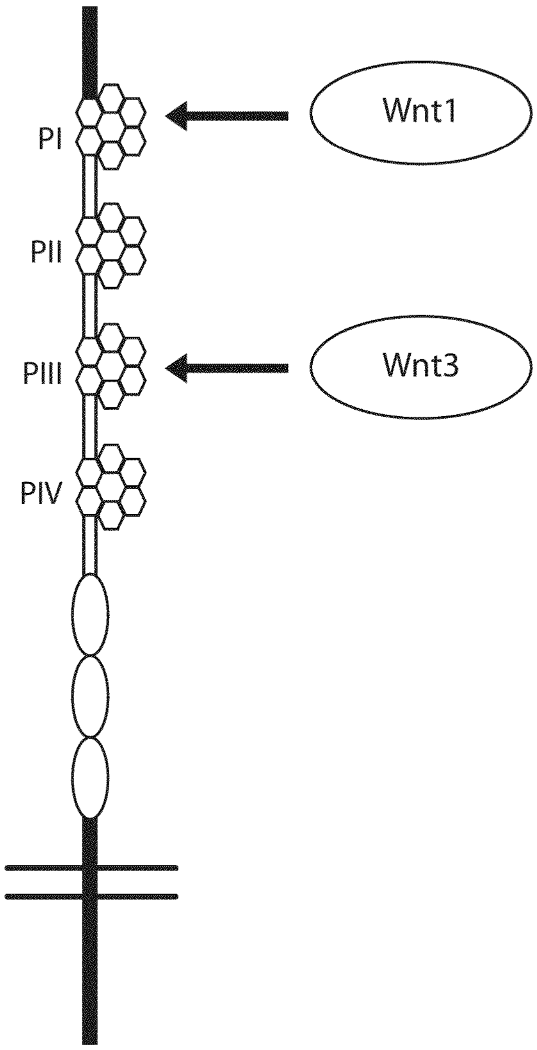
FIG. 13 is a schematic showing the β-propeller regions of LRP6.

Collectively, these results show that different Wnt proteins require different Propeller regions of LRP6 for signaling. The Wnt1 class of Wnt proteins (Wnt1, 1, 2, 6, 7A, 7B, 9, 10A, 10B) requires Propeller 1 of LRP6 for Wnt1 signaling, and they can be inhibited by Propeller 1 specific anti-LRP6 antibodies. The Wnt 3A class of Wnt proteins (Wnt3 and Wnt3a) requires Propeller 3 of LRP6 for Wnt3 signaling, and they can be inhibited by Propeller 3 specific anti-LRP6 antibodies (FIG. 13). Another unexpected finding was the Wnt-potentiating activity of the antibodies in the bivalent IgG format in the presence of Wnt ligands. All antibodies tested in IgG format enhanced either Wnt1 or Wnt3A signaling in the STF Luc reporter gene assay. Interestingly, most Fabs that inhibited Wnt1 and were inactive in the Wnt3A assay, still inhibited Wnt1 as an IgG, but potentiated Wnt3A signaling and vice versa. Most Fabs that inhibited Wnt3A potentiated Wnt1 activity as an IgG. The effect was independent of the IgG format, as several formats were tested (IgG1LALA, IgG2, IgG4, IgG4_Pro). These data shows that different Wnt proteins bind to different Propellers of LRP6 for signaling. Dimerization of LRP6 using bivalent LRP6 antibodies is not sufficient to stimulate Wnt signaling by itself, but can potentiate Wnt signaling initiated by the other class of Wnt proteins. These findings demonstrate that different canonical Wnt ligands use distinct binding sites on LRP6 and that all bivalent antibodies enhance Wnt activity in IgG format in the presence of the non-blocked Wnt Fab (single chain antibodies, unibodies). Monovalent structures of any kind as a final format circumvent the Wnt potentiation. Alternatively, the construction of a bi-specific IgG or IgG-like molecule carrying both the Wnt1- and Wnt3A inhibitory activity circumvent potentiation. Thus, LRP6 antibody constructs can be designed to control and "fine-tune" the Wnt pathway

Example 12

Generating a Biparatopic LRP6 Antibody

This example describes the production and characterization of biparatopic anti-LRP6 IgG-scFv antibodies. Various anti-LRP6 scFv's containing different domain orientations (e.g. VH-VL or VL-VH) and different linker lengths (e.g. $(Gly_4Ser)_3$ or $(Gly_4Ser)_4$) were initially expressed, purified and characterized. Based on results of the scFv study, different biparatopic anti-LRP6 IgG-scFv's were prepared and further evaluated. The scFv may be placed at various positions within the IgG including the C-terminus of CH3 or CL and the N-terminus of VH or VL. Furthermore, various linkers may be used to connect the scFv to the IgG including $Gly_4Ser$ and $(GlyGlySer)_2$.

(a) Materials and Methods (i) Generation of Anti-LRP6 scFv

Genes coding for all scFv-variants were synthesized by Geneart. DNA-fragments coding for scFv in both orientations (VH-VL and VL-VH, separated by two different linkers: $(Gly_4Ser)_3$ and $(Gly_4Ser)_4$, with N-terminal signal sequence and C-terminal 6×His-tag) were directly cloned from Geneart vectors via NdeI/XbaI into vector pFAB15-FkpA, resulting constructs were called pFab15-MOR06475-VH-$(Gly_4Ser)_3$-VL, pFab15-MOR06475-VH-$(Gly_4Ser)_4$-VL, pFab15-MOR06475-VL-$(Gly_4Ser)_3$-VH, pFab15-MOR06475-VL-$(Gly_4Ser)_4$-VH, pFab15-MOR08168-VH-$(Gly_4Ser)_3$-VL, pFab15-MOR08168-VH-$(Gly_4Ser)_4$-VL, pFab15-MOR08168-VL-$(Gly_4Ser)_3$-VH, pFab15-MOR08168-VL-$(Gly_4Ser)_4$-VH, pFab15-MOR08545-VH-$(Gly_4Ser)_3$-VL, pFab15-MOR08545-VH-$(Gly_4Ser)_4$-VL, pFab15-MOR08545-VL-$(Gly_4Ser)_3$-VH and pFab15-MOR08545-VL-$(Gly_4Ser)_4$-VH.

(ii) Generation of Biparatopic Anti-LRP6 IgG-scFv

Anti-LRP6_MOR08168 hIgG1LALA_6475scFv

Vector pRS5a MOR08168 hIgG1LALA containing codon-optimized VH-sequence (synthesized by Geneart) was used as source for generation of biparatopic construct. Initially, AfeI-site was introduced by QuickChange Site-Directed Mutagenesis (Stratagene) at 3'-end of sequence coding for hIgG1LALA (primer no. 1: 5'-agcgtgatgcacgaagcgctgcacaaccactac-3' (SEQ ID NO: 213) and primer no. 2: 5'-gtagtggttgtgcagcgcttcgtgcatcacgctg-3' (SEQ ID NO; 214)). Gene coding for MOR06475scFv (VL-VH-orientation, separated by $(Gly_4Ser)_4$-linker) was synthesized by Geneart. 5'-primer containing AfeI-site and sequence coding for $(GlyGlySer)_2$-linker as well as 3'-primer containing AscI-site were used for amplification of entire MOR06475-scFv-gene (primer no. 3: 5'-tgatgcacgaagcgctgcacaaccacta-cacccagaagagcctgagcctgtcccccggcaag ggcggctccggcggaagcgatatc-3' (SEQ ID NO: 215) and primer no. 4: 5% gagcggccgcccggcgcgcc tcatcagctggacactgtcaccaggg-3' (SEQ ID NO: 216)). PCR-product was then cloned via AfeI/AscI into vector pRS5a MOR08168 hIgG1LALA resulting in the final construct pRS5a MOR08168 hIgG1LALA-6475sc-fv. Gene coding for codon-optimized VL of MOR08168 was synthesized by Geneart. 5'-primer containing Age-site and 3'-primer containing HindIII-site were used for amplification of entire MOR08168-VL-genes (primer no. 5: (5'-gcttccggacaccaccggt gacatcgagctgacccagcc-3' SEQ ID NO: 217) and primer no. 6: 5'-cagcacggtaagctt ggtgcctccgccgaacaccag-3' (SEQ ID NO: 218)). PCR-product was then cloned via AgeI/HindIII into vector pRS5a-hlambda resulting in the final construct pRS5a MOR08168 hlambda.

anti-LRP6_MOR08168 hIgG1LALA_6475scFv_without Lys (K)

Vector pRS5a MOR08168 hIgG1LALA-6475scFv (SEQ ID NO:165) was used as template DNA for removal of C-terminal Lysin at CH3. Quick Change XL Site-Directed Mutagenesis Kit (Stratagene) was used in combination with following primers:

```
5'-ctgtcccccggcggcggctccggc-3'    (SEQ ID NO: 219)

5'-gccggagccgccgccgggggacag-3'    (SEQ ID NO: 220)
```

Site-Directed Mutagensis was done according to Stratagene protocol; resulting new construct was called pRS5a hIgG1LALA MOR08168opt 6475 scFv K. Vector pRS5a MOR08168 hlambda (generation described for anti-LRP6_MOR08168 hIgG1LALA_6475scFv) containing codon-optimized VL-sequence (synthesized by Geneart) was used w/o any modifications for expression of LC.

Anti-LRP6_MOR08168 hIgG1LALA_6475scFv_AspPro to AspAla (DP_to_DA)

Vector pRS5a MOR08168 hIgG1LALA-6475scFv (SEQ ID NO:165) was used as template DNA for substitution of DP to DA in VH of scFv. Quick Change XL Site-Directed Mutagenesis Kit (Stratagene) was used in combination with following primers:

```
                                    (SEQ ID NO: 221)
5'-ccatgaccaacatggacgccgtggacaccgccacc-3'

                                    (SEQ ID NO: 222)
5'-ggtggcggtgtccacggcgtccatgttggtcatgg-3'
```

Site-Directed Mutagensis was done according to Stratagene protocol; resulting new construct was called pRS5a hIgG1LALA MOR08168opt 6475 scFv DP to DA. Vector pRS5a MOR08168 hlambda (generation described for anti-LRP6_MOR08168 hIgG1LALA_6475scFv) containing codon-optimized VL-sequence (synthesized by Geneart) was used w/o any modifications for expression of LC.

Anti-LRP6_MOR08168 hIgG1LALA_6475scFv_AspPro to ThrAla (DP_to_TA)

Vector pRS5a MOR08168 hIgG1LALA-6475scFv (SEQ ID NO:165) was used as template DNA for substitution of DP to TA in VH of scFv. Quick Change XL Site-Directed Mutagenesis Kit (Stratagene) was used in combination with following primers:

```
                                    (SEQ ID NO: 223)
5'-caccatgaccaacatgaccgccgtggacaccgccacc-3'

                                    (SEQ ID NO: 224)
5'-ggtggcggtgtccacggcggtcatgttggtcatggtg-3'
```

Site-Directed Mutagensis was done according to Stratagene protocol; resulting new construct was called pRS5a hIgG1LALA MOR08168opt 6475 scFv DP to TA. Vector pRS5a MOR08168 hlambda (generation described for anti-LRP6_MOR08168 hIgG1LALA_6475scFv) containing codon-optimized VL-sequence (synthesized by Geneart) was used w/o any modifications for expression of LC.

anti-LRP6_MOR08168hIgG1LALA_6475scFv_at_ValLeu (VL)

Vector pRS5a MOR08168 hIgG1LALA containing codon-optimized VH-sequence (synthesized by Geneart) was used w/o any modifications for expression of HC. Gene coding for codon-optimized MOR06475scFv and MOR08168-VL was synthesized by DNA2.0 and was cloned via AgeI/HindIII into vector pRS5a hlambda MOR08168. Resulting vector was called pRS5a hlambda MOR08168 6475scFv at VL.

Anti-LRP6_MOR06475hIgG1LALA_8168scfv_(VH-3-VL), Where 3 Represents a $(Gly_4Ser)_3$ Amino Acid Linker Between the VH and VL Chains.

MOR06475-VH was amplified from vector pM2 hIgG1LALA MOR06475 with following primers:

```
                                    (SEQ ID NO: 225)
5'-gttcctggtcgcgatcctggaaggggtgcactgccaggtgcaattga

aagaaagcg-3'
```

-continued

```
                                    (SEQ ID NO: 226)
5'-cttggtggaggctgagctaac-3'
```

PCR-product was cloned via NruI/BlpI into vector pRS5a hIgG1LALA MOR08168 6475scFv, resulting vector was called pRS5a hIgG1LALA MOR06475 6475scFv. MOR08168scFv was amplified from vector pRS5a MOR08168 scFv (VH-3-VL) with following primers:

```
                                    (SEQ ID NO: 227)
5'-gcacgaagcgctgcacaaccactacacccagaagagcctgagcctg

tcccccggcaagggcggctccggcggaagccaggttcaattggttgaaa

gc-3'

                                    (SEQ ID NO: 228)
5'-gggccctctagagcggccgcccggcgcgcctcatcacagaacggta

agcttggtgcc-3'
```

PCR-product was cloned via AfeI/XbaI into vector pRS5a hIgG1LALA MOR06475 6475scFv, resulting final vector was called pRS5a hIgG1LALA MOR06475 8168scFv (VH-3-VL).

MOR06475-VL was amplified from vector pM2 hkappa MOR06475 with following primers:

```
                                    (SEQ ID NO: 229)
5'-gacaccaccggtgatatcgtgctgacccagagc-3'

                                    (SEQ ID NO: 210)
5'-gcagccaccgtacgtttaatttcaac-3'
```

PCR-product was cloned into vector pRS5a hkappa MOR06654 via AgeI/BsiWI, resulting vector was called pRS5a hkappa MOR06475.

anti-LRP6_MOR06475hIgG1 LALA_8168scfv (VH-4-VL), Where 4 Represents a $(Gly_4Ser)_4$ Amino Acid Linker Between the VH and VL Chains.

MOR06475-VH was amplified from vector pM2 hIgG1LALA MOR06475 with following primers:

```
                                    (SEQ ID NO: 211)
5'-gttcctggtcgcgatcctggaaggggtgcactgccaggtgcaattga

aagaaagcg-3'

                                    (SEQ ID NO: 212)
5'-cttggtggaggctgagctaac-3'
```

PCR-product was cloned via NruI/BlpI into vector pRS5a hIgG1LALA MOR08168 6475scFv, resulting vector was called pRS5a hIgG1LALA MOR06475 6475scFv. MOR08168scFv was amplified from vector pRS5a MOR08168 scFv (VH-4-VL) with following primers:

```
                                    (SEQ ID NO: 213)
5'-gcacgaagcgctgcacaaccactacacccagaagagcctgagcctg

tcccccggcaagggcggctccggcggaagccaggttcaattggttgaaa

gc-3'

                                    (SEQ ID NO: 214)
5'-gggccctctagagcggccgcccggcgcgcctcatcacagaacggta

agcttggtgcc-3'
```

MOR06475-VL was amplified from vector pM2 hkappa MOR06475 with following primers:

(SEQ ID NO: 215)
5'-gacaccaccggtgatatcgtgctgacccagagc-3'

(SEQ ID NO: 216)
5'-gcagccaccgtacgtttaatttcaac-3'

PCR-product was cloned into vector pRS5a hkappa MOR06654 via AgeI/BsiWI, resulting vector was called pRS5a hkappa MOR06475.

(iii) Expression of Anti-LRP6-scFv

Electrocompetent *E. coli* strain W3110 was transformed with plasmid-DNA. Pre-cultures (150 ml LB-medium containing 12.5 μg Tetracyline/ml and 0.4% Glucose, in 500 ml flask) were inoculated with a single colony and incubated over night at 37° C./230 rpm. Expression cultures (6×500 ml SB-medium containing 12.5 μg Tetracycline/ml, in 21 flask) were inoculated with pre-cultures to 0.13600 of 0.1 and incubated at 25° C./230 rpm to O.D600 of ca. 0.6. Then IPTG (Roche) was added to an end concentration of 0.4 mM and cultures were incubated over night at 25° C./230 rpm. Cells were harvested by centrifugation (20 min at 4600 rpm, 4° C.) and cell pellets were frozen at −20° C.

(iv) Purification of Anti-LRP6-scFv

Pellets from 3 1 expressions were suspended in 50 ml Lysis-Buffer (20 mM NaH2PO4, 20 mM Imidazole, 500 mM NaCl, pH 7.4; 1 tablet Complete without EDTA per 50 ml buffer, Roche #11836170001, 10 mM $MgSO_4$ and Benzonase). Cell suspensions were treated by French Press (2× at 1000 bar) and centrifuged for 30 min at 16000×g, 4° C. 1 ml HisTrap HP column (GE Helthcare) was equilibrated with 10 ml Lysis-Buffer. Supernatants were filtrated through Stericup Filter (Millipore) and loaded into equilibrated column (1 ml/min). Column was washed with Lysis-Buffer (20 ml) and bound protein was eluted with 3 ml Elution-Buffer (as Lysis-Buffer but 250 mM Imidazole). Eluate was directly loaded on Superdex75-column (HiLoad 16/60, GE-Healthcare), equilibrated with 130 ml PBS (1 ml/min). Run was done with PBS at 1 ml/min, eluate was collected in 1.5 ml fractions and analyzed on 10% Bis-Tris-Gel (NuPage, Invitrogen). Adequate fractions were pooled, filtrated through 0.2 μm filter and stored at 4° C. All purified proteins were analyzed by LC-MS (with oxidized and reduced samples) and by SEC-MALS (aggregation analysis).

(v) Transient Expression of Biparatopic Anti-LRP6 IgG-scFv 3.2 L HEK293-6E cells were cultivated in M11V3 Media: Lot#D07668B in a BioWave20 at Rocks 10 rpm, Angle 7°, Aeration 25 L/h, $O_2$ 25%, $CO_2$ 6% to a density of 2E6 viable cells/mL. The cells were transiently transfected with 1.8 L DNA:PEI-MIX (plasmid: pRS5a MOR08168 hIgG1 LALA-6475sc-Fv 5 mg+pRS5a MOR08168 hlambda 5 mg+20 mg PEI). 6 hours after transfection 5 L Feeding media (Novartis) with Yeastolate: Lot#09-021 was added to the culture. The cells were then further cultivated at Rocks 24 rpm, Angle: 7°, Aeration 25 L/h, $O_2$ 25%, $CO_2$ 0-6%. Seven days after transfection, cells were removed by crossflow filtration using Fresenius filters 0.2 μm. Afterwards the cell free material was concentrated to 1.75 L with crossflow filtration using 10 kDa cut off filter from Fresenius. After the concentration the concentrate was sterile filtered through a stericup filter (0.22 μm). The sterile supernatant was stored at 4° C. All described biaparatopic anti-LRP6-scFv variants were expressed in a similar manner.

(vi) Purification of Biparatopic Anti-LRP6 IgG-scFv

The purification of the biparatopic IgG was performed on a AKTA 100 explorer Air chromatography system at 6° C. in a cooling cabinet, using a freshly sanitised (0.2 M NaOH/30% isopropanol) XK16/20 column with 25 ml of self-packed MabSelect SuRe resin (all GE Healthcare). All flow rates were 3.5 ml/min, except for loading, at a pressure limit of 5 bar. The column was equilibrated with 3 CV of PBS (made from 10×, Gibco), then the concentrated and sterile filtrated fermentation supernatant (1.35 L) was loaded at 2.0 ml/min o/n. The column was washed with 8 CV of PBS. Then the IgG was eluted with a pH gradient, starting at 50 mM citrate, 70 mM NaCl, pH 4.5, going linearly down in 12 CV to 50 mM citrate, 70 mM NaCl, pH 2.5, followed by a 2 CV constant step of the same pH 2.5 buffer. The biparatopic IgG eluted during the gradient in a single symmetric peak around pH 3.8, and was collected into 4 ml fractions. The fractions were pooled into three pools, left slope, main peak and right slope. The pools were immediately titrated to pH 7.0, slowly and under stirring, using 2 M Tris, pH 9.0. The pools were sterile filtered (Millipore Steriflip, 0.22 μm), OD 280 nm was measured in a Lambda 35 Spectrometer (Perkin Elmer), and the protein concentration was calculated based on the sequence data. The pools were separately tested for aggregation (SEC-MALS) and purity (SDS-PAGE and MS), and based on the results, only the central pool (35 ml at 2.55 mg/ml protein) was further used. All described biaparatopic anti-LRP6-scFv variants were purified in a similar manner.

(vii) Cross-Reactivity Analysis by Protein Microarrays

The microarrays were custom-made high-density protein chips manufactured by Protagen AG (UNIchip® AV-VAR-EP) and contained 384 pre-defined and purified human proteins printed in quadruplicates on a nitrocellulose coated glass slide. The proteins are classified as extracellular or secretory proteins based on gene ontology and expressed as an N-terminal His-tag fusion protein using *Escherichia coli*, and purified using immobilized metal ion affinity chromatography (IMAC). The hybridization of the antibody was done using the TECAN Hybridization Station HS400Pro, programmed with a protocol developed by Protagen AG. The primary antibodies were tested at a final concentration of 5 μg/ml. The secondary labeled antibody, a Cy5-conjugated AffiniPure Goat anti-hsIgG $F(ab')_2$, fragment specific (Jackson Immunoresearch, code no. 109-175-097), was used at a final concentration of 7.5 μg/ml. Microarray image acquisition was done using a GenePix Professional 4200A fluorescence microarray scanner (Axon Instruments, CA) equipped with a red laser (635 nm). Image analysis was performed using the GenePix Pro v6.0 software. Data analysis was done using Protagen UNIchip® Data Analysis Tool v1.8. To determine unspecific cross-reactivity derived from binding of the secondary antibody directly to the printed antigens, the secondary antibody was also incubated on the UNIchip® without the use of the primary antibody. For the determination of the level of cross reactivity normalized to the corresponding antigen, the fluorescent signal intensity value at saturated concentration (20 fmol/spot) was set as 100%. All signal intensities for a given protein, which were more than 4% of the antigen signal, were considered as positive hits, providing they were not also found in the respective control with only the secondary labeled antibody.

(viii) Conformational Stability Measured by Differential Scanning Calorimetry (DSC)

DSC was measured using a capillary cell microcalorimeter VP-DSC from Microcal, equipped with a deep-well plate auto-sampler. Data were analyzed with the software Origin 7.5. The samples (400 μl), were added to 2 ml deep-well plates from Nunc™. The samples in PBS pH 7.0 were analyzed at 1 mg/ml. The reference sample contained 400 μl of the same buffer as the analyte, usually PBS. Heat change associated with thermal denaturation was measured between 20° C. and 100° C., with a heating rate of 3.3° C. $min^{-1}$. The apparent melting temperature (Tm), corresponded to the thermal transition midpoint, where 50% of the analyte is unfolded.

(ix) Serum Stability Studies

Purified proteins were solved in 35 μl rat serum or mouse serum (Gene Tex) resulting in an end concentration of 0.3 mg/ml. Samples were incubated at 37° C. in a plate incubator. 4 μl of each sample were taken at different time-points, 10 μl sample buffer (4×, NuPage, Invitrogen) and 26 μl water were added and samples were frozen at −20° C. 12 μl of each sample were loaded into 12% Bis-Tris-Gel (NuPage, Invitrogen), electrophoresis was done at 200V for 35 min. Protein transfer was done to PVDF-membrane (Invitrogen) in Borate buffer (50 mM Borate, 50 mM Tris) at 30V for 1 h. Membranes were briefly washed in TBST (10 mM Tris-HCl, pH 7.5, 150 mM NaCl, 0.1% Tween80) and then incubated for 2 h at RT/shaker in TBST containing 5% milk powder. Membranes were briefly washed in TBST and then incubated for 1 h at RT/shaker in TBST containing POD-conjugated Goat-anti-human IgG, Fab fragment specific (Dianova), diluted 1:10.000 or anti-His POD (Roche) diluted 1:500. Membranes were washed three times for 5 min at RT/shaker in TBST. Signal detection was done using BM Blue POD Substrate (Roche) or ECL/ECL Plus (GE-Healthcare).

Figure 14:
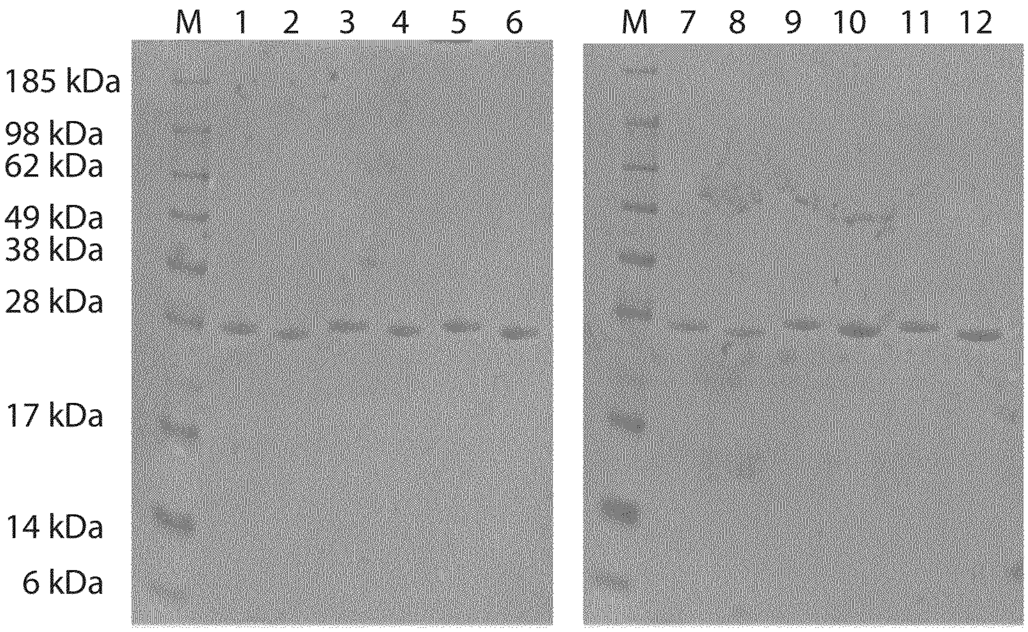
FIG. 14 is a photograph of an SDS-PAGE gel showing that all scFv molecules successfully expressed and purified from *E. coli;*

(b) Results (i) Expression, Purification and Characterisation of Anti-LRP6-ScFvs All scFv's were successfully expressed in *E. coli* W3110 and purified by affinity chromatography followed by size exclusion chromatography. Expected size (MOR06475 $(Gly_4Ser)_3/(Gly_4Ser)_4$: 26.74 and 27.06 kDa respectively, MOR08168 $(Gly_4Ser)_3/(Gly_4Ser)_4$: 26.5 and 26.85 kDa respectively, MOR08545 $(Gly_4Ser)_3/(Gly_4Ser)_4$: 25.99 and 26.31 kDa respectively was confirmed for all purified samples by LC-MS analysis done with reduced and oxidized samples and by SDS PAGE. Purities >95% were obtained. FIG. 14 shows the results of SDS-PAGE analysis in which 1.5 μg of each purified protein were loaded into 10% Bis-Tris gel (NuPage, Invitrogen) M: Marker See Blue Plus2 (Invitrogen); (1): MOR06475-VH-$(Gly_4Ser)_4$-VL; (2) MOR06475-VL-$(Gly_4Ser)_4$-VH; (3) MOR08168-VH-$(Gly_4Ser)_4$-VL; (4) MOR08168-VL-$(Gly_4Ser)_4$-VH; (5) MOR08545-VH-$(Gly_4Ser)_4$-VL; (6) MOR08545-VL-$(Gly_4Ser)_4$-VH (7) MOR06475-VH-$(Gly_4Ser)_3$-VL; (8) MOR06475-VL-$(Gly_4Ser)_3$-VH (9) MOR08168-VH-$(Gly_4Ser)_3$-VL; (10) MOR08168-VL-$(Gly_4Ser)_3$-VH; (11) MOR08545-VH-$(Gly_4Ser)_3$-VL; (12) MOR08545-VL-$(Gly_4Ser)_3$-VH.

Thermal Stability was compared for all SaFv's by DSC. The melting temperature (Tm) was significantly higher for the MOR06475 variants. The highest Tm (64.7° C.) was observed for MOR06475-VL-$(Gly_4Ser)_4$-VH therefore this molecule is believed to be potentially more stable then the other constructs produced.

Figure 17:
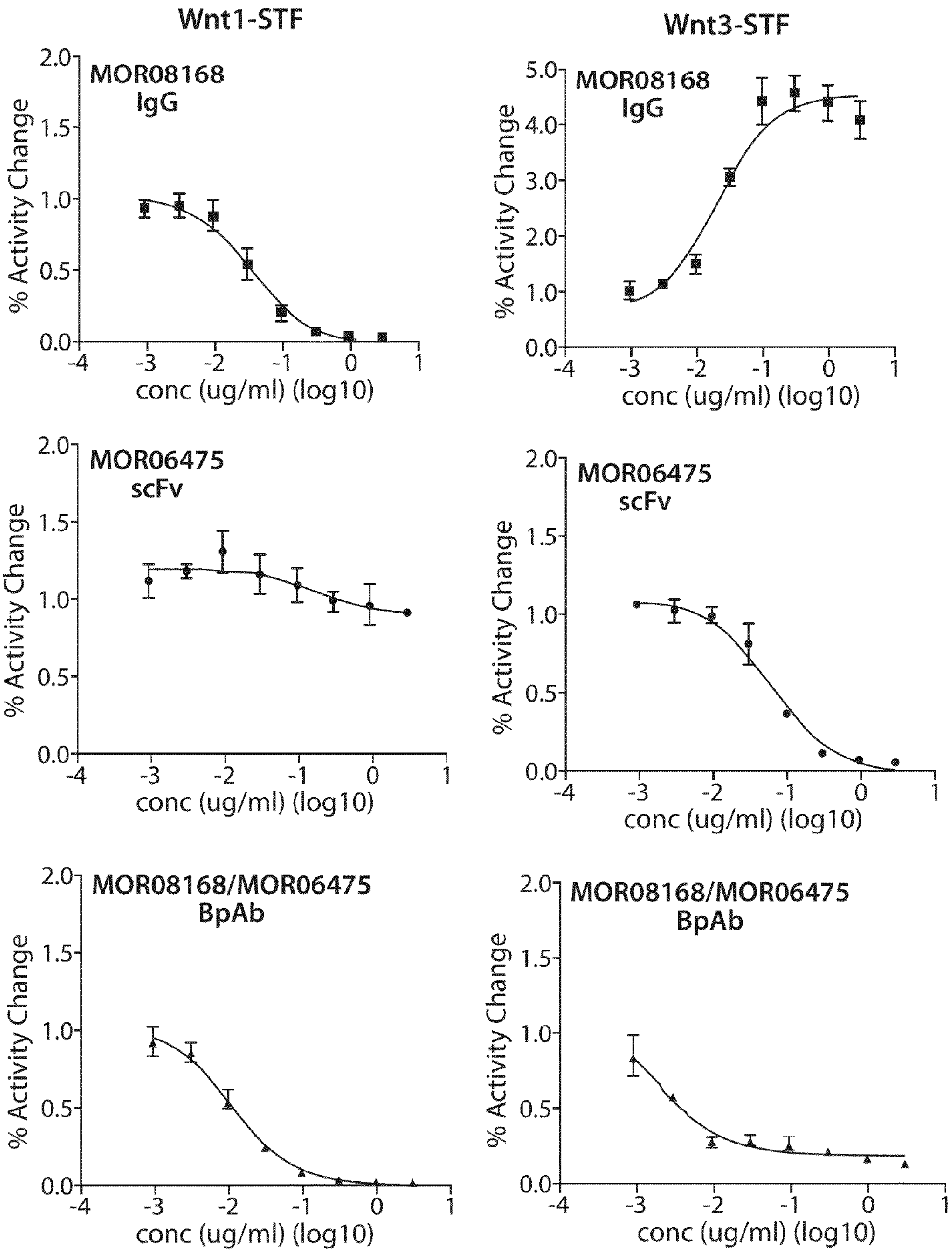
FIG. 17 shows activity in STF assay of a biparatopic antibody and respective component parts separately.

Activity of MOR06475, MOR08168 and MOR08545 scFv and Fab constructs, as well as several biparatopic formats was assessed in the HEK293 STF assay (FIGS. 17 and 18). Collectively, the data show that Propeller 1 IgG (MOR08168) inhibits Propeller 1 ligands such as Wnt1, while potentiating Propeller 3 ligands such as Wnt3 in the STF assay. Propeller 3 scFv6475 inhibits Propeller 3 ligands such as Wnt3, while having no activity on Propeller 1 ligands such as Wnt1. Furthermore, MOR08168/6475 biparatopic antibodies have activity against both Propeller 1 and Propeller 3 ligands, and no potentiating activity at any concentrations applied in the HEK293 Wnt STF assay.

Figure 15:
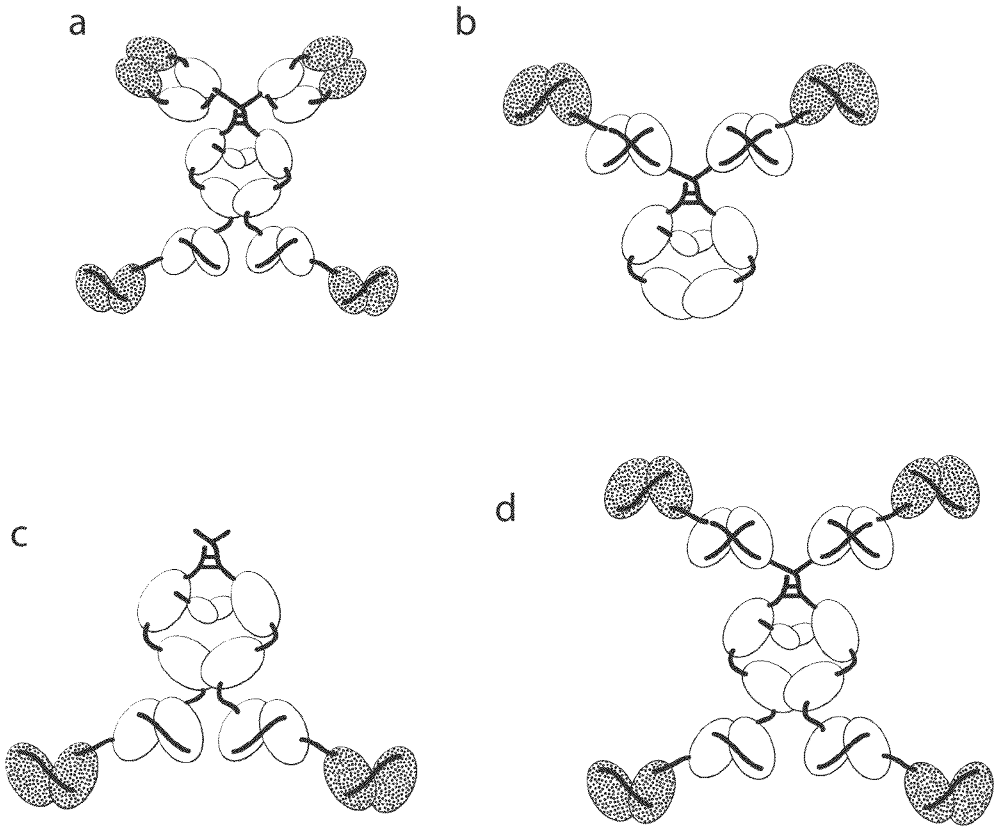
FIG. 15 A-D are schematic example of multivalent antibodies. (15A) scFv scFv attached to the C-terminus of full IgG (15B) scFv scFv attached to the N-terminus of Fc (15C) scFv scFv attached to the C-terminus of Fc (15D) scFv scFv attached to the N and C terminus of Fc.

(ii) Expression, Purification and Characterisation of Biparatopic Anti-LRP6 IgG-scFv A schematic representation of biparatopic anti-LRP61 g-scFv format produced in this study is presented in FIG. 15. FIG. 15A represents a scFv scFv attached to the C-terminus of an IgG; 15B scFv scFv attached to the N-terminus of an Fc; 15C represents an scFv scFv attached to the C-terminus of an Fc; and 15D represents an scFv scFv attached to the N- and C-terminus of an Fc.

The biparatopic antibody in the current experiment is the biparatopic full-IgG with scFv fused to the C-terminus of hIgG1 LALA CH3. In this particular study the scFv was separated by a $(GlyGlySer)_2$-linker from the full-IgG. The scFv consists of VL-VH orientation with a $(Gly_4Ser)_4$ linker.

Figure 16:
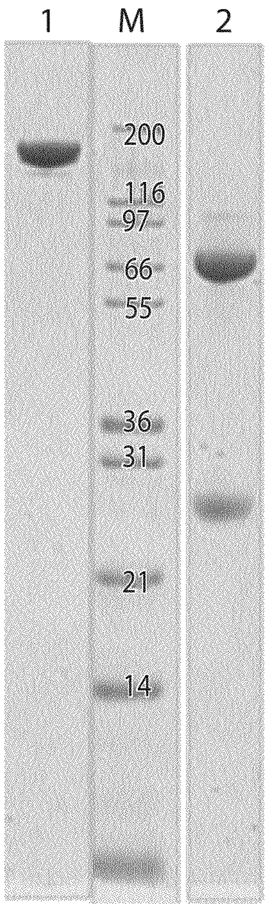
FIG. 16 is a photograph of an SDS-PAGE gel showing purified biparatopic anti-LRP6 IgG scFv under non-reduced (lane 1) and reduced (lane 2) conditions.

Biparatopic anti-LRP6 IgG-scFv's were transiently expressed in HEK293-6E cells and purified by affinity chromatography with gradient elution from pH 4.5 to 2.5. The expected size of 197.4 kDa was determined by LC-MS analysis and SDS-PAGE with a purity greater than 97%. Aggregation, determined by SEC MALS, was less than 5%. FIG. 16 is an SDS-Page analysis of purified biparatopic anti-LRP IgG-scfV. Samples were loaded into 12% Bis-Tris gel (NuPage, Invitrogen). Marker: Invitrogen Mark12; (1): Non-reduced; (2): Reduced Biparatopic anti-LRP6 IgG scFv and parental anti-LRP6 IgG bound to human FcRn at pH 6.0 with a Kd of 0.021 and 0.023 mM respectively, as determined by Biacore. Both formats demonstrated low level binding to human FcRn at pH 7.4, so this BpAb is expected to behave as a standard IgG in vivo (PK characteristics similar to IgG1) (See FIG. 19).

Biparatopic anti-LRP6 IgG scFv was stable in both mouse and rat serum at 37° C., tested up to 336 hours (data not shown) and showed no binding >4% when evaluated on a custom Protagen Unichip containing 384 purified extracellular or secreted proteins (data not shown).

(c) Discussion

Various anti-LRP6 scFv's were initially characterised to enable optimisation of the final biparatopic antibody. ScFv's in both orientations and with two different linker lengths were expressed in *E. coli*. Anti-LRP6 MOR06475, 8168 and 8545 were expressed as VH-VL and VL-VH scFv's with a $(Gly_4Ser)_3$ and $(Gly_4Ser)_4$ linker. All MOR06475 and MOR08168 variants were successfully expressed and purified with a low level (<5%) of aggregates. Correctly processed protein with expected sizes were obtained. Thermal stability data showed that the most stable scFv format was MOR06475-VL-$(Gly_4Ser)_4$-VH with a Tm of 64.7° C. All tested MOR08168 scFv formats showed significantly reduced thermal stability with a Tm of 50-52° C.

Biparatopic anti-LRP6 IgG's with scFv at CH3 and VL as well as modified variants (without C-terminal Lys (K) at CH3, with substitutions AspPro (DP) to AspAla (DA) and AspPro (DP) to ThrAla (TA) in VH of scFv) were successfully expressed and purified with a low level (<5%) of aggregates from cell culture. The expected sizes of approximately 197-198 kDa were determined. Constructs anti-LRP6 MOR08168 hIgG1LALA_6475scFv and anti-LRP6 MOR08168hIgG1 LALA 6475scFv at VL as well as mutated constructs (deletion of C-terminal Lys (K) at CH3 and substitutions AspPro (DP) to AspAla (DA) and AspAla (DP) to ThrAla (TA)) consisted of a scFv with VL-VH orientation and were separated by a $(Gly_4Ser)_4$ linker. A $(GlyGlySer)_2$ linker was used to attach the scFv to the CH3 domain of hIgG1 LALA and to VL of hlambda respectively. As previously discussed, however, the scFv may also consist of VH-VL separated by alternative linkers, furthermore the scFv may also be attached using alternative linkers to other positions within the IgG including the C-terminus of CL and the N-terminus of VH. Constructs with MOR08168scFv consisted of a scFv with VH-VL orientation and were separated by a $(Gly_4Ser)_3$ and $(Gly_4Ser)_4$ linker. A $(GlyGlySer)_2$ linker was used to attach the scFv to the CH3 domain of hIgG1 LALA.

The biparatopic anti-LRP6 MOR08168 hIgG1LALA 6475scFv was stable in serum (tested up to 336 hours). The biparatopic bound as expected to human FcRn at pH6.0, low level binding was seen at pH7.4. The parental antibody bound with similar kinetics.

Example 13

Figure 20:
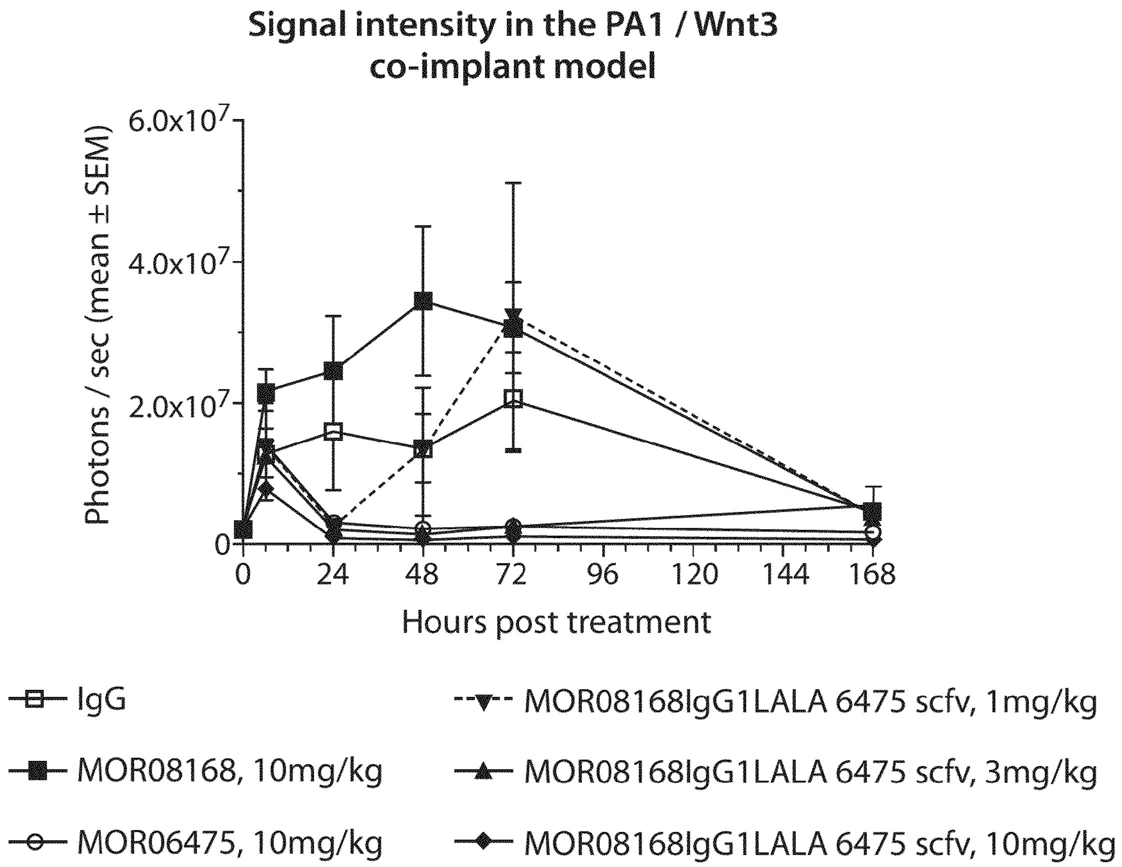
FIG. 20 shows the activity of a biparatopic antibody and a Prop3 antibody but not a Prop1 antibody in a PA-1/Wnt3a L-cell co-culture model.

In Vivo Evaluation of Biparatopic Antibody Anti-LRP6 MOR08168hIgG1LALA 6475 scfv The ability of biparatopic antibody anti-LRP6 MOR08168hIgG1LALA 6475 scfv to inhibit Wnt3 class Wnt signaling in vivo was tested in a co-implant system consisting of PA1-STF reporter cells co-implanted with Wnt3A secreting L cells. Female nude mice were implanted subcutaneously with 10×10e6 PA1-STF cells and 0.5×10e6 L-Wnt3A cells and randomized in groups of 5. 24 hours later, mice received a single intravenous dose of vehicle, MOR08168 LRP6-Propeller 1 Ab (10 mg/kg), MOR06475 LRP6-Propeller 3 Ab (10 mg/kg), or the biparatopic antibody anti-LRP6 MOR08168hIgG1LALA 6475 scfv (1 mg/kg, 3 mg/kg, or 10 mg/kg) and were imaged by Xenogen 6 hours, 24 hours, 48 hours, 72 hours and 168 hours later. The biparatopic antibody anti-LRP6_MOR08168hIgG1LALA 6475 scfv showed a dose-related inhibition of Wnt3A induced signaling, with 1 mg/kg showing maximum inhibition at 24 hours, returning to baseline at 48 hours, and 3 mg/kg and 10 mg/kg showing sustained inhibition for at least 72 hours. The MOR06475 LRP6-Propeller 3 Ab dosed at 10 mg/kg was able to inhibit Wnt3a induced signaling for at least 72 hours, whereas MOR08168 LRP6-Propeller 1 Ab dosed at 10 mg/kg increased Wnt3a induced signaling (FIG. 20).

Figure 21:
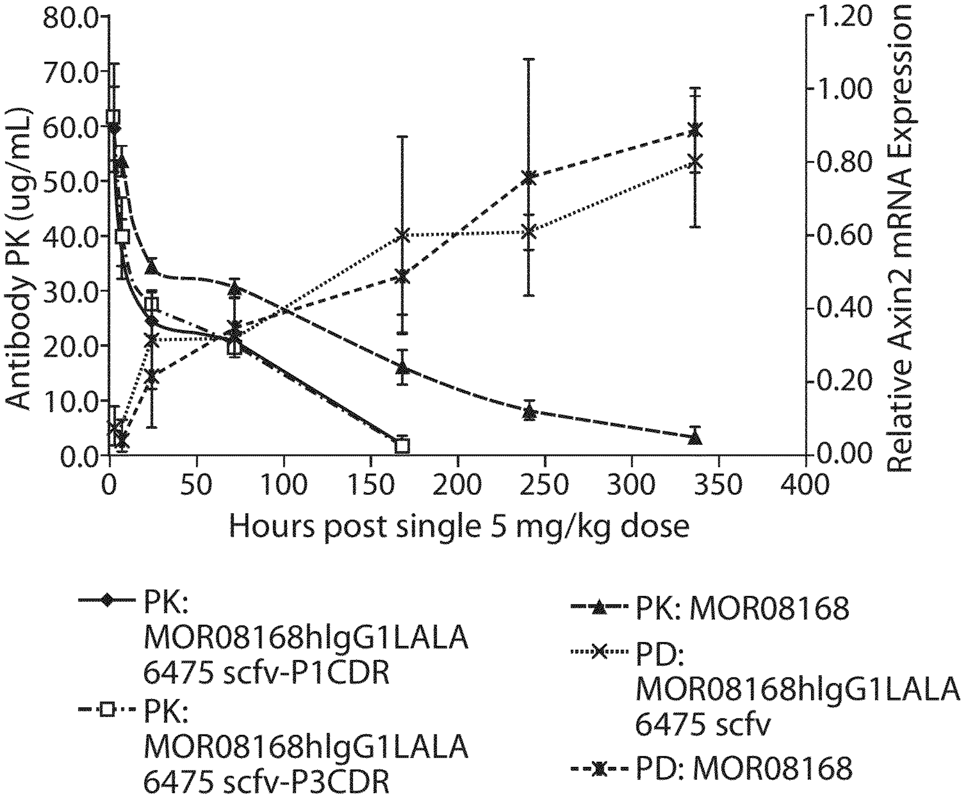
FIG. 21 is a graph showing a comparison between single i.v. doses of a Prop1 LRP6 antibody and a Prop1/3 biparatopic antibody at 5 mg/kg in a rodent.

To measure the effect of the biparatopic antibody anti-LRP6 MOR08168hIgG1LALA 6475 scfv, relative to the MOR08168 LRP6-Propeller 1 Ab, on Wnt signaling in MMTV-Wnt1 tumors, mice implanted with MMTV-Wnt1 tumors were dosed i.v. with a single dose of 5 mg/kg of the biparatopic antibody anti-LRP6 MOR08168hIgG1LALA 6475 scfv or a single dose of 5 mg/kg of the MOR08168 LRP6-Propeller 1 antibody. Serum concentrations of the biparatopic antibody, and propeller 1 antibody, as well as the mRNA expression of β-catenin target gene Axin2, were analyzed over a period of two weeks. The terminal β-phase half-life of the biparatopic antibody was around 48 hours, whereas that of the LRP6 antibody was about 72 hours. A significant decrease of Axin2 mRNA expression was observed in tumors obtained from mice dosed with either the biparatopic antibody, or the propeller 1 antibody, and Axin2 expression gradually recovered with no significant differences observed between the biparatopic antibody anti-LRP6 MOR08168hIgG1LALA 6475 scfv and the MOR08168 LRP6-Propeller 1 antibody (FIG. 21).

Figure 22:
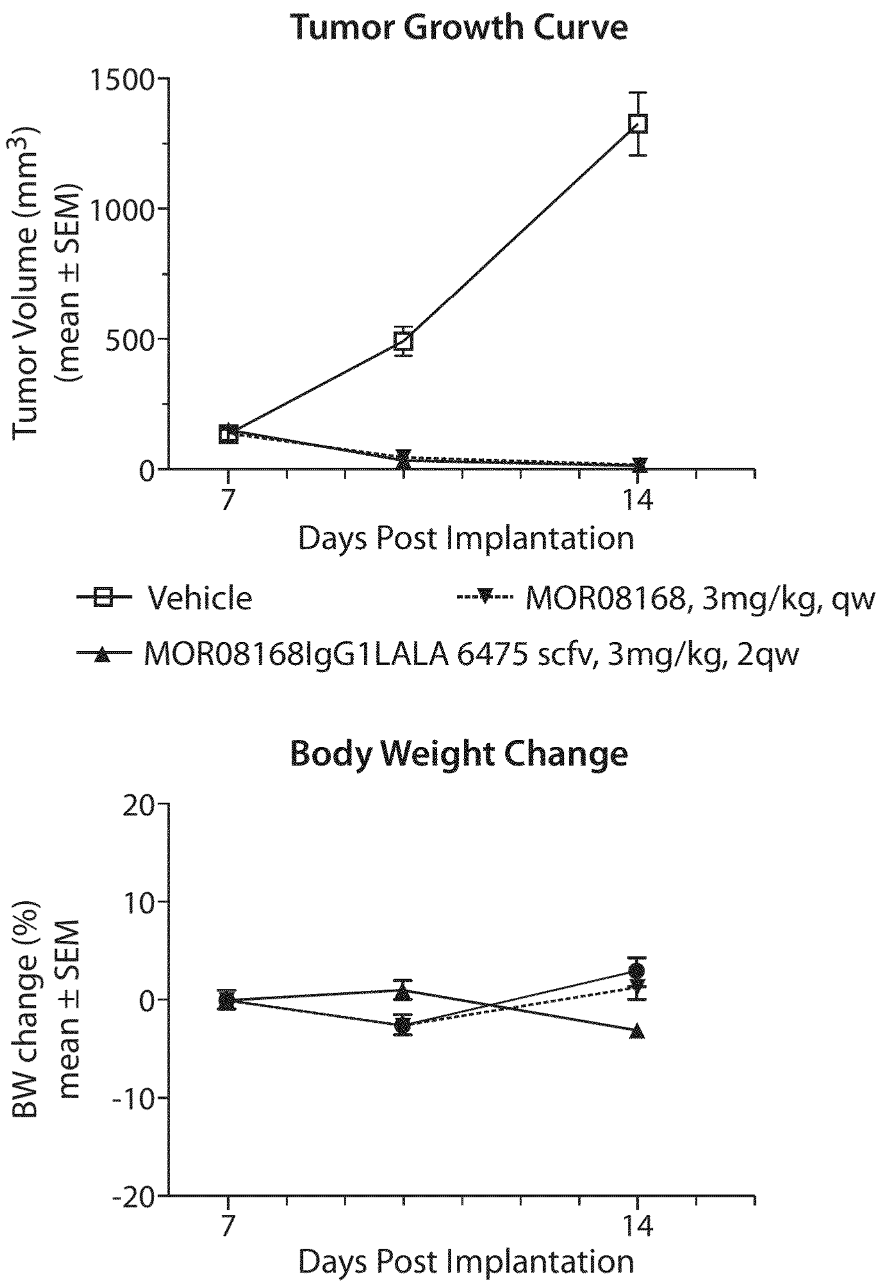
FIG. 22 is a graph showing both Propeller 1 and biparatopic propeller 1/3 antibodies cause in vivo tumor regression in MMTV-Wnt1 model.
Figure 23:
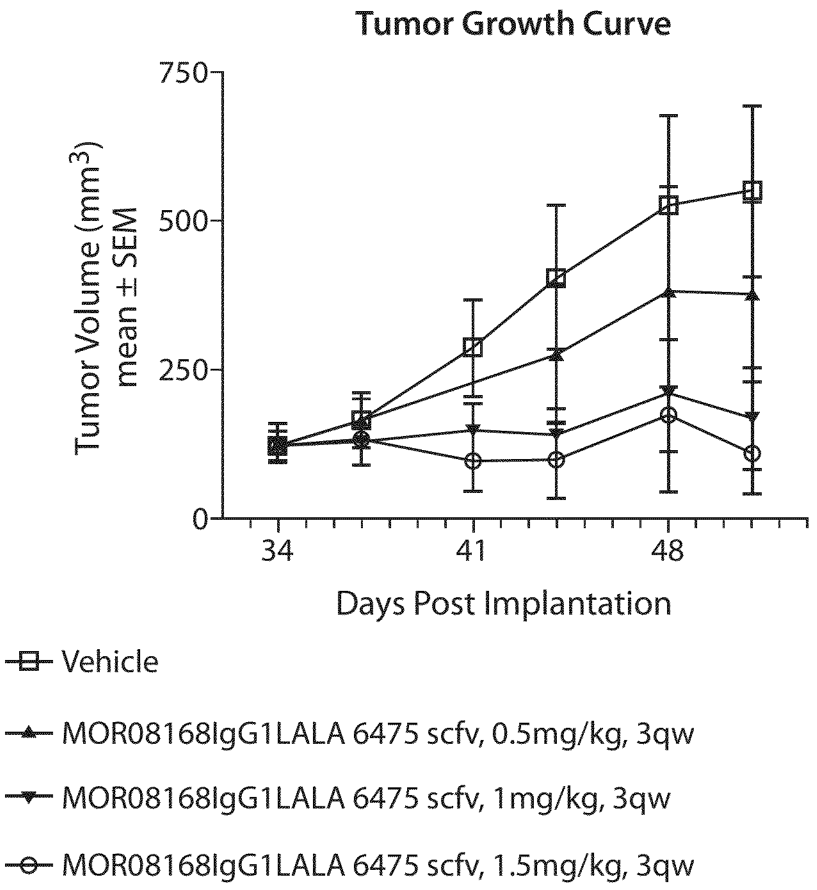
FIG. 23 is a graph showing dose-response relationship of a Prop1/3 binding biparatopic antibody in MMTV-Wnt1 model.

Anti-tumor activity of the biparatopic antibody anti-LRP6 MOR08168hIgG1LALA 6475 scfv was evaluated in the MMTV-Wnt1 allograft model. MMTV-Wnt1 tumor fragments were implanted subcutaneously (s.c.) into female nude mice. 7 days after implantation, mice carrying MMTV-Wnt1 tumors (n=8, average 137 $mm^3$; range: 81-272 $mm^3$) were treated with vehicle IgG, MOR08168 LRP6-Propeller 1 Ab (3 mg/kg, i.v., qw), or biparatopic antibody anti-LRP6 MOR08168hIgG1LALA 6475 scfv (3 mg/kg, i.v., 2qw), and tumors calipered twice a week. Both MOR08168 LRP6-Propeller 1 Ab and biparatopic antibody anti-LRP6 MOR08168hIgG1LALA 6475 scfv antibody induced tumor regressions (−93%, $p<0.05$ and −91%, $p<0.05$ respectively) (See FIG. 22). The dose dependency of the biparatopic antibody anti-LRP6 MOR08168hIgG1LALA 6475 scfv was evaluated and is depicted in FIG. 23.

Figure 24A:
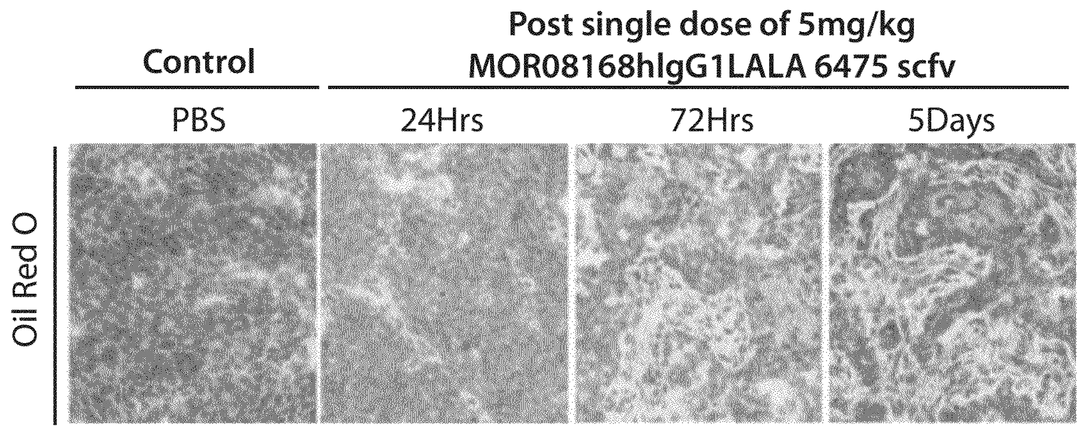
FIG. 24 shows that differentiation of murine MMTV-Wnt1 mammary tumors is induced by antagonistic LRP6 antibodies. A-B) Fragments of MMTV-Wnt1 tumors were implanted subcutaneously into nude mice. Tumor-bearing mice were treated with either a single dose of PBS (control) or 5 mg/kg MOR08168IgG1LALA 6475 scfv. A) Representative images of Oil Red O staining for lipid. B) Quantification of Oil Red O staining. Graph represents mean±SEM values. n=4 in the 72 hour group, n=3 in 24 hour group, n=2 in the 5 Day group, and n=1 for PBS (control)
Figure 24B:
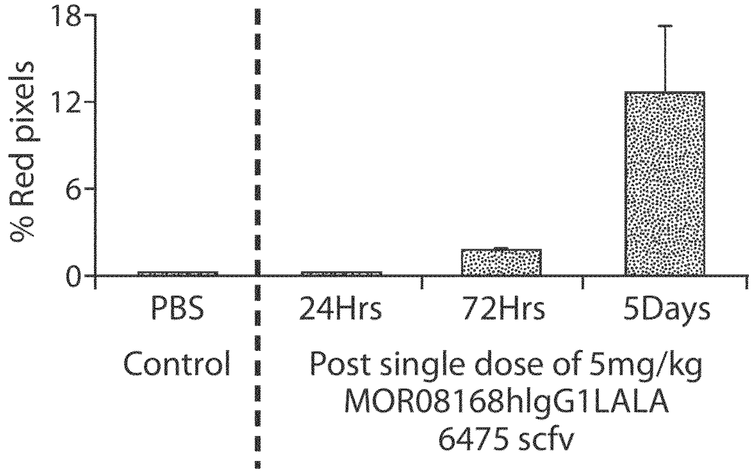

Inhibition of Wnt signaling in colorectal cancer cells by β-catenin siRNA or dominant-negative TCF-4 causes rapid cell cycle arrest and induces an intestinal differentiation program (van der Wetering et al. (2002), Cell, 111, 241-250; van der Wetering et al. (2003), EMBO Reports, 4, 609-615). To determine if inhibition of Wnt signaling by antagonistic LRP6 antibodies has similar consequences in murine MMTV-Wnt1 mammary tumors, secretory differentiation was examined by Oil Red O staining for lipid, a major component of milk. MMTV-Wnt1 tumor bearing mice were treated with either a single dose of PBS (control) or 5 mg/kg anti-LRP6 MOR08168hIgG1LALA 6475 scfv 24 h, 72 h or 5 days after treatment, sections of frozen murine tumor allografts were cut at 5 μm thickness. Slides were air-dried for 30-60 minutes at room temperature and then fixed in ice-cold 10% formalin for 5-10 minutes. Slides were immediately rinsed three times in $dH_2O$. Oil Red O staining was performed using an Oil Red O staining kit (Poly Scientific R&D, Cat #k043). Slides were scanned with ScanScope CS/GL scanner (Aperio Technologies), and tissue sections analyzed with ImageScope v 10.2.1.2315 software (Aperio Technologies), using the IHC color deconvolution algorithm with a positive-pixel count. Representative images of Oil Red O staining are shown in FIG. 24A and quantification in FIG. 24B. The graph represents mean±SEM values. n=4 in the 72 hour group, n=3 in 24 hour group, n=2 in the 5 Day group, and n=1 for PBS (control) and demonstrate an increase in Oil Red O staining during the time course of the experiment. Together, these results suggest that inhibition of Wnt signaling in mammary tumor cells may lead to cell cycle arrest and induction of a secretory differentiation program.

Figure 25:
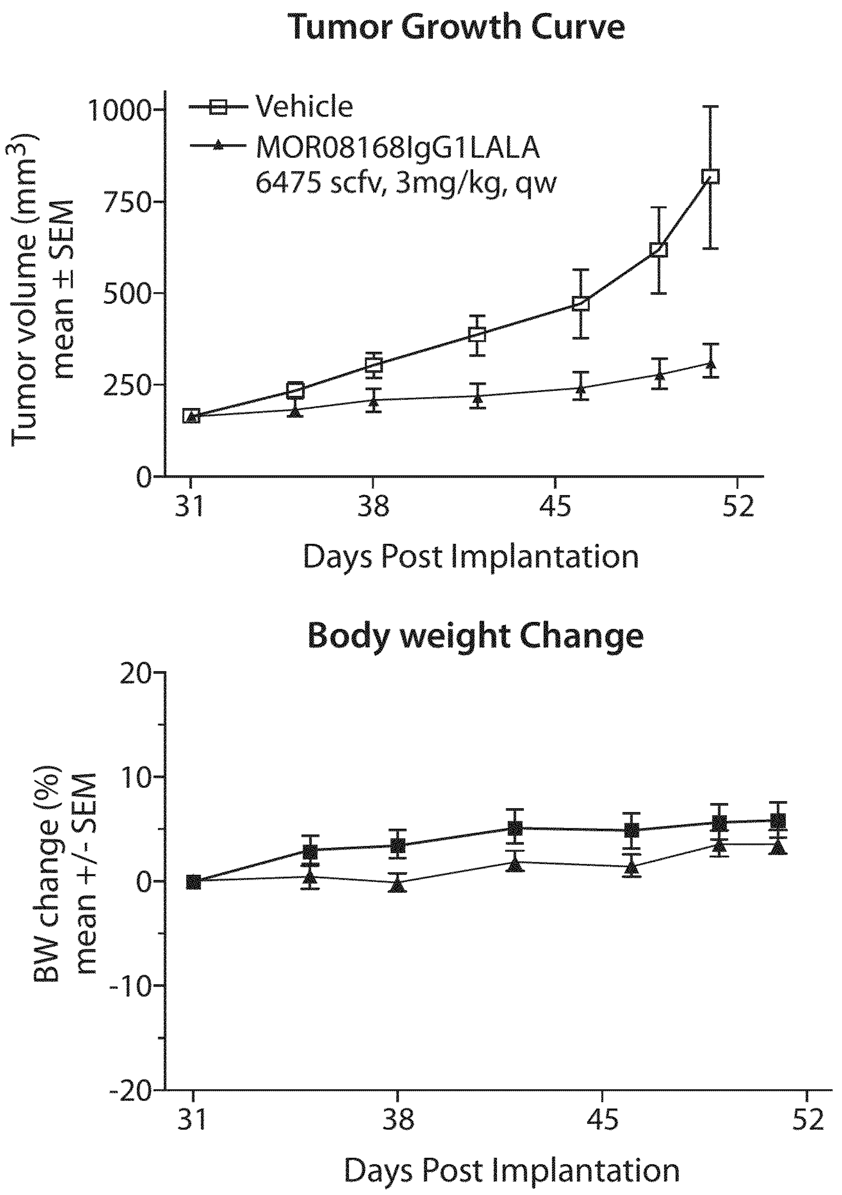
FIG. 25 is a graph showing activity of Prop1/3 binding biparatopic antibody in the E-Cadherin negative MDA-MB231 xenograft model.

Anti-tumor activity of the biparatopic antibody anti-LRP6 MOR08168hIgG1LALA 6475 scfv was further evaluated in the MDA-MB-231 breast xenograft model. 5x10e6 MDA-MB-231 cells in 50% matrigel were implanted subcutaneously (s.c.) into female nude mice. 31 days after implantation, mice carrying MDA-MB-231 tumors (n=7, average 165 $mm^3$; range 99-238 $mm^3$) were treated with vehicle, or biparatopic antibody anti-LRP6 MOR08168hIgG1LALA 6475 scfv (3 mg/kg, i.v., qw), and tumors calipered twice a week. The biparatopic antibody anti-LRP6 MOR08168hIgG1LALA 6475 scfv antibody dosed at 3 mg/kg weekly, significantly delayed tumor growth (T/C=23%, $p<0.05$) (See FIG. 25).

Example 14

In Vivo Evaluation of Additional Biparatopic Antibodies in the MMTV-Wnt1 Model

As described in Example 10, additional anti-LRP6 reverse biparatopic antibodies were generated consisting of the propeller 3 antibody MOR06475 and the propeller 1 MOR08168 scfv domains. The ability of these biparatopic antibodies (MOR06475hIgG1 LALA_8168scfv_(VH-3-VL) and MOR06475hIgG1 LALA_8168scfv_(VH-4-VL) to inhibit Wnt1 signaling in vivo, relative to MOR08168hIgG1LALA 6475 scfv, was determined in the MMTV-Wnt1 model. Mice implanted with MMTV-Wnt1 tumors were dosed i.v. with a single dose of 5 mg/kg of each of the antibodies described above. Serum concentrations of each antibody (MOR08168hIgG1LALA 6475 scfv, MOR06475hIgG1 LALA_8168scfv_(VH-3-VL), and MOR06475hIgG1LALA_8168scfv_(VH-4-VL), as well as the mRNA expression of β-catenin target gene Axin2, were analyzed over a period of 5 days (timepoints evaluated were 0, 2, 7, 24, 72 and 120 h). Both of the reverse biparatopic antibodies showed a significant decrease in axin2 mRNA expression to the same maximal extent as MOR08168hIgG1LALA 6475 scfv. However, the duration of the decrease of axin2 mRNA expression was shorter than that observed with MOR08168hIgG1LALA 6475 scfv, with the signal returning to baseline at the 24 h timepoint for both of the reverse biparatopic molecules. This was consistent with decreased exposure of these molecules, with serum levels dropping to below 5 μg/ml at 24 h compared with 120 h for MOR08168hIgG1LALA 6475 scfv.

Example 15

Binding Affinity of a Biparatopic Antibody to Recombinant LRP6 PD1/2 and PD 3/4

Binding affinities of anti-LRP6 MOR08168hIgG1LALA 6475 scfv, MOR08168, and MOR6475 to Propeller Domains 1-2 of LRP6 (PD1/2, amino acid residues 19 to 629 of Accession No. NP002327) and Propeller Domains 3-4 of LRP6 (PD3/4, amino acids 631-1246 of Accession No. NP002327) were evaluated via surface plasmon resonance (SPR) using a Biacore T-100 (GE Healthcare). For the affinity determinations, anti-human IgG Fcγ specific antibody (#109-005-098, Jackson Immunology) was diluted in 10 mM sodium acetate (pH 5.0) buffer, and then immobilized onto CM4 chip (GE Healthcare, BR-1005-34) for all 4-flow cells to a density of ~2000 RU using standard amine coupling chemistry. The carboxymethyl dextran surface was activated with a 7 min injection of a 1:1 ratio of 0.4 M EDC (1-Ethyl-3-[3-dimethylaminopropyl]carbodiimide hydrochloride) and 0.1 M NHS (N-hydroxysuccinimide). Excess reactive esters were then blocked with 1M ethanolamine. anti-LRP6 MOR08168hIgG1LALA 6475 scfv was prepared at 10 μg/ml in HBS-EP buffer (GE Healthcare), and captured onto a separate flow cell of the CM4 chip to a density of ~70 RU at flow rate 10 μl/min. PD1/2 and PD3/4 were prepared as two fold concentration series starting at 50 nM, and injected at 30 μl/min for 1 min. This allowed a 40 min dissociation phase over the anti-LRP6 MOR08168hIgG1LALA 6475 scfv-captured surface and the control surface without captured ligands. The surfaces were then regenerated two times with 10 mM glycine (pH 2.2). For the dual binding analysis of anti-LRP6 MOR08168hIgG1LALA 6475 scfv to PD1/2 and PD3/4, anti-LRP6 MOR08168hIgG1LALA 6475 scfv was captured onto the CM4 chip immobilized with anti-human IgG Fcγ specific antibody. PD3/4 at a saturating concentration of 100 nM was then flowed over the surface at a flow rate of 30 μl/min for 30 min. A saturating concentration of 100 nM PD1/2 was injected immediately after the PD3/4. The dissociation constant ($K_D$), association ($k_{on}$), and dissociation ($k_{off}$) rates were calculated from the baseline subtracted corrected binding curves using the BIAevaluation software (GE Healthcare).

Figure 26B:
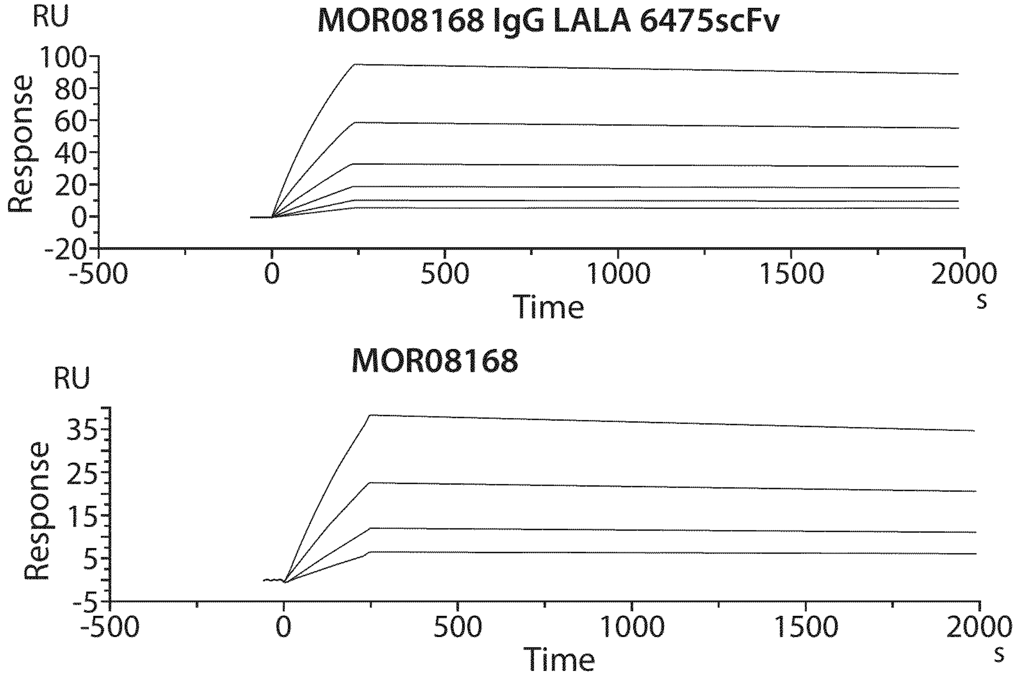
Figure 26C:
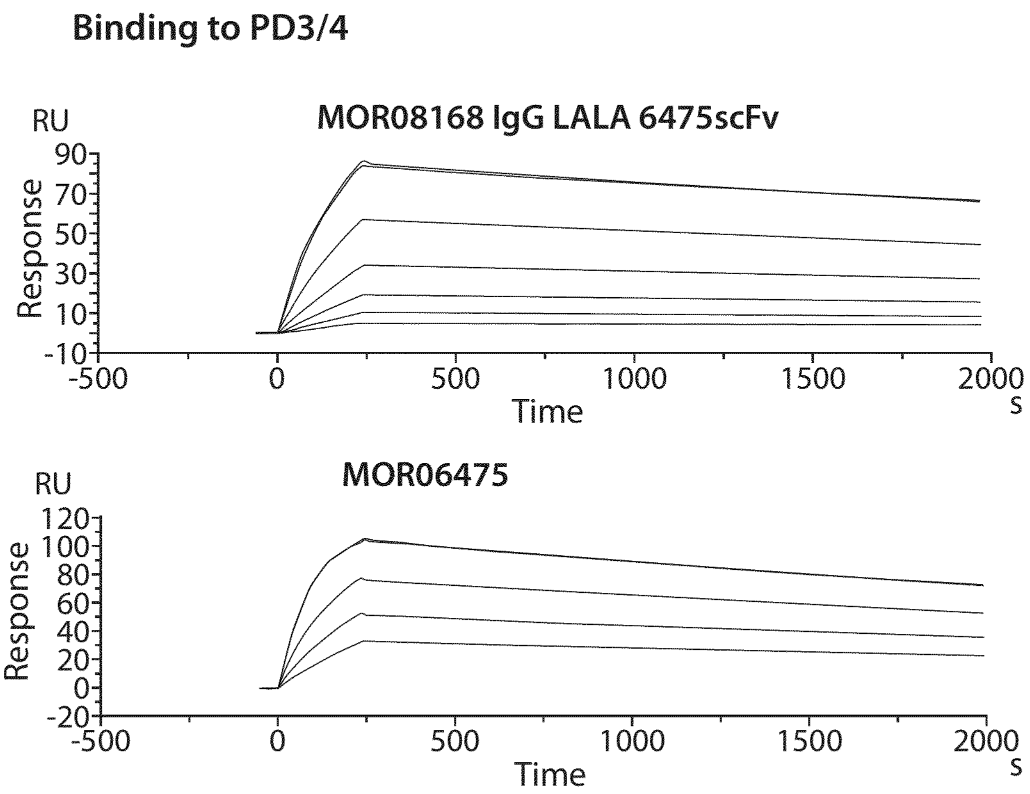
Figure 26D:
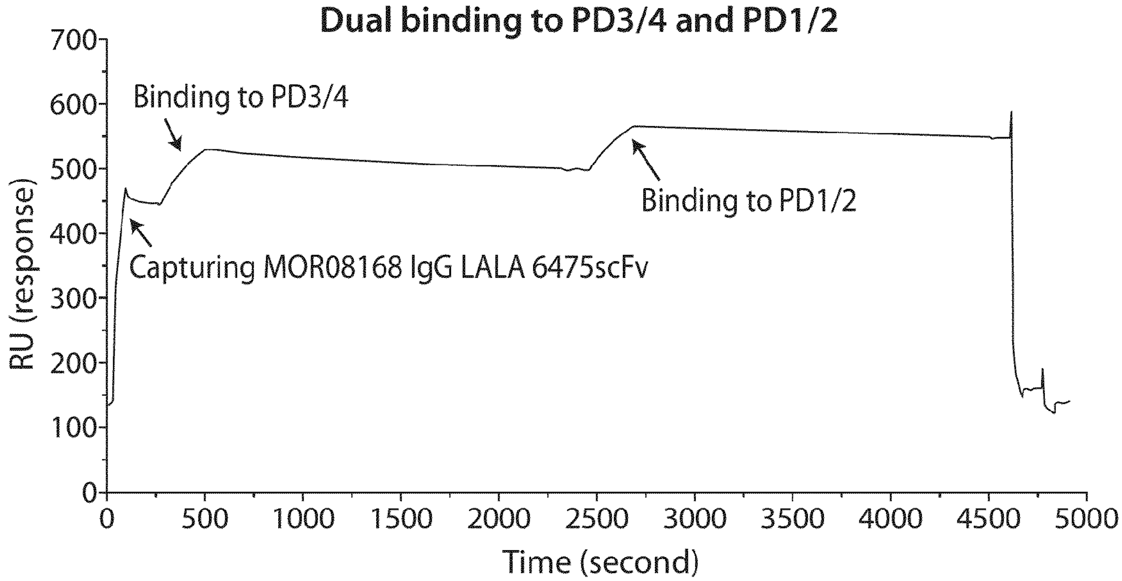

Anti-LRP6 MOR08168hIgG1LALA 6475 scfv (biparatopic antibody) binding to PD1/2 and PD3/4 was compared with that of MOR08168 (propeller 1 antibody) and MOR6475 (propeller 3 antibody). FIG. 26A shows affinities of the molecules for corresponding LRP6 receptor domains, PD1/2 and PD3/4. The determined $K_D$ of anti-LRP6 MOR08168hIgG1LALA 6475 scfv for PD1/2 and PD3/4 was similar to that of MOR08168 to PD1/2 and MOR6475 to PD3/4, respectively. FIG. 26B shows the association and dissociation phases of anti-LRP6 MOR08168hIgG1LALA 6475 scfv binding to each of the proteins. The off-rate for binding of anti-LRP6 MOR08168hIgG1LALA 6475 scfv to PD1/2 is slower than that to PD3/4. Further studies demonstrated in which PD1/2 and PD3/4 were injected sequentially indicated that, as expected, anti-LRP6 MOR08168hIgG1LALA 6475 scfv was capable of binding to both propeller domain constructs (FIG. 26C).

Example 16 scFv Mutations to Improve Thermostability of scFv08168 and scFv06475

This Example describes mutations made in the scFvs of propeller 1 and propeller 3 antibodies and the effect of individual and a combination of mutations to the stability of the scFv as determined by thermal stability. Improvements in the stability of the scFv can be translated to the overall stability of an antibody construct comprising the mutated scFv.

Material and Methods

Constructs

Figure 27:
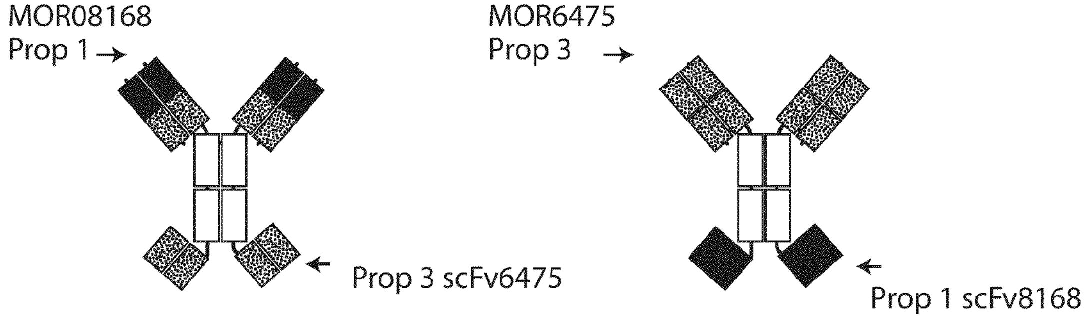
FIG. 27 shows a schematic drawing of IgG based biparatopic antibodies.

For IgG based biparatopic molecules, scFv06475 was fused to the C-terminal of MOR08168 IgG1 via a GlyGlySer linker to make biparatopic antibody designated "901" in FIG. 27 (MOR08168IgG1LALA 6475 scfv), or scFv08168 was fused to the C-terminal of MOR06475 IgG1 via a GGS linker to make biparatopic antibody designated "902" in FIG. 27. For detailed information, please refer to other parts of this patent application.

Rational Design of the Focused Library for scFv06475 and scFv08168

Two approaches were used for selection of point mutations to stabilize scFv06475 and scFv08168: sequence consensus analysis and structure based mutation design using homology modeling in Molecular Operating Environment (MOE).

For sequence consensus analysis, the amino acid sequences of the VH and VL domains of scFv06475, and of the VH and VL domains of scFv08168 were BLASTed against the non-redundant protein sequence database of NCBI. After each BLAST run, the query sequence and the top 250 homologous sequences were aligned by the clustalW program. An in-house computer program was used to count the most common amino acid at every residue position among the aligned sequences. At each position where the amino acid in the query sequence differed from the most common amino acid in the aligned sequence pool, a mutation was designed to mutate the residue from its wild type amino acid to the most common amino acid.

A homology model of scFv06475 and a homology model of scFv08168 were built in MOE. The sequences were first read into the "sequence editor" module of MOE. Existing X-ray structures with homologous sequences were searched in the "antibody modeler" module of MOE. The X-ray structure 3L5X and 1W72 were identified by MOE as the suitable templates to build the homology models for scFv06475 and scFv08168, respectively. Homology models were then built by MOE, using the CHARMM27 force field to minimize the energy.

Models produced by MOE were then subject to five stages of energy minimization and MD simulation in NAMD. The whole models were energy minimized for 5000 steps in the first to the third stage, and with restraints of 30 kcal/mol/$A^2$ applied on different sets of atoms. In the first stage, the restraints were applied to all atoms but the side chain atoms in CDRs. In the second stage, the restraints were applied to all atoms but the residues in CDRs. In the third stage, the restraints were applied only to backbone atoms. The models were then simulated in vacuum for 100 ps at 50K in the fourth stage, with restraints of 30 kcal/mol/$A^2$ applied on the backbone atoms. In the last and the fifth stage, the models were energy minimized for 5000 steps with restraints of 30 kcal/mol/$A^2$ applied on the backbone atoms. The models after these five stages of minimization and MD simulation were taken as the homology models for structure based mutation design.

Mutant models were built upon the wild type homology models. The "mutate" command of the "psfgen" module of VMD was used to mutate residues to the designed amino acids (William Humphrey et al. (1996) J. Molecular Graphics, 14: 33-38. The mutated models were then energy minimized and simulated in six stages. 5000 steps of energy minimization were performed in the first to the fourth stage. Restraints of 30 kcal/mol/$A^2$ were applied on all atoms but the side chain of the mutated residue in the first stage. Restraints of the same strength were applied on all atoms but the mutated residue in the second stage. The restraints on the side chain atoms of the residues within 5 Å to the mutated residue were removed in the third stage. The restraints on the backbone atoms of the residues within 5 Å to the mutated residue were released as well in the fourth stage. With the same restraints as those in the fourth stage applied, the mutated models were simulated in vacuum for 100 ps at 50K. The last snapshots of the simulation trajectories were then energy minimized for 5000 steps again, with the same restraints as those in the fourth stage. These minimized models were taken as the homology models of the mutants.

Plate Based-Library Construction, Expression and Purification in *E. coli* System High throughput mutagenesis was performed using QuikChange XL site-directed mutagenesis kit (Stratagene). Primers were designed according to primer design software Mutaprimer and were ordered from IDT in a 96 well format with normalized concentrations. Mutant strand synthesis reaction volume was scaled down from 50 to 25 μl. The reactions were carried out in the 96 well PCR plate. After the cycling, 0.5 μl DpnI enzyme was added to each amplification reaction and incubated at 37° C. for 2 h to digest the parental dsDNA. Transformation was done by adding 2 μl of DpnI digested mutagenesis reaction into 20 μl Acella chemical competent cells in 96 well PCR plate.

Three individual colonies were picked from each transformation plate for expression and purification. Expression was done in two 96-well deep-well plates using autoinduction media. Aliquots of bacterial culture were saved as glycerol stocks and sent for sequencing analysis. Bacterial pellet combined from the two plates for each individual colony was lysed and purified with MagneHis protein purification system from Promega. KingFisher instrument was set up for high-throughput purification. 1 M NaCl was added into the lysis and wash buffer to improve protein purity. Protein was eluted with 100 μl of 300 mM imidazole in PBS. Protein quantity was briefly checked with Coomasie plus (Thermo) in order to determine the optimal amount of protein for Differential Scanning Fluorimetry (DSF).

Screening of Thermostable Mutations by DSF and Differential Scanning Calorimetry (DSC)

Depending on the protein amount purified for each sample, usually 10 to 20 μl of elution was used for DSF analysis. Specifically, samples of 10-20 μl were mixed with Sypro Orange (Invitrogen) of a final dilution at 1:1000, in a total volume of 25 μl in PBS. The samples were run by BioRad CFX 1000 (25° C. for 2 min, then increment 0.5° C. for 30 second, 25 to 95° C.). Hits were defined as Tm over 2 C above wild type scFv. scFv binding activity was determined by one-point ELISA.

Protein Production in Mammalian Cells

Mutations were introduced into mammalian construct pRS5a that has scFv06475 or scFv08168 with His tag. The constructs were transiently expressed in 50 ml of 293T suspension cells. Briefly, PEI was mixed with DNA 50 μg at 1:3 for optimal transfection efficiency. Cells at 1.4 e6 per ml were use for transfection. Transfected cells were collected after six days of incubation in $CO_2$ chamber 80 rpm shaking in filter paper flask of 250 ml. Supernatant was concentrated to around 1 ml for optimal protein recovery. Protein is purified manually by MagneHis kit according to the instructions from the manufacturer. Purified protein was dialyzed in PBS overnight with changing of buffers. Protein samples either before or after dialysis were used for DSF analysis.

Affinity Measurement for scFvs

Binding $EC_{50}$ of scFvs against LRP6 protein was measured by ELISA. Maxisorp plate was coated with LRP6-Fc (R&D Sysytems, catalog No: 1505-LR) at 3 μg/ml at 4° C. overnight. The plate was blocked with 50 μl of 2% BSA for one hour, and washed five times with the wash solution. The samples were diluted with 1% BSA accordingly. The plate was incubated at RT for 1 h, and washed for 3 times. Detection was done by adding 50 μl pentallis-HRP (Qiagen Mat. No. 1014992) at 1:2000 dilution in 1% BSA, incubated at RT for 1 h, and washed 3 times. 50 μl of substrate reagent A plus B (R&D systems) was added, then incubated for 5-20 min depending on the color. The reaction was stopped by adding 25 μl of the stop solution, followed by plate reading at 450 nm.

Kinetics experiments were performed using BioRad's Proteon XPR36 biosensor. All experiments were performed at room temperature using PBST (phosphate buffered saline with 0.05% Tween-20) as the running buffer. All of the six vertical channels on a GLM chip were activated for 5 min at a flow rate of 30 μl/min using freshly prepared mixture of EDC (400 mM) and sNHS (100 mM). Anti-His mouse IgG1 (R&D systems, catalog No: MAB050) was diluted to 20 μg/ml in 10 mM sodium acetate, PH 5.0 and coupled to the chip for 5 min along separate vertical channels at a flow rate of 30 μl/min. 1 M ethanolamine was then injected for 5 min at 30 μl/min to deactivate the un-reacted sNHS groups. 2 μg/ml MOR08168 scFv wild type or 2 μg/ml MOR08168 D1 mutant was then immobilized on different vertical channels for 15 sec at 100 μl/min followed by two 1 min injection of the running buffer at 30 μl/min in the horizontal direction. The sixth vertical channel was used as the channel reference and no ligand was immobilized on this channel. A dilution series of a 360 KD homodimer antigen LRP6-Fc (R&D systems, catalog No: 1505-LR) was prepared at final concentrations of 300, 100, 33, 11, and 3.7 nM and injected at 30 μl/min along each horizontal channel. Association was monitored for 5 min and dissociation was monitored for 20 min. Buffer was injected in the sixth channel to serve as a row reference for real time baseline drifting correction. Chip surface was regenerated by applying 0.85% phosphoric acid at 100 μl/min for 18 s in the horizontal direction followed by the same running condition in the vertical direction. Kinetics analysis on the Proteon was performed in Proteon Manager v.2.1.1. Each interaction spot data was subtracted by a channel reference followed by a row reference to correct the real time baseline drifting. The processed data were fit globally to a bivalent analyte model.

Results

Figure 28A:
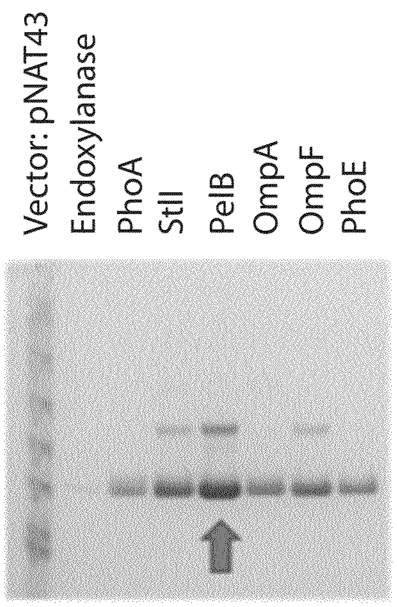
FIG. 28 are photographs of SDS-PAGE gels showing the optimization of anti-LRP6 scFv expression in *E. coli;*
Figure 28B:
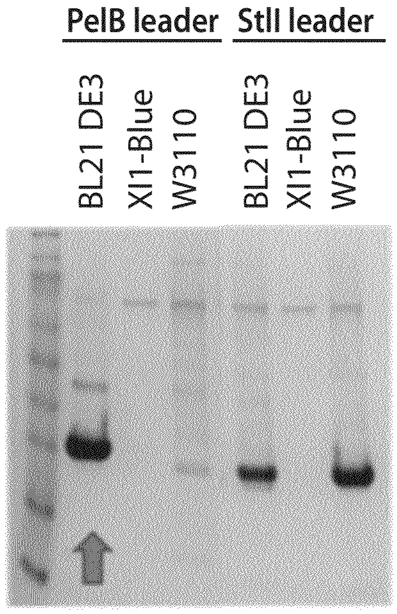

The Plate-Based Mutagenesis, Expression and Purification in *E. coli* Allowed More Efficient Screening from Focused Libraries In order to achieve high yield to facilitate downstream analysis, the effect of the leader sequence on expression was tested. It was shown that the leader with pelB yielded the highest amount of purified protein among the seven leaders tested, as shown in FIG. 28A. Several bacterial strains including BL21 (DE3), XL-1 Blue and W3110 were tested for expression with IPTG induction. The expression level of scFv06475 in BL21 (DE3) was higher than in XL-1 blue and slightly higher than in W3110, as shown in FIG. 28B. In order to facilitate mutagenesis cloning, transformation and expression, Acella (a derivative of BL21) was used for all the subsequent experiments as cloning and expression can be done in the same strain with high efficiency. The protein was purified from cell lysate by KingFisher using MagneHis kit. Estimated yield for scFv08168 was around 10 μg per sample of combined wells from deep well culturing plate, of which 2 was used for DSF thermostability analysis. The plate based HTP screening has shorted the time significantly to around one week from primers to hits with improved thermostability.

scFv Thermostability Improvement by Single Point Mutation from Focused Libraries A hit for improved thermostability was defined as improvement of Tm at least 1° C. above wild type consistently. There were 9 hits from a total of 51 sequence confirmed variants for scFv06475 and 15 hits from a total of 83 sequence confirmed variants for scFv08168. Selected hits were shown in FIG. 28 for scFv06475 and FIG. 29 for scFv08168.

Two approaches were used for selection of point mutations to stabilize scFv06475 and scFv08168: sequence consensus analysis and structure based mutation design. Among the top 250 sequences homologous to the VH domain of scFv06475, VH:34 position was commonly occupied by either Met (45%) or Val (48%) (all numbering system in the text is from Kabat system). Yet this position was a Gly residue in the wild type sequence of scFv06475. Two mutants, VH:G34M and VH:G34V, were designed to mutate the wild type amino acid to the more popular amino acids at this position. As listed in FIG. 28, the VH:G34V mutant consistently showed higher stability than the wild type scFv06475 when expressed and purified by two different protocols. The VH:G34M mutant did not express well in bacterial, likely due to wrong sequence caused by errors in the PCR procedure.

Based on the same sequence consensus analysis, mutations of VH:I34M, VH:G50S, VH:W52aG and VH:H58Y were designed to mutate residues in scFv08168 to the consensus amino acids in its top 250 homologous sequences. As shown in FIG. 30, these mutations improved the Tm of scFv08168 by 7.5° C., 3.0° C., 7.0° C., and 3.5° C., respectively.

In the structure based approach, a homology model of scFv06475 and a homology model of scFv08168 were first built with MOE then energy minimized with NAMD. These models were then visually inspected for potential mutations to enhance local interaction. Mutations on various residues of scFv06475 and scFv08168 were designed, based on five biophysical understandings of protein stability.

The first approach was to increase the size of side chains in the protein core to improve packing. A few hydrophobic residues with side chains facing the protein core were mutated to larger side chains so as to improve the packing around these residues. After screening, three mutations designed by this approach were found to improve the stability of scFv08168. As listed in FIG. 30, the VH:I34F, VL:V47L and VL:G64V mutations improved the melting temperature of the scFv08168 by 4.0° C., 2.5° C., and 2.0° C., respectively.

Figure 33:
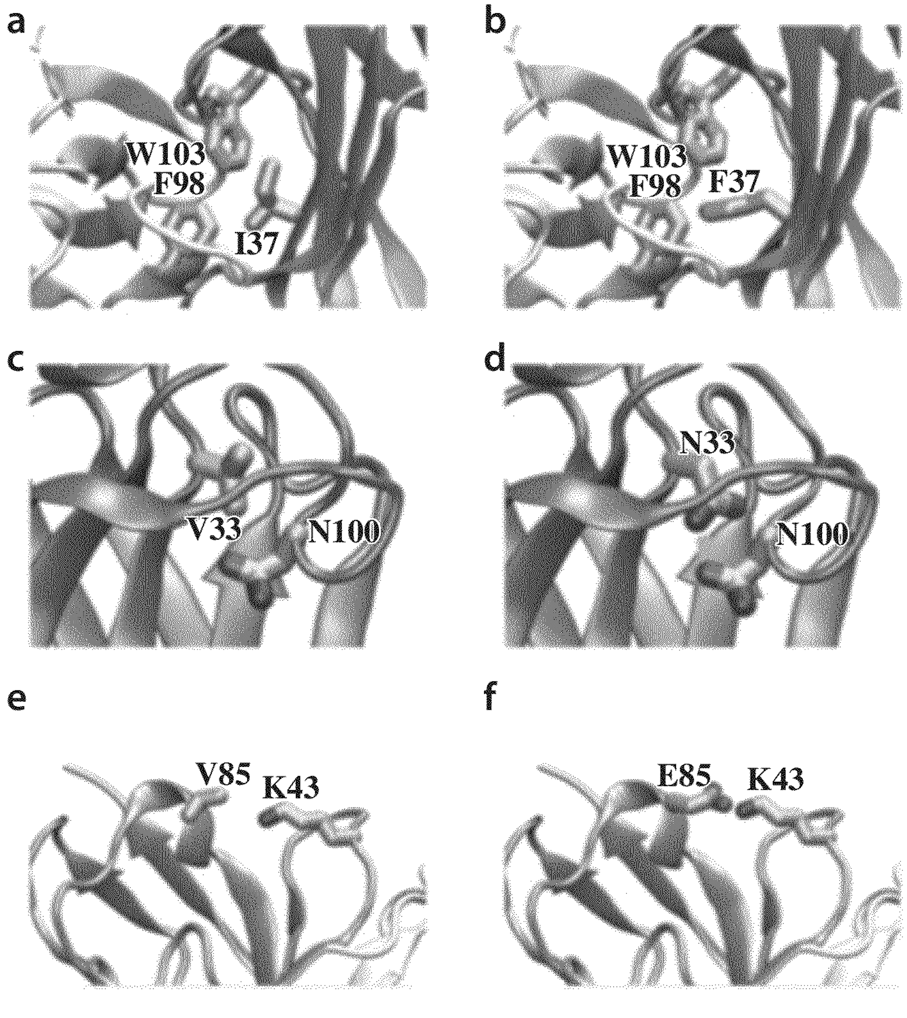
FIG. 33 is an illustration of selected examples of the designed mutations. In all figures, the protein backbone is rendered in ribbon diagram while selected side chains are rendered as sticks. (a): In the homology model of scFv6475, VH:I37 is close to two aromatic residues, which were VL:F98 and VH:W103. (b) In the VH:I37F mutant of scFv6475, VH:F37 and VH:W103 could form a perpendicular pi-pi stacking interaction, while VH:F37 and VL:F98 could form another perpendicular pi-pi stacking interaction. (c) In the homology model of scFv8168, the hydrophobic residue VH:V33 is close to a polar residue VH:N100a. (d) In the VH:V33N mutant of scFv8168, the VH:N33 side chain could form a hydrogen bond with VH:N100a, suggested by homology modeling. The hydrogen bond between the two residues is illustrated by a bond. (e): In the homology model of scFv8168, the charged residue VH:K43 did not form a salt bridge with the hydrophobic residue VH:V85. (f): The two charged side chains of VH:K43 and VH:E85 could form a salt bridge due to the VH:V85E mutation on scFv8168. The distance between the two charge groups could be 2.61 Å.

The second approach was to mutate hydrophobic residues to aromatic residues to form pi-pi stacking interaction. In the wild type scFv06475 homology model, as shown in FIG. 33*a*, the side chain of the VH:I37 residue was in close vicinity to two aromatic residues of VH:W103 and VL:F98. The closest distance between any non-hydrogen side chain atom of VH:I37 and any non-hydrogen side chain atom of VH:W103 was 3.82 A. The counterpart distance between VH:I37 and VL:F98 was 3.77 Å. As shown in FIG. 33*b*, two perpendicular pi-pi stacking interaction were formed when an Phe residue was introduced to this local region through the VH:I37F mutation: one between VH:F37 and VH:W103, and the other between VH:F37 and VL:F98. Newly formed pi-pi stacking interaction must be stronger than the original hydrophobic interaction in this localized region, as the melting temperature of scFv6475 was improved by this mutation from 61 to 64.5° C. (FIG. 28). The VH:M95F mutation also improved the stability of scFv06475 by forming pi-pi stacking interaction with VH:W50 and VH:F100 (FIG. 29). The Tin was improved from 61 to 64.5° C.

The third approach was to mutate non-charged residues to charged residues so as to form salt bridge. The VH:K43 residue of scFv6475 did not form a salt bridge with neighboring residues in the homology model. Since the VH:V85 side chain faced directly to VH:K43 in the homology model of scFv06475 (FIG. 33*e*), it was mutated to negative charged to form a salt bridge with VH:K43. As shown in FIG. 33*f*, the distance between the mutated VH:E85 side chain non-hydrogen atoms and the VH:K43 side chain non-hydrogen atoms could be as short as 2.61 Å, suggesting that a salt bridge could be established between the two residues. Improved stability of scFv6475 upon the VH:V85E mutation listed in FIG. 29 indeed supported the design rationale at this position.

The fourth approach was to mutate hydrophobic residues to polar residues to establish hydrogen bonds. As illustrated in FIG. 33*c*, the hydrophobic VH:V33 residue was close to a polar residue VH:N100a in the homology model of scFv08168. When a polar residue was inserted to this region through the VH:V33N mutation, an extra hydrogen bond could be formed between VH:N33 and VH:N100a. Homology modeling suggested that the distance between the ND2 atom of VH:N33 and one of the OD atoms of VH:N100a could be as short as 2.80 Å, which was within the range of a hydrogen bond, as shown in FIG. 33*d*. As shown in FIG. 29, this VH:V33N mutation improved the stability of scFv08168 by 2.0° C. Likewise, the stability enhancement of the VL:D93N mutation on scFv06475 (see FIG. 29) could be attributed to the improved hydrogen bond geometry with VL:Q27 and VL:Q90.

Based on the surprising observation in the homology model of scFv08168 that two polar residues of VL:T78 and VH S49 were both surrounded by purely hydrophobic side chains, the fifth approach was utilized to mutate the two polar residues in the otherwise hydrophobic environment to non-polar residues. Two polar residues of VL:T78 and VH:S49 were both surrounded by purely hydrophobic side chains. As listed in FIG. 29, the VL:T78V and VH:S49A mutations increased the melting temperature of scFv08168 by 2.5° C. and 5.5° C., respectively.

One point ELISA was carried out to evaluate binding activity. Certain hits were eliminated due to reduced or loss of binding activity towards LRP6. For example, the mutation VH WO52aG of scFv08168 improved Tm by 7° C. but showed much reduced binding activity as compared to wild type scFv08168. Therefore it was not selected for further analysis.

The presence of 300 mM imidazole in the elution buffer sometimes caused an overall shift of Tm by DSF, as observed in scFv06475. But the effect did not affect the ranking of Tm. There was also difference in protein produced in *E. coli* vs. in mammalian cells for scFv06475, as shown in FIG. 28. On the contrary, the presence of imidazole has minimal effect on Tm of scFv8168, as shown in FIG. 30 and FIG. 31. In addition, the Tm value remained unchanged for protein produced from *E. coli* or from mammalian for scFv08168, as shown in FIG. 31. Whether there was shift in Tm or not, the Tm ranking remained the same.

To confirm the effect of thermostability in proteins produced in mammalian cells, these mutations were introduced into construct for mammalian expression vector and expressed in 293T suspension cells. They were purified by MagneHis beads. Tm was checked and hits were confirmed for improved thermostability in proteins expressed in mammalian cells as shown in FIG. 31 for scFv08168. The single point mutation with highest thermostability improvement for scFv08168 is VH:I34M with an improvement of 7.5° C.

Combination of Mutations to Further Improve Thermostability

To further improve thermostability single mutations that improved the thermostability of the scFv combined to make double mutations in scFv08168. As shown in FIG. 31, the additive effects were observed for most of the double mutants including D1, which showed a improvement of 12.5° C. by combination of two mutations of VH:I34M and VH: S49A, whereas the single mutation leaded to 7.5 and 5.5° C. increase in Tm, respectively.

Thermostable Mutants Characterized for Binding and Functional Activity

Affinity analysis ELISA $EC_{50}$ was carried out for both scFv08168 and scFv06475 wild type and variants. As shown in FIG. 32, for scFv08168, the hits showed mostly comparable $EC_{50}$ as wild type scFv08168, with a few mutants appeared to be a little more active than wild type, including the double mutant D1. This was confirmed with Proteon affinity measurement and STF cell based assay activity (performed as described earlier in this application (Materials and Methods, section 8), as shown in FIG. 32. Affinity ranking by Octet of scFv08168 variants showed that they were comparable to wild type (data not shown), In Proteon kinetics analysis, KD of D1 was 2.55 nM, whereas KD of wild type was 3.82 nM (FIG. 32).

For scFv06475, there were two mutations affecting the activity as detected by ELISA and Proteon kinetics analysis. Specifically, in ELISA, VH:G34V and VH:I37F showed $EC_{50}$ to be 27 nM and 4.3 nM respectively as compared to wild type of 0.76 nM. In Proteon analysis, VH:G34V and VH:I39F showed significant drop in off rate (data not shown).

Improved Thermostability of Biparatopic Molecules

For IgG based fusion molecules 902 and mutant version 902T, the first Tm peak shifted from 47° C. to 62° C. This peak corresponded to scFv08168 unfolding. The second peak shifted from 72° C. to 76° C. This peak corresponded to Fab06475, as shown in FIG. 34.

Discussion

Rational design based on sequence analysis and homology modeling has yielded thermostable mutations for scFvs. In the current examples, the hit rate was around 18% for both scFv08168 and scFv06475. The most significant improvement was 7.5° C. increase in Tm over wild type by a single point mutation VH:I34M in scFv08168. On the sequence perspective, this position was highly conserved to Met. Structurally, a larger hydrophobic side chain at this position could improve the packing around this residue. Another point mutation VH:S49A in scFv08168 variant raised Tm by 5° C. This mutation was picked by homology modeling. Though this position is more conserved to Ser than to Ala, structurally Ala may fit better due to the lack of polar side chain around this residue.

For structure based mutation design using homology modeling, a combination of mechanisms was utilized. In scFv06475 and scFv08168, positive hits were discovered by each of the five biophysical considerations: packing improvement, more Pi-Pi stacking, more hydrogen bonds, more salt bridges and removal of buried polar groups. It was by this combination of mechanisms that a total of 10 stabilizing mutations have been identified, as listed in FIGS. 29 and 30.

Combination of mutations identified to improve thermal stability ("beneficial mutations") further improve thermostability if they were located in different areas. This was demonstrated in the case of scFv08168. When beneficial mutation VH:I34M and VH:S49A were combined, Tm was further increased to 62.5° C. vs wild type at 49° C. This was 13.5° C. increase over wild type, where the individual mutation VH:I34M and VH:S49A each raised Tm by 7.5° C. and 5° C. respectively. This was a clear indication for additive effect.

I34M was very close to CDR1-H of scFv08168, however the mutation did not affect the binding affinity as evidenced by a number of assays. CDR plays a role in overall scFv or full antibody stability. Significant improvement may be achieved through engineering of residues close to the CDR region using the methods disclosed, as long as the mutation does not affect binding affinity and specificity.

Most of stabilizing mutations have been located on VH. Out of the 15 stabilizing mutations listed in FIGS. 29 and 30, 11 were mutations on the VH domain whereas only 4 were on the VL domain.

When incorporated into IgG or other formats (e.g. serum albumin fusions), the stabilized VH and VL led to a dramatic improvement in thermostability of the molecules. For IgG fusion, the lower Tm of 47° C. corresponded to the Tm of scFv08168, whereas the higher peak at 72.5° C. correspond to the Tm of CH2 and Fab06475. The incorporation of two mutations VH:I34M and VH:S49A has improved the Tm of scFv08168 from 47° C. to 62° C., whereas the incorporation of VH:M95F in 6475 further improved the Tm of Fab from 72.5° C. to 76° C. The improvement was not only shown on scFv itself, but also on the Fab due to the improved stability of VH and VL. This may provide a more general strategy for improving overall antibody stability.

Rational design coupled with HTP screening in *E. coli* system has offered very quick turnaround time and high hit rate. Tm measured with materials from *E. coli* correlated with that from mammalian, or ranking remained the same. This greatly simplified screening process to implemented as HTP in *E. coli*. Plate based mutagenesis, transformation, expression and purification has shorted the time to less than one week. Using the methods disclosed herein, a number of mutations can be made in scFvs or other antigen binding fragments and screened for thermal stability. These mutated scFvs or antigen binding fragments can then be used as components of larger antibody constructs such as biparatopic antibodies, to confer such stability to the larger antibody construct.

The invention claimed is:

1. An isolated multivalent antibody or antigen-binding fragment thereof having at least two receptor binding domains for two different binding sites of a low density lipoprotein-related protein 6 (LRP6) target receptor, wherein the first receptor binding domain binds to a first binding site on the target receptor and the second receptor binding domain binds to a second binding site on the same LRP6 target receptor, wherein the first and second receptor binding domains are linked together such that the binding of the first and second receptor binding domains to the first and second binding sites of the LRP6 target receptor inhibits a canonical Wnt signal transduction pathway, and wherein the antibody or antigen binding fragment displays no significant potentiation of a Wnt signal;
   wherein the first receptor binding domain is an IgG antibody and the second receptor binding domain is an scFv fragment, wherein the IgG antibody and scFv fragment are linked together by a linker with a spatial distribution that permits the IgG antibody and scFv fragment to bind to the first and second epitopes of LRP6, respectively; and
wherein the heavy chain of the IgG antibody is selected from the group consisting of SEQ ID NO: 18, 66, and 86, and the light chain is selected from the group consisting of SEQ ID NO: 17, and 85.

2. An isolated multivalent antibody or antigen-binding fragment thereof having at least two receptor binding domains for two different binding sites of a low density lipoprotein-related protein 6 (LRP6) target receptor, wherein the first receptor binding domain binds to a first binding site on the target receptor and the second receptor binding domain binds to a second binding site on the same LRP6 target receptor, wherein the first and second receptor binding domains are linked together such that the binding of the first and second receptor binding domains to the first and second binding sites of the LRP6 target receptor inhibits a canonical Wnt signal transduction pathway, and wherein the antibody or antigen binding fragment displays no significant potentiation of a Wnt signal;
   wherein the first receptor binding domain is an IgG antibody and the second receptor binding domain is an scFv fragment, wherein the IgG antibody and scFv fragment are linked together by a linker with a spatial distribution that permits the IgG antibody and scFv fragment to bind to the first and second epitopes of LRP6, respectively; and
wherein the scFv is selected from the group consisting of SEQ ID NO: 142, 144, 146, 148, 150, 152, 154, 156, 158, 160, 162, and 164.

3. An isolated biparatopic antibody or antigen-binding fragment thereof comprising an IgG antibody that binds to a β-propeller 1 domain on a low density lipoprotein-related) protein 6 (LRP6) target receptor and a scFv that binds to a β-propeller 3 domain on the LRP6 target,
   wherein the antibody comprises heavy chain variable region CDR1 of SEQ ID NO: 1; a heavy chain variable region CDR2 of SEQ ID NO: 2; a heavy chain variable region CDR3 of SEQ ID NO: 3; a light chain variable region CDR1 of SEQ ID NO: 4; a light chain variable region CDR2 of SEQ ID NO: 5; and a light chain variable region CDR3 of SEQ ID NO: 6, wherein the antibody binds to a β-propeller 1 domain of LRP6; and a scFv heavy chain variable region CDR1 of SEQ ID NO: 69; a heavy chain variable region CDR2 of SEQ ID NO: 70; a heavy chain variable region CDR3 of SEQ ID NO: 71; a light chain variable region CDR1 of SEQ ID NO: 72; a light chain variable region CDR2 of SEQ ID NO: 73; and a light chain variable region CDR3 of SEQ ID NO: 74, wherein the scFv binds to a β-propeller 3 domain of LRP6, and
   wherein the IgG antibody and the scFv are linked by a linker such that the binding of the IgG antibody and the scFv to the β-propeller 1 domain and the β-propeller 3 domain, respectively inhibits a canonical Wnt signal transduction pathway, and wherein the biparatopic antibody or antigen-binding fragment displays no significant potentiation of a Wnt signal.

4. An isolated multivalent antibody or antigen-binding fragment thereof having at least two receptor binding domains for two different binding sites of a low density lipoprotein-related protein 6 (LRP6) target receptor, wherein the antibody or antigen-binding fragment binds to the-LRP6 β-propeller 1 domain and comprises a heavy chain CDR1 selected from the group consisting of SEQ ID NO: 1, SEQ ID NO: 21, and SEQ ID NO: 47; a CDR2 selected from the group consisting of SEQ ID NO: 2, SEQ ID NO: 22, and SEQ ID NO: 48; and a CDR3 selected from the group consisting of SEQ ID NO: 3, SEQ ID NO: 23, and SEQ ID NO: 49; and a light chain CDR1 selected from the group consisting of SEQ ID NO: 4, SEQ ID NO: 24, and SEQ ID NO: 50; a CDR2 selected from the group consisting of SEQ ID NO: 5, SEQ ID NO: 25, and SEQ ID NO: 51; and a CDR3 selected from the group consisting of SEQ ID NO: 6, SEQ ID NO: 26, and SEQ ID NO: 52.

5. The antibody or antigen-binding fragment of claim 4, wherein the heavy chain is selected from the group consisting of SEQ ID NO: 18, 66, and 86, and the light chain is selected from the group consisting of SEQ ID NO: 17, and 85.

6. An isolated multivalent antibody or antigen-binding fragment thereof having at least two receptor binding domains for two different binding sites of a low density lipoprotein-related protein 6 (LRP6) target receptor, wherein the antibody binds to the LRP6 β-propeller 3 domain and comprises a heavy chain CDR1 selected from the group consisting of SEQ ID NO: 69, SEQ ID NO: 93, and SEQ ID NO: 115; a CDR2 selected from the group consisting of SEQ ID NO: 70, SEQ ID NO: 94, and SEQ ID NO: 116; and a CDR3 selected from the group consisting of SEQ ID NO: 71, SEQ ID NO: 95, and SEQ ID NO: 117; and a light chain CDR1 selected from the group consisting of SEQ ID NO: 72, SEQ ID NO: 96, and SEQ ID NO: 118; a CDR2 selected from the group consisting of SEQ ID NO: 73, SEQ ID NO: 97, and SEQ ID NO: 119; and a CDR3 selected from the group consisting of SEQ ID NO: 74, SEQ ID NO: 98, and SEQ ID NO: 120.

7. The antibody or antigen-binding fragment of claim 6, wherein the first receptor binding domain is an IgG antibody and the second receptor binding domain is an scFv fragment, wherein the IgG antibody and scFv fragment are linked together by a linker with a spatial distribution that permits the IgG antibody and scFv fragment to bind to the first and second epitopes of LRP6, respectively, and wherein the scFv is selected from the group consisting of SEQ ID NO: 142, 144, 146, 148, 150, 152, 154, 156, 158, 160, 162, and 164.

8. An isolated biparatopic antibody or antigen-binding fragment thereof, comprising an IgG antibody comprising a heavy chain variable region CDR1 of SEQ ID NO: 1; a heavy chain variable region CDR2 of SEQ ID NO: 2; a heavy chain variable region CDR3 of SEQ ID NO: 3; a light chain variable region CDR1 of SEQ ID NO: 4; a light chain variable region CDR2 of SEQ ID NO: 5; and a light chain variable region CDR3 of SEQ ID NO: 6, that binds to a β-propeller 1 domain on a low density lipoprotein-related protein 6 (LRP6) target receptor and a scFv comprising a scFv heavy chain variable region CDR1 of SEQ ID NO: 69; a heavy chain variable region CDR2 of SEQ ID NO: 70; a heavy chain variable region CDR3 of SEQ ID NO: 71; a light chain variable region CDR1 of SEQ ID NO: 72; a light chain variable region CDR2 of SEQ ID NO: 73; and a light chain variable region CDR3 of SEQ ID NO: 74, that binds to a β-propeller 3 domain on the LRP6 target.

9. A pharmaceutical composition comprising a multivalent antibody or antigen-binding fragment thereof, having at least first and second receptor binding domains for two different binding sites of a low density lipoprotein-related protein 6 (LRP6) target receptor and a pharmaceutically acceptable carrier, wherein the first receptor binding domain comprises an IgG antibody or antigen-binding fragment thereof having a heavy chain according to SEQ ID NO: 18 and a light chain according to SEQ ID NO 17, and the second receptor binding domain comprises an scFv comprising SEQ ID NO: 144.

* * * * *

SEQUENCE LISTING

<160> NUMBER OF SEQ ID NOS: 208

<210> SEQ ID NO 1
<211> LENGTH: 5
<212> TYPE: PRT
<213> ORGANISM: Homo Sapien

<400> SEQUENCE: 1

Asp Tyr Val Ile Asn
1 5

<210> SEQ ID NO 2
<211> LENGTH: 17
<212> TYPE: PRT
<213> ORGANISM: Homo Sapien

<400> SEQUENCE: 2

Gly Ile Ser Trp Ser Gly Val Asn Thr His Tyr Ala Asp Ser Val Lys
1 5 10 15

Gly

<210> SEQ ID NO 3
<211> LENGTH: 15
<212> TYPE: PRT
<213> ORGANISM: Homo Sapien

<400> SEQUENCE: 3

Leu Gly Ala Thr Ala Asn Asn Ile Arg Tyr Lys Phe Met Asp Val
1 5 10 15

<210> SEQ ID NO 4
<211> LENGTH: 10
<212> TYPE: PRT
<213> ORGANISM: Homo Sapien

<400> SEQUENCE: 4

Ser Gly Asp Ser Leu Arg Asn Lys Val Tyr
1 5 10

<210> SEQ ID NO 5
<211> LENGTH: 6
<212> TYPE: PRT
<213> ORGANISM: Homo Sapien

<400> SEQUENCE: 5

Lys Asn Asn Arg Pro Ser
1 5

<210> SEQ ID NO 6
<211> LENGTH: 10
<212> TYPE: PRT
<213> ORGANISM: Homo Sapien

<400> SEQUENCE: 6

Gln Ser Tyr Asp Gly Gln Lys Ser Leu Val
1 5 10

<210> SEQ ID NO 7
<211> LENGTH: 7
<212> TYPE: PRT
<213> ORGANISM: Homo Sapien

<400> SEQUENCE: 7

Gly Phe Thr Phe Ser Asp Tyr

```
 1               5


<210> SEQ ID NO 8
<211> LENGTH: 6
<212> TYPE: PRT
<213> ORGANISM: Homo Sapien

<400> SEQUENCE: 8

Ser Trp Ser Gly Val Asn
 1               5


<210> SEQ ID NO 9
<211> LENGTH: 15
<212> TYPE: PRT
<213> ORGANISM: Homo Sapien

<400> SEQUENCE: 9

Leu Gly Ala Thr Ala Asn Asn Ile Arg Tyr Lys Phe Met Asp Val
 1               5                   10                  15


<210> SEQ ID NO 10
<211> LENGTH: 6
<212> TYPE: PRT
<213> ORGANISM: Homo Sapien

<400> SEQUENCE: 10

Asp Ser Leu Arg Asn Lys
 1               5


<210> SEQ ID NO 11
<211> LENGTH: 2
<212> TYPE: PRT
<213> ORGANISM: Homo Sapien

<400> SEQUENCE: 11

Lys Asn
 1


<210> SEQ ID NO 12
<211> LENGTH: 7
<212> TYPE: PRT
<213> ORGANISM: Homo Sapien

<400> SEQUENCE: 12

Tyr Asp Gly Gln Lys Ser Leu
 1               5


<210> SEQ ID NO 13
<211> LENGTH: 105
<212> TYPE: PRT
<213> ORGANISM: Homo Sapien

<400> SEQUENCE: 13

Asp Ile Glu Leu Thr Gln Pro Pro Ser Val Ser Val Ala Pro Gly Gln
 1               5                   10                  15

Thr Ala Arg Ile Ser Cys Ser Gly Asp Ser Leu Arg Asn Lys Val Tyr
            20                  25                  30

Trp Tyr Gln Gln Lys Pro Gly Gln Ala Pro Val Leu Val Ile Tyr Lys
        35                  40                  45

Asn Asn Arg Pro Ser Gly Ile Pro Glu Arg Phe Ser Gly Ser Asn Ser
    50                  55                  60

Gly Asn Thr Ala Thr Leu Thr Ile Ser Gly Thr Gln Ala Glu Asp Glu
65                  70                  75                  80
```

```
Ala Asp Tyr Tyr Cys Gln Ser Tyr Asp Gly Gln Lys Ser Leu Val Phe
                85                  90                  95

Gly Gly Gly Thr Lys Leu Thr Val Leu
            100                 105


<210> SEQ ID NO 14
<211> LENGTH: 124
<212> TYPE: PRT
<213> ORGANISM: Homo Sapien

<400> SEQUENCE: 14

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Val Ile Asn Trp Val Arg Gln Ala Pro Gly Lys Gly Leu Glu Trp Val
        35                  40                  45

Ser Gly Ile Ser Trp Ser Gly Val Asn Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Ala Thr Ala Asn Asn Ile Arg Tyr Lys Phe Met Asp
            100                 105                 110

Val Trp Gly Gln Gly Thr Leu Val Thr Val Ser Ser
        115                 120


<210> SEQ ID NO 15
<211> LENGTH: 315
<212> TYPE: DNA
<213> ORGANISM: Homo Sapien

<400> SEQUENCE: 15

gatatcgaac tgacccagcc gccttcagtg agcgttgcac caggtcagac cgcgcgtatc      60

tcgtgtagcg gcgattctct tcgtaataag gtttattggt accagcagaa acccgggcag     120

gcgccagttc ttgtgattta taagaataat cgtccctcag gcatcccgga acgctttagc     180

ggatccaaca gcggcaacac cgcgaccctg accattagcg gcactcaggc ggaagacgaa     240

gcggattatt attgccagtc ttatgatggt cagaagtctc ttgtgtttgg cggcggcacg     300

aagttaaccg tccta                                                      315


<210> SEQ ID NO 16
<211> LENGTH: 372
<212> TYPE: DNA
<213> ORGANISM: Homo Sapien

<400> SEQUENCE: 16

caggtgcaat tggtggaaag cggcggcggc ctggtgcaac cgggcggcag cctgcgtctg      60

agctgcgcgg cctccggatt taccttttct gattatgtta ttaattgggt gcgccaagcc     120

cctgggaagg gtctcgagtg ggtgagcggt atttcttggt ctggtgttaa tactcattat     180

gctgattctg ttaagggtcg ttttaccatt tcacgtgata attcgaaaaa caccctgtat     240

ctgcaaatga acagcctgcg tgcggaagat acggccgtgt attattgcgc gcgtcttggt     300

gctactgcta ataatattcg ttataagttt atggatgttt ggggccaagg caccctggtg     360
```

acggttagct ca 372

<210> SEQ ID NO 17
<211> LENGTH: 211
<212> TYPE: PRT
<213> ORGANISM: Homo Sapien

<400> SEQUENCE: 17

```
Asp Ile Glu Leu Thr Gln Pro Pro Ser Val Ser Val Ala Pro Gly Gln
 1               5                  10                  15

Thr Ala Arg Ile Ser Cys Ser Gly Asp Ser Leu Arg Asn Lys Val Tyr
            20                  25                  30

Trp Tyr Gln Gln Lys Pro Gly Gln Ala Pro Val Leu Val Ile Tyr Lys
        35                  40                  45

Asn Asn Arg Pro Ser Gly Ile Pro Glu Arg Phe Ser Gly Ser Asn Ser
    50                  55                  60

Gly Asn Thr Ala Thr Leu Thr Ile Ser Gly Thr Gln Ala Glu Asp Glu
65                  70                  75                  80

Ala Asp Tyr Tyr Cys Gln Ser Tyr Asp Gly Gln Lys Ser Leu Val Phe
                85                  90                  95

Gly Gly Gly Thr Lys Leu Thr Val Leu Gly Gln Pro Lys Ala Ala Pro
            100                 105                 110

Ser Val Thr Leu Phe Pro Pro Ser Ser Glu Glu Leu Gln Ala Asn Lys
        115                 120                 125

Ala Thr Leu Val Cys Leu Ile Ser Asp Phe Tyr Pro Gly Ala Val Thr
    130                 135                 140

Val Ala Trp Lys Ala Asp Ser Ser Pro Val Lys Ala Gly Val Glu Thr
145                 150                 155                 160

Thr Thr Pro Ser Lys Gln Ser Asn Asn Lys Tyr Ala Ala Ser Ser Tyr
                165                 170                 175

Leu Ser Leu Thr Pro Glu Gln Trp Lys Ser His Arg Ser Tyr Ser Cys
            180                 185                 190

Gln Val Thr His Glu Gly Ser Thr Val Glu Lys Thr Val Ala Pro Thr
        195                 200                 205

Glu Cys Ser
    210
```

<210> SEQ ID NO 18
<211> LENGTH: 454
<212> TYPE: PRT
<213> ORGANISM: Homo Sapien

<400> SEQUENCE: 18

```
Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Val Ile Asn Trp Val Arg Gln Ala Pro Gly Lys Gly Leu Glu Trp Val
        35                  40                  45

Ser Gly Ile Ser Trp Ser Gly Val Asn Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Ala Thr Ala Asn Asn Ile Arg Tyr Lys Phe Met Asp
```

-continued

```
            100                 105                 110

Val Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Ala Ala Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450


<210> SEQ ID NO 19
<211> LENGTH: 633
<212> TYPE: DNA
<213> ORGANISM: Homo Sapien

<400> SEQUENCE: 19

gatatcgaac tgacccagcc gccttcagtg agcgttgcac caggtcagac cgcgcgtatc      60

tcgtgtagcg gcgattctct tcgtaataag gtttattggt accagcagaa acccgggcag     120
```

gcgccagttc ttgtgattta taagaataat cgtccctcag gcatcccgga acgctttagc 180
ggatccaaca gcggcaacac cgcgaccctg accattagcg gcactcaggc ggaagacgaa 240
gcggattatt attgccagtc ttatgatggt cagaagtctc ttgtgtttgg cggcggcacg 300
aagttaaccg tcctaggtca gcccaaggct gccccctcgg tcactctgtt cccgccctcc 360
tctgaggagc ttcaagccaa caaggccaca ctggtgtgtc tcataagtga cttctacccg 420
ggagccgtga cagtggcctg gaaggcagat agcagccccg tcaaggcggg agtggagacc 480
accacaccct ccaaacaaag caacaacaag tacgcggcca gcagctatct gagcctgacg 540
cctgagcagt ggaagtccca cagaagctac agctgccagg tcacgcatga agggagcacc 600
gtggagaaga cagtggcccc tacagaatgt tca 633

<210> SEQ ID NO 20
<211> LENGTH: 1362
<212> TYPE: DNA
<213> ORGANISM: Homo Sapien

<400> SEQUENCE: 20
caggtgcaat tggtggaaag cggcggcggc ctggtgcaac cgggcggcag cctgcgtctg 60
agctgcgcgg cctccggatt taccttttct gattatgtta ttaattgggt gcgccaagcc 120
cctgggaagg gtctcgagtg ggtgagcggt atttcttggt ctggtgttaa tactcattat 180
gctgattctg ttaagggtcg ttttaccatt tcacgtgata attcgaaaaa caccctgtat 240
ctgcaaatga acagcctgcg tgcggaagat acggccgtgt attattgcgc gcgtcttggt 300
gctactgcta ataatattcg ttataagttt atggatgttt ggggccaagg caccctggtg 360
acggttagct cagcctccac caagggtcca tcggtcttcc ccctggcacc ctcctccaag 420
agcacctctg ggggcacagc ggccctgggc tgcctggtca aggactactt ccccgaaccg 480
gtgacggtgt cgtggaactc aggcgccctg accagcggcg tgcacacctt cccggctgtc 540
ctacagtcct caggactcta ctccctcagc agcgtggtga ccgtgccctc cagcagcttg 600
ggcacccaga cctacatctg caacgtgaat cacaagccca gcaacaccaa ggtggacaag 660
agagttgagc ccaaatcttg tgacaaaact cacacatgcc caccgtgccc agcacctgaa 720
gcagcggggg gaccgtcagt cttcctcttc cccccaaaac ccaaggacac cctcatgatc 780
tcccggaccc ctgaggtcac atgcgtggtg gtggacgtga gccacgaaga ccctgaggtc 840
aagttcaact ggtacgtgga cggcgtggag gtgcataatg ccaagacaaa gccgcgggag 900
gagcagtaca acagcacgta ccgggtggtc agcgtcctca ccgtcctgca ccaggactgg 960
ctgaatggca aggagtacaa gtgcaaggtc tccaacaaag ccctcccagc ccccatcgag 1020
aaaaccatct ccaaagccaa agggcagccc cgagaaccac aggtgtacac cctgccccca 1080
tcccgggagg agatgaccaa gaaccaggtc agcctgacct gcctggtcaa aggcttctat 1140
cccagcgaca tcgccgtgga gtgggagagc aatgggcagc cggagaacaa ctacaagacc 1200
acgcctcccg tgctggactc cgacggctcc ttcttcctct acagcaagct caccgtggac 1260
aagagcaggt ggcagcaggg gaacgtcttc tcatgctccg tgatgcatga ggctctgcac 1320
aaccactaca cgcagaagag cctctccctg tctccgggta aa 1362

<210> SEQ ID NO 21
<211> LENGTH: 5
<212> TYPE: PRT
<213> ORGANISM: Homo Sapien

```
<400> SEQUENCE: 21

Val Asn Gly Met His
 1               5


<210> SEQ ID NO 22
<211> LENGTH: 16
<212> TYPE: PRT
<213> ORGANISM: Homo Sapien

<400> SEQUENCE: 22

Val Ile Asp Gly Met Gly His Thr Tyr Tyr Ala Asp Ser Val Lys Gly
 1               5                  10                  15


<210> SEQ ID NO 23
<211> LENGTH: 11
<212> TYPE: PRT
<213> ORGANISM: Homo Sapien

<400> SEQUENCE: 23

Tyr Asp Tyr Ile Lys Tyr Gly Ala Phe Asp Pro
 1               5                  10


<210> SEQ ID NO 24
<211> LENGTH: 11
<212> TYPE: PRT
<213> ORGANISM: Homo Sapien

<400> SEQUENCE: 24

Ser Gly Asp Asn Ile Gly Ser Lys Tyr Val His
 1               5                  10


<210> SEQ ID NO 25
<211> LENGTH: 7
<212> TYPE: PRT
<213> ORGANISM: Homo Sapien

<400> SEQUENCE: 25

Gly Asp Ser Asn Arg Pro Ser
 1               5


<210> SEQ ID NO 26
<211> LENGTH: 10
<212> TYPE: PRT
<213> ORGANISM: Homo Sapien

<400> SEQUENCE: 26

Thr Arg Thr Ser Thr Pro Ile Ser Gly Val
 1               5                  10


<210> SEQ ID NO 27
<211> LENGTH: 7
<212> TYPE: PRT
<213> ORGANISM: Homo Sapien

<400> SEQUENCE: 27

Gly Phe Thr Phe Ser Val Asn
 1               5


<210> SEQ ID NO 28
<211> LENGTH: 5
<212> TYPE: PRT
<213> ORGANISM: Homo Sapien

<400> SEQUENCE: 28
```

-continued

```
Asp Gly Met Gly His
 1               5


<210> SEQ ID NO 29
<211> LENGTH: 11
<212> TYPE: PRT
<213> ORGANISM: Homo Sapien

<400> SEQUENCE: 29

Tyr Asp Tyr Ile Lys Tyr Gly Ala Phe Asp Pro
 1               5                  10


<210> SEQ ID NO 30
<211> LENGTH: 7
<212> TYPE: PRT
<213> ORGANISM: Homo Sapien

<400> SEQUENCE: 30

Asp Asn Ile Gly Ser Lys Tyr
 1               5


<210> SEQ ID NO 31
<211> LENGTH: 3
<212> TYPE: PRT
<213> ORGANISM: Homo Sapien

<400> SEQUENCE: 31

Gly Asp Ser
 1


<210> SEQ ID NO 32
<211> LENGTH: 7
<212> TYPE: PRT
<213> ORGANISM: Homo Sapien

<400> SEQUENCE: 32

Thr Ser Thr Pro Ile Ser Gly
 1               5


<210> SEQ ID NO 33
<211> LENGTH: 107
<212> TYPE: PRT
<213> ORGANISM: Homo Sapien

<400> SEQUENCE: 33

Asp Ile Glu Leu Thr Gln Pro Pro Ser Val Ser Val Ala Pro Gly Gln
 1               5                  10                  15

Thr Ala Arg Ile Ser Cys Ser Gly Asp Asn Ile Gly Ser Lys Tyr Val
            20                  25                  30

His Trp Tyr Gln Gln Lys Pro Gly Gln Ala Pro Val Leu Val Ile Tyr
        35                  40                  45

Gly Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Thr Arg Thr Ser Thr Pro Ile Ser Gly
                85                  90                  95

Val Phe Gly Gly Gly Thr Lys Leu Thr Val Leu
            100                 105


<210> SEQ ID NO 34
<211> LENGTH: 119
```

<212> TYPE: PRT
<213> ORGANISM: Homo Sapien

<400> SEQUENCE: 34

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Val Asn
20 25 30

Gly Met His Trp Val Arg Gln Ala Pro Gly Lys Gly Leu Glu Trp Val
35 40 45

Ser Val Ile Asp Gly Met Gly His Thr Tyr Tyr Ala Asp Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Tyr Asp Tyr Ile Lys Tyr Gly Ala Phe Asp Pro Trp Gly Gln Gly
100 105 110

Thr Leu Val Thr Val Ser Ser
115

<210> SEQ ID NO 35
<211> LENGTH: 107
<212> TYPE: PRT
<213> ORGANISM: Homo Sapien

<400> SEQUENCE: 35

Ser Tyr Glu Leu Thr Gln Pro Pro Ser Val Ser Val Ser Pro Gly Gln
1 5 10 15

Thr Ala Ser Ile Thr Cys Ser Gly Asp Asn Ile Gly Ser Lys Tyr Val
20 25 30

His Trp Tyr Gln Gln Lys Pro Gly Gln Ser Pro Val Leu Val Ile Tyr
35 40 45

Gly Asp Ser Asn Arg Pro Ser Gly Ile Pro Glu Arg Phe Ser Gly Ser
50 55 60

Asn Ser Gly Asn Thr Ala Thr Leu Thr Ile Ser Gly Thr Gln Ala Met
65 70 75 80

Asp Glu Ala Asp Tyr Tyr Cys Thr Arg Thr Ser Thr Pro Ile Ser Gly
85 90 95

Val Phe Gly Gly Gly Thr Lys Leu Thr Val Leu
100 105

<210> SEQ ID NO 36
<211> LENGTH: 119
<212> TYPE: PRT
<213> ORGANISM: Homo Sapien

<400> SEQUENCE: 36

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Val Asn
20 25 30

Gly Met His Trp Val Arg Gln Ala Pro Gly Lys Gly Leu Glu Trp Val
35 40 45

Ser Val Ile Asp Gly Met Gly His Thr Tyr Tyr Ala Asp Ser Val Lys
50 55 60

Gly Arg Phe Thr Ile Ser Arg Asp Asn Ser Lys Asn Thr Leu Tyr Leu

```
65                  70                  75                  80

Gln Met Asn Ser Leu Arg Ala Glu Asp Thr Ala Val Tyr Tyr Cys Ala
                85                  90                  95

Arg Tyr Asp Tyr Ile Lys Tyr Gly Ala Phe Asp Pro Trp Gly Gln Gly
            100                 105                 110

Thr Leu Val Thr Val Ser Ser
        115
```

<210> SEQ ID NO 37
<211> LENGTH: 321
<212> TYPE: DNA
<213> ORGANISM: Homo Sapien

<400> SEQUENCE: 37

```
gatatcgaac tgacccagcc gccttcagtg agcgttgcac caggtcagac cgcgcgtatc     60

tcgtgtagcg gcgataatat tggttctaag tatgttcatt ggtaccagca gaaacccggg    120

caggcgccag ttcttgtgat ttatggtgat tctaatcgtc cctcaggcat cccggaacgc    180

tttagcggat ccaacagcgg caacaccgcg accctgacca ttagcggcac tcaggcggaa    240

gacgaagcgg attattattg cactcgtact tctactccta tttctggtgt gtttggcggc    300

ggcacgaagt taaccgttct t                                              321
```

<210> SEQ ID NO 38
<211> LENGTH: 357
<212> TYPE: DNA
<213> ORGANISM: Homo Sapien

<400> SEQUENCE: 38

```
caggtgcaat tggtggaaag cggcggcggc ctggtgcaac cgggcggcag cctgcgtctg     60

agctgcgcgg cctccggatt taccttttct gttaatggta tgcattgggt gcgccaagcc    120

cctgggaagg gtctcgagtg ggtgagcgtt attgatggta tgggtcatac ttattatgct    180

gattctgtta agggtcgttt taccatttca cgtgataatt cgaaaaacac cctgtatctg    240

caaatgaaca gcctgcgtgc ggaagatacg gccgtgtatt attgcgcgcg ttatgattat    300

attaagtatg gtgcttttga tccttggggc caaggcaccc tggtgacggt tagctca       357
```

<210> SEQ ID NO 39
<211> LENGTH: 212
<212> TYPE: PRT
<213> ORGANISM: Homo Sapien

<400> SEQUENCE: 39

```
Asp Ile Glu Leu Thr Gln Pro Pro Ser Val Ser Val Ala Pro Gly Gln
 1               5                  10                  15

Thr Ala Arg Ile Ser Cys Ser Gly Asp Asn Ile Gly Ser Lys Tyr Val
            20                  25                  30

His Trp Tyr Gln Gln Lys Pro Gly Gln Ala Pro Val Leu Val Ile Tyr
        35                  40                  45

Gly Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Thr Arg Thr Ser Thr Pro Ile Ser Gly
                85                  90                  95

Val Phe Gly Gly Gly Thr Lys Leu Thr Val Leu Gly Gln Pro Lys Ala
            100                 105                 110
```

```
Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Ala
    210


<210> SEQ ID NO 40
<211> LENGTH: 221
<212> TYPE: PRT
<213> ORGANISM: Homo Sapien

<400> SEQUENCE: 40

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Val Asn
            20                  25                  30

Gly Met His Trp Val Arg Gln Ala Pro Gly Lys Gly Leu Glu Trp Val
        35                  40                  45

Ser Val Ile Asp Gly Met Gly His Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Asp Tyr Ile Lys Tyr Gly Ala Phe Asp Pro Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser
    210                 215                 220


<210> SEQ ID NO 41
<211> LENGTH: 636
<212> TYPE: DNA
<213> ORGANISM: Homo Sapien

<400> SEQUENCE: 41
```

```
gatatcgaac tgacccagcc gccttcagtg agcgttgcac caggtcagac cgcgcgtatc      60

tcgtgtagcg gcgataatat tggttctaag tatgttcatt ggtaccagca gaaacccggg     120

caggcgccag ttcttgtgat ttatggtgat tctaatcgtc cctcaggcat cccggaacgc     180

tttagcggat ccaacagcgg caacaccgcg accctgacca ttagcggcac tcaggcggaa     240

gacgaagcgg attattattg cactcgtact tctactccta tttctggtgt gtttggcggc     300

ggcacgaagt taaccgttct tggccagccg aaagccgcac cgagtgtgac gctgtttccg     360

ccgagcagcg aagaattgca ggcgaacaaa gcgaccctgg tgtgcctgat tagcgacttt     420

tatccgggag ccgtgacagt ggcctggaag gcagatagca gccccgtcaa ggcgggagtg     480

gagaccacca caccctccaa acaaagcaac aacaagtacg cggccagcag ctatctgagc     540

ctgacgcctg agcagtggaa gtcccacaga agctacagct gccaggtcac gcatgagggg     600

agcaccgtgg aaaaaaccgt tgcgccgact gaggcc                               636
```

<210> SEQ ID NO 42
<211> LENGTH: 663
<212> TYPE: DNA
<213> ORGANISM: Homo Sapien

<400> SEQUENCE: 42

```
caggtgcaat tggtggaaag cggcggcggc ctggtgcaac cgggcggcag cctgcgtctg      60

agctgcgcgg cctccggatt taccttttct gttaatggta tgcattgggt gcgccaagcc     120

cctgggaagg gtctcgagtg ggtgagcgtt attgatggta tgggtcatac ttattatgct     180

gattctgtta agggtcgttt taccatttca cgtgataatt cgaaaaacac cctgtatctg     240

caaatgaaca gcctgcgtgc ggaagatacg gccgtgtatt attgcgcgcg ttatgattat     300

attaagtatg gtgcttttga tccttggggc caaggcaccc tggtgacggt tagctcagcg     360

tcgaccaaag gtccaagcgt gtttccgctg gctccgagca gcaaaagcac cagcggcggc     420

acggctgccc tgggctgcct ggttaaagat tatttcccgg aaccagtcac cgtgagctgg     480

aacagcgggg cgctgaccag cggcgtgcat acctttccgg cggtgctgca aagcagcggc     540

ctgtatagcc tgagcagcgt tgtgaccgtg ccgagcagca gcttaggcac tcagacctat     600

atttgcaacg tgaaccataa accgagcaac accaaagtgg ataaaaaagt ggaaccgaaa     660

agc                                                                   663
```

<210> SEQ ID NO 43
<211> LENGTH: 107
<212> TYPE: PRT
<213> ORGANISM: Homo Sapien

<400> SEQUENCE: 43

```
Ser Tyr Glu Leu Thr Gln Pro Leu Ser Val Ser Val Ala Leu Gly Gln
 1               5                  10                  15

Thr Ala Arg Ile Thr Cys Gly Gly Asp Asn Ile Gly Ser Lys Tyr Val
            20                  25                  30

His Trp Tyr Gln Gln Lys Pro Gly Gln Ala Pro Val Leu Val Ile Tyr
        35                  40                  45

Gly Asp Ser Asn Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Thr Arg Thr Ser Thr Pro Ile Ser Gly
```

-continued

```
                85                  90                  95

Val Phe Gly Gly Gly Thr Lys Leu Thr Val Leu
            100                 105


<210> SEQ ID NO 44
<211> LENGTH: 119
<212> TYPE: PRT
<213> ORGANISM: Homo Sapien

<400> SEQUENCE: 44

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Val Asn
            20                  25                  30

Gly Met His Trp Val Arg Gln Ala Pro Gly Lys Gly Leu Glu Trp Val
        35                  40                  45

Ser Val Ile Asp Gly Met Gly His Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Asp Tyr Ile Lys Tyr Gly Ala Phe Asp Pro Trp Gly Gln Gly
            100                 105                 110

Thr Leu Val Thr Val Ser Ser
        115


<210> SEQ ID NO 45
<211> LENGTH: 321
<212> TYPE: DNA
<213> ORGANISM: Homo Sapien

<400> SEQUENCE: 45

agctatgaac tgacccagcc gctgtctgtg agcgtggcgc tgggccagac cgcgcgtatt     60

acctgcggtg gcgataacat tggcagcaaa tatgtgcatt ggtatcagca gaaaccgggc    120

caggcgccgg tgctggtgat ttatggcgat agcaaccgtc cgagcggcat tccggaacgt    180

tttagcggca gcaacagcgg caacaccgcg accctgacca tttctcgcgc gcaggcgggt    240

gatgaagcgg attattattg cacccgtacc agcaccccga ttagcggcgt gtttggcggc    300

ggtacgaagt taaccgttct t                                             321


<210> SEQ ID NO 46
<211> LENGTH: 357
<212> TYPE: DNA
<213> ORGANISM: Homo Sapien

<400> SEQUENCE: 46

gaggtgcaat tgctggaaag cggcggcggc ctggtgcaac cgggcggcag cctgcgtctg     60

agctgcgcgg cctccggatt taccttttct gttaatggta tgcattgggt gcgccaagcc    120

cctgggaagg gtctcgagtg ggtgagcgtt attgatggta tgggtcatac ttattatgct    180

gattctgtta agggtcgttt taccatttca cgtgataatt cgaaaaacac cctgtatctg    240

caaatgaaca gcctgcgtgc ggaagatacg gccgtgtatt attgcgcgcg ttatgattat    300

attaagtatg gtgcttttga tccttggggc caaggcaccc tggtgacggt tagctca       357


<210> SEQ ID NO 47
```

-continued

```
<211> LENGTH: 5
<212> TYPE: PRT
<213> ORGANISM: Homo Sapien

<400> SEQUENCE: 47

Asp Tyr Ala Ile His
 1               5


<210> SEQ ID NO 48
<211> LENGTH: 17
<212> TYPE: PRT
<213> ORGANISM: Homo Sapien

<400> SEQUENCE: 48

Gly Ile Ser Tyr Ser Gly Ser Ser Thr His Tyr Ala Asp Ser Val Lys
 1               5                  10                  15

Gly


<210> SEQ ID NO 49
<211> LENGTH: 14
<212> TYPE: PRT
<213> ORGANISM: Homo Sapien

<400> SEQUENCE: 49

Gly Ser His Gly Asn Ile Met Ala Lys Arg Tyr Phe Asp Phe
 1               5                  10


<210> SEQ ID NO 50
<211> LENGTH: 11
<212> TYPE: PRT
<213> ORGANISM: Homo Sapien

<400> SEQUENCE: 50

Ser Gly Asp Asn Ile Arg Lys Lys Tyr Val Tyr
 1               5                  10


<210> SEQ ID NO 51
<211> LENGTH: 7
<212> TYPE: PRT
<213> ORGANISM: Homo Sapien

<400> SEQUENCE: 51

Glu Asp Ser Lys Arg Pro Ser
 1               5


<210> SEQ ID NO 52
<211> LENGTH: 11
<212> TYPE: PRT
<213> ORGANISM: Homo Sapien

<400> SEQUENCE: 52

Ser Thr Ala Asp Ser Gly Ile Asn Asn Gly Val
 1               5                  10


<210> SEQ ID NO 53
<211> LENGTH: 7
<212> TYPE: PRT
<213> ORGANISM: Homo Sapien

<400> SEQUENCE: 53

Gly Phe Thr Phe Ser Asp Tyr
 1               5


<210> SEQ ID NO 54
```

<211> LENGTH: 6
<212> TYPE: PRT
<213> ORGANISM: Homo Sapien

<400> SEQUENCE: 54

Ser Tyr Ser Gly Ser Ser
1 5

<210> SEQ ID NO 55
<211> LENGTH: 14
<212> TYPE: PRT
<213> ORGANISM: Homo Sapien

<400> SEQUENCE: 55

Gly Ser His Gly Asn Ile Met Ala Lys Arg Tyr Phe Asp Phe
1 5 10

<210> SEQ ID NO 56
<211> LENGTH: 7
<212> TYPE: PRT
<213> ORGANISM: Homo Sapien

<400> SEQUENCE: 56

Asp Asn Ile Arg Lys Lys Tyr
1 5

<210> SEQ ID NO 57
<211> LENGTH: 3
<212> TYPE: PRT
<213> ORGANISM: Homo Sapien

<400> SEQUENCE: 57

Glu Asp Ser
1

<210> SEQ ID NO 58
<211> LENGTH: 8
<212> TYPE: PRT
<213> ORGANISM: Homo Sapien

<400> SEQUENCE: 58

Ala Asp Ser Gly Ile Asn Asn Gly
1 5

<210> SEQ ID NO 59
<211> LENGTH: 108
<212> TYPE: PRT
<213> ORGANISM: Homo Sapien

<400> SEQUENCE: 59

Asp Ile Glu Leu Thr Gln Pro Pro Ser Val Ser Val Ala Pro Gly Gln
1 5 10 15

Thr Ala Arg Ile Ser Cys Ser Gly Asp Asn Ile Arg Lys Lys Tyr Val
20 25 30

Tyr Trp Tyr Gln Gln Lys Pro Gly Gln Ala Pro Val Leu Val Ile Tyr
35 40 45

Glu Asp Ser Lys Arg Pro Ser Gly Ile Pro Glu Arg Phe Ser Gly Ser
50 55 60

Asn Ser Gly Asn Thr Ala Thr Leu Thr Ile Ser Gly Thr Gln Ala Glu
65 70 75 80

Asp Glu Ala Asp Tyr Tyr Cys Ser Thr Ala Asp Ser Gly Ile Asn Asn
85 90 95

```
Gly Val Phe Gly Gly Gly Thr Lys Leu Thr Val Leu
            100                 105


<210> SEQ ID NO 60
<211> LENGTH: 123
<212> TYPE: PRT
<213> ORGANISM: Homo Sapien

<400> SEQUENCE: 60

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Ile His Trp Val Arg Gln Ala Pro Gly Lys Gly Leu Glu Trp Val
        35                  40                  45

Ser Gly Ile Ser Tyr Ser Gly Ser Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser His Gly Asn Ile Met Ala Lys Arg Tyr Phe Asp Phe
            100                 105                 110

Trp Gly Gln Gly Thr Leu Val Thr Val Ser Ser
        115                 120


<210> SEQ ID NO 61
<211> LENGTH: 108
<212> TYPE: PRT
<213> ORGANISM: Homo Sapien

<400> SEQUENCE: 61

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Arg Lys Lys Tyr Val
            20                  25                  30

Tyr Trp Tyr Gln Gln Lys Pro Gly Gln Ser Pro Val Leu Val Ile Tyr
        35                  40                  45

Glu Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ser Thr Ala Asp Ser Gly Ile Asn Asn
                85                  90                  95

Gly Val Phe Gly Gly Gly Thr Lys Leu Thr Val Leu
            100                 105


<210> SEQ ID NO 62
<211> LENGTH: 123
<212> TYPE: PRT
<213> ORGANISM: Homo Sapien

<400> SEQUENCE: 62

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Ile His Trp Val Arg Gln Ala Pro Gly Lys Gly Leu Glu Trp Val
```

```
        35                  40                  45

Ser Gly Ile Ser Tyr Ser Gly Ser Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser His Gly Asn Ile Met Ala Lys Arg Tyr Phe Asp Phe
            100                 105                 110

Trp Gly Gln Gly Thr Leu Val Thr Val Ser Ser
        115                 120


<210> SEQ ID NO 63
<211> LENGTH: 324
<212> TYPE: DNA
<213> ORGANISM: Homo Sapien

<400> SEQUENCE: 63

gatatcgaac tgacccagcc gccttcagtg agcgttgcac caggtcagac cgcgcgtatc      60

tcgtgtagcg gcgataatat tcgtaagaag tatgtttatt ggtaccagca gaaacccggg     120

caggcgccag ttcttgtgat ttatgaggat tctaagcgtc cctcaggcat cccggaacgc     180

tttagcggat ccaacagcgg caacaccgcg accctgacca ttagcggcac tcaggcggaa     240

gacgaagcgg attattattg ctctactgct gattctggta ttaataatgg tgtgtttggc     300

ggcggcacga agttaaccgt tctt                                            324


<210> SEQ ID NO 64
<211> LENGTH: 369
<212> TYPE: DNA
<213> ORGANISM: Homo Sapien

<400> SEQUENCE: 64

caggtgcaat tggtggaaag cggcggcggc ctggtgcaac cgggcggcag cctgcgtctg      60

agctgcgcgg cctccggatt taccttttct gattatgcta ttcattgggt gcgccaagcc     120

cctgggaagg gtctcgagtg ggtgagcggt atctcttatt ctggtagctc tacccattat     180

gcggatagcg tgaaaggccg ttttaccatt tcacgtgata attcgaaaaa caccctgtat     240

ctgcaaatga acagcctgcg tgcggaagat acggccgtgt attattgcgc gcgtggttct     300

catggtaata ttatggctaa gcgttatttt gatttttggg gccaaggcac cctggtgacg     360

gttagctca                                                             369


<210> SEQ ID NO 65
<211> LENGTH: 214
<212> TYPE: PRT
<213> ORGANISM: Homo Sapien

<400> SEQUENCE: 65

Asp Ile Glu Leu Thr Gln Pro Pro Ser Val Ser Val Ala Pro Gly Gln
 1               5                  10                  15

Thr Ala Arg Ile Ser Cys Ser Gly Asp Asn Ile Arg Lys Lys Tyr Val
            20                  25                  30

Tyr Trp Tyr Gln Gln Lys Pro Gly Gln Ala Pro Val Leu Val Ile Tyr
        35                  40                  45

Glu Asp Ser Lys Arg Pro Ser Gly Ile Pro Glu Arg Phe Ser Gly Ser
    50                  55                  60
```

-continued

```
Asn Ser Gly Asn Thr Ala Thr Leu Thr Ile Ser Gly Thr Gln Ala Glu
65                  70                  75                  80

Asp Glu Ala Asp Tyr Tyr Cys Ser Thr Ala Asp Ser Gly Ile Asn Asn
                85                  90                  95

Gly Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210


<210> SEQ ID NO 66
<211> LENGTH: 453
<212> TYPE: PRT
<213> ORGANISM: Homo Sapien

<400> SEQUENCE: 66

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Ala Ile His Trp Val Arg Gln Ala Pro Gly Lys Gly Leu Glu Trp Val
        35                  40                  45

Ser Gly Ile Ser Tyr Ser Gly Ser Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser His Gly Asn Ile Met Ala Lys Arg Tyr Phe Asp Phe
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220
```

```
Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 67
<211> LENGTH: 642
<212> TYPE: DNA
<213> ORGANISM: Homo Sapien

<400> SEQUENCE: 67

gatatcgaac tgacccagcc gccttcagtg agcgttgcac caggtcagac cgcgcgtatc      60

tcgtgtagcg gcgataatat tcgtaagaag tatgtttatt ggtaccagca gaaacccggg     120

caggcgccag ttcttgtgat ttatgaggat tctaagcgtc cctcaggcat cccggaacgc     180

tttagcggat ccaacagcgg caacaccgcg accctgacca ttagcggcac tcaggcggaa     240

gacgaagcgg attattattg ctctactgct gattctggta ttaataatgg tgtgtttggc     300

ggcggcacga agttaaccgt cctaggtcag cccaaggctg ccccctcggt cactctgttc     360

ccgccctcct ctgaggagct tcaagccaac aaggccacac tggtgtgtct cataagtgac     420

ttctacccgg gagccgtgac agtggcctgg aaggcagata gcagccccgt caaggcggga     480

gtggagacca ccacaccctc caaacaaagc aacaacaagt acgcggccag cagctatctg     540

agcctgacgc ctgagcagtg gaagtcccac agaagctaca gctgccaggt cacgcatgaa     600

gggagcaccg tggagaagac agtggcccct acagaatgtt ca                        642

<210> SEQ ID NO 68
<211> LENGTH: 1359
```

```
<212> TYPE: DNA
<213> ORGANISM: Homo Sapien

<400> SEQUENCE: 68

caggtgcaat tggtggaaag cggcggcggc ctggtgcaac cgggcggcag cctgcgtctg      60

agctgcgcgg cctccggatt taccttttct gattatgcta ttcattgggt gcgccaagcc     120

cctgggaagg gtctcgagtg ggtgagcggt atctcttatt ctggtagctc tacccattat     180

gcggatagcg tgaaaggccg ttttaccatt tcacgtgata attcgaaaaa caccctgtat     240

ctgcaaatga acagcctgcg tgcggaagat acggccgtgt attattgcgc gcgtggttct     300

catggtaata ttatggccaa gcgttatttt gatttttggg gccaaggcac cctggtgacg     360

gttagctcag cctccaccaa gggtccatcg gtcttccccc tggcaccctc ctccaagagc     420

acctctgggg gcacagcggc cctgggctgc ctggtcaagg actacttccc cgaaccggtg     480

acggtgtcgt ggaactcagg cgccctgacc agcggcgtgc acaccttccc ggctgtccta     540

cagtcctcag gactctactc cctcagcagc gtggtgaccg tgccctccag cagcttgggc     600

acccagacct acatctgcaa cgtgaatcac aagcccagca acaccaaggt ggacaagaga     660

gttgagccca aatcttgtga caaaactcac acatgcccac cgtgcccagc acctgaagca     720

gcggggggac cgtcagtctt cctcttcccc ccaaaaccca aggacaccct catgatctcc     780

cggacccctg aggtcacatg cgtggtggtg gacgtgagcc acgaagaccc tgaggtcaag     840

ttcaactggt acgtggacgg cgtggaggtg cataatgcca agacaaagcc gcgggaggag     900

cagtacaaca gcacgtaccg ggtggtcagc gtcctcaccg tcctgcacca ggactggctg     960

aatggcaagg agtacaagtg caaggtctcc aacaaagccc tcccagcccc catcgagaaa    1020

accatctcca aagccaaagg gcagccccga gaaccacagg tgtacaccct gcccccatcc    1080

cgggaggaga tgaccaagaa ccaggtcagc ctgacctgcc tggtcaaagg cttctatccc    1140

agcgacatcg ccgtggagtg ggagagcaat gggcagccgg agaacaacta caagaccacg    1200

cctcccgtgc tggactccga cggctccttc ttcctctaca gcaagctcac cgtggacaag    1260

agcaggtggc agcaggggaa cgtcttctca tgctccgtga tgcatgaggc tctgcacaac    1320

cactacacgc agaagagcct ctccctgtct ccgggtaaa                           1359


<210> SEQ ID NO 69
<211> LENGTH: 7
<212> TYPE: PRT
<213> ORGANISM: Homo Sapien

<400> SEQUENCE: 69

Asn Arg Gly Gly Gly Val Gly
 1               5


<210> SEQ ID NO 70
<211> LENGTH: 16
<212> TYPE: PRT
<213> ORGANISM: Homo Sapien

<400> SEQUENCE: 70

Trp Ile Asp Trp Asp Asp Asp Lys Ser Tyr Ser Thr Ser Leu Lys Thr
 1               5                  10                  15


<210> SEQ ID NO 71
<211> LENGTH: 9
<212> TYPE: PRT
<213> ORGANISM: Homo Sapien
```

<400> SEQUENCE: 71

Met His Leu Pro Leu Val Phe Asp Ser
1 5

<210> SEQ ID NO 72
<211> LENGTH: 12
<212> TYPE: PRT
<213> ORGANISM: Homo Sapien

<400> SEQUENCE: 72

Arg Ala Ser Gln Phe Ile Gly Ser Arg Tyr Leu Ala
1 5 10

<210> SEQ ID NO 73
<211> LENGTH: 7
<212> TYPE: PRT
<213> ORGANISM: Homo Sapien

<400> SEQUENCE: 73

Gly Ala Ser Asn Arg Ala Thr
1 5

<210> SEQ ID NO 74
<211> LENGTH: 9
<212> TYPE: PRT
<213> ORGANISM: Homo Sapien

<400> SEQUENCE: 74

Gln Gln Tyr Tyr Asp Tyr Pro Gln Thr
1 5

<210> SEQ ID NO 75
<211> LENGTH: 9
<212> TYPE: PRT
<213> ORGANISM: Homo Sapien

<400> SEQUENCE: 75

Gly Phe Ser Leu Ser Asn Arg Gly Gly
1 5

<210> SEQ ID NO 76
<211> LENGTH: 5
<212> TYPE: PRT
<213> ORGANISM: Homo Sapien

<400> SEQUENCE: 76

Asp Trp Asp Asp Asp
1 5

<210> SEQ ID NO 77
<211> LENGTH: 9
<212> TYPE: PRT
<213> ORGANISM: Homo Sapien

<400> SEQUENCE: 77

Met His Leu Pro Leu Val Phe Asp Ser
1 5

<210> SEQ ID NO 78
<211> LENGTH: 8
<212> TYPE: PRT
<213> ORGANISM: Homo Sapien

<400> SEQUENCE: 78

-continued

Ser Gln Phe Ile Gly Ser Arg Tyr
 1               5

<210> SEQ ID NO 79
<211> LENGTH: 3
<212> TYPE: PRT
<213> ORGANISM: Homo Sapien

<400> SEQUENCE: 79

Gly Ala Ser
 1

<210> SEQ ID NO 80
<211> LENGTH: 6
<212> TYPE: PRT
<213> ORGANISM: Homo Sapien

<400> SEQUENCE: 80

Tyr Tyr Asp Tyr Pro Gln
 1               5

<210> SEQ ID NO 81
<211> LENGTH: 108
<212> TYPE: PRT
<213> ORGANISM: Homo Sapien

<400> SEQUENCE: 81

Asp Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Phe Ile Gly Ser Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Gln Gln Tyr Tyr Asp Tyr Pro
                85                  90                  95

Gln Thr Phe Gly Gln Gly Thr Lys Val Glu Ile Lys
            100                 105

<210> SEQ ID NO 82
<211> LENGTH: 119
<212> TYPE: PRT
<213> ORGANISM: Homo Sapien

<400> SEQUENCE: 82

Gln Val Gln Leu Lys Glu Ser Gly Pro Ala Leu Val Lys Pro Thr Gln
 1               5                  10                  15

Thr Leu Thr Leu Thr Cys Thr Phe Ser Gly Phe Ser Leu Ser Asn Arg
            20                  25                  30

Gly Gly Gly Val Gly Trp Ile Arg Gln Pro Pro Gly Lys Ala Leu Glu
        35                  40                  45

Trp Leu Ala Trp Ile Asp Trp Asp Asp Asp Lys Ser Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Met His Leu Pro Leu Val Phe Asp Ser Trp Gly Gln Gly
100 105 110

Thr Leu Val Thr Val Ser Ser
115

<210> SEQ ID NO 83
<211> LENGTH: 324
<212> TYPE: DNA
<213> ORGANISM: Homo Sapien

<400> SEQUENCE: 83
gatatcgtgc tgacccagag cccggcgacc ctgagcctgt ctccgggcga acgtgcgacc 60
ctgagctgca gagcgagcca gtttattggt tctcgttatc tggcttggta ccagcagaaa 120
ccaggtcaag caccgcgtct attaatttat ggtgcttcta atcgtgcaac tggggtcccg 180
gcgcgtttta gcggctctgg atccggcacg gattttaccc tgaccattag cagcctggaa 240
cctgaagact ttgcgactta ttattgccag cagtattatg attatcctca gacctttggc 300
cagggtacga aagttgaaat taaa 324

<210> SEQ ID NO 84
<211> LENGTH: 357
<212> TYPE: DNA
<213> ORGANISM: Homo Sapien

<400> SEQUENCE: 84
caggtgcaat tgaaagaaag cggcccggcc ctggtgaaac cgacccaaac cctgaccctg 60
acctgtacct tttccggatt tagcctgtct aatcgtggtg gtggtgtggg ttggattcgc 120
cagccgcctg ggaaagccct cgagtggctg gcttggatcg attgggatga tgataagtct 180
tatagcacca gcctgaaaac gcgtctgacc attagcaaag atacttcgaa aaatcaggtg 240
gtgctgacta tgaccaacat ggacccggtg gatacggcca cctattattg cgcgcgtatg 300
catcttcctc ttgtttttga ttcttggggc caaggcaccc tggtgacggt tagctca 357

<210> SEQ ID NO 85
<211> LENGTH: 215
<212> TYPE: PRT
<213> ORGANISM: Homo Sapien

<400> SEQUENCE: 85

Asp Ile Val Leu Thr Gln Ser Pro Ala Thr Leu Ser Leu Ser Pro Gly
1 5 10 15

Glu Arg Ala Thr Leu Ser Cys Arg Ala Ser Gln Phe Ile Gly Ser Arg
20 25 30

Tyr Leu Ala Trp Tyr Gln Gln Lys Pro Gly Gln Ala Pro Arg Leu Leu
35 40 45

Ile Tyr Gly Ala Ser Asn Arg Ala Thr Gly Val Pro Ala Arg Phe Ser
50 55 60

Gly Ser Gly Ser Gly Thr Asp Phe Thr Leu Thr Ile Ser Ser Leu Glu
65 70 75 80

Pro Glu Asp Phe Ala Thr Tyr Tyr Cys Gln Gln Tyr Tyr Asp Tyr Pro
85 90 95

Gln Thr Phe Gly Gln Gly Thr Lys Val Glu Ile Lys Arg Thr Val Ala
100 105 110

Ala Pro Ser Val Phe Ile Phe Pro Pro Ser Asp Glu Gln Leu Lys Ser
115 120 125

```
Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 86
<211> LENGTH: 449
<212> TYPE: PRT
<213> ORGANISM: Homo Sapien

<400> SEQUENCE: 86

Gln Val Gln Leu Lys Glu Ser Gly Pro Ala Leu Val Lys Pro Thr Gln
 1               5                  10                  15

Thr Leu Thr Leu Thr Cys Thr Phe Ser Gly Phe Ser Leu Ser Asn Arg
            20                  25                  30

Gly Gly Gly Val Gly Trp Ile Arg Gln Pro Pro Gly Lys Ala Leu Glu
        35                  40                  45

Trp Leu Ala Trp Ile Asp Trp Asp Asp Asp Lys Ser Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Met His Leu Pro Leu Val Phe Asp Ser Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

-continued

```
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 87
<211> LENGTH: 645
<212> TYPE: DNA
<213> ORGANISM: Homo Sapien

<400> SEQUENCE: 87

gatatcgtgc tgacccagag cccggcgacc ctgagcctgt ctccgggcga acgtgcgacc      60

ctgagctgca gagcgagcca gtttattggt tctcgttatc tggcttggta ccagcagaaa     120

ccaggtcaag caccgcgtct attaatttat ggtgcttcta atcgtgcaac tggggtcccg     180

gcgcgtttta gcggctctgg atccggcacg gattttaccc tgaccattag cagcctggaa     240

cctgaagact ttgcgactta ttattgccag cagtattatg attatcctca gacctttggc     300

cagggtacga aagttgaaat taaacgtacg gtggctgcac catctgtctt catcttcccg     360

ccatctgatg agcagttgaa atctggaact gcctctgttg tgtgcctgct gaataacttc     420

tatcccagag aggccaaagt acagtggaag gtggataacg ccctccaatc gggtaactcc     480

caggagagtg tcacagagca ggacagcaag gacagcacct acagcctcag cagcaccctg     540

acgctgagca aagcagacta cgagaaacac aaagtctacg cctgcgaagt cacccatcag     600

ggcctgagct cgcccgtcac aaagagcttc aacaggggag agtgt                     645


<210> SEQ ID NO 88
<211> LENGTH: 1347
<212> TYPE: DNA
<213> ORGANISM: Homo Sapien

<400> SEQUENCE: 88

caggtgcaat tgaaagaaag cggcccggcc ctggtgaaac cgacccaaac cctgaccctg      60

acctgtacct tttccggatt tagcctgtct aatcgtggtg gtggtgtggg ttggattcgc     120

cagccgcctg ggaaagccct cgagtggctg gcttggatcg attgggatga tgataagtct     180

tatagcacca gcctgaaaac gcgtctgacc attagcaaag atacttcgaa aaatcaggtg     240
```

-continued

```
gtgctgacta tgaccaacat ggacccggtg gatacggcca cctattattg cgcgcgtatg    300

catcttcctc ttgtttttga ttcttggggc caaggcaccc tggtgacggt tagctcagcc    360

tccaccaagg gtccatcggt cttccccctg gcaccctcct ccaagagcac ctctgggggc    420

acagcggccc tgggctgcct ggtcaaggac tacttccccg aaccggtgac ggtgtcgtgg    480

aactcaggcg ccctgaccag cggcgtgcac accttcccgg ctgtcctaca gtcctcagga    540

ctctactccc tcagcagcgt ggtgaccgtg ccctccagca gcttgggcac ccagacctac    600

atctgcaacg tgaatcacaa gcccagcaac accaaggtgg acaagagagt tgagcccaaa    660

tcttgtgaca aaactcacac atgcccaccg tgcccagcac ctgaagcagc gggggggaccg   720

tcagtcttcc tcttcccccc aaaacccaag gacaccctca tgatctcccg gacccctgag    780

gtcacatgcg tggtggtgga cgtgagccac gaagaccctg aggtcaagtt caactggtac    840

gtggacggcg tggaggtgca taatgccaag acaaagccgc gggaggagca gtacaacagc    900

acgtaccggg tggtcagcgt cctcaccgtc ctgcaccagg actggctgaa tggcaaggag    960

tacaagtgca aggtctccaa caaagccctc ccagccccca tcgagaaaac catctccaaa   1020

gccaaagggc agccccgaga accacaggtg tacaccctgc ccccatcccg ggaggagatg   1080

accaagaacc aggtcagcct gacctgcctg gtcaaaggct tctatcccag cgacatcgcc   1140

gtggagtggg agagcaatgg gcagccggag aacaactaca agaccacgcc tcccgtgctg   1200

gactccgacg gctccttctt cctctacagc aagctcaccg tggacaagag caggtggcag   1260

caggggaacg tcttctcatg ctccgtgatg catgaggctc tgcacaacca ctacacgcag   1320

aagagcctct ccctgtctcc gggtaaa                                       1347
```

<210> SEQ ID NO 89
<211> LENGTH: 119
<212> TYPE: PRT
<213> ORGANISM: Homo Sapien

<400> SEQUENCE: 89

```
Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Asn Arg
            20                  25                  30

Gly Gly Gly Val Gly Trp Ile Arg Gln Pro Pro Gly Lys Ala Leu Glu
        35                  40                  45

Trp Leu Ala Trp Ile Asp Trp Asp Asp Asp Lys Ser Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Met His Leu Pro Leu Val Phe Asp Ser Trp Gly Gln Gly
            100                 105                 110

Thr Leu Val Thr Val Ser Ser
        115
```

<210> SEQ ID NO 90
<211> LENGTH: 108
<212> TYPE: PRT
<213> ORGANISM: Homo Sapien

<400> SEQUENCE: 90

```
Glu Ile Val Leu Thr Gln Ser Pro Ala Thr Leu Ser Leu Ser Pro Gly
```

-continued

```
 1               5                   10                  15

Glu Arg Ala Thr Leu Ser Cys Arg Ala Ser Gln Phe Ile Gly Ser Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Tyr Asp Tyr Pro
                85                  90                  95

Gln Thr Phe Gly Gln Gly Thr Lys Val Glu Ile Lys
            100                 105


<210> SEQ ID NO 91
<211> LENGTH: 357
<212> TYPE: DNA
<213> ORGANISM: Homo Sapien

<400> SEQUENCE: 91

caggtcacac tgaaagagtc cggccctgcc ctggtcaaac ccacccagac cctgaccctg      60

acatgcacct tcagcggctt cagcctgagc aacagaggcg gcggagtggg ctggatcaga     120

cagcctcccg gcaaggccct ggaatggctg gcctggatcg actgggacga cgacaagagc     180

tacagcacca gcctgaaaac ccggctgacc atcagcaagg acaccagcaa gaaccaggtg     240

gtgctgacca tgaccaacat ggaccccgtg gacaccgcca cctactactg cgcccggatg     300

catctgcccc tggtgttcga tagctggggc cagggcaccc tggtcaccgt cagctca        357


<210> SEQ ID NO 92
<211> LENGTH: 324
<212> TYPE: DNA
<213> ORGANISM: Homo Sapien

<400> SEQUENCE: 92

gaaatcgtgc tgacccagag ccccgccacc ctgtctctga gccctggcga gagagccacc      60

ctgagctgcc gggccagcca gttcatcggc agcagatacc tggcttggta tcagcagaag     120

cccggccagg cccccagact gctgatctac ggcgccagca accgggccac cggcatccct     180

gccagatttt ctggcagcgg cagcggcacc gacttcaccc tgaccatcag cagcctggaa     240

cccgaggact tcgccgtgta ctactgccag cagtactacg actacccccca gaccttcggc     300

cagggcacca aggtggaaat caag                                             324


<210> SEQ ID NO 93
<211> LENGTH: 7
<212> TYPE: PRT
<213> ORGANISM: Homo Sapien

<400> SEQUENCE: 93

Asn Arg Gly Gly Gly Val Gly
 1               5


<210> SEQ ID NO 94
<211> LENGTH: 16
<212> TYPE: PRT
<213> ORGANISM: Homo Sapien

<400> SEQUENCE: 94
```

```
Trp Ile Asp Trp Asp Asp Asp Lys Ser Tyr Ser Thr Ser Leu Lys Thr
 1               5                  10                  15


<210> SEQ ID NO 95
<211> LENGTH: 9
<212> TYPE: PRT
<213> ORGANISM: Homo Sapien

<400> SEQUENCE: 95

Met His Leu Pro Leu Val Phe Asp Ser
 1               5


<210> SEQ ID NO 96
<211> LENGTH: 12
<212> TYPE: PRT
<213> ORGANISM: Homo Sapien

<400> SEQUENCE: 96

Arg Ala Ser Gln Phe Ile Gly Ser Arg Tyr Leu Ala
 1               5                  10


<210> SEQ ID NO 97
<211> LENGTH: 7
<212> TYPE: PRT
<213> ORGANISM: Homo Sapien

<400> SEQUENCE: 97

Gly Ala Ser Asn Arg Ala Thr
 1               5


<210> SEQ ID NO 98
<211> LENGTH: 9
<212> TYPE: PRT
<213> ORGANISM: Homo Sapien

<400> SEQUENCE: 98

Gln Gln Tyr Trp Ser Ile Pro Ile Thr
 1               5


<210> SEQ ID NO 99
<211> LENGTH: 9
<212> TYPE: PRT
<213> ORGANISM: Homo Sapien

<400> SEQUENCE: 99

Gly Phe Ser Leu Ser Asn Arg Gly Gly
 1               5


<210> SEQ ID NO 100
<211> LENGTH: 5
<212> TYPE: PRT
<213> ORGANISM: Homo Sapien

<400> SEQUENCE: 100

Asp Trp Asp Asp Asp
 1               5


<210> SEQ ID NO 101
<211> LENGTH: 9
<212> TYPE: PRT
<213> ORGANISM: Homo Sapien

<400> SEQUENCE: 101

Met His Leu Pro Leu Val Phe Asp Ser
 1               5
```

<210> SEQ ID NO 102
<211> LENGTH: 8
<212> TYPE: PRT
<213> ORGANISM: Homo Sapien

<400> SEQUENCE: 102

Ser Gln Phe Ile Gly Ser Arg Tyr
 1               5

<210> SEQ ID NO 103
<211> LENGTH: 3
<212> TYPE: PRT
<213> ORGANISM: Homo Sapien

<400> SEQUENCE: 103

Gly Ala Ser
 1

<210> SEQ ID NO 104
<211> LENGTH: 6
<212> TYPE: PRT
<213> ORGANISM: Homo Sapien

<400> SEQUENCE: 104

Tyr Trp Ser Ile Pro Ile
 1               5

<210> SEQ ID NO 105
<211> LENGTH: 108
<212> TYPE: PRT
<213> ORGANISM: Homo Sapien

<400> SEQUENCE: 105

Asp Ile Val Leu Thr Gln Ser Pro Ala Thr Leu Ser Leu Ser Pro Gly
 1               5                   10                  15

Glu Arg Ala Thr Leu Ser Cys Arg Ala Ser Gln Phe Ile Gly Ser Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Trp Ser Ile Pro
                85                  90                  95

Ile Thr Phe Gly Gln Gly Thr Lys Val Glu Ile Lys
            100                 105

<210> SEQ ID NO 106
<211> LENGTH: 119
<212> TYPE: PRT
<213> ORGANISM: Homo Sapien

<400> SEQUENCE: 106

Gln Val Gln Leu Lys Glu Ser Gly Pro Ala Leu Val Lys Pro Thr Gln
 1               5                   10                  15

Thr Leu Thr Leu Thr Cys Thr Phe Ser Gly Phe Ser Leu Ser Asn Arg
            20                  25                  30

Gly Gly Gly Val Gly Trp Ile Arg Gln Pro Pro Gly Lys Ala Leu Glu
        35                  40                  45

```
Trp Leu Ala Trp Ile Asp Trp Asp Asp Asp Lys Ser Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Met His Leu Pro Leu Val Phe Asp Ser Trp Gly Gln Gly
            100                 105                 110

Thr Leu Val Thr Val Ser Ser
        115


<210> SEQ ID NO 107
<211> LENGTH: 108
<212> TYPE: PRT
<213> ORGANISM: Homo Sapien

<400> SEQUENCE: 107

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Phe Ile Gly Ser Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Trp Ser Ile Pro
                85                  90                  95

Ile Thr Phe Gly Gln Gly Thr Lys Val Glu Ile Lys
            100                 105


<210> SEQ ID NO 108
<211> LENGTH: 119
<212> TYPE: PRT
<213> ORGANISM: Homo Sapien

<400> SEQUENCE: 108

Gln Val Thr Leu Lys Glu Ser Gly Pro Ala Leu Val Lys Pro Thr Gln
 1               5                  10                  15

Thr Leu Thr Leu Thr Cys Thr Phe Ser Gly Phe Ser Leu Ser Asn Arg
            20                  25                  30

Gly Gly Gly Val Gly Trp Ile Arg Gln Pro Pro Gly Lys Ala Leu Glu
        35                  40                  45

Trp Leu Ala Trp Ile Asp Trp Asp Asp Asp Lys Ser Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Met His Leu Pro Leu Val Phe Asp Ser Trp Gly Gln Gly
            100                 105                 110

Thr Leu Val Thr Val Ser Ser
        115


<210> SEQ ID NO 109
```

<211> LENGTH: 324
<212> TYPE: DNA
<213> ORGANISM: Homo Sapien

<400> SEQUENCE: 109

```
gatatcgtgc tgacccagag cccggcgacc ctgagcctgt ctccgggcga acgtgcgacc     60

ctgagctgca gagcgagcca gtttattggt tctcgttatc tggcttggta ccagcagaaa    120

ccaggtcaag caccgcgtct attaatttat ggtgcttcta atcgtgcaac tggggtcccg    180

gcgcgtttta gcggctctgg atccggcacg gattttaccc tgaccattag cagcctggaa    240

cctgaagact ttgcggtgta ttattgccag cagtattggt ctattcctat tacctttggc    300

cagggtacga aagttgaaat taaa                                           324
```

<210> SEQ ID NO 110
<211> LENGTH: 357
<212> TYPE: DNA
<213> ORGANISM: Homo Sapien

<400> SEQUENCE: 110

```
caggtgcaat tgaaagaaag cggcccggcc ctggtgaaac cgacccaaac cctgaccctg     60

acctgtacct tttccggatt tagcctgtct aatcgtggtg gtggtgtggg ttggattcgc    120

cagccgcctg ggaaagccct cgagtggctg gcttggatcg attgggatga tgataagtct    180

tatagcacca gcctgaaaac gcgtctgacc attagcaaag atacttcgaa aaatcaggtg    240

gtgctgacta tgaccaacat ggacccggtg gatacggcca cctattattg cgcgcgtatg    300

catcttcctc ttgtttttga ttcttggggc caaggcaccc tggtgacggt tagctca       357
```

<210> SEQ ID NO 111
<211> LENGTH: 215
<212> TYPE: PRT
<213> ORGANISM: Homo Sapien

<400> SEQUENCE: 111

```
Asp Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Phe Ile Gly Ser Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Trp Ser Ile Pro
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175
```

```
Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Ala
    210                 215
```

<210> SEQ ID NO 112
<211> LENGTH: 221
<212> TYPE: PRT
<213> ORGANISM: Homo Sapien

<400> SEQUENCE: 112

```
Gln Val Gln Leu Lys Glu Ser Gly Pro Ala Leu Val Lys Pro Thr Gln
 1               5                  10                  15

Thr Leu Thr Leu Thr Cys Thr Phe Ser Gly Phe Ser Leu Ser Asn Arg
            20                  25                  30

Gly Gly Gly Val Gly Trp Ile Arg Gln Pro Pro Gly Lys Ala Leu Glu
        35                  40                  45

Trp Leu Ala Trp Ile Asp Trp Asp Asp Asp Lys Ser Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Met His Leu Pro Leu Val Phe Asp Ser Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser
    210                 215                 220
```

<210> SEQ ID NO 113
<211> LENGTH: 645
<212> TYPE: DNA
<213> ORGANISM: Homo Sapien

<400> SEQUENCE: 113

```
gatatcgtgc tgacccagag cccggcgacc ctgagcctgt ctccgggcga acgtgcgacc      60

ctgagctgca gagcgagcca gtttattggt tctcgttatc tggcttggta ccagcagaaa     120

ccaggtcaag caccgcgtct attaatttat ggtgcttcta atcgtgcaac tggggtcccg     180

gcgcgtttta gcggctctgg atccggcacg gattttaccc tgaccattag cagcctggaa     240

cctgaagact ttgcggtgta ttattgccag cagtattggt ctattcctat tacctttggc     300

cagggtacga aagttgaaat taaacgtacg gtggctgctc cgagcgtgtt tatttttccg     360
```

```
ccgagcgatg aacaactgaa aagcggcacg gcgagcgtgg tgtgcctgct gaacaacttt    420

tatccgcgtg aagcgaaagt tcagtggaaa gtagacaacg cgctgcaaag cggcaacagc    480

caggaaagcg tgaccgaaca ggatagcaaa gatagcacct attctctgag cagcaccctg    540

accctgagca aagcggatta tgaaaaacat aaagtgtatg cgtgcgaagt gacccatcaa    600

ggtctgagca gcccggtgac taaatctttt aatcgtggcg aggcc                    645
```

<210> SEQ ID NO 114
<211> LENGTH: 663
<212> TYPE: DNA
<213> ORGANISM: Homo Sapien

<400> SEQUENCE: 114

```
caggtgcaat tgaaagaaag cggcccggcc ctggtgaaac cgacccaaac cctgaccctg     60

acctgtacct tttccggatt tagcctgtct aatcgtggtg gtggtgtggg ttggattcgc    120

cagccgcctg ggaaagccct cgagtggctg gcttggatcg attgggatga tgataagtct    180

tatagcacca gcctgaaaac gcgtctgacc attagcaaag atacttcgaa aaatcaggtg    240

gtgctgacta tgaccaacat ggacccggtg gatacggcca cctattattg cgcgcgtatg    300

catcttcctc ttgtttttga ttcttggggc caaggcaccc tggtgacggt tagctcagcg    360

tcgaccaaag gtccaagcgt gtttccgctg gctccgagca gcaaaagcac cagcggcggc    420

acggctgccc tgggctgcct ggttaaagat tatttcccgg aaccagtcac cgtgagctgg    480

aacagcgggg cgctgaccag cggcgtgcat acctttccgg cggtgctgca aagcagcggc    540

ctgtatagcc tgagcagcgt tgtgaccgtg ccgagcagca gcttaggcac tcagacctat    600

atttgcaacg tgaaccataa accgagcaac accaaagtgg ataaaaaagt ggaaccgaaa    660

agc                                                                  663
```

<210> SEQ ID NO 115
<211> LENGTH: 5
<212> TYPE: PRT
<213> ORGANISM: Homo Sapien

<400> SEQUENCE: 115

```
Ser Tyr Gly Met Ser
 1               5
```

<210> SEQ ID NO 116
<211> LENGTH: 17
<212> TYPE: PRT
<213> ORGANISM: Homo Sapien

<400> SEQUENCE: 116

```
Asn Ile Ser Asn Asp Gly His Tyr Thr Tyr Tyr Ala Asp Ser Val Lys
 1               5                  10                  15

Gly
```

<210> SEQ ID NO 117
<211> LENGTH: 11
<212> TYPE: PRT
<213> ORGANISM: Homo Sapien

<400> SEQUENCE: 117

```
Phe Gln Ala Ser Tyr Leu Asp Ile Met Asp Tyr
 1               5                  10
```

<210> SEQ ID NO 118

<211> LENGTH: 11
<212> TYPE: PRT
<213> ORGANISM: Homo Sapien

<400> SEQUENCE: 118

Ser Gly Asp Asn Ile Gly Ser Lys Tyr Val His
1 5 10

<210> SEQ ID NO 119
<211> LENGTH: 7
<212> TYPE: PRT
<213> ORGANISM: Homo Sapien

<400> SEQUENCE: 119

Asn Asp Ser Asn Arg Pro Ser
1 5

<210> SEQ ID NO 120
<211> LENGTH: 10
<212> TYPE: PRT
<213> ORGANISM: Homo Sapien

<400> SEQUENCE: 120

Gln Ala Trp Gly Asp Asn Gly Thr Arg Val
1 5 10

<210> SEQ ID NO 121
<211> LENGTH: 7
<212> TYPE: PRT
<213> ORGANISM: Homo Sapien

<400> SEQUENCE: 121

Gly Phe Thr Phe Ser Ser Tyr
1 5

<210> SEQ ID NO 122
<211> LENGTH: 6
<212> TYPE: PRT
<213> ORGANISM: Homo Sapien

<400> SEQUENCE: 122

Ser Asn Asp Gly His Tyr
1 5

<210> SEQ ID NO 123
<211> LENGTH: 11
<212> TYPE: PRT
<213> ORGANISM: Homo Sapien

<400> SEQUENCE: 123

Phe Gln Ala Ser Tyr Leu Asp Ile Met Asp Tyr
1 5 10

<210> SEQ ID NO 124
<211> LENGTH: 7
<212> TYPE: PRT
<213> ORGANISM: Homo Sapien

<400> SEQUENCE: 124

Asp Asn Ile Gly Ser Lys Tyr
1 5

<210> SEQ ID NO 125
<211> LENGTH: 3
<212> TYPE: PRT

<213> ORGANISM: Homo Sapien

<400> SEQUENCE: 125

Asn Asp Ser
1

<210> SEQ ID NO 126
<211> LENGTH: 7
<212> TYPE: PRT
<213> ORGANISM: Homo Sapien

<400> SEQUENCE: 126

Trp Gly Asp Asn Gly Thr Arg
1 5

<210> SEQ ID NO 127
<211> LENGTH: 107
<212> TYPE: PRT
<213> ORGANISM: Homo Sapien

<400> SEQUENCE: 127

Asp Ile Glu Leu Thr Gln Pro Pro Ser Val Ser Val Ala Pro Gly Gln
1 5 10 15

Ser Ile Thr Ile Ser Cys Ser Gly Asp Asn Ile Gly Ser Lys Tyr Val
20 25 30

His Trp Tyr Gln Gln Lys Pro Gly Gln Ala Pro Val Leu Val Ile Tyr
35 40 45

Asn Asp Ser Asn Arg Pro Ser Gly Ile Pro Glu Arg Phe Ser Gly Ser
50 55 60

Asn Ser Gly Asn Thr Ala Thr Leu Thr Ile Ser Gly Thr Gln Ala Glu
65 70 75 80

Asp Glu Ala Asp Tyr Tyr Cys Gln Ala Trp Gly Asp Asn Gly Thr Arg
85 90 95

Val Phe Gly Gly Gly Thr Lys Leu Thr Val Leu
100 105

<210> SEQ ID NO 128
<211> LENGTH: 120
<212> TYPE: PRT
<213> ORGANISM: Homo Sapien

<400> SEQUENCE: 128

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Gly Met Ser Trp Val Arg Gln Ala Pro Gly Lys Gly Leu Glu Trp Val
35 40 45

Ser Asn Ile Ser Asn Asp Gly His Tyr Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Phe Gln Ala Ser Tyr Leu Asp Ile Met Asp Tyr Trp Gly Gln
100 105 110

Gly Thr Leu Val Thr Val Ser Ser
115 120

<210> SEQ ID NO 129
<211> LENGTH: 107
<212> TYPE: PRT
<213> ORGANISM: Homo Sapien

<400> SEQUENCE: 129

Ser Tyr Glu Leu Thr Gln Pro Pro Ser Val Ser Val Ser Pro Gly Gln
1 5 10 15

Thr Ala Ser Ile Thr Cys Ser Gly Asp Asn Ile Gly Ser Lys Tyr Val
20 25 30

His Trp Tyr Gln Gln Lys Pro Gly Gln Ser Pro Val Leu Val Ile Tyr
35 40 45

Asn Asp Ser Asn Arg Pro Ser Gly Ile Pro Glu Arg Phe Ser Gly Ser
50 55 60

Asn Ser Gly Asn Thr Ala Thr Leu Thr Ile Ser Gly Thr Gln Ala Met
65 70 75 80

Asp Glu Ala Asp Tyr Tyr Cys Gln Ala Trp Gly Asp Asn Gly Thr Arg
85 90 95

Val Phe Gly Gly Gly Thr Lys Leu Thr Val Leu
100 105

<210> SEQ ID NO 130
<211> LENGTH: 120
<212> TYPE: PRT
<213> ORGANISM: Homo Sapien

<400> SEQUENCE: 130

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Gly Met Ser Trp Val Arg Gln Ala Pro Gly Lys Gly Leu Glu Trp Val
35 40 45

Ser Asn Ile Ser Asn Asp Gly His Tyr Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Phe Gln Ala Ser Tyr Leu Asp Ile Met Asp Tyr Trp Gly Gln
100 105 110

Gly Thr Leu Val Thr Val Ser Ser
115 120

<210> SEQ ID NO 131
<211> LENGTH: 321
<212> TYPE: DNA
<213> ORGANISM: Homo Sapien

<400> SEQUENCE: 131
gatatcgaac tgacccagcc gccttcagtg agcgttgcac caggtcagag cattaccatc 60
tcgtgtagcg gcgataatat tggttctaag tatgttcatt ggtaccagca gaaacccggg 120
caggcgccag ttcttgtgat ttataatgat tctaatcgtc cctcaggcat cccggaacgc 180
tttagcggat ccaacagcgg caacaccgcg accctgacca ttagcggcac tcaggcggaa 240
gacgaagcgg attattattg ccaggcttgg ggtgataatg gtactcgtgt gtttggcggc 300

-continued

```
ggcacgaagt taaccgttct t                                            321


<210> SEQ ID NO 132
<211> LENGTH: 360
<212> TYPE: DNA
<213> ORGANISM: Homo Sapien

<400> SEQUENCE: 132

caggtgcaat tggtggaaag cggcggcggc ctggtgcaac cgggcggcag cctgcgtctg     60

agctgcgcgg cctccggatt taccttttct tcttatggta tgtcttgggt gcgccaagcc    120

cctgggaagg gtctcgagtg ggtgagcaat atttctaatg atggtcatta tacttattat    180

gctgattctg ttaagggtcg ttttaccatt tcacgtgata attcgaaaaa caccctgtat    240

ctgcaaatga acagcctgcg tgcggaagat acggccgtgt attattgcgc gcgttttcag    300

gcttcttatc ttgatattat ggattattgg ggccaaggca ccctggtgac ggttagctca    360


<210> SEQ ID NO 133
<211> LENGTH: 212
<212> TYPE: PRT
<213> ORGANISM: Homo Sapien

<400> SEQUENCE: 133

Asp Ile Glu Leu Thr Gln Pro Pro Ser Val Ser Val Ala Pro Gly Gln
 1               5                  10                  15

Ser Ile Thr Ile Ser Cys Ser Gly Asp Asn Ile Gly Ser Lys Tyr Val
            20                  25                  30

His Trp Tyr Gln Gln Lys Pro Gly Gln Ala Pro Val Leu Val Ile Tyr
        35                  40                  45

Asn Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ala Trp Gly Asp Asn Gly Thr Arg
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Ala
    210


<210> SEQ ID NO 134
<211> LENGTH: 222
<212> TYPE: PRT
<213> ORGANISM: Homo Sapien

<400> SEQUENCE: 134
```

```
Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ser Asn Ile Ser Asn Asp Gly His Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Gln Ala Ser Tyr Leu Asp Ile Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser
    210                 215                 220
```

<210> SEQ ID NO 135
<211> LENGTH: 636
<212> TYPE: DNA
<213> ORGANISM: Homo Sapien

<400> SEQUENCE: 135

```
gatatcgaac tgacccagcc gccttcagtg agcgttgcac caggtcagag cattaccatc      60

tcgtgtagcg gcgataatat tggttctaag tatgttcatt ggtaccagca gaaacccggg     120

caggcgccag ttcttgtgat ttataatgat tctaatcgtc cctcaggcat cccggaacgc     180

tttagcggat ccaacagcgg caacaccgcg accctgacca ttagcggcac tcaggcggaa     240

gacgaagcgg attattattg ccaggcttgg ggtgataatg gtactcgtgt gtttggcggc     300

ggcacgaagt taaccgttct tggccagccg aaagccgcac cgagtgtgac gctgtttccg     360

ccgagcagcg aagaattgca ggcgaacaaa gcgaccctgg tgtgcctgat tagcgacttt     420

tatccgggag ccgtgacagt ggcctggaag gcagatagca gccccgtcaa ggcgggagtg     480

gagaccacca caccctccaa acaaagcaac aacaagtacg cggccagcag ctatctgagc     540

ctgacgcctg agcagtggaa gtcccacaga agctacagct gccaggtcac gcatgagggg     600

agcaccgtgg aaaaaaccgt tgcgccgact gaggcc                               636
```

<210> SEQ ID NO 136
<211> LENGTH: 666
<212> TYPE: DNA
<213> ORGANISM: Homo Sapien

<400> SEQUENCE: 136
caggtgcaat tggtggaaag cggcggcggc ctggtgcaac cgggcggcag cctgcgtctg 60
agctgcgcgg cctccggatt taccttttct tcttatggta tgtcttgggt gcgccaagcc 120
cctgggaagg gtctcgagtg ggtgagcaat atttctaatg atggtcatta tacttattat 180
gctgattctg ttaagggtcg ttttaccatt tcacgtgata attcgaaaaa caccctgtat 240
ctgcaaatga acagcctgcg tgcggaagat acggccgtgt attattgcgc gcgttttcag 300
gcttcttatc ttgatattat ggattattgg ggccaaggca ccctggtgac ggttagctca 360
gcgtcgacca aaggtccaag cgtgtttccg ctggctccga gcagcaaaag caccagcggc 420
ggcacggctg ccctgggctg cctggttaaa gattatttcc cggaaccagt caccgtgagc 480
tggaacagcg gggcgctgac cagcggcgtg catacctttc cggcggtgct gcaaagcagc 540
ggcctgtata gcctgagcag cgttgtgacc gtgccgagca gcagcttagg cactcagacc 600
tatatttgca acgtgaacca taaaccgagc aacaccaaag tggataaaaa agtggaaccg 660
aaaagc 666

<210> SEQ ID NO 137
<211> LENGTH: 107
<212> TYPE: PRT
<213> ORGANISM: Homo Sapien

<400> SEQUENCE: 137

Ser Tyr Glu Leu Thr Gln Pro Leu Ser Val Ser Val Ala Leu Gly Gln
1 5 10 15

Thr Ala Arg Ile Thr Cys Gly Gly Asp Asn Ile Gly Ser Lys Tyr Val
20 25 30

His Trp Tyr Gln Gln Lys Pro Gly Gln Ala Pro Val Leu Val Ile Tyr
35 40 45

Asn Asp Ser Asn Arg Pro Ser Gly Ile Pro Glu Arg Phe Ser Gly Ser
50 55 60

Asn Ser Gly Asn Thr Ala Thr Leu Thr Ile Ser Arg Ala Gln Ala Gly
65 70 75 80

Asp Glu Ala Asp Tyr Tyr Cys Gln Ala Trp Gly Asp Asn Gly Thr Arg
85 90 95

Val Phe Gly Gly Gly Thr Lys Leu Thr Val Leu
100 105

<210> SEQ ID NO 138
<211> LENGTH: 120
<212> TYPE: PRT
<213> ORGANISM: Homo Sapien

<400> SEQUENCE: 138

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Gly Met Ser Trp Val Arg Gln Ala Pro Gly Lys Gly Leu Glu Trp Val
35 40 45

Ser Asn Ile Ser Asn Asp Gly His Tyr Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys 85 90 95

Ala Arg Phe Gln Ala Ser Tyr Leu Asp Ile Met Asp Tyr Trp Gly Gln
100 105 110

Gly Thr Leu Val Thr Val Ser Ser
115 120

<210> SEQ ID NO 139
<211> LENGTH: 321
<212> TYPE: DNA
<213> ORGANISM: Homo Sapien

<400> SEQUENCE: 139
agctatgaac tgacccagcc gctgagtgtt agcgttgcgc tgggtcagac cgcgcgtatt 60
acctgcggcg gtgataacat tggcagcaaa tatgtgcatt ggtatcagca gaaaccgggc 120
caggcgccgg tgctggtgat ttataacgat agcaaccgtc cgagcggcat tccggaacgt 180
tttagcggca gcaacagcgg caataccgcg accctgacca ttagccgtgc gcaggcgggt 240
gatgaagcgg attattattg ccaggcgtgg ggcgataatg gtacgcgtgt gtttggcggt 300
ggtacgaagt taaccgttct t 321

<210> SEQ ID NO 140
<211> LENGTH: 360
<212> TYPE: DNA
<213> ORGANISM: Homo Sapien

<400> SEQUENCE: 140
gaggtgcaat tgctggaaag cggcggcggc ctggtgcaac cgggcggcag cctgcgtctg 60
agctgcgcgg cctccggatt taccttttct tcttatggta tgtcttgggt gcgccaagcc 120
cctgggaagg gtctcgagtg ggtgagcaat atttctaatg atggtcatta tacttattat 180
gctgattctg ttaagggtcg ttttaccatt tcacgtgata attcgaaaaa caccctgtat 240
ctgcaaatga acagcctgcg tgcggaagat acggccgtgt attattgcgc gcgttttcag 300
gcttcttatc ttgatattat ggattattgg ggccaaggca ccctggtgac ggttagctca 360

<210> SEQ ID NO 141
<211> LENGTH: 726
<212> TYPE: DNA
<213> ORGANISM: Homo Sapien

<400> SEQUENCE: 141
gatatcgttc tgacccagag tccggcaacc ctgagcctga gtccgggtga acgtgccacc 60
ctgagctgtc gtgcaagcca gtttattggt agccgttatc tggcatggta tcagcagaaa 120
ccgggtcagg caccgcgtct gctgatttat ggtgcaagca atcgtgcaac cggtgttccg 180
gcacgtttta gcggtagcgg tagtggcacc gattttaccc tgaccattag cagcctggaa 240
ccggaagatt ttgcaaccta ttattgccag cagtattatg attatccgca gacctttggt 300
cagggcacca aggtggaaat taaaggtggt ggtggtagcg gtggtggtgg ctcaggtggt 360
ggcggtagtc aggttcaatt gaaagaaagc ggtccggcac tggttaaacc gacccagacc 420
ctgaccctga catgtacctt tagcggtttt agcctgagca atcgtggtgg tggtgttggt 480
tggattcgtc agcctccggg taaagcactg gaatggctgg catggattga ttgggatgat 540
gataaaagct atagcaccag cctgaaaacc cgtctgacca ttagtaaaga taccagcaaa 600
aatcaggtgg ttctgaccat gaccaatatg gatccggttg ataccgccac ctattattgt 660
gcacgtatgc atctgccgct ggtttttgat agctggggtc agggtacact agttaccgtt 720
agcagc 726

<210> SEQ ID NO 142
<211> LENGTH: 242
<212> TYPE: PRT
<213> ORGANISM: Homo Sapien

<400> SEQUENCE: 142

Asp Ile Val Leu Thr Gln Ser Pro Ala Thr Leu Ser Leu Ser Pro Gly
1 5 10 15

Glu Arg Ala Thr Leu Ser Cys Arg Ala Ser Gln Phe Ile Gly Ser Arg
20 25 30

Tyr Leu Ala Trp Tyr Gln Gln Lys Pro Gly Gln Ala Pro Arg Leu Leu
35 40 45

Ile Tyr Gly Ala Ser Asn Arg Ala Thr Gly Val Pro Ala Arg Phe Ser
50 55 60

Gly Ser Gly Ser Gly Thr Asp Phe Thr Leu Thr Ile Ser Ser Leu Glu
65 70 75 80

Pro Glu Asp Phe Ala Thr Tyr Tyr Cys Gln Gln Tyr Tyr Asp Tyr Pro
85 90 95

Gln Thr Phe Gly Gln Gly Thr Lys Val Glu Ile Lys Gly Gly Gly Gly
100 105 110

Ser Gly Gly Gly Gly Ser Gly Gly Gly Gly Ser Gln Val Gln Leu Lys
115 120 125

Glu Ser Gly Pro Ala Leu Val Lys Pro Thr Gln Thr Leu Thr Leu Thr
130 135 140

Cys Thr Phe Ser Gly Phe Ser Leu Ser Asn Arg Gly Gly Gly Val Gly
145 150 155 160

Trp Ile Arg Gln Pro Pro Gly Lys Ala Leu Glu Trp Leu Ala Trp Ile
165 170 175

Asp Trp Asp Asp Asp Lys Ser Tyr Ser Thr Ser Leu Lys Thr Arg Leu
180 185 190

Thr Ile Ser Lys Asp Thr Ser Lys Asn Gln Val Val Leu Thr Met Thr
195 200 205

Asn Met Asp Pro Val Asp Thr Ala Thr Tyr Tyr Cys Ala Arg Met His
210 215 220

Leu Pro Leu Val Phe Asp Ser Trp Gly Gln Gly Thr Leu Val Thr Val
225 230 235 240

Ser Ser

<210> SEQ ID NO 143
<211> LENGTH: 741
<212> TYPE: DNA
<213> ORGANISM: Homo Sapien

<400> SEQUENCE: 143
gatatcgtgc tgacacagag ccctgccacc ctgtctctga gccctggcga gagagccacc 60
ctgagctgcc gggccagcca gttcatcggc tcccgctacc tggcctggta tcagcagaag 120
cccggacagg ctcccagact gctgatctac ggcgccagca acagagctac cggcgtgccc 180
gccagatttt ctggcagcgg cagcggcacc gacttcaccc tgaccatcag cagcctggaa 240
cccgaggact tcgccaccta ctactgccag cagtactacg actacccca gaccttcggc 300 cagggcacca aggtggagat caagggcgga ggcggatccg ggggtggcgg aagtggaggc 360
ggaggaagcg gagggggcgg aagccaggtg caattgaaag agtccggccc tgccctggtg 420

```
aagcctaccc agaccctgac cctgacatgc accttcagcg gcttcagcct gagcaacaga    480

ggcggcggag tgggctggat cagacagcct cccggcaagg ccctggaatg gctggcctgg    540

atcgactggg acgacgacaa gagctacagc accagcctga aaacccggct gaccatctcc    600

aaggacacca gcaagaacca ggtggtgctc accatgacca acatggaccc cgtggacacc    660

gccacctatt attgcgcccg gatgcatctg cccctggtgt tcgatagctg gggccaggga    720

accctggtga cagtgtccag c                                              741
```

<210> SEQ ID NO 144
<211> LENGTH: 247
<212> TYPE: PRT
<213> ORGANISM: Homo Sapien

<400> SEQUENCE: 144

```
Asp Ile Val Leu Thr Gln Ser Pro Ala Thr Leu Ser Leu Ser Pro Gly
 1               5                   10                  15

Glu Arg Ala Thr Leu Ser Cys Arg Ala Ser Gln Phe Ile Gly Ser Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Gln Gln Tyr Tyr Asp Tyr Pro
                85                  90                  95

Gln Thr Phe Gly Gln Gly Thr Lys Val Glu Ile Lys Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Lys Glu Ser Gly Pro Ala Leu Val Lys Pro Thr Gln
    130                 135                 140

Thr Leu Thr Leu Thr Cys Thr Phe Ser Gly Phe Ser Leu Ser Asn Arg
145                 150                 155                 160

Gly Gly Gly Val Gly Trp Ile Arg Gln Pro Pro Gly Lys Ala Leu Glu
                165                 170                 175

Trp Leu Ala Trp Ile Asp Trp Asp Asp Asp Lys Ser Tyr Ser Thr Ser
            180                 185                 190

Leu Lys Thr Arg Leu Thr Ile Ser Lys Asp Thr Ser Lys Asn Gln Val
        195                 200                 205

Val Leu Thr Met Thr Asn Met Asp Pro Val Asp Thr Ala Thr Tyr Tyr
    210                 215                 220

Cys Ala Arg Met His Leu Pro Leu Val Phe Asp Ser Trp Gly Gln Gly
225                 230                 235                 240

Thr Leu Val Thr Val Ser Ser
                245
```

<210> SEQ ID NO 145
<211> LENGTH: 726
<212> TYPE: DNA
<213> ORGANISM: Homo Sapien

<400> SEQUENCE: 145

```
caggttcaat tgaaagaaag cggtccggca ctggttaaac cgacccagac cctgaccctg     60
```

-continued

```
acatgtacct ttagcggttt tagcctgagc aatcgtggtg gtggtgttgg ttggattcgt    120

cagcctccgg gtaaagcact ggaatggctg gcatggattg attgggatga tgataaaagc    180

tatagcacca gcctgaaaac ccgtctgacc attagcaaag ataccagcaa aaatcaggtt    240

gttctgacca tgaccaatat ggatccggtt gataccgcaa cctattattg tgcacgtatg    300

catctgccgc tggtttttga tagctggggt cagggtacac tagttaccgt tagcagcggt    360

ggtggtggta gcggtggtgg cggttcaggt ggtggtggca gtgatatcgt tctgacccag    420

agtccggcaa ccctgagcct gagtccgggt gaacgtgcca ccctgagctg tcgtgcaagc    480

cagtttattg gtagccgtta tctggcatgg tatcagcaga aaccgggtca ggcaccgcgt    540

ctgctgattt atggtgcaag caatcgtgca accggtgttc cggcacgttt tagcggtagc    600

ggtagtggca ccgattttac cctgaccatt agtagcctgg aaccggaaga ttttgccacc    660

tattattgcc agcagtatta tgattatccg cagacctttg gtcagggcac caaggtggaa    720

attaaa                                                               726
```

```
<210> SEQ ID NO 146
<211> LENGTH: 242
<212> TYPE: PRT
<213> ORGANISM: Homo Sapien

<400> SEQUENCE: 146

Gln Val Gln Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Asn Arg
            20                  25                  30

Gly Gly Gly Val Gly Trp Ile Arg Gln Pro Pro Gly Lys Ala Leu Glu
        35                  40                  45

Trp Leu Ala Trp Ile Asp Trp Asp Asp Asp Lys Ser Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Met His Leu Pro Leu Val Phe Asp Ser Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asp Ile Val Leu Thr Gln Ser Pro Ala Thr
    130                 135                 140

Leu Ser Leu Ser Pro Gly Glu Arg Ala Thr Leu Ser Cys Arg Ala Ser
145                 150                 155                 160

Gln Phe Ile Gly Ser Arg Tyr Leu Ala Trp Tyr Gln Gln Lys Pro Gly
                165                 170                 175

Gln Ala Pro Arg Leu Leu Ile Tyr Gly Ala Ser Asn Arg Ala Thr Gly
            180                 185                 190

Val Pro Ala Arg Phe Ser Gly Ser Gly Ser Gly Thr Asp Phe Thr Leu
        195                 200                 205

Thr Ile Ser Ser Leu Glu Pro Glu Asp Phe Ala Thr Tyr Tyr Cys Gln
    210                 215                 220

Gln Tyr Tyr Asp Tyr Pro Gln Thr Phe Gly Gln Gly Thr Lys Val Glu
225                 230                 235                 240

Ile Lys
```

<210> SEQ ID NO 147
<211> LENGTH: 741
<212> TYPE: DNA
<213> ORGANISM: Homo Sapien

<400> SEQUENCE: 147
caggttcaat tgaaagaaag cggtccggca ctggttaaac cgacccagac cctgaccctg 60
acatgtacct ttagcggttt tagcctgagc aatcgtggtg gtggtgttgg ttggattcgt 120
cagcctccgg gtaaagcact ggaatggctg gcatggattg attgggatga tgataaaagc 180
tatagcacca gcctgaaaac ccgtctgacc attagcaaag ataccagcaa aaatcaggtt 240
gttctgacca tgaccaatat ggatccggtt gataccgcaa cctattattg tgcacgtatg 300
catctgccgc tggtttttga tagctggggt cagggtacac tagttaccgt tagcagcggt 360
ggtggtggta gcggtggtgg cggttcaggt ggtggtggca gtggcggtgg tggtagtgat 420
atcgttctga cccagagtcc ggcaaccctg agcctgagtc cgggtgaacg tgccaccctg 480
agctgtcgtg caagccagtt tattggtagc cgttatctgg catggtatca gcagaaaccg 540
ggtcaggcac cgcgtctgct gatttatggt gcaagcaatc gtgcaaccgg tgttccggca 600
cgttttagcg gtagcggtag tggcaccgat tttaccctga ccattagtag cctggaaccg 660
gaagattttg ccacctatta ttgccagcag tattatgatt atccgcagac ctttggtcag 720
ggcaccaagg tggaaattaa a 741

<210> SEQ ID NO 148
<211> LENGTH: 247
<212> TYPE: PRT
<213> ORGANISM: Homo Sapien

<400> SEQUENCE: 148

Gln Val Gln Leu Lys Glu Ser Gly Pro Ala Leu Val Lys Pro Thr Gln
1 5 10 15

Thr Leu Thr Leu Thr Cys Thr Phe Ser Gly Phe Ser Leu Ser Asn Arg
20 25 30

Gly Gly Gly Val Gly Trp Ile Arg Gln Pro Pro Gly Lys Ala Leu Glu
35 40 45

Trp Leu Ala Trp Ile Asp Trp Asp Asp Asp Lys Ser Tyr Ser Thr Ser
50 55 60

Leu Lys Thr Arg Leu Thr Ile Ser Lys Asp Thr Ser Lys Asn Gln Val
65 70 75 80

Val Leu Thr Met Thr Asn Met Asp Pro Val Asp Thr Ala Thr Tyr Tyr
85 90 95

Cys Ala Arg Met His Leu Pro Leu Val Phe Asp Ser Trp Gly Gln Gly
100 105 110

Thr Leu Val Thr Val Ser Ser Gly Gly Gly Gly Ser Gly Gly Gly Gly
115 120 125

Ser Gly Gly Gly Gly Ser Gly Gly Gly Gly Ser Asp Ile Val Leu Thr
130 135 140

Gln Ser Pro Ala Thr Leu Ser Leu Ser Pro Gly Glu Arg Ala Thr Leu
145 150 155 160

Ser Cys Arg Ala Ser Gln Phe Ile Gly Ser Arg Tyr Leu Ala Trp Tyr
165 170 175

Gln Gln Lys Pro Gly Gln Ala Pro Arg Leu Leu Ile Tyr Gly Ala Ser
180 185 190

Asn Arg Ala Thr Gly Val Pro Ala Arg Phe Ser Gly Ser Gly Ser Gly

```
        195                 200                 205

Thr Asp Phe Thr Leu Thr Ile Ser Ser Leu Glu Pro Glu Asp Phe Ala
    210                 215                 220

Thr Tyr Tyr Cys Gln Gln Tyr Tyr Asp Tyr Pro Gln Thr Phe Gly Gln
225                 230                 235                 240

Gly Thr Lys Val Glu Ile Lys
                245


<210> SEQ ID NO 149
<211> LENGTH: 732
<212> TYPE: DNA
<213> ORGANISM: Homo Sapien

<400> SEQUENCE: 149

gatatcgaac tgacccagcc tccgagcgtt agcgttgcac cgggtcagac cgcacgtatt      60

agctgtagcg gtgatagcct gcgtaataaa gtttattggt atcagcagaa accgggtcag     120

gcaccggttc tggttattta taaaaataat cgtccgagcg gtattccgga acgttttagc     180

ggtagcaata gcggtaatac cgcaaccctg accattagcg gcacccaggc agaagatgaa     240

gcagattatt attgccagag ctatgatggt cagaaaagcc tggtttttgg tggtggcacc     300

aagcttaccg ttctgggtgg tggtggtagc ggtggtggtg gctcaggtgg tggcggttct     360

caggttcaat tggttgaaag tggtggtggt ctggttcagc ctggtggtag cctgcgtctg     420

agctgtgcag caagcggttt tacctttagc gattatgtga ttaattgggt tcgccaggca     480

ccgggtaaag gtctggaatg ggttagcggt attagctggt caggtgttaa tacccattat     540

gcagatagcg tgaaaggtcg ttttaccatt agccgtgata atagcaaaaa taccctgtat     600

ctgcagatga atagcctgcg tgcagaagat accgcagttt attattgtgc acgtctgggt     660

gcaaccgcaa ataatattcg ctataaattt atggatgtgt ggggtcaggg tacactagtt     720

accgttagca gc                                                         732


<210> SEQ ID NO 150
<211> LENGTH: 244
<212> TYPE: PRT
<213> ORGANISM: Homo Sapien

<400> SEQUENCE: 150

Asp Ile Glu Leu Thr Gln Pro Pro Ser Val Ser Val Ala Pro Gly Gln
 1               5                  10                  15

Thr Ala Arg Ile Ser Cys Ser Gly Asp Ser Leu Arg Asn Lys Val Tyr
            20                  25                  30

Trp Tyr Gln Gln Lys Pro Gly Gln Ala Pro Val Leu Val Ile Tyr Lys
        35                  40                  45

Asn Asn Arg Pro Ser Gly Ile Pro Glu Arg Phe Ser Gly Ser Asn Ser
    50                  55                  60

Gly Asn Thr Ala Thr Leu Thr Ile Ser Gly Thr Gln Ala Glu Asp Glu
65                  70                  75                  80

Ala Asp Tyr Tyr Cys Gln Ser Tyr Asp Gly Gln Lys Ser Leu Val Phe
                85                  90                  95

Gly Gly Gly Thr Lys Leu Thr Val Leu Gly Gly Gly Gly Ser Gly Gly
            100                 105                 110

Gly Gly Ser Gly Gly Gly Gly Ser Gln Val Gln Leu Val Glu Ser Gly
        115                 120                 125

Gly Gly Leu Val Gln Pro Gly Gly Ser Leu Arg Leu Ser Cys Ala Ala
    130                 135                 140
```

```
Ser Gly Phe Thr Phe Ser Asp Tyr Val Ile Asn Trp Val Arg Gln Ala
145                 150                 155                 160

Pro Gly Lys Gly Leu Glu Trp Val Ser Gly Ile Ser Trp Ser Gly Val
                165                 170                 175

Asn Thr His Tyr Ala Asp Ser Val Lys Gly Arg Phe Thr Ile Ser Arg
            180                 185                 190

Asp Asn Ser Lys Asn Thr Leu Tyr Leu Gln Met Asn Ser Leu Arg Ala
        195                 200                 205

Glu Asp Thr Ala Val Tyr Tyr Cys Ala Arg Leu Gly Ala Thr Ala Asn
    210                 215                 220

Asn Ile Arg Tyr Lys Phe Met Asp Val Trp Gly Gln Gly Thr Leu Val
225                 230                 235                 240

Thr Val Ser Ser


<210> SEQ ID NO 151
<211> LENGTH: 747
<212> TYPE: DNA
<213> ORGANISM: Homo Sapien

<400> SEQUENCE: 151

gatatcgaac tgacccagcc tccgagcgtt agcgttgcac cgggtcagac cgcacgtatt      60

agctgtagcg gtgatagcct gcgtaataaa gtttattggt atcagcagaa accgggtcag     120

gcaccggttc tggttattta taaaaataat cgtccgagcg gtattccgga acgttttagc     180

ggtagcaata gcggtaatac cgcaaccctg accattagcg gcacccaggc agaagatgaa     240

gcagattatt attgccagag ctatgatggt cagaaaagcc tggtttttgg tggtggcacc     300

aagcttaccg ttctgggtgg tggtggtagc ggtggtggtg gctcaggtgg tggcggttct     360

ggtggcggtg gttcacaggt tcaattggtt gaaagtggtg gtggtctggt tcagcctggt     420

ggtagcctgc gtctgagctg tgcagcaagc ggttttacct ttagcgatta tgtgattaat     480

tgggttcgcc aggcaccggg taaaggtctg gaatgggtta gcggtattag ctggtcaggt     540

gttaataccc attatgcaga tagcgtgaaa ggtcgtttta ccattagccg tgataatagc     600

aaaaataccc tgtatctgca gatgaatagc ctgcgtgcag aagataccgc agtttattat     660

tgtgcacgtc tgggtgcaac cgcaaataat attcgctata aatttatgga tgtgtggggt     720

cagggtacac tagttaccgt tagcagc                                         747


<210> SEQ ID NO 152
<211> LENGTH: 249
<212> TYPE: PRT
<213> ORGANISM: Homo Sapien

<400> SEQUENCE: 152

Asp Ile Glu Leu Thr Gln Pro Pro Ser Val Ser Val Ala Pro Gly Gln
 1               5                  10                  15

Thr Ala Arg Ile Ser Cys Ser Gly Asp Ser Leu Arg Asn Lys Val Tyr
            20                  25                  30

Trp Tyr Gln Gln Lys Pro Gly Gln Ala Pro Val Leu Val Ile Tyr Lys
        35                  40                  45

Asn Asn Arg Pro Ser Gly Ile Pro Glu Arg Phe Ser Gly Ser Asn Ser
    50                  55                  60

Gly Asn Thr Ala Thr Leu Thr Ile Ser Gly Thr Gln Ala Glu Asp Glu
65                  70                  75                  80

Ala Asp Tyr Tyr Cys Gln Ser Tyr Asp Gly Gln Lys Ser Leu Val Phe
```

```
                85                  90                  95

Gly Gly Gly Thr Lys Leu Thr Val Leu Gly Gly Gly Gly Ser Gly Gly
            100                 105                 110

Gly Gly Ser Gly Gly Gly Gly Ser Gly Gly Gly Gly Ser Gln Val Gln
        115                 120                 125

Leu Val Glu Ser Gly Gly Gly Leu Val Gln Pro Gly Gly Ser Leu Arg
    130                 135                 140

Leu Ser Cys Ala Ala Ser Gly Phe Thr Phe Ser Asp Tyr Val Ile Asn
145                 150                 155                 160

Trp Val Arg Gln Ala Pro Gly Lys Gly Leu Glu Trp Val Ser Gly Ile
                165                 170                 175

Ser Trp Ser Gly Val Asn Thr His Tyr Ala Asp Ser Val Lys Gly Arg
            180                 185                 190

Phe Thr Ile Ser Arg Asp Asn Ser Lys Asn Thr Leu Tyr Leu Gln Met
        195                 200                 205

Asn Ser Leu Arg Ala Glu Asp Thr Ala Val Tyr Tyr Cys Ala Arg Leu
    210                 215                 220

Gly Ala Thr Ala Asn Asn Ile Arg Tyr Lys Phe Met Asp Val Trp Gly
225                 230                 235                 240

Gln Gly Thr Leu Val Thr Val Ser Ser
                245
```

<210> SEQ ID NO 153
<211> LENGTH: 732
<212> TYPE: DNA
<213> ORGANISM: Homo Sapien

<400> SEQUENCE: 153

```
caggttcaat tggttgaaag cggtggtggt ctggttcagc ctggtggtag cctgcgtctg      60

agctgtgcag caagcggttt tacctttagc gattatgtga ttaattgggt tcgtcaggca     120

ccgggtaaag gtctggaatg ggttagcggt attagctggt caggtgttaa tacccattat     180

gcagatagcg tgaaaggtcg ttttaccatt agccgtgata atagcaaaaa taccctgtat     240

ctgcagatga atagcctgcg tgcagaagat accgcagttt attattgtgc acgtctgggt     300

gcaaccgcaa ataatattcg ctataaattt atggatgtgt ggggtcaggg tacactagtt     360

accgttagca gtggtggtgg tggtagcggt ggtggcggat ctggtggcgg tggcagtgat     420

atcgaactga cccagcctcc gagcgttagc gttgcaccgg gtcagaccgc acgtattagc     480

tgtagcggtg atagtctgcg taataaagtt tattggtatc agcagaaacc gggtcaggct     540

ccggttctgg ttatttataa aaataatcgt ccgagcggta ttccggaacg ttttagcggt     600

agcaatagcg gtaataccgc aaccctgacc attagcggca cccaggcaga agatgaagcc     660

gattattatt gtcagagcta tgatggtcag aaaagcctgg tttttggtgg tggcaccaag     720

cttaccgttc tg                                                         732
```

<210> SEQ ID NO 154
<211> LENGTH: 244
<212> TYPE: PRT
<213> ORGANISM: Homo Sapien

<400> SEQUENCE: 154

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30
```

```
Val Ile Asn Trp Val Arg Gln Ala Pro Gly Lys Gly Leu Glu Trp Val
        35                  40                  45

Ser Gly Ile Ser Trp Ser Gly Val Asn Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Ala Thr Ala Asn Asn Ile Arg Tyr Lys Phe Met Asp
            100                 105                 110

Val Trp Gly Gln Gly Thr Leu Val Thr Val Ser Ser Gly Gly Gly Gly
        115                 120                 125

Ser Gly Gly Gly Gly Ser Gly Gly Gly Gly Ser Asp Ile Glu Leu Thr
    130                 135                 140

Gln Pro Pro Ser Val Ser Val Ala Pro Gly Gln Thr Ala Arg Ile Ser
145                 150                 155                 160

Cys Ser Gly Asp Ser Leu Arg Asn Lys Val Tyr Trp Tyr Gln Gln Lys
                165                 170                 175

Pro Gly Gln Ala Pro Val Leu Val Ile Tyr Lys Asn Asn Arg Pro Ser
            180                 185                 190

Gly Ile Pro Glu Arg Phe Ser Gly Ser Asn Ser Gly Asn Thr Ala Thr
        195                 200                 205

Leu Thr Ile Ser Gly Thr Gln Ala Glu Asp Glu Ala Asp Tyr Tyr Cys
    210                 215                 220

Gln Ser Tyr Asp Gly Gln Lys Ser Leu Val Phe Gly Gly Gly Thr Lys
225                 230                 235                 240

Leu Thr Val Leu
```

<210> SEQ ID NO 155
<211> LENGTH: 747
<212> TYPE: DNA
<213> ORGANISM: Homo Sapien

<400> SEQUENCE: 155

```
caggttcaat tggttgaaag cggtggtggt ctggttcagc ctggtggtag cctgcgtctg      60

agctgtgcag caagcggttt tacctttagc gattatgtga ttaattgggt tcgtcaggca     120

ccgggtaaag gtctggaatg ggttagcggt attagctggt caggtgttaa tacccattat     180

gcagatagcg tgaaaggtcg ttttaccatt agccgtgata atagcaaaaa taccctgtat     240

ctgcagatga atagcctgcg tgcagaagat accgcagttt attattgtgc acgtctgggt     300

gcaaccgcaa ataatattcg ctataaattt atggatgtgt ggggtcaggg tacactagtt     360

accgttagca gtggtggtgg tggtagcggt ggtggcggat ctggtggcgg tggttcaggt     420

ggtggtggca gtgatatcga actgacccag cctccgagcg ttagcgttgc accgggtcag     480

accgcacgta ttagctgtag cggtgatagt ctgcgtaata aagtttattg gtatcagcag     540

aaaccgggtc aggctccggt tctggttatt tataaaaata atcgtccgag cggtattccg     600

gaacgtttta gcggtagcaa tagcggtaat accgcaaccc tgaccattag cggcacccag     660

gcagaagatg aagccgatta ttattgtcag agctatgatg gtcagaaaag cctggttttt     720

ggtggtggca ccaagcttac cgttctg                                        747
```

<210> SEQ ID NO 156
<211> LENGTH: 249

<212> TYPE: PRT
<213> ORGANISM: Homo Sapien

<400> SEQUENCE: 156

```
Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Val Ile Asn Trp Val Arg Gln Ala Pro Gly Lys Gly Leu Glu Trp Val
        35                  40                  45

Ser Gly Ile Ser Trp Ser Gly Val Asn Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Ala Thr Ala Asn Asn Ile Arg Tyr Lys Phe Met Asp
            100                 105                 110

Val Trp Gly Gln Gly Thr Leu Val Thr Val Ser Ser Gly Gly Gly Gly
        115                 120                 125

Ser Gly Gly Gly Gly Ser Gly Gly Gly Gly Ser Gly Gly Gly Gly Ser
    130                 135                 140

Asp Ile Glu Leu Thr Gln Pro Pro Ser Val Ser Val Ala Pro Gly Gln
145                 150                 155                 160

Thr Ala Arg Ile Ser Cys Ser Gly Asp Ser Leu Arg Asn Lys Val Tyr
                165                 170                 175

Trp Tyr Gln Gln Lys Pro Gly Gln Ala Pro Val Leu Val Ile Tyr Lys
            180                 185                 190

Asn Asn Arg Pro Ser Gly Ile Pro Glu Arg Phe Ser Gly Ser Asn Ser
        195                 200                 205

Gly Asn Thr Ala Thr Leu Thr Ile Ser Gly Thr Gln Ala Glu Asp Glu
    210                 215                 220

Ala Asp Tyr Tyr Cys Gln Ser Tyr Asp Gly Gln Lys Ser Leu Val Phe
225                 230                 235                 240

Gly Gly Gly Thr Lys Leu Thr Val Leu
                245
```

<210> SEQ ID NO 157
<211> LENGTH: 723
<212> TYPE: DNA
<213> ORGANISM: Homo Sapien

<400> SEQUENCE: 157

```
gatatcgaac tgacccagcc tccgagcgtt agcgttgcac cgggtcagac cgcacgtatt      60

agctgtagcg gtgataatat tggcagcaaa tatgtgcatt ggtatcagca gaaaccgggt     120

caggcaccgg ttctggttat ttatggtgat agcaatcgtc cgagcggtat tccggaacgt     180

tttagcggta gcaatagcgg taataccgca accctgacca ttagcggcac ccaggcagaa     240

gatgaagcag attattattg tacccgtacc agcaccccga ttagcggtgt ttttggtggt     300

ggcaccaagc ttaccgttct gggtggtggt ggtagcggtg gtggtggctc aggtggtggt     360

ggttcacagg ttcaattggt tgaaagtggt ggtggtctgg ttcagcctgg tggtagcctg     420

cgtctgagct gtgcagcaag cggttttacc tttagcgtta atggtatgca ttgggttcgc     480

caggcaccgg gtaaaggtct ggaatgggtt agcgttattg atggtatggg ccatacctat     540
```

-continued tatgccgata gcgttaaagg tcgttttacc attagccgtg ataatagcaa aaataccctg 600
tatctgcaga tgaatagcct gcgtgcagaa gataccgcag tttattattg cgcacgctat 660
gattatatta aatatggtgc ctttgatccg tggggtcagg gtacactagt taccgttagc 720
agc 723

<210> SEQ ID NO 158
<211> LENGTH: 241
<212> TYPE: PRT
<213> ORGANISM: Homo Sapien

<400> SEQUENCE: 158

Asp Ile Glu Leu Thr Gln Pro Pro Ser Val Ser Val Ala Pro Gly Gln
1 5 10 15

Thr Ala Arg Ile Ser Cys Ser Gly Asp Asn Ile Gly Ser Lys Tyr Val
20 25 30

His Trp Tyr Gln Gln Lys Pro Gly Gln Ala Pro Val Leu Val Ile Tyr
35 40 45

Gly Asp Ser Asn Arg Pro Ser Gly Ile Pro Glu Arg Phe Ser Gly Ser
50 55 60

Asn Ser Gly Asn Thr Ala Thr Leu Thr Ile Ser Gly Thr Gln Ala Glu
65 70 75 80

Asp Glu Ala Asp Tyr Tyr Cys Thr Arg Thr Ser Thr Pro Ile Ser Gly
85 90 95

Val Phe Gly Gly Gly Thr Lys Leu Thr Val Leu Gly Gly Gly Gly Ser
100 105 110

Gly Gly Gly Gly Ser Gly Gly Gly Gly Ser Gln Val Gln Leu Val Glu
115 120 125

Ser Gly Gly Gly Leu Val Gln Pro Gly Gly Ser Leu Arg Leu Ser Cys
130 135 140

Ala Ala Ser Gly Phe Thr Phe Ser Val Asn Gly Met His Trp Val Arg
145 150 155 160

Gln Ala Pro Gly Lys Gly Leu Glu Trp Val Ser Val Ile Asp Gly Met
165 170 175

Gly His Thr Tyr Tyr Ala Asp Ser Val Lys Gly Arg Phe Thr Ile Ser
180 185 190

Arg Asp Asn Ser Lys Asn Thr Leu Tyr Leu Gln Met Asn Ser Leu Arg
195 200 205

Ala Glu Asp Thr Ala Val Tyr Tyr Cys Ala Arg Tyr Asp Tyr Ile Lys
210 215 220

Tyr Gly Ala Phe Asp Pro Trp Gly Gln Gly Thr Leu Val Thr Val Ser
225 230 235 240

Ser

<210> SEQ ID NO 159
<211> LENGTH: 738
<212> TYPE: DNA
<213> ORGANISM: Homo Sapien

<400> SEQUENCE: 159
gatatcgaac tgacccagcc tccgagcgtt agcgttgcac cgggtcagac cgcacgtatt 60
agctgtagcg gtgataatat tggcagcaaa tatgtgcatt ggtatcagca gaaaccgggt 120
caggcaccgg ttctggttat ttatggtgat agcaatcgtc cgagcggtat tccggaacgt 180
tttagcggta gcaatagcgg taataccgca accctgacca ttagcggcac ccaggcagaa 240

```
gatgaagcag attattattg tacccgtacc agcaccccga ttagcggtgt ttttggtggt    300

ggcaccaagc ttaccgttct gggtggtggt ggtagcggtg gtggtggctc aggtggtggc    360

ggttctggtg gcggtggttc acaggttcaa ttggttgaaa gtggtggtgg tctggttcag    420

cctggtggta gcctgcgtct gagctgtgca gcaagcggtt ttacctttag cgttaatggt    480

atgcattggg ttcgccaggc accgggtaaa ggtctggaat gggttagcgt tattgatggt    540

atgggccata cctattatgc cgatagcgtt aaaggtcgtt ttaccattag ccgtgataat    600

agcaaaaata ccctgtatct gcagatgaat agcctgcgtg cagaagatac cgcagtttat    660

tattgcgcac gctatgatta tattaaatat ggtgcctttg atccgtgggg tcagggtaca    720

ctagttaccg ttagcagc                                                   738
```

<210> SEQ ID NO 160
<211> LENGTH: 246
<212> TYPE: PRT
<213> ORGANISM: Homo Sapien

<400> SEQUENCE: 160

```
Asp Ile Glu Leu Thr Gln Pro Pro Ser Val Ser Val Ala Pro Gly Gln
 1               5                  10                  15

Thr Ala Arg Ile Ser Cys Ser Gly Asp Asn Ile Gly Ser Lys Tyr Val
            20                  25                  30

His Trp Tyr Gln Gln Lys Pro Gly Gln Ala Pro Val Leu Val Ile Tyr
        35                  40                  45

Gly Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Thr Arg Thr Ser Thr Pro Ile Ser Gly
                85                  90                  95

Val Phe Gly Gly Gly Thr Lys Leu Thr Val Leu Gly Gly Gly Gly Ser
            100                 105                 110

Gly Gly Gly Gly Ser Gly Gly Gly Gly Ser Gly Gly Gly Gly Ser Gln
        115                 120                 125

Val Gln Leu Val Glu Ser Gly Gly Gly Leu Val Gln Pro Gly Gly Ser
    130                 135                 140

Leu Arg Leu Ser Cys Ala Ala Ser Gly Phe Thr Phe Ser Val Asn Gly
145                 150                 155                 160

Met His Trp Val Arg Gln Ala Pro Gly Lys Gly Leu Glu Trp Val Ser
                165                 170                 175

Val Ile Asp Gly Met Gly His Thr Tyr Tyr Ala Asp Ser Val Lys Gly
            180                 185                 190

Arg Phe Thr Ile Ser Arg Asp Asn Ser Lys Asn Thr Leu Tyr Leu Gln
        195                 200                 205

Met Asn Ser Leu Arg Ala Glu Asp Thr Ala Val Tyr Tyr Cys Ala Arg
    210                 215                 220

Tyr Asp Tyr Ile Lys Tyr Gly Ala Phe Asp Pro Trp Gly Gln Gly Thr
225                 230                 235                 240

Leu Val Thr Val Ser Ser
                245
```

<210> SEQ ID NO 161
<211> LENGTH: 723
<212> TYPE: DNA
<213> ORGANISM: Homo Sapien

<400> SEQUENCE: 161

```
caggttcaat tggttgaaag cggtggtggt ctggttcagc ctggtggtag cctgcgtctg     60
agctgtgcag caagcggttt tacctttagc gttaatggta tgcattgggt tcgtcaggca    120
ccgggtaaag gtctggaatg ggttagcgtt attgatggta tgggccatac ctattatgcc    180
gatagcgtta aaggtcgttt taccattagc cgtgataata gcaaaaatac cctgtatctg    240
cagatgaata gcctgcgtgc agaagatacc gcagtttatt attgtgcccg ttatgattat    300
attaaatatg gtgcctttga tccgtggggt cagggtacac tagttaccgt tagcagtggt    360
ggtggtggta gcggtggtgg cggatctggt ggcggtggtt cagatatcga actgacccag    420
cctccgagcg ttagcgttgc accgggtcag accgcacgta ttagctgtag cggtgataat    480
attggcagca aatatgtgca ttggtatcag cagaaaccgg gtcaggctcc ggttctggtt    540
atttatggtg atagcaatcg tccgagcggt attccggaac gttttagcgg tagcaatagc    600
ggtaataccg caaccctgac cattagcggc acccaggcag aagatgaagc cgattattat    660
tgcacccgta ccagcacccc gattagcggt gtttttggtg gtggcaccaa gcttaccgtt    720
ctg                                                                  723
```

<210> SEQ ID NO 162
<211> LENGTH: 241
<212> TYPE: PRT
<213> ORGANISM: Homo Sapien

<400> SEQUENCE: 162

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Val Asn
            20                  25                  30

Gly Met His Trp Val Arg Gln Ala Pro Gly Lys Gly Leu Glu Trp Val
        35                  40                  45

Ser Val Ile Asp Gly Met Gly His Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Asp Tyr Ile Lys Tyr Gly Ala Phe Asp Pro Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asp Ile Glu Leu Thr Gln Pro Pro Ser Val
    130                 135                 140

Ser Val Ala Pro Gly Gln Thr Ala Arg Ile Ser Cys Ser Gly Asp Asn
145                 150                 155                 160

Ile Gly Ser Lys Tyr Val His Trp Tyr Gln Gln Lys Pro Gly Gln Ala
                165                 170                 175

Pro Val Leu Val Ile Tyr Gly Asp Ser Asn Arg Pro Ser Gly Ile Pro
            180                 185                 190

Glu Arg Phe Ser Gly Ser Asn Ser Gly Asn Thr Ala Thr Leu Thr Ile
        195                 200                 205

Ser Gly Thr Gln Ala Glu Asp Glu Ala Asp Tyr Tyr Cys Thr Arg Thr
    210                 215                 220
```

Ser Thr Pro Ile Ser Gly Val Phe Gly Gly Gly Thr Lys Leu Thr Val
225 230 235 240

Leu

<210> SEQ ID NO 163
<211> LENGTH: 738
<212> TYPE: DNA
<213> ORGANISM: Homo Sapien

<400> SEQUENCE: 163
caggttcaat tggttgaaag cggtggtggt ctggttcagc ctggtggtag cctgcgtctg 60
agctgtgcag caagcggttt tacctttagc gttaatggta tgcattgggt tcgtcaggca 120
ccgggtaaag gtctggaatg ggttagcgtt attgatggta tgggccatac ctattatgcc 180
gatagcgtta aaggtcgttt taccattagc cgtgataata gcaaaaatac cctgtatctg 240
cagatgaata gcctgcgtgc agaagatacc gcagtttatt attgtgcccg ttatgattat 300
attaaatatg gtgcctttga tccgtggggt cagggtacac tagttaccgt tagcagtggt 360
ggtggtggta gcggtggtgg cggatctggt ggcggtggtt caggtggtgg tggcagtgat 420
atcgaactga cccagcctcc gagcgttagc gttgcaccgg gtcagaccgc acgtattagc 480
tgtagcggtg ataatattgg cagcaaatat gtgcattggt atcagcagaa accgggtcag 540
gctccggttc tggttattta tggtgatagc aatcgtccga gcggtattcc ggaacgtttt 600
agcggtagca atagcggtaa taccgcaacc ctgaccatta gcggcaccca ggcagaagat 660
gaagccgatt attattgcac ccgtaccagc accccgatta gcggtgtttt tggtggtggc 720
accaagctta ccgttctg 738

<210> SEQ ID NO 164
<211> LENGTH: 246
<212> TYPE: PRT
<213> ORGANISM: Homo Sapien

<400> SEQUENCE: 164

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Val Asn
20 25 30

Gly Met His Trp Val Arg Gln Ala Pro Gly Lys Gly Leu Glu Trp Val
35 40 45

Ser Val Ile Asp Gly Met Gly His Thr Tyr Tyr Ala Asp Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Tyr Asp Tyr Ile Lys Tyr Gly Ala Phe Asp Pro Trp Gly Gln Gly
100 105 110

Thr Leu Val Thr Val Ser Ser Gly Gly Gly Gly Ser Gly Gly Gly Gly
115 120 125

Ser Gly Gly Gly Gly Ser Gly Gly Gly Gly Ser Asp Ile Glu Leu Thr
130 135 140

Gln Pro Pro Ser Val Ser Val Ala Pro Gly Gln Thr Ala Arg Ile Ser
145 150 155 160

Cys Ser Gly Asp Asn Ile Gly Ser Lys Tyr Val His Trp Tyr Gln Gln
165 170 175

```
Lys Pro Gly Gln Ala Pro Val Leu Val Ile Tyr Gly Asp Ser Asn Arg
            180                 185                 190

Pro Ser Gly Ile Pro Glu Arg Phe Ser Gly Ser Asn Ser Gly Asn Thr
        195                 200                 205

Ala Thr Leu Thr Ile Ser Gly Thr Gln Ala Glu Asp Glu Ala Asp Tyr
    210                 215                 220

Tyr Cys Thr Arg Thr Ser Thr Pro Ile Ser Gly Val Phe Gly Gly Gly
225                 230                 235                 240

Thr Lys Leu Thr Val Leu
                245


<210> SEQ ID NO 165
<211> LENGTH: 2121
<212> TYPE: DNA
<213> ORGANISM: Homo Sapien

<400> SEQUENCE: 165

caggtgcaat tggtcgagtc tggcggagga ctggtgcagc ctggtggcag cctgagactg      60

agctgcgccg ccagcggctt caccttcagc gactacgtga tcaactgggt gcgacaggcc     120

cctggaaagg gcctggaatg ggtgtccggc atctcttggt ctggcgtgaa cacccactac     180

gccgacagcg tgaagggccg gttcaccatc agccgggaca acagcaagaa caccctgtac     240

ctgcagatga acagcctgag agccgaggac accgccgtgt actactgtgc cagactgggc     300

gccaccgcca acaacatccg gtacaagttc atggacgtgt ggggccaggg cacactggtg     360

accgtcagct cagctagcac caagggcccc agcgtgttcc ccctggcccc cagcagcaag     420

agcaccagcg gcggcacagc cgccctgggc tgcctggtga aggactactt ccccgagccc     480

gtgaccgtgt cctggaacag cggagccctg acctccggcg tgcacacctt ccccgccgtg     540

ctgcagagca gcggcctgta cagcctgtcc agcgtggtga cagtgcccag cagcagcctg     600

ggcacccaga cctacatctg caacgtgaac cacaagccca gcaacaccaa ggtggacaag     660

agagtggagc ccaagagctg cgacaagacc cacacctgcc cccccctgccc agccccagag     720

gcagcgggcg gaccctccgt gttcctgttc ccccccaagc ccaaggacac cctgatgatc     780

agcaggaccc ccgaggtgac ctgcgtggtg gtggacgtga gccacgagga cccagaggtg     840

aagttcaact ggtacgtgga cggcgtggag gtgcacaacg ccaagaccaa gcccagagag     900

gagcagtaca acagcaccta cagggtggtg tccgtgctga ccgtgctgca ccaggactgg     960

ctgaacggca aggaatacaa gtgcaaggtc tccaacaagg ccctgccagc ccccatcgaa    1020

aagaccatca gcaaggccaa gggccagcca cgggagcccc aggtgtacac cctgcccccc    1080

tcccgggagg agatgaccaa gaaccaggtg tccctgacct gtctggtgaa gggcttctac    1140

cccagcgaca tcgccgtgga gtgggagagc aacggccagc ccgagaacaa ctacaagacc    1200

acccccccag tgctggacag cgacggcagc ttcttcctgt acagcaagct gaccgtggac    1260

aagtccaggt ggcagcaggg caacgtgttc agctgcagcg tgatgcacga agcgctgcac    1320

aaccactaca cccagaagag cctgagcctg tcccccggca agggcggctc cggcggaagc    1380

gatatcgtgc tgacacagag ccctgccacc ctgtctctga gccctggcga gagagccacc    1440

ctgagctgcc gggccagcca gttcatcggc tcccgctacc tggcctggta tcagcagaag    1500

cccggacagg ctcccagact gctgatctac ggcgccagca acagagctac cggcgtgccc    1560

gccagatttt ctggcagcgg cagcggcacc gacttcaccc tgaccatcag cagcctggaa    1620

cccgaggact tcgccaccta ctactgccag cagtactacg actacccccca gaccttcggc    1680
```

```
cagggcacca aggtggagat caagggcgga ggcggatccg gggtggcgg aagtggaggc   1740

ggaggaagcg gagggggcgg aagccaggtg caattgaaag agtccggccc tgccctggtg   1800

aagcctaccc agaccctgac cctgacatgc accttcagcg gcttcagcct gagcaacaga   1860

ggcggcggag tgggctggat cagacagcct cccggcaagg ccctggaatg gctggcctgg   1920

atcgactggg acgacgacaa gagctacagc accagcctga aaacccggct gaccatctcc   1980

aaggacacca gcaagaacca ggtggtgctc accatgacca acatggaccc cgtggacacc   2040

gccacctatt attgcgcccg gatgcatctg cccctggtgt tcgatagctg ggccaggga   2100

accctggtga cagtgtccag c                                              2121
```

```
<210> SEQ ID NO 166
<211> LENGTH: 707
<212> TYPE: PRT
<213> ORGANISM: Homo Sapien

<400> SEQUENCE: 166

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Val Ile Asn Trp Val Arg Gln Ala Pro Gly Lys Gly Leu Glu Trp Val
        35                  40                  45

Ser Gly Ile Ser Trp Ser Gly Val Asn Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Ala Thr Ala Asn Asn Ile Arg Tyr Lys Phe Met Asp
            100                 105                 110

Val Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Ala Ala Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285
```

-continued

```
Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys Gly Gly Ser Gly Gly Ser Asp Ile Val Leu
    450                 455                 460

Thr Gln Ser Pro Ala Thr Leu Ser Leu Ser Pro Gly Glu Arg Ala Thr
465                 470                 475                 480

Leu Ser Cys Arg Ala Ser Gln Phe Ile Gly Ser Arg Tyr Leu Ala Trp
                485                 490                 495

Tyr Gln Gln Lys Pro Gly Gln Ala Pro Arg Leu Leu Ile Tyr Gly Ala
            500                 505                 510

Ser Asn Arg Ala Thr Gly Val Pro Ala Arg Phe Ser Gly Ser Gly Ser
        515                 520                 525

Gly Thr Asp Phe Thr Leu Thr Ile Ser Ser Leu Glu Pro Glu Asp Phe
    530                 535                 540

Ala Thr Tyr Tyr Cys Gln Gln Tyr Tyr Asp Tyr Pro Gln Thr Phe Gly
545                 550                 555                 560

Gln Gly Thr Lys Val Glu Ile Lys Gly Gly Gly Gly Ser Gly Gly Gly
                565                 570                 575

Gly Ser Gly Gly Gly Gly Ser Gly Gly Gly Gly Ser Gln Val Gln Leu
            580                 585                 590

Lys Glu Ser Gly Pro Ala Leu Val Lys Pro Thr Gln Thr Leu Thr Leu
        595                 600                 605

Thr Cys Thr Phe Ser Gly Phe Ser Leu Ser Asn Arg Gly Gly Gly Val
    610                 615                 620

Gly Trp Ile Arg Gln Pro Pro Gly Lys Ala Leu Glu Trp Leu Ala Trp
625                 630                 635                 640

Ile Asp Trp Asp Asp Asp Lys Ser Tyr Ser Thr Ser Leu Lys Thr Arg
                645                 650                 655

Leu Thr Ile Ser Lys Asp Thr Ser Lys Asn Gln Val Val Leu Thr Met
            660                 665                 670

Thr Asn Met Asp Pro Val Asp Thr Ala Thr Tyr Tyr Cys Ala Arg Met
        675                 680                 685

His Leu Pro Leu Val Phe Asp Ser Trp Gly Gln Gly Thr Leu Val Thr
    690                 695                 700

Val Ser Ser
```

705

<210> SEQ ID NO 167
<211> LENGTH: 105
<212> TYPE: PRT
<213> ORGANISM: Homo Sapien

<400> SEQUENCE: 167

Asp Ile Glu Leu Thr Gln Pro Pro Ser Val Ser Val Ala Pro Gly Gln
1 5 10 15

Thr Ala Arg Ile Ser Cys Ser Gly Asp Ser Leu Arg Asn Lys Val Tyr
20 25 30

Trp Tyr Gln Gln Lys Pro Gly Gln Ala Pro Val Leu Val Ile Tyr Lys
35 40 45

Asn Asn Arg Pro Ser Gly Ile Pro Glu Arg Phe Ser Gly Ser Asn Ser
50 55 60

Gly Asn Thr Ala Thr Leu Thr Ile Ser Gly Thr Gln Ala Glu Asp Glu
65 70 75 80

Ala Asp Tyr Tyr Cys Gln Ser Tyr Asp Gly Gln Lys Ser Leu Val Phe
85 90 95

Gly Gly Gly Thr Lys Leu Thr Val Leu
100 105

<210> SEQ ID NO 168
<211> LENGTH: 315
<212> TYPE: DNA
<213> ORGANISM: Homo Sapien

<400> SEQUENCE: 168
gacatcgagc tgacccagcc cccttctgtg tctgtggccc ctggccagac cgccagaatc 60
agctgcagcg gcgacagcct gcggaacaag gtgtactggt atcagcagaa gcccggccag 120
gctcccgtgc tggtgatcta caagaacaac cggcccagcg gcatccctga gcggttcagc 180
ggcagcaaca gcggcaatac cgccaccctg accatcagcg gcacccaggc cgaagatgag 240
gccgactact actgccagag ctacgacggc cagaaaagcc tggtgttcgg cggaggcacc 300
aagcttaccg tgctg 315

<210> SEQ ID NO 169
<211> LENGTH: 633
<212> TYPE: DNA
<213> ORGANISM: Homo Sapien

<400> SEQUENCE: 169
gacatcgagc tgacccagcc cccttctgtg tctgtggccc ctggccagac cgccagaatc 60
agctgcagcg gcgacagcct gcggaacaag gtgtactggt atcagcagaa gcccggccag 120
gctcccgtgc tggtgatcta caagaacaac cggcccagcg gcatccctga gcggttcagc 180
ggcagcaaca gcggcaatac cgccaccctg accatcagcg gcacccaggc cgaagatgag 240
gccgactact actgccagag ctacgacggc cagaaaagcc tggtgttcgg cggaggcacc 300
aagcttaccg tgctgggcca gcccaaagcc gcccctagcg tgaccctgtt cccccccagc 360
agcgaggaac tgcaggccaa caaggccacc ctggtctgcc tgatcagcga cttctaccct 420
ggcgccgtga ccgtggcctg gaaggccgac agcagccccg tgaaggccgg cgtggagaca 480
accaccccca gcaagcagag caacaacaag tacgccgcca gcagctacct gagcctgacc 540
cccgagcagt ggaagagcca cagaagctac agctgccagg tcacccacga gggcagcacc 600

-continued gtggagaaaa ccgtggcccc caccgagtgc agc 633

<210> SEQ ID NO 170
<211> LENGTH: 211
<212> TYPE: PRT
<213> ORGANISM: Homo Sapien

<400> SEQUENCE: 170

```
Asp Ile Glu Leu Thr Gln Pro Pro Ser Val Ser Val Ala Pro Gly Gln
 1               5                  10                  15

Thr Ala Arg Ile Ser Cys Ser Gly Asp Ser Leu Arg Asn Lys Val Tyr
            20                  25                  30

Trp Tyr Gln Gln Lys Pro Gly Gln Ala Pro Val Leu Val Ile Tyr Lys
        35                  40                  45

Asn Asn Arg Pro Ser Gly Ile Pro Glu Arg Phe Ser Gly Ser Asn Ser
    50                  55                  60

Gly Asn Thr Ala Thr Leu Thr Ile Ser Gly Thr Gln Ala Glu Asp Glu
65                  70                  75                  80

Ala Asp Tyr Tyr Cys Gln Ser Tyr Asp Gly Gln Lys Ser Leu Val Phe
                85                  90                  95

Gly Gly Gly Thr Lys Leu Thr Val Leu Gly Gln Pro Lys Ala Ala Pro
            100                 105                 110

Ser Val Thr Leu Phe Pro Pro Ser Ser Glu Glu Leu Gln Ala Asn Lys
        115                 120                 125

Ala Thr Leu Val Cys Leu Ile Ser Asp Phe Tyr Pro Gly Ala Val Thr
    130                 135                 140

Val Ala Trp Lys Ala Asp Ser Ser Pro Val Lys Ala Gly Val Glu Thr
145                 150                 155                 160

Thr Thr Pro Ser Lys Gln Ser Asn Asn Lys Tyr Ala Ala Ser Ser Tyr
                165                 170                 175

Leu Ser Leu Thr Pro Glu Gln Trp Lys Ser His Arg Ser Tyr Ser Cys
            180                 185                 190

Gln Val Thr His Glu Gly Ser Thr Val Glu Lys Thr Val Ala Pro Thr
        195                 200                 205

Glu Cys Ser
    210
```

<210> SEQ ID NO 171
<211> LENGTH: 706
<212> TYPE: PRT
<213> ORGANISM: Homo Sapien

<400> SEQUENCE: 171

```
Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Val Ile Asn Trp Val Arg Gln Ala Pro Gly Lys Gly Leu Glu Trp Val
        35                  40                  45

Ser Gly Ile Ser Trp Ser Gly Val Asn Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Ala Thr Ala Asn Asn Ile Arg Tyr Lys Phe Met Asp
```

```
            100                 105                 110

Val Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Ala Ala Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Gly Gly Ser Gly Gly Ser Asp Ile Val Leu Thr
    450                 455                 460

Gln Ser Pro Ala Thr Leu Ser Leu Ser Pro Gly Glu Arg Ala Thr Leu
465                 470                 475                 480

Ser Cys Arg Ala Ser Gln Phe Ile Gly Ser Arg Tyr Leu Ala Trp Tyr
                485                 490                 495

Gln Gln Lys Pro Gly Gln Ala Pro Arg Leu Leu Ile Tyr Gly Ala Ser
            500                 505                 510

Asn Arg Ala Thr Gly Val Pro Ala Arg Phe Ser Gly Ser Gly Ser Gly
        515                 520                 525
```

```
Thr Asp Phe Thr Leu Thr Ile Ser Ser Leu Glu Pro Glu Asp Phe Ala
    530                 535                 540

Thr Tyr Tyr Cys Gln Gln Tyr Tyr Asp Tyr Pro Gln Thr Phe Gly Gln
545                 550                 555                 560

Gly Thr Lys Val Glu Ile Lys Gly Gly Gly Gly Ser Gly Gly Gly Gly
                565                 570                 575

Ser Gly Gly Gly Gly Ser Gly Gly Gly Gly Ser Gln Val Gln Leu Lys
            580                 585                 590

Glu Ser Gly Pro Ala Leu Val Lys Pro Thr Gln Thr Leu Thr Leu Thr
        595                 600                 605

Cys Thr Phe Ser Gly Phe Ser Leu Ser Asn Arg Gly Gly Gly Val Gly
    610                 615                 620

Trp Ile Arg Gln Pro Pro Gly Lys Ala Leu Glu Trp Leu Ala Trp Ile
625                 630                 635                 640

Asp Trp Asp Asp Asp Lys Ser Tyr Ser Thr Ser Leu Lys Thr Arg Leu
                645                 650                 655

Thr Ile Ser Lys Asp Thr Ser Lys Asn Gln Val Val Leu Thr Met Thr
            660                 665                 670

Asn Met Asp Pro Val Asp Thr Ala Thr Tyr Tyr Cys Ala Arg Met His
        675                 680                 685

Leu Pro Leu Val Phe Asp Ser Trp Gly Gln Gly Thr Leu Val Thr Val
    690                 695                 700

Ser Ser
705
```

<210> SEQ ID NO 172
<211> LENGTH: 2118
<212> TYPE: DNA
<213> ORGANISM: Homo Sapien

<400> SEQUENCE: 172

```
caggtgcaat tggtcgagtc tggcggagga ctggtgcagc ctggtggcag cctgagactg     60
agctgcgccg ccagcggctt caccttcagc gactacgtga tcaactgggt gcgacaggcc    120
cctggaaagg gcctggaatg ggtgtccggc atctcttggt ctggcgtgaa cacccactac    180
gccgacagcg tgaagggccg gttcaccatc agccgggaca acagcaagaa caccctgtac    240
ctgcagatga acagcctgag agccgaggac accgccgtgt actactgtgc cagactgggc    300
gccaccgcca acaacatccg gtacaagttc atggacgtgt ggggccaggg cacactggtg    360
accgtcagct cagctagcac caagggcccc agcgtgttcc ccctggcccc cagcagcaag    420
agcaccagcg gcggcacagc cgccctgggc tgcctggtga aggactactt ccccgagccc    480
gtgaccgtgt cctggaacag cggagccctg acctccggcg tgcacacctt ccccgccgtg    540
ctgcagagca gcggcctgta cagcctgtcc agcgtggtga cagtgcccag cagcagcctg    600
ggcacccaga cctacatctg caacgtgaac cacaagccca gcaacaccaa ggtggacaag    660
agagtggagc ccaagagctg cgacaagacc cacacctgcc ccccctgccc agccccagag    720
gcagcgggcg gaccctccgt gttcctgttc ccccccaagc ccaaggacac cctgatgatc    780
agcaggaccc ccgaggtgac ctgcgtggtg gtggacgtga gccacgagga cccagaggtg    840
aagttcaact ggtacgtgga cggcgtggag gtgcacaacg ccaagaccaa gcccagagag    900
gagcagtaca acagcaccta cagggtggtg tccgtgctga ccgtgctgca ccaggactgg    960
ctgaacggca aggaatacaa gtgcaaggtc tccaacaagg ccctgccagc ccccatcgaa   1020
```

```
aagaccatca gcaaggccaa gggccagcca cgggagcccc aggtgtacac cctgcccccc   1080

tcccgggagg agatgaccaa gaaccaggtg tccctgacct gtctggtgaa gggcttctac   1140

cccagcgaca tcgccgtgga gtgggagagc aacggccagc ccgagaacaa ctacaagacc   1200

acccccccag tgctggacag cgacggcagc ttcttcctgt acagcaagct gaccgtggac   1260

aagtccaggt ggcagcaggg caacgtgttc agctgcagcg tgatgcacga agcgctgcac   1320

aaccactaca cccagaagag cctgagcctg tcccccggcg gcggctccgg cggaagcgat   1380

atcgtgctga cacagagccc tgccaccctg tctctgagcc ctggcgagag agccaccctg   1440

agctgccggg ccagccagtt catcggctcc cgctacctgg cctggtatca gcagaagccc   1500

ggacaggctc ccagactgct gatctacggc gccagcaaca gagctaccgg cgtgcccgcc   1560

agattttctg gcagcggcag cggcaccgac ttcaccctga ccatcagcag cctggaaccc   1620

gaggacttcg ccacctacta ctgccagcag tactacgact acccccagac cttcggccag   1680

ggcaccaagg tggagatcaa gggcggaggc ggatccgggg gtggcggaag tggaggcgga   1740

ggaagcggag gggcggaag ccaggtgcaa ttgaaagagt ccggccctgc cctggtgaag   1800

cctacccaga ccctgaccct gacatgcacc ttcagcggct tcagcctgag caacagaggc   1860

ggcggagtgg gctggatcag acagcctccc ggcaaggccc tggaatggct ggcctggatc   1920

gactgggacg acgacaagag ctacagcacc agcctgaaaa cccggctgac catctccaag   1980

gacaccagca agaaccaggt ggtgctcacc atgaccaaca tggaccccgt ggacaccgcc   2040

acctattatt gcgcccggat gcatctgccc ctggtgttcg atagctgggg ccagggaacc   2100

ctggtgacag tgtccagc                                                 2118


<210> SEQ ID NO 173
<211> LENGTH: 707
<212> TYPE: PRT
<213> ORGANISM: Homo Sapien

<400> SEQUENCE: 173

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Val Ile Asn Trp Val Arg Gln Ala Pro Gly Lys Gly Leu Glu Trp Val
        35                  40                  45

Ser Gly Ile Ser Trp Ser Gly Val Asn Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Ala Thr Ala Asn Asn Ile Arg Tyr Lys Phe Met Asp
            100                 105                 110

Val Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175
```

-continued

```
Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Ala Ala Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys Gly Gly Ser Gly Gly Ser Asp Ile Val Leu
    450                 455                 460

Thr Gln Ser Pro Ala Thr Leu Ser Leu Ser Pro Gly Glu Arg Ala Thr
465                 470                 475                 480

Leu Ser Cys Arg Ala Ser Gln Phe Ile Gly Ser Arg Tyr Leu Ala Trp
                485                 490                 495

Tyr Gln Gln Lys Pro Gly Gln Ala Pro Arg Leu Leu Ile Tyr Gly Ala
            500                 505                 510

Ser Asn Arg Ala Thr Gly Val Pro Ala Arg Phe Ser Gly Ser Gly Ser
        515                 520                 525

Gly Thr Asp Phe Thr Leu Thr Ile Ser Ser Leu Glu Pro Glu Asp Phe
    530                 535                 540

Ala Thr Tyr Tyr Cys Gln Gln Tyr Tyr Asp Tyr Pro Gln Thr Phe Gly
545                 550                 555                 560

Gln Gly Thr Lys Val Glu Ile Lys Gly Gly Gly Gly Ser Gly Gly Gly
                565                 570                 575

Gly Ser Gly Gly Gly Gly Ser Gly Gly Gly Gly Ser Gln Val Gln Leu
            580                 585                 590

Lys Glu Ser Gly Pro Ala Leu Val Lys Pro Thr Gln Thr Leu Thr Leu
```

```
        595                 600                 605

Thr Cys Thr Phe Ser Gly Phe Ser Leu Ser Asn Arg Gly Gly Gly Val
    610                 615                 620

Gly Trp Ile Arg Gln Pro Pro Gly Lys Ala Leu Glu Trp Leu Ala Trp
625                 630                 635                 640

Ile Asp Trp Asp Asp Asp Lys Ser Tyr Ser Thr Ser Leu Lys Thr Arg
                645                 650                 655

Leu Thr Ile Ser Lys Asp Thr Ser Lys Asn Gln Val Val Leu Thr Met
            660                 665                 670

Thr Asn Met Asp Ala Val Asp Thr Ala Thr Tyr Tyr Cys Ala Arg Met
        675                 680                 685

His Leu Pro Leu Val Phe Asp Ser Trp Gly Gln Gly Thr Leu Val Thr
    690                 695                 700

Val Ser Ser
705


<210> SEQ ID NO 174
<211> LENGTH: 2121
<212> TYPE: DNA
<213> ORGANISM: Homo Sapien

<400> SEQUENCE: 174

caggtgcaat tggtcgagtc tggcggagga ctggtgcagc ctggtggcag cctgagactg      60

agctgcgccg ccagcggctt caccttcagc gactacgtga tcaactgggt gcgacaggcc     120

cctggaaagg gcctggaatg ggtgtccggc atctcttggt ctggcgtgaa cacccactac     180

gccgacagcg tgaagggccg gttcaccatc agccgggaca acagcaagaa caccctgtac     240

ctgcagatga acagcctgag agccgaggac accgccgtgt actactgtgc cagactgggc     300

gccaccgcca acaacatccg gtacaagttc atggacgtgt ggggccaggg cacactggtg     360

accgtcagct cagctagcac caagggcccc agcgtgttcc ccctggcccc cagcagcaag     420

agcaccagcg gcggcacagc cgccctgggc tgcctggtga aggactactt ccccgagccc     480

gtgaccgtgt cctggaacag cggagccctg acctccggcg tgcacacctt ccccgccgtg     540

ctgcagagca gcggcctgta cagcctgtcc agcgtggtga cagtgcccag cagcagcctg     600

ggcacccaga cctacatctg caacgtgaac cacaagccca gcaacaccaa ggtggacaag     660

agagtggagc ccaagagctg cgacaagacc cacacctgcc ccccctgccc agccccagag     720

gcagcgggcg gaccctccgt gttcctgttc ccccccaagc ccaaggacac cctgatgatc     780

agcaggaccc ccgaggtgac ctgcgtggtg gtggacgtga gccacgagga cccagaggtg     840

aagttcaact ggtacgtgga cggcgtggag gtgcacaacg ccaagaccaa gcccagagag     900

gagcagtaca acagcaccta cagggtggtg tccgtgctga ccgtgctgca ccaggactgg     960

ctgaacggca aggaatacaa gtgcaaggtc tccaacaagg ccctgccagc ccccatcgaa    1020

aagaccatca gcaaggccaa gggccagcca cgggagcccc aggtgtacac cctgccccccc    1080

tcccgggagg agatgaccaa gaaccaggtg tccctgacct gtctggtgaa gggcttctac    1140

cccagcgaca tcgccgtgga gtgggagagc aacggccagc ccgagaacaa ctacaagacc    1200

accccccccag tgctggacag cgacggcagc ttcttcctgt acagcaagct gaccgtggac    1260

aagtccaggt ggcagcaggg caacgtgttc agctgcagcg tgatgcacga agcgctgcac    1320

aaccactaca cccagaagag cctgagcctg tcccccggca agggcggctc cggcggaagc    1380

gatatcgtgc tgacacagag ccctgccacc ctgtctctga gccctggcga gagagccacc    1440
```

```
ctgagctgcc gggccagcca gttcatcggc tcccgctacc tggcctggta tcagcagaag   1500

cccggacagg ctcccagact gctgatctac ggcgccagca acagagctac cggcgtgccc   1560

gccagatttt ctggcagcgg cagcggcacc gacttcaccc tgaccatcag cagcctggaa   1620

cccgaggact tcgccaccta ctactgccag cagtactacg actacccccca gaccttcggc   1680

cagggcacca aggtggagat caagggcgga ggcggatccg gggtggcgg aagtggaggc   1740

ggaggaagcg gagggggcgg aagccaggtg caattgaaag agtccggccc tgccctggtg   1800

aagcctaccc agaccctgac cctgacatgc accttcagcg gcttcagcct gagcaacaga   1860

ggcggcggag tgggctggat cagacagcct cccggcaagg ccctggaatg gctggcctgg   1920

atcgactggg acgacgacaa gagctacagc accagcctga aaacccggct gaccatctcc   1980

aaggacacca gcaagaacca ggtggtgctc accatgacca acatggacgc cgtggacacc   2040

gccacctatt attgcgcccg gatgcatctg cccctggtgt tcgatagctg gggccaggga   2100

accctggtga cagtgtccag c                                             2121
```

```
<210> SEQ ID NO 175
<211> LENGTH: 707
<212> TYPE: PRT
<213> ORGANISM: Homo Sapien

<400> SEQUENCE: 175

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Val Ile Asn Trp Val Arg Gln Ala Pro Gly Lys Gly Leu Glu Trp Val
        35                  40                  45

Ser Gly Ile Ser Trp Ser Gly Val Asn Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Ala Thr Ala Asn Asn Ile Arg Tyr Lys Phe Met Asp
            100                 105                 110

Val Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Ala Ala Gly Gly Pro Ser Val Phe Leu Phe Pro Pro Lys Pro Lys Asp
                245                 250                 255
```

```
Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys Gly Gly Ser Gly Gly Ser Asp Ile Val Leu
    450                 455                 460

Thr Gln Ser Pro Ala Thr Leu Ser Leu Ser Pro Gly Glu Arg Ala Thr
465                 470                 475                 480

Leu Ser Cys Arg Ala Ser Gln Phe Ile Gly Ser Arg Tyr Leu Ala Trp
                485                 490                 495

Tyr Gln Gln Lys Pro Gly Gln Ala Pro Arg Leu Leu Ile Tyr Gly Ala
            500                 505                 510

Ser Asn Arg Ala Thr Gly Val Pro Ala Arg Phe Ser Gly Ser Gly Ser
        515                 520                 525

Gly Thr Asp Phe Thr Leu Thr Ile Ser Ser Leu Glu Pro Glu Asp Phe
    530                 535                 540

Ala Thr Tyr Tyr Cys Gln Gln Tyr Tyr Asp Tyr Pro Gln Thr Phe Gly
545                 550                 555                 560

Gln Gly Thr Lys Val Glu Ile Lys Gly Gly Gly Gly Ser Gly Gly Gly
                565                 570                 575

Gly Ser Gly Gly Gly Gly Ser Gly Gly Gly Gly Ser Gln Val Gln Leu
            580                 585                 590

Lys Glu Ser Gly Pro Ala Leu Val Lys Pro Thr Gln Thr Leu Thr Leu
        595                 600                 605

Thr Cys Thr Phe Ser Gly Phe Ser Leu Ser Asn Arg Gly Gly Gly Val
    610                 615                 620

Gly Trp Ile Arg Gln Pro Pro Gly Lys Ala Leu Glu Trp Leu Ala Trp
625                 630                 635                 640

Ile Asp Trp Asp Asp Asp Lys Ser Tyr Ser Thr Ser Leu Lys Thr Arg
                645                 650                 655

Leu Thr Ile Ser Lys Asp Thr Ser Lys Asn Gln Val Val Leu Thr Met
            660                 665                 670
```

```
Thr Asn Met Thr Ala Val Asp Thr Ala Thr Tyr Tyr Cys Ala Arg Met
        675                 680                 685

His Leu Pro Leu Val Phe Asp Ser Trp Gly Gln Gly Thr Leu Val Thr
    690                 695                 700

Val Ser Ser
705


<210> SEQ ID NO 176
<211> LENGTH: 2121
<212> TYPE: DNA
<213> ORGANISM: Homo Sapien

<400> SEQUENCE: 176

caggtgcaat tggtcgagtc tggcggagga ctggtgcagc ctggtggcag cctgagactg     60

agctgcgccg ccagcggctt caccttcagc gactacgtga tcaactgggt gcgacaggcc    120

cctggaaagg gcctggaatg ggtgtccggc atctcttggt ctggcgtgaa cacccactac    180

gccgacagcg tgaagggccg gttcaccatc agccgggaca acagcaagaa caccctgtac    240

ctgcagatga acagcctgag agccgaggac accgccgtgt actactgtgc cagactgggc    300

gccaccgcca acaacatccg gtacaagttc atggacgtgt ggggccaggg cacactggtg    360

accgtcagct cagctagcac caagggcccc agcgtgttcc ccctggcccc cagcagcaag    420

agcaccagcg gcggcacagc cgccctgggc tgcctggtga aggactactt ccccgagccc    480

gtgaccgtgt cctggaacag cggagccctg acctccggcg tgcacacctt ccccgccgtg    540

ctgcagagca gcggcctgta cagcctgtcc agcgtggtga cagtgcccag cagcagcctg    600

ggcacccaga cctacatctg caacgtgaac cacaagccca gcaacaccaa ggtggacaag    660

agagtggagc ccaagagctg cgacaagacc cacacctgcc ccccctgccc agccccagag    720

gcagcgggcg gaccctccgt gttcctgttc ccccccaagc ccaaggacac cctgatgatc    780

agcaggaccc ccgaggtgac ctgcgtggtg gtggacgtga gccacgagga cccagaggtg    840

aagttcaact ggtacgtgga cggcgtggag gtgcacaacg ccaagaccaa gcccagagag    900

gagcagtaca acagcaccta cagggtggtg tccgtgctga ccgtgctgca ccaggactgg    960

ctgaacggca aggaatacaa gtgcaaggtc tccaacaagg ccctgccagc ccccatcgaa   1020

aagaccatca gcaaggccaa gggccagcca cgggagcccc aggtgtacac cctgcccccc   1080

tcccgggagg agatgaccaa gaaccaggtg tccctgacct gtctggtgaa gggcttctac   1140

cccagcgaca tcgccgtgga gtgggagagc aacggccagc ccgagaacaa ctacaagacc   1200

acccccccag tgctggacag cgacggcagc ttcttcctgt acagcaagct gaccgtggac   1260

aagtccaggt ggcagcaggg caacgtgttc agctgcagcg tgatgcacga agcgctgcac   1320

aaccactaca cccagaagag cctgagcctg tcccccggca agggcggctc cggcggaagc   1380

gatatcgtgc tgacacagag ccctgccacc ctgtctctga gccctggcga gagagccacc   1440

ctgagctgcc gggccagcca gttcatcggc tcccgctacc tggcctggta tcagcagaag   1500

cccggacagg ctcccagact gctgatctac ggcgccagca acagagctac cggcgtgccc   1560

gccagatttt ctggcagcgg cagcggcacc gacttcaccc tgaccatcag cagcctggaa   1620

cccgaggact tcgccaccta ctactgccag cagtactacg actacccccca gaccttcggc   1680

cagggcacca aggtggagat caagggcgga ggcggatccg gggtggcgg aagtggaggc   1740

ggaggaagcg gagggggcgg aagccaggtg caattgaaag agtccggccc tgccctggtg   1800

aagcctaccc agaccctgac cctgacatgc accttcagcg gcttcagcct gagcaacaga   1860
```

```
ggcggcggag tgggctggat cagacagcct cccggcaagg ccctggaatg gctggcctgg   1920

atcgactggg acgacgacaa gagctacagc accagcctga aaacccggct gaccatctcc   1980

aaggacacca gcaagaacca ggtggtgctc accatgacca acatgaccgc cgtggacacc   2040

gccacctatt attgcgcccg gatgcatctg cccctggtgt tcgatagctg gggccaggga   2100

accctggtga cagtgtccag c                                             2121


<210> SEQ ID NO 177
<211> LENGTH: 464
<212> TYPE: PRT
<213> ORGANISM: Homo Sapien

<400> SEQUENCE: 177

Asp Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Phe Ile Gly Ser Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Gln Gln Tyr Tyr Asp Tyr Pro
                85                  90                  95

Gln Thr Phe Gly Gln Gly Thr Lys Val Glu Ile Lys Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Lys Glu Ser Gly Pro Ala Leu Val Lys Pro Thr Gln
    130                 135                 140

Thr Leu Thr Leu Thr Cys Thr Phe Ser Gly Phe Ser Leu Ser Asn Arg
145                 150                 155                 160

Gly Gly Gly Val Gly Trp Ile Arg Gln Pro Pro Gly Lys Ala Leu Glu
                165                 170                 175

Trp Leu Ala Trp Ile Asp Trp Asp Asp Asp Lys Ser Tyr Ser Thr Ser
            180                 185                 190

Leu Lys Thr Arg Leu Thr Ile Ser Lys Asp Thr Ser Lys Asn Gln Val
        195                 200                 205

Val Leu Thr Met Thr Asn Met Asp Pro Val Asp Thr Ala Thr Tyr Tyr
    210                 215                 220

Cys Ala Arg Met His Leu Pro Leu Val Phe Asp Ser Trp Gly Gln Gly
225                 230                 235                 240

Thr Leu Val Thr Val Ser Ser Gly Gly Ser Gly Gly Ser Asp Ile Glu
                245                 250                 255

Leu Thr Gln Pro Pro Ser Val Ser Val Ala Pro Gly Gln Thr Ala Arg
            260                 265                 270

Ile Ser Cys Ser Gly Asp Ser Leu Arg Asn Lys Val Tyr Trp Tyr Gln
        275                 280                 285

Gln Lys Pro Gly Gln Ala Pro Val Leu Val Ile Tyr Lys Asn Asn Arg
    290                 295                 300

Pro Ser Gly Ile Pro Glu Arg Phe Ser Gly Ser Asn Ser Gly Asn Thr
305                 310                 315                 320

Ala Thr Leu Thr Ile Ser Gly Thr Gln Ala Glu Asp Glu Ala Asp Tyr
```

-continued

```
            325                 330                 335

Tyr Cys Gln Ser Tyr Asp Gly Gln Lys Ser Leu Val Phe Gly Gly Gly
        340                 345                 350

Thr Lys Leu Thr Val Leu Gly Gln Pro Lys Ala Ala Pro Ser Val Thr
    355                 360                 365

Leu Phe Pro Pro Ser Ser Glu Glu Leu Gln Ala Asn Lys Ala Thr Leu
370                 375                 380

Val Cys Leu Ile Ser Asp Phe Tyr Pro Gly Ala Val Thr Val Ala Trp
385                 390                 395                 400

Lys Ala Asp Ser Ser Pro Val Lys Ala Gly Val Glu Thr Thr Thr Pro
                405                 410                 415

Ser Lys Gln Ser Asn Asn Lys Tyr Ala Ala Ser Ser Tyr Leu Ser Leu
            420                 425                 430

Thr Pro Glu Gln Trp Lys Ser His Arg Ser Tyr Ser Cys Gln Val Thr
        435                 440                 445

His Glu Gly Ser Thr Val Glu Lys Thr Val Ala Pro Thr Glu Cys Ser
    450                 455                 460


<210> SEQ ID NO 178
<211> LENGTH: 1392
<212> TYPE: DNA
<213> ORGANISM: Homo Sapien

<400> SEQUENCE: 178

gatatcgtgc tgacacagag ccctgccacc ctgtctctga gccctggcga gagagccacc      60

ctgagctgcc gggccagcca gttcatcggc tcccgctacc tggcctggta tcagcagaag     120

cccggacagg ctcccagact gctgatctac ggcgccagca acagagctac cggcgtgccc     180

gccagatttt ctggcagcgg cagcggcacc gacttcaccc tgaccatcag cagcctggaa     240

cccgaggact tcgccaccta ctactgccag cagtactacg actacccccca gaccttcggc     300

cagggcacca aggtggagat caagggcgga ggcggatccg gggtggcgg aagtggaggc      360

ggaggaagcg gagggggcgg aagccaggtg caattgaaag agtccggccc tgccctggtg     420

aagcctaccc agaccctgac cctgacatgc accttcagcg gcttcagcct gagcaacaga     480

ggcggcggag tgggctggat cagacagcct cccggcaagg ccctggaatg gctggcctgg     540

atcgactggg acgacgacaa gagctacagc accagcctga aaacccggct gaccatctcc     600

aaggacacca gcaagaacca ggtggtgctc accatgacca acatggaccc cgtggacacc     660

gccacctatt attgcgcccg gatgcatctg cccctggtgt tcgatagctg gggccaggga     720

accctggtga cagtgtccag cggcggctcc ggcggaagcg acatcgagct gacccagccc     780

ccttctgtgt ctgtggcgcc cgggcagacc gccagaatca gctgcagcgg cgacagcctg     840

cggaacaagg tgtactggta tcagcagaag cccggccagg ctcccgtgct ggtgatctac     900

aagaacaacc ggcccagcgg catccctgag cggttcagcg gcagcaacag cggcaatacc     960

gccaccctga ccatcagcgg cacccaggcc gaagatgagg ccgactacta ctgccagagc    1020

tacgacggcc agaaaagcct ggtgttcggc ggaggcacca agcttaccgt gctgggccag    1080

cccaaagccg cccctagcgt gaccctgttc ccccccagca gcgaggaact gcaggccaac    1140

aaggccaccc tggtctgcct gatcagcgac ttctaccctg gcgccgtgac cgtggcctgg    1200

aaggccgaca gcagccccgt gaaggccggc gtggagacaa ccacccccag caagcagagc    1260

aacaacaagt acgccgccag cagctacctg agcctgaccc ccgagcagtg gaagagccac    1320

agaagctaca gctgccaggt cacccacgag ggcagcaccg tggagaaaac cgtggccccc    1380
```

accgagtgca gc 1392

<210> SEQ ID NO 179
<211> LENGTH: 124
<212> TYPE: PRT
<213> ORGANISM: Homo Sapien

<400> SEQUENCE: 179

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Tyr
20 25 30

Val Ile Asn Trp Val Arg Gln Ala Pro Gly Lys Gly Leu Glu Trp Val
35 40 45

Ser Gly Ile Ser Trp Ser Gly Val Asn Thr His Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Leu Gly Ala Thr Ala Asn Asn Ile Arg Tyr Lys Phe Met Asp
100 105 110

Val Trp Gly Gln Gly Thr Leu Val Thr Val Ser Ser
115 120

<210> SEQ ID NO 180
<211> LENGTH: 372
<212> TYPE: DNA
<213> ORGANISM: Homo Sapien

<400> SEQUENCE: 180
caggtgcaat tggtcgagtc tggcggagga ctggtgcagc ctggtggcag cctgagactg 60
agctgcgccg ccagcggctt caccttcagc gactacgtga tcaactgggt gcgacaggcc 120
cctggaaagg gcctggaatg ggtgtccggc atctcttggt ctggcgtgaa cacccactac 180
gccgacagcg tgaagggccg gttcaccatc agccgggaca acagcaagaa caccctgtac 240
ctgcagatga acagcctgag agccgaggac accgccgtgt actactgtgc cagactgggc 300
gccaccgcca acaacatccg gtacaagttc atggacgtgt ggggccaggg cacactggtg 360
accgtcagct ca 372

<210> SEQ ID NO 181
<211> LENGTH: 454
<212> TYPE: PRT
<213> ORGANISM: Homo Sapien

<400> SEQUENCE: 181

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Tyr
20 25 30

Val Ile Asn Trp Val Arg Gln Ala Pro Gly Lys Gly Leu Glu Trp Val
35 40 45

Ser Gly Ile Ser Trp Ser Gly Val Asn Thr His Tyr Ala Asp Ser Val
50 55 60

Lys Gly Arg Phe Thr Ile Ser Arg Asp Asn Ser Lys Asn Thr Leu Tyr
65 70 75 80

-continued

```
Leu Gln Met Asn Ser Leu Arg Ala Glu Asp Thr Ala Val Tyr Tyr Cys
                85                  90                  95

Ala Arg Leu Gly Ala Thr Ala Asn Asn Ile Arg Tyr Lys Phe Met Asp
            100                 105                 110

Val Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Ala Ala Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450
```

<210> SEQ ID NO 182
<211> LENGTH: 1362
<212> TYPE: DNA
<213> ORGANISM: Homo Sapien

<400> SEQUENCE: 182

```
caggtgcaat tggtcgagtc tggcggagga ctggtgcagc ctggtggcag cctgagactg     60
agctgcgccg ccagcggctt caccttcagc gactacgtga tcaactgggt gcgacaggcc    120
cctggaaagg gcctggaatg ggtgtccggc atctcttggt ctggcgtgaa cacccactac    180
gccgacagcg tgaagggccg gttcaccatc agccgggaca acagcaagaa caccctgtac    240
ctgcagatga acagcctgag agccgaggac accgccgtgt actactgtgc cagactgggc    300
gccaccgcca acaacatccg gtacaagttc atggacgtgt ggggccaggg cacactggtg    360
accgtcagct cagctagcac caagggcccc agcgtgttcc ccctggcccc cagcagcaag    420
agcaccagcg gcggcacagc cgccctgggc tgcctggtga aggactactt ccccgagccc    480
gtgaccgtgt cctggaacag cggagccctg acctccggcg tgcacacctt ccccgccgtg    540
ctgcagagca gcggcctgta cagcctgtcc agcgtggtga cagtgcccag cagcagcctg    600
ggcacccaga cctacatctg caacgtgaac cacaagccca gcaacaccaa ggtggacaag    660
agagtggagc ccaagagctg cgacaagacc cacacctgcc ccccctgccc agccccagag    720
gcagcgggcg gaccctccgt gttcctgttc ccccccaagc ccaaggacac cctgatgatc    780
agcaggaccc ccgaggtgac ctgcgtggtg gtggacgtga gccacgagga cccagaggtg    840
aagttcaact ggtacgtgga cggcgtggag gtgcacaacg ccaagaccaa gcccagagag    900
gagcagtaca acagcaccta cagggtggtg tccgtgctga ccgtgctgca ccaggactgg    960
ctgaacggca aggaatacaa gtgcaaggtc tccaacaagg ccctgccagc ccccatcgaa   1020
aagaccatca gcaaggccaa gggccagcca cgggagcccc aggtgtacac cctgcccccc   1080
tcccgggagg agatgaccaa gaaccaggtg tccctgacct gtctggtgaa gggcttctac   1140
cccagcgaca tcgccgtgga gtgggagagc aacggccagc ccgagaacaa ctacaagacc   1200
acccccccag tgctggacag cgacggcagc ttcttcctgt acagcaagct gaccgtggac   1260
aagtccaggt ggcagcaggg caacgtgttc agctgcagcg tgatgcacga ggccctgcac   1320
aaccactaca cccagaagag cctgagcctg tcccccggca ag                      1362
```

<210> SEQ ID NO 183
<211> LENGTH: 108
<212> TYPE: PRT
<213> ORGANISM: Homo Sapien

<400> SEQUENCE: 183

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Phe Ile Gly Ser Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Gln Gln Tyr Tyr Asp Tyr Pro
                85                  90                  95

Gln Thr Phe Gly Gln Gly Thr Lys Val Glu Ile Lys
            100                 105
```

<210> SEQ ID NO 184

<211> LENGTH: 324
<212> TYPE: DNA
<213> ORGANISM: Homo Sapien

<400> SEQUENCE: 184
gatatcgtgc tgacccagag cccggcgacc ctgagcctgt ctccgggcga acgtgcgacc 60
ctgagctgca gagcgagcca gtttattggt tctcgttatc tggcttggta ccagcagaaa 120
ccaggtcaag caccgcgtct attaatttat ggtgcttcta atcgtgcaac tggggtcccg 180
gcgcgtttta gcggctctgg atccggcacg gattttaccc tgaccattag cagcctggaa 240
cctgaagact ttgcgactta ttattgccag cagtattatg attatcctca gacctttggc 300
cagggtacga aagttgaaat taaa 324

<210> SEQ ID NO 185
<211> LENGTH: 215
<212> TYPE: PRT
<213> ORGANISM: Homo Sapien

<400> SEQUENCE: 185

Asp Ile Val Leu Thr Gln Ser Pro Ala Thr Leu Ser Leu Ser Pro Gly
1 5 10 15

Glu Arg Ala Thr Leu Ser Cys Arg Ala Ser Gln Phe Ile Gly Ser Arg
20 25 30

Tyr Leu Ala Trp Tyr Gln Gln Lys Pro Gly Gln Ala Pro Arg Leu Leu
35 40 45

Ile Tyr Gly Ala Ser Asn Arg Ala Thr Gly Val Pro Ala Arg Phe Ser
50 55 60

Gly Ser Gly Ser Gly Thr Asp Phe Thr Leu Thr Ile Ser Ser Leu Glu
65 70 75 80

Pro Glu Asp Phe Ala Thr Tyr Tyr Cys Gln Gln Tyr Tyr Asp Tyr Pro
85 90 95

Gln Thr Phe Gly Gln Gly Thr Lys Val Glu Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys
210 215

<210> SEQ ID NO 186
<211> LENGTH: 645
<212> TYPE: DNA
<213> ORGANISM: Homo Sapien

<400> SEQUENCE: 186
gatatcgtgc tgacccagag cccggcgacc ctgagcctgt ctccgggcga acgtgcgacc 60
ctgagctgca gagcgagcca gtttattggt tctcgttatc tggcttggta ccagcagaaa 120

```
ccaggtcaag caccgcgtct attaatttat ggtgcttcta atcgtgcaac tggggtcccg    180

gcgcgtttta gcggctctgg atccggcacg gattttaccc tgaccattag cagcctggaa    240

cctgaagact ttgcgactta ttattgccag cagtattatg attatcctca gacctttggc    300

cagggtacga aagttgaaat taaacgtacg gtggccgctc ccagcgtgtt catcttcccc    360

cccagcgacg agcagctgaa gagcggcacc gccagcgtgg tgtgcctgct gaacaacttc    420

tacccccggg aggccaaggt gcagtggaag gtggacaacg ccctgcagag cggcaacagc    480

caggagagcg tcaccgagca ggacagcaag gactccacct acagcctgag cagcaccctg    540

accctgagca aggccgacta cgagaagcat aaggtgtacg cctgcgaggt gacccaccag    600

ggcctgtcca gccccgtgac caagagcttc aacaggggcg agtgc                    645
```

<210> SEQ ID NO 187
<211> LENGTH: 699
<212> TYPE: PRT
<213> ORGANISM: Homo Sapien

<400> SEQUENCE: 187

```
Gln Val Gln Leu Lys Glu Ser Gly Pro Ala Leu Val Lys Pro Thr Gln
 1               5                  10                  15

Thr Leu Thr Leu Thr Cys Thr Phe Ser Gly Phe Ser Leu Ser Asn Arg
            20                  25                  30

Gly Gly Gly Val Gly Trp Ile Arg Gln Pro Pro Gly Lys Ala Leu Glu
        35                  40                  45

Trp Leu Ala Trp Ile Asp Trp Asp Asp Asp Lys Ser Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Met His Leu Pro Leu Val Phe Asp Ser Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
```

-continued

```
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Gly Ser Gly Gly Ser Gln Val Gln Leu Val Glu Ser Gly Gly
    450                 455                 460

Gly Leu Val Gln Pro Gly Gly Ser Leu Arg Leu Ser Cys Ala Ala Ser
465                 470                 475                 480

Gly Phe Thr Phe Ser Asp Tyr Val Ile Asn Trp Val Arg Gln Ala Pro
                485                 490                 495

Gly Lys Gly Leu Glu Trp Val Ser Gly Ile Ser Trp Ser Gly Val Asn
            500                 505                 510

Thr His Tyr Ala Asp Ser Val Lys Gly Arg Phe Thr Ile Ser Arg Asp
        515                 520                 525

Asn Ser Lys Asn Thr Leu Tyr Leu Gln Met Asn Ser Leu Arg Ala Glu
    530                 535                 540

Asp Thr Ala Val Tyr Tyr Cys Ala Arg Leu Gly Ala Thr Ala Asn Asn
545                 550                 555                 560

Ile Arg Tyr Lys Phe Met Asp Val Trp Gly Gln Gly Thr Leu Val Thr
                565                 570                 575

Val Ser Ser Gly Gly Gly Gly Ser Gly Gly Gly Gly Ser Gly Gly Gly
            580                 585                 590

Gly Ser Asp Ile Glu Leu Thr Gln Pro Pro Ser Val Ser Val Ala Pro
        595                 600                 605

Gly Gln Thr Ala Arg Ile Ser Cys Ser Gly Asp Ser Leu Arg Asn Lys
    610                 615                 620

Val Tyr Trp Tyr Gln Gln Lys Pro Gly Gln Ala Pro Val Leu Val Ile
625                 630                 635                 640

Tyr Lys Asn Asn Arg Pro Ser Gly Ile Pro Glu Arg Phe Ser Gly Ser
                645                 650                 655

Asn Ser Gly Asn Thr Ala Thr Leu Thr Ile Ser Gly Thr Gln Ala Glu
            660                 665                 670

Asp Glu Ala Asp Tyr Tyr Cys Gln Ser Tyr Asp Gly Gln Lys Ser Leu
        675                 680                 685

Val Phe Gly Gly Gly Thr Lys Leu Thr Val Leu
    690                 695
```

<210> SEQ ID NO 188
<211> LENGTH: 2097
<212> TYPE: DNA
<213> ORGANISM: Homo Sapien

<400> SEQUENCE: 188
caggtgcaat tgaaagaaag cggcccggcc ctggtgaaac cgacccaaac cctgaccctg 60
acctgtacct tttccggatt tagcctgtct aatcgtggtg gtggtgtggg ttggattcgc 120
cagccgcctg ggaaagccct cgagtggctg gcttggatcg attgggatga tgataagtct 180
tatagcacca gcctgaaaac gcgtctgacc attagcaaag atacttcgaa aaatcaggtg 240
gtgctgacta tgaccaacat ggacccggtg gatacggcca cctattattg cgcgcgtatg 300
catcttcctc ttgtttttga ttcttggggc caaggcaccc tggtgacggt tagctcagct 360
agcaccaagg gccccagcgt gttcccccctg gcccccagca gcaagagcac cagcggcggc 420
acagccgccc tgggctgcct ggtgaaggac tacttccccg agcccgtgac cgtgtcctgg 480
aacagcggag ccctgacctc cggcgtgcac accttccccg ccgtgctgca gagcagcggc 540
ctgtacagcc tgtccagcgt ggtgacagtg cccagcagca gcctgggcac ccagacctac 600
atctgcaacg tgaaccacaa gcccagcaac accaaggtgg acaagagagt ggagcccaag 660
agctgcgaca agacccacac ctgccccccc tgcccagccc cagaggcagc gggcggaccc 720
tccgtgttcc tgttcccccc caagcccaag gacaccctga tgatcagcag gacccccgag 780
gtgacctgcg tggtggtgga cgtgagccac gaggacccag aggtgaagtt caactggtac 840
gtggacggcg tggaggtgca caacgccaag accaagccca gagaggagca gtacaacagc 900
acctacaggg tggtgtccgt gctgaccgtg ctgcaccagg actggctgaa cggcaaggaa 960
tacaagtgca aggtctccaa caaggccctg ccagccccca tcgaaaagac catcagcaag 1020
gccaagggcc agccacggga gccccaggtg tacaccctgc ccccctcccg ggaggagatg 1080
accaagaacc aggtgtccct gacctgtctg gtgaagggct tctaccccag cgacatcgcc 1140
gtggagtggg agagcaacgg ccagcccgag aacaactaca agaccacccc cccagtgctg 1200
gacagcgacg gcagcttctt cctgtacagc aagctgaccg tggacaagtc caggtggcag 1260
cagggcaacg tgttcagctg cagcgtgatg cacgaagcgc tgcacaacca ctacacccag 1320
aagagcctga gcctgtcccc cggcaagggc ggctccggcg gaagccaggt tcaattggtt 1380
gaaagcggtg gtggtctggt tcagcctggt ggtagcctgc gtctgagctg tgcagcaagc 1440
ggttttacct ttagcgatta tgtgattaat tgggttcgtc aggcaccggg taaaggtctg 1500
gaatgggtta gcggtattag ctggtcaggt gttaataccc attatgcaga tagcgtgaaa 1560
ggtcgtttta ccattagccg tgataatagc aaaaataccc tgtatctgca gatgaatagc 1620
ctgcgtgcag aagataccgc agtttattat tgtgcacgtc tgggtgcaac cgcaaataat 1680
attcgctata aatttatgga tgtgtggggt cagggtacac tagttaccgt tagcagtggt 1740
ggtggtggta gcggtggtgg cggatctggt ggcggtggca gtgatatcga actgacccag 1800
cctccgagcg ttagcgttgc accgggtcag accgcacgta ttagctgtag cggtgatagt 1860
ctgcgtaata aagtttattg gtatcagcag aaaccgggtc aggctccggt tctggttatt 1920
tataaaaata atcgtccgag cggtattccg gaacgtttta gcggtagcaa tagcggtaat 1980
accgcaaccc tgaccattag cggcacccag gcagaagatg aagccgatta ttattgtcag 2040
agctatgatg gtcagaaaag cctggttttt ggtggtggca ccaagcttac cgttctg 2097

<210> SEQ ID NO 189
<211> LENGTH: 704
<212> TYPE: PRT
<213> ORGANISM: Homo Sapien

<400> SEQUENCE: 189

```
Gln Val Gln Leu Lys Glu Ser Gly Pro Ala Leu Val Lys Pro Thr Gln
 1               5                  10                  15

Thr Leu Thr Leu Thr Cys Thr Phe Ser Gly Phe Ser Leu Ser Asn Arg
            20                  25                  30

Gly Gly Gly Val Gly Trp Ile Arg Gln Pro Pro Gly Lys Ala Leu Glu
        35                  40                  45

Trp Leu Ala Trp Ile Asp Trp Asp Asp Asp Lys Ser Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Met His Leu Pro Leu Val Phe Asp Ser Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380
```

```
Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Gly Ser Gly Gly Ser Gln Val Gln Leu Val Glu Ser Gly Gly
    450                 455                 460

Gly Leu Val Gln Pro Gly Gly Ser Leu Arg Leu Ser Cys Ala Ala Ser
465                 470                 475                 480

Gly Phe Thr Phe Ser Asp Tyr Val Ile Asn Trp Val Arg Gln Ala Pro
                485                 490                 495

Gly Lys Gly Leu Glu Trp Val Ser Gly Ile Ser Trp Ser Gly Val Asn
            500                 505                 510

Thr His Tyr Ala Asp Ser Val Lys Gly Arg Phe Thr Ile Ser Arg Asp
        515                 520                 525

Asn Ser Lys Asn Thr Leu Tyr Leu Gln Met Asn Ser Leu Arg Ala Glu
    530                 535                 540

Asp Thr Ala Val Tyr Tyr Cys Ala Arg Leu Gly Ala Thr Ala Asn Asn
545                 550                 555                 560

Ile Arg Tyr Lys Phe Met Asp Val Trp Gly Gln Gly Thr Leu Val Thr
                565                 570                 575

Val Ser Ser Gly Gly Gly Gly Ser Gly Gly Gly Gly Ser Gly Gly Gly
            580                 585                 590

Gly Ser Gly Gly Gly Gly Ser Asp Ile Glu Leu Thr Gln Pro Pro Ser
        595                 600                 605

Val Ser Val Ala Pro Gly Gln Thr Ala Arg Ile Ser Cys Ser Gly Asp
    610                 615                 620

Ser Leu Arg Asn Lys Val Tyr Trp Tyr Gln Gln Lys Pro Gly Gln Ala
625                 630                 635                 640

Pro Val Leu Val Ile Tyr Lys Asn Asn Arg Pro Ser Gly Ile Pro Glu
                645                 650                 655

Arg Phe Ser Gly Ser Asn Ser Gly Asn Thr Ala Thr Leu Thr Ile Ser
            660                 665                 670

Gly Thr Gln Ala Glu Asp Glu Ala Asp Tyr Tyr Cys Gln Ser Tyr Asp
        675                 680                 685

Gly Gln Lys Ser Leu Val Phe Gly Gly Gly Thr Lys Leu Thr Val Leu
    690                 695                 700
```

<210> SEQ ID NO 190
<211> LENGTH: 2112
<212> TYPE: DNA
<213> ORGANISM: Homo Sapien

<400> SEQUENCE: 190

```
caggtgcaat tgaaagaaag cggcccggcc ctggtgaaac cgacccaaac cctgaccctg      60

acctgtacct tttccggatt tagcctgtct aatcgtggtg gtggtgtggg ttggattcgc     120

cagccgcctg ggaaagccct cgagtggctg gcttggatcg attgggatga tgataagtct     180

tatagcacca gcctgaaaac gcgtctgacc attagcaaag atacttcgaa aaatcaggtg     240

gtgctgacta tgaccaacat ggacccggtg gatacggcca cctattattg cgcgcgtatg     300
```

-continued

```
catcttcctc ttgtttttga ttcttggggc caaggcaccc tggtgacggt tagctcagct    360

agcaccaagg gccccagcgt gttcccctg gcccccagca gcaagagcac cagcggcggc    420

acagccgccc tgggctgcct ggtgaaggac tacttccccg agcccgtgac cgtgtcctgg    480

aacagcggag ccctgacctc cggcgtgcac accttccccg ccgtgctgca gagcagcggc    540

ctgtacagcc tgtccagcgt ggtgacagtg cccagcagca gcctgggcac ccagacctac    600

atctgcaacg tgaaccacaa gcccagcaac accaaggtgg acaagagagt ggagcccaag    660

agctgcgaca agacccacac ctgccccccc tgcccagccc cagaggcagc gggcggaccc    720

tccgtgttcc tgttcccccc caagcccaag gacaccctga tgatcagcag gacccccgag    780

gtgacctgcg tggtggtgga cgtgagccac gaggacccag aggtgaagtt caactggtac    840

gtggacggcg tggaggtgca caacgccaag accaagccca gagaggagca gtacaacagc    900

acctacaggg tggtgtccgt gctgaccgtg ctgcaccagg actggctgaa cggcaaggaa    960

tacaagtgca aggtctccaa caaggccctg ccagccccca tcgaaaagac catcagcaag   1020

gccaagggcc agccacggga gccccaggtg tacaccctgc ccccctcccg ggaggagatg   1080

accaagaacc aggtgtccct gacctgtctg gtgaagggct tctaccccag cgacatcgcc   1140

gtggagtggg agagcaacgg ccagcccgag aacaactaca agaccacccc cccagtgctg   1200

gacagcgacg gcagcttctt cctgtacagc aagctgaccg tggacaagtc caggtggcag   1260

cagggcaacg tgttcagctg cagcgtgatg cacgaagcgc tgcacaacca ctacacccag   1320

aagagcctga gcctgtcccc cggcaagggc ggctccggcg gaagccaggt tcaattggtt   1380

gaaagcggtg gtggtctggt tcagcctggt ggtagcctgc gtctgagctg tgcagcaagc   1440

ggttttacct ttagcgatta tgtgattaat tgggttcgtc aggcaccggg taaaggtctg   1500

gaatgggtta gcggtattag ctggtcaggt gttaataccc attatgcaga tagcgtgaaa   1560

ggtcgtttta ccattagccg tgataatagc aaaaataccc tgtatctgca gatgaatagc   1620

ctgcgtgcag aagataccgc agtttattat tgtgcacgtc tgggtgcaac cgcaaataat   1680

attcgctata aatttatgga tgtgtggggt cagggtacac tagttaccgt tagcagtggt   1740

ggtggtggta gcggtggtgg cggatctggt ggcggtggtt caggtggtgg tggcagtgat   1800

atcgaactga cccagcctcc gagcgttagc gttgcaccgg gtcagaccgc acgtattagc   1860

tgtagcggtg atagtctgcg taataaagtt tattggtatc agcagaaacc gggtcaggct   1920

ccggttctgg ttatttataa aaataatcgt ccgagcggta ttccggaacg ttttagcggt   1980

agcaatagcg gtaataccgc aaccctgacc attagcggca cccaggcaga agatgaagcc   2040

gattattatt gtcagagcta tgatggtcag aaaagcctgg tttttggtgg tggcaccaag   2100

cttaccgttc tg                                                       2112
```

<210> SEQ ID NO 191
<211> LENGTH: 105
<212> TYPE: PRT
<213> ORGANISM: Homo Sapien

<400> SEQUENCE: 191

```
Asp Ile Glu Leu Thr Gln Pro Pro Ser Val Ser Val Ala Pro Gly Gln
1               5                   10                  15

Thr Ala Arg Ile Ser Cys Ser Gly Asp Ser Leu Arg Asn Lys Val Tyr
            20                  25                  30

Trp Tyr Gln Gln Lys Pro Gly Gln Ala Pro Val Leu Val Ile Tyr Lys
        35                  40                  45
```

Asn Asn Arg Pro Ser Gly Ile Pro Glu Arg Phe Ser Gly Ser Asn Ser
    50                  55                  60

Gly Asn Thr Ala Thr Leu Thr Ile Ser Gly Thr Gln Ala Glu Asp Glu
65                  70                  75                  80

Ala Asp Tyr Tyr Cys Gln Ser Tyr Asp Gly Gln Lys Ser Leu Val Phe
                85                  90                  95

Gly Gly Gly Thr Lys Leu Thr Val Leu
            100                 105

<210> SEQ ID NO 192
<211> LENGTH: 315
<212> TYPE: DNA
<213> ORGANISM: Homo Sapien

<400> SEQUENCE: 192
gacatcgagc tgactcagcc ccctagcgtg tcagtggctc ctggccagac cgctagaatt      60
agctgtagcg gcgatagcct gcgtaacaag gtctactggt atcagcagaa gcccggccag     120
gcccctgtgc tggtcatcta taagaacaat aggcctagcg gcatccccga gcggtttagc     180
ggctctaata gcggcaacac cgctaccctg actattagcg gcactcaggc cgaggacgag     240
gccgactact actgtcagtc ctacgacggc cagaagtcac tggtctttgg cggcggaact     300
aagctgaccg tgctg                                                      315

<210> SEQ ID NO 193
<211> LENGTH: 211
<212> TYPE: PRT
<213> ORGANISM: Homo Sapien

<400> SEQUENCE: 193

Asp Ile Glu Leu Thr Gln Pro Pro Ser Val Ser Val Ala Pro Gly Gln
 1               5                  10                  15

Thr Ala Arg Ile Ser Cys Ser Gly Asp Ser Leu Arg Asn Lys Val Tyr
            20                  25                  30

Trp Tyr Gln Gln Lys Pro Gly Gln Ala Pro Val Leu Val Ile Tyr Lys
        35                  40                  45

Asn Asn Arg Pro Ser Gly Ile Pro Glu Arg Phe Ser Gly Ser Asn Ser
    50                  55                  60

Gly Asn Thr Ala Thr Leu Thr Ile Ser Gly Thr Gln Ala Glu Asp Glu
65                  70                  75                  80

Ala Asp Tyr Tyr Cys Gln Ser Tyr Asp Gly Gln Lys Ser Leu Val Phe
                85                  90                  95

Gly Gly Gly Thr Lys Leu Thr Val Leu Gly Gln Pro Lys Ala Ala Pro
            100                 105                 110

Ser Val Thr Leu Phe Pro Pro Ser Ser Glu Glu Leu Gln Ala Asn Lys
        115                 120                 125

Ala Thr Leu Val Cys Leu Ile Ser Asp Phe Tyr Pro Gly Ala Val Thr
    130                 135                 140

Val Ala Trp Lys Ala Asp Ser Ser Pro Val Lys Ala Gly Val Glu Thr
145                 150                 155                 160

Thr Thr Pro Ser Lys Gln Ser Asn Asn Lys Tyr Ala Ala Ser Ser Tyr
                165                 170                 175

Leu Ser Leu Thr Pro Glu Gln Trp Lys Ser His Arg Ser Tyr Ser Cys
            180                 185                 190

Gln Val Thr His Glu Gly Ser Thr Val Glu Lys Thr Val Ala Pro Thr
        195                 200                 205

Glu Cys Ser
210

<210> SEQ ID NO 194
<211> LENGTH: 633
<212> TYPE: DNA
<213> ORGANISM: Homo Sapien

<400> SEQUENCE: 194
gacatcgagc tgactcagcc ccctagcgtg tcagtggctc ctggccagac cgctagaatt 60
agctgtagcg gcgatagcct gcgtaacaag gtctactggt atcagcagaa gcccggccag 120
gcccctgtgc tggtcatcta taagaacaat aggcctagcg gcatccccga gcggtttagc 180
ggctctaata gcggcaacac cgctaccctg actattagcg gcactcaggc cgaggacgag 240
gccgactact actgtcagtc ctacgacggc cagaagtcac tggtctttgg cggcggaact 300
aagctgaccg tgctgggaca gcctaaggct gcccccagcg tgaccctgtt cccccccagc 360
agcgaggagc tgcaggccaa caaggccacc ctggtgtgcc tgatcagcga cttctaccca 420
ggcgccgtga ccgtggcctg gaaggccgac agcagccccg tgaaggccgg cgtggagacc 480 accacccccca gcaagcagag caacaacaag tacgccgcca gcagctacct gagcctgacc 540
cccgagcagt ggaagagcca caggtcctac agctgccagg tgacccacga gggcagcacc 600
gtggaaaaga ccgtggcccc aaccgagtgc agc 633

<210> SEQ ID NO 195
<211> LENGTH: 707
<212> TYPE: PRT
<213> ORGANISM: Homo Sapien

<400> SEQUENCE: 195

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Tyr
20 25 30

Val Ile Asn Trp Val Arg Gln Ala Pro Gly Lys Gly Leu Glu Trp Val
35 40 45

Ser Gly Ile Ser Trp Ser Gly Val Asn Thr His Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Leu Gly Ala Thr Ala Asn Asn Ile Arg Tyr Lys Phe Met Asp
100 105 110

Val Trp Gly Gln Gly Thr Leu Val Thr Val Ser Ser Ala Ser Thr Lys
115 120 125

Gly Pro Ser Val Phe Pro Leu Ala Pro Ser Ser Lys Ser Thr Ser Gly
130 135 140

Gly Thr Ala Ala Leu Gly Cys Leu Val Lys Asp Tyr Phe Pro Glu Pro
145 150 155 160

Val Thr Val Ser Trp Asn Ser Gly Ala Leu Thr Ser Gly Val His Thr
165 170 175

Phe Pro Ala Val Leu Gln Ser Ser Gly Leu Tyr Ser Leu Ser Ser Val
180 185 190

Val Thr Val Pro Ser Ser Ser Leu Gly Thr Gln Thr Tyr Ile Cys Asn
195 200 205

```
Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Ala Ala Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys Gly Gly Ser Gly Gly Ser Asp Ile Val Leu
    450                 455                 460

Thr Gln Ser Pro Ala Thr Leu Ser Leu Ser Pro Gly Glu Arg Ala Thr
465                 470                 475                 480

Leu Ser Cys Arg Ala Ser Gln Phe Ile Gly Ser Arg Tyr Leu Ala Trp
                485                 490                 495

Tyr Gln Gln Lys Pro Gly Gln Ala Pro Arg Leu Leu Ile Tyr Gly Ala
            500                 505                 510

Ser Asn Arg Ala Thr Gly Val Pro Ala Arg Phe Ser Gly Ser Gly Ser
        515                 520                 525

Gly Thr Asp Phe Thr Leu Thr Ile Ser Ser Leu Glu Pro Glu Asp Phe
    530                 535                 540

Ala Thr Tyr Tyr Cys Gln Gln Tyr Tyr Asp Tyr Pro Gln Thr Phe Gly
545                 550                 555                 560

Gln Gly Thr Lys Val Glu Ile Lys Gly Gly Gly Gly Ser Gly Gly Gly
                565                 570                 575

Gly Ser Gly Gly Gly Gly Ser Gly Gly Gly Gly Ser Gln Val Gln Leu
            580                 585                 590

Lys Glu Ser Gly Pro Ala Leu Val Lys Pro Thr Gln Thr Leu Thr Leu
        595                 600                 605

Thr Cys Thr Phe Ser Gly Phe Ser Leu Ser Asn Arg Gly Gly Gly Val
    610                 615                 620
```

```
Gly Trp Ile Arg Gln Pro Pro Gly Lys Ala Leu Glu Trp Leu Ala Trp
625                 630                 635                 640

Ile Asp Trp Asp Asp Asp Lys Ser Tyr Ser Thr Ser Leu Lys Thr Arg
                645                 650                 655

Leu Thr Ile Ser Lys Asp Thr Ser Lys Asn Gln Val Val Leu Thr Met
            660                 665                 670

Thr Asn Met Asp Pro Val Asp Thr Ala Thr Tyr Tyr Cys Ala Arg Met
        675                 680                 685

His Leu Pro Leu Val Phe Asp Ser Trp Gly Gln Gly Thr Leu Val Thr
    690                 695                 700

Val Ser Ser
705


<210> SEQ ID NO 196
<211> LENGTH: 2121
<212> TYPE: DNA
<213> ORGANISM: Homo Sapien

<400> SEQUENCE: 196

caggtgcagc tggtggaatc aggcggagga ctggtccagc ctggcggatc acttagactg      60

agctgtgccg ctagtggctt cacctttagc gactatgtga ttaactgggt ccgacaggcc     120

cctggcaagg gactggaatg ggtgtcaggc attagttgga gcggcgtgaa cactcactac     180

gccgatagcg tgaagggccg gttcactatt agccgggata actctaagaa caccctgtac     240

ctgcagatga atagcctgag agccgaggac accgccgtct actactgcgc tagactgggc     300

gctaccgcta acaacatccg ctataagttc atggacgtgt ggggccaggg caccctggtc     360

acagtgtctt cagctagcac taagggcccc tcagtgttcc ccctggcccc tagctctaag     420

tctactagcg gtggcaccgc cgctctgggc tgcctggtca aggactactt ccccgagccc     480

gtgaccgtgt cttggaatag cggcgctctg actagcggag tgcacacctt ccccgccgtg     540

ctgcagtcta gcggcctgta tagcctgtct agcgtcgtga ccgtgcctag ctctagcctg     600

ggcactcaga cctatatctg taacgtgaac cacaagccta gtaacactaa ggtggacaag     660

cgggtggaac ctaagtcttg cgataagact cacacctgtc ccccctgccc tgccccagaa     720

gctgctggcg gacctagcgt gttcctgttc ccacctaagc ctaaagacac cctgatgatt     780

agtaggaccc ccgaagtgac ctgcgtggtg gtggacgtca gccacgagga ccctgaagtg     840

aagttcaatt ggtatgtgga cggcgtggaa gtgcacaacg ctaagactaa gcctagagag     900

gaacagtata actccaccta tagggtggtg tcagtgctga ccgtgctgca ccaggactgg     960

ctgaacggca aagagtataa gtgtaaagtc tctaacaagg ccctgcctgc ccctatcgaa    1020

aagactatct ctaaggctaa gggccagcct agagaacccc aggtctacac cctgcccccct    1080

agtagagaag agatgactaa gaatcaggtg tccctgacct gtctggtcaa gggcttctac    1140

cctagcgata tcgccgtgga gtgggagtct aacggccagc ccgagaacaa ctataagact    1200

accccccctg tgctggatag cgacggctct ttcttcctgt actctaaact gaccgtggac    1260

aagtctaggt ggcagcaggg caacgtgttc agctgtagcg tgatgcacga ggccctgcac    1320

aatcactaca ctcagaagtc actgagcctg agtcccggca agggcggctc aggcggtagc    1380

gatatcgtgc tgactcagtc acccgctacc ctgagtctga gccctggcga gcgggctaca    1440

ctgagctgta gagctagtca gtttatcggc tcacgctacc tggcctggta tcagcagaag    1500

cccggccagg cccctagact gctgatctac ggcgctagta atagagctac cggcgtgccc    1560

gctaggttta gcggctcagg atcaggcacc gactttaccc tgactattag tagcctggaa    1620
```

```
cccgaggact tcgctaccta ctactgtcag cagtactacg actaccctca gaccttcggc   1680

cagggaacta aggtcgagat taagggcggt ggcggtagcg gcggaggcgg atcaggtggt   1740

ggtggtagtg gcggcggagg tagtcaggtc cagctgaaag agtcaggccc tgccctggtc   1800

aagcctactc agaccctgac cctgacctgc acttttagcg gctttagcct gagtaataga   1860

ggcggcggag tgggctggat tagacagcct ccaggcaaag ccctggagtg gctggcctgg   1920

atcgactggg acgacgataa gtcctactcc actagcctga aaactaggct gacaatcagc   1980

aaggacacta gtaaaaacca ggtggtgctg actatgacta atatggaccc cgtggacacc   2040

gctacctatt attgcgctag aatgcacctc ccactggtgt tcgatagctg gggtcaggga   2100

actctggtca cagtcagtag c                                              2121
```

<210> SEQ ID NO 197
<211> LENGTH: 105
<212> TYPE: PRT
<213> ORGANISM: Homo Sapien

<400> SEQUENCE: 197

```
Ser Tyr Glu Leu Thr Gln Pro Pro Ser Val Ser Val Ala Pro Gly Gln
 1               5                  10                  15

Thr Ala Arg Ile Ser Cys Ser Gly Asp Ser Leu Arg Asn Lys Val Tyr
            20                  25                  30

Trp Tyr Gln Gln Lys Pro Gly Gln Ala Pro Val Leu Val Ile Tyr Lys
        35                  40                  45

Asn Asn Arg Pro Ser Gly Ile Pro Glu Arg Phe Ser Gly Ser Asn Ser
    50                  55                  60

Gly Asn Thr Ala Thr Leu Thr Ile Ser Gly Thr Gln Ala Glu Asp Glu
65                  70                  75                  80

Ala Asp Tyr Tyr Cys Gln Ser Tyr Asp Gly Gln Lys Ser Leu Val Phe
                85                  90                  95

Gly Gly Gly Thr Lys Leu Thr Val Leu
            100                 105
```

<210> SEQ ID NO 198
<211> LENGTH: 315
<212> TYPE: DNA
<213> ORGANISM: Homo Sapien

<400> SEQUENCE: 198

```
tcttacgagc tgacccagcc cccttccgtg tctgtggctc ctggccagac cgccagaatc     60

tcttgctccg gcgactccct gcggaacaag gtgtactggt atcagcagaa gcccggccag    120

gcccctgtgc tggtcatcta caagaacaac cggccctccg gcatccccga gagattctct    180

ggctccaact ccggcaacac cgccaccctg acaatctctg gcacacaggc cgaggacgag    240

gccgactact actgccagtc ctacgacggc cagaaatcac tggtgttcgg cggaggcacc    300

aagctgacag tgctg                                                     315
```

<210> SEQ ID NO 199
<211> LENGTH: 211
<212> TYPE: PRT
<213> ORGANISM: Homo Sapien

<400> SEQUENCE: 199

```
Ser Tyr Glu Leu Thr Gln Pro Pro Ser Val Ser Val Ala Pro Gly Gln
 1               5                  10                  15
```

```
Thr Ala Arg Ile Ser Cys Ser Gly Asp Ser Leu Arg Asn Lys Val Tyr
            20                  25                  30

Trp Tyr Gln Gln Lys Pro Gly Gln Ala Pro Val Leu Val Ile Tyr Lys
        35                  40                  45

Asn Asn Arg Pro Ser Gly Ile Pro Glu Arg Phe Ser Gly Ser Asn Ser
    50                  55                  60

Gly Asn Thr Ala Thr Leu Thr Ile Ser Gly Thr Gln Ala Glu Asp Glu
65                  70                  75                  80

Ala Asp Tyr Tyr Cys Gln Ser Tyr Asp Gly Gln Lys Ser Leu Val Phe
                85                  90                  95

Gly Gly Gly Thr Lys Leu Thr Val Leu Gly Gln Pro Lys Ala Ala Pro
            100                 105                 110

Ser Val Thr Leu Phe Pro Pro Ser Ser Glu Glu Leu Gln Ala Asn Lys
        115                 120                 125

Ala Thr Leu Val Cys Leu Ile Ser Asp Phe Tyr Pro Gly Ala Val Thr
    130                 135                 140

Val Ala Trp Lys Ala Asp Ser Ser Pro Val Lys Ala Gly Val Glu Thr
145                 150                 155                 160

Thr Thr Pro Ser Lys Gln Ser Asn Asn Lys Tyr Ala Ala Ser Ser Tyr
                165                 170                 175

Leu Ser Leu Thr Pro Glu Gln Trp Lys Ser His Arg Ser Tyr Ser Cys
            180                 185                 190

Gln Val Thr His Glu Gly Ser Thr Val Glu Lys Thr Val Ala Pro Thr
        195                 200                 205

Glu Cys Ser
    210


<210> SEQ ID NO 200
<211> LENGTH: 633
<212> TYPE: DNA
<213> ORGANISM: Homo Sapien

<400> SEQUENCE: 200

tcttacgagc tgacccagcc cccttccgtg tctgtggctc ctggccagac cgccagaatc      60

tcttgctccg gcgactccct gcggaacaag gtgtactggt atcagcagaa gcccggccag     120

gcccctgtgc tggtcatcta caagaacaac cggccctccg gcatccccga gagattctct     180

ggctccaact ccggcaacac cgccaccctg acaatctctg gcacacaggc cgaggacgag     240

gccgactact actgccagtc ctacgacggc cagaaatcac tggtgttcgg cggaggcacc     300

aagctgacag tgctgggaca gcctaaggct gcccccagcg tgaccctgtt cccccccagc     360

agcgaggagc tgcaggccaa caaggccacc ctggtgtgcc tgatcagcga cttctaccca     420

ggcgccgtga ccgtggcctg gaaggccgac agcagccccg tgaaggccgg cgtggagacc     480

accacccccca gcaagcagag caacaacaag tacgccgcca gcagctacct gagcctgacc     540

cccgagcagt ggaagagcca caggtcctac agctgccagg tgacccacga gggcagcacc     600

gtggaaaaga ccgtggcccc aaccgagtgc agc                                  633


<210> SEQ ID NO 201
<211> LENGTH: 707
<212> TYPE: PRT
<213> ORGANISM: Homo Sapien

<400> SEQUENCE: 201

Gln Val Gln Leu Val Glu Ser Gly Gly Gly Leu Val Gln Pro Gly Gly
 1               5                  10                  15
```

-continued

```
Ser Leu Arg Leu Ser Cys Ala Ala Ser Gly Phe Thr Phe Ser Asp Tyr
            20                  25                  30

Val Ile Asn Trp Val Arg Gln Ala Pro Gly Lys Gly Leu Glu Trp Val
        35                  40                  45

Ser Gly Ile Ser Trp Ser Gly Val Asn Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Ala Thr Ala Asn Asn Ile Arg Tyr Lys Phe Met Asp
            100                 105                 110

Val Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Ala Ala Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430
```

```
Ser Val Met His Glu Ala Leu His Asn His Tyr Thr Gln Lys Ser Leu
        435                 440                 445

Ser Leu Ser Pro Gly Lys Gly Gly Ser Gly Gly Ser Asp Ile Val Leu
    450                 455                 460

Thr Gln Ser Pro Ala Thr Leu Ser Leu Ser Pro Gly Glu Arg Ala Thr
465                 470                 475                 480

Leu Ser Cys Arg Ala Ser Gln Phe Ile Gly Ser Arg Tyr Leu Ala Trp
                485                 490                 495

Tyr Gln Gln Lys Pro Gly Gln Ala Pro Arg Leu Leu Ile Tyr Gly Ala
            500                 505                 510

Ser Asn Arg Ala Thr Gly Val Pro Ala Arg Phe Ser Gly Ser Gly Ser
        515                 520                 525

Gly Thr Asp Phe Thr Leu Thr Ile Ser Ser Leu Glu Pro Glu Asp Phe
    530                 535                 540

Ala Thr Tyr Tyr Cys Gln Gln Tyr Tyr Asp Tyr Pro Gln Thr Phe Gly
545                 550                 555                 560

Gln Gly Thr Lys Val Glu Ile Lys Gly Gly Gly Gly Ser Gly Gly Gly
                565                 570                 575

Gly Ser Gly Gly Gly Gly Ser Gly Gly Gly Gly Ser Gln Val Gln Leu
            580                 585                 590

Lys Glu Ser Gly Pro Ala Leu Val Lys Pro Thr Gln Thr Leu Thr Leu
        595                 600                 605

Thr Cys Thr Phe Ser Gly Phe Ser Leu Ser Asn Arg Gly Gly Gly Val
    610                 615                 620

Gly Trp Ile Arg Gln Pro Pro Gly Lys Ala Leu Glu Trp Leu Ala Trp
625                 630                 635                 640

Ile Asp Trp Asp Asp Asp Lys Ser Tyr Ser Thr Ser Leu Lys Thr Arg
                645                 650                 655

Leu Thr Ile Ser Lys Asp Thr Ser Lys Asn Gln Val Val Leu Thr Met
            660                 665                 670

Thr Asn Met Asp Pro Val Asp Thr Ala Thr Tyr Tyr Cys Ala Arg Met
        675                 680                 685

His Leu Pro Leu Val Phe Asp Ser Trp Gly Gln Gly Thr Leu Val Thr
    690                 695                 700

Val Ser Ser
705
```

<210> SEQ ID NO 202
<211> LENGTH: 2121
<212> TYPE: DNA
<213> ORGANISM: Homo Sapien

<400> SEQUENCE: 202

```
caggtgcagc tggtggaatc aggcggagga ctggtccagc ctggcggatc acttagactg     60

agctgtgccg ctagtggctt cacctttagc gactatgtga ttaactgggt ccgacaggcc    120

cctggcaagg gactggaatg ggtgtcaggc attagttgga gcggcgtgaa cactcactac    180

gccgatagcg tgaagggccg gttcactatt agccgggata actctaagaa caccctgtac    240

ctgcagatga atagcctgag agccgaggac accgccgtct actactgcgc tagactgggc    300

gctaccgcta acaacatccg ctataagttc atggacgtgt ggggccaggg caccctggtc    360

acagtgtctt cagctagcac taagggcccc tcagtgttcc ccctggcccc tagctctaag    420

tctactagcg gtggcaccgc cgctctgggc tgcctggtca aggactactt ccccgagccc    480

gtgaccgtgt cttggaatag cggcgctctg actagcggag tgcacacctt ccccgccgtg    540
```

```
ctgcagtcta gcggcctgta tagcctgtct agcgtcgtga ccgtgcctag ctctagcctg    600

ggcactcaga cctatatctg taacgtgaac cacaagccta gtaacactaa ggtggacaag    660

cgggtggaac ctaagtcttg cgataagact cacacctgtc ccccctgccc tgccccagaa    720

gctgctggcg gacctagcgt gttcctgttc ccacctaagc ctaaagacac cctgatgatt    780

agtaggaccc ccgaagtgac ctgcgtggtg gtggacgtca gccacgagga ccctgaagtg    840

aagttcaatt ggtatgtgga cggcgtggaa gtgcacaacg ctaagactaa gcctagagag    900

gaacagtata actccaccta tagggtggtg tcagtgctga ccgtgctgca ccaggactgg    960

ctgaacggca aagagtataa gtgtaaagtc tctaacaagg ccctgcctgc ccctatcgaa   1020

aagactatct ctaaggctaa gggccagcct agagaacccc aggtctacac cctgcccccct   1080

agtagagaag agatgactaa gaatcaggtg tccctgacct gtctggtcaa gggcttctac   1140

cctagcgata tcgccgtgga gtgggagtct aacggccagc ccgagaacaa ctataagact   1200

acccccccctg tgctggatag cgacggctct ttcttcctgt actctaaact gaccgtggac   1260

aagtctaggt ggcagcaggg caacgtgttc agctgtagcg tgatgcacga ggccctgcac   1320

aatcactaca ctcagaagtc actgagcctg agtcccggca agggcggctc aggcggtagc   1380

gatatcgtgc tgactcagtc acccgctacc ctgagtctga gccctggcga gcgggctaca   1440

ctgagctgta gagctagtca gtttatcggc tcacgctacc tggcctggta tcagcagaag   1500

cccggccagg cccctagact gctgatctac ggcgctagta atagagctac cggcgtgccc   1560

gctaggttta gcggctcagg atcaggcacc gactttaccc tgactattag tagcctggaa   1620

cccgaggact tcgctaccta ctactgtcag cagtactacg actaccctca gaccttcggc   1680

cagggaacta aggtcgagat taagggcggt ggcggtagcg gcggaggcgg atcaggtggt   1740

ggtggtagtg gcggcggagg tagtcaggtc cagctgaaag agtcaggccc tgccctggtc   1800

aagcctactc agaccctgac cctgacctgc actttagcg gctttagcct gagtaataga   1860

ggcggcggag tgggctggat tagacagcct ccaggcaaag ccctggagtg gctggcctgg   1920

atcgactggg acgacgataa gtcctactcc actagcctga aactaggct gacaatcagc   1980

aaggacacta gtaaaaacca ggtggtgctg actatgacta atatggaccc cgtggacacc   2040

gctacctatt attgcgctag aatgcacctc ccactggtgt tcgatagctg gggtcaggga   2100

actctggtca cagtcagtag c                                            2121
```

<210> SEQ ID NO 203
<211> LENGTH: 105
<212> TYPE: PRT
<213> ORGANISM: Homo Sapien

<400> SEQUENCE: 203

```
Ser Tyr Glu Leu Thr Gln Pro Leu Ser Val Ser Val Ala Leu Gly Gln
 1               5                  10                  15

Thr Ala Arg Ile Thr Cys Ser Gly Asp Ser Leu Arg Asn Lys Val Tyr
            20                  25                  30

Trp Tyr Gln Gln Lys Pro Gly Gln Ala Pro Val Leu Val Ile Tyr Lys
        35                  40                  45

Asn Asn Arg Pro Ser Gly Ile Pro Glu Arg Phe Ser Gly Ser Asn Ser
    50                  55                  60

Gly Asn Thr Ala Thr Leu Thr Ile Ser Arg Ala Gln Ala Gly Asp Glu
65                  70                  75                  80

Ala Asp Tyr Tyr Cys Gln Ser Tyr Asp Gly Gln Lys Ser Leu Val Phe
```

```
                85                  90                  95

Gly Gly Gly Thr Lys Leu Thr Val Leu
            100                 105


<210> SEQ ID NO 204
<211> LENGTH: 315
<212> TYPE: DNA
<213> ORGANISM: Homo Sapien

<400> SEQUENCE: 204

agctacgagc tgactcagcc cctgagcgtg tcagtggctc tgggccagac cgctagaatc      60

acctgtagcg gcgatagcct gagaaacaag gtctactggt atcagcagaa gcccggccag     120

gcccctgtgc tggtcatcta taagaacaat aggcctagcg gcatccccga gcggtttagc     180

ggctctaata gcggcaacac cgctaccctg actattagta gggctcaggc cggcgacgag     240

gccgactact actgtcagtc ctacgacggc cagaagtcac tggtctttgg cggcggaact     300

aagctgaccg tgctg                                                      315


<210> SEQ ID NO 205
<211> LENGTH: 211
<212> TYPE: PRT
<213> ORGANISM: Homo Sapien

<400> SEQUENCE: 205

Ser Tyr Glu Leu Thr Gln Pro Leu Ser Val Ser Val Ala Leu Gly Gln
 1               5                  10                  15

Thr Ala Arg Ile Thr Cys Ser Gly Asp Ser Leu Arg Asn Lys Val Tyr
            20                  25                  30

Trp Tyr Gln Gln Lys Pro Gly Gln Ala Pro Val Leu Val Ile Tyr Lys
        35                  40                  45

Asn Asn Arg Pro Ser Gly Ile Pro Glu Arg Phe Ser Gly Ser Asn Ser
    50                  55                  60

Gly Asn Thr Ala Thr Leu Thr Ile Ser Arg Ala Gln Ala Gly Asp Glu
65                  70                  75                  80

Ala Asp Tyr Tyr Cys Gln Ser Tyr Asp Gly Gln Lys Ser Leu Val Phe
                85                  90                  95

Gly Gly Gly Thr Lys Leu Thr Val Leu Gly Gln Pro Lys Ala Ala Pro
            100                 105                 110

Ser Val Thr Leu Phe Pro Pro Ser Ser Glu Glu Leu Gln Ala Asn Lys
        115                 120                 125

Ala Thr Leu Val Cys Leu Ile Ser Asp Phe Tyr Pro Gly Ala Val Thr
    130                 135                 140

Val Ala Trp Lys Ala Asp Ser Ser Pro Val Lys Ala Gly Val Glu Thr
145                 150                 155                 160

Thr Thr Pro Ser Lys Gln Ser Asn Asn Lys Tyr Ala Ala Ser Ser Tyr
                165                 170                 175

Leu Ser Leu Thr Pro Glu Gln Trp Lys Ser His Arg Ser Tyr Ser Cys
            180                 185                 190

Gln Val Thr His Glu Gly Ser Thr Val Glu Lys Thr Val Ala Pro Thr
        195                 200                 205

Glu Cys Ser
    210


<210> SEQ ID NO 206
<211> LENGTH: 633
<212> TYPE: DNA
```

<213> ORGANISM: Homo Sapien

<400> SEQUENCE: 206

```
agctacgagc tgactcagcc cctgagcgtg tcagtggctc tgggccagac cgctagaatc     60

acctgtagcg gcgatagcct gagaaacaag gtctactggt atcagcagaa gcccggccag    120

gcccctgtgc tggtcatcta taagaacaat aggcctagcg gcatccccga gcggtttagc    180

ggctctaata gcggcaacac cgctaccctg actattagta gggctcaggc cggcgacgag    240

gccgactact actgtcagtc ctacgacggc cagaagtcac tggtctttgg cggcggaact    300

aagctgaccg tgctgggaca gcctaaggct gcccccagcg tgaccctgtt ccccccccagc   360

agcgaggagc tgcaggccaa caaggccacc ctggtgtgcc tgatcagcga cttctaccca    420

ggcgccgtga ccgtggcctg gaaggccgac agcagccccg tgaaggccgg cgtggagacc    480

accaccccca gcaagcagag caacaacaag tacgccgcca gcagctacct gagcctgacc    540

cccgagcagt ggaagagcca caggtcctac agctgccagg tgacccacga gggcagcacc    600

gtggaaaaga ccgtggcccc aaccgagtgc agc                                 633
```

<210> SEQ ID NO 207
<211> LENGTH: 707
<212> TYPE: PRT
<213> ORGANISM: Homo Sapien

<400> SEQUENCE: 207

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Val Ile Asn Trp Val Arg Gln Ala Pro Gly Lys Gly Leu Glu Trp Val
        35                  40                  45

Ser Gly Ile Ser Trp Ser Gly Val Asn Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Gly Ala Thr Ala Asn Asn Ile Arg Tyr Lys Phe Met Asp
            100                 105                 110

Val Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240
```

-continued

```
Ala Ala Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys Gly Gly Ser Gly Gly Ser Asp Ile Val Leu
    450                 455                 460

Thr Gln Ser Pro Ala Thr Leu Ser Leu Ser Pro Gly Glu Arg Ala Thr
465                 470                 475                 480

Leu Ser Cys Arg Ala Ser Gln Phe Ile Gly Ser Arg Tyr Leu Ala Trp
                485                 490                 495

Tyr Gln Gln Lys Pro Gly Gln Ala Pro Arg Leu Leu Ile Tyr Gly Ala
            500                 505                 510

Ser Asn Arg Ala Thr Gly Val Pro Ala Arg Phe Ser Gly Ser Gly Ser
        515                 520                 525

Gly Thr Asp Phe Thr Leu Thr Ile Ser Ser Leu Glu Pro Glu Asp Phe
    530                 535                 540

Ala Thr Tyr Tyr Cys Gln Gln Tyr Tyr Asp Tyr Pro Gln Thr Phe Gly
545                 550                 555                 560

Gln Gly Thr Lys Val Glu Ile Lys Gly Gly Gly Gly Ser Gly Gly Gly
                565                 570                 575

Gly Ser Gly Gly Gly Gly Ser Gly Gly Gly Gly Ser Gln Val Gln Leu
            580                 585                 590

Lys Glu Ser Gly Pro Ala Leu Val Lys Pro Thr Gln Thr Leu Thr Leu
        595                 600                 605

Thr Cys Thr Phe Ser Gly Phe Ser Leu Ser Asn Arg Gly Gly Gly Val
    610                 615                 620

Gly Trp Ile Arg Gln Pro Pro Gly Lys Ala Leu Glu Trp Leu Ala Trp
625                 630                 635                 640

Ile Asp Trp Asp Asp Asp Lys Ser Tyr Ser Thr Ser Leu Lys Thr Arg
                645                 650                 655

Leu Thr Ile Ser Lys Asp Thr Ser Lys Asn Gln Val Val Leu Thr Met
```

-continued

```
            660                 665                 670

Thr Asn Met Asp Pro Val Asp Thr Ala Thr Tyr Tyr Cys Ala Arg Met
        675                 680                 685

His Leu Pro Leu Val Phe Asp Ser Trp Gly Gln Gly Thr Leu Val Thr
    690                 695                 700

Val Ser Ser
705


<210> SEQ ID NO 208
<211> LENGTH: 2121
<212> TYPE: DNA
<213> ORGANISM: Homo Sapien

<400> SEQUENCE: 208

gaggtgcagc tgctggaatc aggcggagga ctggtgcagc ctggcggatc actgagactg     60

agctgtgccg ctagtggctt cacctttagc gactatgtga ttaactgggt ccgacaggcc    120

cctggcaagg gactggaatg ggtgtcaggc attagttgga gcggcgtgaa cactcactac    180

gccgatagcg tgaagggccg gttcactatt agccgggata actctaagaa caccctgtac    240

ctgcagatga atagcctgag agccgaggac accgccgtct actactgcgc tagactgggc    300

gctaccgcta acaacatccg ctataagttc atggacgtgt ggggccaggg caccctggtc    360

acagtgtctt cagctagcac taagggcccc tcagtgttcc ccctggcccc tagctctaag    420

tctactagcg gtggcaccgc cgctctgggc tgcctggtca aggactactt ccccgagccc    480

gtgaccgtgt cttggaatag cggcgctctg actagcggag tgcacacctt ccccgccgtg    540

ctgcagtcta gcggcctgta tagcctgtct agcgtcgtga ccgtgcctag ctctagcctg    600

ggcactcaga cctatatctg taacgtgaac cacaagccta gtaacactaa ggtggacaag    660

cgggtggaac ctaagtcttg cgataagact cacacctgtc ccccctgccc tgccccagaa    720

gctgctggcg gacctagcgt gttcctgttc ccacctaagc ctaaagacac cctgatgatt    780

agtaggaccc ccgaagtgac ctgcgtggtg gtggacgtca gccacgagga ccctgaagtg    840

aagttcaatt ggtatgtgga cggcgtggaa gtgcacaacg ctaagactaa gcctagagag    900

gaacagtata actccaccta tagggtggtg tcagtgctga ccgtgctgca ccaggactgg    960

ctgaacggca aagagtataa gtgtaaagtc tctaacaagg ccctgcctgc ccctatcgaa   1020

aagactatct ctaaggctaa gggccagcct agagaacccc aggtctacac cctgcccccct  1080

agtagagaag agatgactaa gaatcaggtg tccctgacct gtctggtcaa gggcttctac   1140

cctagcgata tcgccgtgga gtgggagtct aacggccagc ccgagaacaa ctataagact   1200

acccccccctg tgctggatag cgacggctct ttcttcctgt actctaaact gaccgtggac  1260

aagtctaggt ggcagcaggg caacgtgttc agctgtagcg tgatgcacga ggccctgcac   1320

aatcactaca ctcagaagtc actgagcctg agtcccggca agggcggctc aggcggtagc   1380

gatatcgtgc tgactcagtc acccgctacc ctgagtctga gccctggcga gcgggctaca   1440

ctgagctgta gagctagtca gtttatcggc tcacgctacc tggcctggta tcagcagaag   1500

cccggccagg cccctagact gctgatctac ggcgctagta atagagctac cggcgtgccc   1560

gctaggttta gcggctcagg atcaggcacc gactttaccc tgactattag tagcctggaa   1620

cccgaggact tcgctaccta ctactgtcag cagtactacg actaccctca gaccttcggc   1680

cagggaacta aggtcgagat taagggcggt ggcggtagcg gcggaggcgg atcaggtggt   1740

ggtggtagtg gcggcggagg tagtcaggtc cagctgaaag agtcaggccc tgccctggtc   1800
```

-continued

```
aagcctactc agaccctgac cctgacctgc acttttagcg gctttagcct gagtaataga    1860

ggcggcggag tgggctggat tagacagcct ccaggcaaag ccctggagtg gctggcctgg    1920

atcgactggg acgacgataa gtcctactcc actagcctga aaactaggct gacaatcagc    1980

aaggacacta gtaaaaacca ggtggtgctg actatgacta atatggaccc cgtggacacc    2040

gctacctatt attgcgctag aatgcacctc ccactggtgt tcgatagctg gggtcaggga    2100

actctggtca cagtcagtag c                                              2121
```